US012723046B2

(12) United States Patent
Agejas Chicharro et al.

(10) Patent No.: US 12,723,046 B2
(45) Date of Patent: Sep. 1, 2026

(54) cGAS INHIBITORS

(71) Applicant: Eli Lilly and Company, Indianapolis, IN (US)

(72) Inventors: Francisco Javier Agejas Chicharro, Madrid (ES); Adel Ahmed, Fishers, IN (US); Cheryl Ann Carson, Indianapolis, IN (US); Scott Eugene Conner, Carmel, IN (US); Graham Robert Cumming, Madrid (ES); Kevin Charles Fortner, Indianapolis, IN (US); Douglas L. Gernert, Indianapolis, IN (US); Steven J. Green, Indianapolis, IN (US); Charles W. Lugar, McCordsville, IN (US); Jothirajah Marimuthu, Carmel, IN (US); Christina Martinez Brokaw, Zionsville, IN (US); Shanthi Nagarajan, San Diego, CA (US); Emmanuel Onobun, Indianapolis, IN (US); Eric George Tromiczak, Indianapolis, IN (US); Thibault Francois Varin, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 426 days.

(21) Appl. No.: 18/390,364

(22) Filed: Dec. 20, 2023

(65) Prior Publication Data

US 2024/0246979 A1 Jul. 25, 2024

Related U.S. Application Data

(60) Provisional application No. 63/476,422, filed on Dec. 21, 2022.

(30) Foreign Application Priority Data

Nov. 10, 2023 (EP) .................................... 23383152

(51) Int. Cl.
*C07D 487/04* (2006.01)
*A61K 31/55* (2006.01)
*A61P 37/06* (2006.01)

(52) U.S. Cl.
CPC ............ *C07D 487/04* (2013.01); *A61K 31/55* (2013.01); *A61P 37/06* (2018.01)

(58) Field of Classification Search
None
See application file for complete search history.

(56) References Cited

FOREIGN PATENT DOCUMENTS

| | | |
|---|---|---|
| CN | 111018864 | 4/2020 |
| CN | 115197206 | 10/2022 |
| WO | 2005107471 | 11/2005 |
| WO | 2019/153002 | 8/2019 |
| WO | 2020/186027 | 3/2020 |
| WO | 2020/252240 | 12/2020 |
| WO | 2020/257621 | 12/2020 |
| WO | 2022/066851 | 3/2022 |
| WO | 2022/137085 | 6/2022 |
| WO | 2023109912 | 6/2023 |

OTHER PUBLICATIONS

Qian Pengcheng, Ye Longwu, Foreign Patent Application: CN111089399A, Publication Date: May 1, 2020 (Year: 2020).*
Written Opinion, PCT Application No. PCT/US2023/085023, dated May 6, 2024, 6 pages.
Ablasser, et al., "cGAS produces a 2'- 5' -linked cyclic dinucleotide second messenger that activates STING," Nature, vol. 498, pp. 380-384 (2013).
Sun, et al., "Cyclic GMP_AMP Synthase Is a Cytosolic DNA Sensor That Activates the Type I Interferon Pathway," Science, vol. 339, pp. 786-791 (2013).
Gao, et al., Science, vol. 341, pp. 903-906 (2013).
Civril, et al., Nature, vol. 498, pp. 332-337 (2013).
Gray, et al., "Cutting Edge: cGAS Is Required for Lethal Autoimmune Disease in the Trex1-Deficient Mouse Model of Aicardi-Goutieres Syndrome," The Journal of Immunology, vol. 195, No. 5, pp. 1939-1943 (2015).
Caielli, et al., Erythroid Mitochondrial Retention Triggers Myeloid-dependent Type I interferon in human SLE, Cell, vol. 184, No. 17, pp. 4464-4479 (2021).
Xiao, et al., "cGAS activation causes lupus-like autoimmune disorders in a TREX1 mutant mouse model," Journal of Autoimmunity, vol. 100, pp. 84-94 (2019).
Furie, et al., "Monoclonal antibody targeting BDCA2 ameliorates skin lesions in systemic lupus erythematosus," The Journal of Clinical Investigation, vol. 129, No. 3, pp. 1359-1371 (Mar. 2019).
Smith, et al., "Using the circulating proteome to assess type I interferon activity in systemic lupus erythematosus", Scientific Reports, vol. 10, p. 4462 (2020).
Tanaka, et al., "Filgotinib, a novel JAK1-preferential inhibitor for the treatment of rheumatoid arthritis: An overview from clinical trials," Mod. Rheumatol., vol. 32, No. 1 pp. 1-11 (2022).

(Continued)

*Primary Examiner* — Kortney L. Klinkel
*Assistant Examiner* — Cierra M Rochelle
(74) *Attorney, Agent, or Firm* — Nielsen IP Law LLC

(57) ABSTRACT

The present invention relates to novel cGAS inhibitor compounds, having a formula of:

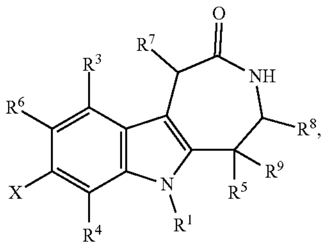

to pharmaceutical compositions comprising the compounds, and to methods of using the compounds and compositions to treat certain pathological conditions such as immune-mediated diseases.

26 Claims, No Drawings

(56) References Cited

OTHER PUBLICATIONS

Skopelia-Gardner, et al., "The early local and systemic Type I interferon responses to ultraviolet B light exposure are cGAS dependent," Scientific Reports, vol. 10, No. 7908 (2020).
An, et al., "Expression of Cyclic GMP-AMP Synthase in Patients With Systemic Lupus Erythematosus," Arthritis Rheumatol., vol. 69, No. 4, pp. 800-807 (2017).

* cited by examiner cGAS INHIBITORS

FIELD

The present invention relates to novel cGAS inhibitor compounds, to pharmaceutical compositions comprising the compounds, and to methods of using the compounds and compositions to treat certain pathological conditions, such as immune-mediated diseases.

BACKGROUND

Cyclic GAMP-AMP synthase (cGAS) is a critical cytosolic DNA sensor that catalyzes the formation of 2'3'-Cyclic GMP-AMP (cGAMP), a second messenger that binds to Stimulator of interferon genes (STING) to trigger downstream signaling resulting in the production of proinflammatory cytokines and type I interferons (Ablasser, A. et al. *Nature,* 2013, 498, 380-384, Sun, L. et al. *Science,* 2013, 339, 786-791). cGAS recognizes dsDNA and retroviral DNA intermediates (Gao, D. et al. *Science,* 2013, 341, 903-906) in a nonsequence-specific manner and dimerizes to activate its nucleotidyl transferase function (Civril, F. et al. *Nature,* 2013, 498, 332-337), triggering potent antiviral effector functions through the interferon signature genes induced by the type I interferons. Failure to degrade cytosolic DNA and mitochondrial DNA leakage from cellular stress have also been implicated in pathogenic cGAS activation in diseases such as Aicardi-Goutières syndrome (Gray, E. E. et al. *J Immunol,* 2015, 195, 1939-1943) and systemic lupus erythematosus (SLE) (Caielli, S. et al. *Cell,* 2021, 184, 4464-4479). cGAS deficiency rescues the autoimmune phenotype and fatality of TREX1 knockout mice that accumulate DNA in the cytosol, mimicking features of Aicardi-Goutières syndrome (Xiao, N. et al. *J Autoimmun,* 2019, 100, 84-94). SLE is a heterogenous disease characterize by the widespread loss of tolerance of nuclear antigens such as anti-dsDNA antibodies and a high interferon gene signature. Reduction of the interferon gene signature in clinical trials has been correlated to amelioration of symptoms and interferon signature gene panels has been used both as a biomarker and pharmacodynamic marker in SLE clinical trials (Furie, R, et al. *J Clin Invest,* 2019, 129, 1359-1371, Smith, M. A. et al. *Sci Rep,* 2020, 10, 4462, Tanaka, T. et al. *Mod Rheumatol,* 2022, 00, 1-11). UV light exposure in skin has been shown to activate cGAS (Skopelja-Gardner, S. et al. *Sci Rep,* 2020, 10, 7908) and elevations in cGAMP has been reported to be elevated in SLE (An, J. et al. *Arthritis Rheumatol,* 2017, 69, 800-807). In addition, mitochondrial dysfunction in SLE also promotes cGAS activation (Caielli, S. et al. *Cell,* 2021, 184, 4464-4479).

WO2019153002 discloses 2,3,4,5-tetrahydro-1H-pyrido[4,3-b]indole inhibitors of cGAS for treating autoinflammatory diseases. WO2022137085 discloses 2-heteroaryl-1H-indole compounds for treating cGAS-related diseases. However, various preclinical scaffolds have been shown to face challenges such as poor cell activity, unsatisfactory potency, and/or unfavorable pharmacokinetic characteristics. There has not been any cGAS inhibitor currently approved as FDA-approved drugs on the market. Ventus Therapeutics announced in January 2023 VENT-03, a cGAS inhibitor development candidate. Despite this, it appears that VENT-03 has not yet entered clinic at this time. There thus remains a need for novel, oral, selective, and/or potent cGAS inhibitors for the treatment of immune-mediated diseases, including cGAS-mediated immune disorders, such as cGAS-mediated aspects of SLE. The present invention provides novel cGAS inhibitors, and compositions thereof, for use in the treatment of such diseases.

SUMMARY

In some embodiments, the present invention provides a compound of Formula IIa:

(IIa)

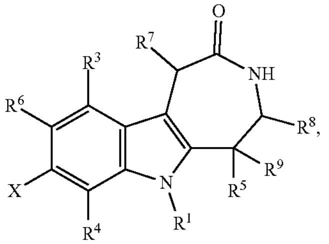

wherein:

X and $R^4$ are independently halo;

$R^1$, $R^7$, $R^8$, and $R^9$ are independently $R^b$;

$R^6$ is H or F;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H, or —$R^{bb}$—OH;

$R^5$ is H, —$R^{bb}$H, —$R^{bb}$C(O)$OR^b$, —$R^{bb}$C(O)N$(R^b)_2$, —$R^{bb}$N$(R^b)_2$, —$R^{bb}$N$(R^b)$($R^{bb}CF_3$), —$R^{bb}OR^b$, or

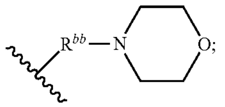

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

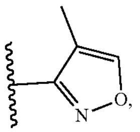,

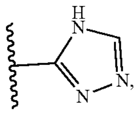, or

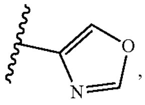, or a pharmaceutically acceptable salt thereof.

In some embodiments, provided herein is a pharmaceutical composition, comprising a compound disclosed herein, or a pharmaceutically acceptable salt thereof, with one or more pharmaceutically acceptable carriers, diluents, or excipients.

In some embodiments, provided herein is a method of treating an immune-mediated disease in a patient, such as systemic lupus erythematosus, lupus nephritis, dermatomyositis, and Aicardi-Goutières syndrome, comprising administering to a patient in need of such treatment an effective amount of a compound disclosed herein, or a pharmaceutically acceptable salt thereof, or a pharmaceutically composition thereof.

In some embodiments, provided herein is a compound, as disclosed herein, or a pharmaceutically acceptable salt thereof, for use in therapy.

DETAILED DESCRIPTION

In some embodiments, the present invention provides a compound of Formula IIa:

(IIa)

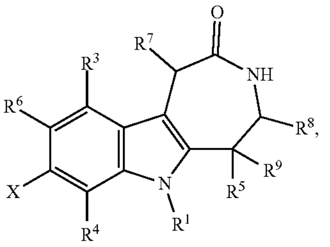

wherein:

X and $R^4$ are independently halo;

$R^1$, $R^7$, $R^8$, and $R^9$ are independently $R^b$;

$R^6$ is H or F;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H, or —$R^{bb}$—OH;

$R^5$ is H, —$R^{bb}$H, —$R^{bb}$C(O)$OR^b$, —$R^{bb}$C(O)N($R^b$)$_2$, —$R^{bb}$N($R^b$)$_2$, —$R^{bb}$N($R^b$)($R^{bb}CF_3$), —$R^{bb}OR^b$, or

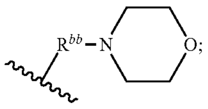

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is 5-membered heteroaryl including N, or a pharmaceutically acceptable salt thereof.

In some embodiments, $R^e$ is

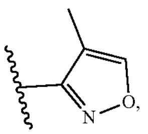
,
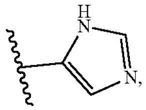
, or
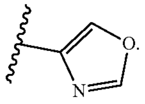
.

In some embodiments, the present invention provides a compound of Formula IIb:

(IIb)

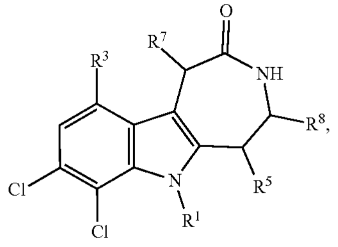

or a pharmaceutically acceptable salt thereof, wherein each variable is according to those defined for Formula IIa above.

In some embodiments, $R^5$ is H, —$R^{bb}$H, —$R^{bb}$C(O)$OR^b$, —$R^{bb}$C(O)N($R^b$)$_2$, —$R^{bb}$N($R^b$)$_2$, —$R^{bb}$N($R^b$)($R^{bb}CF_3$), —$R^{bb}$—$OR^b$, or

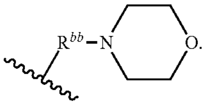

In some embodiments, $R^5$ is H, —$CH_3$, —$CH_2CH_3$, —$CH_2CH_2CH_3$,

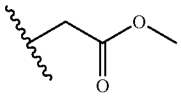
,
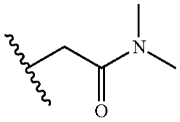
,
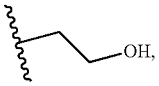

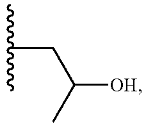

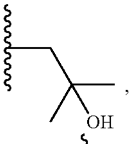
,
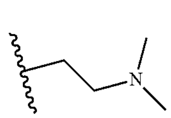
,

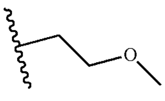
,
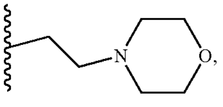

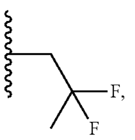

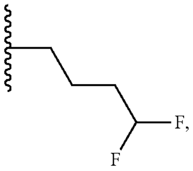
or

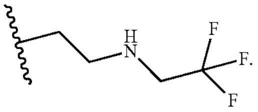

In some embodiments, $R^5$ is —$R^{bb}$H, —$R^{bb}$C(O)O$R^b$, —$R^{bb}$C(O)N($R^b$)$_2$, —$R^{bb}$N($R^b$)$_2$, —$R^{bb}$N($R^b$)($R^{bb}$CF$_3$), —$R^{bb}$—O$R^b$ or

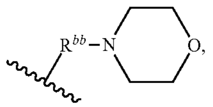

and the

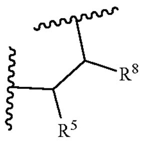

is

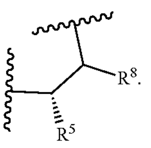

In some embodiments, $R^5$ is —$R^{bb}$H, —$R^{bb}$C(O)O$R^b$, —$R^{bb}$C(O)N($R^b$)$_2$, —$R^{bb}$N($R^b$)$_2$, —$R^{bb}$N($R^b$)($R^{bb}$CF$_3$), —$R^{bb}$—O$R^b$ or

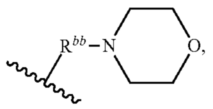

and the

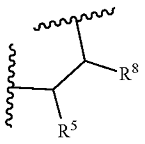

is

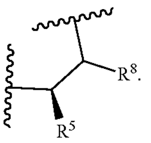

In some embodiments, the present invention provides a compound of Formula IVa:

(IVa)

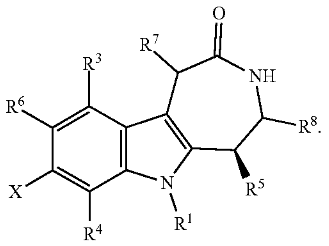

In some embodiments, $R^5$ is H.

In some embodiments, $R^7$ is H.

In some embodiments, $R^7$ is —$R^{bb}$H, and the

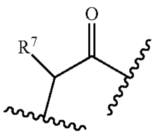

is

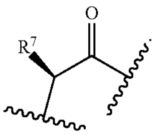

In some embodiments, $R^7$ is —$R^{bb}$H, and the

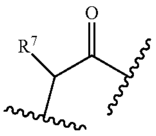

is

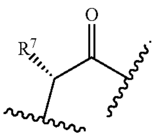

In some embodiments, the present invention provides a compound of Formula IVb:

IVb

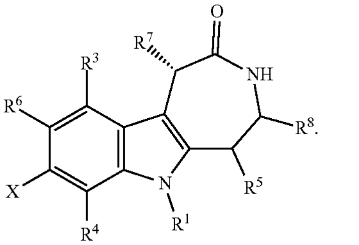

In some embodiments, $R^7$ is methyl.

In some embodiments, $R^3$ is $-NH-R^{bb}-OR^b$, $-NHC(O)-R^{bb}-OR^b$, $-NHC(O)C(O)_2$, $-O-R^{bb}-C(O)NH_2$, $-O-R^{bb}-OR^b$, $-O-R^{bb}-O-C(O)-R^b$, $-O-R^{bb}-H$, $-O-R^{bb}-CN$, $-NH-R^{bb}-H$, $-R^{bb}-OH$, or $R^{bb}-CN$.

In some embodiments, $R^3$ is $-NH-R^c$, $-NH-C(O)-R^c$, or $-O-R^c$.

In some embodiments, $R^3$ is selected from

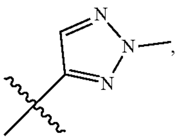
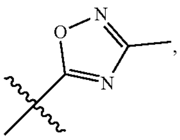
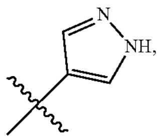
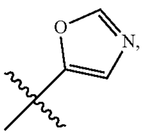
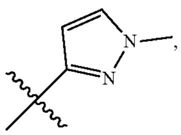
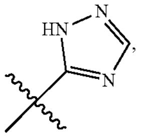
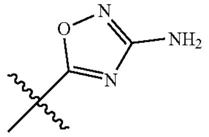
and
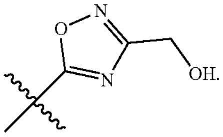

In some embodiments, $R^3$ is selected from $-NH-(CH_2)_2-OH$, $-NH-(CH_2)_2-O(CH_3)$, $-NH-(CH_2)((CH)(CH_3))-OH$, $-NHC(O)-CH_2-OH$, $-NHC(O)-CH_2-O(CH_3)$, $-NHC(O)-CH(CH_3)-OH$, $-NH-(CH_2)(CF_2)(CH_2)-OH$, $-NH-(CH_2)-CHF_2$, $-NH-(CH_2)_2-CHF_2$, $-O-CH_2-C(O)NH_2$, $-O-(CH_2)(CH(CH_3))-OH$, $-O(CH_2)_3-OH$, $-O(CH_2)_2-O(CH_3)$, $-O-(CH_2)(CF_2)(CH_2)-OH$, $-NH-(CH_2)(CF_2)(CH_2)-OH$, $-O(CH_2)CH_2F$, $-O(CH_2)_2CH_2F$, $-O-CH_2-CN$, $-NH(CH_2)_3$, $-(CH_2)_3OH$, and $-CH_2-CN$.

In some embodiments, $R^8$ is H.

In some embodiments, $R^8$ is methyl.

In some embodiments, $R^1$ is H.

In some embodiments, $R^1$ is methyl.

In some embodiments, $R^1$ is $C_{1-3}$ alkyl substituted with one or more fluoro.

In some embodiments, $R^1$ is trifluoroethyl.

In some embodiments, $R^1$ is $-CH_2CF_3$.

In some embodiments, the compound has formula IIc:

(IIc)

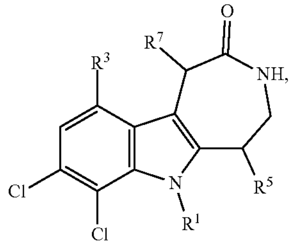

wherein:

$R^1$ is H, $-CH_3$, or $-CHF_2$;

$R^5$ is H, $-CH_3$, $CH_2CH_3$, or $-CH_2CH_2CH_3$;

$R^7$ is H, $-CH_3$, $CH_2CH_3$, or $-CH_2CH_2CH_3$;

$R^3$ is $-NH-(CH_2)_2-OH$, $-NH-(CH_2)_2-O(CH_3)$, $-NH-(CH_2)((CH)(CH_3))-OH$, $-NHC(O)-CH_2-OH$, $-NHC(O)-CH_2-O(CH_3)$, $-NHC(O)-CH(CH_3)-OH$, $-NH-(CH_2)(CF_2)(CH_2)-OH$, $-NH-(CH_2)-CHF_2$, $-NH-(CH_2)_2-CHF_2$, $-O-CH_2-C(O)NH_2$, $-O-(CH_2)(CH(CH_3))-OH$, $-O(CH_2)_3-OH$, $-O(CH_2)_2-O(CH_3)$, $-O-(CH_2)(CF_2)(CH_2)-OH$, $-NH-(CH_2)(CF_2)(CH_2)-OH$, $-O(CH_2)CH_2F$, $-O(CH_2)_2CH_2F$, $-O-CH_2-CN$, $-NH(CH_2)_3$, $-(CH_2)_3OH$, $-CH_2-CN$,

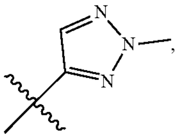
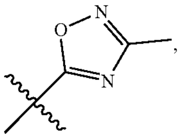
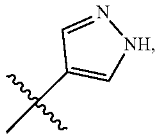
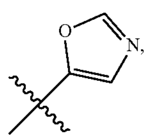
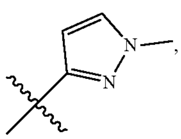
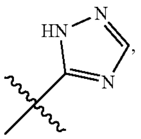
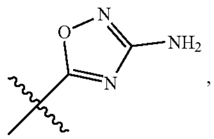
,
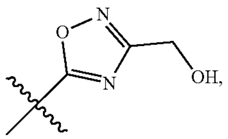

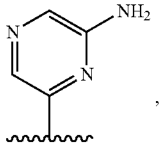
,
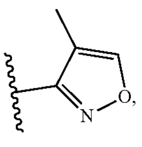
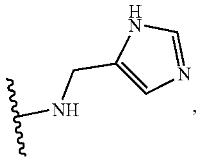
, and
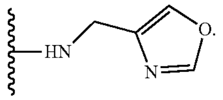

In some embodiments, the compound has formula IId:
(IId)
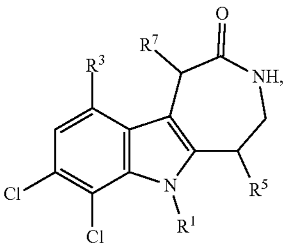
wherein $R^1$, $R^5$, and $R^7$ is each independently H or —$CHF_2$, and $R^3$ is —NHC(O)—$CH_2$—OH, —O—$(CH_2)_2$—O—$(CH_3)$, —NH—C(O)—CH$(CH_3)$—OH, or
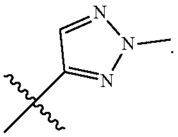 [SMILES: *c1cnn(C)n1]
In some embodiments, the compound is selected from the group consisting of:
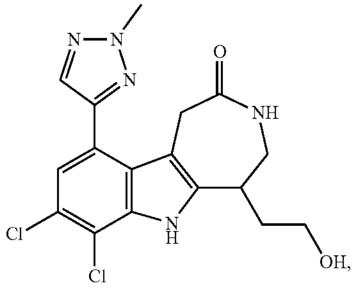
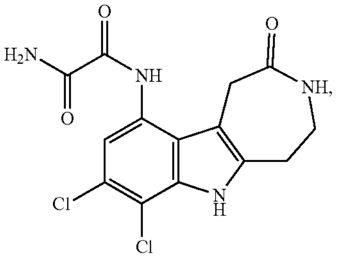
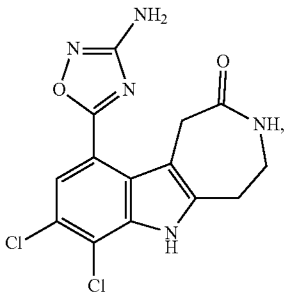
-continued
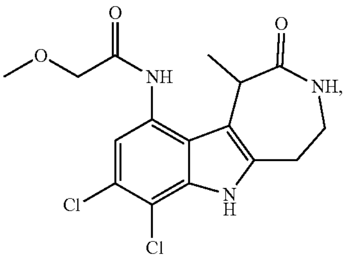
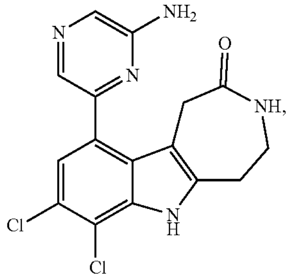
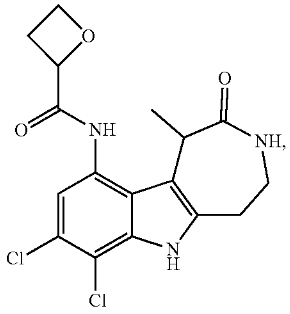
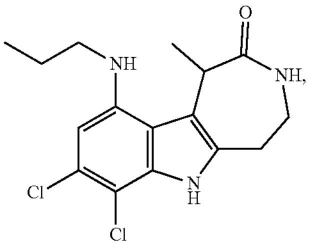
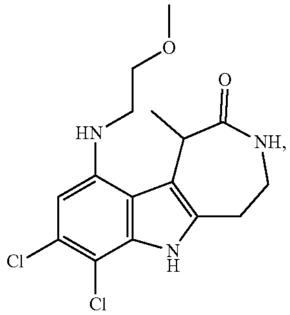
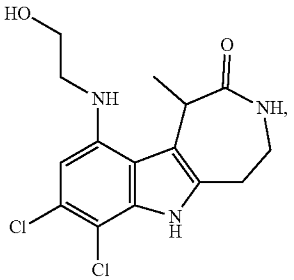

-continued
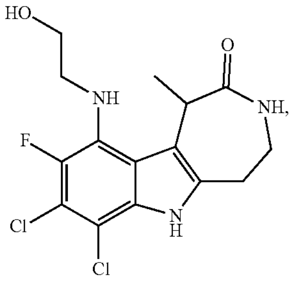
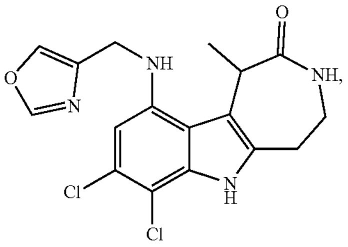
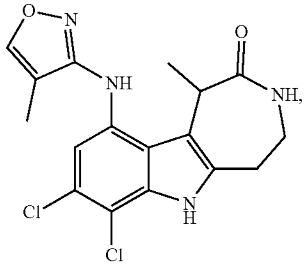
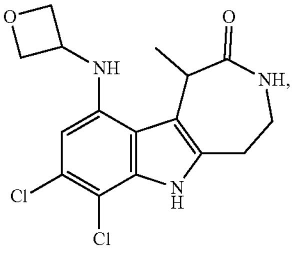
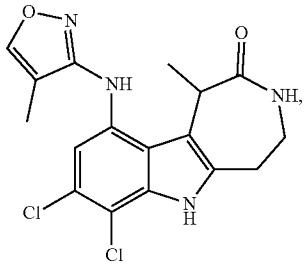
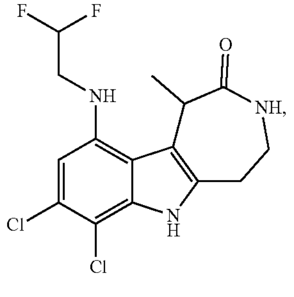
-continued
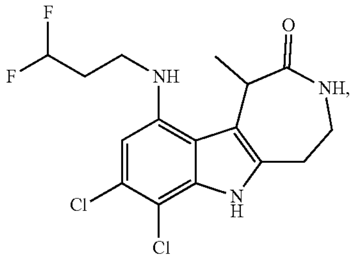
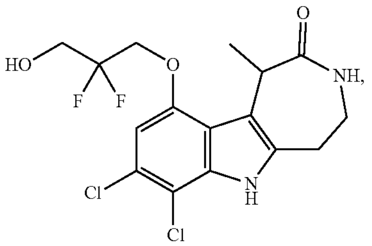
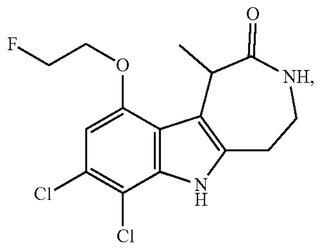
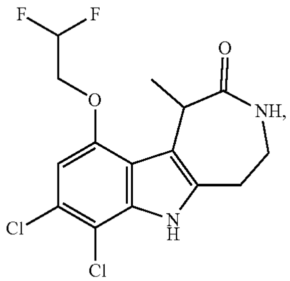
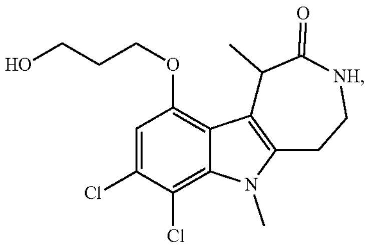
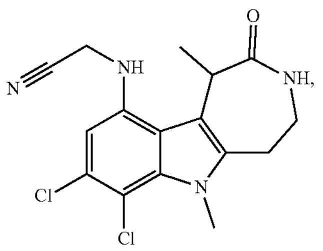

-continued
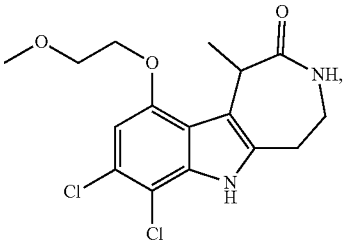
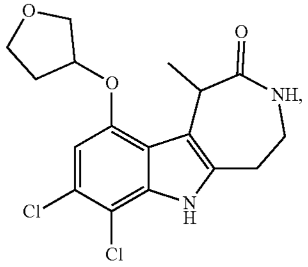
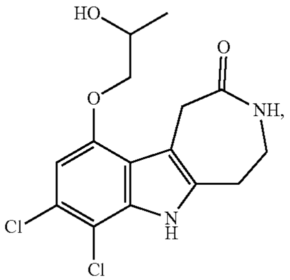
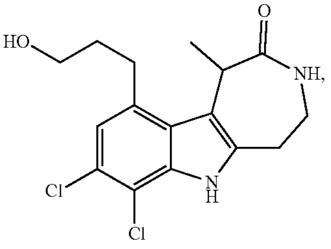
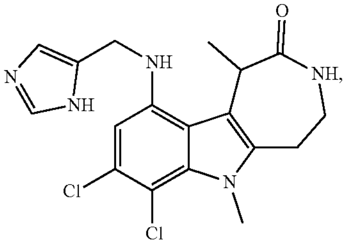
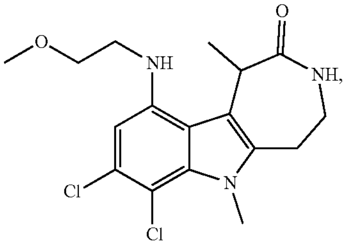
-continued
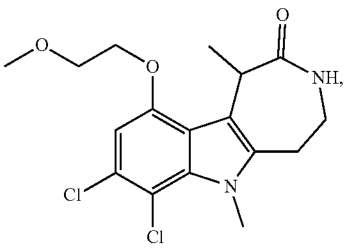
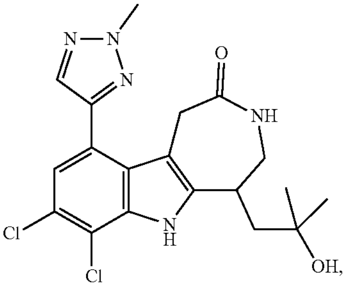
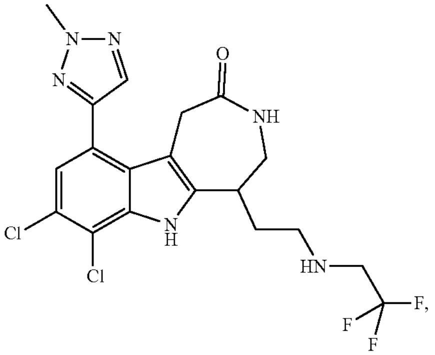
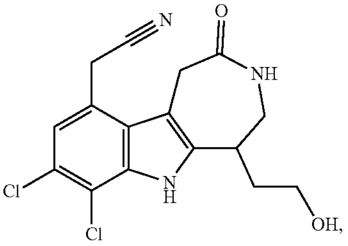
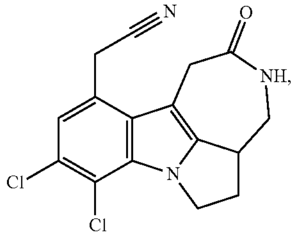
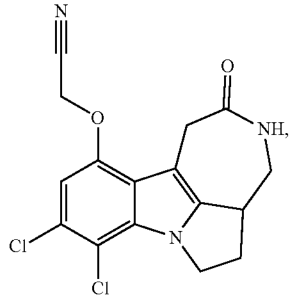

-continued
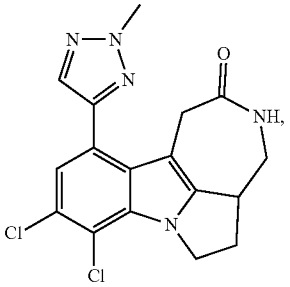
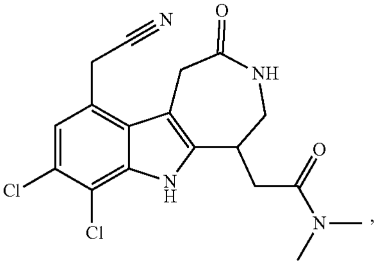
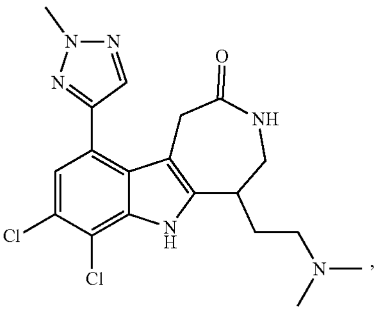
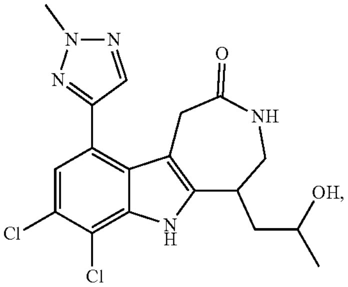
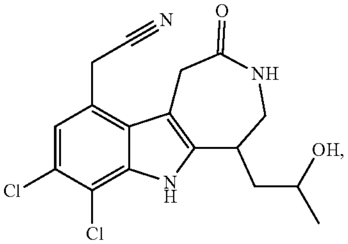
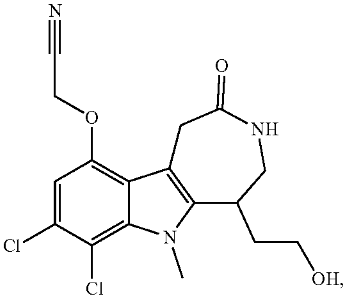
-continued
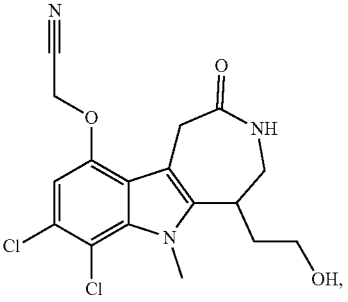
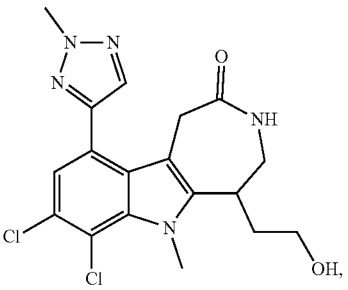
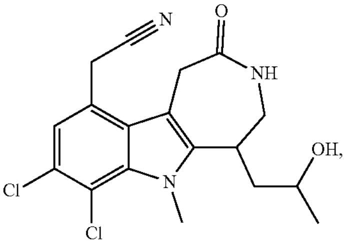
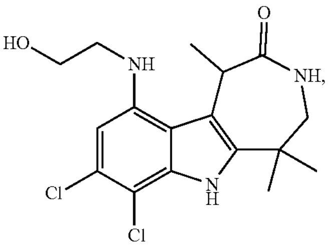
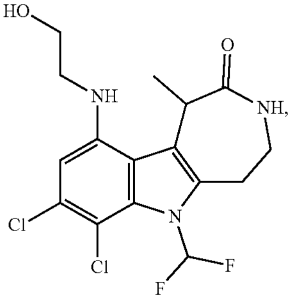
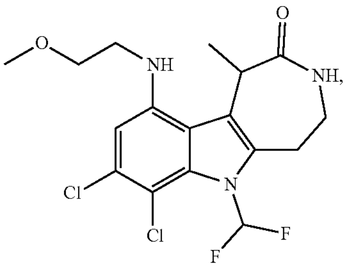

-continued
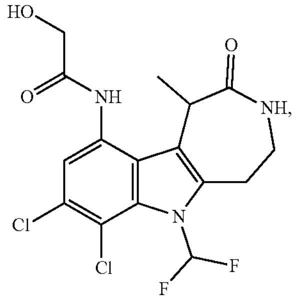
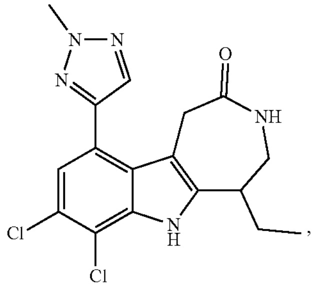
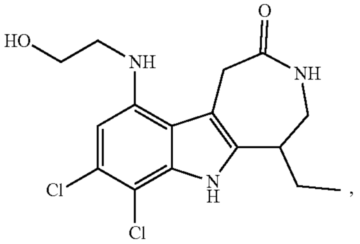
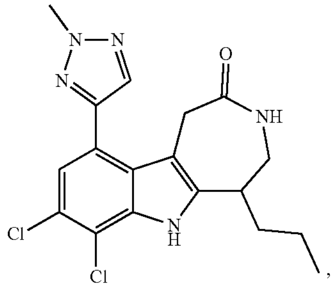
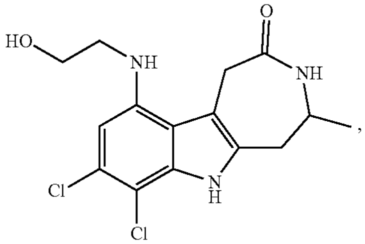
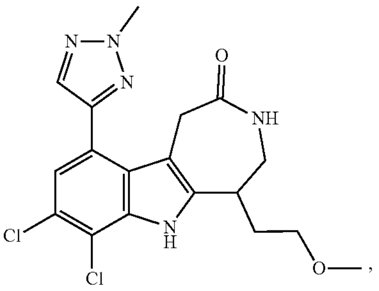
-continued
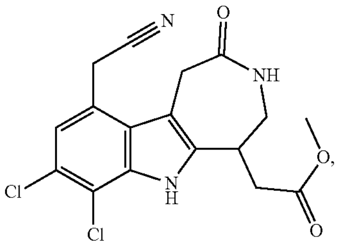
and
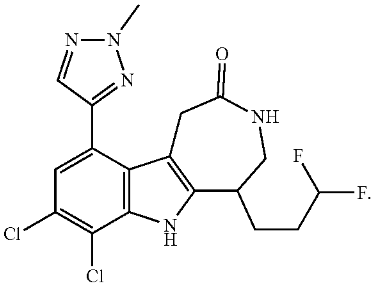
In some embodiments, the compound is selected from the group consisting of:
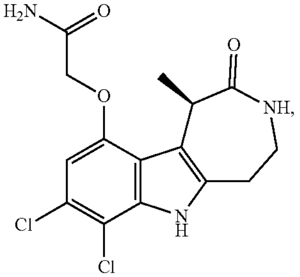
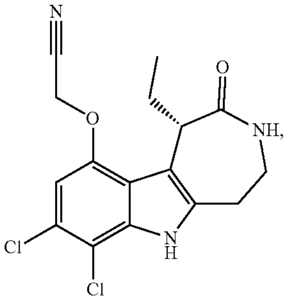
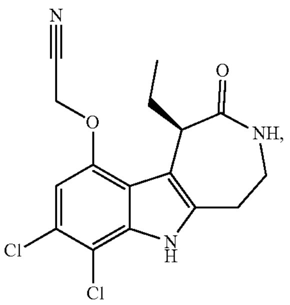

-continued
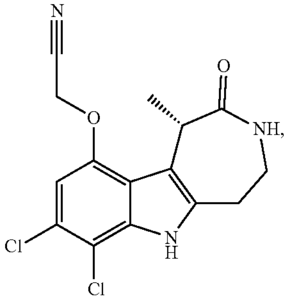
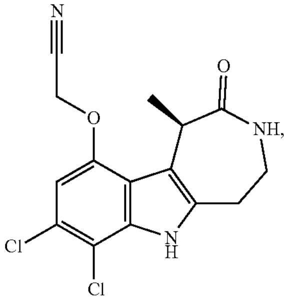
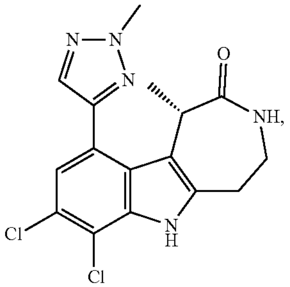
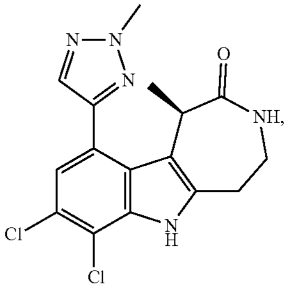
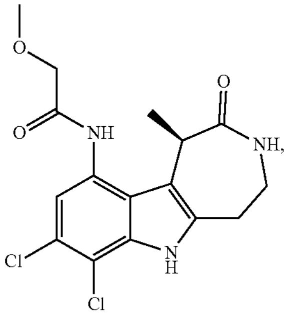
-continued
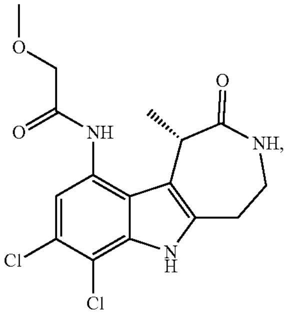
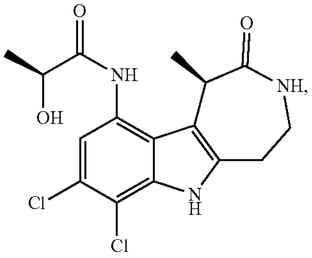
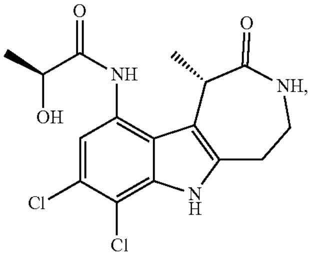
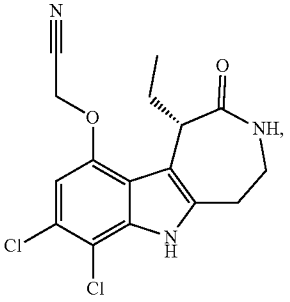
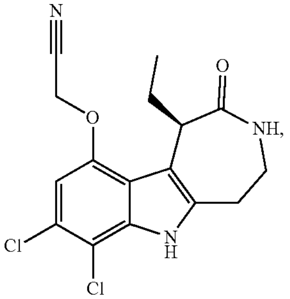

-continued
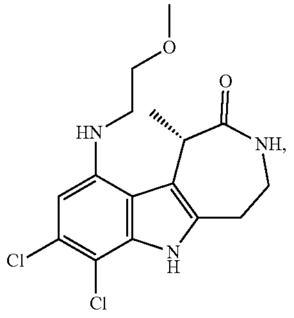
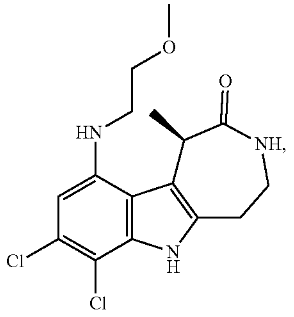
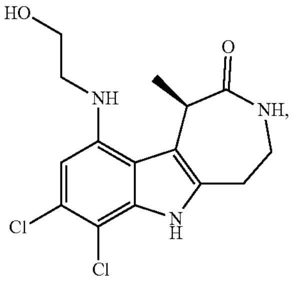
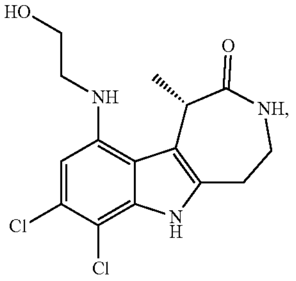
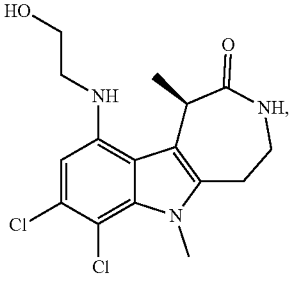
-continued
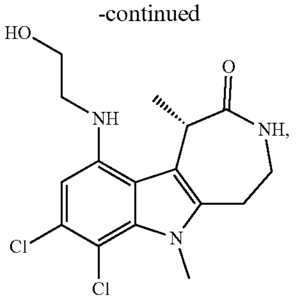
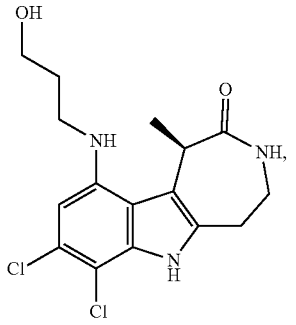
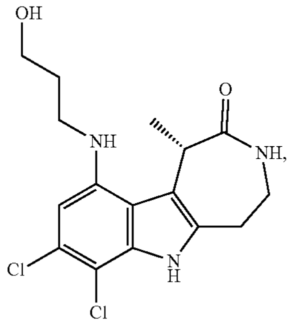
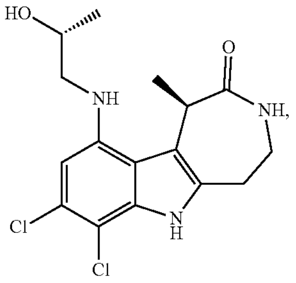
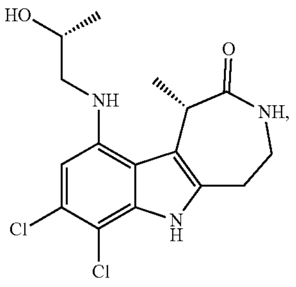

-continued
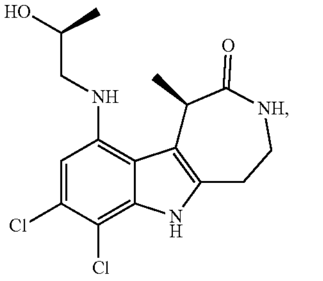
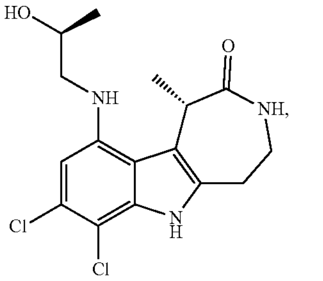
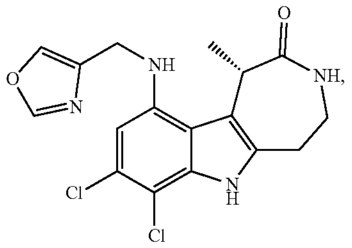
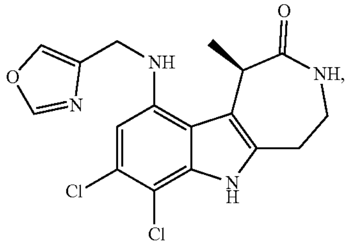
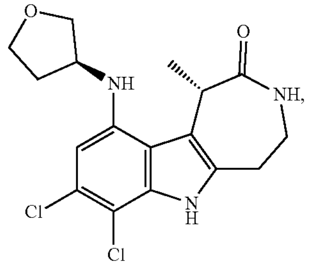
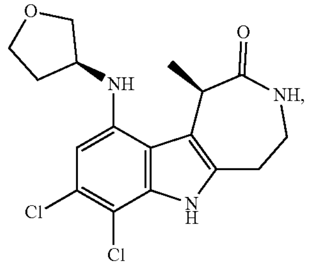
-continued
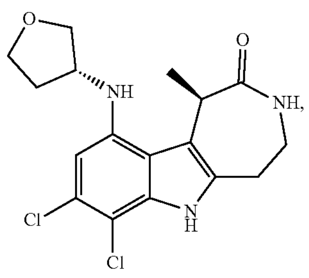
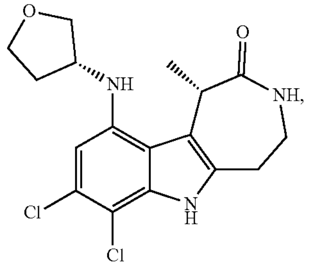
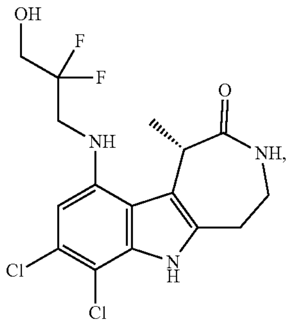
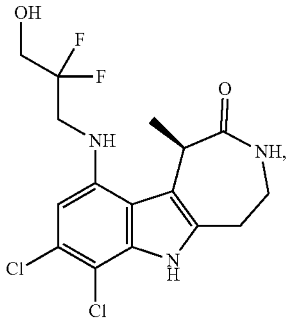
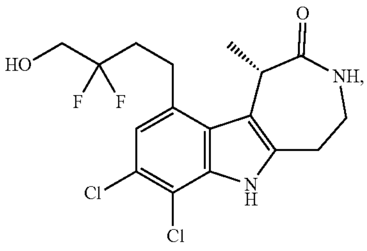
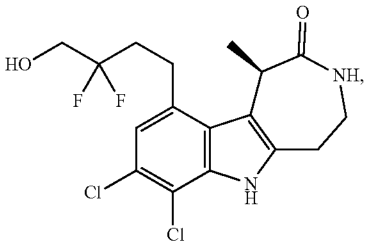

-continued
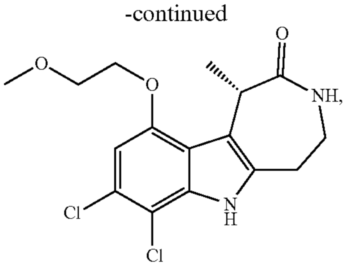
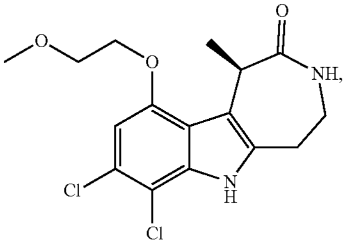
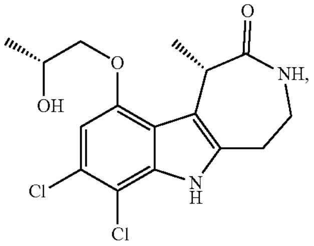
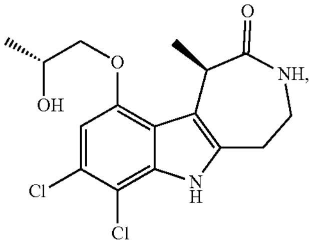
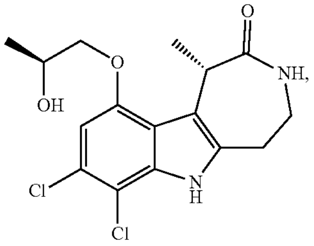
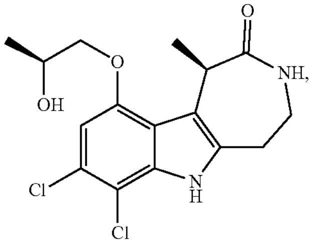
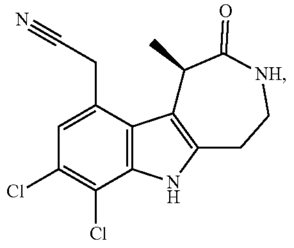
-continued
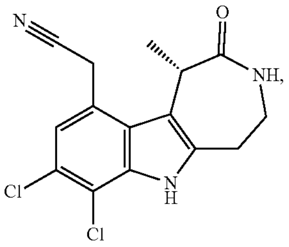
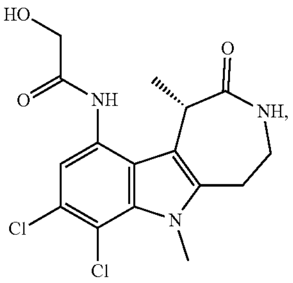
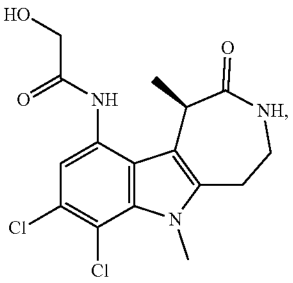
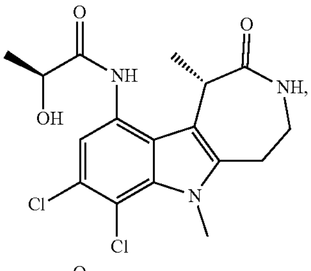
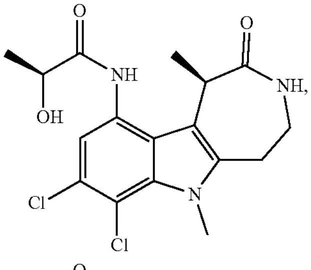
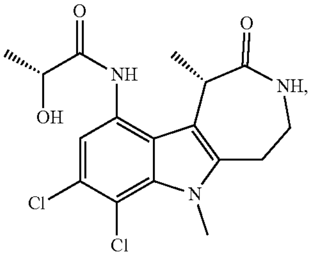

-continued
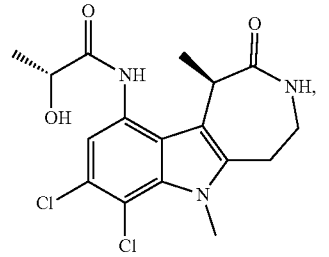
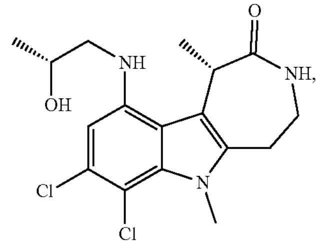
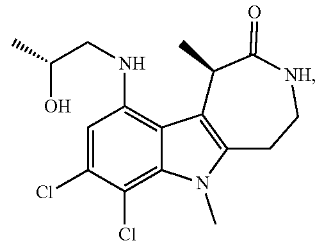
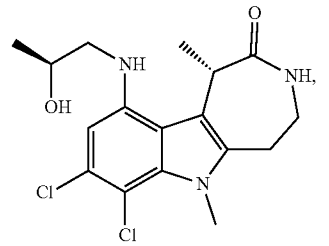
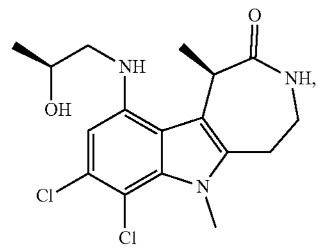
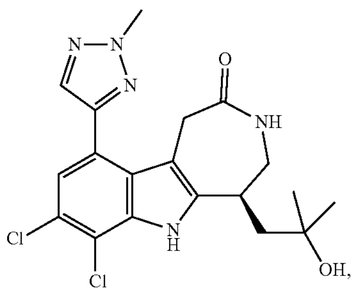
-continued
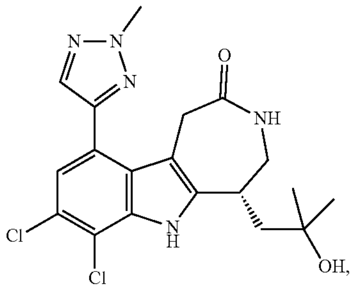
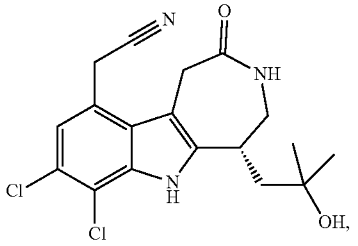
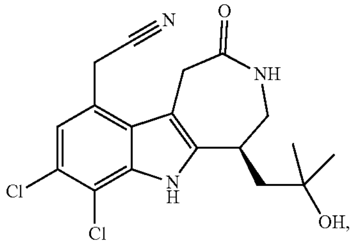
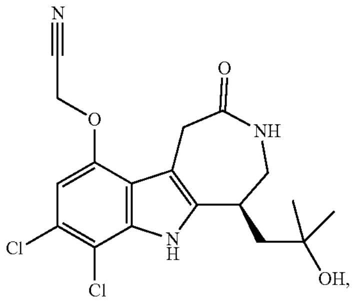
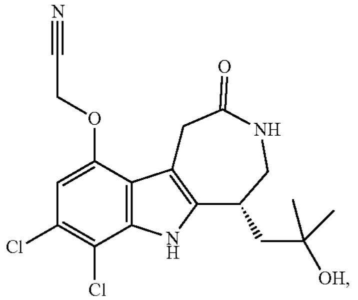
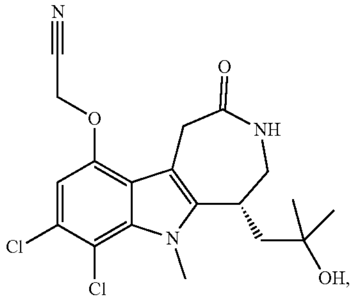

-continued
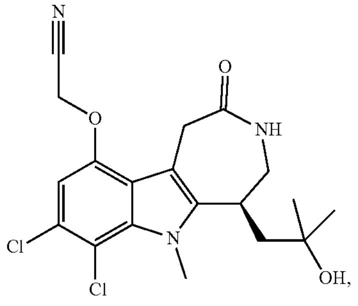
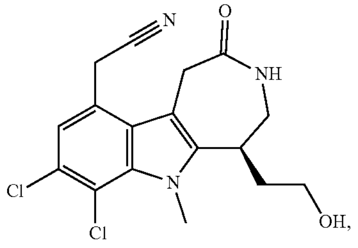
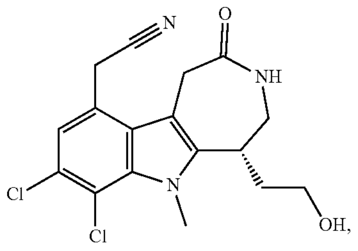
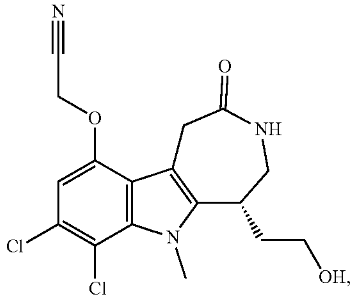
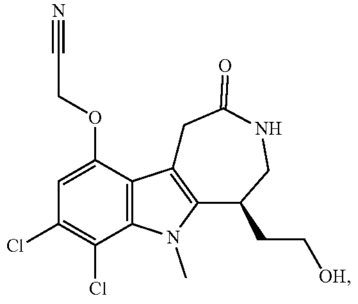
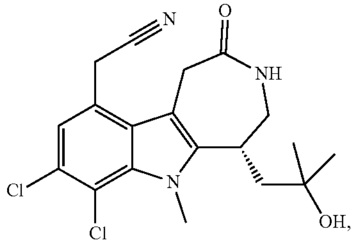
-continued
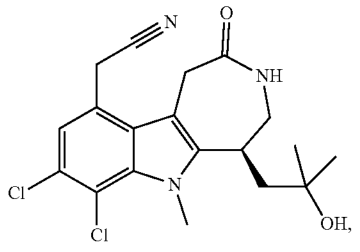
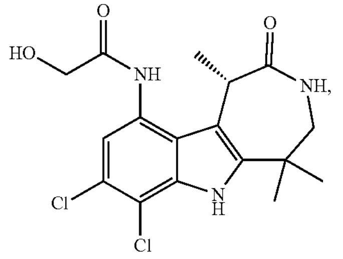
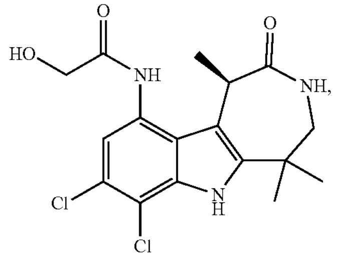
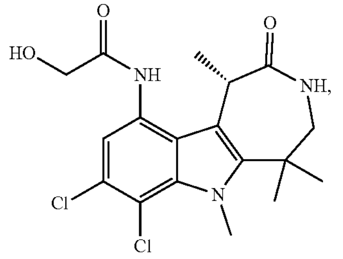
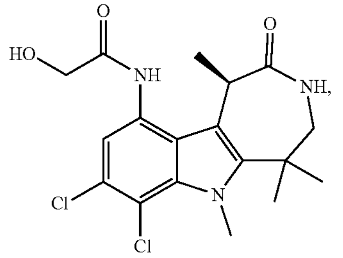
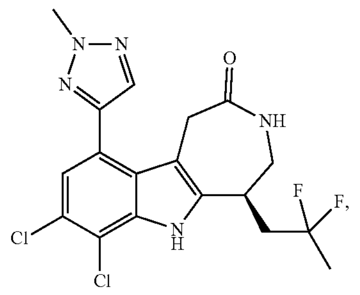

-continued
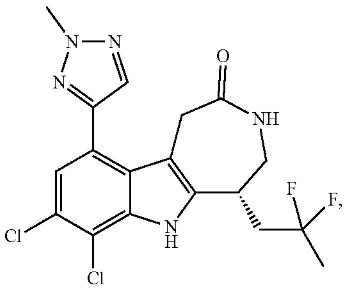
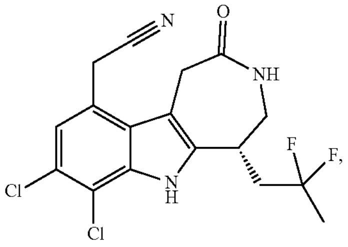
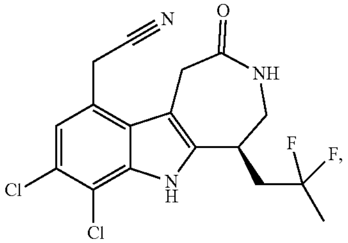
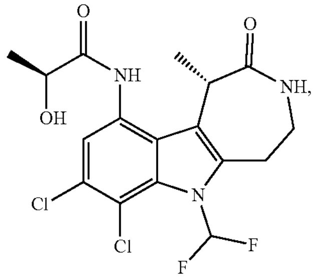
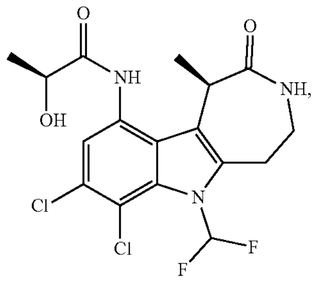
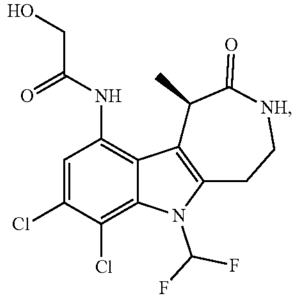
-continued
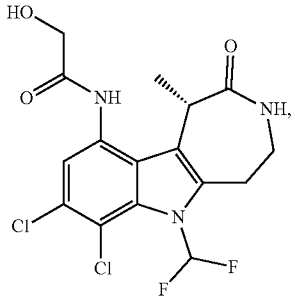
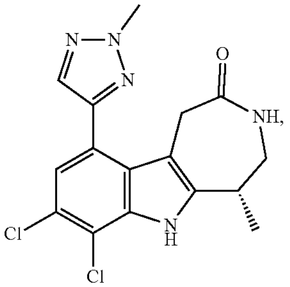
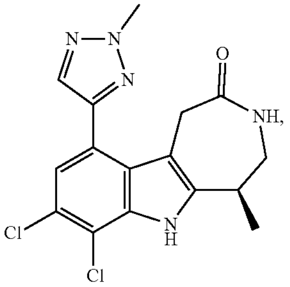
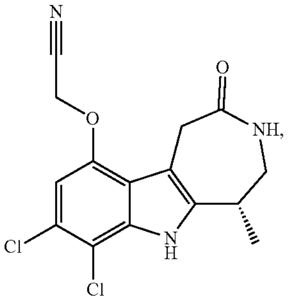
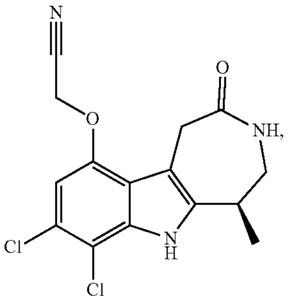
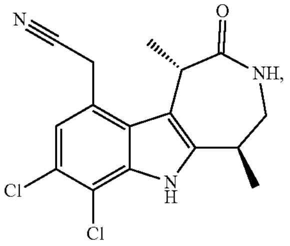

-continued
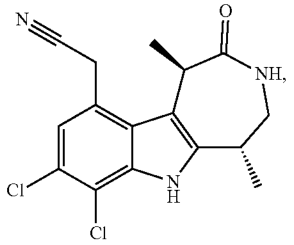
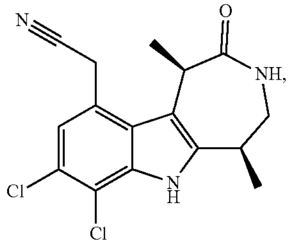
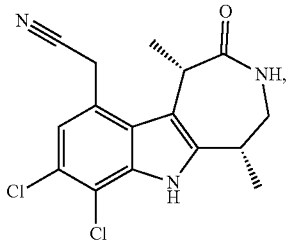
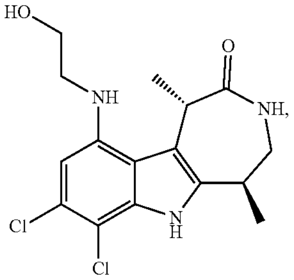
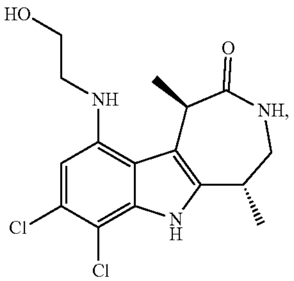
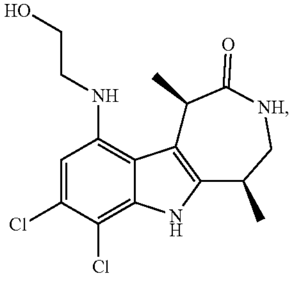
-continued
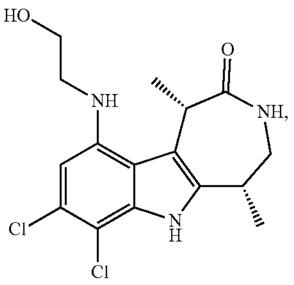
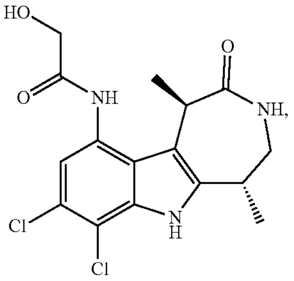
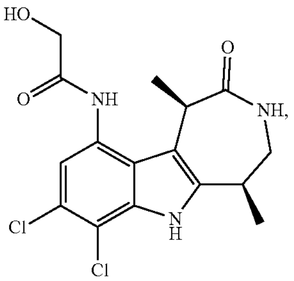
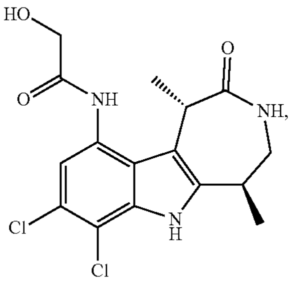
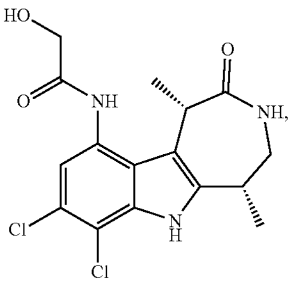
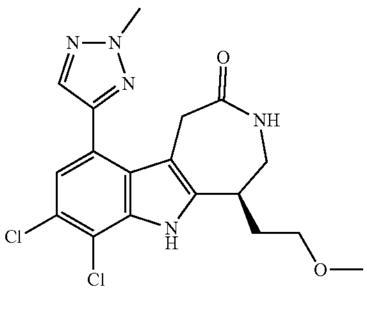
, -continued
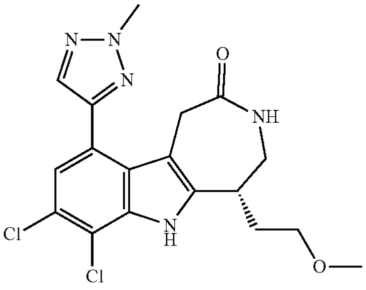
,
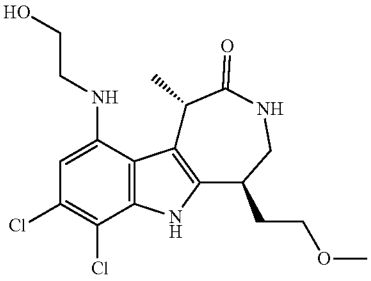
,
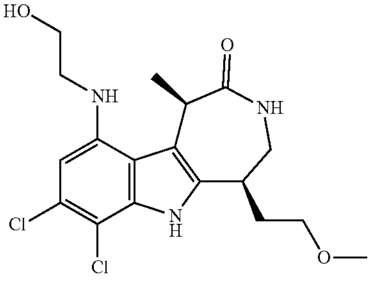
,
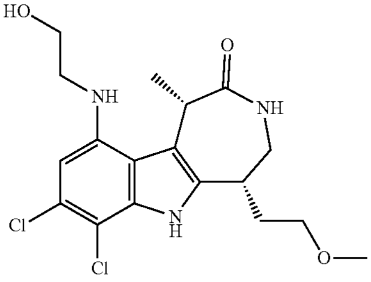
,
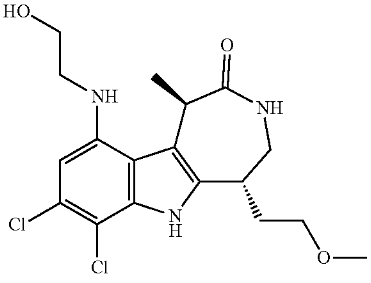
,
-continued
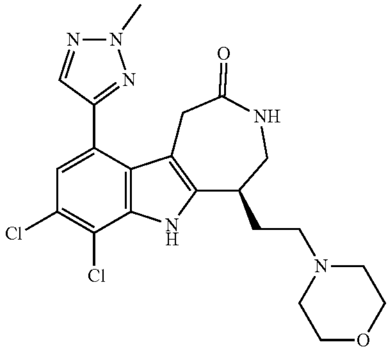
, and
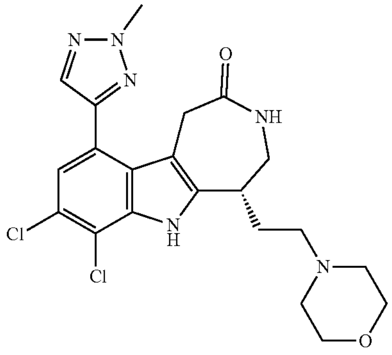
.
In some embodiments, the compound is selected from:
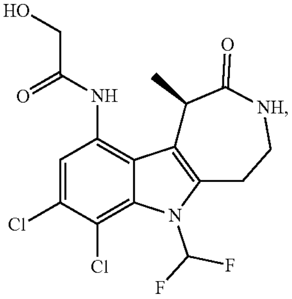
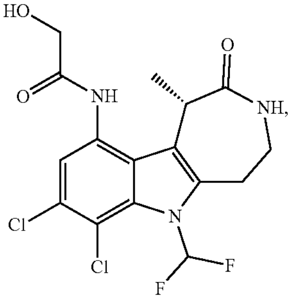
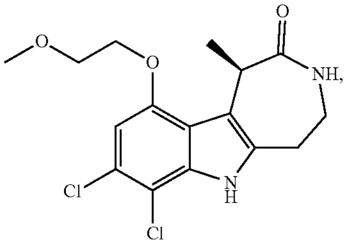

-continued
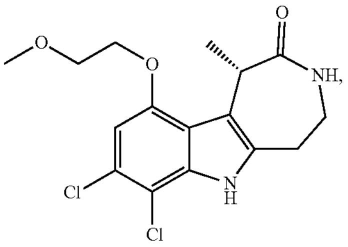
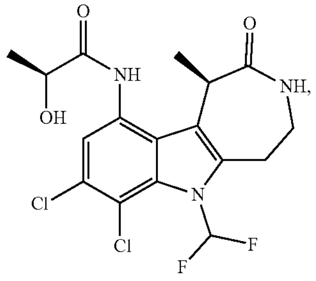
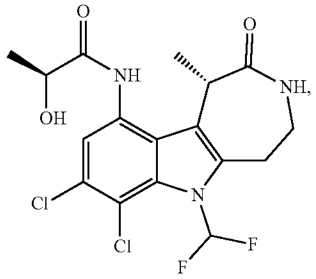
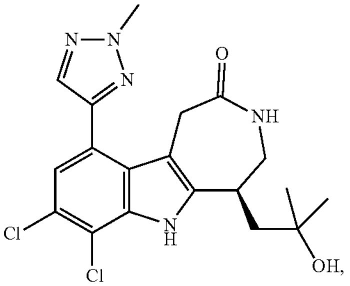
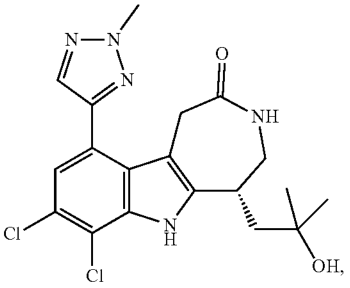
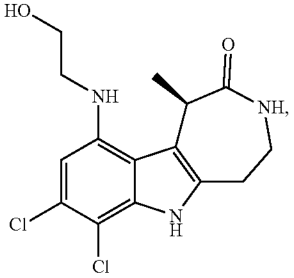
-continued
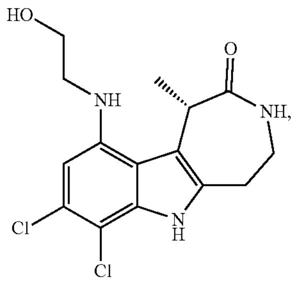
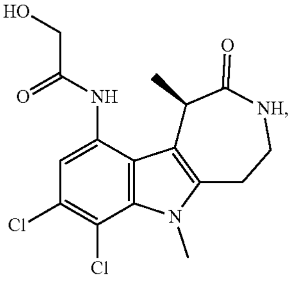
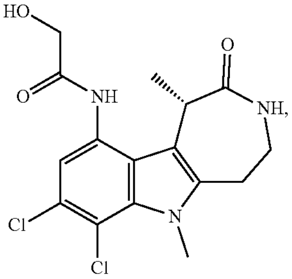
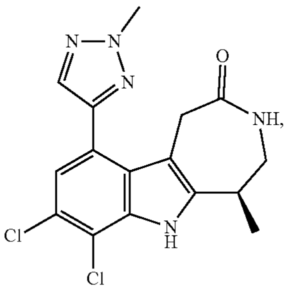
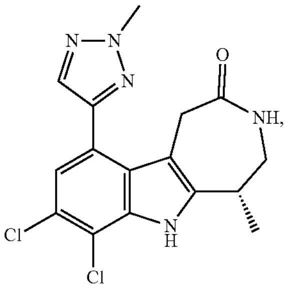
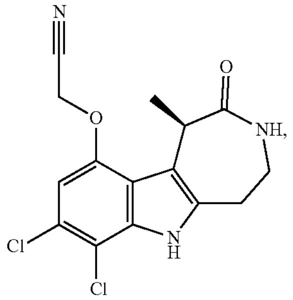
and -continued

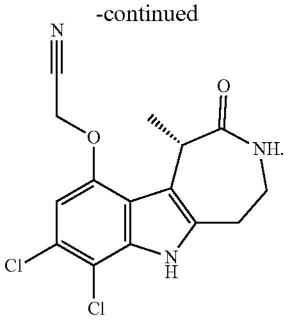

In some embodiments, provided herein is a pharmaceutical composition, comprising a compound disclosed herein, or a pharmaceutically acceptable salt thereof, with one or more pharmaceutically acceptable carriers, diluents, or excipients.

In some embodiments, provided herein is a method of treating an immune-mediated disease in a patient, comprising administering to a patient in need of such treatment an effective amount of a compound disclosed herein, or a pharmaceutically acceptable salt thereof, or a pharmaceutically composition thereof.

In some embodiments, the immune-mediated disease is selected from systemic lupus erythematosus, lupus nephritis, dermatomyositis, and Aicardi-Goutières syndrome.

In some embodiments, provided herein is a method of treating a disease associated with cGAS activation in a patient, comprising administering to a patient in need of such treatment an effective amount of a compound disclosed herein, or a pharmaceutically acceptable salt thereof, or a pharmaceutically composition thereof.

In some embodiments, provided herein is a compound, as disclosed herein, or a pharmaceutically acceptable salt thereof, for use in therapy.

In some embodiments, provided herein is a compound, as disclosed herein, or a pharmaceutically acceptable salt thereof, for use in treatment of a disease selected from systemic lupus erythematosus, lupus nephritis, dermatomyositis, and Aicardi-Goutières syndrome.

In some embodiments, the present invention provides a compound of Formula Ia:

Ia

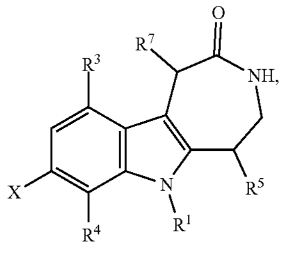

wherein:

X and $R^4$ are each independently halo;

$R^1$ and $R^7$ are each independently $R^b$;

$R^3$ is —NH—$R^{bb}$—OH, —NHC(O)—$R^{bb}$—OH, —O—$R^{bb}$—C(O)$NH_2$, —O—$R^{bb}$—OH, —O—$R^{bb}$—O—C(O)—$R^b$, —O—$R^{bb}$—H, —O—$R^{bb}$—CN, —NH—$R^{bb}$—H, —$R^{bb}$—CN, or a five-membered heteroaryl with 2 or 3 heteroatoms, wherein the five-membered heteroaryl is optionally substituted with —$R^{bb}$—H or —$R^{bb}$—OH;

$R^5$ is H, —$R^{bb}$C(O)$Q^1R^b$, or —$R^{bb}$OH;

$Q^1$ is O or $NR^b$;

each occurrence of $R^b$ is independently H or —$R^{bb}$H; and each occurrence of $R^{bb}$ is independently substituted or unsubstituted $C_{1-3}$ alkylene, or a pharmaceutically acceptable salt thereof.

In some embodiments, X of the compound of Formula Ia is chloro.

In some embodiments, $R^4$ of the compound of any embodiment above is chloro.

In some embodiments, $R^1$ of the compound of any embodiment above is H provided that $R^3$ is not —O—$R^{bb}$—CN. In some embodiments, $R^1$ of the compound of any embodiment above is methyl and $R^3$ of the compound is —O—$R^{bb}$—CN.

In some embodiments, $R^5$ of the compound of any embodiment above $R^5$ is H, provided that $R^3$ is not the 5-membered heteroaryl.

In some embodiments, $R^5$ of the compound of any embodiment above is —$CH_2C(O)NHCH_3$, —$CH_2C(O)N(CH_3)_2$, —$CH_2C(O)OCH_2CH_3$, or —$CH_2C(O)OH$. In some embodiments, $R^5$ of the compound of any embodiment above is —$CH_2CH_2OH$.

In some embodiments, $R^3$ of the compound of any embodiment above is the five-membered heteroaryl.

In some embodiments, $R^3$ of the compound of any embodiment above is the five-membered heteroaryl with 3 heteroatoms.

In some embodiments, $R^3$ of the compound of any embodiment above is selected from:

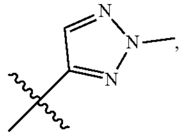 , 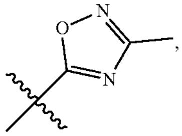 , 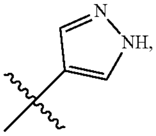

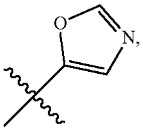 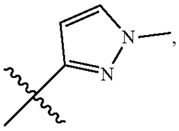 , 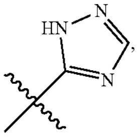 , and

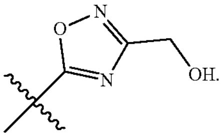

In some embodiments, $R^3$ of the compound of any embodiment above is selected from —NH—$R^{bb}$—OH, —NHC(O)—$R^{bb}$—OH, —O—$R^{bb}$—C(O)$NH_2$, —O—$R^{bb}$—OH, —O—$R^{bb}$—O—C(O)—$R^b$, —O—$R^{bb}$—H, —O—$R^{bb}$—CN, —NH—$R^{bb}$—H, and —$R^{bb}$—CN. In some embodiments, $R^3$ of the compound of any embodiment above is selected from —NHC(O)—$R^{bb}$—OH, —O—$R^{bb}$—C(O)$NH_2$, and —O—$R^{bb}$—H.

In some embodiments, $R^{bb}$ of the compound of any embodiment above is $CH_2$.

In some embodiments, the compound of Formula Ia is selected from the group consisting of:
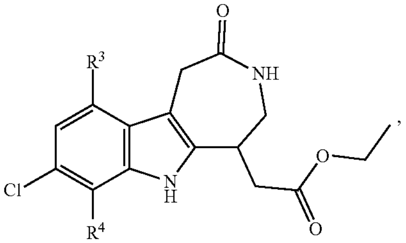
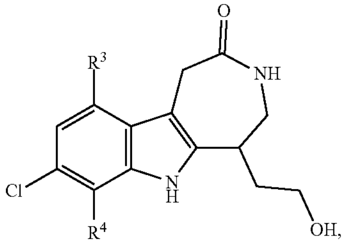
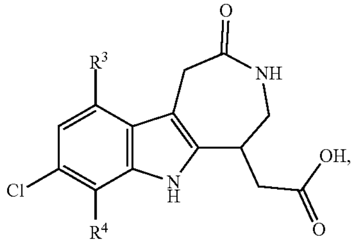
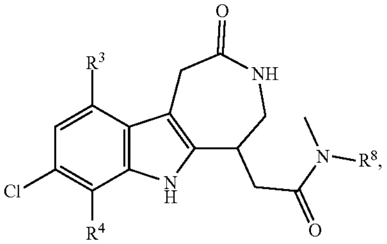
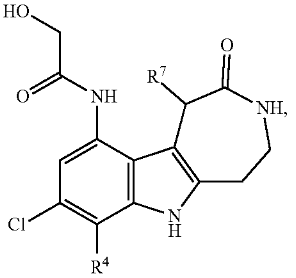
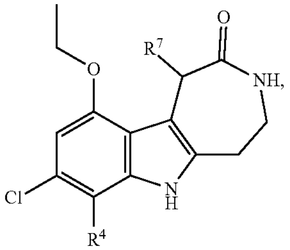
-continued
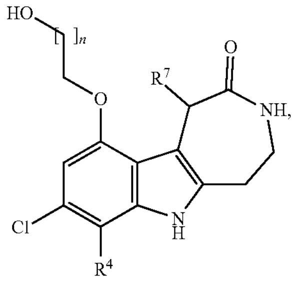
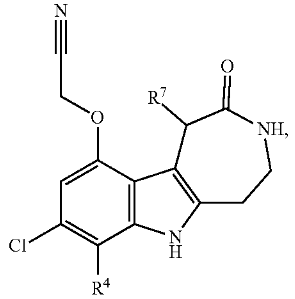
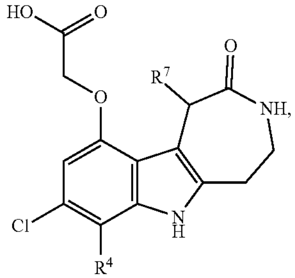
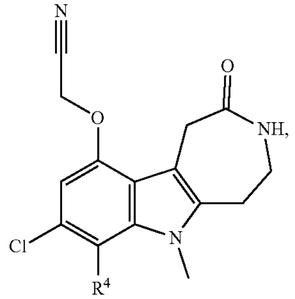
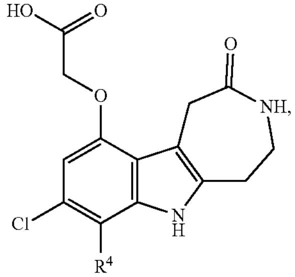

-continued
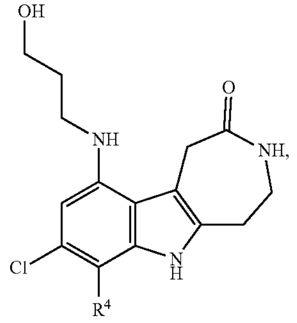
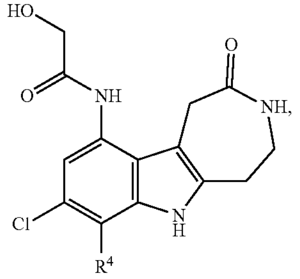
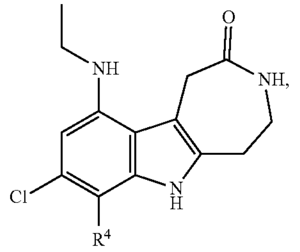
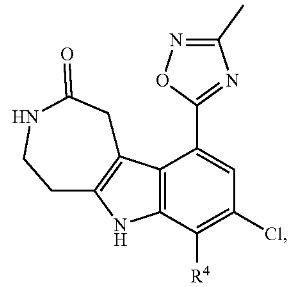
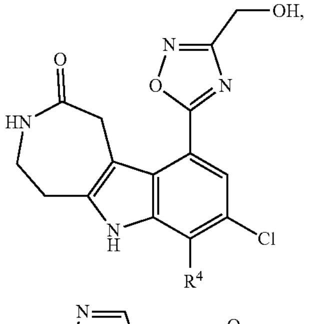
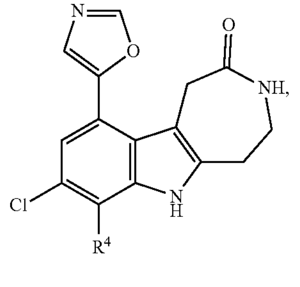
-continued
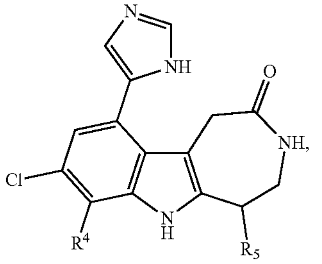
and
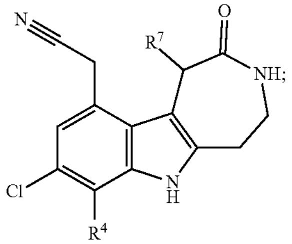
or a pharmaceutically acceptable salt thereof, wherein each substituent is as defined above with respect to Formula Ia, and n is 0, 1, or 2.
In some embodiments, the compound of Formula Ia is selected from the group consisting of:
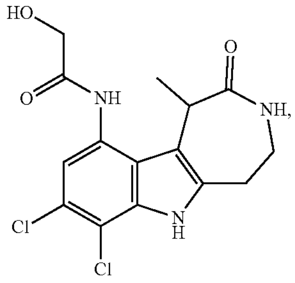
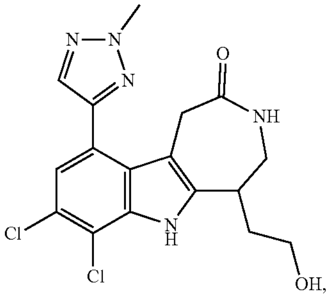
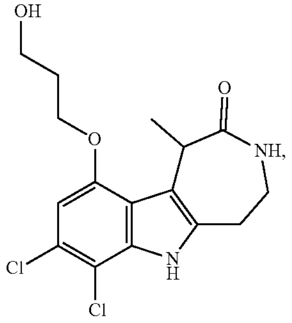

-continued
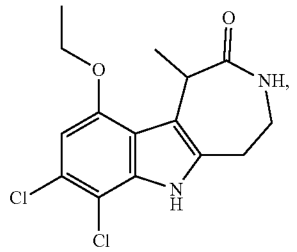
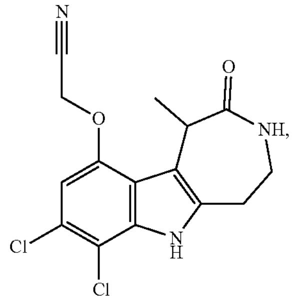
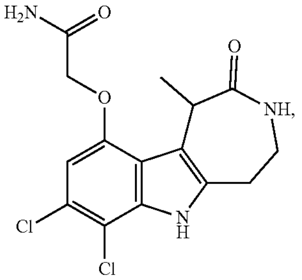
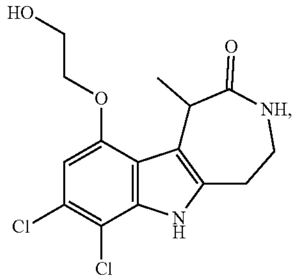
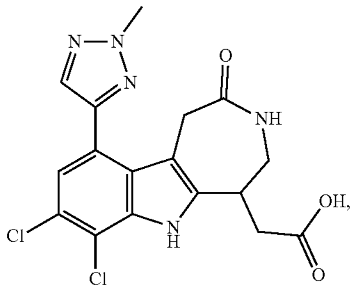
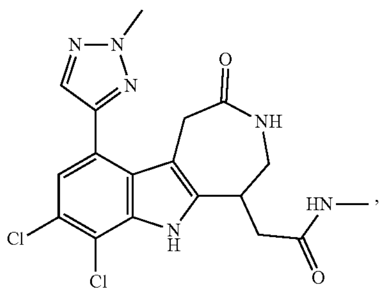
-continued
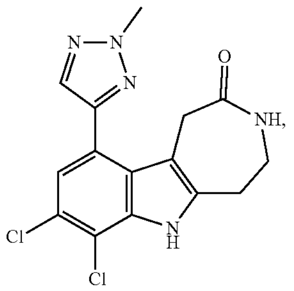
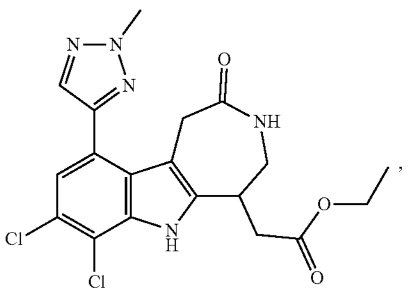
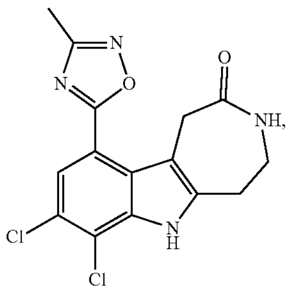
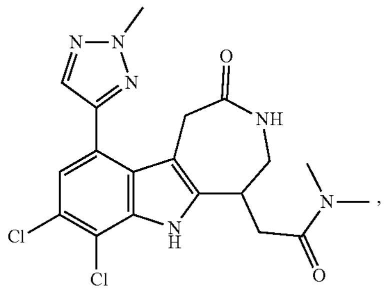
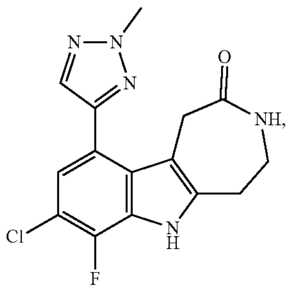
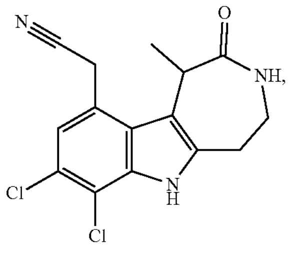

-continued
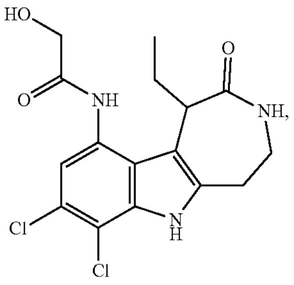
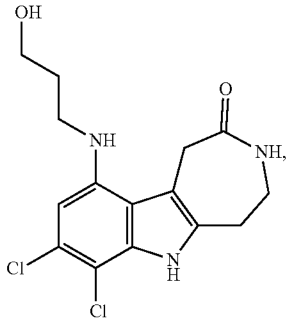
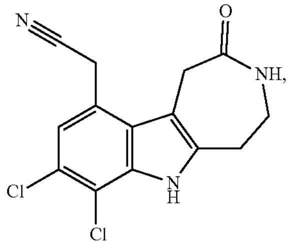
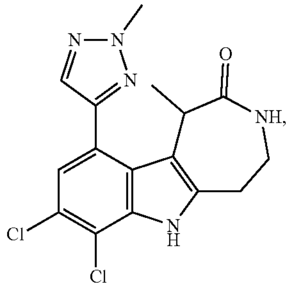
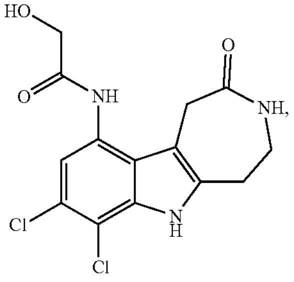
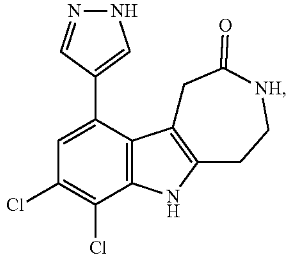
-continued
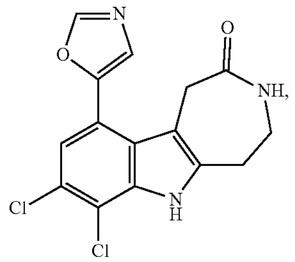
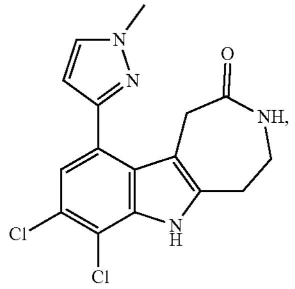
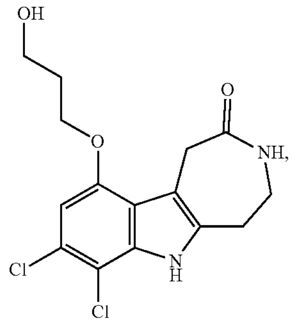
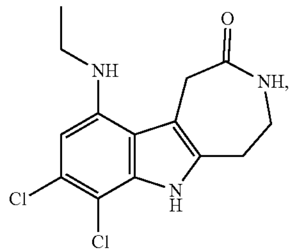
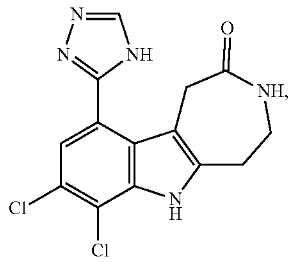
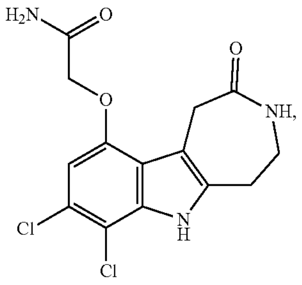

-continued
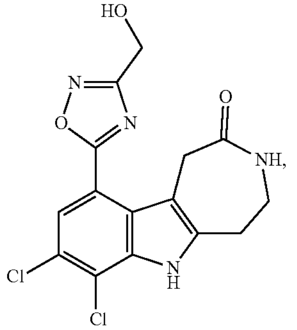
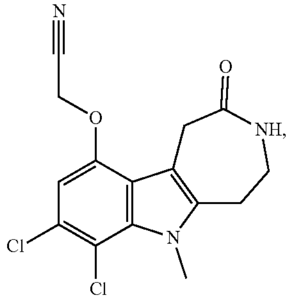
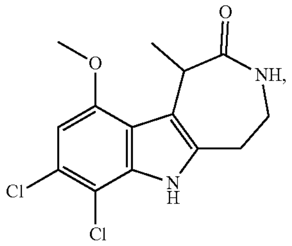
and
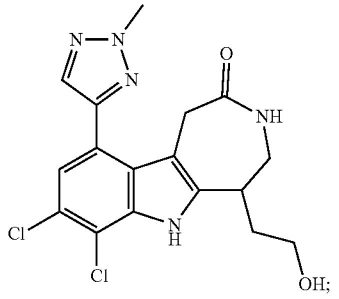
or a pharmaceutically acceptable salt thereof.
In some embodiments, the present invention provides a compound of Formula Ib:
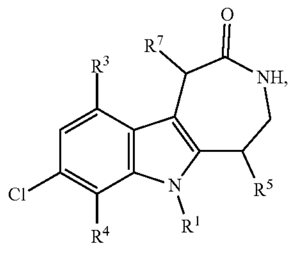
Ib
or a pharmaceutically acceptable salt thereof, wherein each variable is as defined above with respect to Formula Ia.
In some embodiments, the compound of Formula Ia is selected from the group consisting of:
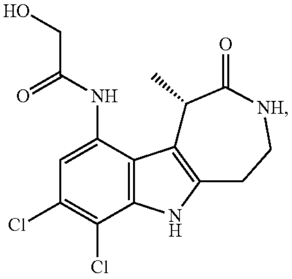
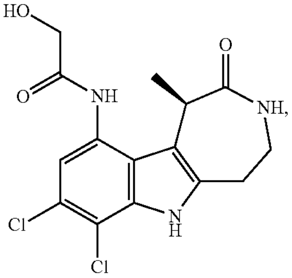
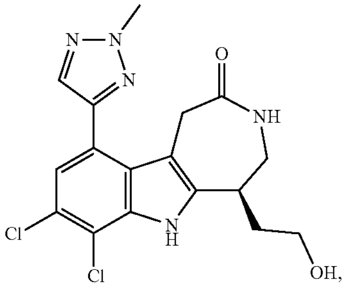
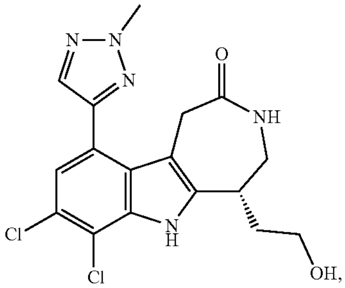
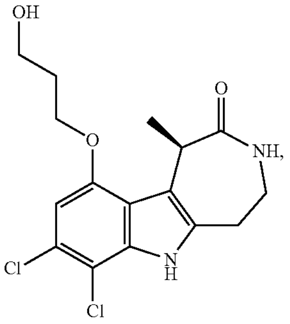

-continued
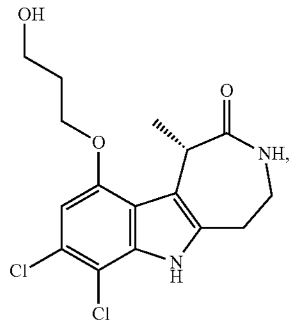
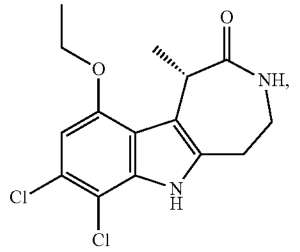
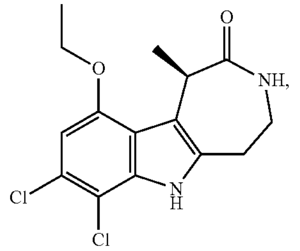
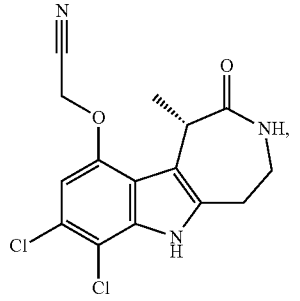
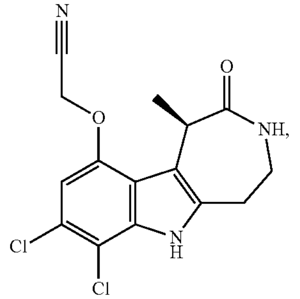
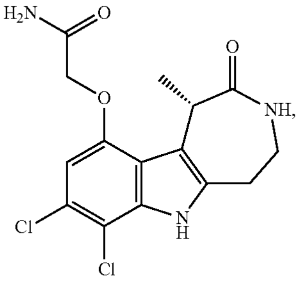
and
-continued
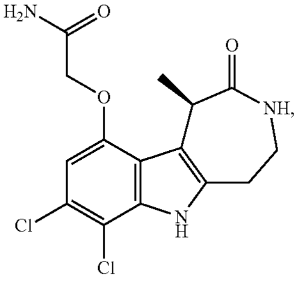
or a pharmaceutically acceptable salt thereof.
In some embodiments, the compound of Formula Ia is of Formula Ia-1:
Ia-1
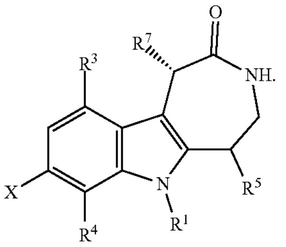
In some embodiments, the compound of Formula Ia is of Formula Ia-2:
Ia-2
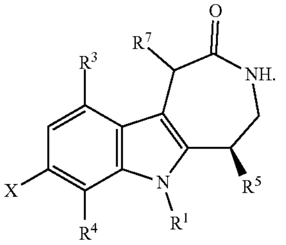
In some embodiments, the compound provided herein are selected from the group consisting of:
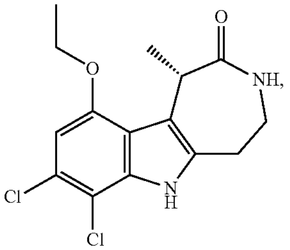

-continued

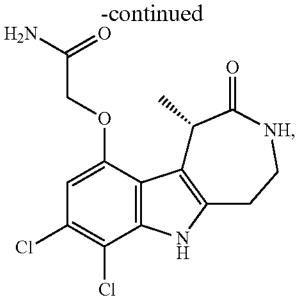

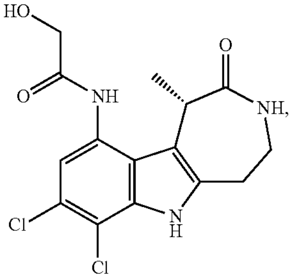

and

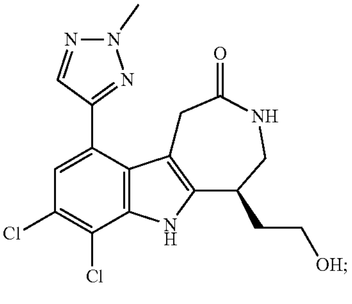

or a pharmaceutically acceptable salt thereof.

In some embodiments, provided here is a pharmaceutical composition, comprising a compound according to any one of embodiments above, or a pharmaceutically acceptable salt thereof, with one or more pharmaceutically acceptable carriers, diluents, or excipients.

In some embodiments, provided here is a method of treating an immune-mediated disease in a patient, comprising administering to a patient in need of such treatment an effective amount of a compound according to any one of embodiments above, or a pharmaceutically acceptable salt thereof, or a pharmaceutically composition described above.

In some embodiments, provided here is a method of treating systemic lupus erythematosus in a patient, comprising administering to a patient in need of such treatment an effective amount of a compound according to any one of embodiments above, or a pharmaceutically acceptable salt thereof, or a pharmaceutically composition described above.

In some embodiments, provided here is a method of treating lupus nephritis in a patient, comprising administering to a patient in need of such treatment an effective amount of a compound according to any one of embodiments above, or a pharmaceutically acceptable salt thereof, or a pharmaceutically composition described above.

In some embodiments, provided here is a method of treating dermatomyositis in a patient, comprising administering to a patient in need of such treatment an effective amount of a compound according to any one of embodiments above, or a pharmaceutically acceptable salt thereof, or a pharmaceutically composition described above.

In some embodiments, provided here is a method of treating Aicardi-Goutières syndrome in a patient, comprising administering to a patient in need of such treatment an effective amount of a compound according to any one of embodiments above, or a pharmaceutically acceptable salt thereof, or a pharmaceutically composition described above.

In some embodiments, provided here is a method of treating a disease associated with cGAS activation in a patient, comprising administering to a patient in need of such treatment an effective amount of a compound according to any one of embodiments above, or a pharmaceutically acceptable salt thereof, or a pharmaceutically composition describe above.

In some embodiments, provided here is a compound according to any one of embodiments described above, or a pharmaceutically acceptable salt thereof, for use in therapy.

In some embodiments, provided here is a compound selected from the group consisting of:

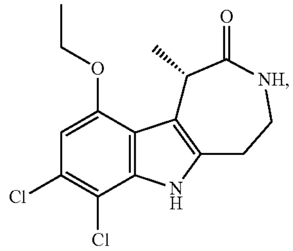

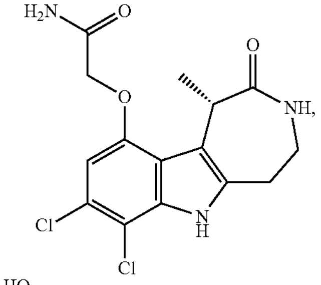

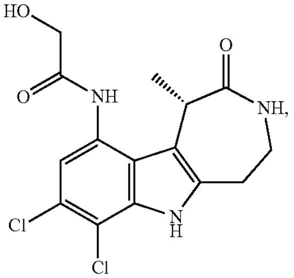

and

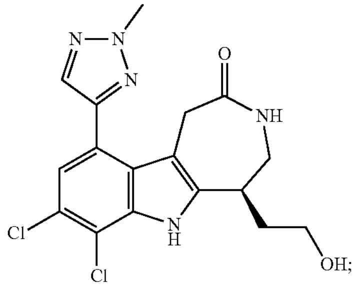

or a pharmaceutically acceptable salt thereof for use in therapy.

In some embodiments, provided here is a compound according to any one of embodiments described above, or a pharmaceutically acceptable salt thereof, for use in the treatment of an immune-mediated disease. In some embodiments, the immune-mediated disease is selected from the group consisting of systemic lupus erythematosus, lupus nephritis, dermatomyositis, and Aicardi-Goutières syndrome.

In some embodiments, provided here is a compound selected from the group consisting of:

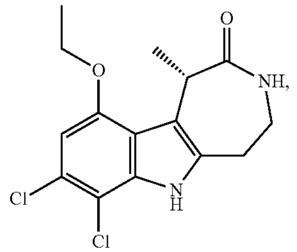

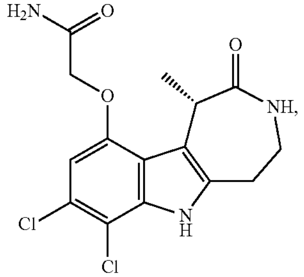

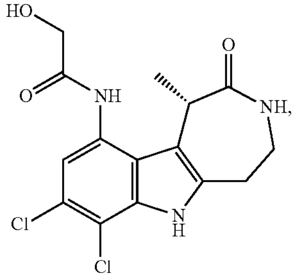

and

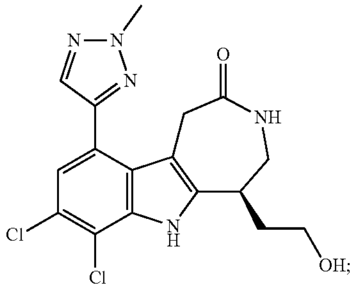

or a pharmaceutically acceptable salt thereof for use in the treatment of an immune-mediated diseases. In some embodiments, the immune-mediated disease is selected from the group consisting of systemic lupus erythematosus, lupus nephritis, dermatomyositis, and Aicardi-Goutières syndrome.

In some embodiments, provided here is a compound according to any one of embodiments described above, or a pharmaceutically acceptable salt thereof, for use in the treatment of systemic lupus erythematosus.

In some embodiments, provided here is a compound according to any one of embodiments described above, or a pharmaceutically acceptable salt thereof, for use in the treatment of lupus nephritis.

In some embodiments, provided here is a compound according to any one of embodiments described above, or a pharmaceutically acceptable salt thereof, for use in the treatment of dermatomyositis.

In some embodiments, provided here is a compound according to any one of embodiments described above, or a pharmaceutically acceptable salt thereof, for use in the treatment of Aicardi-Goutières syndrome.

In some embodiments, provided here is a method of treating a disease associated with cGAS activation in a patient, comprising administering to a patient in need of such treatment an effective amount of a compound provided herein, or a pharmaceutically acceptable salt thereof, or pharmaceutically composition according to any of the above embodiments.

The present application further provides the following additional embodiments:

Embodiment 1. A compound of formula IIIa:

(IIIa)

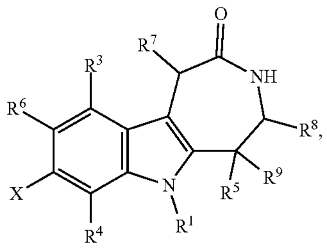

wherein:

X and $R^4$ are independently halo;

$R^1$, $R^7$, $R^8$, and $R^9$ are independently $R^b$;

$R^6$ is H or F;

$R^3$ is —NH—$R^{bb}$—O$R^b$, —NHC(O)—$R^{bb}$—O$R^b$, —NHC(O)—C(O)—$NH_2$, —NH—$R^c$, —NH—C(O)—$R^c$, —O—$R^c$, —O—$R^{bb}$—C(O)$NH_2$, —O—$R^{bb}$—O$R^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H, or —$R^{bb}$—OH;

$R^5$ is H, —$R^{bb}$H, —$R^{bb}$C(O)O$R^b$, —$R^{bb}$C(O)N$(R^b)_2$, —$R^{bb}$N$(R^b)_2$, —$R^{bb}$N$(R^b)$($R^{bb}CF_3$), —$R^{bb}$O$R^b$, or

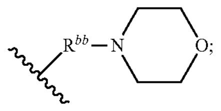

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

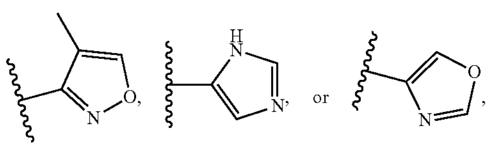

or or a pharmaceutically acceptable salt thereof.

Embodiment 2. A compound of formula IIIb:

(IIIb)

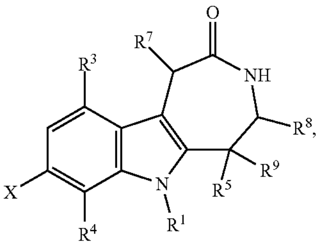

wherein:

X and $R^4$ are independently halo;

$R^1$, $R^7$, $R^8$, and $R^9$ are independently $R^b$;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H or $R^{bb}$—OH;

$R^5$ is H, —$R^{bb}$H, —$R^{bb}$C(O)$OR^b$, —$R^{bb}$C(O)N($R^b$)$_2$, —$R^{bb}$N($R^b$)$_2$, —$R^{bb}$N($R^b$)($R^{bb}CF_3$), —$R^{bb}OR^b$, or

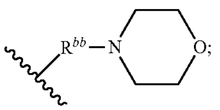

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

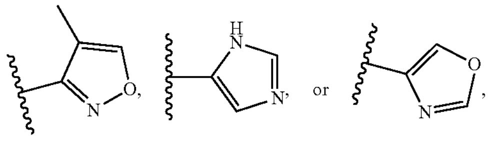

or or a pharmaceutically acceptable salt thereof.

Embodiment 3. The compound of embodiment 1 or 2, wherein X is Cl, or a pharmaceutically acceptable salt thereof.

Embodiment 4. The compound of any of embodiments 1 to 3, wherein $R^4$ is Cl, or a pharmaceutically acceptable salt thereof.

Embodiment 5. A compound of formula IIIc:

(IIIc)

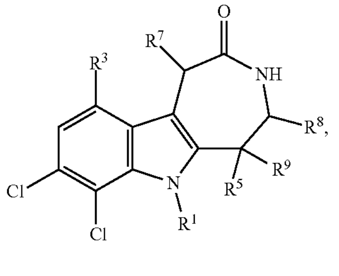

wherein:

$R^1$, $R^7$, $R^8$, and $R^9$ are independently $R^b$;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, NH—$R^{bb}$—H, —$R^{bb}$—OH, —$R^{bb}$—CN, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H or —$R^{bb}$—OH;

$R^5$ is H, —$R^{bb}$H, —$R^{bb}$C(O)$OR^b$, —$R^{bb}$C(O)N($R^b$)$_2$, —$R^{bb}$N($R^b$)$_2$, —$R^{bb}$N($R^b$)($R^{bb}CF_3$), $R^{bb}OR^b$, or

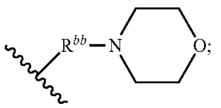

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

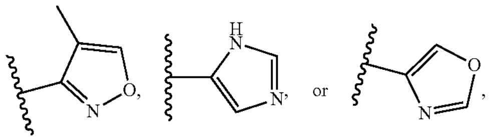

or or a pharmaceutically acceptable salt thereof.

Embodiment 6. The compound of any of embodiments 1 to 5, wherein $R^9$ is H or methyl, or a pharmaceutically acceptable salt thereof.

Embodiment 7. The compound of embodiment 6, wherein $R^9$ is methyl, or a pharmaceutically acceptable salt thereof.

Embodiment 8. A compound of formula IIId:

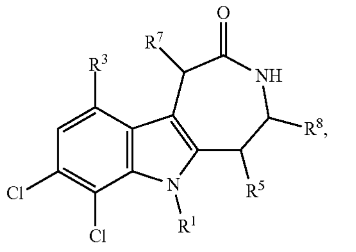

(IIId)

wherein:

$R^1$, $R^7$, and $R^8$ are independently $R^b$;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H or —$R^{bb}$—OH;

$R^5$ is H, —$R^{bb}$H, —$R^{bb}$C(O)$OR^b$, —$R^{bb}$C(O)N$(R^b)_2$, —$R^{bb}$N$(R^b)_2$, —$R^{bb}$N$(R^b)$($R^{bb}CF_3$), —$R^{bb}OR^b$, or

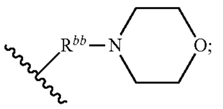

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

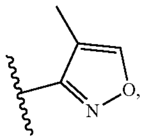 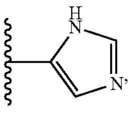 or 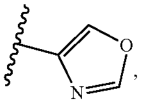

or a pharmaceutically acceptable salt thereof.

Embodiment 9. The compound of any of embodiments 1 to 8, wherein $R^5$ is H, —$R^{bb}$H, —$R^{bb}$C(O)$OR^b$, —$R^{bb}$—C(O)N$(R^b)_2$, —$R^{bb}$N$(R^b)_2$, —$R^{bb}$N$(R^b)$($R^{bb}CF_3$), —$R^{bb}$—$OR^b$, or

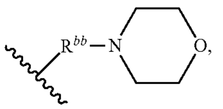

or a pharmaceutically acceptable salt thereof.

Embodiment 10. The compound of any of embodiments 1 to 8, wherein $R^5$ is H, —$CH_3$, —$CH_2CH_3$, —$CH_2CH_2CH_3$,

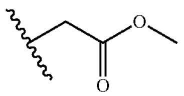 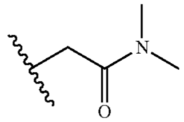 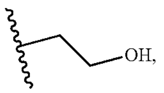

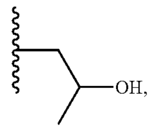 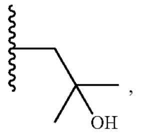 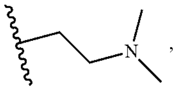

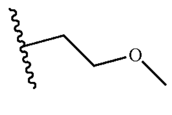 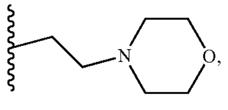

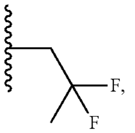 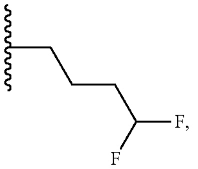 or

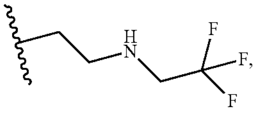

or a pharmaceutically acceptable salt thereof.

Embodiment 11. The compound of embodiment 9, wherein $R^5$ is H, methyl, ethyl, n-propyl, or isopropyl, or a pharmaceutically acceptable salt thereof.

Embodiment 12. The compound of any of embodiments 1-11, wherein $R^5$ is other than H, and the

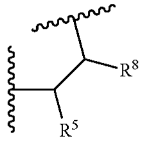

is

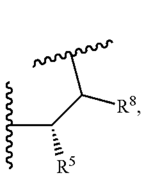

or a pharmaceutically acceptable salt thereof.

Embodiment 13. The compound of embodiment 11, wherein $R^5$ is H, or a pharmaceutically acceptable salt thereof.

Embodiment 14. The compound of any of embodiments 1-8, wherein $R^1$ and $R^5$ with atoms attached therewith collectively form a 5-member heterocycle, or a pharmaceutically acceptable salt thereof.

Embodiment 15. The compound of any of embodiments 1-8, wherein

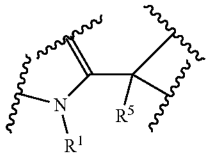

is

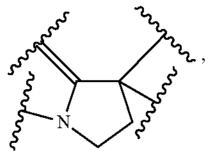 [SMILES: *N1CCC(*)(*)C1=*]

or a pharmaceutically acceptable salt thereof.

Embodiment 16. The compound of any of embodiments 1-15, wherein $R^7$ is H, or a pharmaceutically acceptable salt thereof.

Embodiment 17. The compound of any of embodiments 1-14, wherein $R^7$ is —$R^{bb}$H, and the

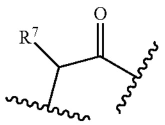

is

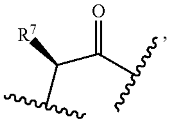

or a pharmaceutically acceptable salt thereof.

Embodiment 18. The compound of any of embodiments 1-14 and 17, wherein $R^7$ is methyl, ethyl, or propyl, or a pharmaceutically acceptable salt thereof.

Embodiment 19. The compound of embodiment 17, wherein $R^7$ is methyl, or a pharmaceutically acceptable salt thereof.

Embodiment 20. The compound of any of embodiments 1 to 19, wherein $R^3$ is —NH—$R^{bb}$—$OR^b$, or a pharmaceutically acceptable salt thereof.

Embodiment 21. The compound of any of embodiments 1 to 19, wherein $R^3$ is —NHC(O)—$R^{bb}$—$OR^b$, or a pharmaceutically acceptable salt thereof.

Embodiment 22. The compound of any of embodiments 1 to 19, wherein $R^3$ is —NHC(O)—C(O)—$NH_2$, or a pharmaceutically acceptable salt thereof.

Embodiment 23. The compound of any of embodiments 1 to 19, wherein $R^3$ is —NH—$R^c$, or a pharmaceutically acceptable salt thereof.

Embodiment 24. The compound of any of embodiments 1 to 19, wherein $R^3$ is —NH—C(O)—$R^c$, or a pharmaceutically acceptable salt thereof.

Embodiment 25. The compound of any of embodiments 1 to 19, wherein $R^3$ is —O—$R^c$, or a pharmaceutically acceptable salt thereof.

Embodiment 26. The compound of any of embodiments 23 to 25, wherein $R^c$ is a 4- or 5-membered heterocycle of oxygen, or a pharmaceutically acceptable salt thereof.

Embodiment 27. The compound of any of embodiments 23 to 25, wherein $R^c$ is a $C_{4-6}$ carbocycle substituted with hydroxy, or a pharmaceutically acceptable salt thereof.

Embodiment 28. The compound of any of embodiments 1 to 19, wherein $R^3$ is

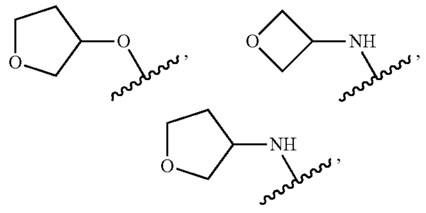

or a pharmaceutically acceptable salt thereof.

Embodiment 29. The compound of any of embodiments 1 to 19, wherein $R^3$ is

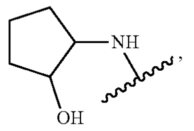 [SMILES: *NC1CCCC1O]

or a pharmaceutically acceptable salt thereof.

Embodiment 30. The compound of any of embodiments 1 to 19, wherein $R^3$ is

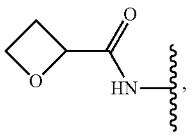 [SMILES: *NC(=O)C1CCO1]

or a pharmaceutically acceptable salt thereof.

Embodiment 31. The compound of any of embodiments 1 to 19, wherein $R^3$ is —O—$R^{bb}$—$OR^b$, or a pharmaceutically acceptable salt thereof.

Embodiment 32. The compound of any of embodiments 1 to 19, wherein $R^3$ is —O—$R^{bb}$—O—C(O)—$R^b$, or a pharmaceutically acceptable salt thereof.

Embodiment 33. The compound of any of embodiments 1 to 19, wherein $R^3$ is —O—$R^{bb}$—H, or a pharmaceutically acceptable salt thereof.

Embodiment 34. The compound of any of embodiments 1 to 19, wherein $R^3$ is —O—$R^{bb}$—CN, or a pharmaceutically acceptable salt thereof.

Embodiment 35. The compound of any of embodiments 1 to 19, wherein $R^3$ is —NH—$R^{bb}$—H, or a pharmaceutically acceptable salt thereof.

Embodiment 36. The compound of any of embodiments 1 to 19, wherein $R^3$ is —$R^{bb}$—OH, or a pharmaceutically acceptable salt thereof.

Embodiment 37. The compound of any of embodiments 1 to 19, wherein $R^3$ is —$R^{bb}$—CN, or a pharmaceutically acceptable salt thereof.

Embodiment 38. The compound of any of embodiments 1 to 19, wherein $R^3$ is —NH—$R^e$, or a pharmaceutically acceptable salt thereof.

Embodiment 39. The compound of any of embodiments 1 to 19, wherein $R^3$ is —NH—$CH_2$—$R^e$, or a pharmaceutically acceptable salt thereof.

Embodiment 40. The compound of any of embodiments 1 to 19, wherein $R^3$ is a five-membered heteroaryl with 2 or 3 heteroatoms optionally substituted with —$NH_2$, or a pharmaceutically acceptable salt thereof.

Embodiment 41. The compound of any of embodiments 1 to 19, wherein $R^3$ is a five-membered heteroaryl with 2 or 3 heteroatoms optionally substituted with —$R^{bb}$—H, or a pharmaceutically acceptable salt thereof.

Embodiment 42. The compound of any of embodiments 1 to 19, wherein $R^3$ is a five-membered heteroaryl with 2 or 3 heteroatoms optionally substituted with —$R^{bb}$—OH, or a pharmaceutically acceptable salt thereof.

Embodiment 43. The compound of any of embodiments 1-19, wherein $R^3$ is selected from

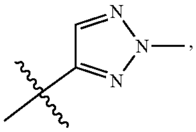,
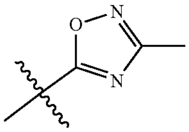,
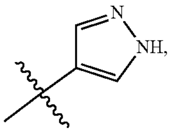
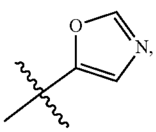
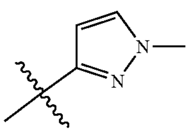,
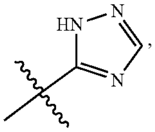,
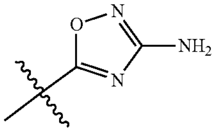 and
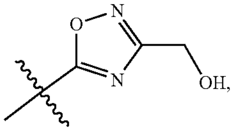

or a pharmaceutically acceptable salt thereof.

Embodiment 44. The compound of any of embodiments 1 to 19, wherein $R^3$ is a six-membered heteroaryl with 2 or 3 heteroatoms, or a pharmaceutically acceptable salt thereof.

Embodiment 45. The compound of any of embodiments 1 to 19, wherein $R^3$ is a

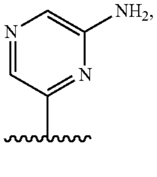 [SMILES: *c1cncc(N)n1]

or a pharmaceutically acceptable salt thereof.

Embodiment 46. The compound of any of embodiments 1 to 19, wherein $R^3$ is selected from

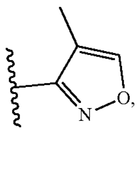
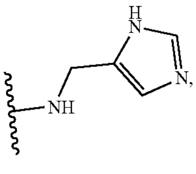 and

-continued

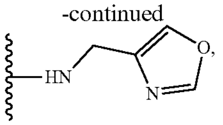

or a pharmaceutically acceptable salt thereof.

Embodiment 47. The compound of any of embodiments 1 to 19, wherein $R^3$ is selected from —NH—$R^{bb}$—OH, —NHC(O)—$R^{bb}$—OH, —O—$R^{bb}$—C(O)$N_2$, —O—$R^{bb}$—OH, —O—$R^{bb}$—O—C(O)—$R^b$, —O—$R^{bb}$—H, —O—$R^{bb}$—CN, —NH—$R^{bb}$—H, and —$R^{bb}$—CN, or a pharmaceutically acceptable salt thereof.

Embodiment 48. The compound of embodiment 47, wherein $R^3$ is —O—$R^{bb}$—C(O)$NH_2$, or a pharmaceutically acceptable salt thereof.

Embodiment 49. The compound of any of embodiments 1 to 19, wherein $R^3$ is selected from —NH—$(CH_2)_2$—OH, —NH—$(CH_2)_2$—O($CH_3$), —NH—($CH_2$)(CH($CH_3$))—OH, —NHC(O)—$CH_2$—OH, —NHC(O)—$CH_2$—O($CH_3$), —NHC(O)—CH($CH_3$)—OH, —NH—($CH_2$)($CF_2$)($CH_2$)—OH, —NH—($CH_2$)—$CHF_2$, —NH—$(CH_2)_2$—$CHF_2$, —O—$CH_2$—C(O)$NH_2$, —O—($CH_2$)(CH($CH_3$))—OH, —O$(CH_2)_3$—OH, —O$(CH_2)_2$—O($CH_3$), —O—($CH_2$)($CF_2$)($CH_2$)—OH, —NH—($CH_2$)($CF_2$)($CH_2$)—OH, —O($CH_2$)$CH_2$F, —O$(CH_2)_2$$CH_2$F, —O—$CH_2$—CN, —NH$(CH_2)_3$, —$(CH_2)_3$OH, and —$CH_2$—CN, or a pharmaceutically acceptable salt thereof.

Embodiment 49A. The compound of any of embodiments 1 to 19, wherein $R^3$ is —NH—CO—CH($CH_3$)—OH. In some embodiments, $R^3$ is

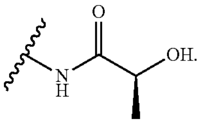 [SMILES: *NC(=O)[C@H](C)O]

Embodiment 50. The compound of any of embodiments 1-49, wherein $R^8$ is H, or a pharmaceutically acceptable salt thereof.

Embodiment 51. The compound of any of embodiments 1-49, wherein $R^8$ is methyl, or a pharmaceutically acceptable salt thereof.

Embodiment 52. The compound of any of embodiments 1-51, wherein $R^1$ is H, or a pharmaceutically acceptable salt thereof.

Embodiment 53. The compound of any of embodiments 1-51, wherein $R^1$ is methyl, or a pharmaceutically acceptable salt thereof.

Embodiment 54. The compound of any of embodiments 1-51, wherein $R^1$ is —$CHF_2$, or a pharmaceutically acceptable salt thereof.

Embodiment 55. A compound of formula IIIe:

(IIIe)

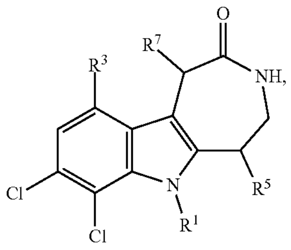

wherein:

$R^1$ is H, —$CH_3$, or —$CHF_2$;

$R^5$ is H, —$CH_3$, $CH_2CH_3$, or —$CH_2CH_2CH_3$;

$R^7$ is H, —$CH_3$, $CH_2CH_3$, or —$CH_2CH_2CH_3$;

$R^3$ is —NH—$(CH_2)_2$—OH, —NH—$(CH_2)_2$—O($CH_3$), —NH—($CH_2$)((CH)($CH_3$))—OH, —NHC(O)—$CH_2$—OH, —NHC(O)—$CH_2$—O($CH_3$), —NHC(O)—CH($CH_3$)—OH, —NH—($CH_2$)($CF_2$)($CH_2$)—OH, —NH—($CH_2$)—$CHF_2$, —NH—$(CH_2)_2$—$CHF_2$, —O—$CH_2$—C(O)$NH_2$, —O—($CH_2$)(CH($CH_3$))—OH, —O$(CH_2)_3$—OH, —O$(CH_2)_2$—O($CH_3$), —O—($CH_2$)($CF_2$)($CH_2$)—OH, —NH—($CH_2$)($CF_2$)($CH_2$)—OH, —O($CH_2$)$CH_2$F, —O$(CH_2)_2CH_2$F, —O—$CH_2$—CN, —NH$(CH_2)_3$, —$(CH_2)_3$OH, —$CH_2$—CN,

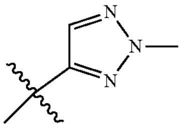 , 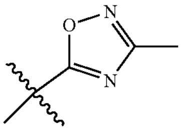 ,

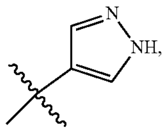 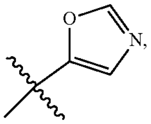 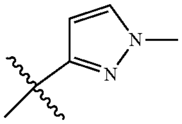 ,

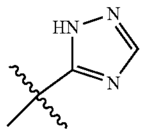 , 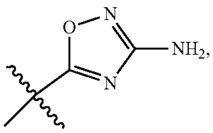

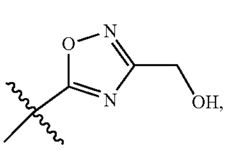 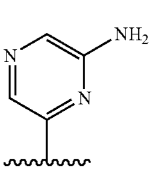 , 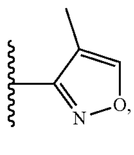

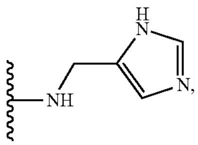 and 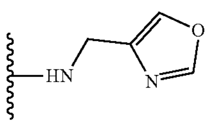 , or a pharmaceutically acceptable salt thereof.

Embodiment 56. A compound of formula IIIf:

(IIIf)

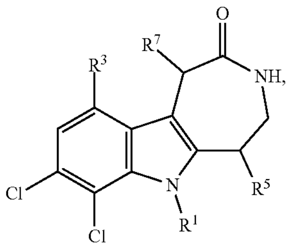

wherein $R^1$, $R^5$, and $R^7$ is each independently H or —$CHF_2$, and $R^3$ is —NHC(O)—$CH_2$—OH, —O—$(CH_2)_2$—O—($CH_3$), —NH—C(O)—CH($CH_3$)—OH, or

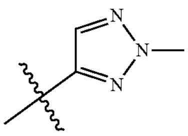 , or a pharmaceutically acceptable salt thereof.

Embodiment 57. The compound of embodiment 1, wherein the compound is selected from:

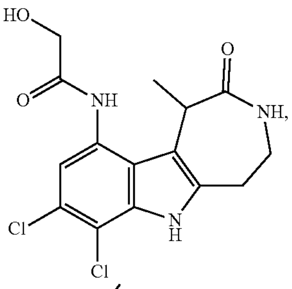

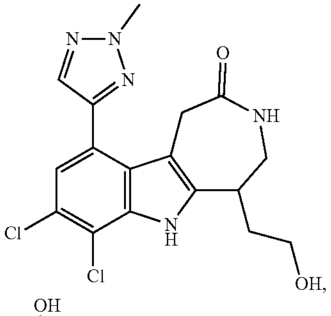

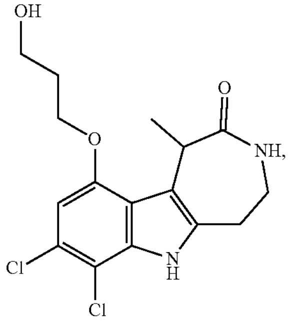

-continued
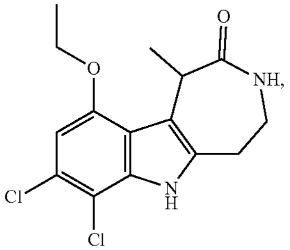
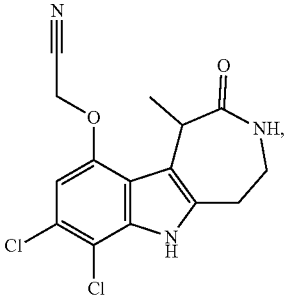
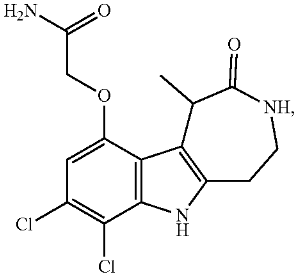
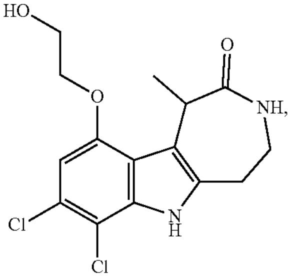
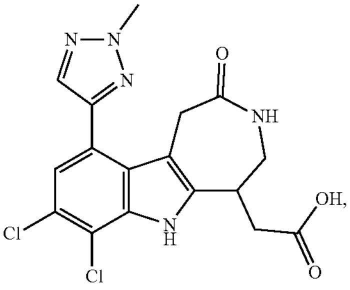
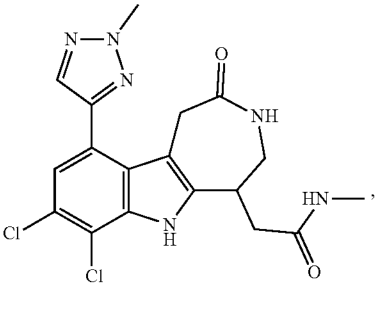
-continued
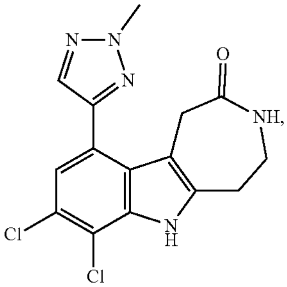
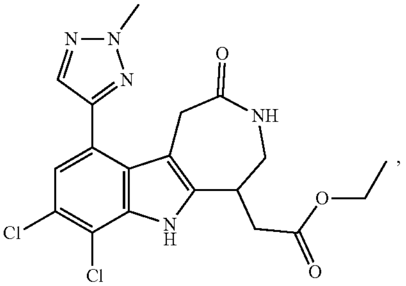
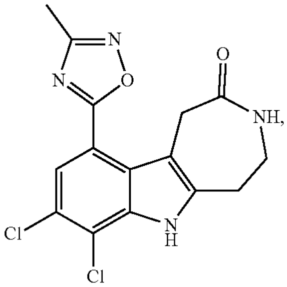
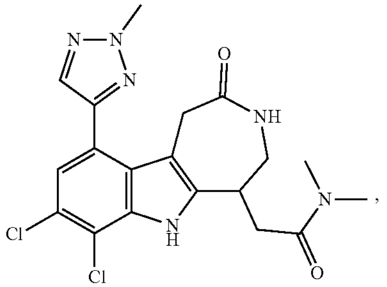
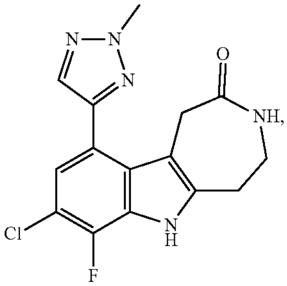
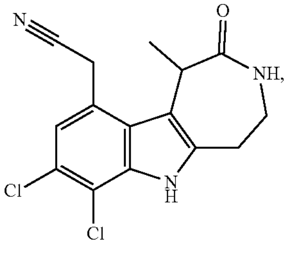

-continued
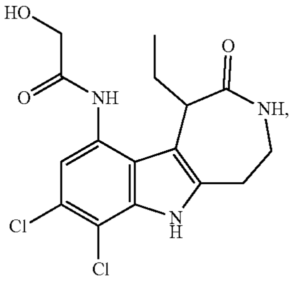
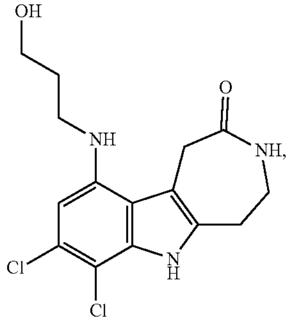
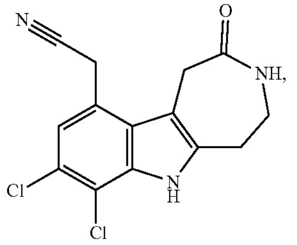
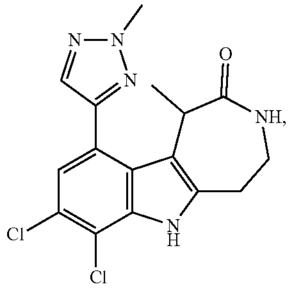
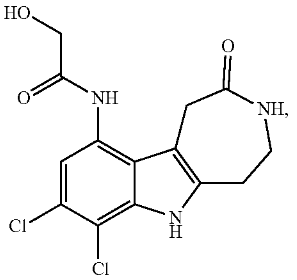
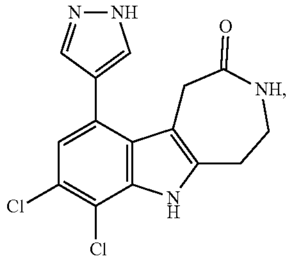
-continued
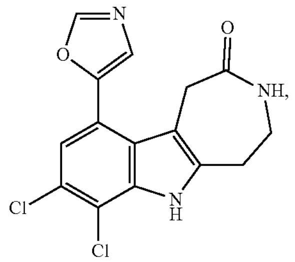
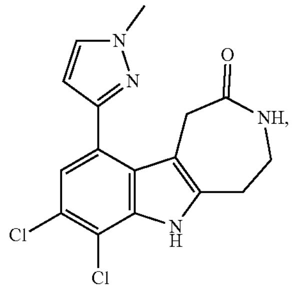
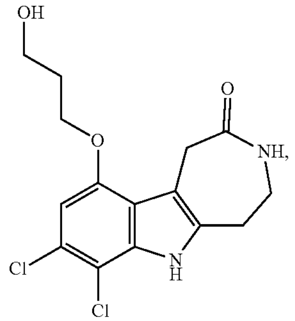
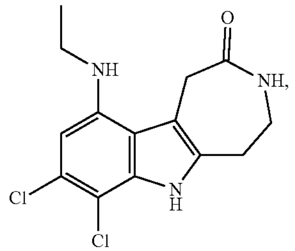
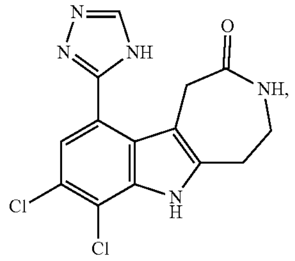
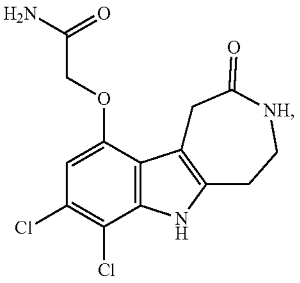

-continued
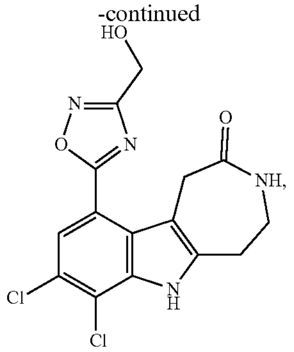
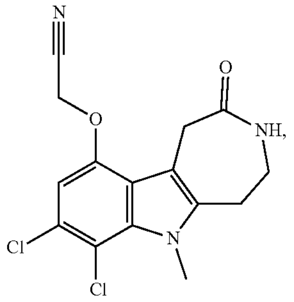
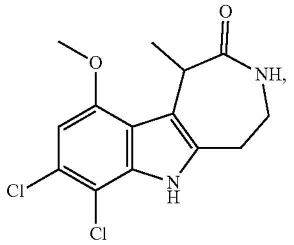
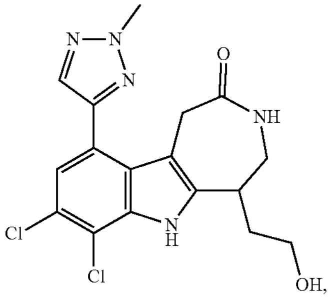
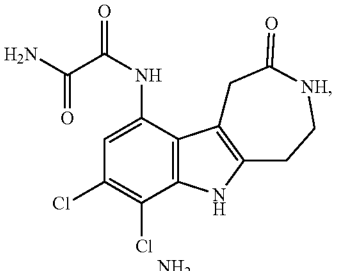
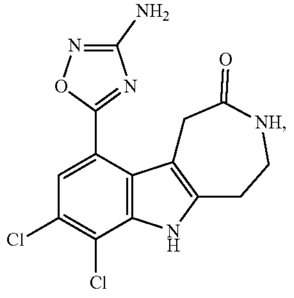
-continued
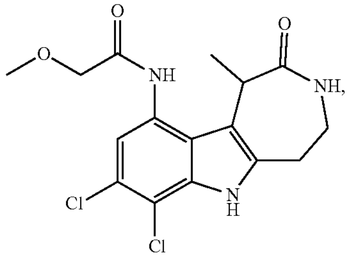
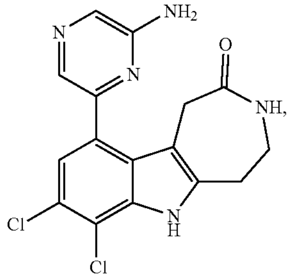
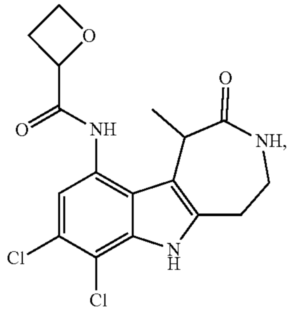
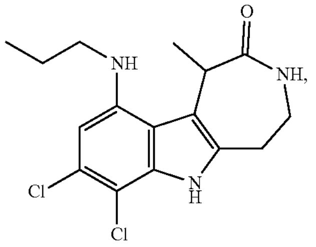
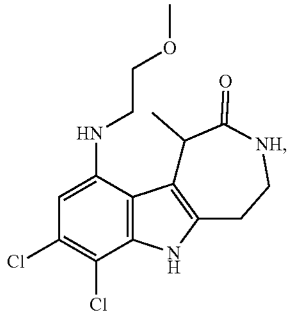
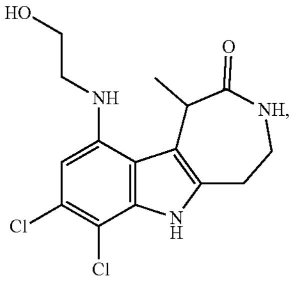

-continued
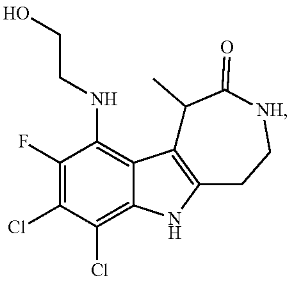
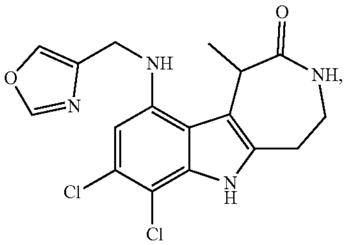
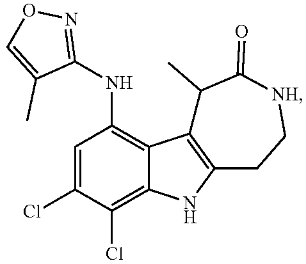
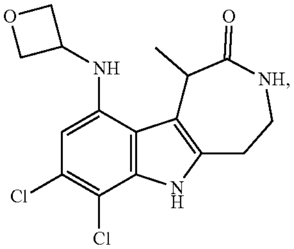
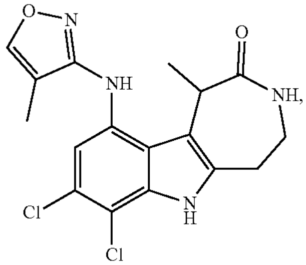
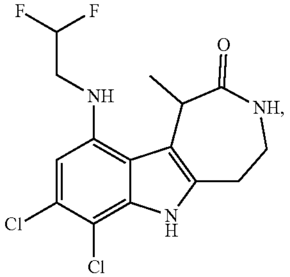
-continued
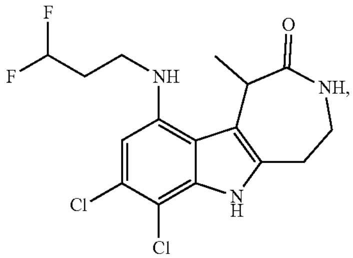
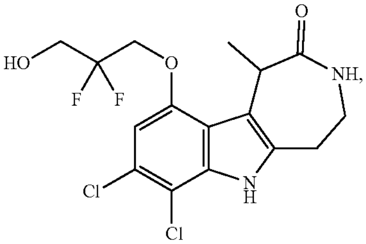
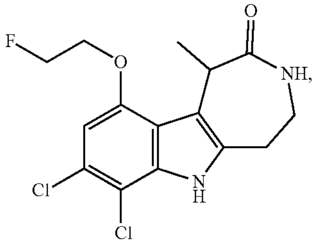
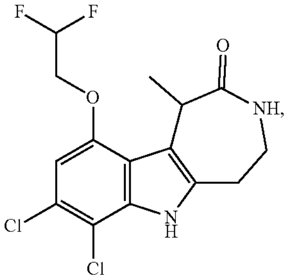
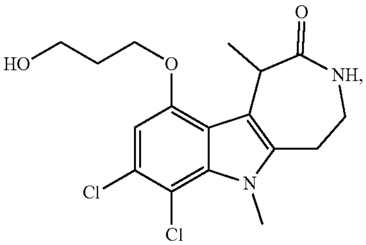
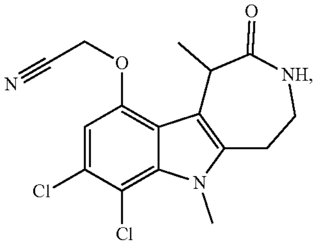

-continued
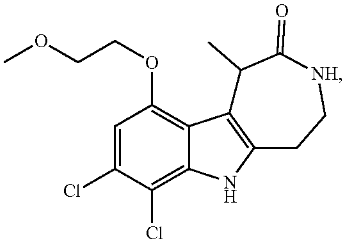
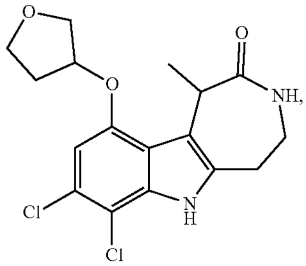
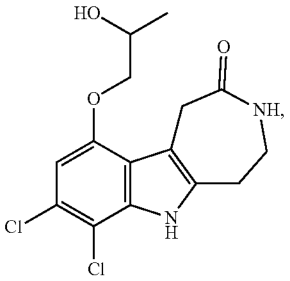
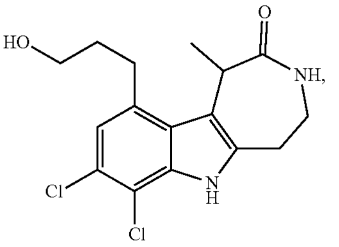
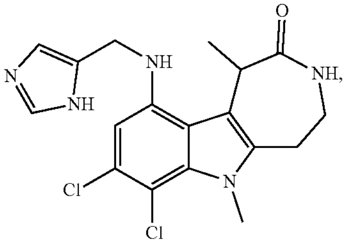
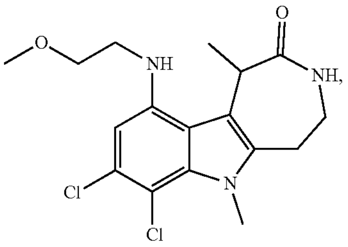
-continued
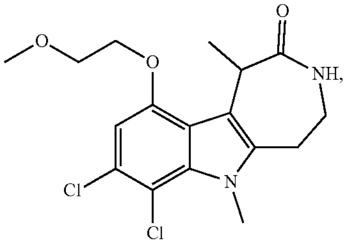
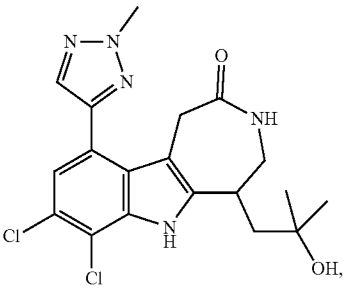
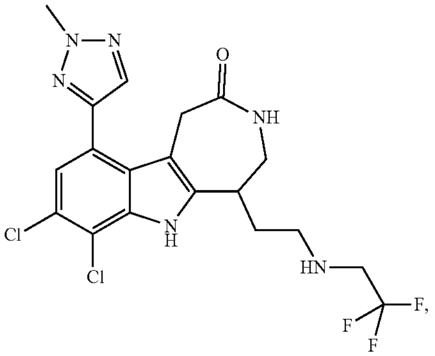
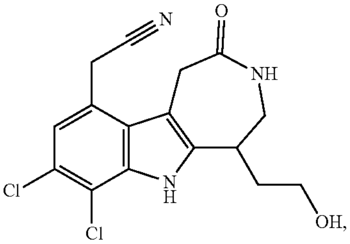
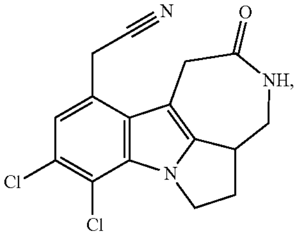
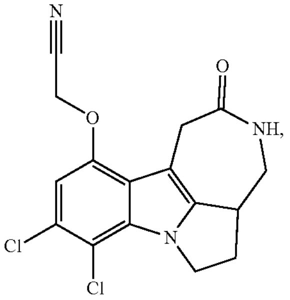

-continued
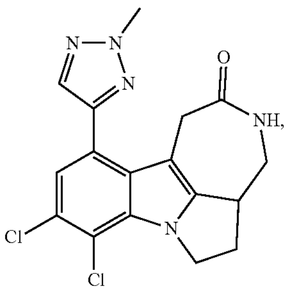
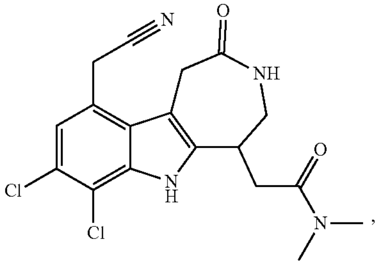
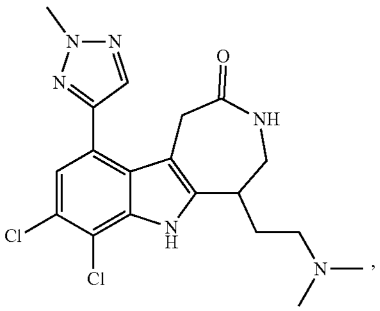
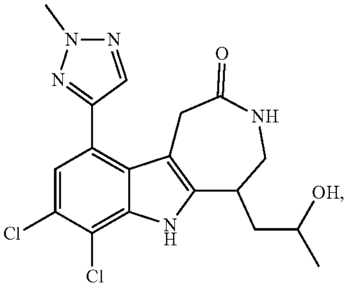
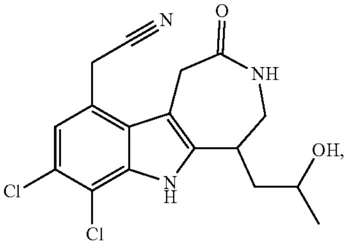
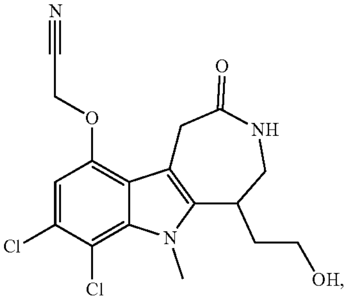
-continued
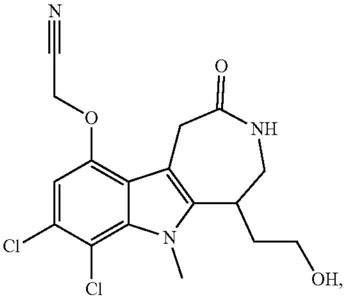
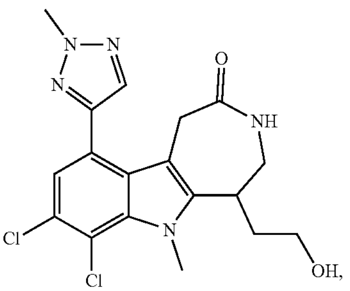
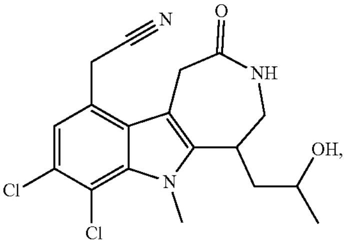
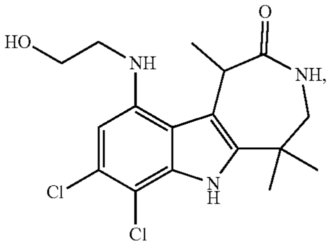
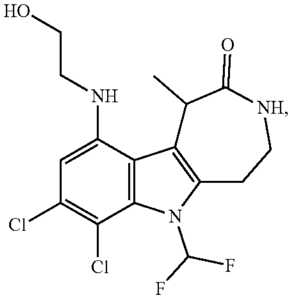
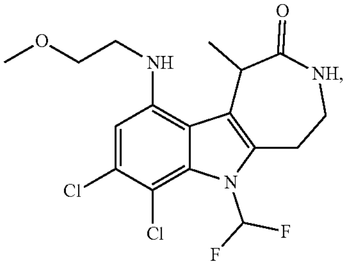

-continued
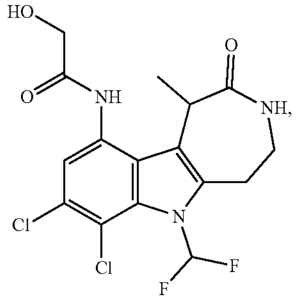
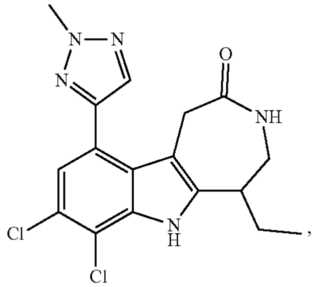
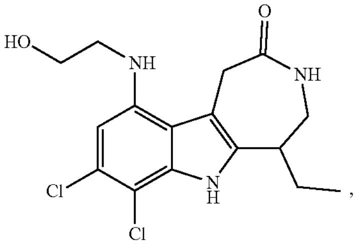
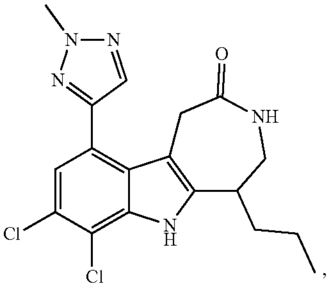
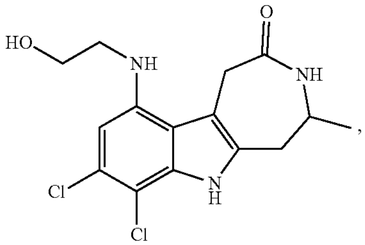
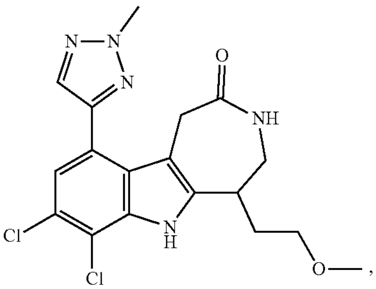
-continued
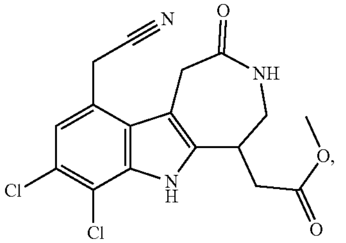
and
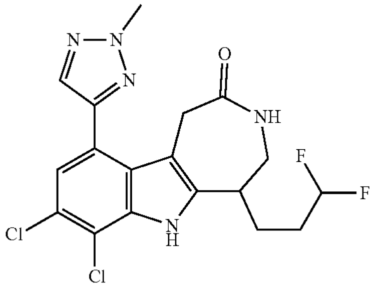
or a pharmaceutically acceptable salt thereof.
Embodiment 58. The compound of embodiment 1, wherein the compound is selected from the group consisting of:
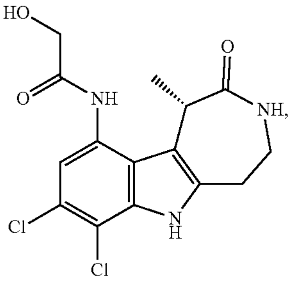
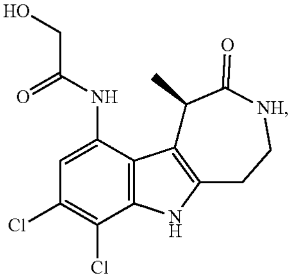
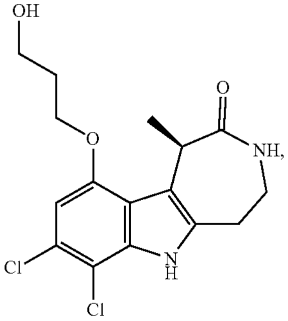

-continued
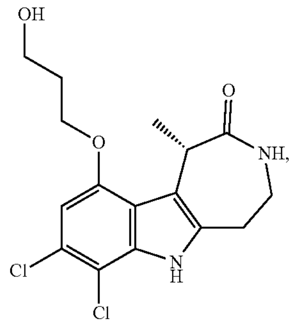
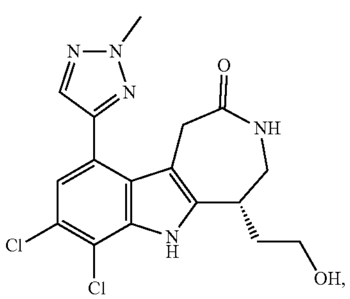
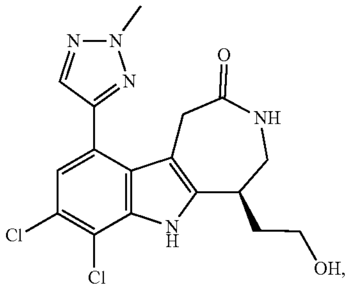
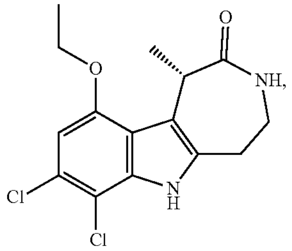
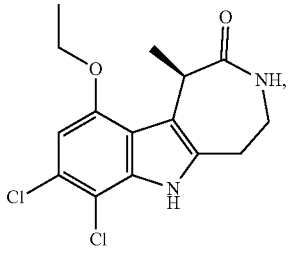
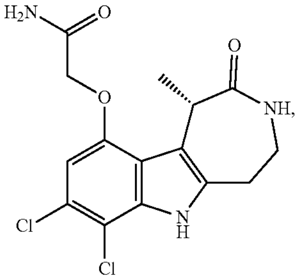
-continued
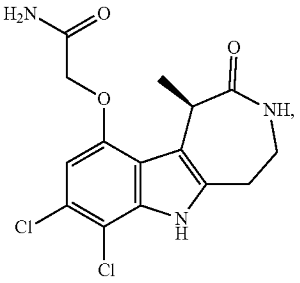
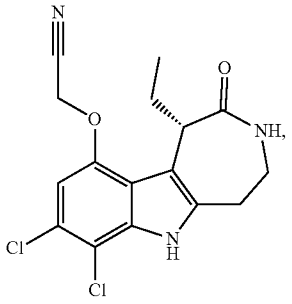
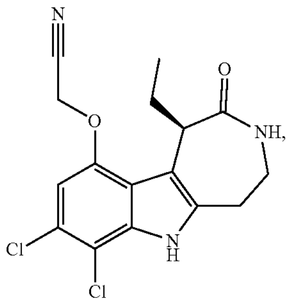
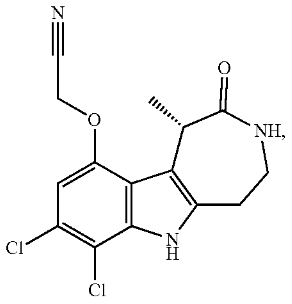
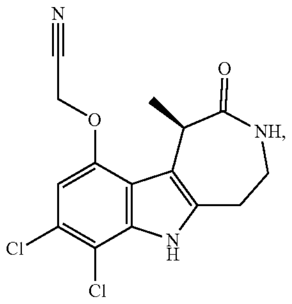

-continued
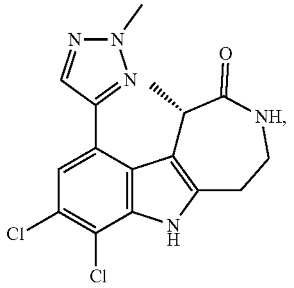
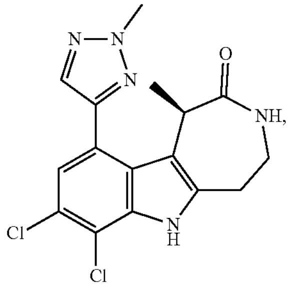
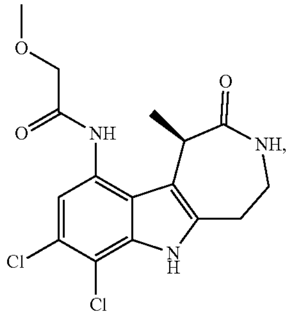
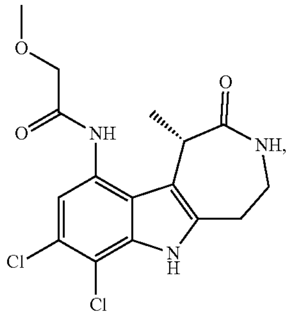
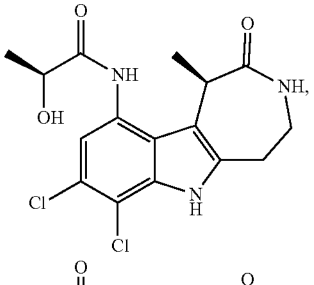
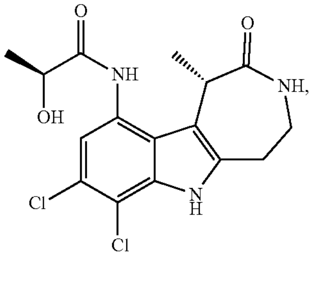
-continued
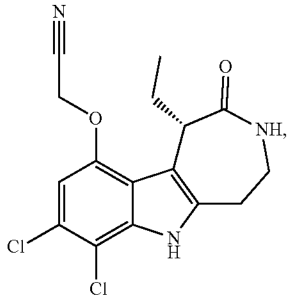
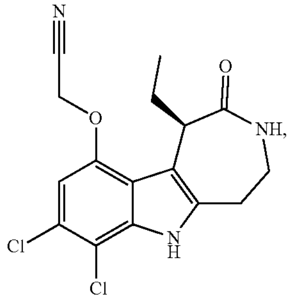
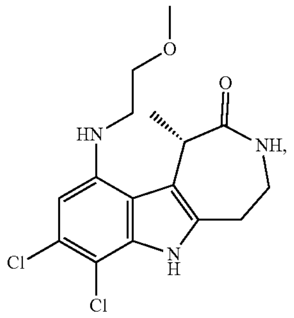
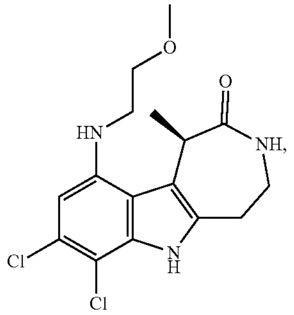
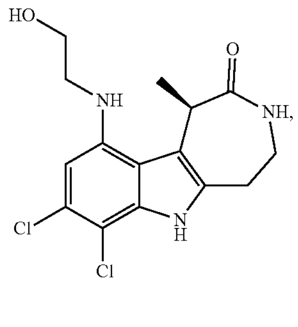

-continued
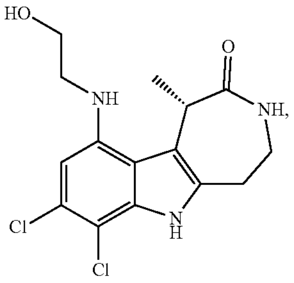
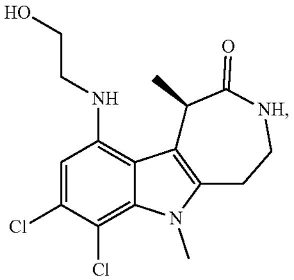
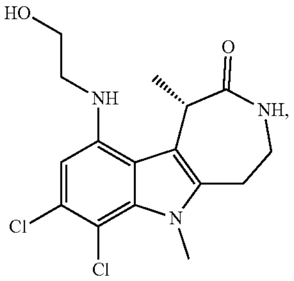
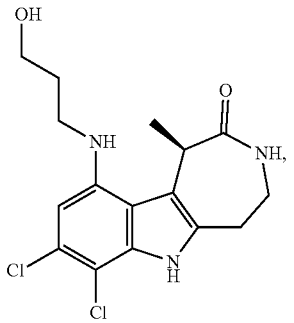
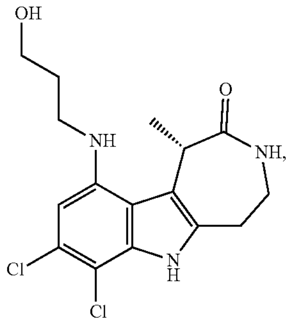
-continued
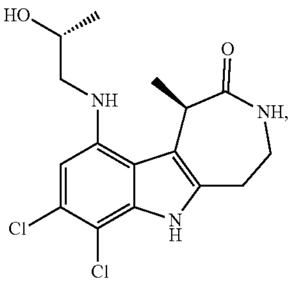
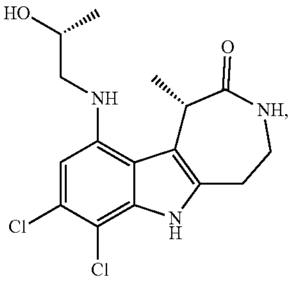
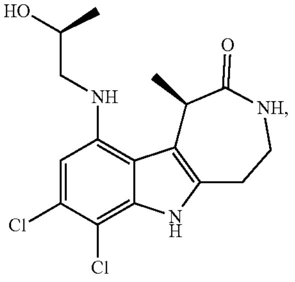
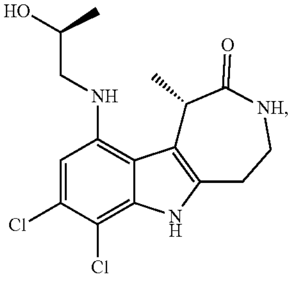
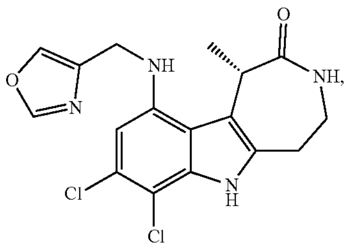
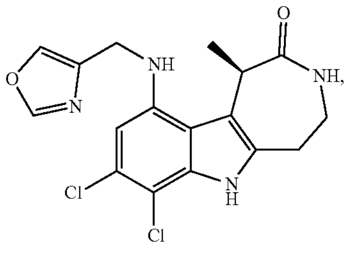

-continued
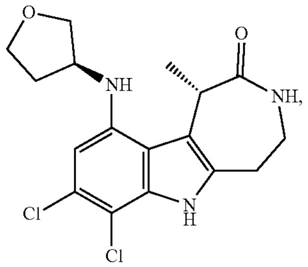
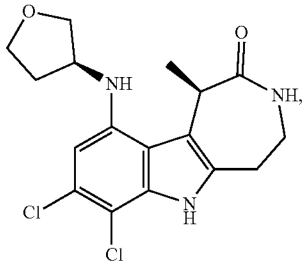
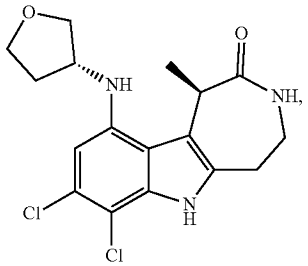
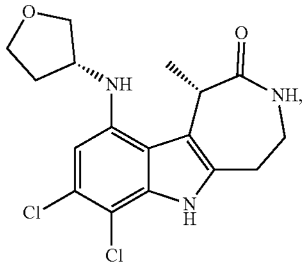
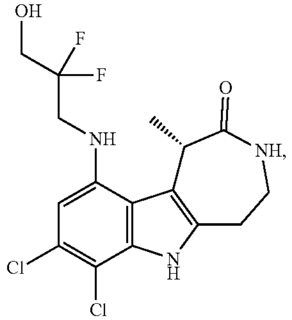
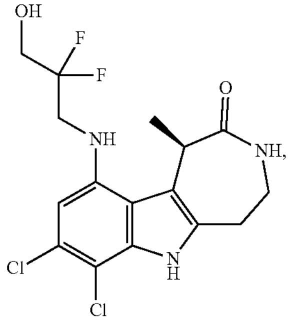
-continued
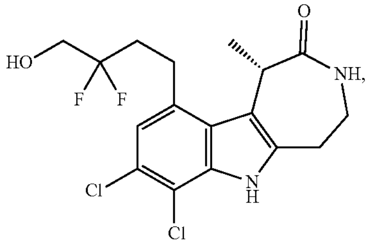
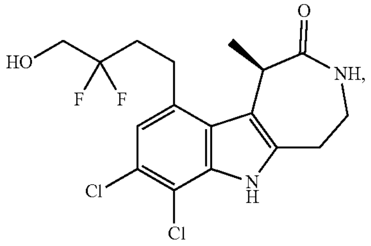
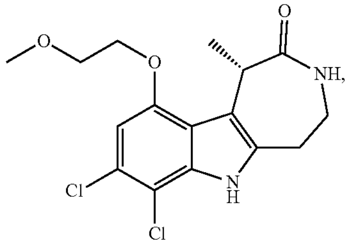
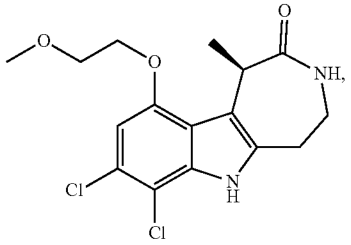
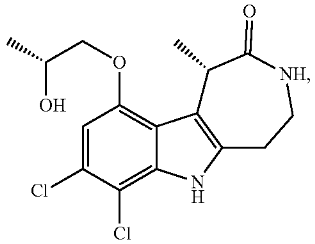
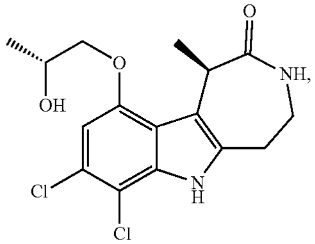
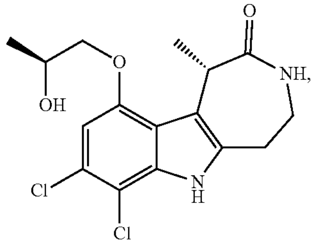

-continued
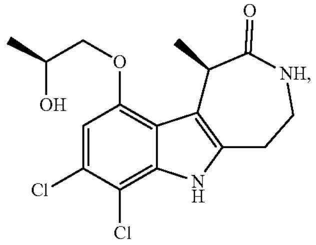
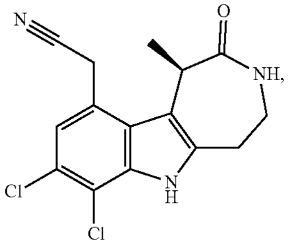
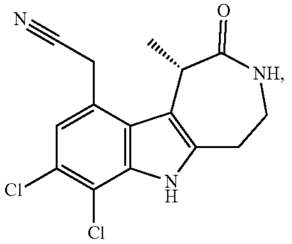
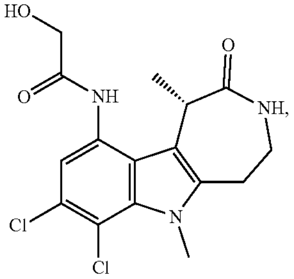
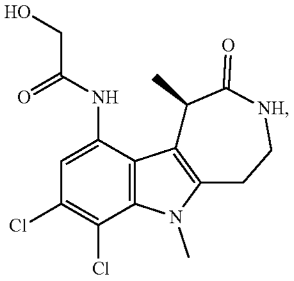
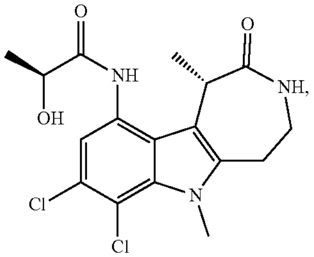
-continued
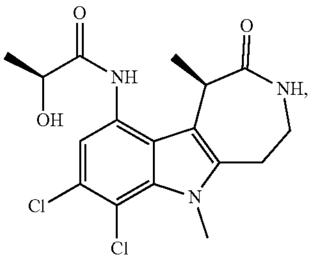
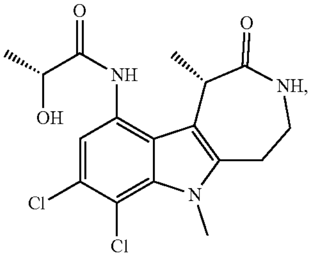
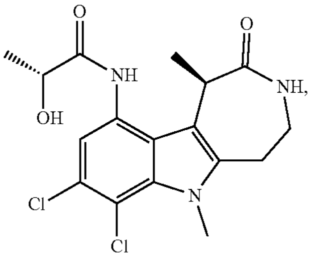
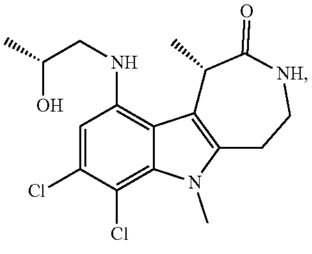
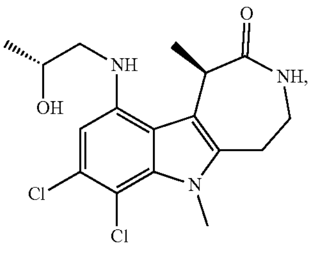
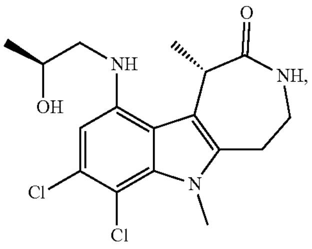

-continued
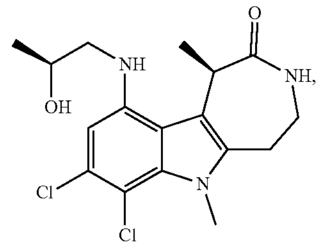
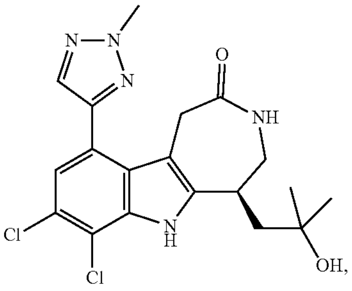
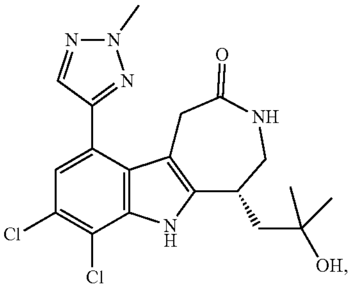
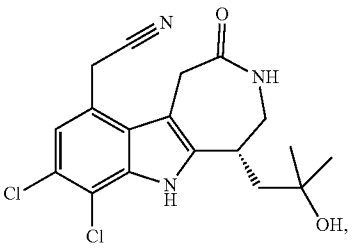
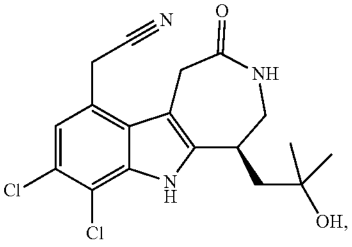
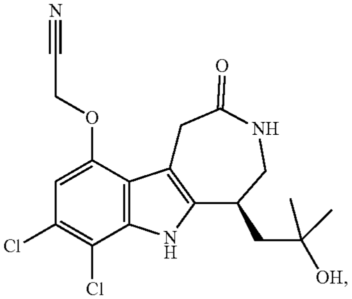
-continued
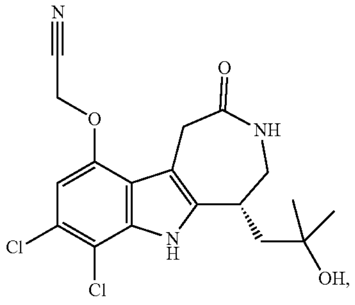
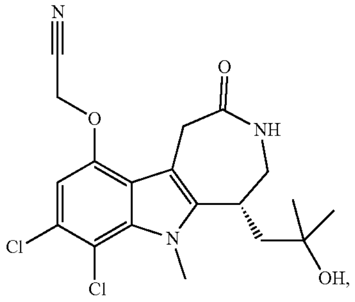
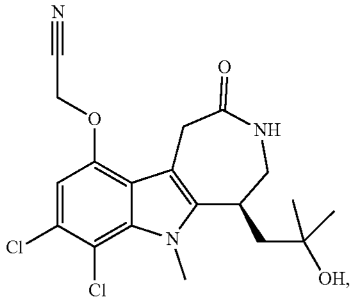
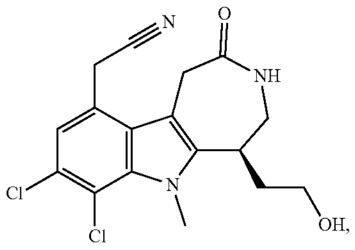
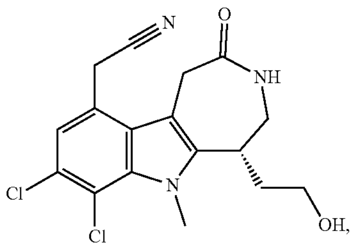
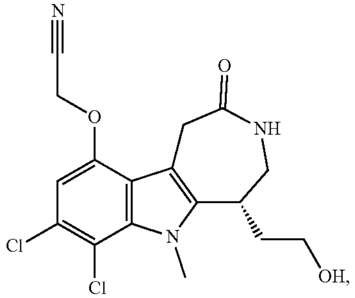

-continued
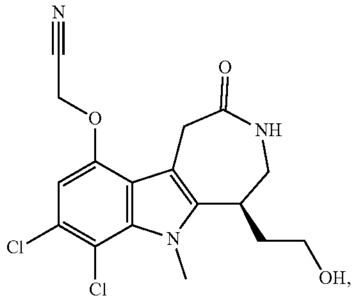
,
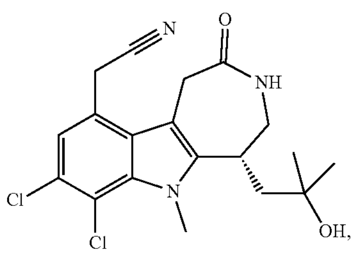
,
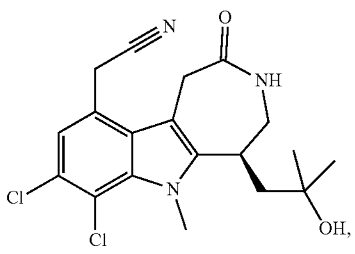
,
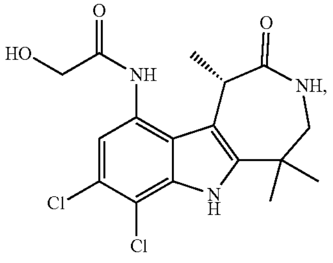
,
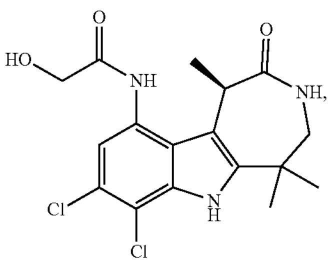
,
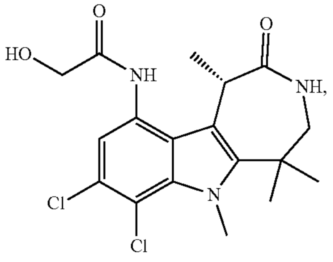
-continued
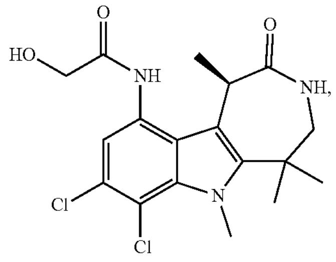
,
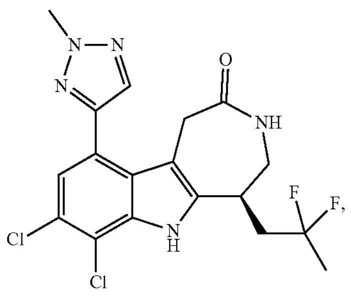
,
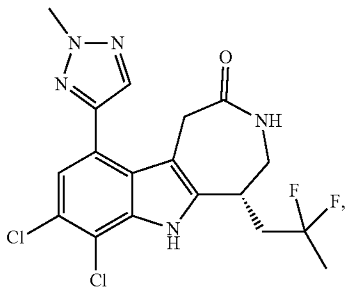
,
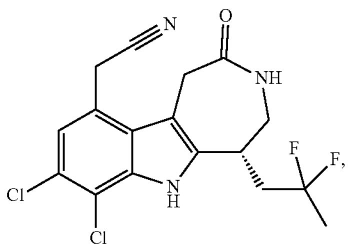
,
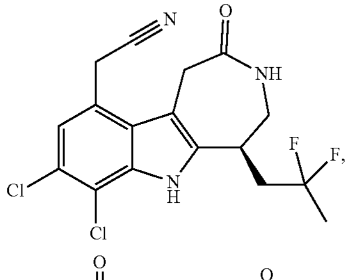
,
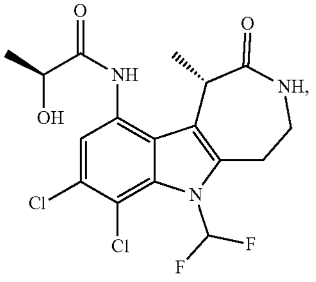
, -continued
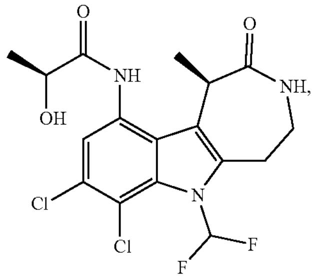
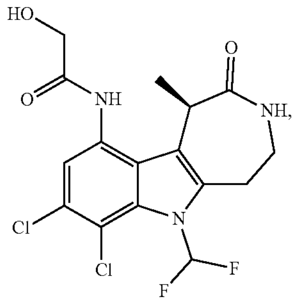
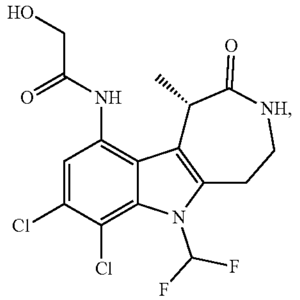
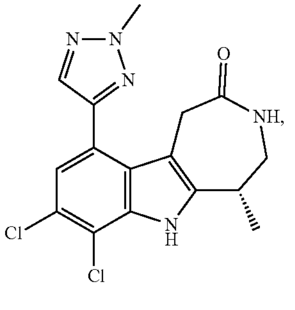
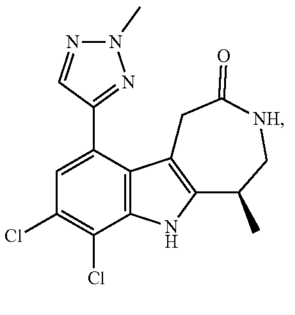
-continued
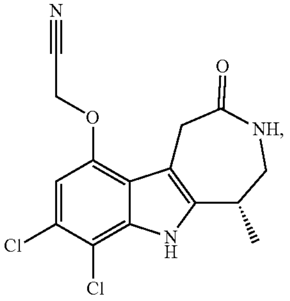
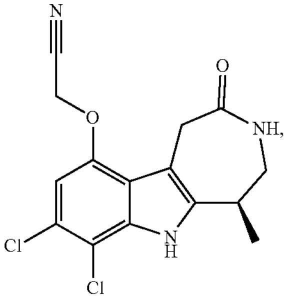
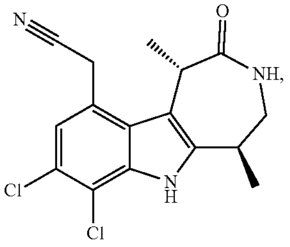
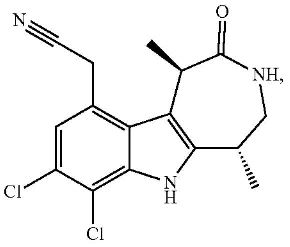
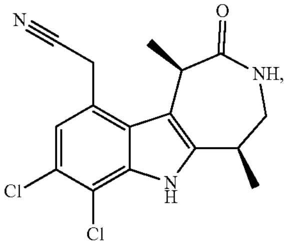
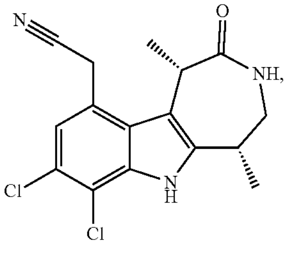

-continued
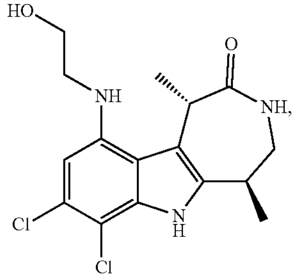
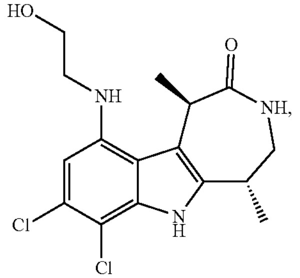
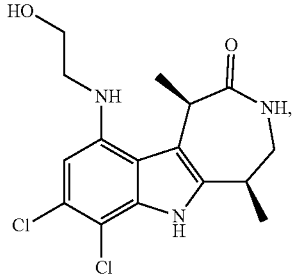
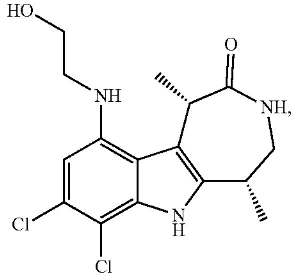
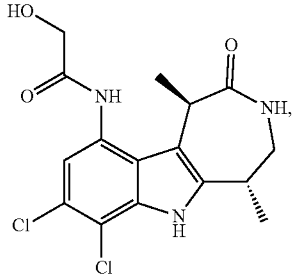
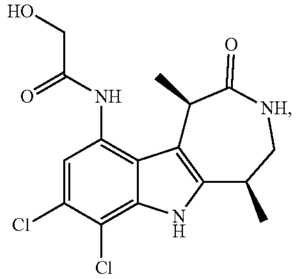
-continued
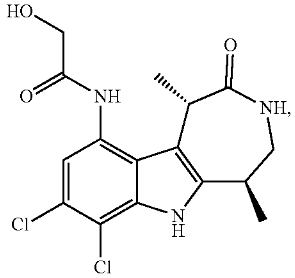
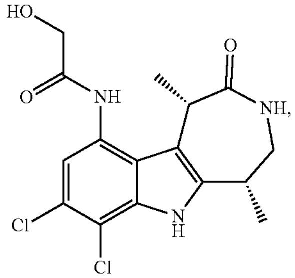
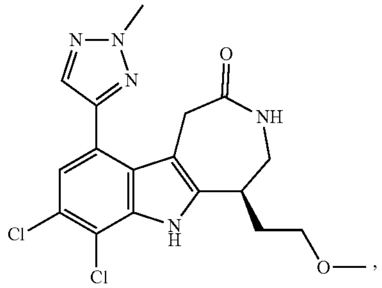
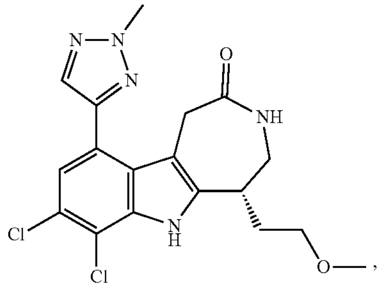
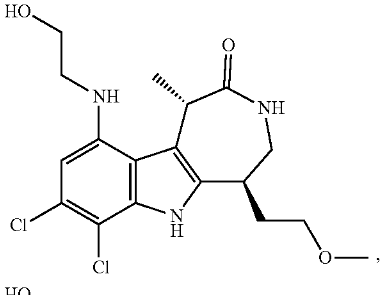
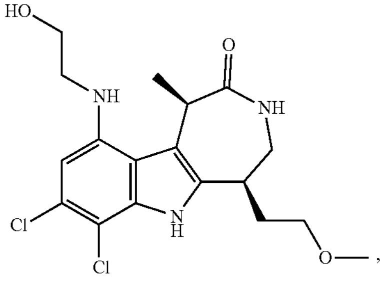

-continued
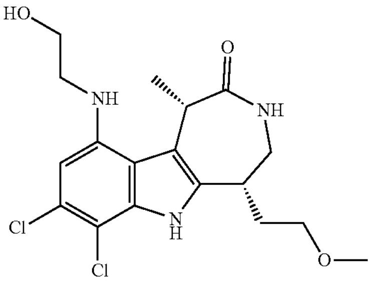
,
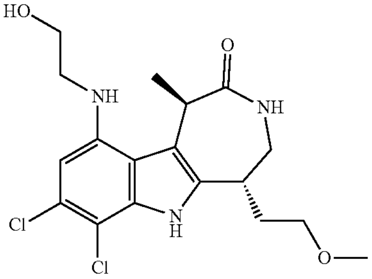
,
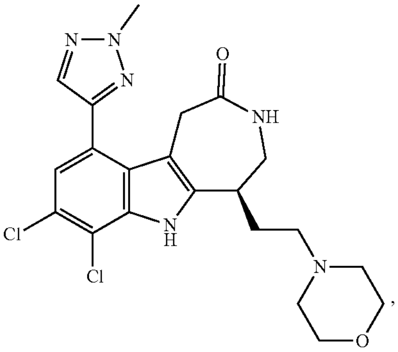
, and
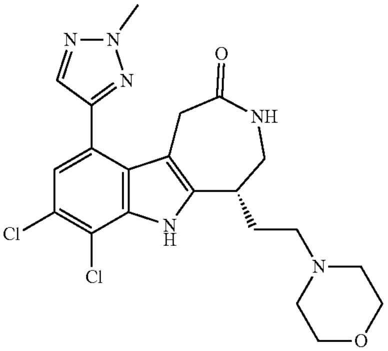
.
or a pharmaceutically acceptable salt thereof.
Embodiment 59. A compound selected from:
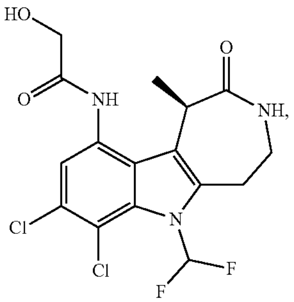
-continued
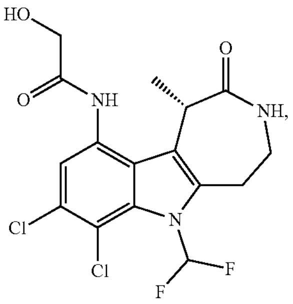
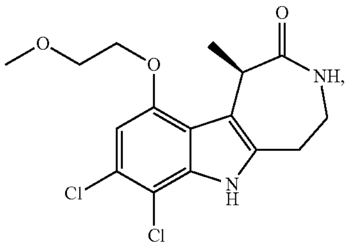
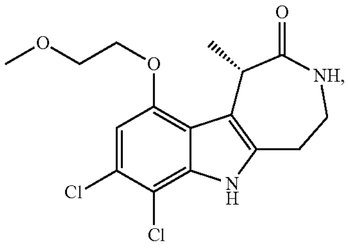
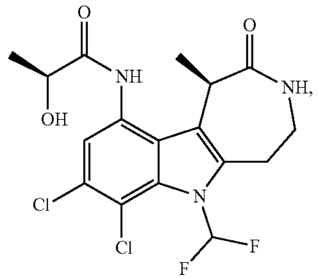
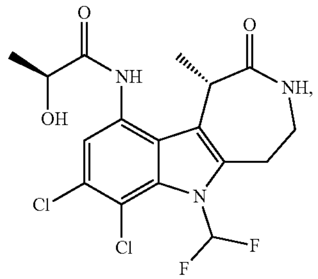
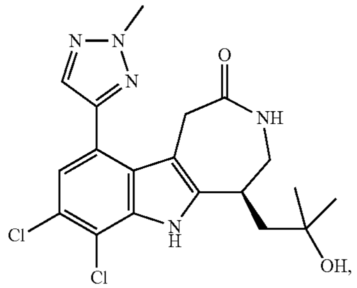

-continued

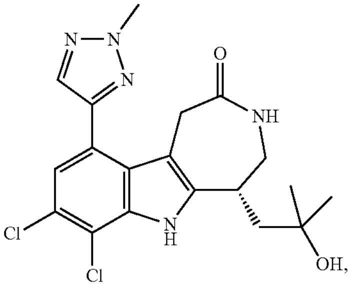

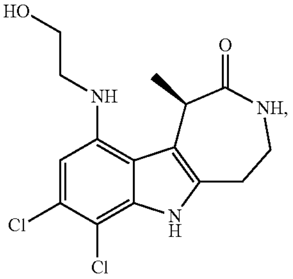

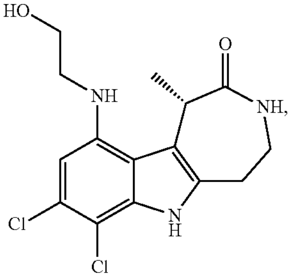

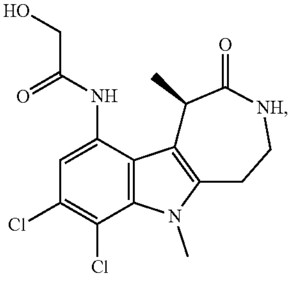

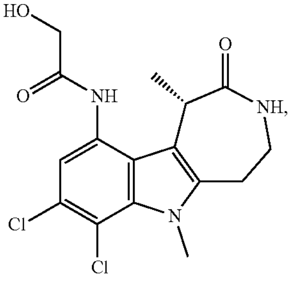

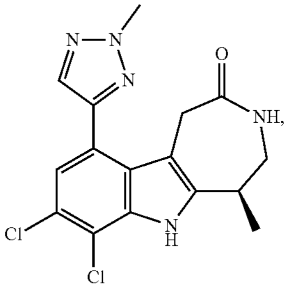

-continued

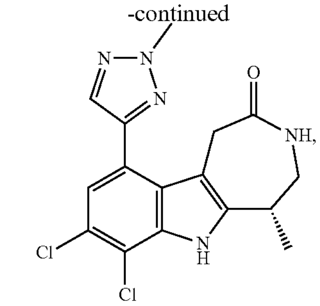

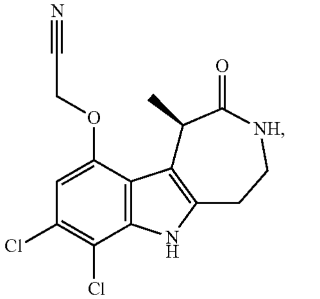

and

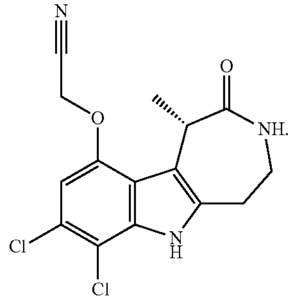

Embodiment 60. A pharmaceutical composition, comprising a compound according to any one of embodiments 1 to 59, or a pharmaceutically acceptable salt thereof, with one or more pharmaceutically acceptable carriers, diluents, or excipients.

Embodiment 61. A method of treating an immune-mediated disease in a patient, comprising administering to a patient in need of such treatment an effective amount of a compound according to any one of embodiments 1 to 59, or a pharmaceutically acceptable salt thereof, or a pharmaceutically composition according to embodiment 60.

Embodiment 62. A method of treating systemic lupus erythematosus in a patient, comprising administering to a patient in need of such treatment an effective amount of a compound according to any one of embodiments 1 to 59, or a pharmaceutically acceptable salt thereof, or a pharmaceutically composition according to embodiment 60.

Embodiment 63. A method of treating lupus nephritis in a patient, comprising administering to a patient in need of such treatment an effective amount of a compound according to any one of embodiments 1 to 59, or a pharmaceutically acceptable salt thereof, or a pharmaceutically composition according to embodiment 60.

Embodiment 64. A method of treating dermatomyositis in a patient, comprising administering to a patient in need of such treatment an effective amount of a compound according to any one of embodiments 1 to 59, or a pharmaceutically acceptable salt thereof, or a pharmaceutically composition according to embodiment 60.

Embodiment 65. A method of treating Aicardi-Goutières syndrome in a patient, comprising administering to a patient in need of such treatment an effective amount of a compound according to any one of embodiments 1 to 59, or a pharmaceutically acceptable salt thereof, or a pharmaceutically composition according to embodiment 60.

Embodiment 66. A method of treating a disease associated with cGAS activation in a patient, comprising administering to a patient in need of such treatment an effective amount of a compound according to any one of embodiments 1 to 59, or a pharmaceutically acceptable salt thereof, or a pharmaceutically composition according to embodiment 60.

Embodiment 67. A compound according to any one of embodiments 1 to 59, or a pharmaceutically acceptable salt thereof, for use in therapy.

Embodiment 68. A compound according to any one of embodiments 1 to 59, or a pharmaceutically acceptable salt thereof, for use in the treatment of an immune-mediated disease.

Embodiment 69. A compound according to any one of embodiments 1 to 59, or a pharmaceutically acceptable salt thereof, for use in the treatment of systemic lupus erythematosus.

Embodiment 70. A compound according to any one of embodiments 1 to 59, or a pharmaceutically acceptable salt thereof, for use in the treatment of lupus nephritis.

Embodiment 71. A compound according to any one of embodiments 1 to 59, or a pharmaceutically acceptable salt thereof, for use in the treatment of dermatomyositis.

Embodiment 72. A compound according to any one of embodiments 1 to 59, or a pharmaceutically acceptable salt thereof, for use in the treatment of Aicardi-Goutières syndrome.

Embodiment 73. Use of a compound according to any one of embodiments 1 to 59 for the manufacture of a medicament for the treatment of an immune-mediated disease in a patient in need thereof.

Embodiment 74. Use of a compound according to any one of embodiments 1 to 59 for the manufacture of a medicament for the treatment of systemic lupus erythematosus in a patient in need thereof.

Embodiment 75. Use of a compound according to any one of embodiments 1 to 59 for the manufacture of a medicament for the treatment of lupus nephritis in a patient in need thereof.

Embodiment 76. Use of a compound according to any one of embodiments 1 to 59 for the manufacture of a medicament for the treatment of dermatomyositis in a patient in need thereof.

Embodiment 77. Use of a compound according to any one of embodiments 1 to 59 for the manufacture of a medicament for the treatment of Aicardi-Goutières syndrome in a patient in need thereof.

Embodiment 78. A pharmaceutical composition comprising a compound of according to any one of embodiments 1 to 59, or a pharmaceutically acceptable salt thereof, for use in the treatment of an immune-mediated disease in a patient in need thereof.

Embodiment 79. A pharmaceutical composition comprising a compound of according to any one of embodiments 1 to 59, or a pharmaceutically acceptable salt thereof, for use in the treatment of systemic lupus erythematosus in a patient in need thereof.

Embodiment 80. A pharmaceutical composition comprising a compound of according to any one of embodiments 1 to 59, or a pharmaceutically acceptable salt thereof, for use in the treatment of lupus nephritis in a patient in need thereof.

Embodiment 81. A pharmaceutical composition comprising a compound of according to any one of embodiments 1 to 59, or a pharmaceutically acceptable salt thereof, for use in the treatment of dermatomyositis in a patient in need thereof.

Embodiment 82. A pharmaceutical composition comprising a compound of according to any one of embodiments 1 to 59, or a pharmaceutically acceptable salt thereof, for use in the treatment of Aicardi-Goutières syndrome in a patient in need thereof.

Embodiment A1. A compound of formula:

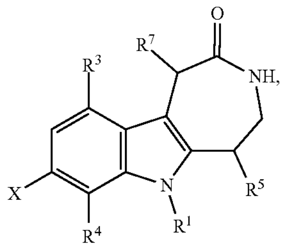

wherein:

X and $R^4$ are independently halo;

$R^1$ and $R^7$ are independently $R^b$;

$R^3$ is —NH—$R^{bb}$—OH, —NHC(O)—$R^{bb}$—OH, —O—$R^{bb}$—C(O)$NH_2$, —O—$R^{bb}$—OH, —O—$R^{bb}$—O—C(O)—$R^b$, —O—$R^{bb}$—H, —O—$R^{bb}$—CN, —NH—$R^{bb}$—H, —$R^{bb}$—CN, or a five-membered heteroaryl with 2 or 3 heteroatoms, wherein the five-membered heteroaryl is optionally substituted with —$R^{bb}$—H or —$R^{bb}$—OH;

$R^5$ is H, —$R^{bb}$C(O)$Q^1R^b$, or —$R^{bb}$OH;

$Q^1$ is O or $NR^b$;

each occurrence of $R^b$ is independently H or —$R^{bb}$H; and each occurrence of $R^{bb}$ is independently substituted or unsubstituted $C_{1-3}$ alkylene, or a pharmaceutically acceptable salt thereof.

Embodiment A2. The compound of embodiment A1, wherein X is chloro.

Embodiment A3. The compound of embodiment A1 or A2, wherein $R^4$ is chloro.

Embodiment A4. The compound of any one of the preceding embodiments A1-A3, wherein $R^1$ is H provided that $R^3$ is not —O—$R^{bb}$—CN.

Embodiment A5. The compound of embodiment A1, wherein $R^1$ is methyl and $R^3$ is —O—$R^{bb}$—CN.

Embodiment A6. The compound of any one of the preceding embodiments A1-A5, wherein $R^5$ is H provided that $R^3$ is not the five-membered heteroaryl.

Embodiment A7. The compound of any one of the preceding embodiments A1-A6, wherein $R^5$ is —$CH_2C(O)NHCH_3$, —$CH_2C(O)N(CH_3)_2$, —$CH_2C(O)OCH_2CH_3$, or —$CH_2C(O)OH$.

Embodiment A8. The compound of any of the embodiments A1-A6, wherein $R^5$ is —$CH_2CH_2OH$.

Embodiment A9. The compound of any one of the preceding embodiments A1-A8, wherein $R^3$ is the five-membered heteroaryl.

Embodiment A10. The compound of any one of the preceding embodiments A1-A9, wherein $R^3$ is selected from:

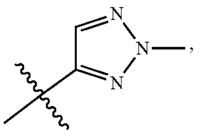
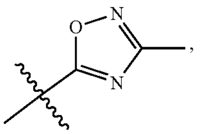
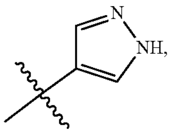
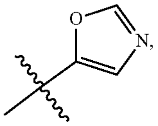
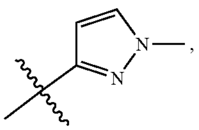
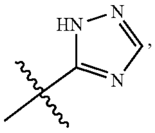
and
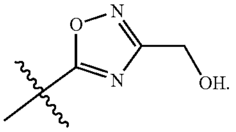
Embodiment A11. The compound of any one of the preceding embodiments A1-A10, wherein $R^3$ is selected from —NH—$R^{bb}$—OH, —NHC(O)—$R^{bb}$—OH, —O—$R^{bb}$—C(O)$NH_2$, —O—$R^{bb}$—OH, —O—$R^{bb}$—O—C(O)—$R^b$, —O—$R^{bb}$—H, —O—$R^{bb}$—CN, —NH—$R^{bb}$—H, and —$R^{bb}$—CN.
Embodiment A12. The compound of embodiment A1, wherein the compound is selected from the group consisting of:
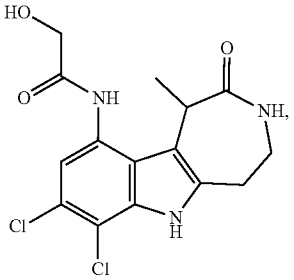
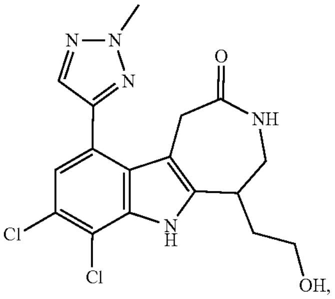
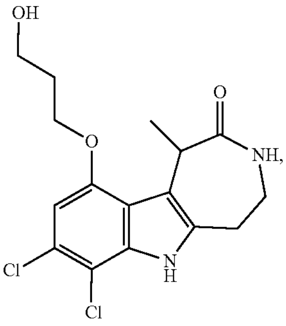
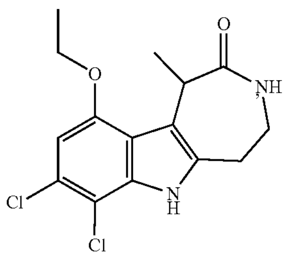
-continued
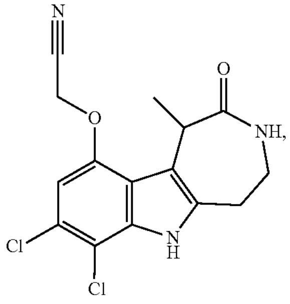
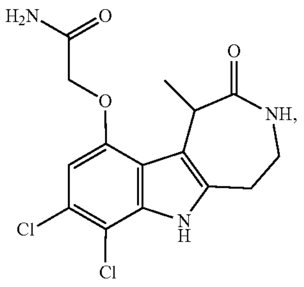
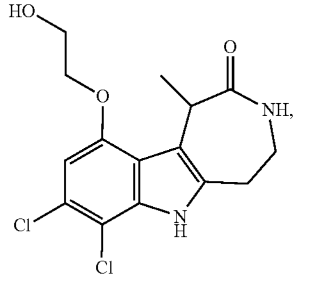
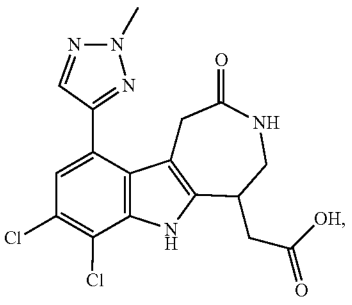
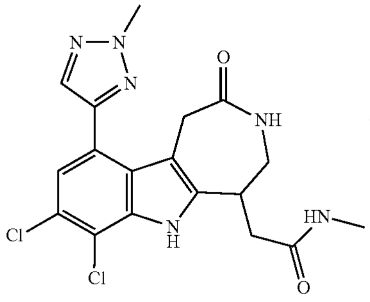
, -continued
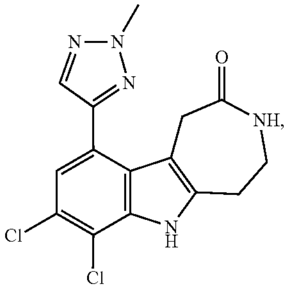
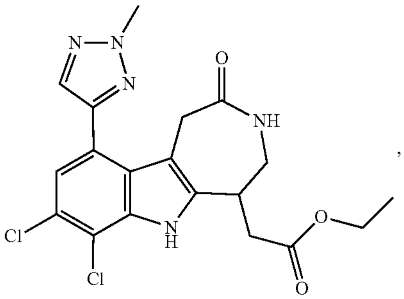
,
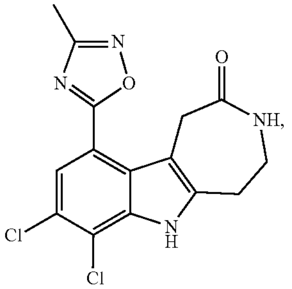
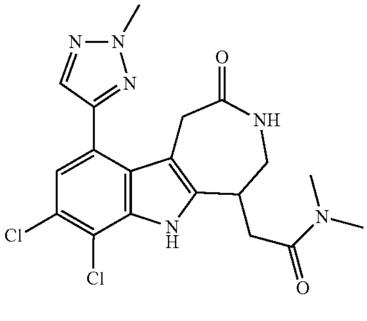
,
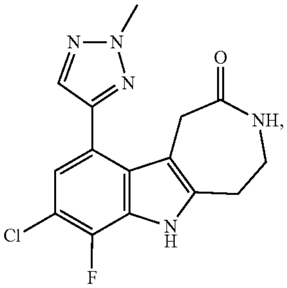
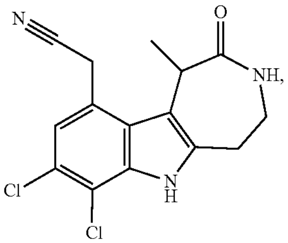
-continued
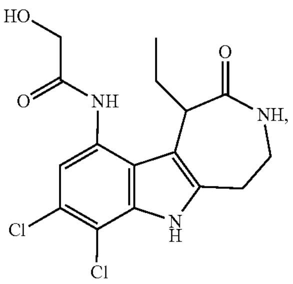
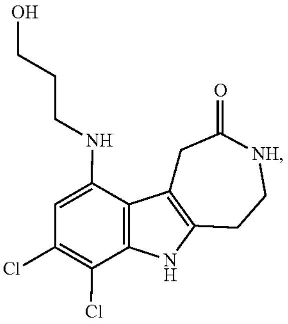
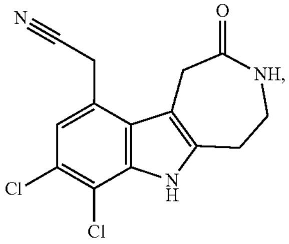
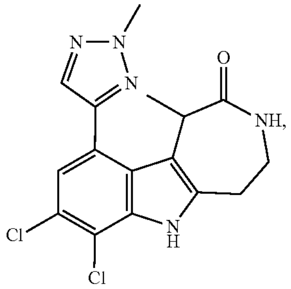
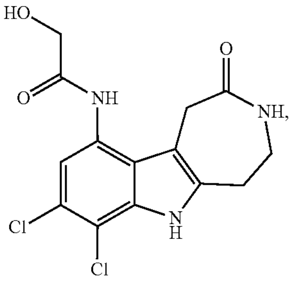
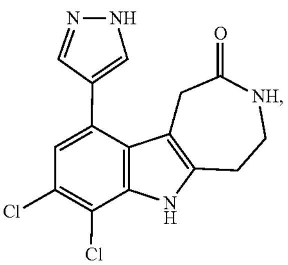
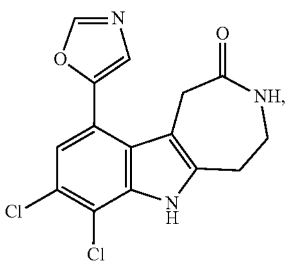

-continued
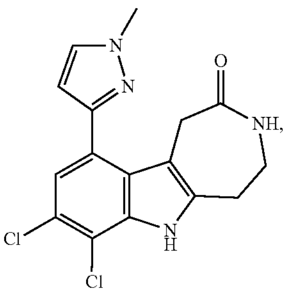
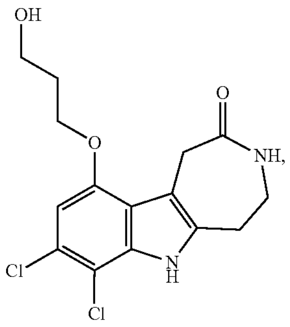
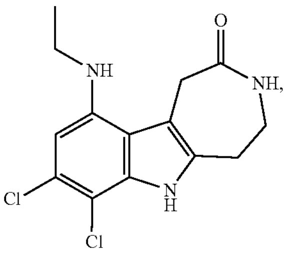
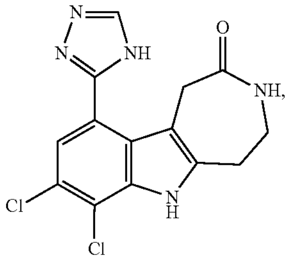
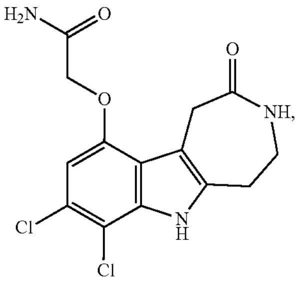
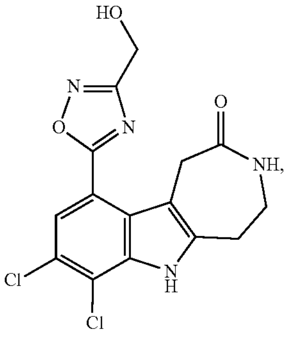
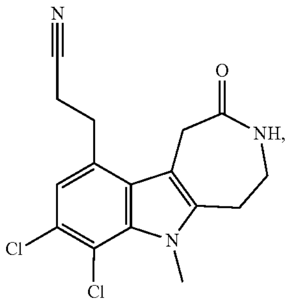
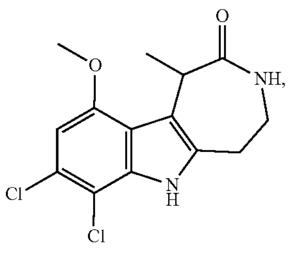
and
-continued
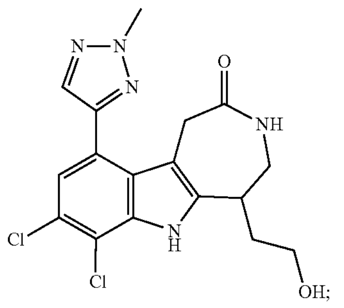
or a pharmaceutically acceptable salt thereof.
Embodiment A13. The compound of embodiment A1, wherein the compound is selected from the group consisting of:
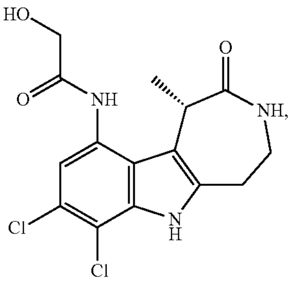
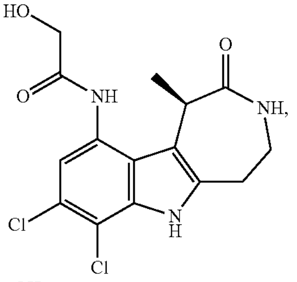
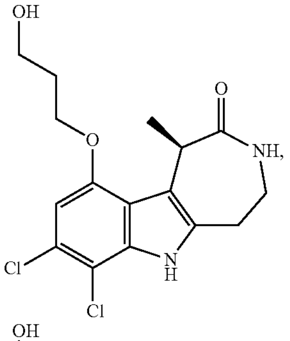
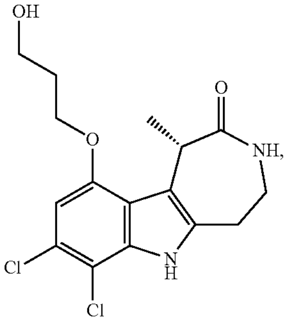

-continued

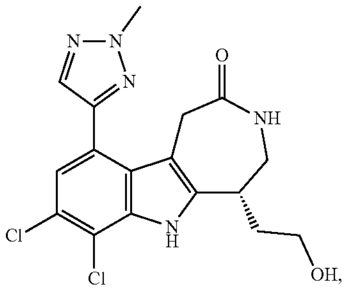

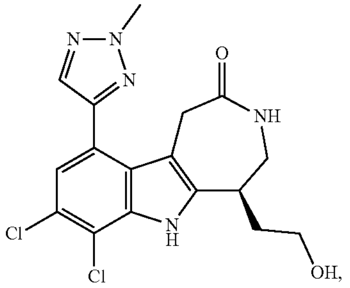

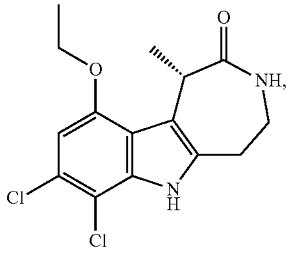

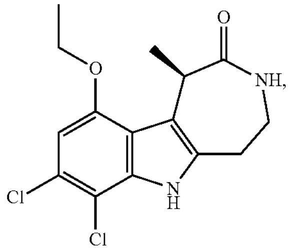

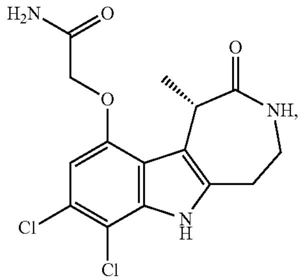

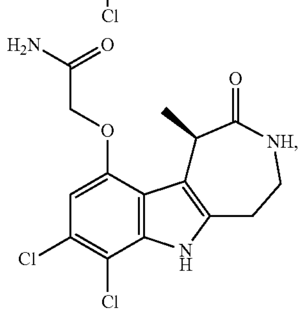

-continued

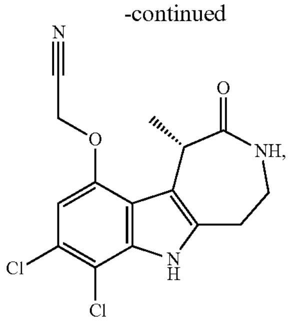

and

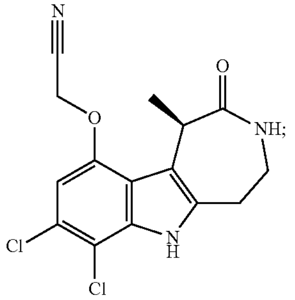

or a pharmaceutically acceptable salt thereof.

Embodiment A14. A pharmaceutical composition, comprising a compound according to any one of embodiments A1 to A13, or a pharmaceutically acceptable salt thereof, with one or more pharmaceutically acceptable carriers, diluents, or excipients.

Embodiment A15. A method of treating an immune-mediated disease in a patient, comprising administering to a patient in need of such treatment an effective amount of a compound according to any one of embodiments A1 to A13, or a pharmaceutically acceptable salt thereof, or a pharmaceutically composition according to embodiment A14.

Embodiment A16. A method of treating systemic lupus erythematosus in a patient, comprising administering to a patient in need of such treatment an effective amount of a compound according to any one of embodiments A1 to A13, or a pharmaceutically acceptable salt thereof, or a pharmaceutically composition according to embodiment A14.

Embodiment A17. A method of treating lupus nephritis in a patient, comprising administering to a patient in need of such treatment an effective amount of a compound according to any one of embodiments A1 to A13, or a pharmaceutically acceptable salt thereof, or a pharmaceutically composition according to embodiment A14.

Embodiment A18. A method of treating dermatomyositis in a patient, comprising administering to a patient in need of such treatment an effective amount of a compound according to any one of embodiments A1 to A13, or a pharmaceutically acceptable salt thereof, or a pharmaceutically composition according to embodiment A14.

Embodiment A19. A method of treating Aicardi-Goutières syndrome in a patient, comprising administering to a patient in need of such treatment an effective amount of a compound according to any one of embodiments A1 to A13, or a pharmaceutically acceptable salt thereof, or a pharmaceutically composition according to embodiment A14.

Embodiment A20. A method of treating a disease associated with cGAS activation in a patient, comprising administering to a patient in need of such treatment an effective amount of a compound according to any one of embodiments A1 to A13, or a pharmaceutically acceptable salt thereof, or a pharmaceutically composition according to embodiment A14.

Embodiment A21. A compound according to any one of embodiments A1 to A13, or a pharmaceutically acceptable salt thereof, for use in therapy.

Embodiment A22. A compound according to any one of embodiments A1 to A13, or a pharmaceutically acceptable salt thereof, for use in the treatment of an immune-mediated disease.

Embodiment A23. A compound according to any one of embodiments A1 to A13, or a pharmaceutically acceptable salt thereof, for use in the treatment of systemic lupus erythematosus.

Embodiment A24. A compound according to any one of embodiments A1 to A13, or a pharmaceutically acceptable salt thereof, for use in the treatment of lupus nephritis.

Embodiment A25. A compound according to any one of embodiments A1 to A13, or a pharmaceutically acceptable salt thereof, for use in the treatment of dermatomyositis.

Embodiment A26. A compound according to any one of embodiments A1 to A13, or a pharmaceutically acceptable salt thereof, for use in the treatment of Aicardi-Goutières syndrome.

Embodiment B1. A compound of formula IVa:

(IVa)

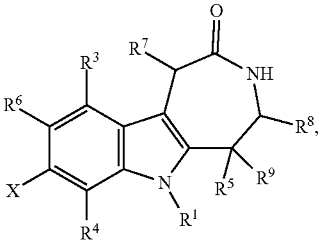

wherein:

X and $R^4$ are independently halo;

$R^1$, $R^7$, $R^8$, and $R^9$ are independently $R^b$;

$R^6$ is H or F;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$CH_2$—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —NH—$R^e$, —O—$CH_2$—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H, or —$R^{bb}$—OH;

$R^5$ is H, —$R^{bb}$H, —$R^{bb}$C(O)$OR^b$, —$R^{bb}$C(O)N($R^b$)$_2$, —$R^{bb}$N($R^b$)$_2$, —$R^{bb}$N($R^b$)($R^{bb}CF_3$), —$R^{bb}OR^b$, or

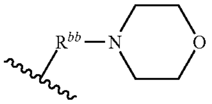;

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

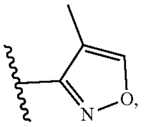, 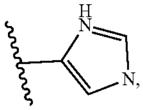, or 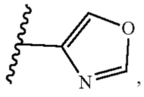, or a pharmaceutically acceptable salt thereof.

Embodiment B2. A compound of formula IVb:

(IVb)

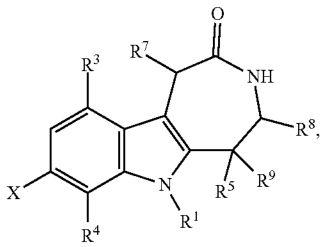

wherein:

X and $R^4$ are independently halo;

$R^1$, $R^7$, $R^8$, and $R^9$ are independently $R^b$;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$CH_2$—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —O—$CH_2$—$R^e$, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H or —$R^{bb}$—OH;

$R^5$ is H, —$R^{bb}$H, —$R^{bb}$C(O)$OR^b$, —$R^{bb}$C(O)N($R^b$)$_2$, —$R^{bb}$N($R^b$)$_2$, —$R^{bb}$N($R^b$)($R^{bb}CF_3$), —$R^{bb}OR^b$, or

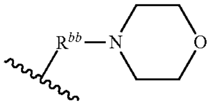;

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

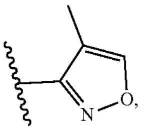, 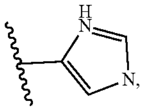, or 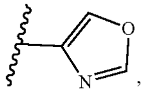, or a pharmaceutically acceptable salt thereof.

Embodiment B5. A compound of formula IVc:

(IVc)

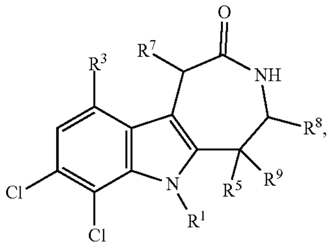

wherein:

$R^1$, $R^7$, $R^8$, and $R^9$ are independently $R^b$;

$R^3$ is —NH—$R^{bb}$—O$R^b$, —NHC(O)—$R^{bb}$—O$R^b$, —NHC(O)—C(O)—$NH_2$, —NH—$R^c$, —NH—C(O)—$R^c$, —O—$R^c$, —O—$CH_2$—$R^c$, —O—$R^{bb}$—C(O)$NH_2$, —O—$R^{bb}$—O$R^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —O—$CH_2$—$R^e$, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H or —$R^{bb}$—OH;

$R^5$ is H, —$R^{bb}$H, —$R^{bb}$C(O)O$R^b$, —$R^{bb}$C(O)N($R^b$)$_2$, —$R^{bb}$N($R^b$)$_2$, —$R^{bb}$N($R^b$)($R^{bb}CF_3$), —$R^{bb}$O$R^b$, or

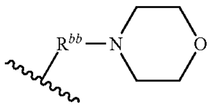

;

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

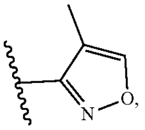 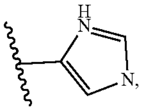 or 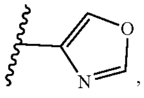

or a pharmaceutically acceptable salt thereof.

Embodiment B8. A compound of formula IVd:

(IVd)

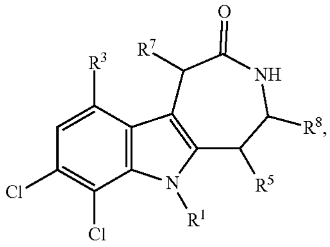

wherein:

$R^1$, $R^7$, and $R^8$ are independently $R^b$;

$R^3$ is —NH—$R^{bb}$—O$R^b$, —NHC(O)—$R^{bb}$—O$R^b$, —NHC(O)—C(O)—$NH_2$, —NH—$R^c$, —NH—C(O)—$R^c$, —O—$R^c$, —O—$CH_2$—$R^c$, —O—$R^{bb}$—C(O)$NH_2$, —O—$R^{bb}$—O$R^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —O—$CH_2$—$R^e$, —NH—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H or —$R^{bb}$—OH;

$R^5$ is H, —$R^{bb}$H, —$R^{bb}$C(O)O$R^b$, —$R^{bb}$C(O)N($R^b$)$_2$, —$R^{bb}$N($R^b$)$_2$, —$R^{bb}$N($R^b$)($R^{bb}CF_3$), —$R^{bb}$O$R^b$, or

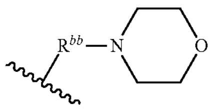

;

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is

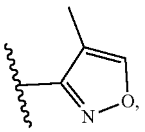 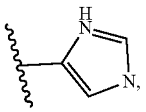 or 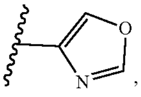

or a pharmaceutically acceptable salt thereof.

Embodiments B3, B4, B6, B7, and B9-B19 are according to embodiments 3, 4, 6, 7, and 9-19 above, respectively, except that the references to embodiments 1, 2, 5, and 8 are each replaced with references to the embodiments B1, B2, B5, and B8, respectively.

Embodiment B20. The compound of any of embodiments B1 to B19, wherein $R^3$ is

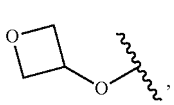

or a pharmaceutically acceptable salt thereof.

Embodiment B21. The compound of any of embodiments B1 to B19, wherein $R^3$ is —O—$CH_2$—$R^c$, or a pharmaceutically acceptable salt thereof.

Embodiment B22. The compound of any of embodiments B1 to B19, wherein $R^3$ is

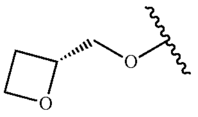

or a pharmaceutically acceptable salt thereof.

Embodiment B23. The compound of any of embodiments B1 to B19, wherein $R^3$ is —O—$(CH_2)_2$—$OCH_3$, or a pharmaceutically acceptable salt thereof.

Embodiment B24 The compound of any of embodiments B1 to B19, wherein $R^3$ is selected from —O—$CH_2$—$R^e$.

Embodiment B25. The compound of any of embodiments B1 to B19, wherein $R^3$ is

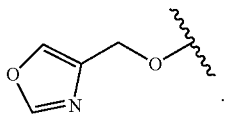 [SMILES: *OCc1cocn1]

.

Embodiment B26. The compound of any of embodiments B1 to B19, wherein $R^3$ is —NH—CO—$CH(CH_3)$—OH.

Embodiment B27. The compound of any of embodiments B1 to B19, wherein $R^3$ is

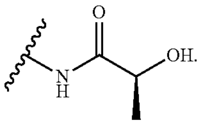 [SMILES: *NC(=O)[C@H](C)O]

Embodiment B28. The compound of any of embodiments B1-B27, wherein $R^8$ is H, or a pharmaceutically acceptable salt thereof.

Embodiment B29. The compound of any of embodiments B1-B27, wherein $R^8$ is methyl, or a pharmaceutically acceptable salt thereof.

Embodiment B30. The compound of any of embodiments 1-B29, wherein $R^1$ is H, or a pharmaceutically acceptable salt thereof.

Embodiment B31. The compound of any of embodiments 1-B29, wherein $R^1$ is methyl, or a pharmaceutically acceptable salt thereof.

Embodiment B32. The compound of any of embodiments 1-B29, wherein $R^1$ is $C_{1-3}$ alkyl substituted with one or more fluoro.

Embodiment B33. The compound of any of embodiments 1-B29, wherein $R^1$ is —$CHF_2$, or a pharmaceutically acceptable salt thereof.

Embodiment B34. The compound of any of embodiments 1-B29, wherein $R^1$ is trifluoroethyl.

Embodiment B35. The compound of any of embodiments 1-B29, wherein $R^1$ is —$CH_2CF_3$.

Embodiment B36. A compound of formula IVe:

(IVe)

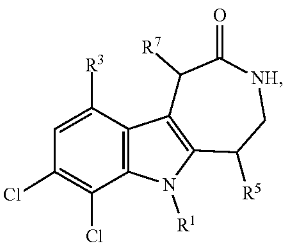

wherein:

$R^1$ is H or $C_{1-3}$ alkyl optionally substituted with one or more fluoro;

$R^5$ is H, —$CH_3$, —$CH_2CH_3$, or —$CH_2CH_2CH_3$;

$R^7$ is H, —$CH_3$, —$CH_2CH_3$, or —$CH_2CH_2CH_3$;

$R^3$ is —NH—$(CH_2)_2$—OH, —NH—$(CH_2)_2$—$O(CH_3)$, —NH—$(CH_2)((CH)(CH_3))$—OH, —NHC(O)—$CH_2$—OH, —NHC(O)—$CH_2$—$O(CH_3)$, —NHC(O)—$CH(CH_3)$—OH, —NH—$(CH_2)(CF_2)(CH_2)$—OH, —NH—$(CH_2)$—$CHF_2$, —NH—$(CH_2)_2$—$CHF_2$, —O—$CH_2$—$C(O)NH_2$, —O—$(CH_2)(CH(CH_3))$—OH, —$O(CH_2)_3$—OH, —$O(CH_2)_2$—$O(CH_3)$, —O—$(CH_2)(CF_2)(CH_2)$—OH, —NH—$(CH_2)(CF_2)(CH_2)$—OH, —$O(CH_2)CH_2F$, —$O(CH_2)_2CH_2F$, —O—$CH_2$—CN, —$NH(CH_2)_3$, —$(CH_2)_3OH$, —$CH_2$—CN,

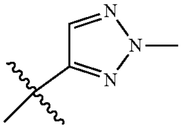
,
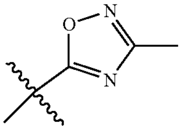
,
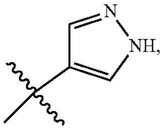
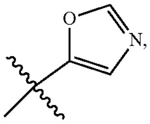
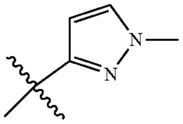
,
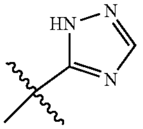
,
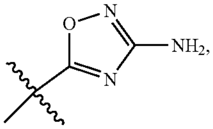
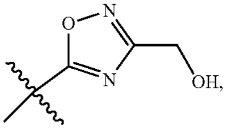
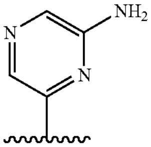
,
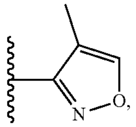
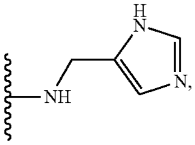
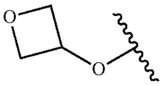
,
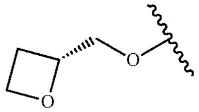
,
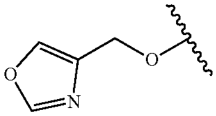
, and
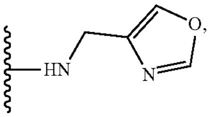

or a pharmaceutically acceptable salt thereof.

Embodiment B37. A compound of formula IVf:

(IVf)

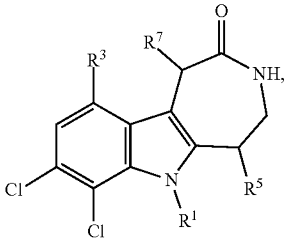

wherein $R^1$, $R^5$, and $R^7$ is each independently H, —$CH_2CF_3$, or —$CHF_2$, and $R^3$ is —NHC(O)—$CH_2$—OH, —O—$(CH_2)_2$—O—$(CH_3)$, —NH—C(O)—$CH(CH_3)$—OH, or

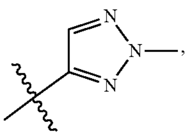 [SMILES: *c1cnn(C)n1]
or a pharmaceutically acceptable salt thereof.
Embodiment B38. The compound of embodiment B1, wherein the compound is selected from:
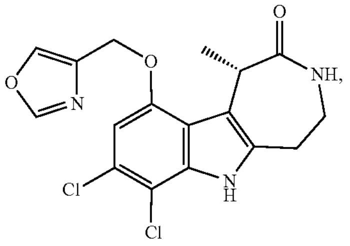
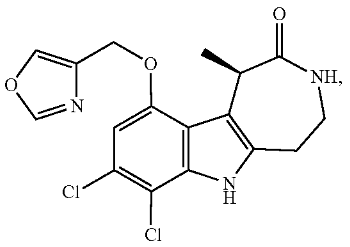
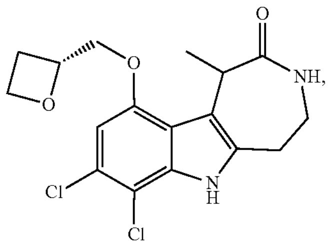
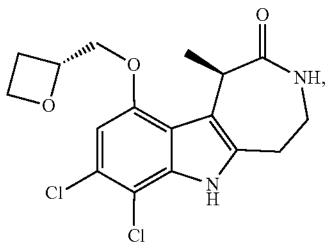
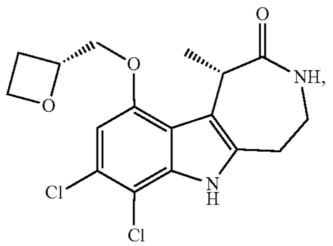
-continued
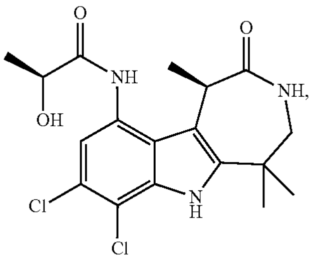
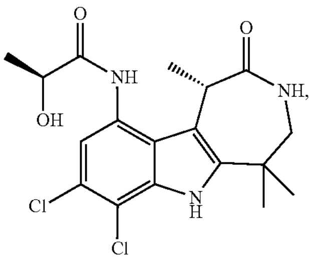
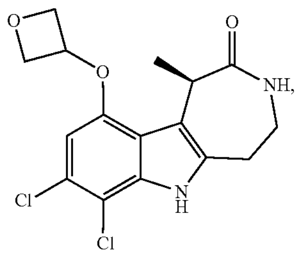
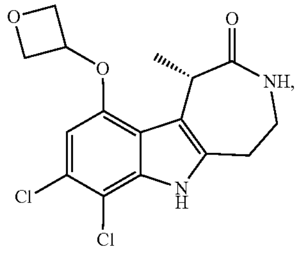
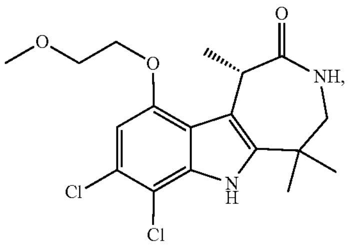
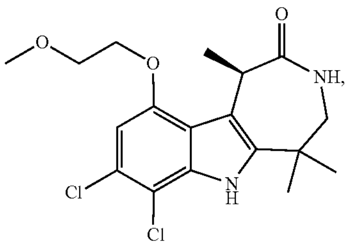

-continued
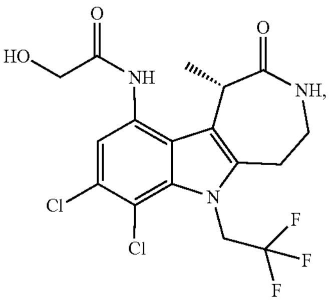
and
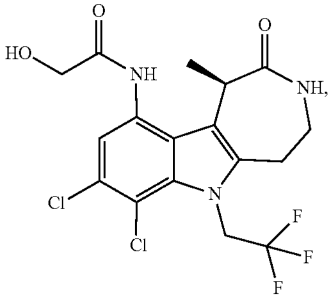 [SMILES: C[C@H]1C(=O)NCCc2c1c1c(NC(=O)CO)cc(Cl)c(Cl)c1n2CC(F)(F)F]
or a pharmaceutically acceptable salt thereof.
Embodiment B39. A compound, selected from:
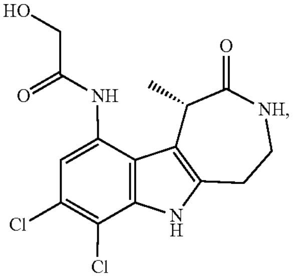
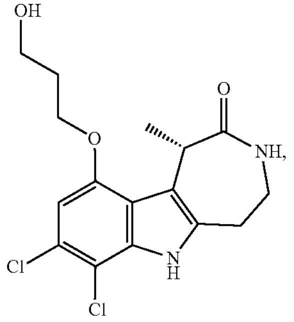
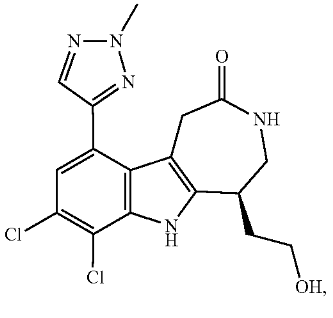
-continued
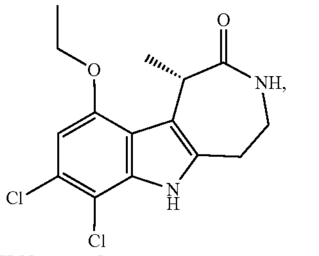
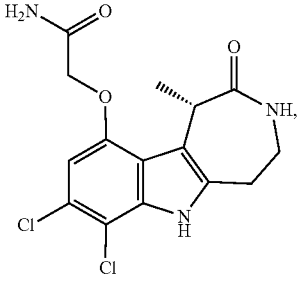
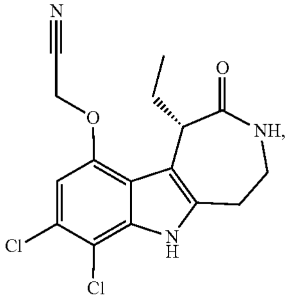
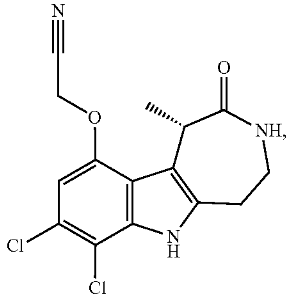
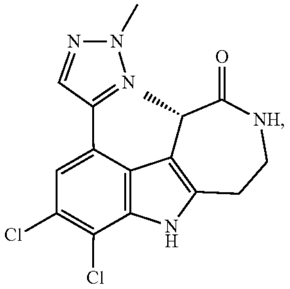
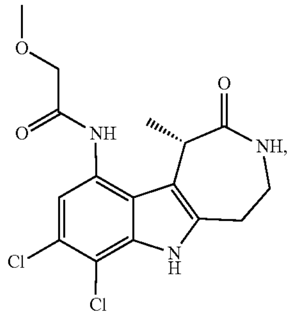
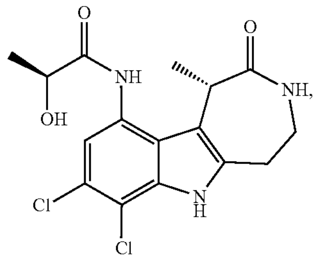
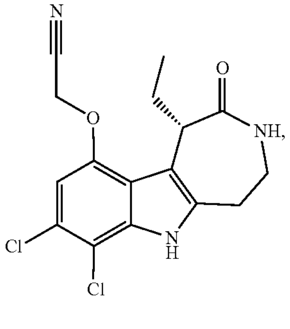
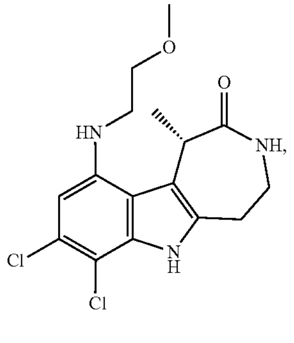

-continued
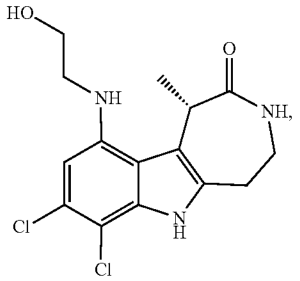
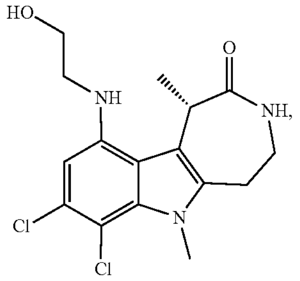
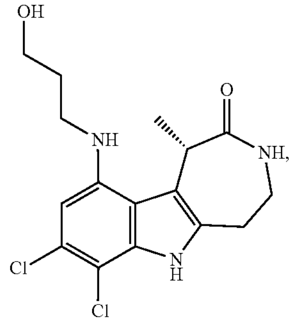
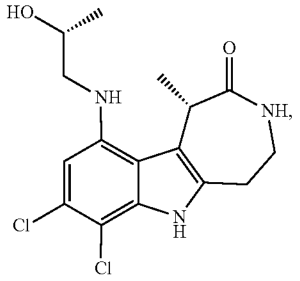
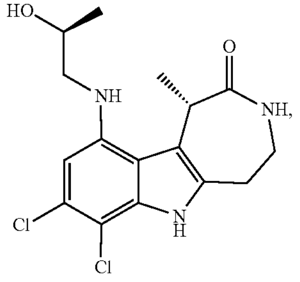
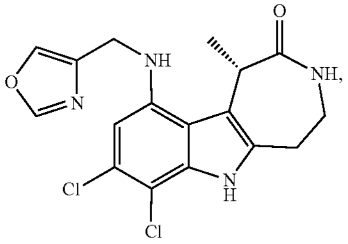
-continued
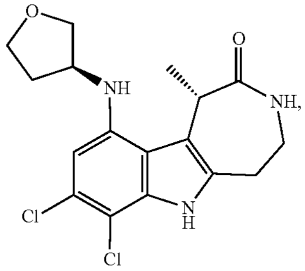
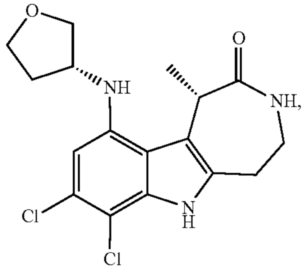
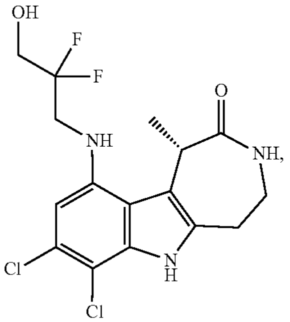
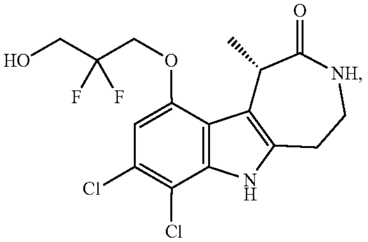
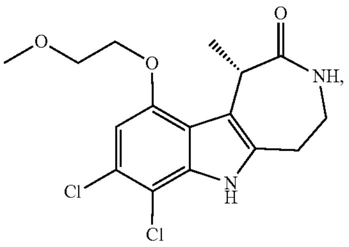
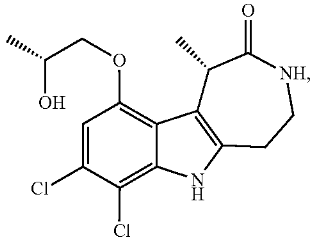

-continued
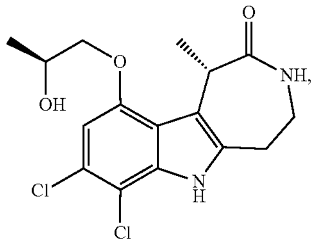
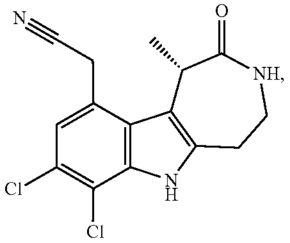
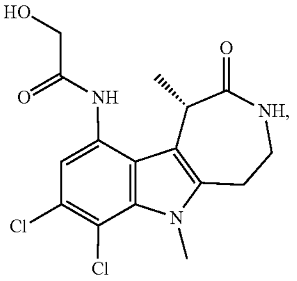
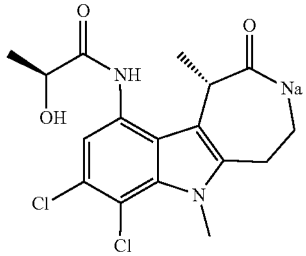
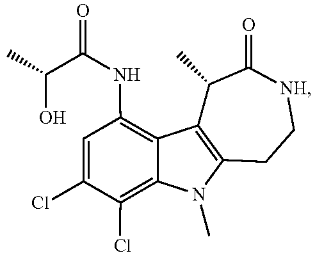
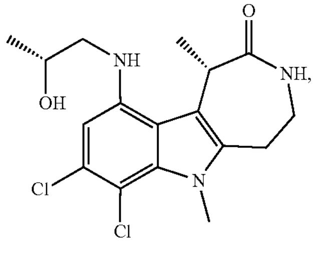
-continued
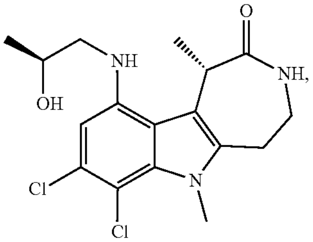
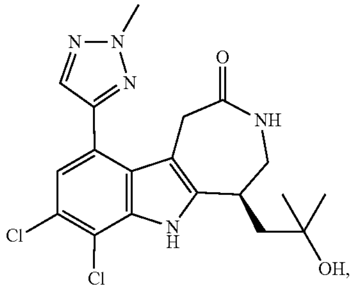
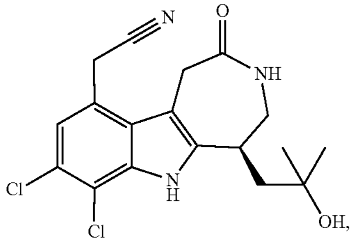
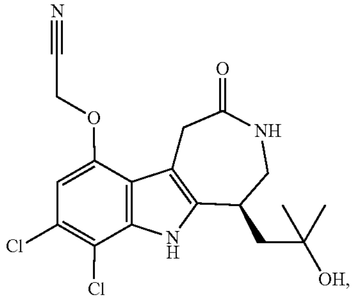
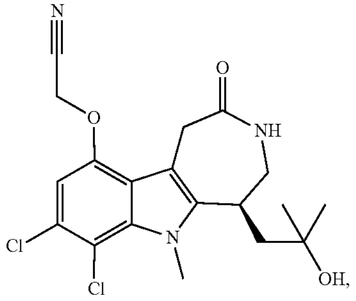
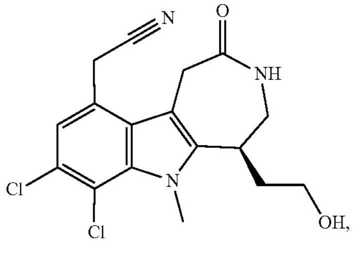

-continued
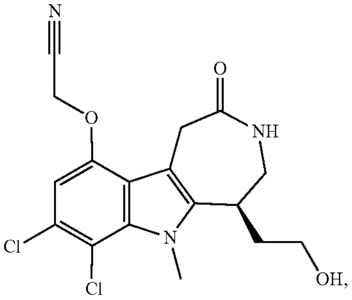
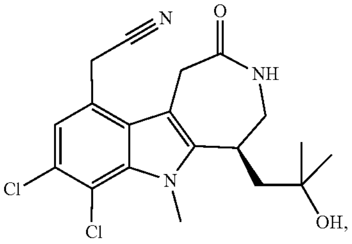
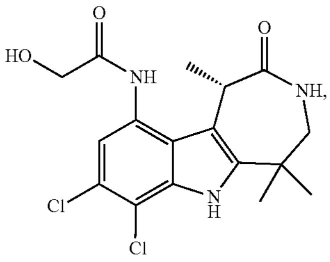
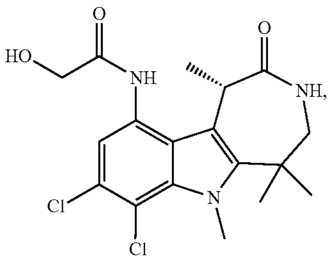
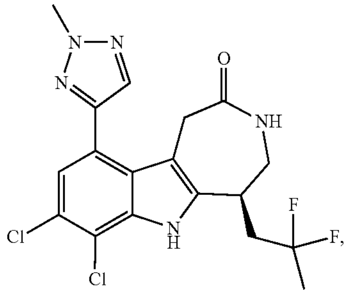
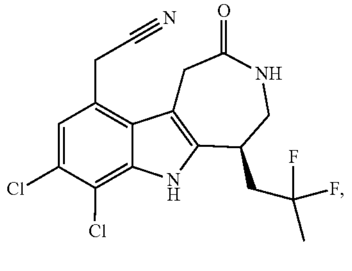
-continued
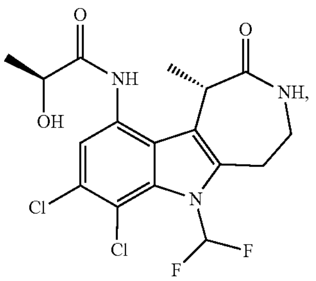
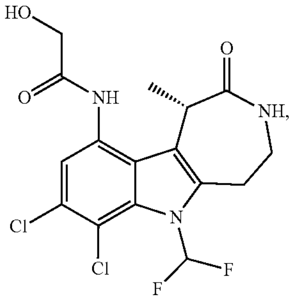
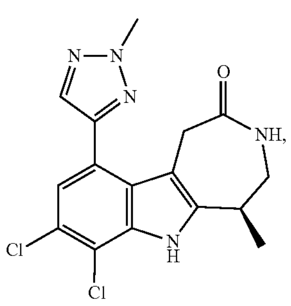
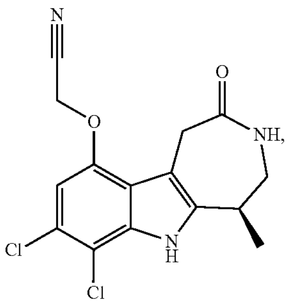
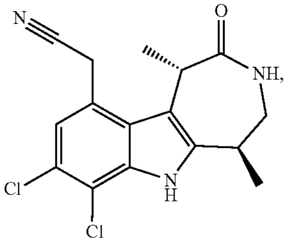
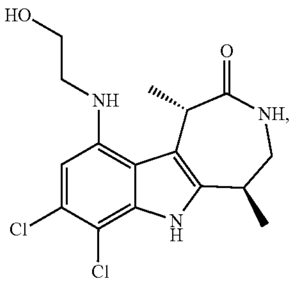
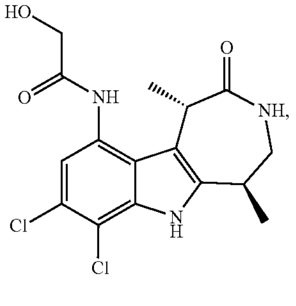

-continued

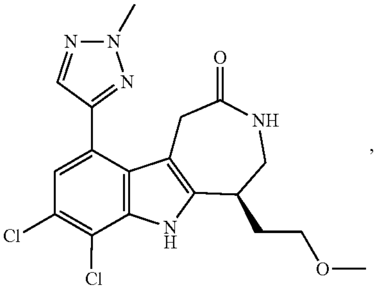

,

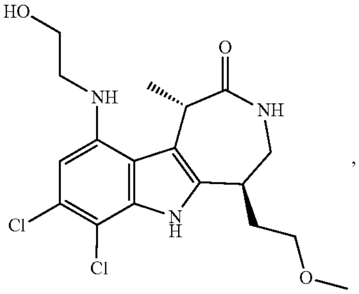

,

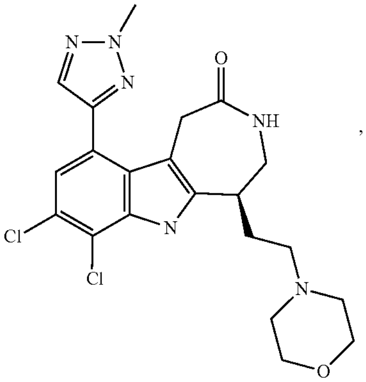

,

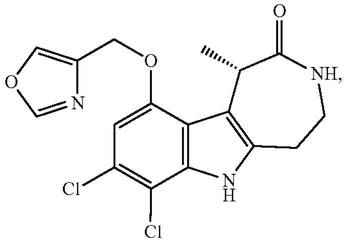

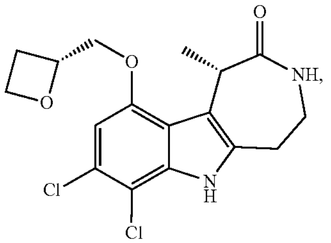

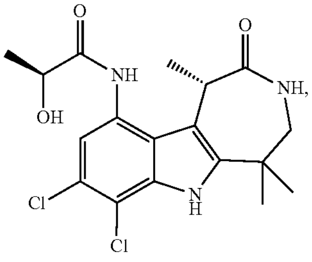

-continued

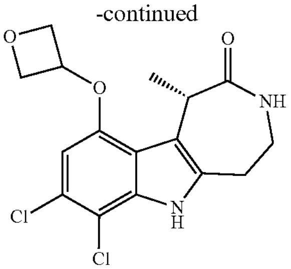

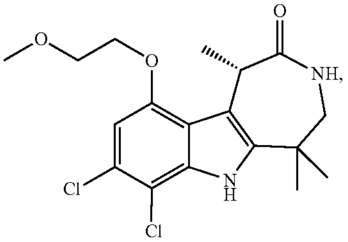

and

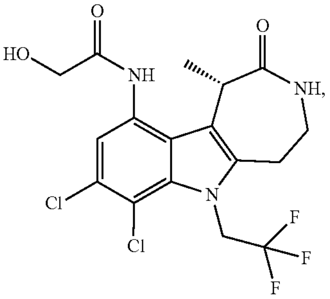

or a pharmaceutically acceptable salt thereof.

Embodiment B40. A pharmaceutical composition, comprising a compound according to any one of embodiments B1 to B39, or a pharmaceutically acceptable salt thereof, with one or more pharmaceutically acceptable carriers, diluents, or excipients.

Embodiments B41 to B59 are omitted. Embodiments B61 to B82 are according to embodiments 60 to 82, respectively, with the exception that the references to embodiments 1 to 59 are replaced with the references to embodiments B1 to B39, and the references to embodiment 60 is replaced with references to embodiment B40.

As used herein, the term "alkyl", used alone or as part of a larger moiety, refers to a saturated, straight, or branched chain hydrocarbon group containing one or more carbon atoms. Alkyl is generally monovalent. For example, "ethyl" can be represented as $CH_3CH_2\cdot$, where the dot represents a radical or dangling bond. The term "alkylene" refers to a bivalent saturated, straight, or branched chain hydrocarbon group that can be regarded as derived from an alkyl by removing an end atom. For example, an "ethylene" can be represented as $\cdot CH_2CH_2\cdot$, and can be regarded as derived from ethyl by removing a hydrogen atom from an end of the ethyl group. As used herein, the term "propyl" includes n-propyl and isopropyl. Likewise, the term "propylene" includes n-propylene ($\cdot CH_2CH_2CH_2\cdot$) and isopropylene ($\cdot CH_2CH(CH_3)\cdot$).

The term "alkyl" and "alkylene" may be preceded with a designation of number of carbon atoms in the main carbon chain of the moiety. For example, "$C_{1-3}$ alkyl" refers to alkyl having 1 to 3 carbon atoms in the main chain. Moreover, "$C_{1-3}$ alkylene" refers to alkylene having 1 to 3 carbon atoms on the main chain between the two radicals or dangling bonds. That is, the designation of number of carbon atoms does not consider substituents. As such, a "substituted" $C_{1-3}$ alkylene may include more carbon atoms when the substitution is alkyl. For example, an R group of $C_3$ alkylene substituted with a methyl includes a total of 4 carbon atoms in the R group.

As used herein, the term "halo" refers to halogen as a substituent, and specifically chloro, fluoro, bromo, or iodo.

As used herein, the term "heteroaryl", unless specified, refers to groups having 5 to 10 ring atoms, preferably 5, 6, 9, or 10 ring atoms, having 6, 10, or 14 it-electrons shared in a cyclic array, and having heteroatoms. The term "heteroatom" refers to nitrogen, oxygen, or sulfur, and includes any oxidized form of nitrogen or sulfur, and any quaternized form of a basic nitrogen.

As used herein, the term "heterocyclic ring" or "heterocycle" refers to an optionally substituted saturated ring system containing at least two carbon atoms and at least one heteroatom. Exemplary heteroatoms are oxygen, nitrogen, and sulfur. Exemplary heterocyclic rings or heterocycles include oxirane, aziridine, oxetane, oxolane, pyrrolidine, piperidine and morpholine. As used herein, the phrase "heterocycle of" followed with the name of a heteroatom refers to a heterocycle including that specified heteroatom alone and no other heteroatom. In other words, the ring system contains carbon atoms and at least one of the specified heteroatom, but no other ring atom. For example, a "heterocycle of oxygen" encompasses oxirane, oxolane, dioxolane, among others, but does not encompass oxathiolane, morpholine, thiomorpholine, or the like.

As used herein, the term "solvate" refers to a type of compound that includes a solvent molecule bound by non-covalent intermolecular forces. The solvate can be that of a disclosed compound or that of a pharmaceutically acceptable salt thereof. The solvate is a "hydrate" when the solvent molecule is water. The solvate may be stoichiometric or non-stoichiometric. Pharmaceutically acceptable solvates may include 1 to about 10, or one to 2, 3 or 4, solvent molecules.

As used herein, the term "stereoisomer" refers to an isomer made up of the same atoms bonded by the same bonds but having different and non-interchangeable structures in the three-dimensional space. The term of stereoisomer includes "enantiomer" which refers to two stereoisomers that are mirror images of one another and are not superimposable over one another. A one-to-one mixture of a pair of enantiomers is referred to as a "racemic" mixture. The term of stereoisomer also includes "diastereoisomers" (or "diastereomer") which refers to two stereoisomers that have at least two asymmetric atoms, but which are not mirror-images of each other. The absolute stereochemistry of a stereoisomer may be specified according to the Cahn-Ingold Prelog R S system, where the stereochemistry at each chiral center is designated as either R or S. When stereoisomers are resolved yet whose absolute configuration is unknown, those stereocenters are designated (+) or (−) depending on the direction (dextro- or laevorotatory) that they rotate the plane of polarization at the wavelength of the sodium D line. In structural illustrations, plain lines (——) depict bonds approximately in the plane of the drawing; bonds to atoms above the plane are shown with a bold wedge (▬) starting from an atom in the plane of the drawing at the narrow end of the wedge; and bonds to atoms below the plane are shown with a hashed wedge of short parallel lines (▬) starting from an atom in the plane of the drawing at the narrow end of the hashed wedge. For compounds having a stereocenter where all bonds connected to the stereocenter are structurally represented with plain lines (——), or the compounds are represented with chemical nomenclature without a stereoisomer designation, they shall be construed to mean any of the possible stereoisomers, a racemic mixture thereof, or a mixture with one or more stereoisomers enriched relative to others, unless explicitly stated otherwise. In other words, for any compound disclosed here that includes a stereocenter to which all bonds connected are illustrated in plain lines, the disclosure contemplates each and every possible stereoisomer thereof, as well as any mixture of those stereoisomers.

The term stereoisomer also includes "geometric isomers" such as "cis-trans isomer". These are isomers where arrangements of groups around a double bond or a ring differ from one another despite the same molecular formula. The term of stereoisomer may further include "rotational isomers" or "rotamers" which is defined as stereoisomers that arise from hindered single-bond rotation. For simplicity, the term "stereoisomer" is used here interchangeable with the term "isomer". Unless explicitly stated otherwise (such as by referencing the retention time for the specified separation condition), "isomer 1" refers to the stereoisomer that eludes out first from the column during separation (e.g. a chiral separation of a racemic mixture or a separation of a pair of cis-trans isomers) under a stated separation condition; and "isomer 2" refers to the stereoisomer that eludes out the second during the same separation. An asterisk (*) is used to denote the chiral center (or stereocenter) in the structures for "isomer 1" and "isomer 2". Moreover, when the asterisk is used on a stereocenter to which a bold wedge (▬) or a hashed wedge (▬) is also attached, the solid wedge and hashed wedge represents relative stereochemistry only, and are not designations of absolute stereochemistry. Such representations may be used to convey that absolute stereochemistry at that denoted stereocenter is unknown, or that the pair of enantiomers based on that denoted stereocenter is not separated (i.e., representing a racemic mixture of the enantiomers).

As used herein, the term "patient" refers to a human.

As used herein, the term "treating" includes restraining, slowing, stopping, or reversing the progression or severity of an existing symptom or disorder.

As used herein, the term "effective amount" refers to the amount or dose of compound of the invention, or a pharmaceutically acceptable salt thereof which, upon single or multiple dose administration to the patient, provides the desired effect in the patient under diagnosis or treatment. An effective amount can be determined by one skilled in the art by the use of known techniques. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. The compounds of the present invention are generally effective over a wide dosage range. For example, dosages per day normally fall within the range of about 0.1 to about 15 mg/kg of body weight.

As used herein, the term "immune-mediated disease" encompasses a group of autoimmune or inflammatory disorders in which immunological pathways play an important etiological and/or pathogenetic role. Such diseases are sometimes characterized by an alteration in cellular homeostasis. Immune-mediated diseases may be triggered by environmental factors, dietary habits, infectious agents, and genetic predisposition. Some immune-mediated diseases may be associated with cGAS activation. Immune-mediated disease includes, for example, systemic lupus erythematosus, lupus nephritis, dermatomyositis, and Aicardi-Goutières syndrome. Immune-mediated diseases may also include interferonopathies.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art (See, e.g. Remington: The Science and Practice of Pharmacy, A. Adej are, Editor, 23rd Edition, Elsevier Academic Press, 2020).

The compounds of the present invention, or pharmaceutically acceptable salts thereof, may be prepared according to the following Preparations and Examples by methods well known and appreciated in the art. Suitable reaction conditions for the steps of these Preparations and Examples are well known in the art and appropriate substitutions of solvents and co-reagents are within the skill of the art. Likewise, it will be appreciated by those skilled in the art that synthetic intermediates may be isolated and/or purified by various well-known techniques as needed or desired, and that frequently, it will be possible to use various intermediates directly in subsequent synthetic steps with little or no purification. As an illustration, compounds of the preparations and examples can be isolated, for example, by silica gel purification, isolated directly by filtration, or crystallization. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, and is well appreciated by the skilled chemist. All substituents, unless otherwise indicated, are as previously defined, and all reagents are well known and appreciated in the art. Abbreviations used throughout the disclosure are provided in Table 1 below, unless commonly understood.

TABLE 1

Abbreviations and definitions

| Term | Definition |
|---|---|
| ACN | Acetonitrile |
| ATP | Adenosine triphosphate |
| BOC/Boc | tert-Butyloxycarbonyl |
| t-BuONa | Sodium tert-butoxide |
| tert-BuBrettPhos-Pd-G3 | [(2-Di-tert-butylphosphino-3,6-dimethoxy-2',4',6'-triisopropyl-1,1'-biphenyl)-2-(2'-amino-1,1'-biphenyl)]palladium(II) methanesulfonate |
| cGAMP | Cyclic guanosine monophosphate-adenosine monophosphate |
| DCM | Dichloromethane |
| DIBAL-H | Diisobutylaluminum hydride |
| DIPEA | N,N-Diisopropylethylamine |
| DMEA | Dimethylethylamine |
| DMF | N,N-Dimethylformamide |
| DMSO | Dimethyl sulfoxide |
| DMAP | 4-Dimethylaminopyridine |
| DMPU | N,N'-Dimethylpropyleneurea |
| DTT | Dithiothreitol |
| ES/MS | Electrospray mass spectrometry |
| $Et_2O$ | Diethyl ether |
| $Et_3N$ | Triethylamine |
| EtOAc | Ethyl acetate |
| EtOH | Ethanol |

TABLE 1-continued

Abbreviations and definitions

| Term | Definition |
|---|---|
| GTP | Guanosine-5'-triphosphate |
| HPLC | High performance liquid chromatography |
| hr(s) | Hour/hours |
| iPrOH | Isopropyl alcohol |
| IPTG | Isopropyl β-D-1-thiogalactopyranoside |
| LC | Liquid chromatography |
| LCMS | Liquid chromatography mass spectrometry |
| LDA | Lithium diisopropylamide |
| MeOH | Methanol |
| min | Minute(s) |
| MS | Mass spectrometry |
| MTBE | Methyl tert-butyl ether |
| NBS | N-Bromosuccinimide |
| NIS | N-Iodosuccinimide |
| NMO | N-Methylmorpholine N-oxide |
| NMR | Nuclear magnetic resonance |
| $Pd_2(dba)_3$ | Tris(dibenzylideneacetone)dipalladium(0) |
| $Pd(dppf)Cl_2$ | [1,1'-Bis(diphenylphosphino)ferrocene] dichloropalladium(II) |
| PE | Petroleum Ether |
| RT | Retention time |
| SEM- | 2-(Trimethylsilyl)ethoxymethyl |
| SFC | Supercritical fluid chromatography |
| SCX | Strong Cation Exchange |
| TBAF | Tetra-n-butylammonium Fluoride |
| TBTU | 2-(1H-Benzotriazole-1-yl)-1,1,3,3-tetramethyluronium tetrafluorobora |
| TFA | Trifluoroacetic acid |
| THF | Tetrahydrofuran |
| TosMIC | Toluenesulfonylmethyl isocyanide |
| Triton X-100 | 2-[4-(2,4,4-trimethylpentan-2-yl)phenoxy] ethanol |
| TsCl | 4-Toluenesulfonyl chloride |
| Xantphos | (9,9-Dimethyl-9H-xanthene-4,5-diyl)bis (diphenylphosphane) |
| XantPhos-Pd-G2 | Chloro[(4,5-bis(diphenylphosphino)-9,9-dimethylxanthene)-2-(2'-amino-1,1'-biphenyl)] palladium(II) |

Scheme 1. General Scheme for the Preparation of Boronic Acid Pinacol Ester 2

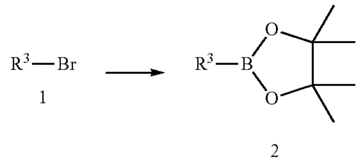

Scheme 1 depicts a general scheme for the synthesis of boronic acid pinacol ester. The synthesis of boronic acid pinacol ester compound 2 is carried out via a catalysed (e.g. with $Pd(dppf)Cl_2$ as the catalyst) cross-coupling reaction of bis(pinacolato)diboron with aryl bromo compound 1 in suitable conditions (e.g. 1,4-dioxane as solvent, potassium acetate as a base). The mixture is then agitated at a suitable temperature (e.g., 60~105° C.) for several minutes until the reaction completes. The reaction progress can be monitored, for example, with thin layer chromatography (TLC) or other suitable methods. The reaction mixture is concentrated and purified (e.g. via silica gel chromatography) to give pinacol ester compound 2.

Scheme 2. General Scheme for the Preparation of Compound 4.

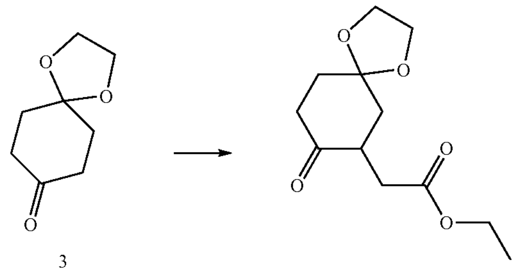

3 4

Scheme 2 depicts a scheme for the synthesis of intermediate compound 4. The synthesis of 4 starts by treating 1,4-dioxaspiro[4.5]decan-8-one (3) with a base, such as, LDA at low temperature in a suitable solvent (e.g. THF) and allowing the resulting intermediate (e.g. enolate) to react with a suitable reagent (e.g. ethyl bromoacetate). The mixture is then stirred for several minutes until the reaction completes. The reaction progress can be monitored, for example, with thin layer chromatography (TLC) or other suitable methods. The reaction mixture is concentrated and purified (e.g. via silica gel chromatography) to give intermediate compound 4.

Scheme 3. General Scheme for Synthesis of the Compound of Formula 1s

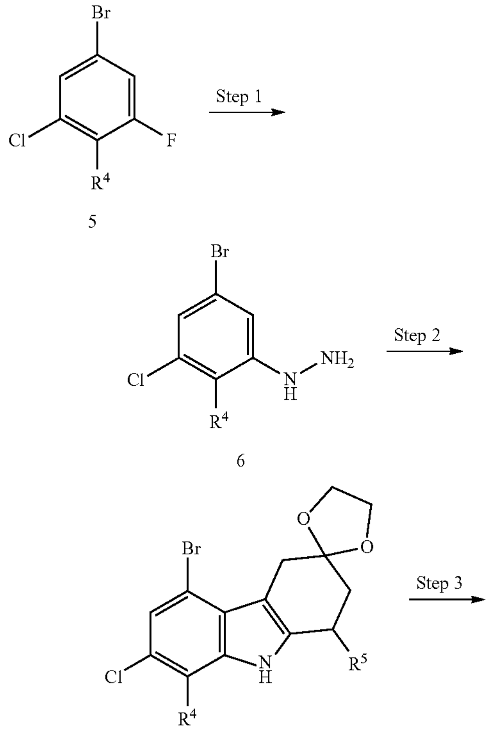

5 6 7

-continued

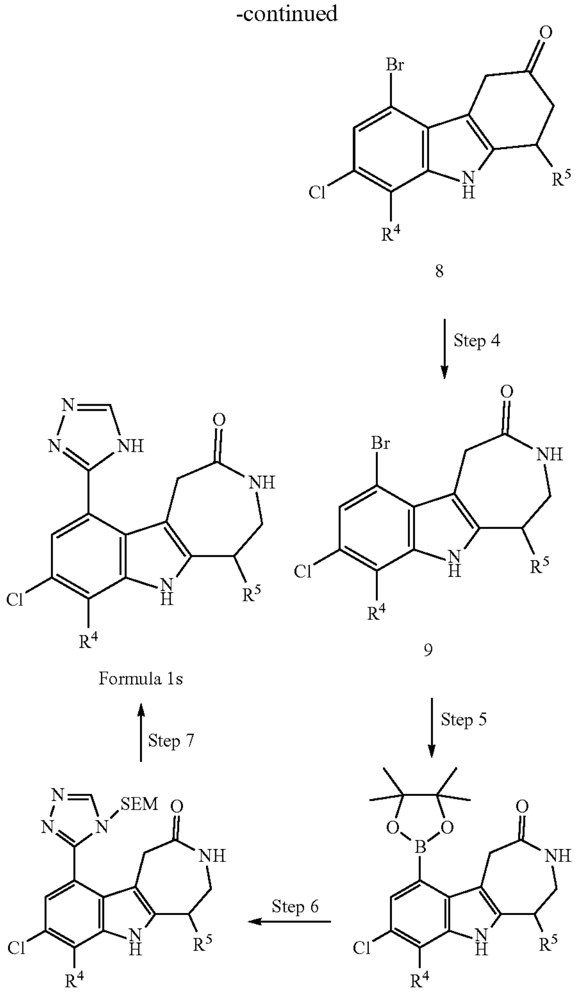

8 9 Formula 1s 9b 9a

Scheme 3 depicts a general scheme for the synthesis of compound of Formula 1s and the intermediates thereof. In step 1, a fluoro-bearing compound 5 is contacted with hydrazine under conditions sufficient to provide intermediate compound 6. For example, a solution of compound 5 under $N_2$ in a suitable solvent (e.g., DMSO) is heated with hydrazine hydrate at a suitable temperature (e.g., 70-80° C.) for several hours until the reaction completes. The reaction is quenched (e.g., with water), extracted with a suitable solvent (e.g., EtOAc), dried (e.g., over anhydrous sodium sulfate), concentrated under reduced pressure, and purified (e.g., via silica gel chromatography) to give intermediate compound 6.

In step 2, compound 6 is contacted with 1,4-dioxaspiro[4.5]decan-8-one under conditions sufficient to provide compound 7. For example, a solution of compound 6 in a suitable solvent (e.g., toluene) and a suitable catalyst (e.g., zinc chloride) is heated to a suitable temperature (e.g., 110-130° C.) for several hours, and then cooled to ambient temperature. The reaction is extracted with a suitable solvent (e.g., EtOAc), dried (e.g., over anhydrous sodium sulfate), concentrated under reduced pressure, and purified (e.g., via silica gel chromatography) to give compound 7.

In step 3, compound 7 is converted under conditions sufficient to provide compound 8. For example, compound 7 is dissolved in a suitable solvent (e.g., acetone) and treated with an appropriate acid (e.g., TFA) and heated at a suitable temperature (e.g., 60-80° C.) for several hours until the reaction completes. The reaction mixture is triturated from a suitable solvent (e.g., MTBE/EtOAc) and concentrated under reduced pressure to give intermediate compound 8.

In step 4, compound 8 is contacted with an azide compound under conditions sufficient (e.g., Schmidt reaction condition) to provide compound 9. For example, compound 8 is cooled and dissolved in a suitable solvent (e.g., methanesulfonic acid), treated with an azide (e.g., sodium azide), and warmed to ambient temperature for a few minutes. The reaction mixture is quenched by the addition of the reaction mixture to a suitable aqueous base (e.g., aqueous sodium bicarbonate). The solids are collected by suction filtration, washed, dried, and purified (e.g., via silica gel chromatography) to give compound 9. Alternatively, the quenched reaction mixture is extracted with a suitable solvent (e.g., EtOAc), dried (e.g., over anhydrous sodium sulfate), concentrated under reduced pressure, and purified (e.g., via silica gel chromatography) to give compound 9.

In step 5, compound 9 is converted under sufficient reaction conditions to provide a boronic acid pinacol ester compound 9a. For example, an aryl bromide compound 9 is reacted with bis(pinacolato)diboron, under suitable conditions (e.g., $Pd(dppf)Cl_2$ catalyst, solvent such as 1,4-dioxane or DMF, and an appropriate base such as potassium acetate) and heated for several hours under suitable temperature (e.g., 60 to 105° C.) to give intermediate compound 9a.

In step 6, compound 9a is contacted with a protected triazole compound under conditions sufficient to provide compound 9b. For example, compound 9a is heated with 3-bromo-1-((2-(trimethyl silyl)ethoxy)methyl)-1H-1,2,4-triazole in a suitable solvent (such as 1,4-dioxane and water), in presence of $Pd(dppf)Cl_2$ and an appropriate base (such as potassium carbonate or sodium carbonate) at suitable temperature (e.g., 60 to 105° C.) for several hours until completion. The reaction mixture is cooled to ambient temperature, filtered, and rinsed through silica. The filtrate is concentrated under reduced pressure, purified (e.g., by silica gel flash chromatography) to give intermediate compound 9b.

In step 7, compound 9b is deprotected under conditions sufficient (e.g., using an acid such as TFA in a solvent such as DCM at ambient temperature) to give the compound of Formula 1s.

Scheme 3'. General Scheme for Synthesis of the Compound of Formula 9'

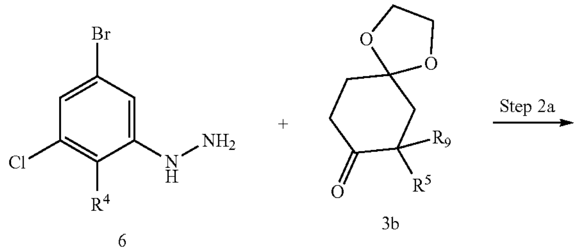

6

3b

-continued

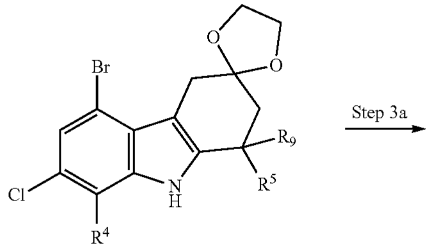

7'

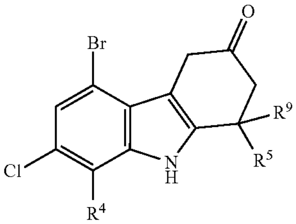

8'

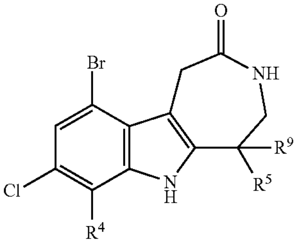

9'

Scheme 3' depicts a general scheme for the synthesis of compound of Formula 9' and the intermediates thereof. In step 2a, compound 6 is contacted with compound 3b, 1,4-dioxaspiro[4.5]decan-8-one substituted with $R^5$ and/or $R^9$, under conditions sufficient to provide compound 7'. For example, a solution of compound 6 in a suitable solvent (e.g., toluene or xylenes) and a suitable catalyst (e.g., zinc chloride) is heated to a suitable temperature (e.g., 110-130° C.) for several hours, and then cooled to ambient temperature. The reaction is extracted with a suitable solvent (e.g., EtOAc), dried (e.g., over anhydrous sodium sulfate), concentrated under reduced pressure, and purified (e.g., via silica gel chromatography) to give compound 7'. Steps 3a and 4a are performed according to Scheme 3 above to provide the compound of Formula 9'.

Scheme 3'a. General Scheme for Synthesis of the Compound of Formula 8

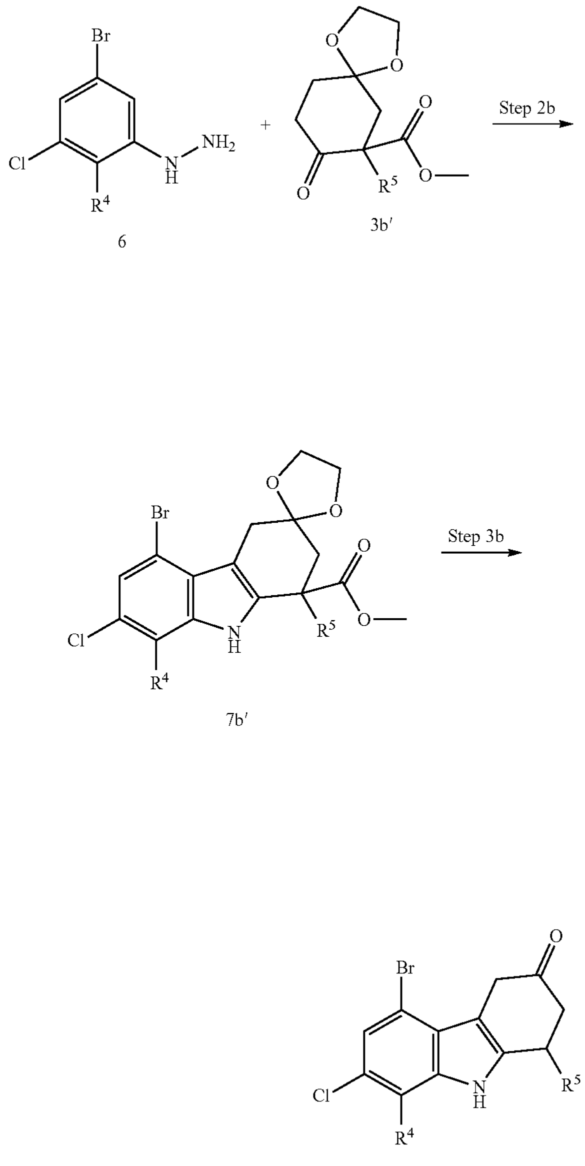

6 3b' 7b' 8

Scheme 3'a depicts a general scheme for the synthesis of compound of Formula 8 and the intermediates thereof. In step 2b, compound 6 is contacted with compound 3b', 1,4-dioxaspiro[4.5]decan-8-one substituted with $R^5$ and an alkyl carboxylate, under conditions sufficient to provide compound 7b'. For example, a solution of compound 6 in a suitable solvent (e.g., MeOH) and acetic acid is heated to reflux for a few hours to provide a hydrazone compound. The hydrazone compound is then contacted with a suitable catalyst (e.g., zinc chloride) to provide the compound 7b'. In step 3b, the compound 7b' is hydrolyzed under sufficient conditions, such as in presence of sodium hydroxide, and subsequently acidified to form a carboxylic acid compound. The carboxylic acid compound is contacted with a suitable acid (e.g. acetic acid) and heated under conditions sufficient to provide the compound 8.

Scheme 3". General Scheme for Synthesis of the compound of Formula 1s'

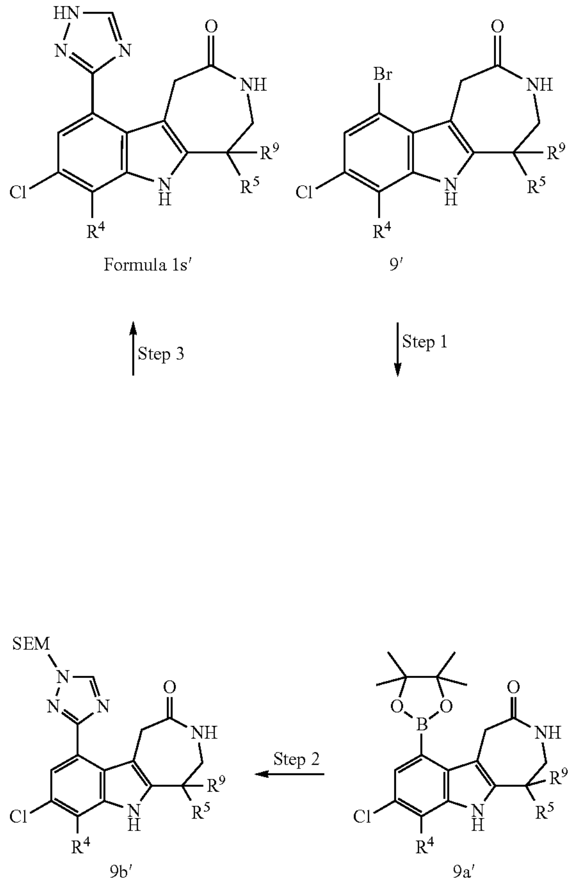

Formula 1s' 9' 9b' 9a'

Scheme 3" depicts a general scheme for the synthesis of compound of Formula 1s' and the intermediates thereof. In step 1, compound 9' is converted under sufficient reaction conditions to provide a boronic acid pinacol ester compound 9a'. For example, an aryl bromide is reacted with bis (pinacolato)diboron, under suitable conditions (e.g., $Pd(dppf)Cl_2$ catalyst, solvent such as 1,4-dioxane, and an appropriate base such as potassium acetate) and heated for several hours under suitable temperature (e.g., 60 to 105° C.) to form pinacol ester 9a'.

In step 2, a Suzuki reaction is shown where compound 9a' is contacted with a protected triazole compound under conditions sufficient to provide compound 9b'. For example, compound 9a' is heated with 3-bromo-1-((2-(trimethylsilyl) ethoxy)methyl)-1H-1,2,4-triazole in a suitable solvent (e.g., 1,4-dioxane and water), in presence of $Pd(dppf)Cl_2$ and an appropriate base (e.g., potassium carbonate or sodium carbonate) at suitable temperature (e.g., 60 to 105° C.) for several hours until completion. The reaction mixture is cooled to ambient temperature, filtered, and rinsed through silica. The filtrate is concentrated under reduced pressure, purified (e.g., by silica gel flash chromatography) to give intermediate compound 9b'.

In step 3, compound 9b' is deprotected under conditions sufficient (e.g., using an acid such as TFA in a solvent such as DCM at ambient temperature) to give the compound of Formula 1s'.

Scheme 4. General Scheme for Synthesis of the Compounds of Formula 1b-1d

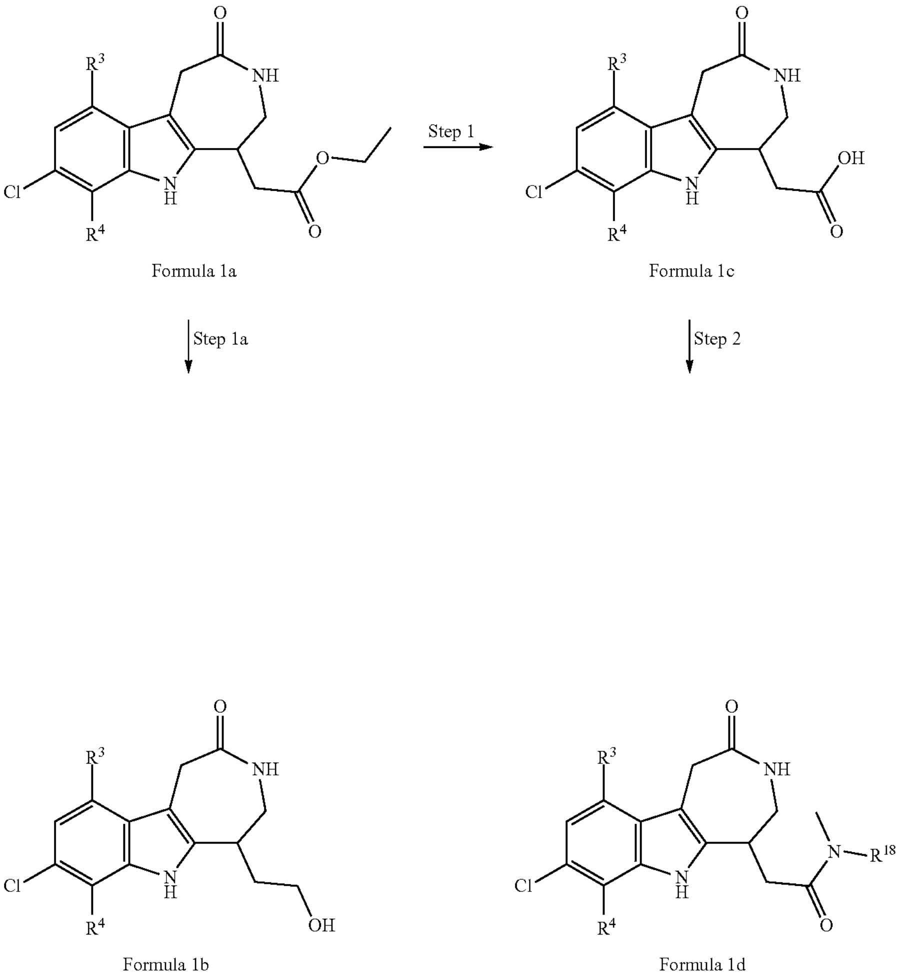

Scheme 4 depicts a general scheme for the synthesis of compounds of Formula 1a, Formula 1b, Formula 1c, and Formula 1d.

In step 1, the compound of Formula 1a is hydrolyzed under conditions sufficient to provide compound of Formula 1c. For example, a solution of compound of Formula 1a in a suitable solvent (e. g. a mixture of THF and MeOH) is treated with an appropriate base (e.g., NaOH). The mixture is stirred at ambient temperature, and an appropriate acid (e.g. HCl) is added. The reaction mixture is diluted with an appropriate solvent and the organic layer extracted. The organics are dried (e.g. over sodium sulfate), filtered, and concentrated under reduced pressure. The residue is dissolved in a solvent (e.g. DCM), and dried under reduced pressure to give the compound of Formula 1c.

In step 2, the compound of Formula 1c is contacted with a suitable amine under conditions sufficient to provide a compound of Formula 1d. For example, the compound of Formula 1c in a suitable solvent (e.g. DMF), an amide-coupling reagent (e.g. 2,4,6-triisopropyl-1,3,5,2,4,6-trioxatriphosphorinane-2,4,6-trioxide in EtOAc), and an amine (e.g. methylamine or dimethylamine) are mixed and stirred at ambient temperature for several hours. The reaction mixture is diluted with saturated aqueous sodium bicarbonate, and the layers separated. The organic layer is washed with water and then with saturated aqueous NaCl, dried (e.g. over anhydrous sodium sulfate), filtered, concentrated under reduced pressure, and purified (e.g. via silica gel flash chromatography) to give the compound of Formula 1d.

Alternatively, in step 1a, a solution of the compound of Formula 1a is contacted with a suitable reducing agent to provide the compound of Formula 1b. For example, the compound of Formula 1a is cooled in an appropriate solvent (e.g. DCM). A reducing agent (e.g. DIBAL-H) is added and the reaction mixture warmed to ambient temperature. The mixture is then cooled and quenched with an appropriate solvent (e.g. EtOAc). The mixture is warmed to ambient temperature and diluted with suitable solvents. The layers are separated, the aqueous layer extracted with a suitable solvent (e.g. DCM), and the combined organic layers are dried (e.g. over anhydrous sodium sulfate), filtered, concentrated under reduced pressure, and purified (e.g. via silica gel flash chromatography) to give the compound of Formula 1b.

Scheme 4'. General Scheme for Synthesis of the Compounds of Formula 1a, Formula 1b, Formula 1b-i, Formula 1c, Formula 1c-i, Formula 1c-ii, Formula 1c-iii, and Formula 1d

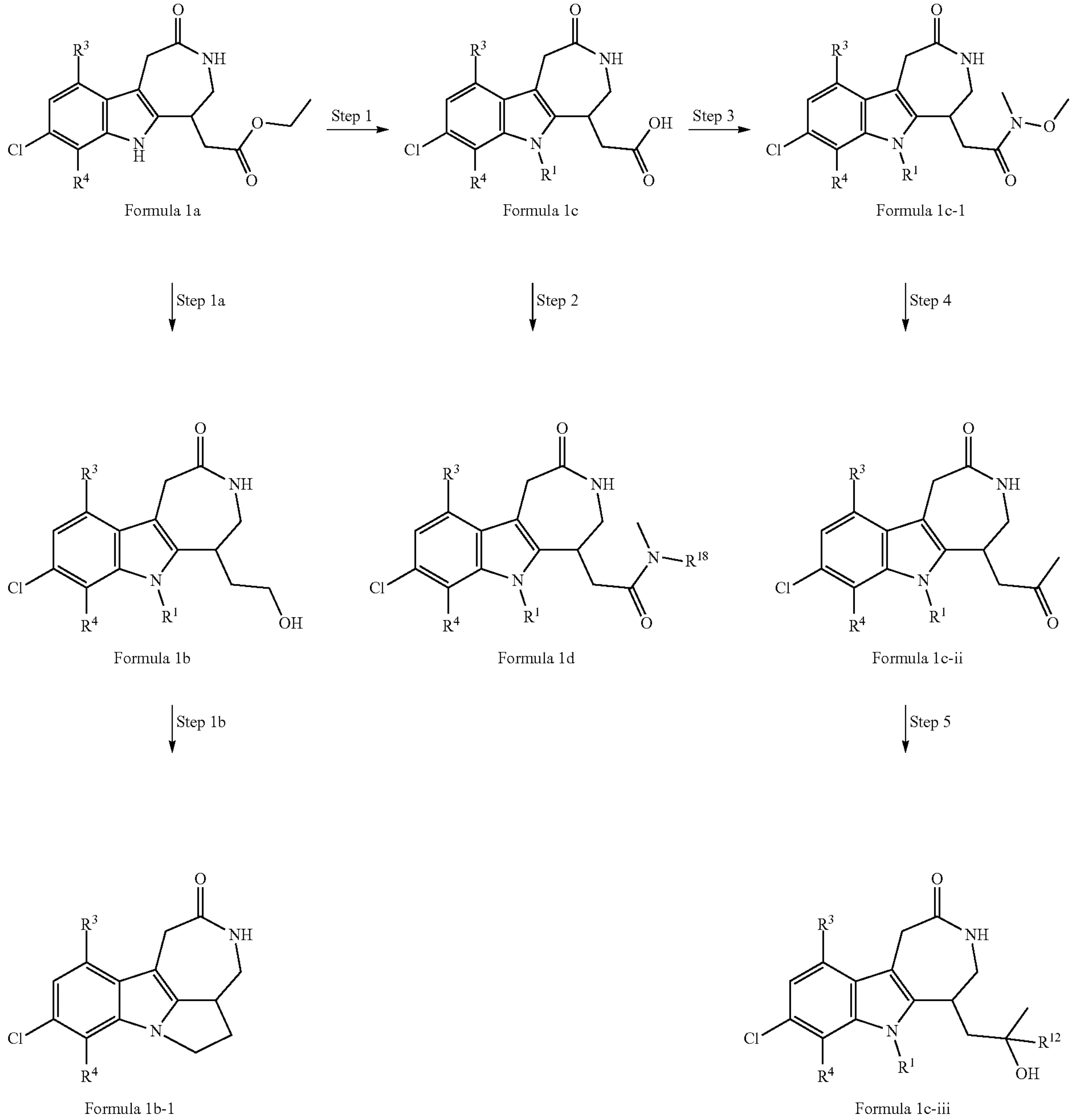

Formula 1a, Formula 1c, Formula 1c-1, Formula 1b, Formula 1d, Formula 1c-ii, Formula 1b-1, Formula 1c-iii Scheme 4' depicts a general scheme for the synthesis of compounds of Formula 1b-i, Formula 1c-i, Formula 1c-ii, and Formula 1c-iii, where $R^{12}$ and $R^{18}$ are each methyl or H.

Steps 1 and 2 are performed according to Scheme 4 above. Step 3 shows a Weinreb amide formation reaction in which compound of Formula 1c is reacted with N,O-dimethylhydroxylamine hydrochloride, in the presence of a coupling reagent such as HATU, a solvent such as DMF, and a base such as DIPEA and at a suitable temperature, such as at about 25° C. to give compound of Formula 1c-i.

Step 4 shows a Weinreb ketone synthesis reaction in which compound of Formula 1c-i is reacted with an organomagnesium such as MeMgBr, in the presence of a solvent such as THF, and at a suitable temperature to give compound of Formula 1c-ii.

Step 5 shows a ketone reduction reaction in which compound of Formula 1c-ii is reacted with $NaBH_4$ in the presence of a solvent such as MeOH at a suitable temperature, such as about 20° C. to give compound of Formula 1c-iii.

Step 1a can be performed according to Scheme 4 above. Step 1b shows cyclization of Formula 1b in a Mitsunobu reaction to give the compound of Formula 1b-i. The reaction is carried out in the presence of a reagent such as diisopropyl azodicarboxylate, a catalyst such as triphenylphosphine, in the presence of a solvent such as THF, and at a suitable temperature, preferably at 0° C.

Scheme 5. General Scheme for Synthesis of Compound 12 and Compound of Formula 1e

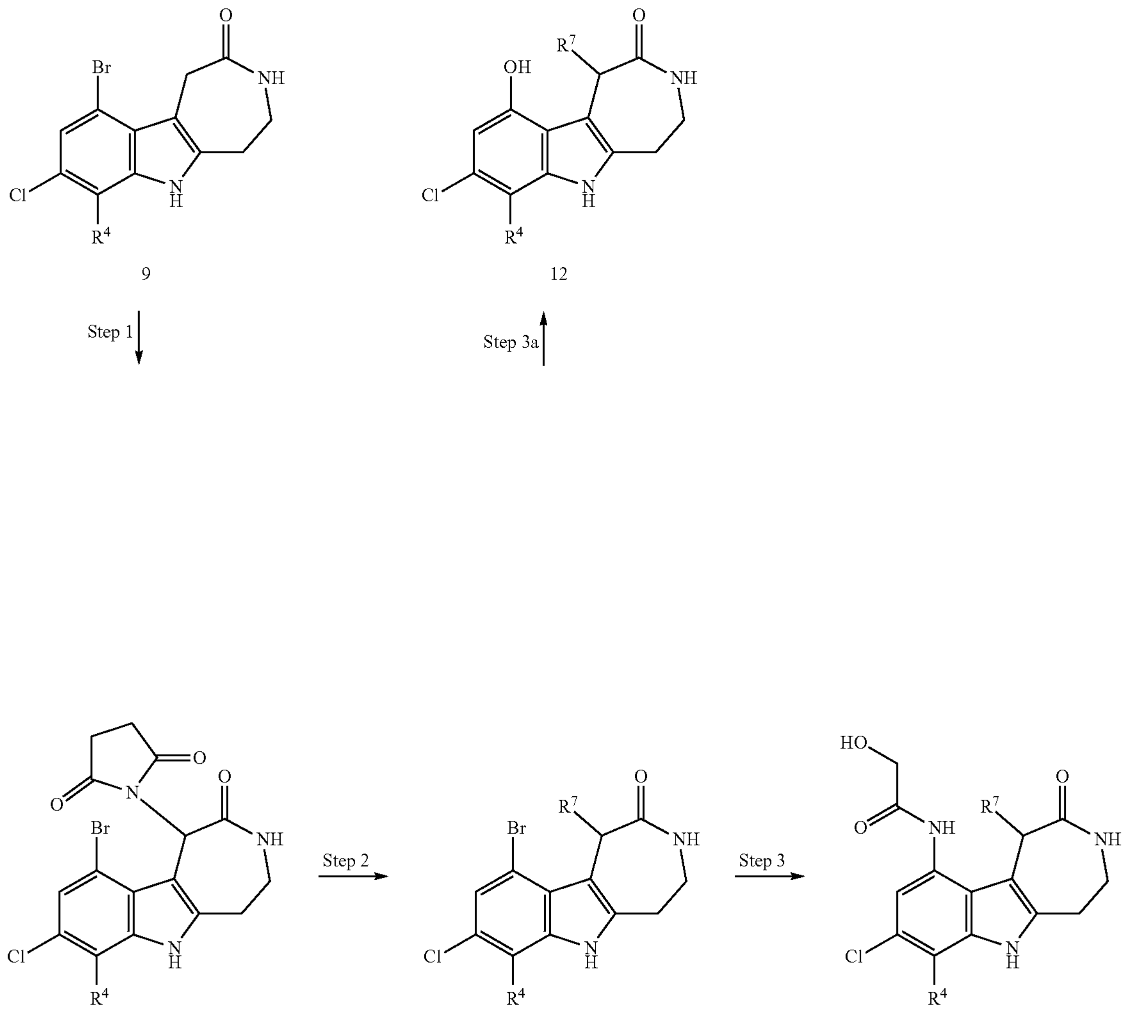

9, 12, 10, 11, Formula 1e

Scheme 5 depicts a general scheme for the synthesis of Compound 12 and the compound of Formula 1e, and the intermediates thereof.

In step 1, compound 9 is contacted with NBS or NIS under conditions sufficient to provide compound 10. For example, a solution of compound 9 in a suitable solvent (e.g. DMF) is treated with an appropriate base (e.g. cesium carbonate). The mixture is then cooled, NBS or NIS is added, and the reaction is allowed to warm to ambient temperature. The reaction mixture is quenched (e.g. with aqueous LiCl), filtered, and washed with water to give compound 10.

In step 2, compound 10 is contacted with a suitable Grignard reagent under conditions sufficient to provide compound 11. For example, compound 10 is treated with alkyl magnesium bromide in a suitable solvent (e.g. THF). The reaction mixture is quenched with water and an appropriate acid (e.g. HCl). The reaction is extracted with a suitable solvent (e.g. EtOAc), dried (e.g. over magnesium sulfate), concentrated under reduced pressure, and purified (e.g. via silica gel chromatography) to give compound 11.

In step 3, compound 11 is contacted with 2-hydroxyacetamide under conditions sufficient to provide the compound of Formula 1e. For example, a solution of compound 11 in a suitable solvent (e.g. 1,4-dioxane) is treated with an appropriate base (e.g. cesium carbonate) and 2-hydroxyacetamide in presence of a suitable catalyst (e.g. $Pd_2(dba)_3$) and ligand (Xantphos). The mixture is heated to reflux for a few minutes, cooled to ambient temperature, and partitioned between water and EtOAc. The combined organic layers are dried (e.g. over sodium sulfate), filtered, concentrated under reduced pressure, and purified (e.g. via silica gel chromatography) to give the compound of Formula 1e.

Alternatively, in step 3a, compound 11 is converted under conditions sufficient into compound 12. For example, compound 11 is dissolved in an appropriate solvent, then a base (e.g. sodium tert-butoxide or cesium hydroxide) and a catalyst (e.g. tert-BuBrettPhos-Pd-G3) are added. The reaction mixture is heated to a suitable temperature, such as at about 65° C. for a few hours, cooled to ambient temperature and quenched with an appropriate acid (e.g. HCl). The reaction is then extracted with a suitable solvent (e.g. EtOAc), dried (e.g. over magnesium sulfate), concentrated under reduced pressure, and purified (e.g. via silica gel chromatography) to give compound 12.

Scheme 5'. General Scheme for Synthesis of Compounds of Formulas 1e and 1e-i.

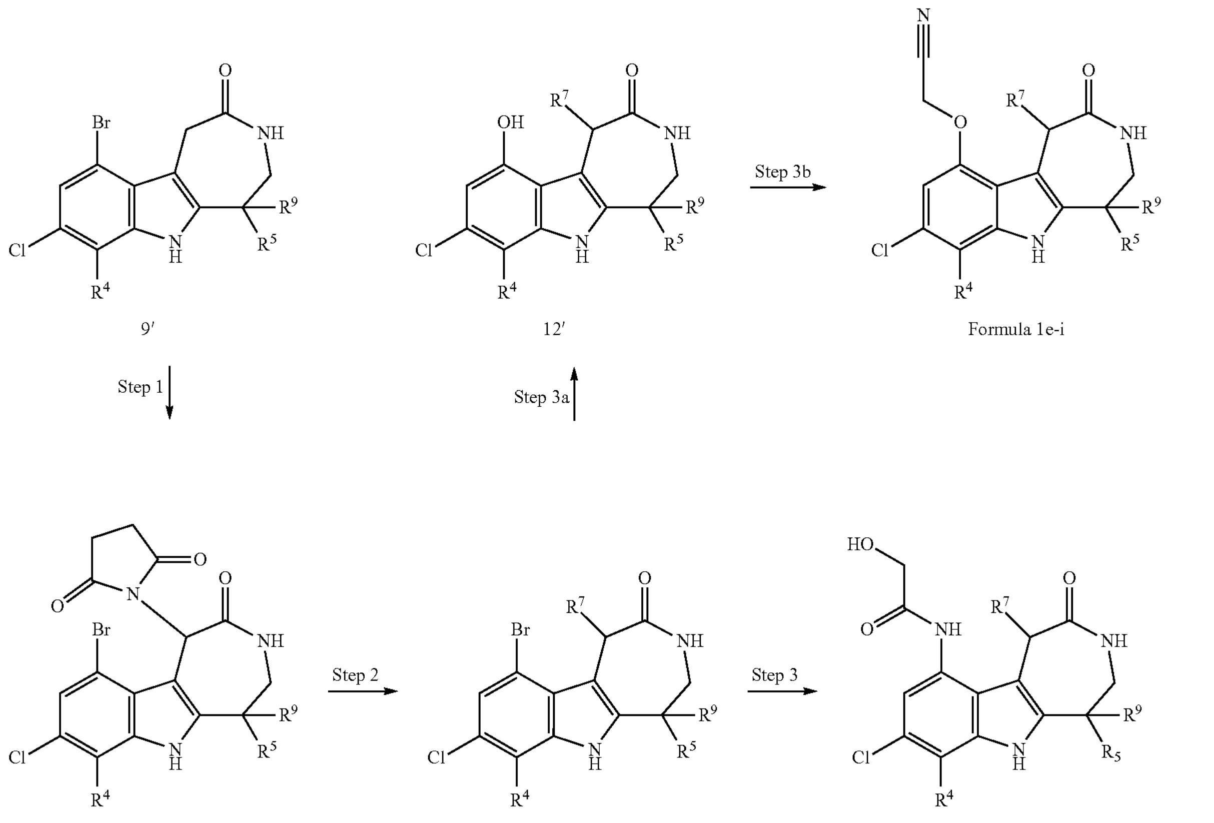

9'

12'

Formula 1e-i

10'

11'

Formula 1e'

Scheme 5' depicts a general scheme for the synthesis of Compound 12', the compound of Formula 1e', and the compound of Formula 1e-i, and the intermediates thereof. Steps 1, 2, and 3a are performed according to Scheme 5 above from the compound 9'. In some embodiments, the alkyl magnesium bromide used in step 2 is methyl magnesium bromide.

In step 3, compound 11' is contacted with 2-hydroxyacetamide under conditions sufficient to provide the compound of Formula 1e'. For example, a solution of compound 11' in a suitable solvent (e.g. 1,4-dioxane) is treated with an appropriate base (e.g. cesium carbonate) and 2-hydroxyacetamide in presence of a suitable catalyst (e.g. $Pd_2(dba)_3$) with ligand (Xantphos) or tert-BuBrettPhos-Pd-G). The mixture is heated to reflux for a few minutes, cooled to ambient temperature, and partitioned between water and EtOAc. The combined organic layers are dried (e.g. over sodium sulfate), filtered, concentrated under reduced pressure, and purified (e.g. via silica gel chromatography) to give the compound of Formula 1e'. One skilled in the art will recognize that there are many catalyst, ligand, base, and solvent combinations that may be used to perform this transformation.

Alternatively, in step 3a, compound 11' is converted under conditions sufficient into compound 12' by a hydroxylation reaction. For example, compound 11' is dissolved in an appropriate solvent (e.g., 1,4-dioxane and water), then a base (e.g. sodium tert-butoxide or cesium hydroxide) and a catalyst (e.g. tert-BuBrettPhos-Pd-G3) are added. The reaction mixture is heated to a suitable temperature, such as at about 65° C. for a few hours, cooled to ambient temperature, and quenched with an appropriate acid (e.g. HCl). The reaction is then extracted with a suitable solvent (e.g. EtOAc), dried (e.g. over magnesium sulfate), concentrated under reduced pressure, and purified (e.g. via silica gel chromatography) to give compound 12'. One skilled in the art will recognize that there are many catalyst, ligand, base, and solvent combinations that may be used to perform this transformation.

In Step 3b, the phenol in compound 12' is alkylated by reacting compound 12' with an alkylating reagent such as chloroacetonitrile or bromoacetonitrile in the presence of a base such as potassium carbonate, and a solvent such as DMF, and at a suitable temperature, for example, at ambient temperature to give Formula 1e-i.

Scheme 5A . General Scheme for Synthesis of Compound of Formula 1e-ii

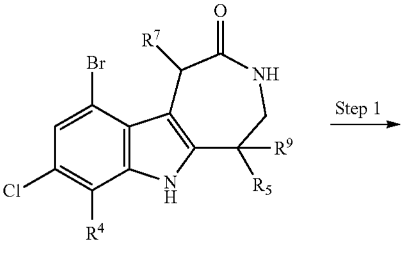

11'

-continued

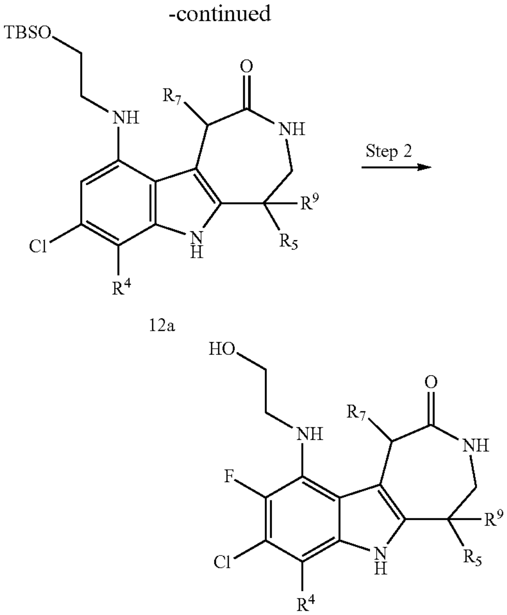

12a

Formula 1e-ii

Scheme 5A depicts synthesis of compound Formula 1e-ii through intermediate 12a.

In Step 1, compound 11' is reacted with 2-(tert-butyldimethylsiloxy)ethanamine, in the presence of a catalyst such as $Pd_2(dba)_3$, and a ligand such as 4,5-bis(diphenylphosphino)-9,9-dimethylxanthene, a solvent such as 1,4-dioxane, and a base such as cesium carbonate, and at a suitable temperature, for example about 100-115° C. to give compound 12a.

In step 2, compound 12a is fluorinated by reacting with 1-fluoro-2,4,6-trimethylpyridinium tetrafluoroborate in the presence of a solvent such as ACN and at ambient temperature. HCl is added to the reaction allowing deprotection of tert-butyldimethylsilyl to give the fluorinated compound of Formula 1e-ii.

Scheme 6. General Scheme for Synthesis of Compounds of Formulas 1f, 1g, 1h, and 1i

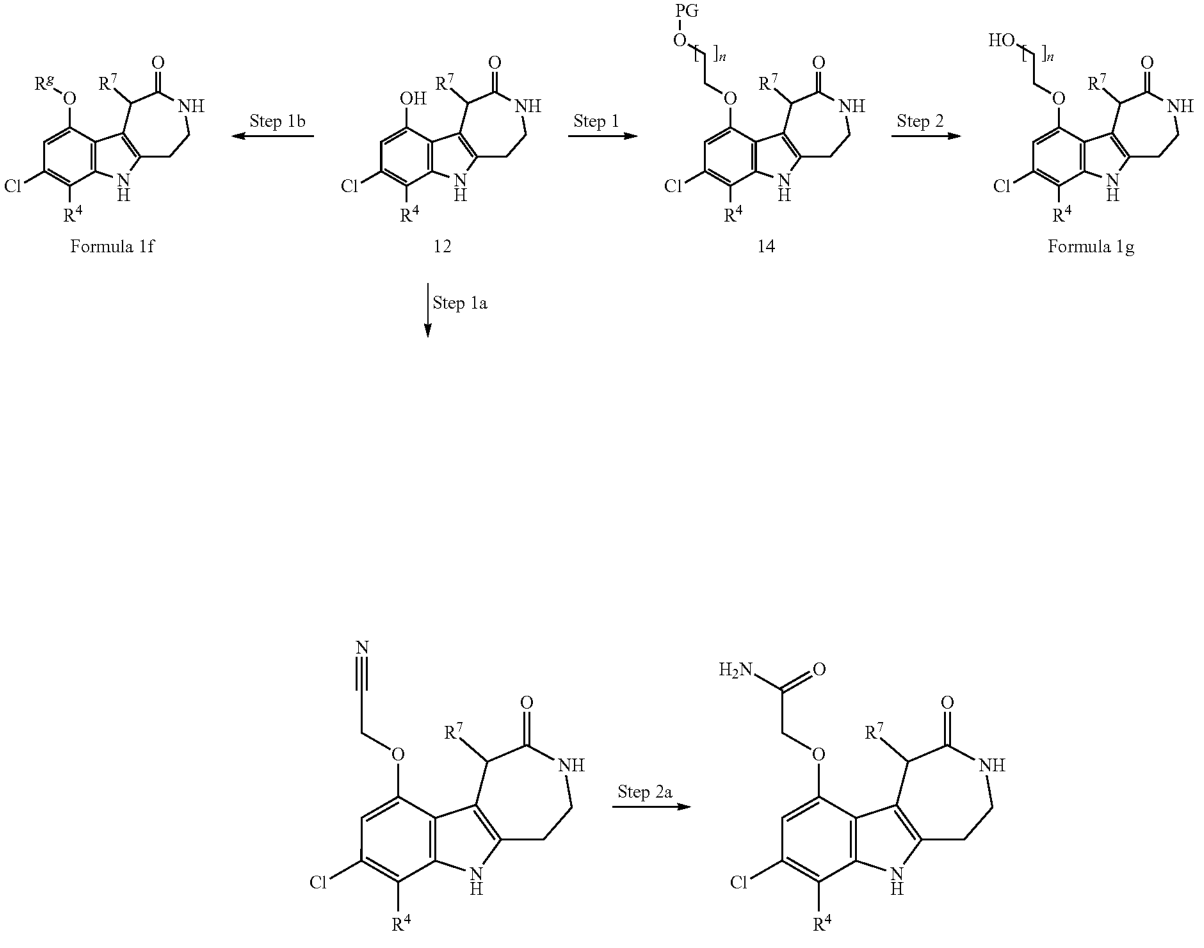

Formula 1f

12

14

Formula 1g

Formula 1h

Formula 1i

Scheme 6 depicts a general scheme for the synthesis of compounds of Formula 1f, Formula 1g, Formula 1h, Formula 1i, and the intermediates thereof. PG is a suitable protecting group, and $R^g$ is methyl or ethyl.

In step 1, compound 12 is contacted with an alkyl bromide under conditions sufficient to provide compound 14. For example, compound 12 is dissolved in a suitable solvent (e.g. DMF), followed by the addition of an appropriate base (e.g. $K_2CO_3$) and an alkyl bromide (such as 3-bromopropyl acetate or 2-(2-bromoethoxy)tetrahydro-2H-pyran). The mixture is then stirred at ambient temperature, then an appropriate catalyst (e.g., NaI) is added. Stirring continues for several hours. The reaction is cooled to ambient temperature and diluted with an appropriate solvent (e.g. EtOAc). Diatomaceous earth is added, followed by filtering, and then rinsing with EtOAc. The filtrate is washed (e.g. with saturated aqueous sodium bicarbonate and saturated aqueous NaCl), dried (e.g. over anhydrous sodium sulfate), filtered, concentrated under reduced pressure, and purified (e.g. via silica gel flash chromatography) to give compound 14.

In step 2, compound 14 is deprotected under conditions sufficient to give the compound of Formula 1g, e.g. using an acid (such as HCl) and appropriate solvent (such as 1,4-dioxane), or a base (such LiOH) in a solvent (such as MeOH).

Alternatively in Step 1a, compound 12 is contacted with a haloacetonitrile reagent to give the compound of Formula 1h. For example, compound 12 is dissolved in a suitable solvent (e.g. DMF) and cooled to 0° C. A suitable base (e.g. potassium carbonate) is added, followed by addition of bromoacetonitrile, and the reaction is stirred at ambient temperature. The mixture is poured into saturated aqueous sodium bicarbonate and extracted with EtOAc. The organic layers are washed (e.g. with saturated aqueous NaCl), dried (e.g. over anhydrous sodium sulfate), filtered, concentrated under reduced pressure, and purified (e.g. via silica gel flash chromatography) to give the compound of Formula 1h.

In step 2a, the compound of Formula 1h is hydrolyzed under conditions sufficient to give the compound of Formula 1i. For example, the compound of Formula 1h is dissolved in an appropriate solvent (e.g. DMSO). $H_2O_2$ and a base (e.g. potassium carbonate) are added. The reaction is stirred for an appropriate amount of time, quenched with aqueous sodium thiosulfate, then water and EtOAc are added. The organic layers are washed (e.g. with saturated aqueous NaCl), dried (e.g. over anhydrous sodium sulfate), filtered, concentrated under reduced pressure, and purified (e.g. via silica gel flash chromatography) to give the compound of Formula 1i.

Still alternatively, in step 1b, compound 12 is contacted with a suitable alkylating agent under conditions sufficient to provide the compound of Formula 1f. For example, compound 12 and an appropriate base (such as potassium carbonate) are stirred in an appropriate solvent (e.g. DMSO). An alkyl halide (such as iodoethane or iodomethane) is added and stirred at an appropriate temperature (e.g. about 50° C.). The reaction is then cooled to ambient temperature, washed (e.g. with saturated aqueous NaCl), dried (e.g. over anhydrous magnesium sulfate), filtered, concentrated onto diatomaceous earth, and purified (e.g. via silica gel flash chromatography) to give the compound of Formula 1f.

Scheme 6'. General Scheme for Synthesis of Compounds of Formulas 1f', 1g', 1h', and 1i'

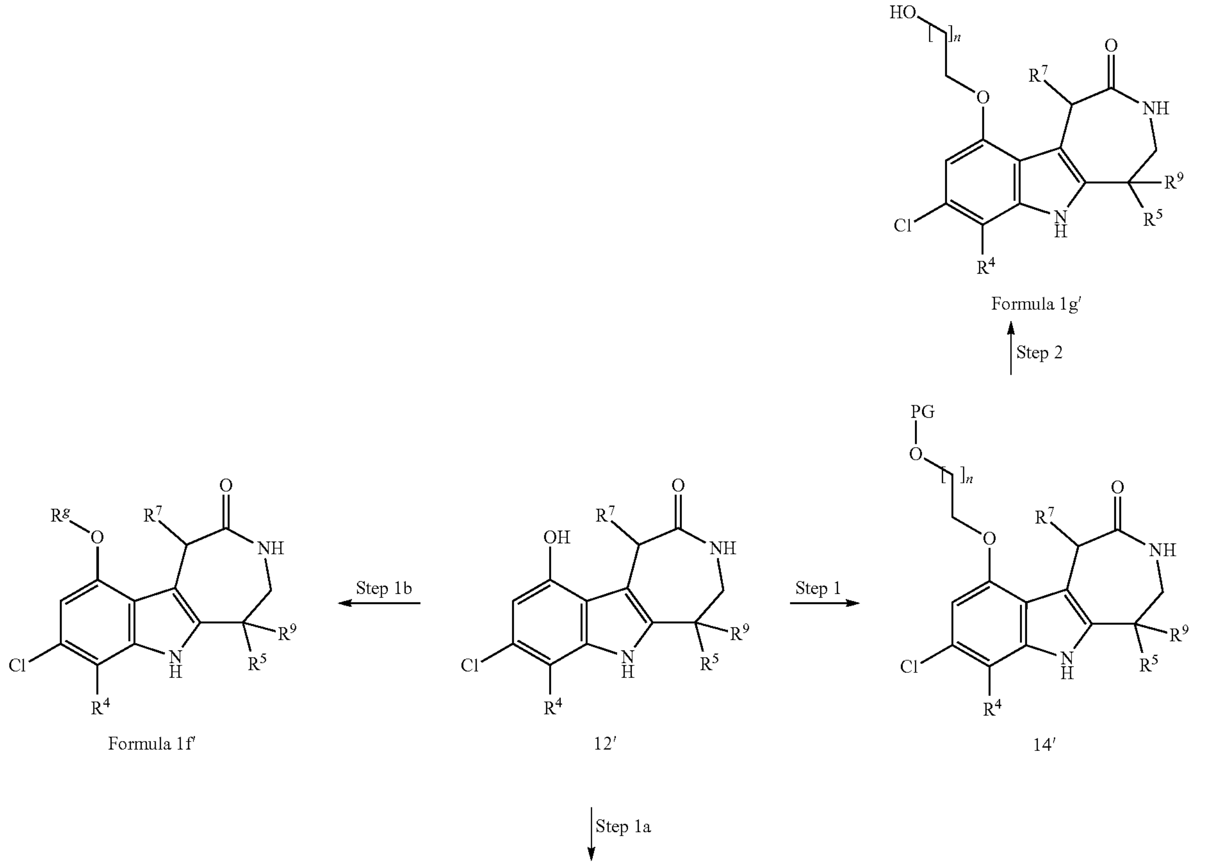

Formula 1g'

Formula 1f'

12'

14'

-continued

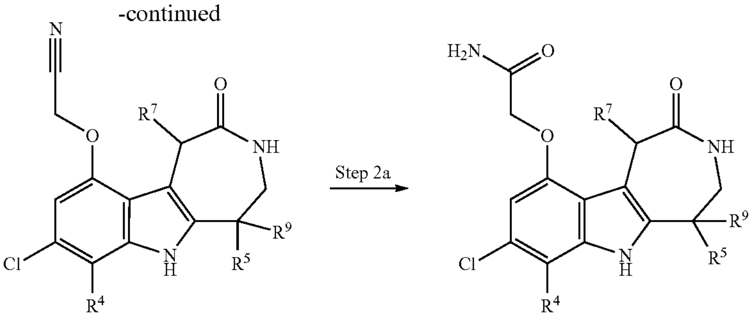

Formula 1h′ Formula 1i′

Scheme 6' depicts a general scheme for the synthesis of compounds of Formula 1f', Formula 1g', Formula 1h', Formula 1i', and the intermediates thereof. PG is a suitable protecting group; $R^g$ is methyl or ethyl.

In step 1, compound 12' is contacted with a reagent under conditions sufficient to provide compound 14'. For example, compound 12 is dissolved in a suitable solvent (e.g. DMF), followed by the addition of an appropriate base (e.g. $K_2CO_3$) and an alkyl halide (such as 3-bromopropyl acetate or 2-(2-bromoethoxy)tetrahydro-2H-pyran). The mixture is then stirred at ambient temperature, then an appropriate catalyst (e.g., NaI) is added. Stirring continues for several hours. The reaction is cooled to ambient temperature and diluted with an appropriate solvent (e.g. EtOAc). Diatomaceous earth is added, followed by filtering, and then rinsing with EtOAc. The filtrate is washed (e.g. with saturated aqueous sodium bicarbonate and saturated aqueous NaCl), dried (e.g. over anhydrous sodium sulfate), filtered, concentrated under reduced pressure, and purified (e.g. via silica gel flash chromatography) to give compound 14'. Steps 1, 1a, 1b, 2, and 2a are performed according to Scheme 6 above to provide the compounds of Formula 1f', 1g', 1h', and 1i'.

Scheme 7. General Scheme for Synthesis of the compounds of Formula 1j and 1k

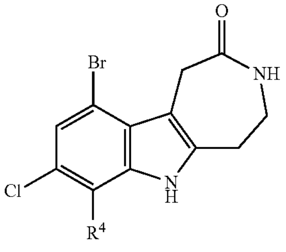

9

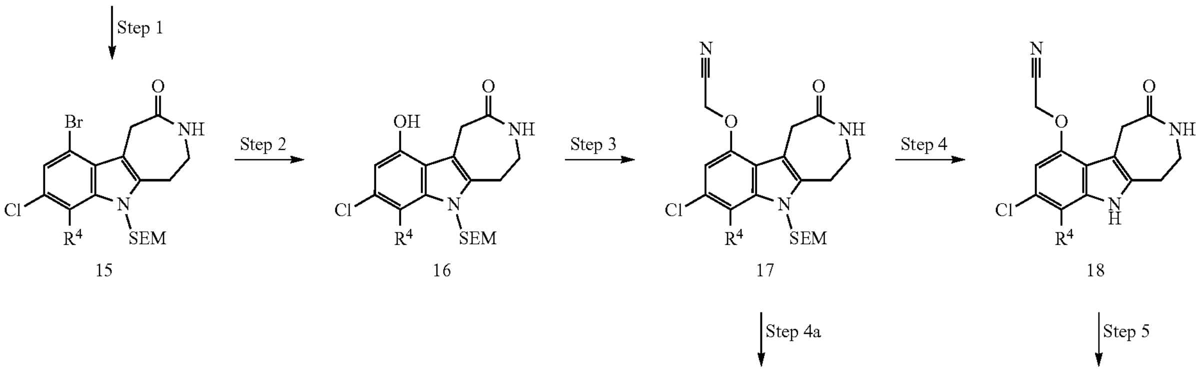

15 16 17 18

-continued

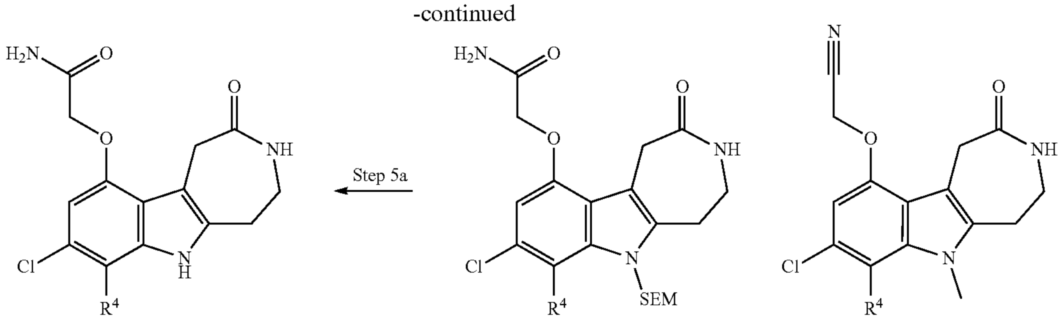

Formula 1k 19 Formula 1j

Scheme 7 depicts a general scheme for the synthesis of the compounds of Formula 1j, Formula 1k, and the intermediates thereof. In step 1, compound 9 is contacted with a suitable reagent to provide compound 15 with its indole nitrogen protected. For example, compound 9 is dissolved in an appropriate solvent such as THF. A protecting group reagent such as SEM-Cl and a base (such as sodium hydride) are added and stirred at an appropriate temperature for a few hours. The reaction is quenched with saturated aqueous sodium bicarbonate, washed (e.g. with saturated aqueous sodium bicarbonate and extracting into EtOAc), dried (e.g. over anhydrous sodium sulfate), filtered, concentrated under reduced pressure, and purified (e.g. via silica gel flash chromatography) to give compound 15.

In step 2, compound 15 is contacted with an aqueous base under conditions sufficient to form compound 16. For example, compound 15 is dissolved in a solvent such as 1,4-dioxane and water. A base (such as t-BuONa) and a catalyst (such as tert-BuBrettPhos-Pd-G) are added, and the mixture is heated to an appropriate temperature. The mixture is cooled to ambient temperature and acid (such as aqueous HCl) is added. The reaction mixture is diluted with EtOAc, washed (e.g. with saturated aqueous NaCl), dried (e.g. over anhydrous sodium sulfate), filtered, concentrated under reduced pressure, and purified (e.g. via silica gel flash chromatography) to give compound 16.

In step 3, compound 16 is contacted with an alkyl bromide under conditions sufficient to give compound 17. For example, compound 16 is dissolved in a suitable solvent (e.g. DMF) and cooled to 0° C. A suitable base (e.g. potassium carbonate) is added followed by the addition of bromoacetonitrile, and the reaction is stirred at ambient temperature until completion. The mixture is poured into saturated aqueous sodium bicarbonate and extracted with EtOAc. The organic layers are washed (e.g. with saturated aqueous NaCl), dried (e.g. over anhydrous sodium sulfate), filtered, concentrated under reduced pressure, and purified (e.g. via silica gel flash chromatography) to give compound 17.

In step 4, compound 17 is deprotected under conditions sufficient to give compound 18. For example, compound 17 is dissolved in an appropriate solvent such as DCM, and an appropriate acid such as TFA added. The mixture is concentrated, diluted with an appropriate solvent such as THF, diluted with aqueous ammonia, and stirred at ambient temperature for a few hours. The reaction is diluted with EtOAc, washed (e.g. with saturated aqueous NaCl), dried (e.g. over anhydrous sodium sulfate), filtered, concentrated under reduced pressure, and purified (e.g. via silica gel flash chromatography) to give compound 18.

In step 5, compound 18 is indole alkylated under sufficient conditions to give compound Formula 1j. For example, compound 18 and a base (e.g., cesium carbonate) are stirred in an appropriate solvent (e.g., DMF). A haloalkane (e.g., iodomethane or iodoethane) is added, and the mixture stirred at an appropriate temperature for a few hours. The mixture is diluted with water, extracted with EtOAc, concentrated under reduced pressure, and purified (e.g., by prep-HPLC) to give the compound of Formula 1j.

Alternatively, in step 4a, compound 17 is converted under sufficient conditions into compound 19. For example, compound 17 is dissolved in an appropriate solvent (e.g. DMSO), then $H_2O_2$ and a base (e.g. potassium carbonate) are added. The reaction is stirred for a sufficient amount of time, then diluted with an appropriate solvent (such as EtOAc), washed with saturated aqueous NaCl, dried over anhydrous sodium sulfate, filtered, and concentrated under reduced pressure. The reaction is then triturated with an appropriate solvent such as ACN to give intermediate 19.

In step 5a, compound 19 is deprotected under conditions sufficient to give Formula 1k. For example, compound 19 is dissolved in an appropriate solvent such as DCM. An appropriate acid (such as TFA) is added, and the mixture stirred for a few hours at ambient temperature until completion. The mixture is then concentrated, diluted with an appropriate solvent (such as THF), diluted with aqueous ammonia, and stirred at an appropriate temperature for a few hours. The reaction is diluted with EtOAc, washed (e.g. with saturated aqueous NaCl), dried (e.g. over anhydrous sodium sulfate), filtered, concentrated under reduced pressure, and purified (e.g. via Prep-HPLC) to give the compound of Formula 1k.

Scheme 7'. General Scheme for Synthesis of the compounds of Formula 1j' and 1k'

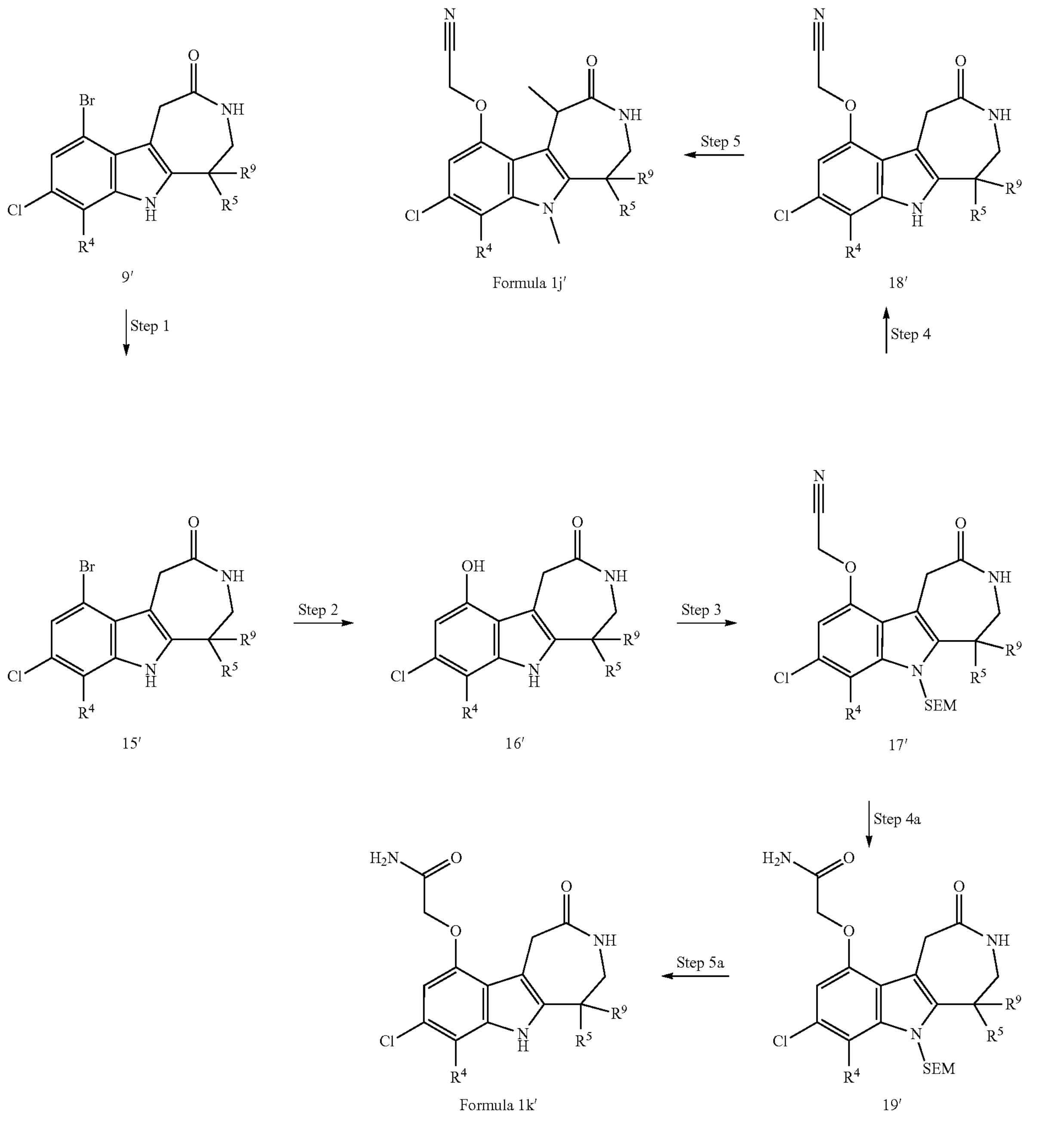

Scheme 7' depicts a general scheme for the synthesis of the compounds of Formula 1j', Formula 1k', and the intermediates thereof. Steps 1, 2, 3, 4, and 5 are performed according to Scheme 7 above using the suitable starting material to provide the compound of Formula 1j'. In step 4a, compound 17' is converted under sufficient conditions into compound 19'. For example, compound 17' is dissolved in an appropriate solvent (e.g., DMSO), then $H_2O_2$ and a base (e.g., potassium carbonate) are added. The reaction is stirred, then diluted with an appropriate solvent (such as EtOAc), washed with saturated aqueous NaCl, dried over anhydrous sodium sulfate, filtered, and concentrated under reduced pressure. The reaction is then triturated with an appropriate solvent such as ACN to give intermediate 19'. In step 5a, compound 19' is deprotected under conditions sufficient to give Formula 1k'. For example, compound 19' is dissolved in an appropriate solvent such as DCM. An appropriate acid (such as TFA) is added and the mixture stirred for a few hours at ambient temperature until completion. The mixture is then concentrated, diluted with an appropriate solvent (such as THF), diluted with aqueous ammonia, and stirred at an appropriate temperature for a few hours. The reaction is diluted with EtOAc, washed (e.g. with saturated aqueous NaCl), dried (e.g. over anhydrous sodium sulfate), filtered, concentrated under reduced pressure, and purified (e.g. via Prep-HPLC) to give the compound of Formula 1k'.

Scheme 8. General Scheme for Synthesis of Formula 11

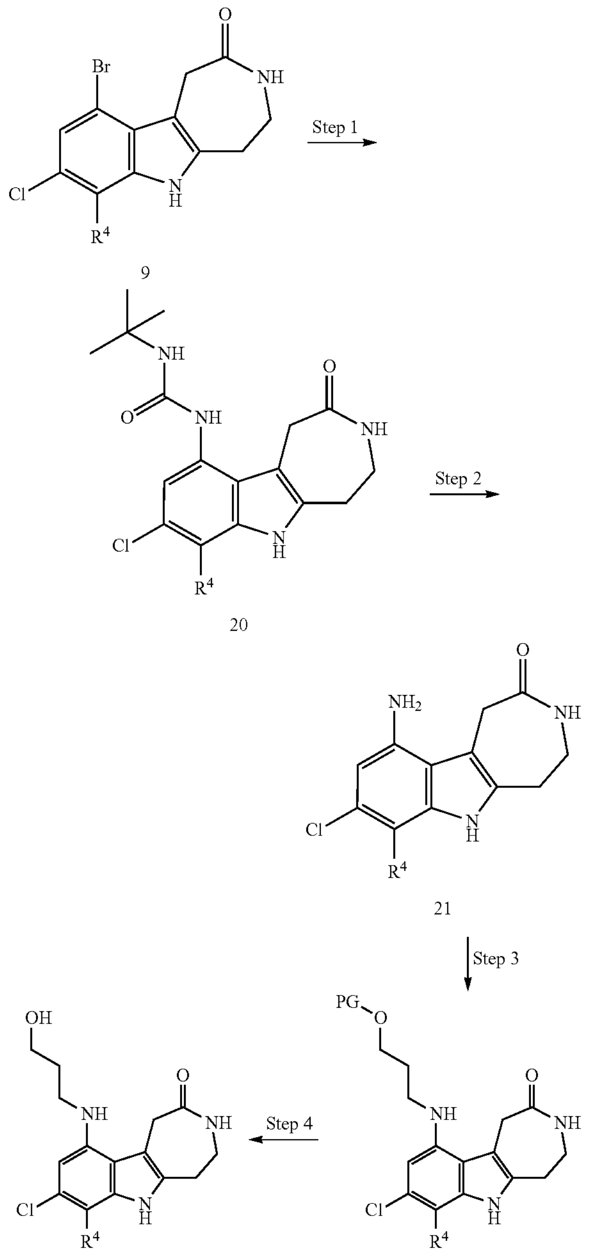

9, 20, 21, 22, Formula 11

Scheme 8 depicts the synthesis of the compound of Formula 11 and the intermediates thereof. In step 1, halide-bearing compound 9 is contacted with tert-butyl carbamate under conditions sufficient to provide compound 20. For example, compound 9 is dissolved in an appropriate solvent (such as 1,4-dioxane) and an appropriate base (such as cesium carbonate) is added. tert-Butyl carbamate is then added along with a catalyst (such as XantPhos-Pd-$G_2$). The mixture is stirred for a few hours at an appropriate temperature until completion. The reaction is concentrated under reduced pressure and purified (e.g. via silica gel flash chromatograph) to give compound 20.

In step 2, compound 20 is deprotected under conditions sufficient to provide compound 21. For example, compound 20 is contacted with an acid (such as HCl in EtOH), and then concentrated under reduced pressure and triturated with solvent such as EtOAc to give compound 21.

In step 3, compound 21 is contacted with a suitable aldehyde under conditions sufficient (e.g. reductive amination condition) to provide compound 22. For example, compound 21 is dissolved in appropriate solvents such as MeOH, and acetic acid, with a base such as DIPEA. An aldehyde (such as 3-[tert butyl(dimethyl)silyl]oxypropanal) and a reducing agent (such as sodium cyanoborohydride) are added to the solution. The mixture is stirred for several hours at an appropriate temperature (such as ambient temperature) until completion. The reaction is quenched with an appropriate solvent (such as water) and extracted with EtOAc. The organics are dried (e.g. over anhydrous sodium sulfate), filtered, concentrated under reduced pressure, and purified (e.g. via silica gel flash chromatography) to give compound 22.

In step 4, compound 22 is contacted with an acid under conditions sufficient to give the compound of Formula 11. For example, compound 22 is suspended in an acid and solvent system such as HCl/MeOH at an appropriate temperature and stirred. At completion, the reaction mixture is concentrated under reduced pressure, purified (e.g. by prep-HPLC), and lyophilized to give the compound of Formula 11.

Scheme 8'. General Scheme for of Formula 11'

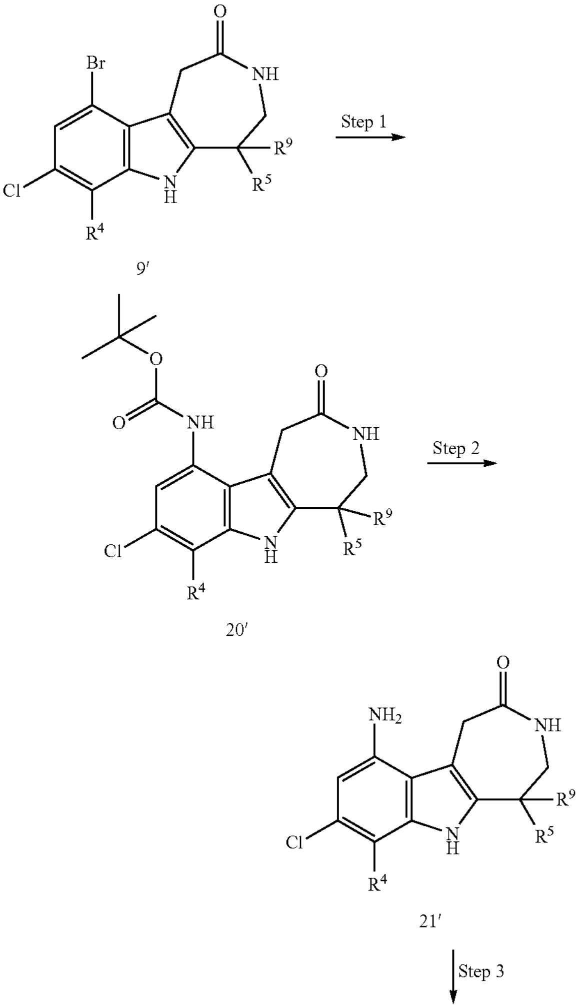

9', 20', 21'

-continued

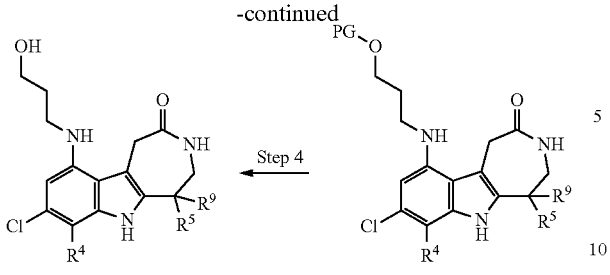

Formula 1l'

22'

Scheme 8' depicts the synthesis of the compound of Formula 1l' and the intermediates thereof. Steps 1, 2, 3, and 4 are performed according to Scheme 8 above from compound of Formula 9'.

Scheme 9. General Scheme for Synthesis of Compounds of Formula 1m and 1n

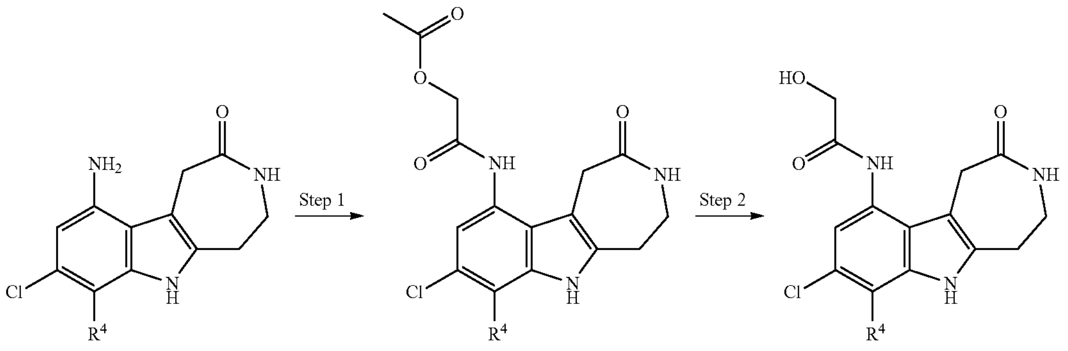

21

23

Formula 1m

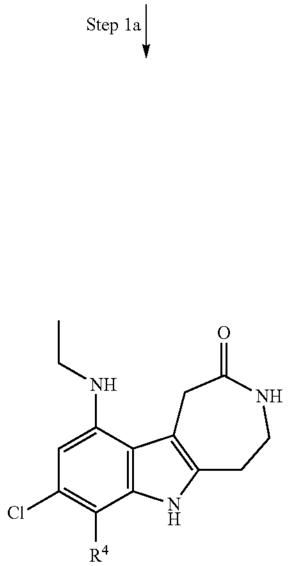

Formula 1n

Scheme 9 depicts synthesis of the compounds of Formula 1m, Formula 1n, and the intermediates thereof. In step 1, compound 21 is contacted with acetoxyacetyl chloride under conditions sufficient to provide compound 23. For example, compound 21 is reacted with acetoxyacetyl chloride in an appropriate solvent (such as DCM) in presence of an appropriate base (such as $Et_3N$) at ambient temperature. The reaction is then quenched using an appropriate solvent, dried (e.g. over anhydrous sodium sulfate), filtered, and concentrated under reduced pressure to give compound 23.

In step 2, compound 23 is contacted with a base to give the compound of Formula 1m. For example, compound 23 is dissolved in an appropriate solvent (such as THF and water), and a base (such as lithium hydroxide monohydrate) is added. The mixture is stirred for a few minutes at an appropriate temperature until reaction completes. The reaction is then diluted with water, extracted, dried (e.g., over anhydrous sodium sulfate), filtered, concentrated under reduced pressure, and purified (e.g., via prep-HPLC) to give the compound of Formula 1m.

Alternatively, in step 1a, compound 21 is contacted with an aldehyde under conditions sufficient to provide the compound of Formula 1n. For example, compound 21 is dissolved in an appropriate solvent (such as MeOH), and an acid (such as acetic acid) added to adjust the pH. Acetaldehyde is added, along with a reducing agent (such as sodium cyanoborohydride). The mixture is stirred for several hours at ambient temperature. The reaction is then diluted, washed (e.g. with saturated aqueous sodium bicarbonate and saturated aqueous NaCl), dried (e.g. over sodium sulfate), filtered, concentrated under reduced pressure, and purified (e.g. via silica gel flash chromatography and prep-HPLC) to give the compound of Formula 1n.

Scheme 9'. General Scheme for Synthesis of Compounds of Formula 1m' and Formula 1n'

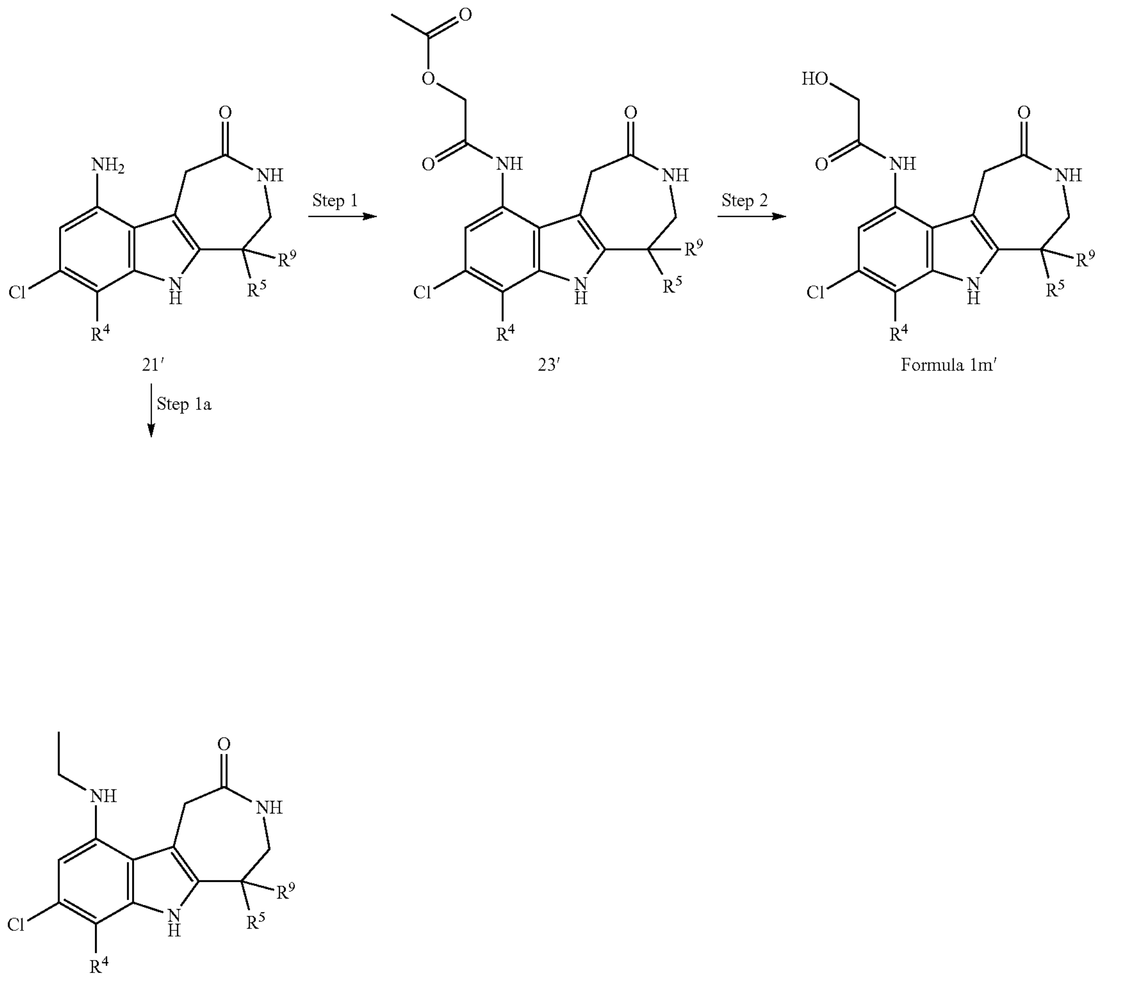

21'
23'
Formula 1m'
Formula 1n'

Scheme 9' depicts synthesis of the compounds of Formula 1m', Formula 1n', and the intermediates thereof. Steps 1, 2, 3, and 4 are performed according to Scheme 9 above from compound of Formula 21'.

Scheme 10. General Scheme for Synthesis of the compounds of Formula 1o and 1p

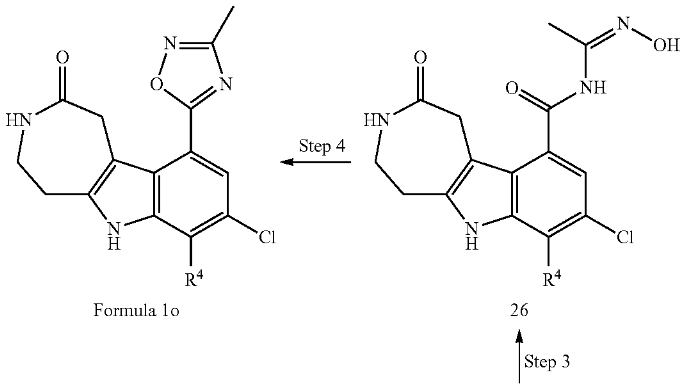

Formula 1o
26

-continued

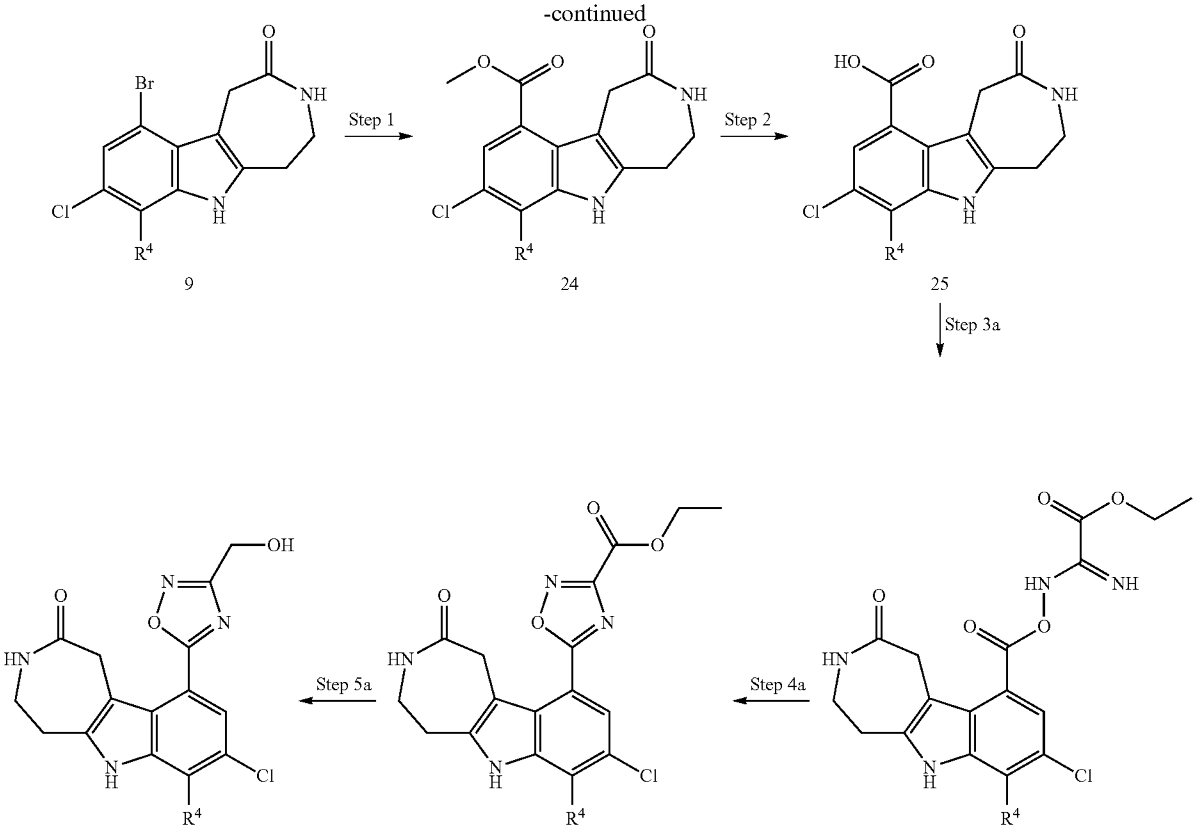

9 24 25

Formula 1p 28 27

Scheme 10 depicts synthesis of compounds of Formula 1o, Formula 1p, and intermediates thereof. In step 1, halide-bearing compound 9 is converted under conditions sufficient (e.g. a palladium-catalyzed carbonylation reaction) to provide an ester-bearing compound 24. For example, compound 9 is suspended in suitable solvents such as MeOH and DMF with a suitable catalyst (such as $Pd(dppf)Cl_2$), and a base (such as $Et_3N$). The reaction is sparged with CO, stirred under a CO atmosphere at an appropriate temperature and pressure for several hours, and then diluted with a solvent (such as EtOAc). The reaction is washed sequentially with water and saturated aqueous NaCl, dried (e.g. over sodium sulfate), filtered, concentrated under reduced pressure, and purified (e.g. via silica gel flash chromatography to give compound 24.

In step 2, compound 24 is hydrolyzed under conditions sufficient to give the carboxylic acid compound 25. For example, compound 24 is taken up in a suitable organic solvent (e.g. THF, water, or mixture thereof), treated with a base (e.g. lithium hydroxide monohydrate), and stirred at ambient temperature for several hours until completion. The pH of the solution is adjusted to about 4, and the resulting solid is filtered and washed (e.g. with water) to give compound 25.

In step 3, compound 25 is contacted with N'-hydroxyacetimidamide under conditions sufficient to give compound 26. For example, compound 25 is suspended with a coupling agent (such as TBTU) in a solvent (such as DMF) with a base (such as DIPEA). N'-Hydroxyacetimidamide and catalytic DMAP are added to the mixture and stirred at an appropriate temperature for a few hours until completion. The reaction is then diluted with EtOAc, washed sequentially with water and saturated aqueous NaCl, dried (e.g. over sodium sulfate), filtered, and concentrated under reduced pressure to give intermediate compound 26.

In step 4, compound 26 is contacted with a fluoride source under conditions sufficient (e.g. a ring closure condition) to provide the compound of Formula 1o. For example, compound 26 is dissolved in an appropriate solvent (such as 1,4-dioxane), and KF is added. The mixture is sparged with $N_2$ and stirred for several hours at a suitable temperature (e.g., 100 to 120° C.) until the reaction is complete. The reaction is then cooled to ambient temperature, the precipitate filtered, and triturated to give the compound of Formula 1o.

Alternatively, in step 3a, compound 25 is contacted with ethyl (N'-hydroxycarbamimidoyl)formate under conditions sufficient (e.g. amide coupling condition) to give compound 27. The coupling process is analogous to the process described above for step 3.

In step 4a, compound 27 is contacted with a fluoride source under conditions sufficient (e.g. ring closure condition) to provide compound 28, for example, in a process analogous to the process described above for step 4.

In step 5a, compound 28 is contacted with a reducing agent under conditions sufficient to give a compound of Formula 1p. For example, compound 28 is dissolved in an appropriate solvent (such as THF), and lithium borohydride is added. The mixture is stirred for a few minutes and then quenched with saturated aqueous $NH_4Cl$, and diluted with DCM and water. The organic layers are dried (e.g. over sodium sulfate), filtered, concentrated under reduced pressure, and purified (e.g. by Prep-HPLC) to give the compound of Formula 1p.

Scheme 10'. General Scheme for Synthesis of the Compounds of Formula 1o' and 1p'

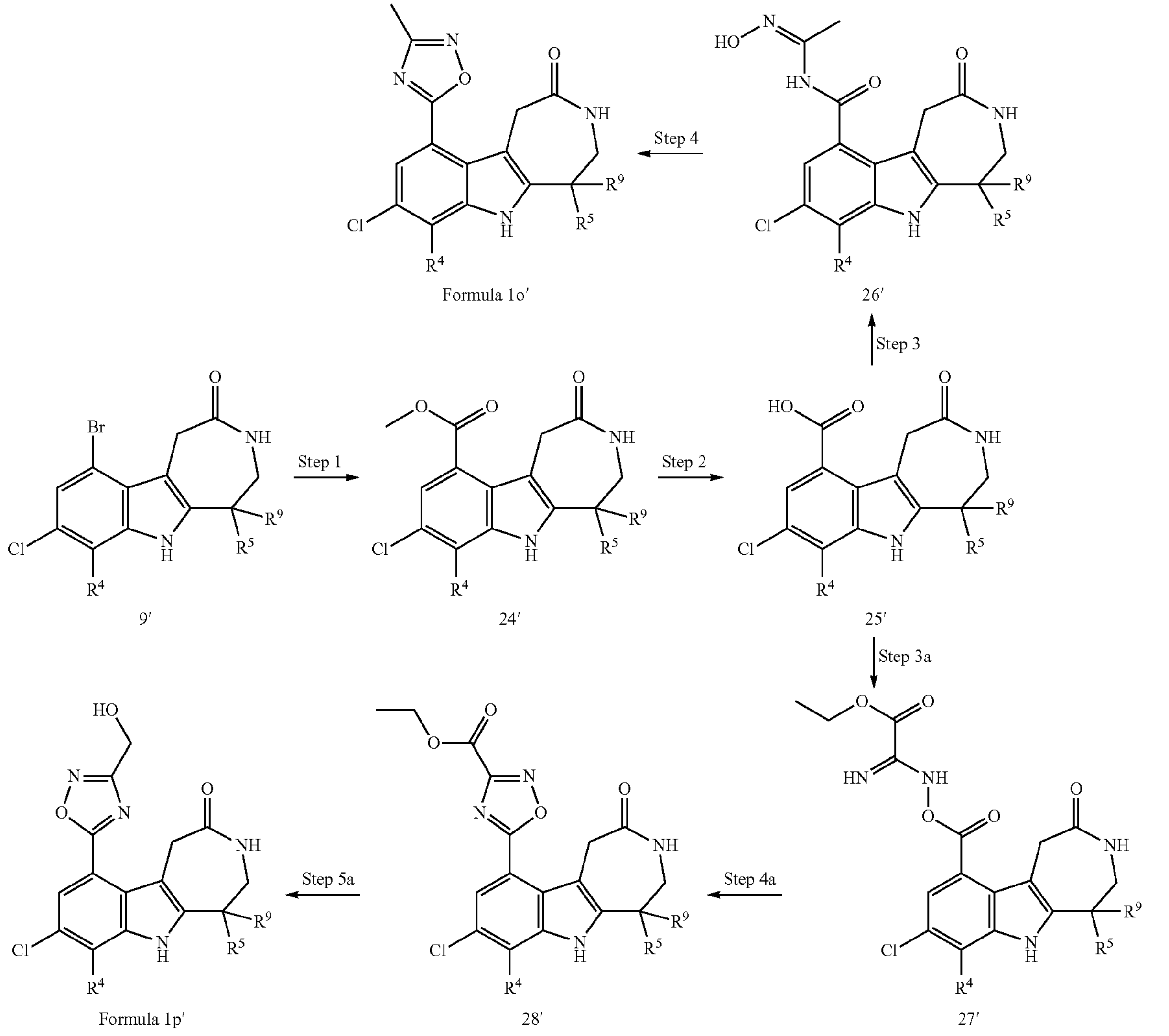

Formula 1o', 26', 9', 24', 25', Formula 1p', 28', 27'

Scheme 10' depicts synthesis of compounds of Formula 1o', Formula 1p', and intermediates thereof. Steps 1, 2, 3, 4, 3a, 4a, and 5a are performed according to Scheme 10 above from the starting material of compound of Formula 9'.

Scheme 11. General Scheme for Synthesis of Formula 1q

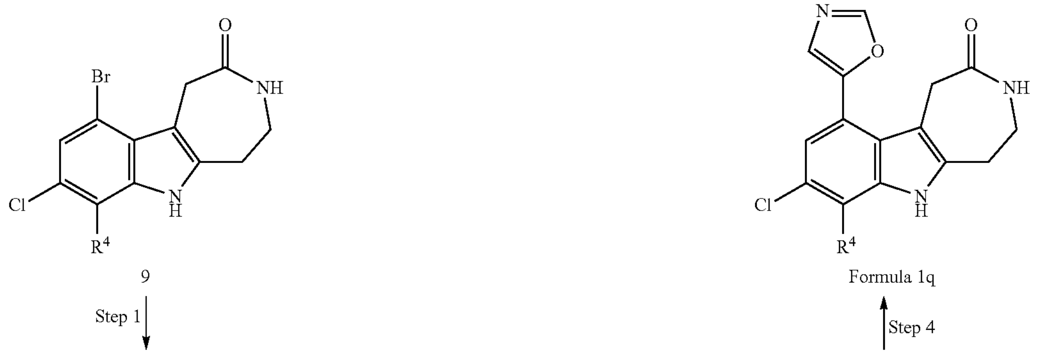

9, Formula 1q

-continued

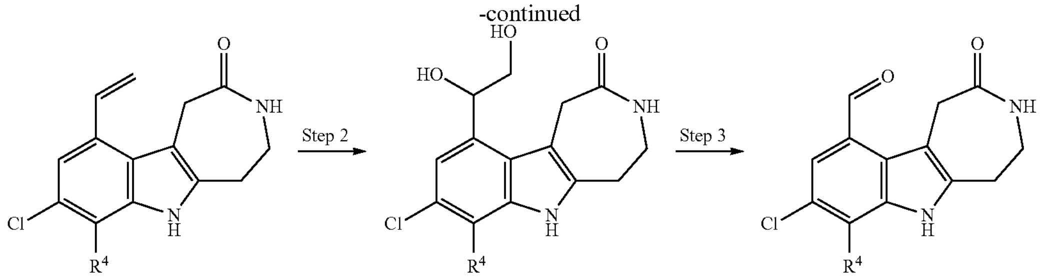

29 30 31

Scheme 11 depicts the synthesis of the compound of Formula 1q and intermediates thereof. In step 1, aryl bromide compound 9 is contacted with a vinyltrifluoroborate salt under conditions sufficient (e.g. palladium-catalyzed cross-coupling reaction) to give compound 29. For example, compound 9 is suspended with potassium vinyltrifluoroborate and Pd(dppf)$Cl_2$ catalyst in a solvent (such as 1,4-dioxane and water), in presence of a base (such as sodium carbonate). The mixture is sparged with $N_2$ and stirred at a suitable temperature (e.g., 90° C.) for several hours until completion. The mixture is filtered, washed with solvent (such as 1,4-dioxane), concentrated under reduced pressure, and purified (e.g. via silica gel flash chromatography) to give intermediate compound 29.

In step 2, compound 29 is contacted with a suitable dihydroxylation reagent under conditions sufficient to give a diol compound 30. For example, compound 29 is dissolved with oxidant (such as NMO) in solvents (such as THF and water). A dihydroxylation catalyst such as potassium osmate dihydrate is added and the mixture stirred for several hours until reaction completion. The reaction is diluted with EtOAc, washed (e.g. with saturated aqueous sodium bicarbonate and saturated aqueous NaCl), dried (e.g. over sodium sulfate), filtered, and concentrated under reduced pressure to give intermediate compound 30.

In step 3, compound 30 is contacted with an oxidant under conditions sufficient (e.g. oxidative cleavage condition) to give intermediate compound 31. For example, compound 30 is suspended with sodium periodate in appropriate solvents (such as water and acetone). The mixture is stirred at ambient temperature until the reaction is complete. The reaction mixture is then filtered and concentrated under reduced pressure to give compound 31.

In step 4, compound 31 is contacted with TosMIC under conditions sufficient to give the compound of Formula 1q. For example, compound 31 is dissolved in an appropriate solvent (such as MeOH) with a base (such as potassium carbonate). TosMIC is added and the mixture stirred at a suitable temperature (e.g., 65-80° C.) for a few hours until completion. The reaction is then cooled to ambient temperature, diluted with EtOAc, washed (e.g. with saturated aqueous NaCl), dried (e.g. over sodium sulfate), filtered, concentrated under reduced pressure, and purified (e. g., by prep-HPLC) to give the compound of Formula 1q.

Scheme 11'. General Scheme for Synthesis of Formula 1q'

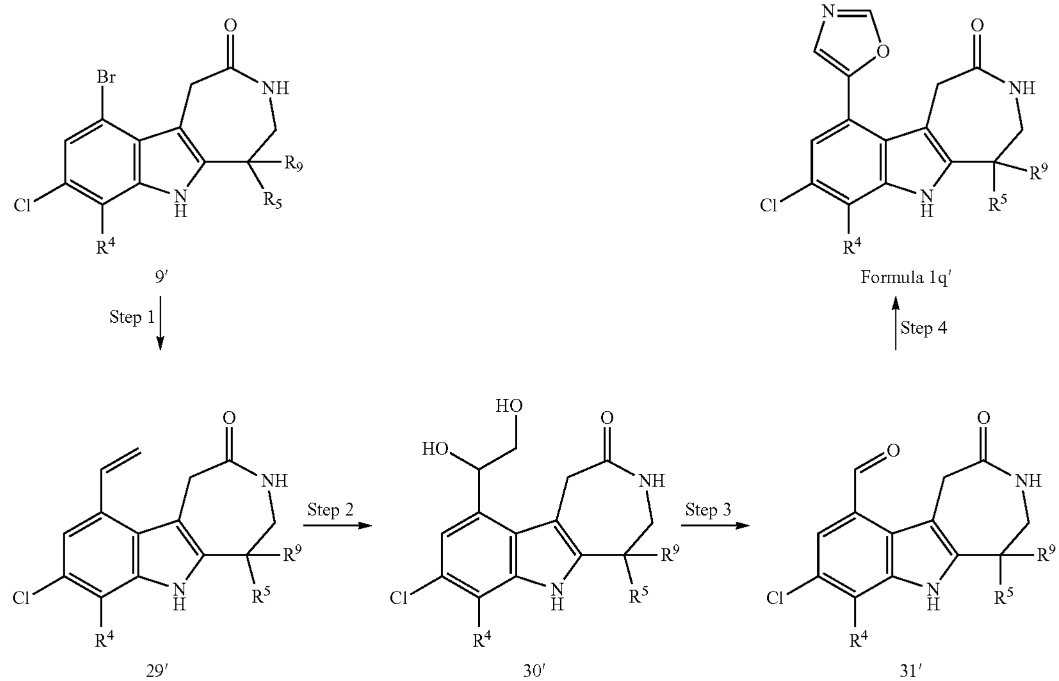

9' Formula 1q' 29' 30' 31'

Scheme 11' depicts synthesis of compounds of Formula 1q' and intermediates thereof. Steps 1, 2, 3, and 4 are performed according to Scheme 11 above from the starting material of compound of Formula 9'.

Scheme 12. General Scheme for Synthesis of Formula 1r

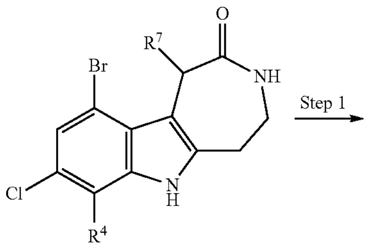

9

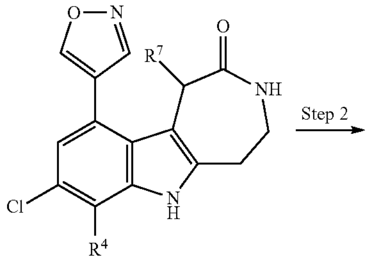

32

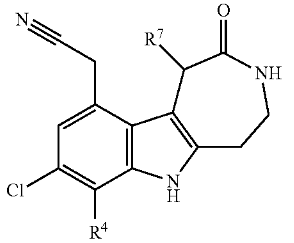

Formula 1r

Scheme 12 depicts the synthesis of the compound of Formula 1r and intermediates thereof. In step 1, compound 9 is contacted with 4-isoxazoleboronic acid pinacol ester under conditions sufficient (e.g. Suzuki reaction condition) to provide compound 32. For example, 4-isoxazoleboronic acid pinacol ester is added to compound 9 along with an appropriate base (such as KF) and Pd(dppf)$Cl_2$ catalyst in appropriate solvents (such as DMSO and water). The mixture is sparged with $N_2$ and stirred at a suitable temperature (e.g., 100-130° C.) for a few hours. The reaction is diluted with water, extracted with EtOAc, dried (e.g. over anhydrous sodium sulfate), filtered, concentrated under reduced pressure, and purified (e.g. via silica gel chromatography) to give compound 32 (or a ring-opened isomer thereof).

In step 2, compound 32 is contacted with a fluoride source under conditions sufficient to provide the compound of Formula 1r. Compound 32 is dissolved with KF in an appropriate solvent system (such as DMF and water) and stirred for several hours at a suitable temperature (e.g., 100-120° C.) until reaction completion. The reaction is concentrated under reduced pressure to remove water and purified (e.g. by prep-HPLC) to give compound of Formula 1r.

Scheme 12'. General Scheme for Synthesis of Formula 1r'

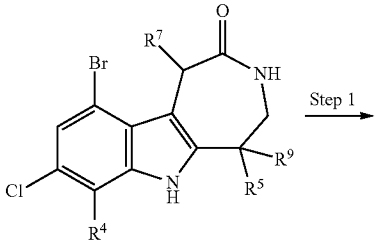

9'

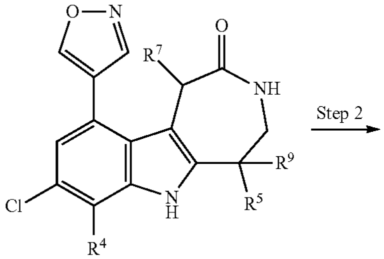

32'

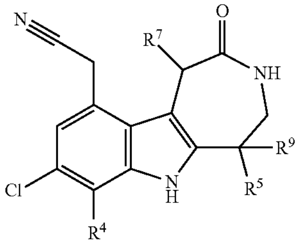

Formula 1r'

Scheme 12' depicts synthesis of compounds of Formula 1r' and intermediate 32' (or a ring-opened isomer thereof). Steps 1 and 2 are performed according to Scheme 12 above from the starting material of compound 9'.

Scheme 13. General Scheme for Synthesis of the compound of Formula 1s-a

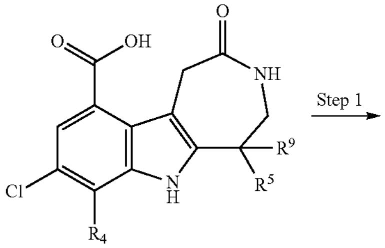

25

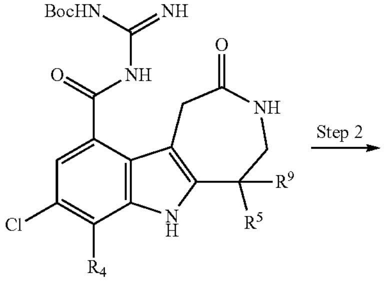

33

-continued

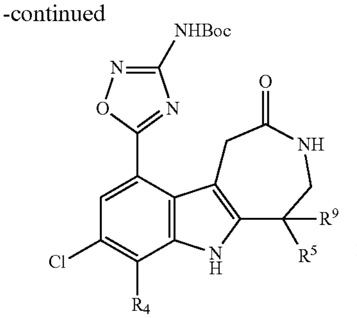

34

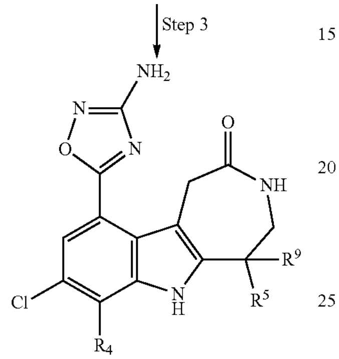

Formula 1t

Scheme 13 depicts synthesis of compound of Formula 1t through intermediates 33 and 34.

In step 1, compound 25 is reacted with tert-butyl N-carbamimidoylcarbamate in presence of a coupling reagent such as ((1H-benzo[d][1,2,3]triazol-1-yl)oxy)tri(pyrrolidin-1-yl)phosphonium, a base such as 4-methylmorpholine, and a solvent such as DMF at a suitable temperature, for example, at ambient temperature, to give compound 33.

In Step 2, compound 33 is reacted with (diacetoxyiodo) benzene in the presence of a solvent such as DMF, and at ambient temperature to allow for intramolecular cyclization giving compound 34.

In Step 3, compound 34 is Boc deprotected in the presence of an acid such as TFA, a solvent such as DCM, and at ambient temperature to give compound of Formula 1t.

Scheme 14. General Scheme for Synthesis of the Compound of Formula 1u

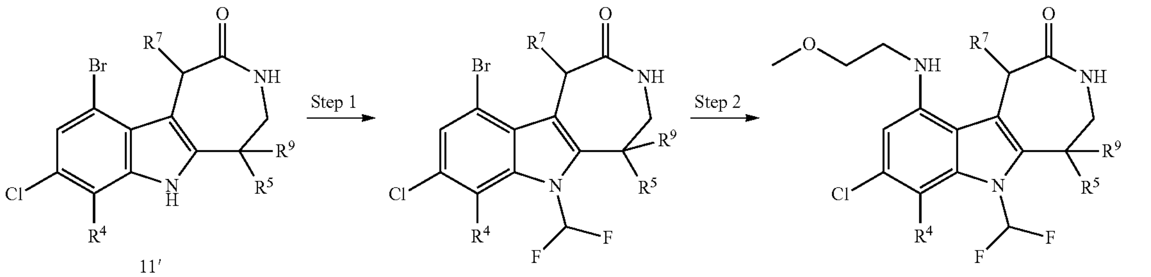

11′ 35′ Formula 1u

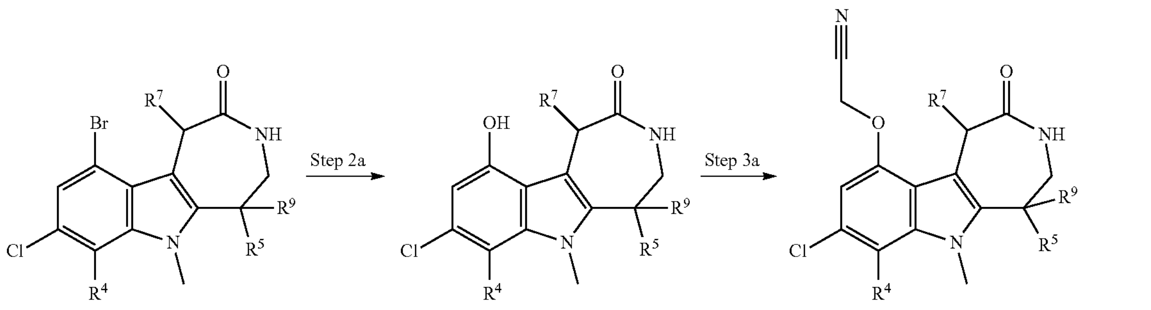

37′ 38′ Formula 1v

Scheme 14 depicts synthesis of compounds of Formula 1u and Formula 1v and the intermediates thereof.

Step 1 shows difluoromethylation of the indole through reacting compound 11' with a difluoromethylation reagent such as ethyl-2-bromo-2,2-difluoroacetate in the presence of a base such as sodium hydride, a solvent such as DMF, and at a suitable temperature, for example, at 60° C. to give compound 35'.

Step 2 shows converting compound 35' to the compound of Formula 1u through Buchwald amination or amidation reaction employing a suitable catalyst such as $Pd_2(dba)_3$ and Xantphos, a solvent such as 1,4-dioxane, and a base such as cesium carbonate with appropriate coupling partner (primary amides or amines) such as 2-methoxyethan-1-amine. Reactions may be run at elevated temperatures (RT-reflux) under an inert atmosphere.

Step 1a shows methylation of indole in compound 11' to give compound 37' by reacting compound 11' with a methylating reagent such as MeI in the presence of a base such as cesium carbonate, and a solvent such as DMF, and at a suitable temperature, for example, at ambient temperature.

In step 2a, compound 37' is contacted with a base under conditions sufficient to form compound 38'. For example, compound 37' is dissolved in a solvent such as 1,4-dioxane and water. A base (such as t-BuONa) and a catalyst (such as tert-BuBrettPhos-Pd-$G_3$) are added, and the mixture is heated to an appropriate temperature. The mixture is cooled to ambient temperature and acid (such as aqueous HCl) is added. The reaction mixture is diluted with EtOAc, washed (e.g., with saturated aqueous NaCl), dried (e.g., over anhydrous sodium sulfate), filtered, concentrated under reduced pressure, and purified (e.g., via silica gel flash chromatography) to give compound 38'.

In Step 3a, compound 38' is contacted with a haloacetonitrile reagent under conditions sufficient to give compound Formula 1v. For example, compound 38' is dissolved in a suitable solvent (e.g., DMF) and cooled to 0° C. A suitable base (e.g., potassium carbonate) is added followed by the addition of bromoacetonitrile, and the reaction is stirred at ambient temperature until completion. The mixture is poured into saturated aqueous sodium bicarbonate and extracted with EtOAc. The organic layers are washed (e.g., with saturated aqueous NaCl), dried (e.g., over anhydrous sodium sulfate), filtered, concentrated under reduced pressure, and purified (e.g., via silica gel flash chromatography) to give compound Formula 1v.

Scheme 14'. General Scheme for Synthesis of the Compound of Formula 1x

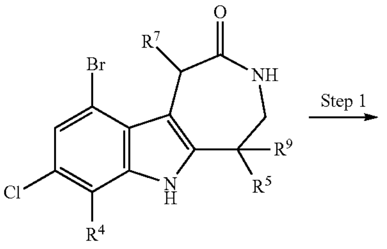

11'

-continued

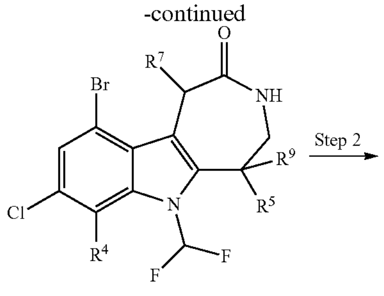

35'

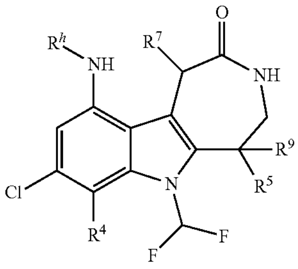

Formula 1x

Scheme 14' depicts synthesis of compounds of Formula 1x and the intermediates thereof. $R^h$ may be —C(O)—$R^{bb}$—$OR^b$ or —$CH_2$—$R^{bb}$—$OR^b$, where $R^{bb}$ and $R^b$ are as defined above with respect to embodiment 1.

Step 1 is performed according to Scheme 14 above. Step 2 shows converting compound 35' to the compound of Formula 1x through Buchwald amination or amidation reaction employing a suitable catalyst such as $Pd_2(dba)_3$ and Xantphos, a solvent such as 1,4-dioxane, and a base such as cesium carbonate with appropriate coupling partner (primary amides or amines) such as 2-methoxyethan-1-amine. Reactions may be run at elevated temperatures (RT-reflux) under an inert atmosphere.

Scheme 15. General Scheme for Synthesis of Formula 1w

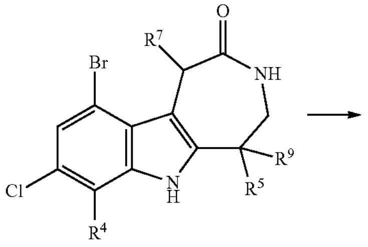

11'

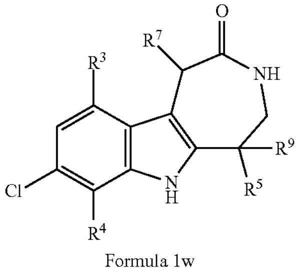

Formula 1w

Scheme 15 depicts the synthesis of the compound of Formula 1w. Compound 11' is contacted with boronic acid pinacol ester 2 under conditions sufficient (e.g., Suzuki reaction conditions) to provide the compound of Formula 1w. For example, boronic acid pinacol ester 2 is added to compound 11' along with an appropriate base (such as sodium carbonate or potassium carbonate) and $Pd(dppf)Cl_2$ catalyst in appropriate solvents (such as 1,4-dioxane and water). The mixture is sparged with $N_2$ and stirred at a suitable temperature (e.g., 90-120° C.) for a few hours. The reaction is diluted with water, extracted with EtOAc, dried (e.g., over anhydrous sodium sulfate), filtered, concentrated under reduced pressure, and purified (e.g., via silica gel chromatography) to give the compound of Formula 1w.

Scheme 15'. General Scheme for Synthesis of Formula 1w'

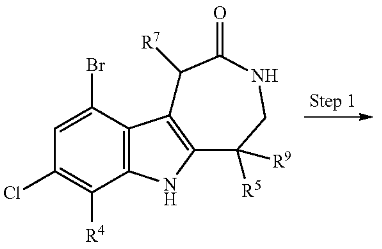

11'

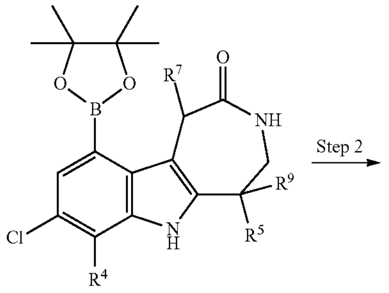

39

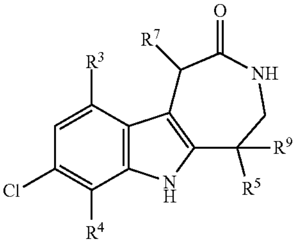

Formula 1w'

Scheme 15' depicts the synthesis of the compound of Formula 1w' and intermediates thereof. In step 1, compound 11' is converted under sufficient reaction conditions to provide a boronic acid pinacol ester compound 39. For example, an aryl bromide compound 11' is reacted with bis(pinacolato)diboron, under suitable conditions (e.g., $Pd(dppf)Cl_2$ catalyst, solvent such as 1,4 dioxane and THF, and an appropriate base such as potassium acetate) and heated for several hours under suitable temperature (e.g., 90° C.) to form crude boronic acid pinacol ester intermediate 39.

In step 2, a Suzuki reaction is shown where compound 39 is contacted with an appropriate aryl bromide or aryl iodide under conditions sufficient to provide the compound of Formula 1w'. For example, crude compound 39 is heated with an appropriate aryl bromide, a suitable solvent (e.g., 1,4 dioxane), in presence of $Pd(dppf)Cl_2$ and an appropriate base (e.g., potassium acetate, or sodium carbonate) at suitable temperature (e.g., 60 to 105° C.) for several hours until completion. The reaction mixture is cooled to ambient temperature, filtered, and rinsed through silica. The filtrate is concentrated under reduced pressure, purified (e.g., by silica gel flash chromatography) to give the compound of Formula 1w'.

The disclosure provides compounds that may be prepared as a racemic mixture or as single enantiomers. The single enantiomers may be separated via supercritical fluid chromatography. Exemplary separation condition is as follows:

Column: Chiralpak AD-H, 21×150 mm;

Mobile Phase: 30% MeOH: 70% $CO_2$, or 25% MeOH: 75% $CO_2$

Flow Rate: 80 mL/min;

Column temperature: 40° C.;

Detection: 225 nM.

These separation conditions, with any suitable modifications as a person skilled in the art deems proper, can be applied to separate enantiomers from their respective racemic mixtures, even when no specific separation conditions are provided below.

The disclosure below provides preparation methods and test results for exemplified compounds. For clarity, specific examples below that include stereocenters but without a particular stereoisomer designation shall be construed as racemic mixtures of the relevant stereoisomers.

Intermediate 1

(5-Bromo-3-chloro-2-fluorophenyl)hydrazine

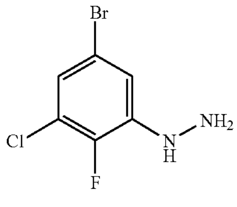 [SMILES: NNc1cc(Br)cc(Cl)c1F]

Added hydrazine hydrate (4.85 g, 48.44 mmol, 50 mass %) to a solution of 5-bromo-1-chloro-2,3-difluoro-benzene (10 g, 44 mmol) in DMSO (50 mL) under nitrogen. Stirred at 75° C. for 4 hrs. Poured the reaction mixture into ice cold water and stirred at ambient temperature for 15 min. Diluted with EtOAc and separated the layers. Washed the organic layer with saturated aqueous NaCl, dried over anhydrous sodium sulfate, filtered, and concentrated under reduced pressure to give (5-bromo-3-chloro-2-fluorophenyl)hydrazine (8.0 g, 76%) as an off-white solid. $^1H$ NMR (DMSO-d6): 7.38 (br s, 1H), 7.21 (dd, J=7.2, 2.4 Hz, 1H), 6.86 (dd, J=5.7, 2.4 Hz, 1H), 4.22 (d, J=1.6 Hz, 2H).

Intermediate 2

5-Bromo-7-chloro-8-fluoro-1,2,4,9-tetrahydrospiro[carbazole-3,2'-[1,3]dioxolane]

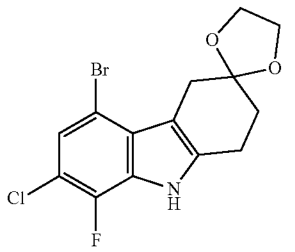 [SMILES: Fc1c(Cl)cc(Br)c2c3c([nH]c12)CCC1(C3)OCCO1]

Combined (5-bromo-3-chloro-2-fluorophenyl)hydrazine (8.0 g, 33.2 mmol), 1,4-dioxaspiro[4.5]decan-8-one (5.62 g, 36.05 mmol), and toluene (160 mL). Heated to 120° C. with stirring for 3 hrs. then cooled to ambient temperature. Added zinc chloride (5.9 g, 42.2 mmol) and heated to 120° C. with stirring for 3 days. Concentrated under reduced pressure. Diluted with EtOAc and washed with water and then with saturated aqueous NaCl, dried over anhydrous sodium sulfate, filtered, and concentrated under reduced pressure. Purified by silica gel flash chromatography eluting with hexanes/EtOAc to give 5-bromo-7-chloro-8-fluoro-1,2,4,9-tetrahydrospiro[carbazole-3,2'-[1,3]dioxolane] (5.5 g, 45%) as an off-white solid. $^1$H NMR (DMSO-d6): 11.84 (s, 1H), 7.23 (d, J=5.9 Hz, 1H), 4.02-3.91 (m, 4H), 3.12 (s, 2H), 2.81 (t, J=6.4 Hz, 2H), 1.93 (t, J=6.4 Hz, 2H).

Intermediate 3

5-Bromo-7-chloro-8-fluoro-1,2,4,9-tetrahydro-3H-carbazol-3-one

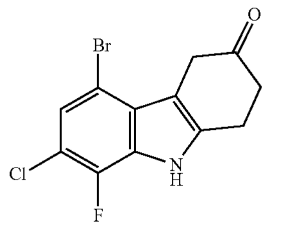 [SMILES: O=C1CCc2[nH]c3c(F)c(Cl)cc(Br)c3c2C1]

Cooled a mixture of 5-bromo-7-chloro-8-fluoro-1,2,4,9-tetrahydrospiro[carbazole-3,2'-[1,3]dioxolane] (8.0 g, 22.3 mmol) and ACN (80 mL) to 0° C. Added TFA (8.0 mL) at 0° C. Stirred at 70° C. for 16 hrs. Concentrated under reduced pressure. Triturated from 1:1 EtOAc/MTBE, collected the solid by suction filtration, washed twice with MTBE, and dried under reduced pressure to give 5-bromo-7-chloro-8-fluoro-1,2,4,9-tetrahydro-3H-carbazol-3-one (4.5 g, 64%) as a light brown solid. $^1$H NMR (DMSO-d6): 12.06 (s, 1H), 7.27 (d, J=6.0 Hz, 1H), 3.78 (s, 2H), 3.09 (t, J=7.2 Hz, 2H), 2.70 (t, J=7.2 Hz, 2H).

Intermediate 4

10-Bromo-8-chloro-7-fluoro-3,4,5,6-tetrahydroazepino[4,5-b]indol-2(1H)-one

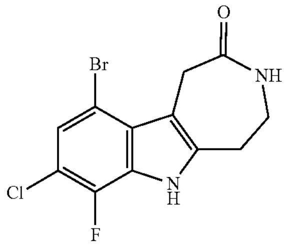

Cooled a mixture of 5-bromo-7-chloro-8-fluoro-1,2,4,9-tetrahydro-3H-carbazol-3-one (5.7 g, 18.0 mmol) in methanesulfonic acid (28.0 mL) to −15° C. Added sodium azide (1.4 g, 21.6 mmol), warmed to ambient temperature, and stirred for 30 min. Poured the reaction mixture into ice cold water, diluted with more water, and stirred at ambient temperature for 15 min. Added the mixture slowly to saturated aqueous sodium bicarbonate. Stirred at ambient temperature for 20 min. Collected the solid by suction filtration, washed with water, and dried under reduced pressure. Purified by silica gel flash chromatography eluting with DCM/MeOH to give 10-bromo-8-chloro-7-fluoro-3,4,5,6-tetrahydroazepino[4,5-b]indol-2(1H)-one (0.98 g, 16%) as a brown solid. ES/MS (m/z): 328.8/330.8/332.8 (M−H). $^1$H NMR (DMSO-d6): 11.99 (br s, 1H), 7.74 (t, J=6.3 Hz, 1H), 7.29 (d, J=6.0 Hz, 1H), 4.14 (s, 2H), 3.58-3.48 (m, 2H), 2.95-2.86 (m, 2H).

Example 1

8-Chloro-7-fluoro-10-(2-methyl-2H-1,2,3-triazol-4-yl)-3,4,5,6-tetrahydroazepino[4,5-b]indol-2(1H)-one

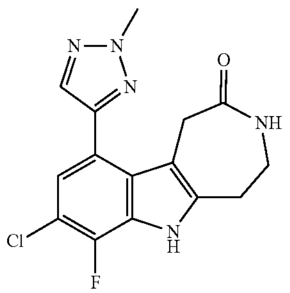

Combined 4-bromo-2-methyl-triazole (145 mg, 0.909 mmol), 1,4-dioxane (10 mL), bis(pinacolato)diboron (307 mg, 1.21 mmol), potassium acetate (118 mg, 1.21 mmol) and purged with argon for 5 min. Added Pd(dppf)$Cl_2$·DCM (9.9 mg, 0.0121 mmol), and purge again with argon. Heated to 60° C. for 30 min. Added 10-bromo-8-chloro-7-fluoro-3,4,5,6-tetrahydroazepino[4,5-b]indol-2(1H)-one (200 mg, 0.606 mmol) and heated to 100° C. for 16 hrs. Cooled to ambient temperature and filtered through diatomaceous earth rinsing with EtOAc. Washed the filtrate with water and then with saturated aqueous NaCl, dried over anhydrous sodium sulfate, filtered, and concentrated under reduced pressure. Purified by reverse phase chromatography followed by SFC chromatography to give 8-chloro-7-fluoro-10-(2-methyl-2H-1,2,3-triazol-4-yl)-3,4,5,6-tetrahydroazepino[4,5-b]indol-2(1H)-one (50 mg, 0.15 mmol, 26%) as an off-white solid. ES/MS (m/z): 333.8/335.8 (M+H). $^1$H NMR (DMSO-d6): 11.83 (br s, 1H), 7.93 (s, 1H), 7.67 (t, J=6.4 Hz, 1H), 7.03 (d, J=6.5 Hz, 1H), 4.23 (s, 3H), 3.54-3.46 (m, 2H), 2.96-2.88 (m, 2H).

Intermediate 5

(5-Bromo-2,3-dichlorophenyl)hydrazine

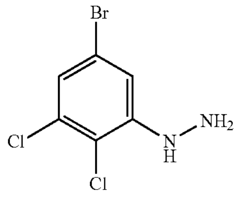 [SMILES: NNc1cc(Br)cc(Cl)c1Cl]

Added hydrazine hydrate (13.0 mL, 135 mmol, 51 mass %) to a solution of 5-bromo-1,2-dichloro-3-fluoro-benzene (16.5 g, 64.3 mmol) in DMSO (64 mL) under $N_2$. Stirred at 75° C. for 3 hrs. Cooled to ambient temperature and added about 150 mL of water. Stirred at ambient temperature for 30 min and poured into 200 mL of water. Collected the solid, washed three times with water, and dried under reduced pressure at 60° C. to give (5-bromo-2,3-dichlorophenyl) hydrazine (16.73 g, 99+%) as a white solid. ES/MS (m/z): 252.6/254.6/256.6 (M−H).

Intermediate 6

5-Bromo-7,8-dichloro-1,2,4,9-tetrahydrospiro[carbazole-3,2'-[1,3]dioxolane]

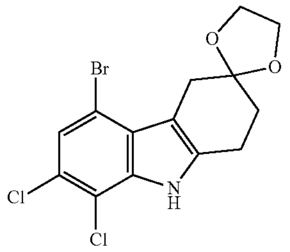

Combined (5-bromo-2,3-dichlorophenyl)hydrazine (5.00 g, 19.5 mmol), 1,4-dioxaspiro[4.5]decan-8-one (3.15 g, 19.6 mmol, 97 mass %), and toluene (126 mL). Refluxed for 30 min and cooled to ambient temperature. Added zinc chloride (3.20 g, 23.5 mmol). Refluxed for 3 days. Added zinc chloride (3.20 g, 23.5 mmol) and refluxed for 2 days. Cooled to ambient temperature, diluted with EtOAc and 1N aqueous sodium hydroxide. Separated the layers. Added 5N aqueous HCl to the aqueous layer until pH 7. Extracted the aqueous layer with EtOAc (3×). Washed the combined organic layers with saturated aqueous NaCl, dried over anhydrous sodium sulfate, filtered, and concentrated under reduced pressure. Dissolved the residue in hot EtOAc and cooled to ambient temperature slowly. Collected the solid by suction filtration and washed twice with EtOAc to give 5-bromo-7,8-dichloro-1,2,4,9-tetrahydrospiro[carbazole-3,2'-[1,3]dioxolane] (3.56 g, 8.97 mmol, 95 mass %, 46% yield) as a brown solid.

Concentrated the filtrate, purified the residue by silica gel flash chromatography eluting with hexanes/EtOAc, and dried under reduced pressure to yield additional 5-bromo-7,8-dichloro-1,2,4,9-tetrahydrospiro[carbazole-3,2'-[1,3]dioxolane] (950 mg, 13%) as a pale-yellow solid. ES/MS (m/z): 376.0/378.0/380.0 (M+H).

Intermediate 7

5-Bromo-7,8-dichloro-1,2,4,9-tetrahydro-3H-carbazol-3-one

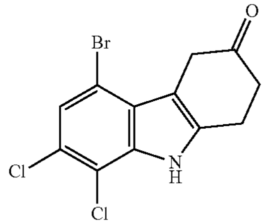

Combined 5-bromo-7,8-dichloro-1,2,4,9-tetrahydrospiro[carbazole-3,2'-[1,3]dioxolane](2.22 g, 5.77 mmol, 98 mass %) and acetone (29 mL). Purged with $N_2$ and added TFA (0.92 mL, 12 mmol). Stirred at reflux for 4 days. Cooled to ambient temperature, concentrated, and dried under reduced pressure. Combined the residue and acetone (29 mL). Purged with $N_2$ and added TFA (0.92 mL, 12 mmol). Stirred at reflux for 20 hrs. Cooled to ambient temperature and concentrated under reduced pressure. Suspended the residue in $Et_2O$ and allowed to stand overnight. Collected the solid by suction filtration and washed twice with $Et_2O$ to give 5-bromo-7,8-dichloro-1,2,4,9-tetrahydro-3H-carbazol-3-one (1.32 g, 65%) as a yellow solid.

Concentrated the filtrate, suspended the residue in $Et_2O$, and allowed to stand overnight. Collected the solid and washed twice with $Et_2O$ to yield additional 5-bromo-7,8-dichloro-1,2,4,9-tetrahydro-3H-carbazol-3-one (109 mg, 5%) as a light brown solid. ES/MS (m/z): 329.8/331.8/333.8 (M−H).

Intermediate 8

10-Bromo-7,8-dichloro-3,4,5,6-tetrahydroazepino[4,5-b]indol-2(1H)-one

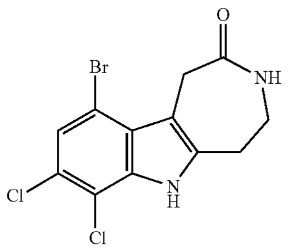 [SMILES: O=C1Cc2c([nH]c3c(Cl)c(Cl)cc(Br)c23)CCN1]

Cooled a suspension of 5-bromo-7,8-dichloro-1,2,4,9-tetrahydro-3H-carbazol-3-one (1.32 g, 3.77 mmol, 95 mass %) in methanesulfonic acid (25 mL) in an ice water bath until the solvent was almost frozen. Added sodium azide (321 mg, 4.89 mmol) slowly and stirred at 0° C. Allowed reaction to warm to ambient temperature slowly while stirring overnight. Added the reaction mixture dropwise to a stirring mixture of ice and 2M aqueous potassium carbonate. Collected the solid and washed twice with water. Triturated the solid with EtOAc. Collected the solid and washed twice with EtOAc. Concentrated the filtrate and purified the residue by silica gel flash chromatography eluting with DCM/MeOH. Combined pure fractions with the solid from the trituration with EtOAc. Dissolved the product in DCM and concentrated under reduced pressure. Dried under reduced pressure to give 10-bromo-7,8-dichloro-3,4,5,6-tetrahydroazepino[4,5-b]indol-2(1H)-one (601 mg, 44%) as a brown solid. ES/MS (m/z): 344.8/346.8/348.8 (M−H).

Example 2

7,8-Dichloro-10-(2-methyl-2H-1,2,3-triazol-4-yl)-3,4,5,6-tetrahydroazepino[4,5-b]indol-2(1H)-one

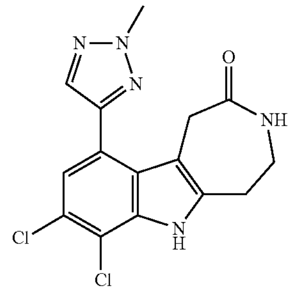 [SMILES: Cn1ncc(-c2cc(Cl)c(Cl)c3[nH]c4c(c23)CC(=O)NCC4)n1]

Combined 4-bromo-2-methyl-triazole (205 mg, 1.20 mmol, 95 mass %), bis(pinacolato)diboron (374 mg, 1.44 mmol), potassium acetate (238 mg, 2.40 mmol), Pd(dppf)$Cl_2$ (72 mg, 0.096 mmol), and DMF (6.0 mL) under $N_2$. Purged with $N_2$ and heated to 100° C. for 5 hrs. Cooled to ambient temperature and diluted with EtOAc. Washed twice with water and then with saturated aqueous NaCl, dried over anhydrous sodium sulfate, filtered, and concentrated under reduced pressure. Dissolved in DCM and concentrated under reduced pressure twice. Purified by silica gel flash chromatography eluting with hexanes/EtOAc to give impure 2-methyl-4-(4,4,5,5-tetramethyl-1,3,2-dioxaborolan-2-yl)-2H-1,2,3-triazole. Combined with 10-bromo-7,8-dichloro-3,4,5,6-tetrahydroazepino[4,5-b]indol-2(1H)-one (50 mg, 0.14 mmol, 97 mass %), sodium carbonate (44 mg, 0.42 mmol), Pd(dppf)$Cl_2$ (16 mg, 0.021 mmol), 1,4-dioxane (1.0 mL) and water (0.2 mL) under $N_2$. Purged with $N_2$ and heated to 100° C. for 2 hrs. Cooled to ambient temperature and added Pd(dppf)$Cl_2$ (16 mg, 0.021 mmol). Purged with $N_2$, and heated to 100° C. for 1.5 hrs. and cooled to ambient temperature. Filtered through a plug of silica gel and rinsed through the silica with 9:1 DCM/MeOH. Concentrated the filtrate under reduced pressure. Purified by silica gel flash chromatography eluting with DCM/MeOH. Purified further by HPLC to give 7,8-dichloro-10-(2-methyl-2H-1,2,3-triazol-4-yl)-3,4,5,6-tetrahydroazepino[4,5-b]indol-2(1H)-one (10 mg, 20%) as an off-white solid. ES/MS (m/z): ($^{35}Cl/^{37}Cl$) 350.0/352.0 (M+H). $^1H$ NMR (DMSO-d6): 11.63 (s, 1H), 7.97 (s, 1H), 7.67 (t, J=6.4 Hz, 1H), 7.16 (s, 1H), 4.24 (s, 3H), 3.55-3.46 (m, 2H), 2.99-2.91 (m, 2H).

Example 3

7,8-Dichloro-10-(1-methyl-1H-pyrazol-3-yl)-3,4,5,6-tetrahydroazepino[4,5-b]indol-2(1H)-one

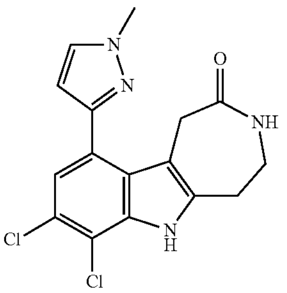 [SMILES: Cn1ccc(-c2cc(Cl)c(Cl)c3[nH]c4c(c23)CC(=O)NCC4)n1]

Combined 10-bromo-7,8-dichloro-3,4,5,6-tetrahydroazepino[4,5-b]indol-2(1H)-one (150 mg, 0.418 mmol, 97 mass %), 1-methyl-3-(4,4,5,5-tetramethyl-1,3,2-dioxaborolan-2-yl)pyrazole (155 mg, 0.730 mmol, 98 mass %), sodium carbonate (133 mg, 1.25 mmol), Pd(dppf)$Cl_2$ (47 mg, 0.063 mmol), 1,4-dioxane (2.8 mL) and water (0.56 mL) under $N_2$. Purged with $N_2$ and heated to 120° C. for 2 hrs. Cooled to ambient temperature and diluted the reaction mixture with EtOAc. Washed twice with water and then with saturated aqueous NaCl, dried over anhydrous sodium sulfate, filtered, and concentrated under reduced pressure. Purified by silica gel flash chromatography eluting with DCM/MeOH and dried under reduced pressure at 60° C. to give 7,8-dichloro-10-(1-methyl-1H-pyrazol-3-yl)-3,4,5,6-tetrahydroazepino[4,5-b]indol-2(1H)-one (62 mg, 42%) as a light brown solid. ES/MS (m/z): ($^{35}Cl/^{37}Cl$) 348.6/350.6 (M+H). $^1H$ NMR (DMSO-d6): 11.49 (s, 1H), 7.80 (d, J=2.2 Hz, 1H), 7.62 (t, J=6.3 Hz, 1H), 7.08 (s, 1H), 6.42 (d, J=2.2 Hz, 1H), 3.92 (s, 3H), 3.54-3.47 (m, 2H), 3.43 (s, 2H), 2.96-2.90 (m, 2H).

Intermediate 9

2-Methyl-4-(4,4,5,5-tetramethyl-1,3,2-dioxaborolan-2-yl)-2H-1,2,3-triazole

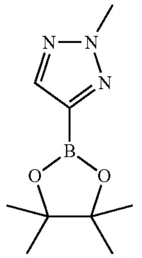

Combined 4-bromo-2-methyl-triazole (400 mg, 2.40 mmol, 97 mass %), bis(pinacolato)diboron (683 mg, 2.64 mmol, 98 mass %), potassium acetate (712 mg, 7.18 mmol), Pd(dppf)$Cl_2$ (197 mg, 0.264 mmol), and 1,4-dioxane (12.0 mL) under $N_2$. Purged with $N_2$, and heated to 100° C. for 1.5 hrs. and cooled to ambient temperature. Repeated the reaction twice on identical scale and combined all three reaction mixtures. Filtered the mixture through a plug of silica gel and rinsed through the silica with EtOAc. Concentrated the filtrate under reduced pressure. Purified by silica gel flash chromatography eluting with hexanes/EtOAc. Dissolved the product in DCM, concentrated, and dried under reduced pressure, to give 2-methyl-4-(4,4,5,5-tetramethyl-1,3,2-dioxaborolan-2-yl)-2H-1,2,3-triazole (1.22 g, 80%) as a light brown solid. ES/MS (m/z): 209.8 (M+H). $^1$H NMR ($CDCl_3$): 7.89 (s, 1H), 4.25 (s, 3H), 1.36 (s, 12H).

Intermediate 10

Ethyl 2-(8-oxo-1,4-dioxaspiro[4.5]decan-7-yl)acetate

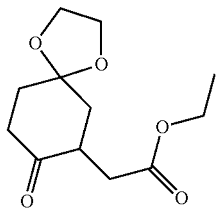 [SMILES: CCOC(=O)CC1CC2(CCC1=O)OCCO2]

Dissolved 1,4-dioxaspiro[4.5]decan-8-one (7.00 g, 43.5 mmol, 97 mass %) in THF (145 mL) and cooled to −78° C. Added LDA (25 mL, 50 mmol, 2.0M in THF/heptane/ethylbenzene) dropwise over 20 min. Stirred the solution for 30 min at −78° C. Added ethyl bromoacetate (5.66 mL, 50.0 mmol, 98 mass %) dropwise over 10 min. Stirred the solution for 1 hr at −78° C., warmed to ambient temperature, and stirred for 1 hr. Quenched with saturated aqueous $NH_4Cl$. Diluted with EtOAc and water and separated the layers. Washed the organic layer with saturated aqueous NaCl, dried over anhydrous sodium sulfate, filtered, and concentrated under reduced pressure to give the crude product. Repeated the reaction using an identical procedure except for using 1,4-dioxaspiro[4.5]decan-8-one (4.90 g, 30.4 mmol, 97 mass %) in THF (100 mL), LDA (17 mL, 34 mmol, 2.0M in THF/heptane/ethylbenzene), and ethyl bromoacetate (3.96 mL, 35.0 mmol, 98 mass %) and then combined the crude products. Purified about half of the crude product by silica gel flash chromatography eluting with hexanes/EtOAc. Combined the mixed fractions with the other half of the crude product and purified by silica gel flash chromatography (DCM/EtOAc). Combined the mostly pure fractions from each chromatography run, concentrated under reduced pressure, and crystallized the residue from EtOAc/hexanes. Collected the solid, washed three times with hexanes, and dried under reduced pressure to give racemic ethyl 2-(8-oxo-1,4-dioxaspiro[4.5]decan-7-yl)acetate (4.81 g, 26% yield) as a white solid.

Concentrated the filtrate from the crystallization and concentrated under reduced pressure. Purified by silica gel flash chromatography eluting with DCM/EtOAc. Combined the mostly pure fractions, concentrated under reduced pressure, and crystallized the residue from EtOAc/hexanes. Collected the solid, washed three times with hexanes, and dried under reduced pressure to give additional racemic ethyl 2-(8-oxo-1,4-dioxaspiro[4.5]decan-7-yl)acetate (1.00 g, 5%) as a white solid. ES/MS (m/z): 243.0 (M+H). $^1$H NMR ($CDCl_3$): 4.18-4.08 (m, 2H), 4.08-3.98 (m, 4H), 3.20 (sextet, J=6.5 Hz, 1H), 2.77-2.66 (m, 2H), 2.40 (ddd, J=14.4, 5.0, 2.8 Hz, 1H), 2.19 (dd, J=6.1, 16.6 Hz, 1H), 2.15-1.93 (m, 3H), 1.81 (t, J=13.3 Hz, 1H), 1.25 (t, J=7.1 Hz, 3H).

Intermediate 11

Ethyl 2-(5-bromo-7,8-dichloro-1,2,4,9-tetrahydrospiro[carbazole-3,2'-[1,3]dioxolan]-1-yl)acetate

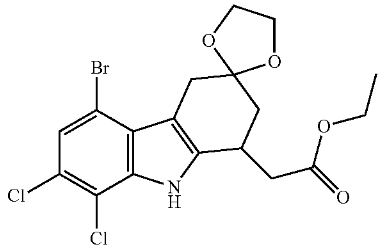 [SMILES: CCOC(=O)CC1CC2(Cc3c1[nH]c1c(Cl)c(Cl)cc(Br)c31)OCCO2]

Combined (5-bromo-2,3-dichlorophenyl)hydrazine (4.93 g, 18.9 mmol, 98 mass %), racemic ethyl 2-(8-oxo-1,4-dioxaspiro[4.5]decan-7-yl)acetate, (4.81 g, 18.9 mmol), and toluene (126 mL). Refluxed for 22 hrs. and cooled to ambient temperature to generate the crude hydrazone solution. Charged a separate flask with zinc chloride (3.09 g, 22.7 mmol) and heated the contents under reduced pressure until the zinc chloride became a free-flowing solid. Cooled to ambient temperature, added the contents of the flask containing the hydrazone solution, and purged with $N_2$. Refluxed for 6 days and cooled to ambient temperature. Diluted with EtOAc and saturated aqueous sodium bicarbonate. Added 5N aqueous HCl until pH 7. Separated the layers and extracted the aqueous layer with EtOAc. Dried the combined organic layers over anhydrous sodium sulfate, filtered, and concentrated under reduced pressure. Purified by silica gel flash chromatography eluting with hexanes/EtOAc and dried under reduced pressure to give racemic ethyl 2-(5-bromo-7,8-dichloro-1,2,4,9-tetrahydrospiro[carbazole-3,2'-[1,3]dioxolan]-1-yl)acetate (1.82 g, 21%). ES/MS (m/z): 462.0/464.0/466.0 (M+H).

Intermediate 12

Ethyl 2-(5-bromo-7,8-dichloro-3-oxo-2,3,4,9-tetrahydro-1H-carbazol-1-yl)acetate

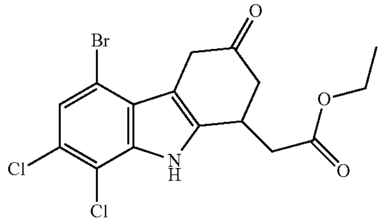 [SMILES: CCOC(=O)CC1CC(=O)Cc2c1[nH]c1c(Cl)c(Cl)cc(Br)c21]

Combined ethyl 2-(5-bromo-7,8-dichloro-1,2,4,9-tetrahydrospiro[carbazole-3,2'-[1,3]dioxolan]-1-yl)acetate (1.82 g, 3.89 mmol, 99 mass %) and acetone (19.4 mL). Purged with $N_2$ and added TFA (0.62 mL, 8.2 mmol). Heated the mixture to 85° C. for 4 days. Cooled to ambient temperature, concentrated, and dried under reduced pressure. Combined the residue and acetone (19.4 mL). Purged with $N_2$ and added TFA (0.62 mL). Heated mixture to 85° C. for 20 hrs. Cooled to ambient temperature and concentrated under reduced pressure. Suspended the residue in $Et_2O$ and allowed to stand overnight. Collected the solid by suction filtration and washed twice with $Et_2O$ to give racemic ethyl 2-(5-bromo-7,8-dichloro-3-oxo-2,3,4,9-tetrahydro-1H-carbazol-1-yl)acetate (1.19 g, 69%) as a pale-yellow solid. ES/MS (m/z): 417.8/419.8/421.8 (M+H).

Intermediate 13

Ethyl 2-(10-bromo-7,8-dichloro-2-oxo-1,2,3,4,5,6-hexahydroazepino[4,5-b]indol-5-yl)acetate

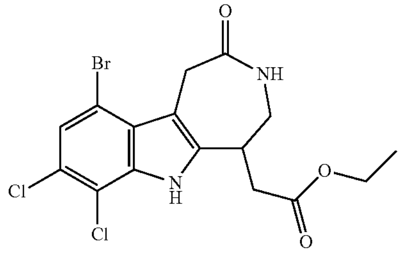 [SMILES: CCOC(=O)CC1CNC(=O)Cc2c1[nH]c1c(Cl)c(Cl)cc(Br)c21]

Cooled a suspension of ethyl 2-(5-bromo-7,8-dichloro-3-oxo-2,3,4,9-tetrahydro-1H-carbazol-1-yl)acetate (1.19 g, 2.70 mmol, 95 mass %) in methanesulfonic acid (18 mL) in an ice water bath until the solvent was almost frozen. Added sodium azide (230 mg, 3.50 mmol) slowly and stirred for 4 hrs. at 0° C. Allowed the reaction to warm to ambient temperature while stirring overnight. Added the reaction mixture dropwise to a stirring mixture of ice and 2M aqueous potassium carbonate. Diluted with EtOAc and separated the layers. Washed the organic layer with saturated aqueous NaCl, dried over anhydrous sodium sulfate, filtered, and concentrated under reduced pressure. Triturated with DCM and then with EtOAc. Concentrated the filtrate and purified the residue by silica gel flash chromatography eluting with DCM/EtOAc and dried under reduced pressure to give racemic ethyl 2-(10-bromo-7,8-dichloro-2-oxo-1,2,3,4,5,6-hexahydroazepino[4,5-b]indol-5-yl)acetate (442 mg, 0.927 mmol, 91 mass %, 34% yield) as a pale-yellow solid.

Combined mixed fractions with the solid from the trituration with DCM. Concentrated the filtrate and purified the residue by silica gel flash chromatography eluting with DCM/EtOAc. Dissolved the product in DCM and concentrated under reduced pressure. Purified the residue with reverse phase chromatography to yield additional racemic ethyl 2-(10-bromo-7,8-dichloro-2-oxo-1,2,3,4,5,6-hexahydroazepino[4,5-b]indol-5-yl)acetate (94 mg, 8%) as an off-white solid. ES/MS (m/z): 433.0/435.0/437.0 (M+H). $^1H$ NMR (DMSO-d6): 11.74 (s, 1H), 7.86-7.78 (m, 1H), 7.43 (s, 1H), 4.23 (d, J=15.7 Hz, 1H), 4.19-4.06 (m, 2H), 4.06 (d, J=15.7 Hz, 1H), 3.73-3.62 (m, 1H), 3.48-3.38 (m, 2H), 2.93 (dd, J=17.1, 1.5 Hz, 1H), 2.64 (dd, J=17.1, 10.1 Hz, 1H), 1.22 (t, J=7.1 Hz, 3H).

Example 4

Ethyl 2-(7,8-dichloro-10-(2-methyl-2H-1,2,3-triazol-4-yl)-2-oxo-1,2,3,4,5,6-hexahydroazepino[4,5-b]indol-5-yl)acetate

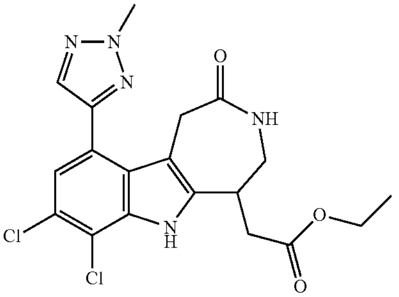 [SMILES: CCOC(=O)CC1CNC(=O)Cc2c1[nH]c1c(Cl)c(Cl)cc(-c3cnn(C)n3)c21]

Combined ethyl 2-(10-bromo-7,8-dichloro-2-oxo-1,2,3,4,5,6-hexahydroazepino[4,5-b]indol-5-yl)acetate (242 mg, 0.507 mmol, 91 mass %), 2-methyl-4-(4,4,5,5-tetramethyl-1,3,2-dioxaborolan-2-yl)-2H-1,2,3-triazole (166 mg, 0.762 mmol, 96 mass %), sodium carbonate (161 mg, 1.52 mmol), $Pd(dppf)Cl_2$ (57 mg, 0.076 mmol), 1,4-dioxane (3.4 mL) and water (0.68 mL) under $N_2$. Purged with $N_2$ and heated to 100° C. for 2.5 hrs. Cooled to ambient temperature and diluted the reaction mixture with EtOAc. Filtered the solution through a plug of silica gel and rinsed through the silica with 9:1 EtOAc/MeOH. Concentrated the filtrate under reduced pressure. Purified by silica gel flash chromatography eluting with EtOAc/MeOH. Dissolved the product in DCM, concentrated, and dried under reduced pressure at 60° C. to give racemic ethyl 2-(7,8-dichloro-10-(2-methyl-2H-1,2,3-triazol-4-yl)-2-oxo-1,2,3,4,5,6-hexahydroazepino[4,5-b]indol-5-yl)acetate (176 mg, 76%) as a cream-colored solid. ES/MS (m/z): ($^{35}Cl/^{37}Cl$) 436.0/438.0 (M+H). $^1H$ NMR (DMSO-d6): 11.62 (s, 1H), 7.96 (s, 1H), 7.78-7.75 (m, 1H), 7.17 (s, 1H), 4.24 (s, 3H), 4.20-4.06 (m, 2H), 3.69-3.60 (m, 1H), 3.43 (d, J=15.8 Hz, 1H), 3.49-3.37 (m, 2H), 3.24 (d, J=15.8 Hz, 1H), 2.99 (dd, J=17.2, 1.8 Hz, 1H), 2.61 (dd, J=17.2, 10.4 Hz, 1H), 1.22 (t, J=7.1 Hz, 3H).

Example 5

2-(7,8-Dichloro-10-(2-methyl-2H-1,2,3-triazol-4-yl)-2-oxo-1,2,3,4,5,6-hexahydroazepino[4,5-b]indol-5-yl)acetic acid

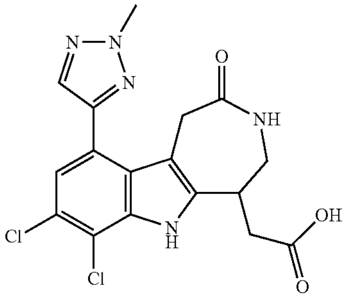 [SMILES: Cn1ncc(-c2cc(Cl)c(Cl)c3[nH]c4c(c23)CC(=O)NCC4CC(=O)O)n1]

Combined ethyl 2-(7,8-dichloro-10-(2-methyl-2H-1,2,3-triazol-4-yl)-2-oxo-1,2,3,4,5,6-hexahydroazepino[4,5-b]indol-5-yl)acetate (124 mg, 0.276 mmol, 97 mass %), THF (1.4 mL), MeOH (1.4 mL), and 5N aqueous NaOH (0.11 mL). Stirred at ambient temperature for 6 hrs. Added 5N aqueous HCl until pH 2. Diluted with EtOAc and saturated aqueous NaCl. Separated the layers and extracted the aqueous layer with EtOAc (5×). Dried the combined organic layers over anhydrous sodium sulfate, filtered, concentrated, and dried under reduced pressure at 70° C. to give racemic 2-(7,8-dichloro-10-(2-methyl-2H-1,2,3-triazol-4-yl)-2-oxo-1,2,3,4,5,6-hexahydroazepino[4,5-b]indol-5-yl)acetic acid (71 mg, 61%) as a cream-colored solid. Extracted the aqueous layer with 9:1 DCM/iPrOH (3×). Dried the combined organic layers over anhydrous sodium sulfate, filtered, concentrated, and dried under reduced pressure at 70° C. Dissolved the residue in DCM, concentrated (2×), and dried under reduced pressure at 70° C. to yield a second crop of racemic 2-(7,8-dichloro-10-(2-methyl-2H-1,2,3-triazol-4-yl)-2-oxo-1,2,3,4,5,6-hexahydroazepino[4,5-b]indol-5-yl) acetic acid (6 mg, 5%) as an off-white solid. ES/MS (m/z): ($^{35}Cl/^{37}Cl$) 408.0/410.0 (M+H). $^1H$ NMR (DMSO-d6): 12.37 (s, 1H), 11.62 (s, 1H), 7.96 (s, 1H), 7.78 (t, J=6.3 Hz, 1H), 7.16 (s, 1H), 4.24 (s, 3H), 3.70-3.60 (m, 1H), 3.43 (d, J=15.8 Hz, 1H), 3.47-3.37 (m, 2H), 3.24 (d, J=15.8 Hz, 1H), 2.92 (d, J=18.3 Hz, 1H), 2.53 (dd, J=17.6, 10.1 Hz, 1H).

Example 6

2-(7,8-Dichloro-10-(2-methyl-2H-1,2,3-triazol-4-yl)-2-oxo-1,2,3,4,5,6-hexahydroazepino[4,5-b]indol-5-yl)-N-methylacetamide

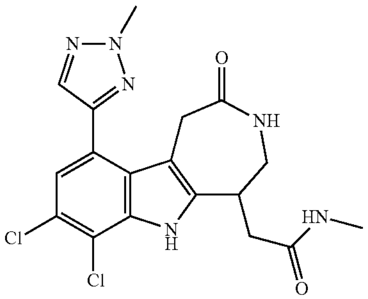 [SMILES: CNC(=O)CC1CNC(=O)Cc2c1[nH]c1c(Cl)c(Cl)cc(-c3cnn(C)n3)c21]

Combined 2-(7,8-dichloro-10-(2-methyl-2H-1,2,3-triazol-4-yl)-2-oxo-1,2,3,4,5,6-hexahydroazepino[4,5-b]indol-5-yl)acetic acid (30 mg, 0.071 mmol), DMF (0.7 mL), methylamine (0.18 mL, 0.36 mmol, 2.0M in THF), and 2,4,6-triisopropyl-1,3,5,2,4,6-trioxatriphosphorinane-2,4,6-trioxide (86 μL, 50% in EtOAc). Stirred at ambient temperature for 3 hrs. Added methylamine (0.18 mL, 0.36 mmol, 2.0M in THF) and 2,4,6-triisopropyl-1,3,5,2,4,6-trioxatriphosphorinane-2,4,6-trioxide (86 μL, 50% in EtOAc) and stirred at ambient temperature for 1.5 hrs. Diluted with EtOAc, saturated aqueous sodium bicarbonate, water, and saturated aqueous NaCl. Separated the layers and extracted the aqueous layer with EtOAc (3×) and with 9:1 DCM/iPrOH (3×). Dried the combined organic layers over anhydrous sodium sulfate, filtered, and concentrated under reduced pressure. Purified by silica gel flash chromatography eluting with DCM/MeOH. Dissolved the product in DCM then concentrated and dried under reduced pressure at 70° C. to give 2-(7,8-dichloro-10-(2-methyl-2H-1,2,3-triazol-4-yl)-2-oxo-1,2,3,4,5,6-hexahydroazepino[4,5-b]indol-5-yl)-N-methylacetamide (16 mg, 51%) as an off-white solid. ES/MS (m/z): ($^{35}Cl/^{37}Cl$) 421.0/423.0 (M+H). $^1H$ NMR (DMSO-d6): 11.68 (s, 1H), 7.97 (s, 1H), 7.89 (q, J=4.5 Hz, 1H), 7.71 (t, J=6.3 Hz, 1H), 7.16 (s, 1H), 4.24 (s, 3H), 3.63-3.54 (m, 1H), 3.48-3.33 (m, 2H), 3.39 (d, J=16.1 Hz, 1H), 3.28 (d, J=16.1 Hz, 1H), 2.77 (dd, J=15.3, 3.7 Hz, 1H), 2.64 (d, J=4.5 Hz, 3H), 2.38 (dd, J=15.3, 9.7 Hz, 1H).

Example 7

2-(7,8-Dichloro-10-(2-methyl-2H-1,2,3-triazol-4-yl)-2-oxo-1,2,3,4,5,6-hexahydroazepino[4,5-b]indol-5-yl)-N,N-dimethylacetamide

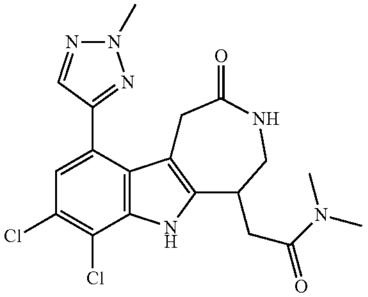 [SMILES: CN(C)C(=O)CC1CNC(=O)Cc2c1[nH]c1c(Cl)c(Cl)cc(-c3cnn(C)n3)c21]

Combined 2-(7,8-dichloro-10-(2-methyl-2H-1,2,3-triazol-4-yl)-2-oxo-1,2,3,4,5,6-hexahydroazepino[4,5-b]indol-5-yl)acetic acid (30 mg, 0.071 mmol), DMF (0.7 mL), dimethylamine (0.18 mL, 0.36 mmol, 2.0M in THF), and 2,4,6-triisopropyl-1,3,5,2,4,6-trioxatriphosphorinane-2,4,6-trioxide (86 μL, 50% in EtOAc). Stirred at ambient temperature for 3 hrs. Diluted with EtOAc and saturated aqueous sodium bicarbonate and separated the layers. Washed the organic layer with water and then with saturated aqueous NaCl, dried over anhydrous sodium sulfate, filtered, and concentrated under reduced pressure. Purified by silica gel flash chromatography eluting with DCM/MeOH. Dissolved the product in DCM then concentrated and dried under reduced pressure at 70° C. to give 2-(7,8-dichloro-10-(2-methyl-2H-1,2,3-triazol-4-yl)-2-oxo-1,2,3,4,5,6-hexahydroazepino[4,5-b]indol-5-yl)-N,N-dimethylacetamide (18 mg, 57%) as a cream-colored solid. ES/MS (m/z): ($^{35}Cl$/$^{37}Cl$) 435.0/437.0 (M+H). $^1$H NMR (DMSO-d6): 11.58 (s, 1H), 7.96 (s, 1H), 7.72 (t, J=6.4 Hz, 1H), 7.16 (s, 1H), 4.24 (s, 3H), 3.66 (ddd, J=14.5, 6.4, 2.9 Hz, 1H), 3.55-3.47 (m, 1H), 3.47 (d, J=15.9 Hz, 1H), 3.36 (dt, J=14.5, 6.4 Hz, 1H), 3.22 (d, J=15.9 Hz, 1H), 2.97 (s, 3H), 2.90 (s, 3H), 2.82 (dd, J=16.9, 3.2 Hz, 1H), 2.67 (dd, J=16.9, 9.5 Hz, 1H).

Example 8

7,8-Dichloro-5-(2-hydroxyethyl)-10-(2-methyl-2H-1,2,3-triazol-4-yl)-3,4,5,6-tetrahydroazepino[4,5-b]indol-2(1H)-one

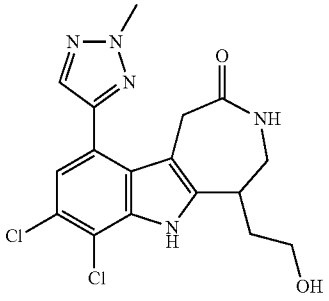 [SMILES: Cn1ncc(-c2cc(Cl)c(Cl)c3[nH]c4c(c23)CC(=O)NCC4CCO)n1]

Cooled a solution of ethyl 2-(7,8-dichloro-10-(2-methyl-2H-1,2,3-triazol-4-yl)-2-oxo-1,2,3,4,5,6-hexahydroazepino[4,5-b]indol-5-yl)acetate (60 mg, 0.13 mmol) in DCM (1.9 mL) under $N_2$ to −78° C. Added DIBAL-H (0.54 mL, 0.65 mmol, 1.2 M in toluene) dropwise. Warmed the reaction mixture to ambient temperature, stirred for 10 min, cooled to −78° C., and quenched with EtOAc. Warmed to ambient temperature and diluted with DCM and saturated aqueous potassium sodium tartrate. Stirred for 15 min and separated the layers. Extracted the aqueous layer twice with DCM. Dried the combined organic layers over anhydrous sodium sulfate, filtered, and concentrated under reduced pressure. Purified by silica gel flash chromatography eluting with DCM/MeOH. Dried under reduced pressure at 70° C. to give 7,8-dichloro-5-(2-hydroxyethyl)-10-(2-methyl-2H-1,2,3-triazol-4-yl)-3,4,5,6-tetrahydroazepino[4,5-b]indol-2(1H)-one (19 mg, 0.047 mmol, 36%) as an off-white solid. ES/MS (m/z): ($^{35}Cl$/$^{37}Cl$) 394.0/396.0 (M+H). $^1$H NMR (DMSO-d6): 11.55 (s, 1H), 7.96 (s, 1H), 7.69 (t, J=6.4 Hz, 1H), 7.15 (s, 1H), 4.66 (t, J=4.7 Hz, 1H), 4.24 (s, 3H), 3.65-3.55 (m, 3H), 3.41 (d, J=15.9 Hz, 1H), 3.43-3.35 (m, 1H), 3.24 (d, J=15.9 Hz, 1H), 3.16-3.08 (m, 1H), 2.10-1.99 (m, 1H), 1.78-1.67 (m, 1H).

Example 8A (R)-7,8-Dichloro-5-(2-hydroxyethyl)-10-(2-methyl-2H-1,2,3-triazol-4-yl)-3,4,5,6-tetrahydroazepino[4,5-b]indol-2(1H)-one Or (S)-7,8-Dichloro-5-(2-hydroxyethyl)-10-(2-methyl-2H-1,2,3-triazol-4-yl)-3,4,5,6-tetrahydroazepino[4,5-b]indol-2(1H)-one (isomer 1) and Example 8B (R)-7,8-Dichloro-5-(2-hydroxyethyl)-10-(2-methyl-2H-1,2,3-triazol-4-yl)-3,4,5,6-tetrahydroazepino[4,5-b]indol-2(1H)-one Or (S)-7,8-Dichloro-5-(2-hydroxyethyl)-10-(2-methyl-2H-1,2,3-triazol-4-yl)-3,4,5,6-tetrahydroazepino[4,5-b]indol-2(1H)-one (isomer 2)

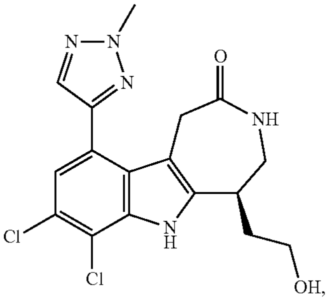

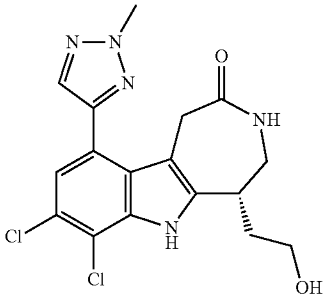

Purified racemic 7,8-dichloro-5-(2-hydroxyethyl)-10-(2-methyl-2H-1,2,3-triazol-4-yl)-3,4,5,6-tetrahydroazepino[4,5-b]indol-2(1H)-one (67 mg, 0.17 mmol) by supercritical fluid chromatography to yield the titled compounds (Isomer 1—Rt=1.31 min (97% ee), 28 mg, 41%; Isomer 2—Rt=2.40 min (97% ee), 24 mg, 36%). Column: Chiralpak AD-H, 21×150 mm; Mobile Phase: 30% MeOH: 70% $CO_2$; Flow Rate: 80 mL/min; Column temperature: 40° C.; Detection: 225 nM. ES/MS (m/z): ($^{35}Cl$/$^{37}Cl$) 394.0/396.0 (M+H). $^1$H NMR (DMSO-d6): 11.55 (s, 1H), 7.96 (s, 1H), 7.69 (t, J=6.4 Hz, 1H), 7.15 (s, 1H), 4.66 (t, J=4.7 Hz, 1H), 4.24 (s, 3H), 3.65-3.55 (m, 3H), 3.41 (d, J=15.9 Hz, 1H), 3.43-3.35 (m, 1H), 3.24 (d, J=15.9 Hz, 1H), 3.16-3.08 (m, 1H), 2.10-1.99 (m, 1H), 1.78-1.67 (m, 1H).

Intermediate 14

1-(10-Bromo-7,8-dichloro-2-oxo-1,2,3,4,5,6-hexahydroazepino[4,5-b]indol-1-yl)pyrrolidine-2,5-dione

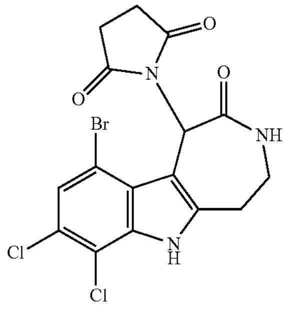 [SMILES: O=C1NCCc2[nH]c3c(Cl)c(Cl)cc(Br)c3c2C1N1C(=O)CCC1=O]

Dissolved 10-bromo-7,8-dichloro-3,4,5,6-tetrahydroazepino[4,5-b]indol-2(1H)-one (1.72 g, 4.94 mmol) in DMF (50 mL) and added cesium carbonate (2 g, 6 mmol). Cooled to 0° C. Added NBS (1.8 g, 10 mmol) and allowed to warm to ambient temperature over 18 hrs. Quenched with an aqueous solution of 10% LiCl and stirred for 30 min. Filtered the reaction and washed the solid with water to give 1-(10-bromo-7,8-dichloro-2-oxo-1,2,3,4,5,6-hexahydroazepino[4,5-b]indol-1-yl)pyrrolidine-2,5-dione as a brown solid. (1.45 g, 66%). ES/MS (m/z): 344.8/347.0/348.8 (M+H-succinimide).

Intermediate 15

10-Bromo-7,8-dichloro-1-methyl-3,4,5,6-tetrahydroazepino[4,5-b]indol-2(1H)-one

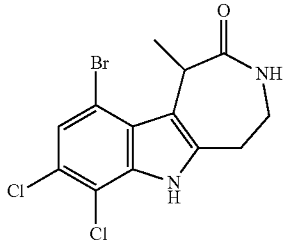 [SMILES: CC1C(=O)NCCc2[nH]c3c(Cl)c(Cl)cc(Br)c3c21]

Dissolved 3M methyl magnesium bromide solution in $Et_2O$ (6 mL, 18 mmol) in THF (20 mL) and cooled to 0° C. Added a solution of 1-(10-bromo-7,8-dichloro-2-oxo-1,2,3,4,5,6-hexahydroazepino[4,5-b]indol-1-yl)pyrrolidine-2,5-dione (1.45 g, 3.26 mmol) in THF (10 mL) dropwise. After complete addition, quenched the reaction with water and 1N HCl. Extracted with EtOAc. Dried the combined organic layers over magnesium sulfate, filtered, and concentrated under reduced pressure. Purified the residue via silica gel chromatography eluting with DCM/MeOH to give 10-bromo-7,8-dichloro-1-methyl-3,4,5,6-tetrahydroazepino[4,5-b]indol-2(1H)-one as a yellow-brown solid. (800 mg, 68%). ES/MS (m/z): 360.8/363.0/364.8 (M+H).

Intermediate 16

7,8-Dichloro-10-hydroxy-1-methyl-3,4,5,6-tetrahydroazepino[4,5-b]indol-2(1H)-one

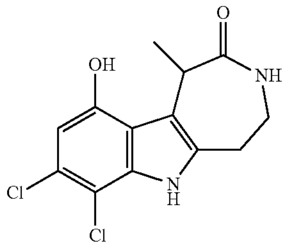 [SMILES: CC1C(=O)NCCc2[nH]c3c(Cl)c(Cl)cc(O)c3c21]

Dissolved 10-bromo-7,8-dichloro-1-methyl-3,4,5,6-tetrahydroazepino[4,5-b]indol-2(1H)-one (521 mg, 1.44 mmol) in 1,4-dioxane (30 mL) and sparged with nitrogen for 5 min. Added tert-BuBrettPhos-Pd-G3 (61 mg, 0.071 mmol), sodium t-butoxide (346 mg, 3.6 mmol), and water (6 mL). Heated to 65° C. for 2 hrs. Cooled to ambient temperature and quenched with 1N HCl. Extracted with EtOAc. Dried the combined organic layers over magnesium sulfate, filtered, and concentrated under reduced pressure. Purified by silica gel chromatography eluting with DCM/MeOH to give 7,8-dichloro-10-hydroxy-1-methyl-3,4,5,6-tetrahydroazepino[4,5-b]indol-2(1H)-one as a brown powder (246 mg, 57%). ES/MS (m/z): ($^{35}Cl/^{37}Cl$) 299.0/301.0 (M+H).

Intermediate 17

10-Bromo-7,8-dichloro-1-ethyl-3,4,5,6-tetrahydroazepino[4,5-b]indol-2(1H)-one

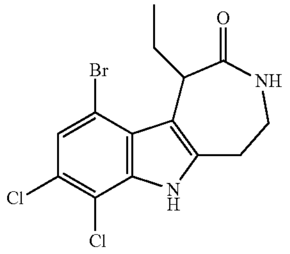 [SMILES: CCC1C(=O)NCCc2[nH]c3c(Cl)c(Cl)cc(Br)c3c21]

Dissolved 3M ethylmagnesium bromide solution in $Et_2O$ (0.75 mL, 2.3 mmol) in THF (4 mL) and cooled to 0° C. Added a solution of 1-(10-bromo-7,8-dichloro-2-oxo-1,2,3,4,5,6-hexahydroazepino[4,5-b]indol-1-yl)pyrrolidine-2,5-dione (200 mg, 0.449 mmol) in THF (2 mL) dropwise. After complete addition, quenched the reaction with water and 1N HCl. Extracted with EtOAc. Dried the combined organic layers over magnesium sulfate, filtered, and concentrated under reduced pressure. Purified the residue via silica gel chromatography eluting with DCM/MeOH to give 10-bromo-7,8-dichloro-1-ethyl-3,4,5,6-tetrahydroazepino[4,5-b]indol-2(1H)-one as a yellow solid. (138.1 mg, 82%). ES/MS (m/z): 374.8/376.8/378.8 (M+H).

Example 9

7,8-Dichloro-1-methyl-10-(2-methyl-2H-1,2,3-triazol-4-yl)-3,4,5,6-tetrahydroazepino[4,5-b]indol-2(1H)-one

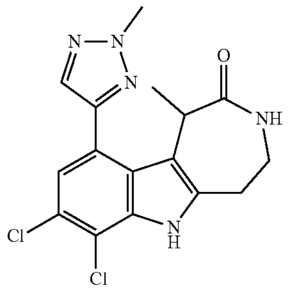

Dissolved 10-bromo-7,8-dichloro-1-methyl-3,4,5,6-tetrahydroazepino[4,5-b]indol-2(1H)-one (180 mg, 0.398 mmol), 2-methyl-4-(4,4,5,5-tetramethyl-1,3,2-dioxaborolan-2-yl)-2H-1,2,3-triazole (366 mg, 0.875 mmol), Pd(dppf)$Cl_2$ (53 mg, 0.072 mmol) and sodium carbonate (170 mg, 1.60 mmol) in 1,4-dioxane (6 mL) and water (1.5 mL). Sparged with $N_2$ and stirred at 90° C. overnight. Concentrated under reduced pressure and purified by silica gel chromatography eluting with DCM/MeOH. Purified by prep-HPLC to give 7,8-dichloro-1-methyl-10-(2-methyl-2H-1,2,3-triazol-4-yl)-3,4,5,6-tetrahydroazepino[4,5-b]indol-2(1H)-one (29 mg, 20%) as a yellow solid. ES/MS (m/z): ($^{35}Cl/^{37}Cl$) 364.2/366.2 (M+H). $^1H$ NMR (DMSO-d6): 11.57 (s, 1H), 7.95 (s, 1H), 7.67 (t, J=5.7 Hz, 1H), 7.08 (s, 1H), 4.24 (s, 3H), 3.69-3.61 (m, 2H), 3.25 (m, 1H), 3.08-2.88 (m, 2H), 1.19 (d, J=7.5 Hz, 3H).

Example 10

7,8-Dichloro-10-methoxy-1-methyl-3,4,5,6-tetrahydroazepino[4,5-b]indol-2(1H)-one

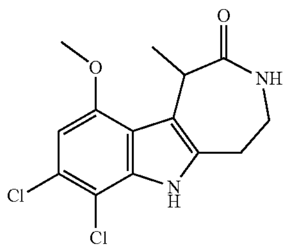

Dissolved 7,8-dichloro-10-hydroxy-1-methyl-3,4,5,6-tetrahydroazepino[4,5-b]indol-2(1H)-one (25 mg, 84 μmol) in DMSO (1 mL) and added potassium carbonate (35 mg, 0.25 mmol) followed by iodomethane (23 mg, 0.16 mmol). Heated to 50° C. under nitrogen for 1 hr. Cooled and quenched with saturated aqueous ammonium chloride solution. Extracted with EtOAc, dried the organic over anhydrous magnesium sulfate, filtered, and concentrated under reduced pressure. Purified by reverse phase flash chromatography to give 7,8-dichloro-10-methoxy-1-methyl-3,4,5,6-tetrahydroazepino[4,5-b]indol-2(1H)-one (14 mg, 55%). ES-MS (m/z): ($^{35}Cl/^{37}Cl$) 313.2/315.2 (M+H). 1H NMR (DMSO-d6): 11.28 (s, 1H), 7.72-7.68 (m, 1H), 6.68 (s, 1H), 4.29-4.26 (q, J=7.5 Hz, 1H), 3.89 (s, 3H), 3.69-3.61 (m, 1H), 3.29-3.24 (m, 1H), 2.97-2.93 (m, 1H), 2.87-2.78 (m, 1H), 1.49 (d, J=7.5 Hz, 3H).

Example 11

N-(7,8-Dichloro-1-ethyl-2-oxo-1,2,3,4,5,6-hexahydroazepino[4,5-b]indol-10-yl)-2-hydroxyacetamide

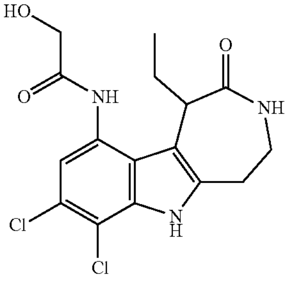 [SMILES: CCC1C(=O)NCCc2[nH]c3c(Cl)c(Cl)cc(NC(=O)CO)c3c21]

Dissolved 10-bromo-7,8-dichloro-1-ethyl-3,4,5,6-tetrahydroazepino[4,5-b]indol-2(1H)-one (50 mg, 0.133 mmol) in 1,4-dioxane (1.5 mL). Added cesium carbonate (130 mg, 0.4 mmol) and 2-hydroxyacetamide (30 mg, 0.4 mmol) and sparged with $N_2$ for 5 min. Added $Pd_2(dba)_3$ (12 mg, 0.013 mmol) and Xantphos (15 mg, 0.026 mmol) and heated to reflux for 90 min. Cooled to ambient temperature and partitioned between water and EtOAc. Dried the organic layers over sodium sulfate, filtered, and concentrated under reduced pressure. Purified the residue via silica gel reverse phase chromatography to give N-(7,8-dichloro-1-ethyl-2-oxo-1,2,3,4,5,6-hexahydroazepino[4,5-b]indol-10-yl)-2-hydroxyacetamide as a yellow solid. (7 mg, 14%). ES/MS (m/z): ($^{35}Cl/^{37}Cl$) 370.0/372.0 (M+H). $^1H$ NMR (DMSO-d6): 11.45 (br s, 1H), 9.01 (br s, 1H), 7.74 (t, J=6.0 Hz, 1H), 7.40 (s, 1H), 6.05 (br s, 1H), 4.09-4.00 (m, 2H), 3.95 (dd, J=5.8, 11.2 Hz, 1H), 3.74-3.62 (m, 1H), 3.28-3.20 (m, 1H), 3.01 (d, J=17.7 Hz, 1H), 2.91-2.82 (m, 1H), 1.94-1.80 (m, 2H), 1.02 (t, J=7.3 Hz, 3H).

Example 12

N-(7,8-Dichloro-1-methyl-2-oxo-1,2,3,4,5,6-hexahydroazepino[4,5-b]indol-10-yl)-2-hydroxyacetamide

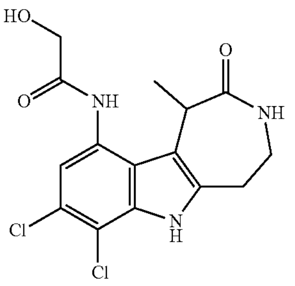 [SMILES: CC1C(=O)NCCc2[nH]c3c(Cl)c(Cl)cc(NC(=O)CO)c3c21]

Dissolved 10-bromo-7,8-dichloro-1-methyl-3,4,5,6-tetrahydroazepino[4,5-b]indol-2(1H)-one (370 mg, 1.02 mmol) in 1,4-dioxane (5 mL). Added cesium carbonate (1 g, 3 mmol) and 2-hydroxyacetamide (230 mg, 3.06 mmol) and sparged with $N_2$ for 5 min. Added $Pd_2(dba)_3$ (94 mg, 0.103 mmol) and Xantphos (120 mg, 0.207 mmol) and heated to 90° C. for 90 min. Cooled the reaction to ambient temperature and partitioned between water and EtOAc. Dried the organic layers over sodium sulfate, filtered, and concentrated under reduced pressure. Purified the residue via silica gel flash chromatography eluting with DCM/MeOH to give N-(7,8-dichloro-1-methyl-2-oxo-1,2,3,4,5,6-hexahydroazepino[4,5-b]indol-10-yl)-2-hydroxyacetamide as a yellow solid. (38.2 mg, 10% yield). ES/MS (m/z): ($^{35}Cl/^{37}Cl$) 355.9/357.8 (M+H).

Example 12A (S)—N-(7,8-Dichloro-1-methyl-2-oxo-1,2,3,4,5,6-hexahydroazepino[4,5-b]indol-10-yl)-2-hydroxyacetamide Or (R)—N-(7,8-Dichloro-1-methyl-2-oxo-1,2,3,4,5,6-hexahydroazepino[4,5-b]indol-10-yl)-2-hydroxyacetamide (isomer 1) and Example 12B (S)—N-(7,8-Dichloro-1-methyl-2-oxo-1,2,3,4,5,6-hexahydroazepino[4,5-b]indol-10-yl)-2-hydroxyacetamide Or (R)—N-(7,8-Dichloro-1-methyl-2-oxo-1,2,3,4,5,6-hexahydroazepino[4,5-b]indol-10-yl)-2-hydroxyacetamide (isomer 2)

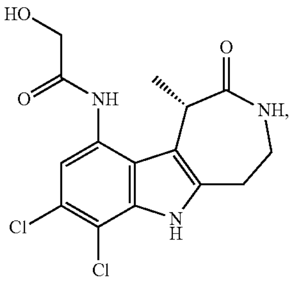

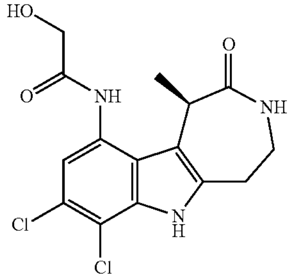

N-(7,8-dichloro-1-methyl-2-oxo-1,2,3,4,5,6-hexahydroazepino[4,5-b]indol-10-yl)-2-hydroxyacetamide (38 mg, 0.107 mmol) was separated via chiral chromatography (Chiralpak AD-H, 20×150, 25% MeOH/$CO_2$, Flow Rate: 80 mL/min, column temperature: 40° C.) to give N-(7,8-dichloro-1-methyl-2-oxo-1,2,3,4,5,6-hexahydroazepino[4,5-b]indol-10-yl)-2-hydroxyacetamide as separated enantiomers. (Isomer 1: 8.7 mg, 23%, Rt: 1.92 min, 98% ee; Isomer 2: 7.5 mg, 20%, Rt: 2.38 min, 96% ee). ES/MS (m/z): ($^{35}Cl/^{37}Cl$) 355.9/357.8 (M+H).

Example 13

3-((7,8-Dichloro-1-methyl-2-oxo-1,2,3,4,5,6-hexahydroazepino[4,5-b]indol-10-yl)oxy)propyl acetate

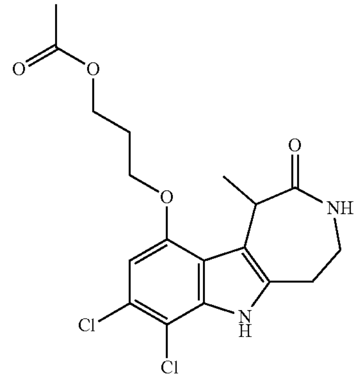 [SMILES: CC(=O)OCCCOc1cc(Cl)c(Cl)c2[nH]c3c(c12)C(C)C(=O)NCC3]

Dissolved 7,8-dichloro-10-hydroxy-1-methyl-3,4,5,6-tetrahydroazepino[4,5-b]indol-2(1H)-one (100 mg, 0.33 mmol) in DMF (4.0 mL). Added $K_2CO_3$ (50 mg, 0.36 mmol) with stirring. Cooled to 0° C. and added 3-bromopropyl acetate (47 μL, 0.37 mmol). Continued stirring at ambient temperature. Added NaI (5.0 mg, 0.033 mmol) and stirred at 60° C. for 24 hrs. Cooled to ambient temperature and diluted with EtOAc. Added diatomaceous earth, filtered, and rinsed diatomaceous earth with EtOAc (3×). Washed combined EtOAc with saturated aqueous sodium bicarbonate and saturated aqueous NaCl. Dried organics over anhydrous sodium sulfate, filtered, and concentrated under reduced pressure. Purified by silica gel flash chromatography eluting with DCM/MeOH to give 3-((7,8-dichloro-1-methyl-2-oxo-1,2,3,4,5,6-hexahydroazepino[4,5-b]indol-10-yl)oxy)propyl acetate as a racemic mixture (65 mg, 49%). ES/MS (m/z): ($^{35}Cl/^{37}Cl$) 398.8/400.8 (M+H). $^1H$ NMR (DMSO-d6): 11.28 (s, 1H), 7.72 (t, J=5.8 Hz, 1H), 6.69 (s, 1H), 4.30-4.23 (m, 5H), 3.30 (s, 2H), 2.98-2.92 (m, 1H), 2.88-2.78 (m, 1H). 2.11 (m, 2H), 2.04 (s, 3H), 1.51 (d, J=7.4 Hz, 3H).

Example 14

7,8-Dichloro-10-(3-hydroxypropoxy)-1-methyl-3,4,5,6-tetrahydroazepino[4,5-b]indol-2(1H)-one (racemic)

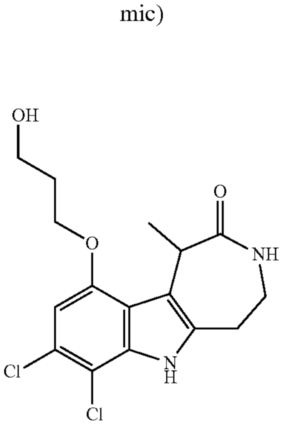

Added 3-((7,8-dichloro-1-methyl-2-oxo-1,2,3,4,5,6-hexahydroazepino[4,5-b]indol-10-yl)oxy)propyl acetate (55 mg, 0.14 mmol), 1,4-dioxane (1.4 mL), lithium hydroxide (0.21 g, 0.092 mmol, 1.0 M in $H_2O$) and MeOH (1.0 mL) at ambient temperature and stirred for 30 min. Added 5N HCl (55 μL, 0.28 mmol) and diluted with EtOAc. Poured into 1:1 water/saturated aqueous NaCl. Extracted the organic layer, washed with saturated aqueous NaCl, dried over anhydrous sodium sulfate, filtered, and concentrated under reduced pressure. Dried under reduced pressure at 40° C. overnight to give 7,8-dichloro-10-(3-hydroxypropoxy)-1-methyl-3,4,5,6-tetrahydroazepino[4,5-b]indol-2(1H)-one (48 mg, 98%). ES/MS (m/z): ($^{35}Cl/^{37}Cl$) 356.8/358.8 (M+H).

Example 14A (S)-7,8-Dichloro-10-(3-hydroxypropoxy)-1-methyl-3,4,5,6-tetrahydroazepino[4,5-b]indol-2(1H)-one Or (R)-7,8-Dichloro-10-(3-hydroxypropoxy)-1-methyl-3,4,5,6-tetrahydroazepino[4,5-b]indol-2(1H)-one (isomer 1) and Example 14B (S)-7,8-Dichloro-10-(3-hydroxypropoxy)-1-methyl-3,4,5,6-tetrahydroazepino[4,5-b]indol-2(1H)-one Or (R)-7,8-Dichloro-10-(3-hydroxypropoxy)-1-methyl-3,4,5,6-tetrahydroazepino[4,5-b]indol-2(1H)-one (isomer 2)

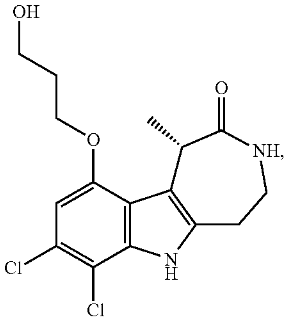

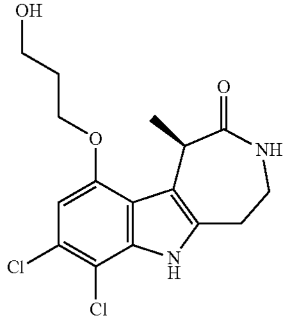

Purified 7,8-dichloro-10-(3-hydroxypropoxy)-1-methyl-3,4,5,6-tetrahydroazepino[4,5-b]indol-2(1H)-one (0.046 g, 0.13 mmol) by supercritical fluid chromatography to give the 7,8 dichloro-10-(3-hydroxypropoxy)-1-methyl-3,4,5,6-tetrahydroazepino[4,5-b]indol-2(1H)-one as separated enantiomers (Isomer 1: 11 mg, 24%, Rt=1.62 min, 96% ee; Isomer 2: 15 mg, 33%, Rt=2.35 min, 96% ee). Column: Chiralpak AD-H, 21×150 mm; Mobile Phase: 30% EtOH: 70% $CO_2$; Flow Rate: 80 mL/min; Column temperature: 40° C.; ES/MS (m/z): ($^{35}Cl/^{37}Cl$) 356.8/358.8 (M+H). $^1H$ NMR (DMSO-d6): 11.26 (s, 1H), 7.71 (t, J=5.7 Hz, 1H), 6.66 (s, 1H), 4.62 (t, J=5.2 Hz, 1H), 4.32-4.26 (m, 1H), 4.15-4.10 (m, 2H), 3.63 (m, 3H), 3.30-3.32 (m, 1H), 2.95 (m, 1H), 2.87-2.79 (m, 1H), 1.96-1.90 (m, 2H), 1.51 (d, J=7.4 Hz, 3H).

Example 15

7,8-Dichloro-10-ethoxy-1-methyl-3,4,5,6-tetrahydroazepino[4,5-b]indol-2(1H)-one

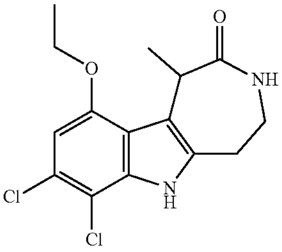

Dissolved 7,8-dichloro-10-hydroxy-1-methyl-3,4,5,6-tetrahydro-1H-azepino[4,5-b]indol-2-one (77 mg, 0.26 mmol) and potassium carbonate (76 mg, 0.77 mmol) in DMSO (2.5 mL, 35 mmol). Added iodoethane (80 μL, 0.51 mmol) and stirred at 50° C. for 1 hr. Cooled the reaction to ambient temperature and diluted with EtOAc. Washed with water and saturated aqueous NaCl. Dried over anhydrous magnesium sulfate, filtered, and concentrated onto diatomaceous earth. Purified by silica gel flash chromatography eluting with DCM/MeOH to give 7,8-dichloro-10-ethoxy-1-methyl-3,4,5,6-tetrahydroazepino[4,5-b]indol-2(1H)-one (43 mg, 51%). ES/MS (m/z): ($^{35}Cl/^{37}Cl$) 327.0/329.0 (M+H).

Example 15A (S)-7,8-Dichloro-10-ethoxy-1-methyl-3,4,5,6-tetrahydroazepino[4,5-b]indol-2(1H)-one Or (R)-7,8-Dichloro-10-ethoxy-1-methyl-3,4,5,6-tetrahydroazepino[4,5-b]indol-2(1H)-one (isomer 1) and Example 15B (S)-7,8-Dichloro-10-ethoxy-1-methyl-3,4,5,6-tetrahydroazepino[4,5-b]indol-2(1H)-one Or (R)-7,8-Dichloro-10-ethoxy-1-methyl-3,4,5,6-tetrahydroazepino[4,5-b]indol-2(1H)-one (isomer 2)

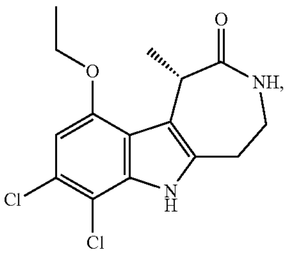

-continued

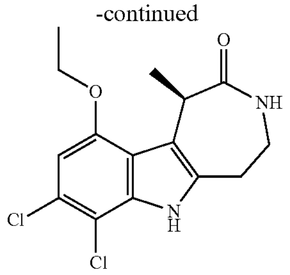

Purified 7,8-dichloro-10-ethoxy-1-methyl-3,4,5,6-tetrahydroazepino[4,5-b]indol-2(1H)-one (0.043 g, 0.13 mmol) by supercritical fluid chromatography to give, 8-dichloro-10-ethoxy-1-methyl-3,4,5,6-tetrahydroazepino[4,5-b]indol-2(1H)-one as separated enantiomers (Isomer 1—Rt=1.52 min (97% ee), 13.9 mg, 32%; Isomer 2—Rt=2.20 min (97% ee), 14.4 mg, 34%). Column: Chiralpak AD-H, 21×150 mm; Mobile Phase: 30% EtOH: 70% $CO_2$; Flow Rate: 80 mL/min; Column temperature: 40° C. ES/MS (m/z): ($^{35}Cl/^{37}Cl$) 327.0/329.0 (M+H). $^1H$ NMR (DMSO-d6): 11.25 (s, 1H), 7.72-7.69 (m, 1H), 6.66 (s, 1H), 4.33-4.27 (m, 2H), 4.19-4.10 (m, 2H), 3.69-3.64 (m, 1H), 3.30 (s, OH), 2.97-2.82 (m, 2H), 1.51 (d, J=7.4 Hz, 3H), 1.40 (t, J=7.0 Hz, 3H).

Example 16

2-((7,8-Dichloro-1-methyl-2-oxo-1,2,3,4,5,6-hexahydroazepino[4,5-b]indol-10-yl)oxy)acetonitrile

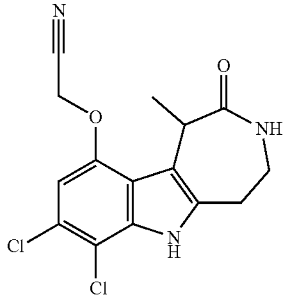 [SMILES: CC1C(=O)NCCc2[nH]c3c(Cl)c(Cl)cc(OCC#N)c3c21]

Dissolved 7,8-dichloro-10-hydroxy-1-methyl-3,4,5,6-tetrahydroazepino[4,5-b]indol-2(1H)-one (322 mg, 1.076 mmol) in DMF (11 mL) and cooled to 0° C. Added potassium carbonate (71 mg, 0.51 mmol) followed by bromoacetonitrile (90 μL, 1.29 mmol). Allowed reaction to stir and slowly warm to ambient temperature. Poured the reaction into saturated aqueous sodium bicarbonate and extracted with EtOAc (3×). Washed the combined organic layers with saturated aqueous NaCl, dried over anhydrous magnesium sulfate, filtered, and concentrated under reduced pressure. Purified by silica gel flash chromatography eluting with 1:1 THF:DCM/MeOH to give 2-((7,8-dichloro-1-methyl-2-oxo-1,2,3,4,5,6-hexahydroazepino[4,5-b]indol-10-yl)oxy)acetonitrile (210 mg, 58%). ES/MS (m/z): ($^{35}Cl/^{37}Cl$) 338.0/340.0 (M+H).

Example 16A (S)-2-((7,8-Dichloro-1-methyl-2-oxo-1,2,3,4,5,6-hexahydroazepino[4,5-b]indol-10-yl)oxy)acetonitrile Or (R)-2-((7,8-Dichloro-1-methyl-2-oxo-1,2,3,4,5,6-hexahydroazepino[4,5-b]indol-10-yl)oxy)acetonitrile (isomer 1) and

Example 16B (S)-2-((7,8-Dichloro-1-methyl-2-oxo-1,2,3,4,5,6-hexahydroazepino[4,5-b]indol-10-yl)oxy)acetonitrile Or (R)-2-((7,8-Dichloro-1-methyl-2-oxo-1,2,3,4,5,6-hexahydroazepino[4,5-b]indol-10-yl)oxy)acetonitrile (isomer 2)

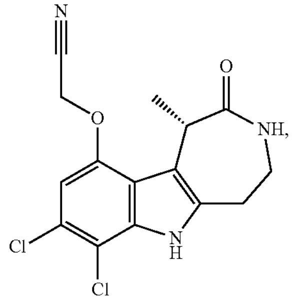

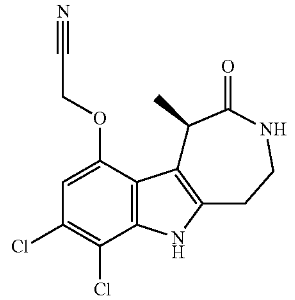

Purified 2-((7,8-dichloro-1-methyl-2-oxo-1,2,3,4,5,6-hexahydroazepino[4,5-b]indol-10-yl)oxy)acetonitrile (0.210 g, 0.62 mmol) by supercritical fluid chromatography to give 2-((7,8-dichloro-1-methyl-2-oxo-1,2,3,4,5,6-hexahydroazepino[4,5-b]indol-10-yl)oxy)acetonitrile as separated enantiomers (Isomer 1—Rt=1.35 min (98% ee), 43 mg, 20%; Isomer 2—Rt=2.29 (98% ee), 53 mg, 25%). Column: Chiralpak AD-H, 21×150 mm; Mobile Phase: 30% MeOH: 70% $CO_2$; Flow Rate: 80 mL/min; Column temperature: 40° C. ES/MS (m/z): ($^{35}Cl/^{37}Cl$) 338.0/340.0 (M+H). $^1H$ NMR (Acetone): 10.52 (s, 1H), 7.12-6.96 (m, 1H), 6.92 (s, 1H), 5.35 (s, 2H), 3.93-3.84 (m, 1H), 3.54-3.47 (m, 2H), 3.12-3.02 (m, 2H), 1.65-1.62 (m, 3H).

Example 17

2-((7,8-Dichloro-1-methyl-2-oxo-1,2,3,4,5,6-hexahydroazepino[4,5-b]indol-10-yl)oxy)acetamide

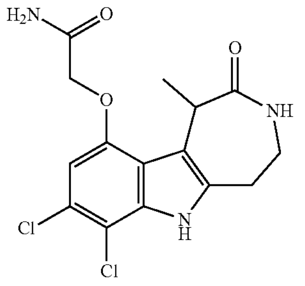 [SMILES: CC1C(=O)NCCc2[nH]c3c(Cl)c(Cl)cc(OCC(N)=O)c3c21]

Dissolved 2-[(7,8-dichloro-1-methyl-2-oxo-3,4,5,6-tetrahydro-1H-azepino[4,5-b]indol-10-yl)oxy]acetonitrile (49 mg, 0.145 mmol) and potassium carbonate (36 mg, 0.26 mmol) in DMSO (1.0 mL). Added $H_2O_2$ (30 mass % in water) (68 μL, 0.67 mmol) dropwise and stirred for 2.5 hrs. Quenched with saturated sodium thiosulfate, water and extracted with EtOAc. Washed the organic layer with saturated aqueous NaCl (2×), dried over anhydrous sodium sulfate, filtered, and concentrated under reduced pressure to give 2-((7,8-dichloro-1-methyl-2-oxo-1,2,3,4,5,6-hexahydroazepino[4,5-b]indol-10-yl)oxy)acetamide (52 mg, 99+%). ES/MS (m/z): ($^{35}Cl/^{37}Cl$) 356.2/358.2 (M+H).

Example 17A (S)-2-((7,8-Dichloro-1-methyl-2-oxo-1,2,3,4,5,6-hexahydroazepino[4,5-b]indol-10-yl)oxy)acetamide Or (R)-2-((7,8-Dichloro-1-methyl-2-oxo-1,2,3,4,5,6-hexahydroazepino[4,5-b]indol-10-yl)oxy)acetamide (isomer 1) and Example 17B (S)-2-((7,8-Dichloro-1-methyl-2-oxo-1,2,3,4,5,6-hexahydroazepino[4,5-b]indol-10-yl)oxy)acetamide Or (R)-2-((7,8-Dichloro-1-methyl-2-oxo-1,2,3,4,5,6-hexahydroazepino[4,5-b]indol-10-yl)oxy)acetamide (isomer 2)

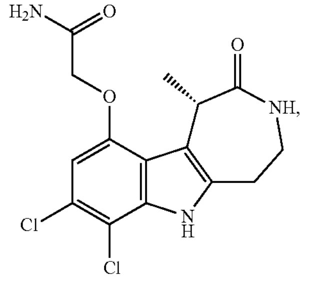

-continued

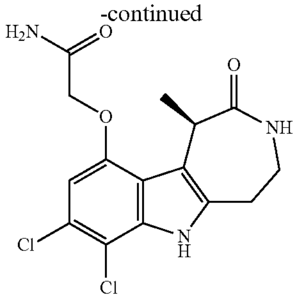

Purified 2-((7,8-dichloro-1-methyl-2-oxo-1,2,3,4,5,6-hexahydroazepino[4,5-b]indol-10-yl)oxy)acetamide (0.200 g, 0.561 mmol) by supercritical fluid chromatography to give 2-((7,8-dichloro-1-methyl-2-oxo-1,2,3,4,5,6-hexahydroazepino[4,5-b]indol-10-yl)oxy)acetamide as separated enantiomers (Isomer 1—Rt=2.15 min (98% ee), 52 mg, 26%; Isomer 2—Rt=2.84 min (94% ee), 55 mg, 27%). Column: Chiralpak AD-H, 21×150 mm; Mobile Phase: 25% MeOH: 75% $CO_2$; Flow Rate: 80 mL/min; Column temperature: 40° C. ES/MS (m/z): ($^{35}Cl/^{37}Cl$) 356.0/358.0 (M+H). $^1H$ NMR (DMSO-d6): 11.30 (s, 1H), 7.72-7.69 (m, 1H), 7.40-7.36 (m, 2H), 6.57 (s, 1H), 4.64-4.56 (m, 2H), 4.36-4.29 (m, 2H), 3.70-3.66 (m, 1H), 3.00-2.84 (m, 2H), 1.53 (d, J=7.4 Hz, 3H).

Intermediate 21

7,8-Dichloro-1-methyl-10-(2-((tetrahydro-2H-pyran-2-yl)oxy)ethoxy)-3,4,5,6-tetrahydroazepino[4,5-b]indol-2(1H)-one

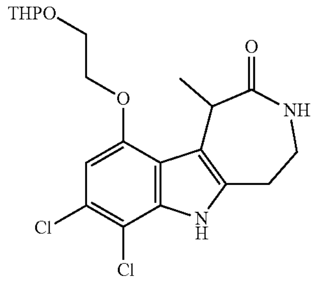

Dissolved 7,8-dichloro-10-hydroxy-1-methyl-3,4,5,6-tetrahydroazepino[4,5-b]indol-2(1H)-one (50 mg, 0.167 mmol) in DMF (2.0 mL), then added potassium carbonate (25 mg, 0.18 mmol). Cooled to 0° C., then added 2-(2-bromoethoxy)tetrahydro-2H-pyran (27 μL, 0.19 mmol). Stirred at ambient temperature. Added sodium iodide (5.0 mg, 0.033 mmol) and stirred at 60° C. for 6 hrs. Cooled to ambient temperature and diluted with EtOAc. Extracted with saturated aqueous sodium bicarbonate (2×). Filtered the material and washed filtrate with saturated aqueous NaCl. Dried organics over anhydrous sodium sulfate, filtered, and concentrated under reduced pressure. Purified by silica gel flash chromatography eluting with DCM/MeOH to give 7,8-dichloro-1-methyl-10-(2-((tetrahydro-2H-pyran-2-yl)oxy)ethoxy)-3,4,5,6-tetrahydroazepino[4,5-b]indol-2(1H)-one (8.0 mg, 11%). ES/MS (m/z): ($^{35}Cl/^{37}Cl$) 448.8.8/450.8 (M+Na).

Example 18

7,8-Dichloro-10-(2-hydroxyethoxy)-1-methyl-3,4,5,6-tetrahydroazepino[4,5-b]indol-2(1H)-one

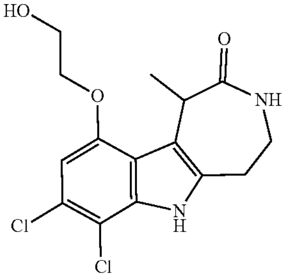 [SMILES: CC1C(=O)NCCc2[nH]c3c(Cl)c(Cl)cc(OCCO)c3c21]

Dissolved 7,8-dichloro-1-methyl-10-(2-((tetrahydro-2H-pyran-2-yl)oxy)ethoxy)-3,4,5,6-tetrahydroazepino[4,5-b]indol-2(1H)-one (8.0 mg, 0.019 mmol) in MeOH (1.0 mL). Added hydrochloric acid (4N in 1,4-dioxane) (1.0 mL, 4.0 mmol) at ambient temperature and stirred for 1 hr. Dried the reaction under a flow of $N_2$ and diluted the crude material with EtOAc. Washed with water (2×) and saturated aqueous NaCl. Dried over anhydrous sodium sulfate, filtered, and concentrated under reduced pressure to give 7,8-dichloro-10-(2-hydroxyethoxy)-1-methyl-3,4,5,6-tetrahydroazepino[4,5-b]indol-2(1H)-one (6.5 mg, 91%). ES/MS (m/z): ($^{35}$Cl/$^{37}$Cl) 342.8/344.8 (M+H). $^1$H NMR (DMSO-d6): 11.25 (s, 1H), 7.70-7.65 (m, 1H), 6.68 (s, 1H), 4.86 (t, J=5.1 Hz, 1H), 4.35-4.30 (m, 2H), 4.15-4.06 (m, 2H), 3.79 (q, J=5.1 Hz, 2H), 3.73-3.71 (m, 1H), 2.97-2.85 (m, 2H), 1.52 (d, J=7.4 Hz, 3H).

Example 19

7,8-Dichloro-10-(1H-pyrazol-4-yl)-3,4,5,6-tetrahydroazepino[4,5-b]indol-2(1H)-one

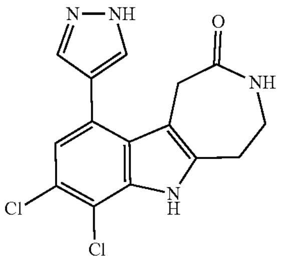 [SMILES: O=C1Cc2c([nH]c3c(Cl)c(Cl)cc(-c4cn[nH]c4)c23)CCN1]

Added together 10-bromo-7,8-dichloro-3,4,5,6-tetrahydroazepino[4,5-b]indol-2(1H)-one (50 mg, 0.14 mmol), 1-(tetrahydro-2H-pyran-2-yl)-4-(4,4,5,5-tetramethyl-1,3,2-dioxaborolan-2-yl)-1H-pyrazole (63 mg, 0.22 mmol), $Pd(dppf)_2Cl_2$ (12 mg, 0.014 mmol), and sodium carbonate (30 mg, 0.287 mmol). Added 1,4-dioxane (2.0 mL) and water (0.2 mL). Flushed the reaction mixture with $N_2$ for 10 min and stirred at 90° C. for 1 hr. Allowed the reaction to cool to ambient temperature, filtered, and concentrated under reduced pressure. Dissolved the crude residue in DCM (1.5 mL) and added TFA (1.5 mL). Stirred at ambient temperature for 2 hrs. and concentrated under reduced pressure. Purified by silica gel reverse phase chromatography to give 7,8-dichloro-10-(1H-pyrazol-4-yl)-3,4,5,6-tetrahydroazepino[4,5-b]indol-2(1H)-one (21 mg, 44%). ES/MS (m/z): ($^{35}$Cl/$^{37}$Cl) 335.0/337.0 (M+H). $^1$H NMR (DMSO-d6): 13.12-13.10 (m, 1H), 11.47 (s, 1H), 7.98-7.93 (m, 1H), 7.66-7.61 (m, 2H), 6.97 (s, 1H), 3.53-3.46 (m, 4H), 2.94-2.92 (m, 2H).

Intermediate 22

10-Bromo-7,8-dichloro-6-((2-(trimethyl silyl)ethoxy)methyl)-3,4,5,6-tetrahydroazepino[4,5-b]indol-2(1H)-one

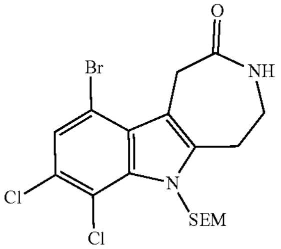 [SMILES: C[Si](C)(C)CCOCn1c2c(c3c(Br)cc(Cl)c(Cl)c31)CC(=O)NCC2]

Dissolved 10-bromo-7,8-dichloro-3,4,5,6-tetrahydroazepino[4,5-b]indol-2(1H)-one (3.00 g, 7.76 mmol) in THF (50 mL). Added sodium hydride (750 mg, 18.6 mmol, 60% in mineral oil) portion-wise at 0° C. and stirred for 1 hr. Added SEM-Cl (2.80 mL, 16.0 mmol) dropwise at 0° C. and stirred for 3 hrs. Quenched with saturated aqueous sodium bicarbonate. Added EtOAc, washed sequentially with water and saturated aqueous NaCl, dried over anhydrous sodium sulfate, filtered, and concentrated under reduced pressure. Purified by flash column chromatography (hexanes/EtOAc) to give 10-bromo-7,8-dichloro-6-((2-(trimethylsilyl)ethoxy)methyl)-3,4,5,6-tetrahydroazepino[4,5-b]indol-2(1H)-one (3.30 g, 76%) as a yellow solid. ES/MS (m/z): 476.9/478.8/480.8 (M+H).

Intermediate 23

7,8-Dichloro-10-hydroxy-6-((2-(trimethyl silyl)ethoxy)methyl)-3,4,5,6-tetrahydroazepino[4,5-b]indol-2(1H)-one

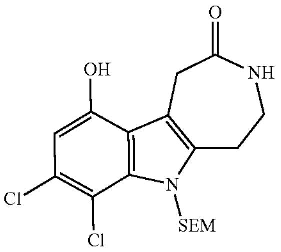 [SMILES: C[Si](C)(C)CCOCn1c2c(c3c(O)cc(Cl)c(Cl)c31)CC(=O)NCC2]

Dissolved 10-bromo-7,8-dichloro-6-((2-(trimethyl silyl)ethoxy)methyl)-3,4,5,6-tetrahydroazepino[4,5-b]indol-2(1H)-one (1.00 g, 1.78 mmol), tert-BuBrettPhos-Pd-G (175 mg, 0.200 mmol) and t-BuONa (585 mg, 5.97 mmol) in 1,4-dioxane (12.0 mL) and water (3.0 mL). Sparged with $N_2$, then heated at 65° C. for 5 hrs. Cooled to ambient temperature, acidified with 1N aqueous HCl, diluted with EtOAc, washed with saturated aqueous NaCl, dried over sodium sulfate, filtered, and concentrated under reduced pressure. Purified by silica gel flash chromatography eluting with DCM/MeOH to give 7,8-dichloro-10-hydroxy-6-((2-(trimethyl silyl)ethoxy)methyl)-3,4,5,6-tetrahydroazepino[4,5-b]indol-2(1H)-one (700 mg, 66%) as a brown solid. ES/MS (m/z): ($^{35}$Cl/$^{37}$Cl) 415.1/417.1 (M+H).

Intermediate 24

2-((7,8-Dichloro-2-oxo-6-((2-(trimethylsilyl)ethoxy)methyl)-1,2,3,4,5,6-hexahydroazepino[4,5-b]indol-10-yl)oxy)acetonitrile

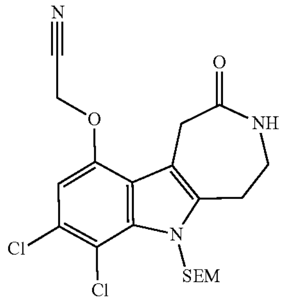 [SMILES: C[Si](C)(C)CCOCn1c2c(c3c(OCC#N)cc(Cl)c(Cl)c31)CC(=O)NCC2]

Suspended 10-bromo-7,8-dichloro-6-((2-(trimethylsilyl)ethoxy)methyl)-3,4,5,6-tetrahydroazepino[4,5-b]indol-2(1H)-one (250 mg, 0.421 mmol) and potassium carbonate (175 mg, 1.27 mmol) in DMF (3 mL). Added bromoacetonitrile (160 mg, 1.29 mmol) at 0° C. and stirred at ambient temperature for 5 hrs. Diluted with EtOAc, washed with saturated aqueous NaCl, dried over sodium sulfate, filtered, and concentrated under reduced pressure. Purified by silica gel flash chromatography eluting with DCM/MeOH to give 2-((7,8-dichloro-2-oxo-6-((2-(trimethylsilyl)ethoxy)methyl)-1,2,3,4,5,6-hexahydroazepino[4,5-b]indol-10-yl)oxy)acetonitrile (220 mg, 86%) as a yellow solid. ES/MS (m/z): ($^{35}$Cl/$^{37}$Cl) 454.1/456.0 (M+H).

Intermediate 25

2-((7,8-Dichloro-2-oxo-6-((2-(trimethylsilyl)ethoxy)methyl)-1,2,3,4,5,6-hexahydroazepino[4,5-b]indol-10-yl)oxy)acetamide

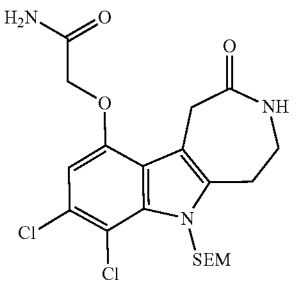 [SMILES: C[Si](C)(C)CCOCn1c2c(c3c(OCC(N)=O)cc(Cl)c(Cl)c31)CC(=O)NCC2]

Suspended 2-((7,8-dichloro-2-oxo-6-((2-(trimethylsilyl)ethoxy)methyl)-1,2,3,4,5,6-hexahydroazepino[4,5-b]indol-10-yl)oxy)acetonitrile (220 mg, 0.363 mmol) and potassium carbonate (300 mg, 2.17 mmol) in DMSO (3 mL). Added 35% aqueous $H_2O_2$ (510 mg, 4.49 mmol) dropwise at 0° C. and stirred at ambient temperature for 2 hrs. Diluted with EtOAc, washed with saturated aqueous NaCl, dried over sodium sulfate, filtered, and concentrated under reduced pressure. Triturated with ACN (2 mL) to give 2-((7,8-dichloro-2-oxo-6-((2-(trimethyl silyl)ethoxy)methyl)-1,2,3,4,5,6-hexahydroazepino[4,5-b]indol-10-yl)oxy)acetamide (150 mg, 78%) as a light yellow solid. ES/MS (m/z): ($^{35}$Cl/$^{37}$Cl) 472.1/474.0 (M+H).

Example 20

2-((7,8-Dichloro-2-oxo-1,2,3,4,5,6-hexahydroazepino[4,5-b]indol-10-yl)oxy)acetamide

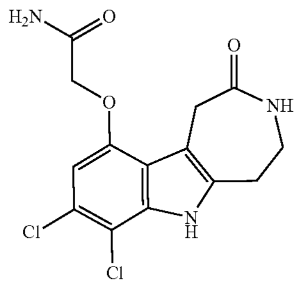 [SMILES: NC(=O)COc1cc(Cl)c(Cl)c2[nH]c3c(c12)CC(=O)NCC3]

Dissolved 2-((7,8-dichloro-2-oxo-6-((2-(trimethylsilyl)ethoxy)methyl)-1,2,3,4,5,6-hexahydroazepino[4,5-b]indol-10-yl)oxy)acetamide (130 mg, 0.248 mmol) in DCM (2 mL) and added TFA (1 mL) at 0° C., then stirred at ambient temperature for 2 hrs. Concentrated, diluted with THF (3 mL), added 28% aqueous $NH_3 \cdot H_2O$ (1 mL) and stirred for 1.5 hr at ambient temperature. Diluted with water, extracted with EtOAc, washed the organic layer with saturated aqueous NaCl, dried over sodium sulfate, filtered, and concentrated under reduced pressure. Purified by prep-HPLC to give 2-((7,8-dichloro-2-oxo-1,2,3,4,5,6-hexahydroazepino[4,5-b]indol-10-yl)oxy)acetamide (20.51 mg, 24%) as a white solid. ES/MS (m/z): ($^{35}$Cl/$^{37}$Cl) 342.2/344.2 (M+H). $^1$H NMR (DMSO-d6): 11.43-11.41 (m, 1H), 7.73-7.70 (m, 1H), 7.48-7.47 (m, 2H), 6.61-6.55 (m, 1H), 4.63-4.55 (m, 2H), 4.04-4.02 (m, 2H), 3.00-2.98 (m, 2H)

Intermediate 26

2-((7,8-Dichloro-2-oxo-1,2,3,4,5,6-hexahydroazepino[4,5-b]indol-10-yl)oxy)acetonitrile

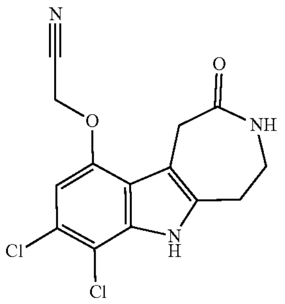 [SMILES: N#CCOc1cc(Cl)c(Cl)c2[nH]c3c(c12)CC(=O)NCC3]

Dissolved 2-((7,8-dichloro-2-oxo-6-((2-(trimethylsilyl)ethoxy)methyl)-1,2,3,4,5,6-hexahydroazepino[4,5-b]indol-10-yl)oxy)acetonitrile (65 mg, 0.14 mmol) in DCM (2 mL). Added TFA (1 mL) and stirred at ambient temperature for 2 hrs. Concentrated and diluted with THF (3 mL), then added 28% aqueous $NH_3 \cdot H_2O$ (1 mL). Stirred at ambient temperature for 1.5 hrs. Diluted with water (25 mL), extracted with EtOAc, washed with saturated aqueous NaCl, dried over anhydrous sodium sulfate, filtered, and concentrated under reduced pressure. Purified by prep-HPLC to give 2-((7,8-dichloro-2-oxo-1,2,3,4,5,6-hexahydroazepino[4,5-b]indol-10-yl)oxy)acetonitrile (30 mg, 64%) as a white solid. ES/MS (m/z): ($^{35}Cl/^{37}Cl$) 324.2/326.2 (M+H).

Example 21

2-((7,8-Dichloro-6-methyl-2-oxo-1,2,3,4,5,6-hexahydroazepino[4,5-b]indol-10-yl)oxy)acetonitrile

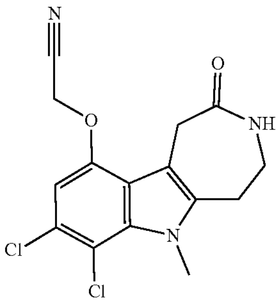 [SMILES: Cn1c2c(c3c(OCC#N)cc(Cl)c(Cl)c31)CC(=O)NCC2]

Added cesium carbonate (74 mg, 0.23 mmol) and iodomethane (32 mg, 0.23 mmol) to 2-((7,8-dichloro-2-oxo-1,2,3,4,5,6-hexahydroazepino[4,5-b]indol-10-yl)oxy)acetonitrile (25 mg, 0.076 mmol) in DMF (1 mL). Stirred at ambient temperature for 2 hrs. Diluted with water (20 mL), extracted with EtOAc, and concentrated organics under reduced pressure. Purified by prep-HPLC to give 2-((7,8-dichloro-6-methyl-2-oxo-1,2,3,4,5,6-hexahydroazepino[4,5-b]indol-10-yl)oxy)acetonitrile (6.7 mg, 26%) as a white solid. ES/MS (m/z): ($^{35}Cl/^{37}Cl$) 338.2/340.2 (M+H). $^1H$ NMR (DMSO-d6): 7.72 (t, J=6.3 Hz, 1H), 6.95 (s, 1H), 5.34 (s, 2H), 3.98 (s, 2H), 3.94 (s, 3H), 3.58-3.53 (m, 2H), 2.89-2.86 (m, 2H).

Intermediate 27 tert-Butyl (7,8-dichloro-2-oxo-1,2,3,4,5,6-hexahydroazepino[4,5-b]indol-10-yl)carbamate

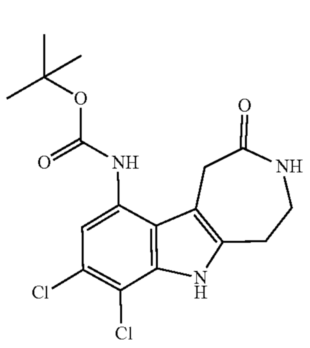 [SMILES: CC(C)(C)OC(=O)Nc1cc(Cl)c(Cl)c2[nH]c3c(c12)CC(=O)NCC3]

Dissolved 10-bromo-7,8-dichloro-3,4,5,6-tetrahydroazepino[4,5-b]indol-2(1H)-one (500 mg, 1.36 mmol) in 1,4-dioxane (9 mL). Added cesium carbonate (1 g, 3 mmol), XantPhos-Pd-$G_2$ (140 mg, 0.141 mmol) and tert-butyl carbamate (330 mg, 2.76 mmol) at ambient temperature. Sparged with $N_2$ and stirred overnight at 100° C. Concentrated under reduced pressure and purified by silica gel flash chromatograph eluting with petroleum ether/EtOAc to give tert-butyl (7,8-dichloro-2-oxo-1,2,3,4,5,6-hexahydroazepino[4,5-b]indol-10-yl)carbamate (290 mg, 33%) as a brown solid. ES/MS (m/z): ($^{35}Cl/^{37}Cl$) 328.0/329.9 (M+H-tBu) and 384.0/386.0 (M+H).

Intermediate 28

10-Amino-7,8-dichloro-3,4,5,6-tetrahydroazepino[4,5-b]indol-2(1H)-one hydrochloride

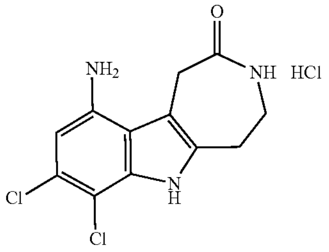

Dissolved mixture of tert-butyl (7,8-dichloro-2-oxo-1,2,3,4,5,6-hexahydroazepino[4,5-b]indol-10-yl)carbamate (290 mg, 0.457 mmol, 61% purity) and 10-amino-7,8-dichloro-3,4,5,6-tetrahydroazepino[4,5-b]indol-2(1H)-one hydrochloride (290 mg, 0.232 mmol, 23% purity) in 4N HCl/EtOH (4 mL) and stirred 1 hr at ambient temperature. Concentrated under reduced pressure and triturated with EtOAc to give 10-amino-7,8-dichloro-3,4,5,6-tetrahydroazepino[4,5-b]indol-2(1H)-one hydrochloride (246 mg, 0.621 mmol, 90%) as yellow oil. ES/MS (m/z): ($^{35}Cl/^{37}Cl$) 284.0/286.0 (M+H).

Intermediate 29

10-((3-((tert-Butyldimethylsilyl)oxy)propyl)amino)-7,8-dichloro-3,4,5,6-tetrahydroazepino[4,5-b]indol-2(1H)-one

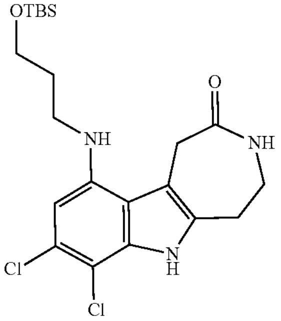 [SMILES: CC(C)(C)[Si](C)(C)OCCCNc1cc(Cl)c(Cl)c2[nH]c3c(c12)CC(=O)NCC3]

Dissolved 10-amino-7,8-dichloro-3,4,5,6-tetrahydroazepino[4,5-b]indol-2(1H)-one hydrochloride (100 mg, 0.285 mmol) in MeOH (3 mL). Added DIPEA to adjust to pH 8.

Stirred for 30 min at ambient temperature. Added acetic acid (40 mg, 0.67 mmol) to the mixture and stirred for 30 min at ambient temperature. Added 3-[tert-butyl(dimethyl)silyl] oxypropanal (140 mg, 0.743 mmol) to the mixture and stirred for 30 min at ambient temperature. Added sodium cyanoborohydride (60 mg, 0.91 mmol) and stirred overnight at ambient temperature. Quenched with water, extracted with EtOAc, dried over anhydrous sodium sulfate, filtered, and concentrated under reduced pressure. Purified by silica gel flash chromatography eluting with DCM/MeOH to give 10-((3-((tert-butyldimethylsilyl)oxy)propyl)amino)-7,8-dichloro-3,4,5,6-tetrahydroazepino[4,5-b]indol-2(1H)-one (160 mg, 99%) as a yellow solid. ES/MS (m/z): ($^{35}Cl/^{37}Cl$) 456.0/458.0 (M+H)

Example 22

7,8-Dichloro-10-((3-hydroxypropyl)amino)-3,4,5,6-tetrahydroazepino[4,5-b]indol-2(1H)-one

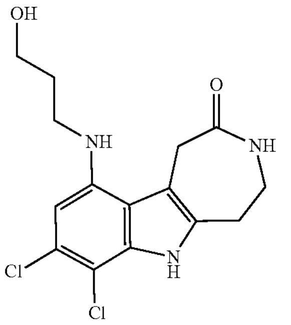 [SMILES: O=C1Cc2c([nH]c3c(Cl)c(Cl)cc(NCCCO)c23)CCN1]

Suspended 10-((3-((tert-butyldimethylsilyl)oxy)propyl) amino)-7,8-dichloro-3,4,5,6-tetrahydroazepino[4,5-b]indol-2(1H)-one (160 mg, 0.283 mmol) in 4N HCl in MeOH (4 mL) and stirred for 1 hr at ambient temperature. Concentrated under reduced pressure and purified by prep-HPLC. Lyophilized to give 7,8-dichloro-10-((3-hydroxypropyl) amino)-3,4,5,6-tetrahydroazepino[4,5-b]indol-2(1H)-one (20 mg, 20%) as a grey solid. ES/MS (m/z): ($^{35}Cl/^{37}Cl$) 342.2/344.2 (M+H). $^1H$ NMR (DMSO-d6): 11.07-11.05 (m, 1H), 7.73-7.68 (m, 1H), 6.21 (s, 1H), 5.47-5.43 (m, 1H), 4.70 (t, J=4.9 Hz, 1H), 3.94-3.90 (m, 2H), 3.63-3.61 (m, 2H), 3.51-3.45 (m, 2H), 3.18-3.15 (m, 2H), 2.92-2.90 (m, 2H), 1.83-1.77 (m, 2H).

Intermediate 30

10-(3-((tert-Butyldimethylsilyl)oxy)propoxy)-7,8-dichloro-6-((2-(trimethyl silyl)ethoxy)methyl)-3,4,5,6-tetrahydroazepino[4,5-b]indol-2(1H)-one

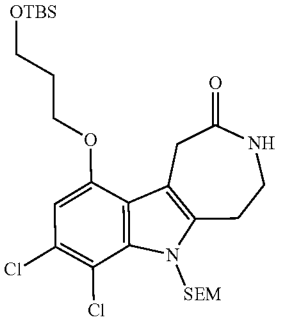 [SMILES: CC(C)(C)[Si](C)(C)OCCCOc1cc(Cl)c(Cl)c2c1c1c(n2COCC[Si](C)(C)C)CCNC(=O)C1]

Dissolved 7,8-dichloro-10-hydroxy-6-((2-(trimethylsilyl) ethoxy)methyl)-3,4,5,6-tetrahydroazepino[4,5-b]indol-2 (1H)-one (50 mg, 0.11 mmol) in DMF (2 mL). Added potassium carbonate (20 mg, 0.14 mmol) and 3-bromopropoxy-tert-butyl-dimethyl-silane (55 mg, 0.22 mmol) at 0° C. Warmed to ambient temperature and stirred for 2 hrs. Quenched with water, extracted with EtOAc, dried over anhydrous sodium sulfate, filtered, and concentrated under reduced pressure to give 10-(3-((tert-butyldimethylsilyl) oxy)propoxy)-7,8-dichloro-6-((2-(trimethylsilyl)ethoxy) methyl)-3,4,5,6-tetrahydroazepino[4,5-b]indol-2(1H)-one (80 mg, 75%) as a yellow gum. ES/MS (m/z): ($^{35}Cl/^{37}Cl$) 587.2/589.2 (M+H).

Example 23

7,8-Dichloro-10-(3-hydroxypropoxy)-3,4,5,6-tetrahydroazepino[4,5-b]indol-2(1H)-one

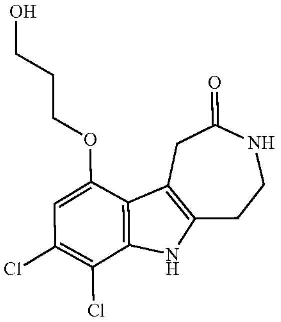 [SMILES: O=C1Cc2c([nH]c3c(Cl)c(Cl)cc(OCCCO)c23)CCN1]

Dissolved 10-(3-((tert-butyldimethylsilyl)oxy)propoxy)-7,8-dichloro-6-((2-(trimethylsilyl)ethoxy)methyl)-3,4,5,6-tetrahydroazepino[4,5-b]indol-2(1H)-one (80 mg, 0.081 mmol) in DCM (2 mL). Added TFA (2 mL), then stirred for 1.5 hr at ambient temperature. Concentrated and dissolved in THF (1 mL). Added 2N aqueous LiOH (1 mL). Stirred for 1 hr at ambient temperature. Quenched with water, extracted with EtOAc, dried over anhydrous sodium sulfate, filtered, and concentrated under reduced pressure. Purified by prep-HPLC to give 7,8-dichloro-10-(3-hydroxypropoxy)-3,4,5,6-tetrahydroazepino[4,5-b]indol-2(1H)-one (7.7 mg, 26%) as a white solid. ES/MS (m/z): ($^{35}Cl/^{37}Cl$) 343.2/345.2 (M+H). $^1H$ NMR (DMSO-d6): 11.32 (s, 1H), 7.66 (t, J=6.2 Hz, 1H), 6.67 (s, 1H), 4.62 (t, J=5.1 Hz, 1H), 4.12 (t, J=6.0 Hz, 2H), 3.96 (s, 2H), 3.64-3.60 (m, 2H), 3.56-3.50 (m, 2H), 2.91-2.86 (m, 2H), 1.93 (quintet, J=6.0 Hz, 2H).

Intermediate 31

2-((7,8-Dichloro-2-oxo-1,2,3,4,5,6-hexahydroazepino[4,5-b]indol-10-yl)amino)-2-oxoethyl acetate

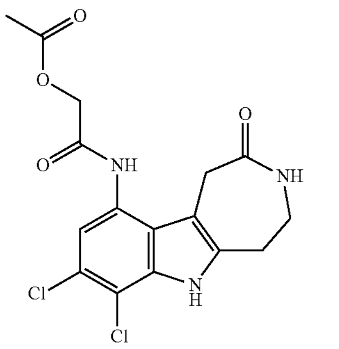 [SMILES: CC(=O)OCC(=O)Nc1cc(Cl)c(Cl)c2[nH]c3c(c12)CC(=O)NCC3]

Dissolved 10-amino-7,8-dichloro-3,4,5,6-tetrahydroazepino[4,5-b]indol-2(1H)-one hydrochloride (200 mg, 0.498 mmol) in DCM (4 mL), then added $Et_3N$ (0.5 mL, 4 mmol) and stirred for 0.5 hr at ambient temperature. Added acetoxyacetyl chloride (270 mg, 1.98 mmol) and stirred overnight at ambient temperature. Quenched with water, extracted with EtOAc, dried over anhydrous sodium sulfate, filtered, and concentrated under reduced pressure to give 2-((7,8-dichloro-2-oxo-1,2,3,4,5,6-hexahydroazepino[4,5-b]indol-10-yl)amino)-2-oxoethyl acetate (157 mg, 37%) as a yellow solid. ES/MS (m/z): ($^{35}Cl/^{37}Cl$) 383.9/385.9 (M+H).

Example 24

N-(7,8-Dichloro-2-oxo-1,2,3,4,5,6-hexahydroazepino[4,5-b]indol-10-yl)-2-hydroxyacetamide

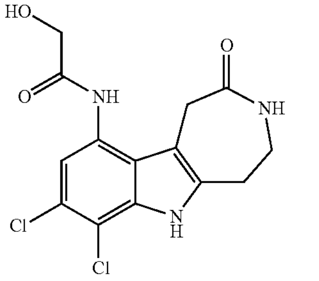 [SMILES: O=C1Cc2c([nH]c3c(Cl)c(Cl)cc(NC(=O)CO)c23)CCN1]

Dissolved 2-((7,8-dichloro-2-oxo-1,2,3,4,5,6-hexahydroazepino[4,5-b]indol-10-yl)amino)-2-oxoethyl acetate (176 mg, 0.206 mmol) in THF (5 mL) and water (1 mL). Added lithium hydroxide monohydrate (100 mg, 2.38 mmol) and stirred for 1 hr at ambient temperature. Diluted with water, extracted with EtOAc, dried over anhydrous sodium sulfate, filtered, and concentrated under reduced pressure. Purified by prep-HPLC to give N-(7,8-dichloro-2-oxo-1,2,3,4,5,6-hexahydroazepino[4,5-b]indol-10-yl)-2-hydroxyacetamide (27 mg, 38%) as a white solid. ES/MS (m/z): ($^{35}Cl/^{37}Cl$) 342.2/344.1 (M+H). $^1H$ NMR (DMSO-d6): 11.07-11.05 (m, 1H), 7.73-7.68 (m, 1H), 6.21 (s, 1H), 5.47-5.43 (m, 1H), 4.70 (t, J=4.9 Hz, 1H), 3.94-3.90 (m, 2H), 3.63-3.61 (m, 2H), 3.51-3.45 (m, 2H), 3.18-3.15 (m, 2H), 2.92-2.90 (m, 2H), 1.83-1.77 (m, 2H).

Intermediate 32

Methyl 7,8-dichloro-2-oxo-1,2,3,4,5,6-hexahydroazepino[4,5-b]indole-10-carboxylate

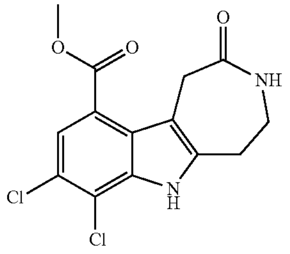 [SMILES: COC(=O)c1cc(Cl)c(Cl)c2[nH]c3c(c12)CC(=O)NCC3]

Suspended 10-bromo-7,8-dichloro-3,4,5,6-tetrahydroazepino[4,5-b]indol-2(1H)-one (1.00 g, 2.73 mmol), Pd(dppf)$Cl_2$ (303 mg, 0.410 mmol) and $Et_3N$ (1.20 mL, 8.60 mmol) in MeOH (9 mL) and DMF (3 mL). Sparged with CO then stirred at 70° C. overnight under CO (50 psi). Diluted with EtOAc, washed sequentially with water and saturated aqueous NaCl, dried over sodium sulfate, filtered, and concentrated under reduced pressure. Purified by silica gel flash chromatography eluting with DCM/MeOH to give methyl 7,8-dichloro-2-oxo-1,2,3,4,5,6-hexahydroazepino[4,5-b]indole-10-carboxylate (567 mg, 57%) as a brown solid. ES/MS (m/z): ($^{35}Cl/^{37}Cl$) 327.0/329.0 (M+H).

Intermediate 33

7,8-Dichloro-2-oxo-1,2,3,4,5,6-hexahydroazepino[4,5-b]indole-10-carboxylic acid

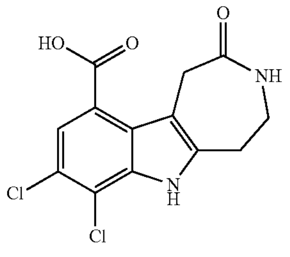 [SMILES: O=C1Cc2c([nH]c3c(Cl)c(Cl)cc(C(=O)O)c23)CCN1]

Dissolved methyl 7,8-dichloro-2-oxo-1,2,3,4,5,6-hexahydroazepino[4,5-b]indole-10-carboxylate (642 mg, 1.77 mmol) in THF (4 mL) and water (2 mL). Added lithium hydroxide monohydrate (408 mg, 9.72 mmol) and stirred for 1 hr at ambient temperature. Added 1N aqueous HCl to pH=4 and filtered to give 7,8-dichloro-2-oxo-1,2,3,4,5,6-hexahydroazepino[4,5-b]indole-10-carboxylic acid (680 mg, 98%) as a brown solid. ES/MS (m/z): ($^{35}Cl/^{37}Cl$) 313.2/315.2 (M+H).

Intermediate 34

7,8-Dichloro-N-(1-(hydroxyimino)ethyl)-2-oxo-1,2,3,4,5,6-hexahydroazepino[4,5-b]indole-10-carboxamide

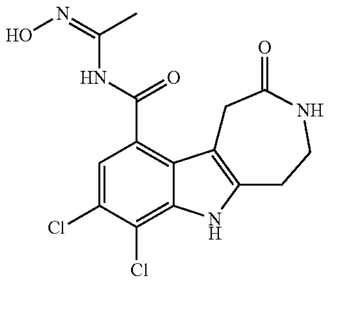 [SMILES: C/C(=N/O)NC(=O)c1cc(Cl)c(Cl)c2[nH]c3c(c12)CC(=O)NCC3]

Suspended 7,8-dichloro-2-oxo-1,2,3,4,5,6-hexahydroazepino[4,5-b]indole-10-carboxylic acid (200 mg, 0.511 mmol), N'-hydroxyacetimidamide (40 mg, 0.51 mmol), TBTU (185 mg, 0.565 mmol), and DIPEA (0.27 mL, 1.50 mmol) in DMF (2 mL). Stirred at 20° C. for 45 min. Added N'-hydroxyacetimidamide (40 mg, 0.51 mmol) and DMAP (7 mg, 0.06 mmol). Stirred at 20° C. overnight. Diluted with EtOAc, washed sequentially with water and saturated aqueous NaCl, dried over sodium sulfate, filtered, and concentrated under reduced pressure to give 7,8-dichloro-N-(1-(hydroxyimino)ethyl)-2-oxo-1,2,3,4,5,6-hexahydroazepino[4,5-b]indole-10-carboxamide (227 mg, 99%) as brown oil. ES/MS (m/z): ($^{35}$Cl/$^{37}$Cl) 369.0/371.0 (M+H).

Example 25

7,8-Dichloro-10-(3-methyl-1,2,4-oxadiazol-5-yl)-3,4,5,6-tetrahydroazepino[4,5-b]indol-2(1H)-one

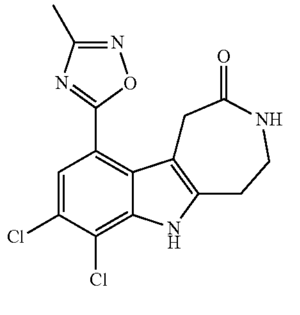 [SMILES: Cc1noc(-c2cc(Cl)c(Cl)c3[nH]c4c(c23)CC(=O)NCC4)n1]

Suspended 7,8-dichloro-N-(1-(hydroxyimino)ethyl)-2-oxo-1,2,3,4,5,6-hexahydroazepino[4,5-b]indole-10-carboxamide (227 mg, 0.504 mmol) in 1,4-dioxane (3 mL). Added KF (86 mg, 1.5 mmol) and stirred for 5 days at 110° C. Filtered and concentrated under reduced pressure. Purified by prep-HPLC give 7,8-dichloro-10-(3-methyl-1,2,4-oxadiazol-5-yl)-3,4,5,6-tetrahydroazepino[4,5-b]indol-2(1H)-one (14.88 mg, 8%) as a white solid. ES/MS (m/z): ($^{35}$Cl/$^{37}$Cl) 351.2/353.2 (M+H). $^{1}$H NMR (DMSO-d6): 12.03 (s, 1H), 7.77-7.72 (m, 1H), 7.65 (s, 1H), 3.58-3.53 (m, 4H), 3.01-2.98 (m, 2H), 2.48 (s, 3H).

Intermediate 35

Ethyl 2-(((7,8-dichloro-2-oxo-1,2,3,4,5,6-hexahydroazepino[4,5-b]indole-10-carbonyl)oxy)amino)-2-iminoacetate

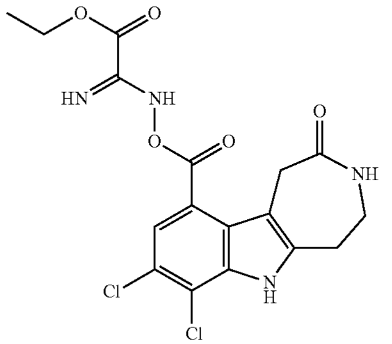 [SMILES: CCOC(=O)C(=N)NOC(=O)c1cc(Cl)c(Cl)c2[nH]c3c(c12)CC(=O)NCC3]

Dissolved 7,8-dichloro-2-oxo-1,2,3,4,5,6-hexahydroazepino[4,5-b]indole-10-carboxylic acid (488 mg, 1.29 mmol) in DMF (4 mL). Added TBTU (470 mg, 1.43 mmol) and DIEA (0.700 mL, 4.00 mmol). Stirred at ambient temperature for 0.75 hrs then added ethyl (N'-hydroxycarbamimidoyl)formate (200 mg, 1.44 mmol) and DMAP (16 mg, 0.13 mmol). Stirred at ambient temperature for 3 hrs. Filtered and triturated the precipitate with ACN (10 mL) at ambient temperature for 1 hr to give ethyl 2-(((7,8-dichloro-2-oxo-1,2,3,4,5,6-hexahydroazepino[4,5-b]indole-10-carbonyl)oxy)amino)-2-iminoacetate (360 mg, 61%) as a brown solid. ES/MS (m/z): ($^{35}$Cl/$^{37}$Cl) 427.0/429.0 (M+H).

Intermediate 36

Ethyl 5-(7,8-dichloro-2-oxo-1,2,3,4,5,6-hexahydroazepino[4,5-b]indol-10-yl)-1,2,4-oxadiazole-3-carboxylate

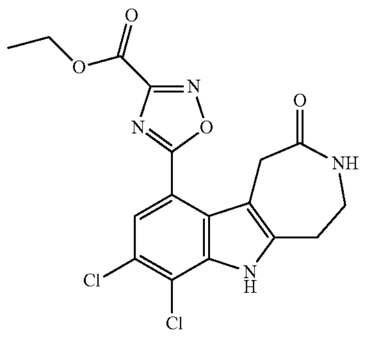 [SMILES: CCOC(=O)c1noc(-c2cc(Cl)c(Cl)c3[nH]c4c(c23)CC(=O)NCC4)n1]

Dissolved ethyl 2-(((7,8-dichloro-2-oxo-1,2,3,4,5,6-hexahydroazepino[4,5-b]indole-10-carbonyl)oxy)amino)-2-iminoacetate (360 mg, 0.800 mmol) in 1,4-dioxane (9 mL). Added KF (470 mg, 8.08 mmol), sparged with $N_2$ and stirred at 115° C. overnight. Added KF (700 mg, 12.0 mmol), sparged with $N_2$ and stirred at 115° C. overnight again. Added KF (690 mg, 11.9 mmol), sparged with $N_2$ and stirred at 115° C. for 5 hrs until the reaction was complete. Cooled to ambient temperature and poured the reaction mixture into water (30 mL). Filtered the precipitate and triturated with ACN to give ethyl 5-(7,8-dichloro-2-oxo-1,2,3,4,5,6-hexahydroazepino[4,5-b]indol-10-yl)-1,2,4-oxadiazole-3-carboxylate (230 mg, 69%) as an off-white solid. ES/MS (m/z): ($^{35}Cl/^{37}Cl$) 408.8/410.8 (M+H).

Example 26

7,8-Dichloro-10-(3-(hydroxymethyl)-1,2,4-oxadiazol-5-yl)-3,4,5,6-tetrahydroazepino[4,5-b]indol-2(1H)-one

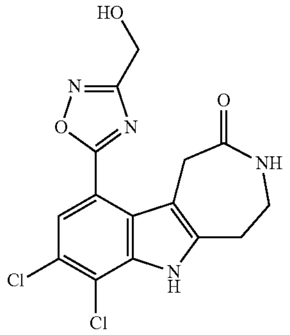 [SMILES: O=C1Cc2c([nH]c3c(Cl)c(Cl)cc(-c4nc(CO)no4)c23)CCN1]

Dissolved ethyl 5-(7,8-dichloro-2-oxo-1,2,3,4,5,6-hexahydroazepino[4,5-b]indol-10-yl)-1,2,4-oxadiazole-3-carboxylate (185 mg, 0.445 mmol) in THF (8 mL). Added lithium borohydride (30 mg, 1.4 mmol) at 0° C. and stirred for 30 minutes. Quenched with saturated aqueous $NH_4Cl$ (10 mL) and diluted with DCM (50 mL) and water (40 mL). Removed the solid by filtration and extracted the filtrate with DCM. Dried the organic layers over $Na_2SO_4$, filtered and concentrated under reduced pressure. Purified by Prep-HPLC to give 7,8-dichloro-10-(3-(hydroxymethyl)-1,2,4-oxadiazol-5-yl)-3,4,5,6-tetrahydroazepino[4,5-b]indol-2(1H)-one (35 mg, 21%) as a white solid. ES-MS (m/z): ($^{35}Cl/^{37}Cl$) 367.2/369.2 (M+H). $^1H$ NMR (DMSO): 12.08-12.07 (m, 1H), 7.75 (t, J=6.5 Hz, 1H), 7.67 (s, 1H), 5.83 (t, J=6.2 Hz, 1H), 4.69 (d, J=6.3 Hz, 2H), 3.58-3.54 (m, 4H), 3.01-2.99 (m, 2H).

Intermediate 37

7,8-Dichloro-10-vinyl-3,4,5,6-tetrahydroazepino[4,5-b]indol-2(1H)-one

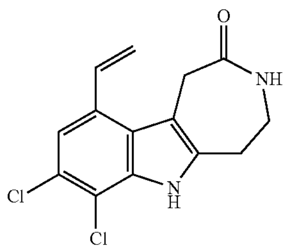 [SMILES: C=Cc1cc(Cl)c(Cl)c2[nH]c3c(c12)CC(=O)NCC3]

Suspended 10-bromo-7,8-dichloro-3,4,5,6-tetrahydroazepino[4,5-b]indol-2(1H)-one (500 mg, 1.39 mmol), potassium vinyltrifluoroborate (290 mg, 2.10 mmol), Pd(dppf)$Cl_2$ (105 mg, 0.142 mmol) and sodium carbonate (445 mg, 4.20 mmol) in 1,4-dioxane (4 mL) and water (1 mL). Sparged with $N_2$ and stirred at 90° C. overnight. Filtered and washed the solid with 1,4-dioxane, then concentrated the filtrate under reduced pressure. Purified by silica gel flash chromatography eluting with DCM/MeOH to give 7,8-dichloro-10-vinyl-3,4,5,6-tetrahydroazepino[4,5-b]indol-2(1H)-one (275 mg, 62%) as a yellow solid. ES/MS (m/z): ($^{35}Cl/^{37}Cl$) 295.0/297.0 (M+H).

Intermediate 38

7,8-Dichloro-10-(1,2-dihydroxyethyl)-3,4,5,6-tetrahydroazepino[4,5-b]indol-2(1H)-one

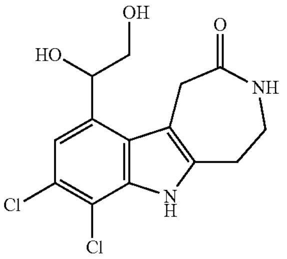 [SMILES: O=C1Cc2c([nH]c3c(Cl)c(Cl)cc(C(O)CO)c23)CCN1]

Dissolved 7,8-dichloro-10-vinyl-3,4,5,6-tetrahydroazepino[4,5-b]indol-2(1H)-one (275 mg, 0.866 mmol) and NMO (314 mg, 2.60 mmol) in THF (4 mL) and water (1 mL). Added potassium osmate dihydrate (87 mg, 0.26 mmol) and stirred overnight at ambient temperature. Diluted with EtOAc, washed sequentially with saturated aqueous sodium bicarbonate and saturated aqueous NaCl. Dried organics over sodium sulfate, filtered, and concentrated under reduced pressure to give 7,8-dichloro-10-(1,2-dihydroxyethyl)-3,4,5,6-tetrahydroazepino[4,5-b]indol-2(1H)-one (153 mg, 27%) as a dark green solid. ES/MS (m/z): ($^{35}Cl/^{37}Cl$) 310.9.0/312.9 (M+H, —$H_2O$).

Intermediate 39

7,8-Dichloro-2-oxo-1,2,3,4,5,6-hexahydroazepino[4,5-b]indole-10-carbaldehyde

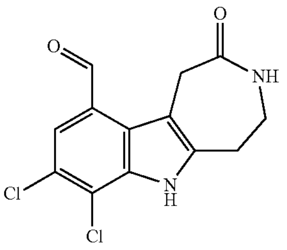 [SMILES: O=Cc1cc(Cl)c(Cl)c2[nH]c3c(c12)CC(=O)NCC3]

Suspended 7,8-dichloro-10-(1,2-dihydroxyethyl)-3,4,5,6-tetrahydroazepino[4,5-b]indol-2(1H)-one (153 mg, 0.237 mmol) and sodium periodate (103 mg, 0.481 mmol) in acetone (3 mL) and water (1.5 mL). Stirred at ambient temperature for 1 hr until the reaction was complete. Filtered and concentrated under reduced pressure to give 7,8-dichloro-2-oxo-1,2,3,4,5,6-hexahydroazepino[4,5-b]indole-10-carbaldehyde (120 mg, crude) as a yellow solid. ES/MS (m/z): ($^{35}Cl/^{37}Cl$) 297.0/299.0 (M+H).

Example 27

7,8-Dichloro-10-(oxazol-5-yl)-3,4,5,6-tetrahydroazepino[4,5-b]indol-2(1H)-one

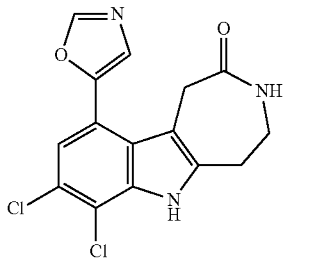 [SMILES: O=C1Cc2c([nH]c3c(Cl)c(Cl)cc(-c4cnco4)c23)CCN1]

Suspended 7,8-dichloro-2-oxo-1,2,3,4,5,6-hexahydroazepino[4,5-b]indole-10-carbaldehyde (120 mg, 0.263 mmol) in MeOH (3 mL). Added TosMIC (63 mg, 0.32 mmol) and potassium carbonate (73 mg, 0.53 mmol) and stirred for 2 hrs. at 70° C. Cooled to ambient temperature, diluted with EtOAc, washed with saturated aqueous NaCl, dried over sodium sulfate, filtered, and concentrated under reduced pressure. Purified by prep-HPLC to give 7,8-dichloro-10-(oxazol-5-yl)-3,4,5,6-tetrahydroazepino[4,5-b]indol-2(1H)-one (15 mg, 16%) as a white solid. ES/MS (m/z): ($^{35}Cl/^{37}Cl$) 336.2/338.2 (M+H). $^1H$ NMR (DMSO-d6): 11.79 (s, 1H), 8.53 (s, 1H), 7.70 (t, J=6.3 Hz, 1H), 7.45 (s, 1H), 7.26 (s, 1H), 3.38-3.35 (m, 2H), 2.97-2.94 (m, 2H).

Intermediate 40

7,8-Dichloro-10-(isoxazol-4-yl)-3,4,5,6-tetrahydroazepino[4,5-b]indol-2(1H)-one

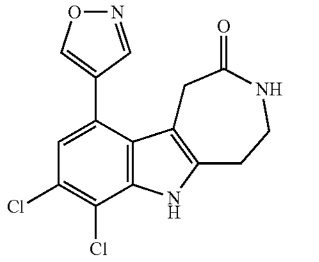 [SMILES: O=C1Cc2c([nH]c3c(Cl)c(Cl)cc(-c4cnoc4)c23)CCN1]

Suspended 10-bromo-7,8-dichloro-3,4,5,6-tetrahydroazepino[4,5-b]indol-2(1H)-one (100 mg, 0.260 mmol), 4-isoxazoleboronic acid pinacol ester (60 mg, 0.30 mmol), potassium fluoride (45 mg, 0.78 mmol) and Pd(dppf)$Cl_2$ (20 mg, 0.030 mmol) in DMSO (8 mL) and water (2 mL). Sparged with $N_2$ then stirred at 130° C. for 2 hrs. Filtered and concentrated under reduced pressure to give 7,8-dichloro-10-(isoxazol-4-yl)-3,4,5,6-tetrahydroazepino[4,5-b]indol-2(1H)-one or a ring-opened isomer (80 mg, crude) as a brown gum. ES/MS (m/z): ($^{35}Cl/^{37}Cl$) 335.8/337.8 (M+H).

Example 28

2-(7,8-Dichloro-2-oxo-1,2,3,4,5,6-hexahydroazepino[4,5-b]indol-10-yl)acetonitrile

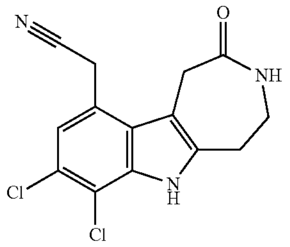 [SMILES: N#CCc1cc(Cl)c(Cl)c2[nH]c3c(c12)CC(=O)NCC3]

Dissolved 7,8-dichloro-10-(isoxazol-4-yl)-3,4,5,6-tetrahydroazepino[4,5-b]indol-2(1H)-one (80 mg, 0.21 mmol) and potassium fluoride (80 mg, 1.38 mmol) in DMF (3 mL) and water (3 mL). Stirred at 100° C. overnight. Filtered and concentrated under reduced pressure. Purified by prep-HPLC to give 2-(7,8-dichloro-2-oxo-1,2,3,4,5,6-hexahydroazepino[4,5-b]indol-10-yl)acetonitrile (20 mg, 30%) as a white solid. ES/MS (m/z): ($^{35}Cl/^{37}Cl$) 308.2/310.2 (M+H). $^1H$ NMR (DMSO-d6): 11.66-11.64 (m, 1H), 7.79 (t, J=6.2 Hz, 1H), 7.18 (s, 1H), 4.35 (s, 2H), 3.87 (s, 2H), 3.56-3.48 (m, 2H), 2.97-2.93 (m, 2H).

Intermediate 41

7,8-Dichloro-10-(4,4,5,5-tetramethyl-1,3,2-dioxaborolan-2-yl)-3,4,5,6-tetrahydroazepino[4,5-b]indol-2(1H)-one

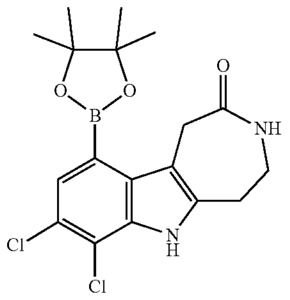 [SMILES: CC1(C)OB(c2cc(Cl)c(Cl)c3[nH]c4c(c23)CC(=O)NCC4)OC1(C)C]

Suspended 10-bromo-7,8-dichloro-3,4,5,6-tetrahydroazepino[4,5-b]indol-2(1H)-one (600 mg, 1.67 mmol), bis(pinacolato)diboron (900 mg, 3.37 mmol), potassium acetate (500 mg, 5.04 mmol), and Pd(dppf)$Cl_2$ (100 mg, 0.135 mmol) in 1,4-dioxane (10 mL) and THF (5 mL). Sparged with $N_2$ and heated at 90° C. overnight. Cooled to RT and use directly in subsequent transformation (crude recovery: 3.30 g, roughly 20 mass %).

Intermediate 42

7,8-Dichloro-10-(1-((2-(trimethylsilyl)ethoxy)methyl)-1H-1,2,4-triazol-3-yl)-3,4,5,6-tetrahydroazepino[4,5-b]indol-2(1H)-one

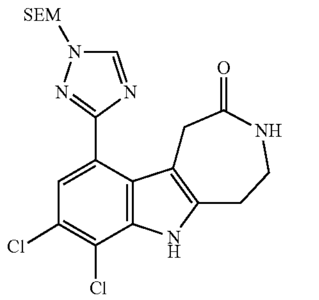 [SMILES: C[Si](C)(C)CCOCn1cnc(-c2cc(Cl)c(Cl)c3[nH]c4c(c23)CC(=O)NCC4)n1]

Suspended 7,8-dichloro-10-(4,4,5,5-tetramethyl-1,3,2-dioxaborolan-2-yl)-3,4,5,6-tetrahydroazepino[4,5-b]indol-2(1H)-one (2.20 g, crude), 3-bromo-1-((2-(trimethylsilyl)ethoxy)methyl)-1H-1,2,4-triazole (CAS 1260599-41-4, 400 mg, 1.15 mmol), $Pd(dppf)Cl_2$ (85 mg, 0.12 mmol) and $K_2CO_3$ (500 mg, 3.44 mmol) in 1,4-dioxane (16 mL) and water (4 mL). Sparged with $N_2$ and stirred at 100° C. overnight. Cooled to ambient temperature and concentrated under reduced pressure. Purified by silica gel flash chromatography eluting with DCM/MeOH to give 7,8-dichloro-10-(1-((2-(trimethylsilyl)ethoxy)methyl)-1H-1,2,4-triazol-3-yl)-3,4,5,6-tetrahydroazepino[4,5-b]indol-2(1H)-one (220 mg, 24%) as a brown solid. ES/MS (m/z): ($^{35}Cl/^{37}Cl$) 465.8/467.9 (M+H).

Example 29

7,8-Dichloro-10-(4H-1,2,4-triazol-3-yl)-3,4,5,6-tetrahydroazepino[4,5-b]indol-2(1H)-one

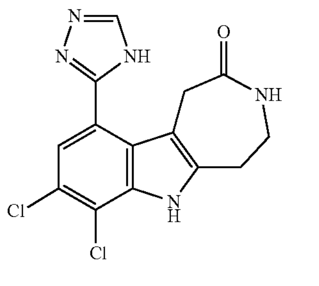 [SMILES: O=C1Cc2c([nH]c3c(Cl)c(Cl)cc(-c4nnc[nH]4)c23)CCN1]

Dissolved 7,8-dichloro-10-(1-((2-(trimethylsilyl)ethoxy)methyl)-1H-1,2,4-triazol-3-yl)-3,4,5,6-tetrahydroazepino[4,5-b]indol-2(1H)-one (200 mg, 0.240 mmol) in DCM (4 mL) and added TFA (2 mL). Stirred for 2 hrs at ambient temperature and concentrated under reduced pressure. Purified by prep-HPLC to give 7,8-dichloro-10-(4H-1,2,4-triazol-3-yl)-3,4,5,6-tetrahydroazepino[4,5-b]indol-2(1H)-one (48 mg, 58%) as a white solid. ES/MS (m/z): ($^{35}Cl/^{37}Cl$) 336.2/338.2 (M+H). $^1H$ NMR (DMSO-d6): 14.35-14.28 (m, 1H), 11.67 (d, J=70.5 Hz, 1H), 8.72-8.13 (m, 1H), 7.69-7.61 (m, 1H), 7.31 (d, J=12.1 Hz, 1H), 3.51 (s, 4H), 2.96 (s, 2H).

Example 30

7,8-Dichloro-10-(ethylamino)-3,4,5,6-tetrahydroazepino[4,5-b]indol-2(1H)-one

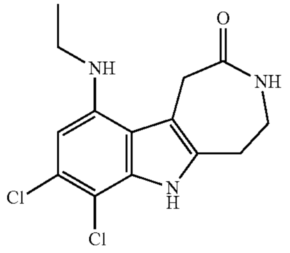 [SMILES: CCNc1cc(Cl)c(Cl)c2[nH]c3c(c12)CC(=O)NCC3]

Dissolved 10-amino-7,8-dichloro-3,4,5,6-tetrahydroazepino[4,5-b]indol-2(1H)-one hydrochloride (150 mg, 0.459 mmol) in MeOH (15 mL) and added acetic acid to adjust to pH 5. Stirred at ambient temperature for 30 min. Added acetaldehyde (30 mg, 0.68 mmol) and stirred at ambient temperature for 30 min. Added sodium cyanoborohydride (91 mg, 1.38 mmol) and stirred at ambient temperature for 5 hrs. Diluted with EtOAc, washed sequentially with saturated aqueous sodium bicarbonate and saturated aqueous NaCl, dried over sodium sulfate, filtered, and concentrated under reduced pressure. Purified by silica gel flash chromatography eluting with DCM/MeOH, then prep-HPLC to give 7,8-dichloro-10-(ethylamino)-3,4,5,6-tetrahydroazepino[4,5-b]indol-2(1H)-one (18 mg, 12%) as a white solid. ES/MS (m/z): ($^{35}Cl/^{37}Cl$) 312.2/314.2 (M+H). $^1H$ NMR (DMSO-d6): 11.07-11.05 (m, 1H), 7.74-7.70 (m, 1H), 6.21 (s, 1H), 5.36-5.21 (m, 1H), 3.93 (s, 2H), 3.51-3.49 (m, 2H), 3.14-3.10 (m, 2H), 2.90-2.88 (m, 2H), 1.24-1.20 (m, 3H).

Intermediate 43

7,8-Dichloro-10-(isoxazol-4-yl)-1-methyl-3,4,5,6-tetrahydroazepino[4,5-b]indol-2(1H)-one

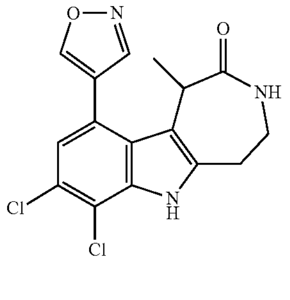 [SMILES: CC1C(=O)NCCc2[nH]c3c(Cl)c(Cl)cc(-c4cnoc4)c3c21]

Dissolved 7,8-dichloro-10-hydroxy-1-methyl-3,4,5,6-tetrahydroazepino[4,5-b]indol-2(1H)-one (200 mg, 0.359 mmol), 4-isoxazoleboronic acid pinacol ester (150 mg, 0.754 mmol), KF (150 mg, 2.58 mmol), and $Pd(dppf)Cl_2$ (50 mg, 0.068 mmol) in DMSO (5 mL) and water (1.25 mL). Sparged with $N_2$ and stirred at 100° C. for 1 hr. Diluted with water (20 mL), extracted with EtOAc, dried over anhydrous sodium sulfate, filtered, and concentrated under reduced pressure. Purified by silica gel chromatography eluting with DCM/MeOH to give 7,8-dichloro-10-(isoxazol-4-yl)-1-methyl-3,4,5,6-tetrahydroazepino[4,5-b]indol-2(1H)-one or a ring-opened isomer (130 mg, 68%) as a brown solid. ES/MS (m/z): ($^{35}Cl/^{37}Cl$) 349.8/351.8 (M+H).

Example 31

2-(7,8-Dichloro-1-methyl-2-oxo-1,2,3,4,5,6-hexahydroazepino[4,5-b]indol-10-yl)acetonitrile

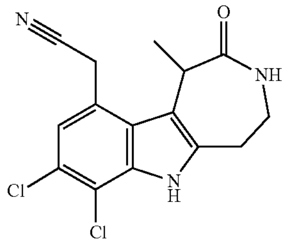 [SMILES: CC1C(=O)NCCc2[nH]c3c(Cl)c(Cl)cc(CC#N)c3c21]

Dissolved 7,8-dichloro-10-(isoxazol-4-yl)-1-methyl-3,4,5,6-tetrahydroazepino[4,5-b]indol-2(1H)-one (130 mg, 0.245 mmol), KF (120 mg, 2.07 mmol) in DMF (3 mL) and water (3 mL). Stirred at 100° C. overnight. Concentrated under reduced pressure to remove water. Purified by prep-HPLC to give 2-(7,8-dichloro-1-methyl-2-oxo-1,2,3,4,5,6-hexahydroazepino[4,5-b]indol-10-yl)acetonitrile (26 mg, 32%) as a yellow solid. ES/MS (m/z): ($^{35}Cl/^{37}Cl$) 322.2/324.2 (M+H). $^1H$ NMR (DMSO-d6): 11.60 (s, 1H), 7.83-7.79 (m, 1H), 7.21 (s, 1H), 4.35-4.23 (m, 2H), 4.05-4.00 (m, 1H), 3.75-3.73 (m, 1H), 3.28-3.25 (m, 1H), 3.07-2.92 (m, 2H), 1.58 (d, J=7.5 Hz, 3H).

Example 32

$N^1$-(7,8-Dichloro-2-oxo-1,2,3,4,5,6-hexahydroazepino[4,5-b]indol-10-yl)oxalamide

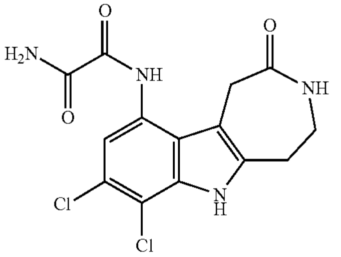 [SMILES: NC(=O)C(=O)Nc1cc(Cl)c(Cl)c2[nH]c3c(c12)CC(=O)NCC3]

Combined 10-amino-7,8-dichloro-3,4,5,6-tetrahydroazepino[4,5-b]indol-2(1H)-one (100 mg, 0.282 mmol, 80 mass %), oxamic acid (76 mg, 0.853 mmol) and DIPEA (0.25 mL, 0.853 mmol) in DMF (3 mL). Added 1-[bis(dimethylamino)methylene]-1H-1,2,3-triazolo[4,5-b]pyridinium 3-oxide hexafluorophosphate (220 mg, 0.567 mmol). Stirred at 20° C. for 2 hrs. Quenched with water (30 mL) and extracted with EtOAc (20 mL×3). Washed combined organic layers with saturated aqueous NaCl (50 mL), dried over anhydrous $Na_2SO_4$, filtered, and concentrated under reduced pressure. Purified by silica gel flash chromatography eluting with MeOH in DCM and concentrated under reduced pressure. The residue was further purified by prep-HPLC to give $N^1$-(7,8-dichloro-2-oxo-1,2,3,4,5,6-hexahydroazepino[4,5-b]indol-10-yl)oxalamide (12 mg, 11%) as a yellow solid. ES/MS (m/z): ($^{35}Cl/^{37}Cl$) 355.0/356.9 (M+H).

Intermediate 44 tert-Butyl N—[N-(7,8-dichloro-2-oxo-3,4,5,6-tetrahydro-1H-azepino[4,5-b]indole-10-carbonyl)carbamimidoyl]carbamate

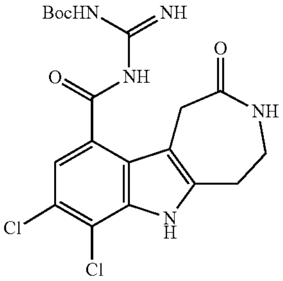 [SMILES: CC(C)(C)OC(=O)NC(=N)NC(=O)c1cc(Cl)c(Cl)c2[nH]c3c(c12)CC(=O)NCC3]

Combined 7,8-dichloro-2-oxo-1,2,3,4,5,6-hexahydroazepino[4,5-b]indole-10-carboxylic acid (400 mg, 0.894 mmol, 70 mass %), ((1H-benzo[d][1,2,3]triazol-1-yl)oxy)tri(pyrrolidin-1-yl)phosphonium (560 mg, 1.076 mmol) and 4-methylmorpholine (460 mg, 4.50 mmol) in DMF (10 mL). Stirred at ambient temperature for 15 min. Added tert-butyl N-carbamimidoylcarbamate (285 mg, 1.79 mmol). Stirred overnight at ambient temperature. Quenched with water (20 mL), extracted with EtOAc (30 mL). The organic layer was washed with water (10 mL×5) and saturated aqueous NaCl (20 mL×2), dried over anhydrous $Na_2SO_4$, filtered, and concentrated under reduced pressure. Purified by silica gel flash chromatography eluting with MeOH in DCM to give tert-butyl N—[N-(7,8-dichloro-2-oxo-3,4,5,6-tetrahydro-1H-azepino[4,5-b]indole-10-carbonyl)carbamimidoyl]carbamate (400 mg, 82 mass %, 81%) as a yellow solid. ES/MS (m/z): ($^{35}Cl/^{37}Cl$) 453.8/455.8 (M+H).

Intermediate 45 tert-Butyl (5-(7,8-dichloro-2-oxo-1,2,3,4,5,6-hexahydroazepino[4,5-b]indol-10-yl)-1,2,4-oxadiazol-3-yl)carbamate

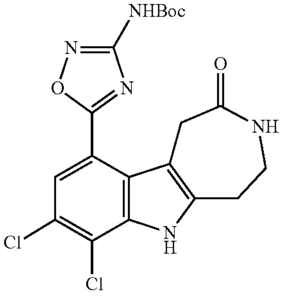 [SMILES: CC(C)(C)OC(=O)Nc1noc(-c2cc(Cl)c(Cl)c3[nH]c4c(c23)CC(=O)NCC4)n1]

Dissolved tert-butyl N— [N-(7,8-dichloro-2-oxo-3,4,5,6-tetrahydro-1H-azepino[4,5-b]indole-10-carbonyl)carbamimidoyl]carbamate (200 mg, 0.361 mmol, 82 mass %) in DMF (5 mL). Added (diacetoxyiodo)benzene at 0° C. Stirred at ambient temperature overnight. Diluted the reaction mixture with water (10 mL) and extracted with EtOAc (10 mL) (×3). Washed combined organic layers with saturated aqueous sodium bicarbonate solution (10 mL). Dried the organic layer over anhydrous $Na_2SO_4$, filtered, and concentrated under reduced pressure. Purified residue by silica gel flash chromatography eluting with MeOH in DCM to give tert-butyl (5-(7,8-dichloro-2-oxo-1,2,3,4,5,6-hexahydroazepino[4,5-b]indol-10-yl)-1,2,4-oxadiazol-3-yl)carbamate (140 mg, 53%) as a yellow solid. ES/MS (m/z): ($^{35}Cl/^{37}Cl$) 452.1/454.0 (M+H) and 396.0/397.9 (M+H-tBu).

Example 33

10-(3-Amino-1,2,4-oxadiazol-5-yl)-7,8-dichloro-3,4,5,6-tetrahydroazepino[4,5-b]indol-2(1H)-one

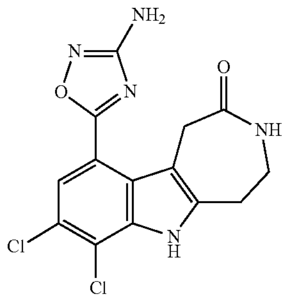 [SMILES: Nc1noc(-c2cc(Cl)c(Cl)c3[nH]c4c(c23)CC(=O)NCC4)n1]

Added TFA (1 mL, 12.9 mmol) to tert-butyl (5-(7,8-dichloro-2-oxo-1,2,3,4,5,6-hexahydroazepino[4,5-b]indol-10-yl)-1,2,4-oxadiazol-3-yl)carbamate (140 mg, 0.192 mmol, 62 mass %) in DCM (3 mL). Stirred at ambient temperature for 1 hr. Concentrated under reduced pressure and purified by prep-HPLC to give 10-(3-amino-1,2,4-oxadiazol-5-yl)-7,8-dichloro-3,4,5,6-tetrahydroazepino[4,5-b]indol-2(1H)-one (32 mg, 47%) as a yellow solid. ES/MS (m/z): ($^{35}Cl/^{37}Cl$) 352.0/354.0 (M+H).

Example 34

10-(6-Aminopyrazin-2-yl)-7,8-dichloro-3,4,5,6-tetrahydroazepino[4,5-b]indol-2(1H)-one

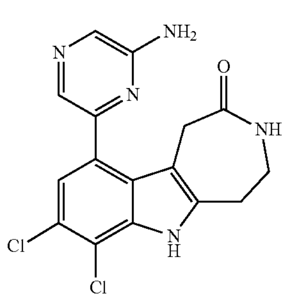 [SMILES: Nc1cncc(-c2cc(Cl)c(Cl)c3[nH]c4c(c23)CC(=O)NCC4)n1]

Combined 7,8-dichloro-10-(4,4,5,5-tetramethyl-1,3,2-dioxaborolan-2-yl)-3,4,5,6-tetrahydroazepino[4,5-b]indol-2(1H)-one (350 mg, 0.656 mmol, 74 mass %), 6-bromopyrazin-2-amine (116 mg, 0.656 mmol), $Pd(dppf)Cl_2$ (49 mg, 0.066 mmol) and $Na_2CO_3$ (175 mg, 1.64 mmol) in 1,4-dioxane (4 mL) and $H_2O$ (1 mL). Stirred at 90° C. for 3 hrs, under $N_2$ atmosphere. Concentrated under reduced pressure, diluted the residue with water, extracted with EtOAc (3×). Combined the organic layers, dried over anhydrous $Na_2SO_4$, filtered, and concentrated under reduced pressure. Purified by silica gel flash chromatography eluting with MeOH in DCM. Concentrated under reduced pressure and triturated with ACN, stirred at 20° C. for 1 hr, to give 10-(6-aminopyrazin-2-yl)-7,8-dichloro-3,4,5,6-tetrahydroazepino[4,5-b]indol-2(1H)-one (54.76 mg, 22%) as a white solid. ES-MS (m/z): ($^{35}Cl/^{37}Cl$) 362.0/364.0 (M+H).

Intermediate 46

7,8-Dichloro-1-ethyl-10-hydroxy-3,4,5,6-tetrahydroazepino[4,5-b]indol-2(1H)-one

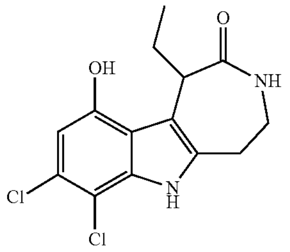 [SMILES: CCC1C(=O)NCCc2[nH]c3c(Cl)c(Cl)cc(O)c3c21]

Combined 10-bromo-7,8-dichloro-1-ethyl-3,4,5,6-tetrahydroazepino[4,5-b]indol-2(1H)-one (500 mg, 0.651 mmol, 49 mass %), cesium hydroxide monohydrate (115 mg, 0.651 mmol), tert-BuBrettPhos-Pd-$G_3$ (59 mg, 0.065 mmol) in 1,4-dioxane (10 mL) and $H_2O$ (2.5 mL). Degassed and purged with $N_2$ three times. Stirred and heated at 65° C. for 2 hrs under $N_2$ atmosphere. Cooled to ambient temperature. Concentrated under reduced pressure. Purified by silica gel flash chromatography eluting with MeOH in DCM and concentrated under reduced pressure to give 7,8-dichloro-1-ethyl-10-hydroxy-3,4,5,6-tetrahydroazepino[4,5-b]indol-2(1H)-one (200 mg, 66%) as a light yellow oil. ES/MS (m/z): ($^{35}Cl/^{37}Cl$) 312.9/314.8 (M+H).

Intermediate 47

2-((7,8-Dichloro-1-ethyl-2-oxo-1,2,3,4,5,6-hexahydroazepino[4,5-b]indol-10-yl)oxy)acetonitrile

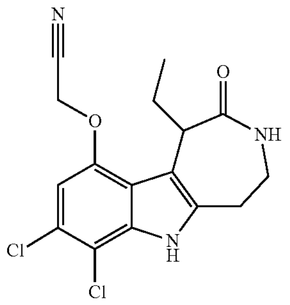 [SMILES: CCC1C(=O)NCCc2[nH]c3c(Cl)c(Cl)cc(OCC#N)c3c21]

Combined 7,8-dichloro-1-ethyl-10-hydroxy-3,4,5,6-tetrahydroazepino[4,5-b]indol-2(1H)-one (200 mg, 0.428 mmol, 67 mass %) and $K_2CO_3$ (91 mg, 0.64 mmol) in DMF (5 mL), and added 2-chloroacetonitrile (66 mg, 0.86 mmol). Stirred at ambient temperature for 16 hrs. Diluted with water and extracted with EtOAc (2×). Combined organic layers, washed with saturated aqueous NaCl (2×) and dried over anhydrous $Na_2SO_4$, filtered, and concentrated under reduced pressure. Purified by silica gel flash chromatography eluting with EtOAc in PE and concentrated under reduced pressure to give racemic 2-((7,8-dichloro-1-ethyl-2-oxo-1,2,3,4,5,6-hexahydroazepino[4,5-b]indol-10-yl)oxy)acetonitrile (65 mg, 32%) as a light yellow oil. ES/MS (m/z): ($^{35}Cl/^{37}Cl$) 351.8/353.8 (M+H).

Example 35

(R)-2-((7,8-Dichloro-1-ethyl-2-oxo-1,2,3,4,5,6-hexahydroazepino[4,5-b]indol-10-yl)oxy)acetonitrile Or (S)-2-((7,8-Dichloro-1-ethyl-2-oxo-1,2,3,4,5,6-hexahydroazepino[4,5-b]indol-10-yl)oxy)acetonitrile (isomer 1) and Example 36

(R)-2-((7,8-Dichloro-1-ethyl-2-oxo-1,2,3,4,5,6-hexahydroazepino[4,5-b]indol-10-yl)oxy)acetonitrile Or (S)-2-((7,8-Dichloro-1-ethyl-2-oxo-1,2,3,4,5,6-hexahydroazepino[4,5-b]indol-10-yl)oxy)acetonitrile (isomer 2)

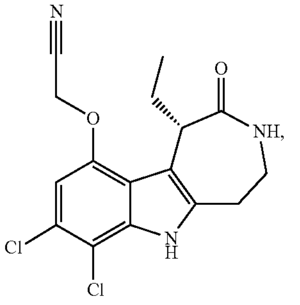

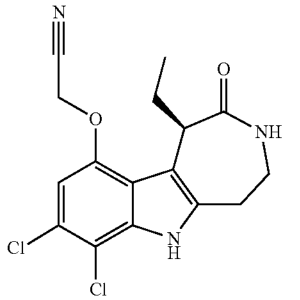

Purified racemic 2-((7,8-dichloro-1-ethyl-2-oxo-1,2,3,4,5,6-hexahydroazepino[4,5-b]indol-10-yl)oxy)acetonitrile (65 mg, 0.14 mmol, 75 mass %) by SFC to give the titled compounds (Isomer 1—Rt=1.572 min (100% ee), 16 mg, 32% as an off-white solid; Isomer 2—Rt=1.718 min (99.6% ee), 15 mg, 32% as an off-white solid). Mobile Phase: 40% EtOH (0.1% $NH_3H_2O$): 60% $CO_2$; Column: DAICEL CHIRALCEL OJ (30×250 mm, 10 μm); FlowRate: 80 mL/min. ES/MS (m/z) ($^{35}Cl/^{37}Cl$): 352.1/354.0 (M+H).

Example 37

(R)-7,8-Dichloro-1-methyl-10-(2-methyl-2H-1,2,3-triazol-4-yl)-3,4,5,6-tetrahydroazepino[4,5-b]indol-2(1H)-one Or (S)-7,8-Dichloro-1-methyl-10-(2-methyl-2H-1,2,3-triazol-4-yl)-3,4,5,6-tetrahydroazepino[4,5-b]indol-2(1H)-one (isomer 1) and Example 38

(R)-7,8-Dichloro-1-methyl-10-(2-methyl-2H-1, 2, 3-triazol-4-yl)-3,4,5,6-tetrahydroazepino[4,5-b]indol-2(1H)-one Or (S)-7,8-Dichloro-1-methyl-10-(2-methyl-2H-1,2,3-triazol-4-yl)-3,4,5,6-tetrahydroazepino[4,5-b]indol-2(1H)-one (isomer 2)

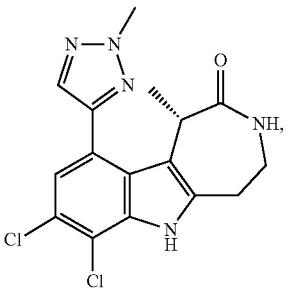

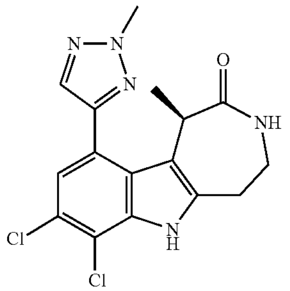

Purified racemic 7,8-dichloro-1-methyl-10-(2-methyl-2H-1,2,3-triazol-4-yl)-3,4,5,6-tetrahydroazepino[4,5-b]indol-2(1H)-one (26.5 mg, 0.073 mmol) by SFC to give the titled compounds (Isomer 1—Rt=1.61 min (100% ee), 9.9 mg, 37%; Isomer 2—Rt=2.22 min (94% ee), 9.6 mg, 36%). Column: Chiralpak AD-H, 21×150 mm; Mobile Phase: 25% MeOH: 75% $CO_2$; Flow Rate: 80 mL/min; Column temperature: 40° C.; Detection: 225 nM. ES/MS (m/z): ($^{35}Cl/^{37}Cl$) 364.0/366.0 (M+H).

Example 39

N-(7,8-Dichloro-1-methyl-2-oxo-1,2,3,4,5,6-hexahydroazepino[4,5-b]indol-10-yl)-2-methoxyacetamide

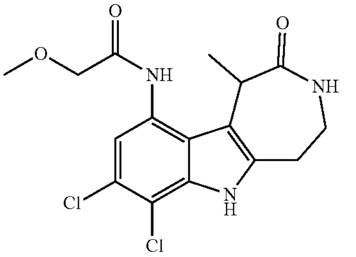 [SMILES: COCC(=O)Nc1cc(Cl)c(Cl)c2[nH]c3c(c12)C(C)C(=O)NCC3]

Combined 10-bromo-7,8-dichloro-1-methyl-3,4,5,6-tetrahydroazepino[4,5-b]indol-2(1H)-one (150 mg, 0.302 mmol, 73 mass %), 2-methoxyacetamide (59 mg, 0.67 mmol), $Pd_2(dba)_3$ (28 mg, 0.030 mmol), Xantphos (35 mg, 0.061 mmol) and cesium carbonate (345 mg, 1.06 mmol) in 1,4-dioxane (10 mL) and THF (1 mL). Degassed and purged with $N_2$ (x3). Stirred at 110° C. for 16 hrs, under $N_2$ atmosphere. Filtered and added water to the filtrate, extracted with EtOAc. Combined the organic layers, washed with saturated aqueous NaCl, dried over anhydrous $Na_2SO_4$, filtered, and concentrated under reduced pressure. Purified by flash silica gel chromatography eluting with MeOH in DCM and concentrated under reduced pressure, and further purified by prep-HPLC to give N-(7,8-dichloro-1-methyl-2-oxo-1,2,3,4,5,6-hexahydroazepino[4,5-b]indol-10-yl)-2-methoxyacetamide (55.37 mg, 48%) as a yellow solid. ES/MS (m/z): ($^{35}Cl/^{37}Cl$) 370.0/371.9 (M+H).

Example 40

(R)—N-(7,8-Dichloro-1-methyl-2-oxo-1,2,3,4,5,6-hexahydroazepino[4,5-b]indol-10-yl)-2-methoxyacetamide Or (S)—N-(7,8-Dichloro-1-methyl-2-oxo-1,2,3,4,5,6-hexahydroazepino[4,5-b]indol-10-yl)-2-methoxyacetamide (isomer 1) and Example 41

(R)—N-(7,8-Dichloro-1-methyl-2-oxo-1,2,3,4,5,6-hexahydroazepino[4,5-b]indol-10-yl)-2-methoxyacetamide Or (S)—N-(7,8-Dichloro-1-methyl-2-oxo-1,2,3,4,5,6-hexahydroazepino[4,5-b]indol-10-yl)-2-methoxyacetamide (isomer 2)

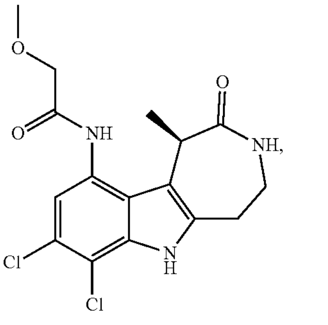

-continued

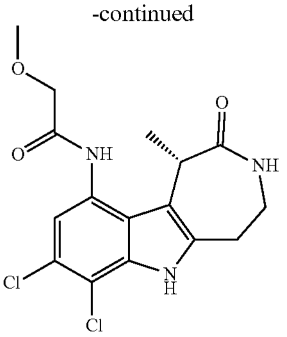

Purified racemic N-(7,8-dichloro-1-methyl-2-oxo-1,2,3,4,5,6-hexahydroazepino[4,5-b]indol-10-yl)-2-methoxyacetamide (151.6 mg, 0.409 mmol) by SFC to give the titled compounds (Isomer 1—Rt=1.29 min (98% ee), 55.2 mg, 36%; Isomer 2—Rt=2.38 min (100% ee), 49.0 mg, 32%). Column: Chiralpak AD-H, 21×150 mm; Mobile Phase: 25% EtOH with 0.5%% DMEA: 75% $CO_2$; Flow Rate: 80 mL/min; Column temperature: 40° C.; Detection: 254 nM. ES/MS (m/z): ($^{35}Cl/^{37}Cl$) 370.2/372.2 (M+H).

Example 42

(S)—N—((R)-7,8-Dichloro-1-methyl-2-oxo-1,2,3,4,5,6-hexahydroazepino[4,5-b]indol-10-yl)-2-hydroxypropanamide Or (S)—N—((S)-7,8-Dichloro-1-methyl-2-oxo-1,2,3,4,5,6-hexahydroazepino[4,5-b]indol-10-yl)-2-hydroxypropanamide (isomer 1)

Example 43

(S)—N—((R)-7,8-Dichloro-1-methyl-2-oxo-1,2,3,4,5,6-hexahydroazepino[4,5-b]indol-10-yl)-2-hydroxypropanamide Or (S)—N—((S)-7,8-Dichloro-1-methyl-2-oxo-1,2,3,4,5,6-hexahydroazepino[4,5-b]indol-10-yl)-2-hydroxypropanamide (isomer 2)

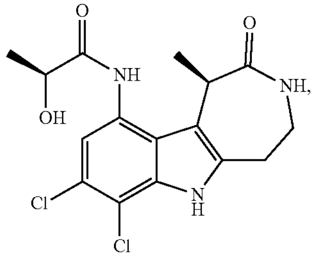

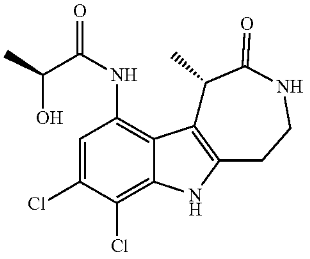

Combined 10-bromo-7,8-dichloro-1-methyl-3,4,5,6-tetrahydroazepino[4,5-b]indol-2(1H)-one (270 mg, 0.664 mmol, 89 mass %), (S)-2-hydroxypropanamide (124 mg, 1.33 mmol), XantPhos-Pd-$G_2$ (62 mg, 0.066 mmol) and cesium carbonate (683 mg, 1.99 mmol) in 1,4-dioxane (10 mL) and THF (1 mL). Degassed and purged with $N_2$ (×3). Stirred at 80° C. for 2 hrs, under $N_2$ atmosphere. Cooled to ambient temperature. Diluted with water, extracted with EtOAc (2×). Combined organic layers, washed with saturated aqueous NaCl (2×), dried over anhydrous $Na_2SO_4$, filtered, and concentrated under reduced pressure. Purified by silica gel flash chromatography eluting with MeOH in DCM and concentrated under reduced pressure. Then further purified by prep-HPLC to give the titled compounds (Isomer 1—Rt=1.475 min (98% de), 68 mg, 27% as a white solid; Isomer 2—Rt=1.547 min (97.3% de), 33 mg, 13% as a white solid). ES/MS (m/z): ($^{35}Cl/^{37}Cl$) 370.0/372.0 (M+H).

Intermediate 47A

10-Amino-7,8-dichloro-1-methyl-3,4,5,6-tetrahydroazepino[4,5-b]indol-2(1H)-one

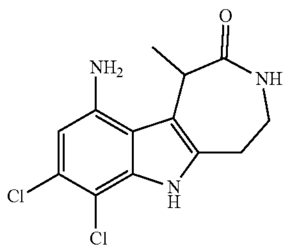 [SMILES: CC1C(=O)NCCc2[nH]c3c(Cl)c(Cl)cc(N)c3c21]

Combined 10-bromo-7,8-dichloro-1-methyl-3,4,5,6-tetrahydroazepino[4,5-b]indol-2(1H)-one (240 mg, 663 μmol), tris(dibenzylideneacetone)dipalladium(0) (60.7 mg, 66.3 μmol), 4,5-bis(diphenylphosphino)-9,9-dimethyl xanthene (76.7 mg, 133 μmol), tert-butyl carbamate (155 mg, 1.33 mmol), then added 1,4-dioxane (5 mL). Bubbled in $N_2$ for 5 min. Added cesium carbonate (756 mg, 2.32 mmol) and bubbled in $N_2$ for additional 2 min, then sealed and heated to 100° C. overnight. Cooled to ambient temperature, added EtOAc, and washed with water. Washed with saturated sodium bicarbonate, saturated aqueous NaCl, dried over sodium sulfate, filtered, concentrated. Redissolved in DCM (3 mL). Added 2 drops anisole (50 mg, 50 μL, 0.46 mmol) and then added TFA (1.5 g, 1.0 mL, 13 mmol). Stirred at ambient temperature for 1 hr. Quenched with saturated aqueous sodium bicarbonate solution and added EtOAc. Extracted, then washed with saturated aqueous sodium bicarbonate solution, saturated aqueous NaCl, dried over sodium sulfate, filtered, Concentrated under reduced pressure and purified by normal phase silica gel column chromatography eluting with MeOH in DCM to give 10-amino-7,8-dichloro-1-methyl-3,4,5,6-tetrahydroazepino[4,5-b]indol-2(1H)-one (0.13 g, 66%) as an orange foam. ES/MS (m/z): ($^{35}Cl/^{37}Cl$) 297.8/299.8 (M+H).

Example 44

N-(7,8-Dichloro-1-methyl-2-oxo-1,2,3,4,5,6-hexahydroazepino[4,5-b]indol-10-yl)oxetane-2-carboxamide

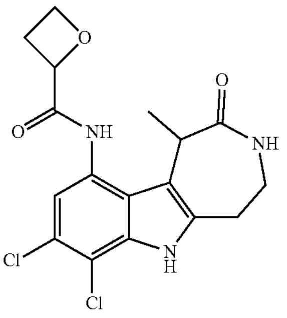 [SMILES: CC1C(=O)NCCc2[nH]c3c(Cl)c(Cl)cc(NC(=O)C4CCO4)c3c21]

Dissolved 10-amino-7,8-dichloro-1-methyl-3,4,5,6-tetrahydroazepino[4,5-b]indol-2(1H)-one (50 mg, 0.17 mmol) in DMF (2 mL), and added DIPEA (73 μL, 0.42 mmol) and rac-oxetane-2-carboxylic acid (26 mg, 0.25 mmol). Added propylphosphonic anhydride (50% in DMF) (0.12 mL, 0.20 mmol), then stirred at ambient temperature overnight. Added additional DIPEA (73 μL, 0.42 mmol) followed by propylphosphonic anhydride (50% in DMF) (0.15 g, 0.14 mL, 0.25 mmol). Diluted with EtOAc and washed with 0.1N HCl, saturated aqueous sodium bicarbonate (2×), and saturated aqueous NaCl. Dried organics over $Na_2SO_4$, filtered, and concentrated under reduced pressure. Purified via flash chromatography eluting with MeOH in DCM to give N-(7,8-dichloro-1-methyl-2-oxo-1,2,3,4,5,6-hexahydroazepino[4,5-b]indol-10-yl)oxetane-2-carboxamide (35 mg, 55%). ES/MS (m/z): ($^{35}Cl/^{37}Cl$) 381.9/383.9 (M+H).

Example 45

7,8-Dichloro-1-methyl-10-(propylamino)-3,4,5,6-tetrahydroazepino[4,5-b]indol-2(1H)-one

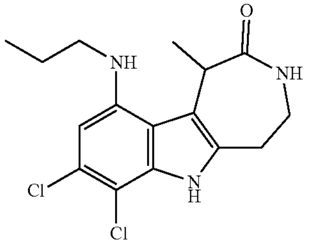 [SMILES: CCCNc1cc(Cl)c(Cl)c2[nH]c3c(c12)C(C)C(=O)NCC3]

Combined 10-bromo-7,8-dichloro-1-methyl-3,4,5,6-tetrahydroazepino[4,5-b]indol-2(1H)-one (120 mg, 0.298 mmol, 90 mass %), propan-1-amine (93 mg, 1.5 mmol), $Pd_2(dba)_3$ (37 mg, 0.039 mmol), Xantphos (45 mg, 0.075 mmol) and cesium carbonate (245 mg, 0.746 mmol) in 1,4-dioxane (4 mL) and THF (0.2 mL). Stirred at 105° C. under $N_2$ atmosphere for 16 hrs. Concentrated under reduced pressure and diluted with water, extracted with EtOAc (3×). Combined organic layers, dried over anhydrous $Na_2SO_4$, filtered, and concentrated under reduced pressure. Purified by prep-TLC eluting with MeOH in DCM, then further purified by prep-HPLC. Concentrated under reduced pressure and lyophilized to give 7,8-dichloro-1-methyl-10-(propylamino)-3,4,5,6-tetrahydroazepino[4,5-b]indol-2(1H)-one (33 mg, 32%) as a gray solid. ES/MS (m/z): ($^{35}Cl/^{37}Cl$) 340.0/342.0 (M+H).

Example 46

7,8-Dichloro-10-((2-methoxyethyl)amino)-1-methyl-3,4,5,6-tetrahydroazepino[4,5-b]indol-2(1H)-one

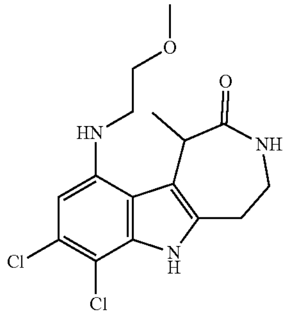 [SMILES: COCCNc1cc(Cl)c(Cl)c2[nH]c3c(c12)C(C)C(=O)NCC3]

Added 10-bromo-7,8-dichloro-1-methyl-3,4,5,6-tetrahydroazepino[4,5-b]indol-2(1H)-one (80 mg, 0.22 mmol), 2-methoxyethan-1-amine (33 mg, 0.44 mmol), XantPhos-Pd-G2 (39 mg, 0.044 mmol), potassium phosphate tribasic monohydrate (0.20 g, 0.88 mmol) in 1,4-dioxane (2 mL) to a screw cap vial under nitrogen. Sealed and heated at 100° C. overnight. Added 0.5 mL saturated aqueous NaCl solution. Extracted with 1 mL EtOAc. Separated organic layer and dried over a diatomaceous earth cartridge and washed with additional EtOAc. Organic layer concentrated under a $N_2$ stream to give racemic 7,8-dichloro-10-((2-methoxyethyl)amino)-1-methyl-3,4,5,6-tetrahydroazepino[4,5-b]indol-2(1H)-one (30 mg, 37%). ES/MS (m/z): ($^{35}Cl/^{37}Cl$) 356.0/358.0 (M+H).

Example 47

(R)-7,8-Dichloro-10-((2-methoxyethyl)amino)-1-methyl-3,4,5,6-tetrahydroazepino[4,5-b]indol-2(1H)-one Or (S)-7,8-Dichloro-10-((2-methoxyethyl)amino)-1-methyl-3,4,5,6-tetrahydroazepino[4,5-b]indol-2(1H)-one (isomer 1) and Example 48

(R)-7,8-Dichloro-10-((2-methoxyethyl)amino)-1-methyl-3,4,5,6-tetrahydroazepino[4,5-b]indol-2(1H)-one Or (S)-7,8-Dichloro-10-((2-methoxyethyl)amino)-1-methyl-3,4,5,6-tetrahydroazepino[4,5-b]indol-2(1H)-one (isomer 2)

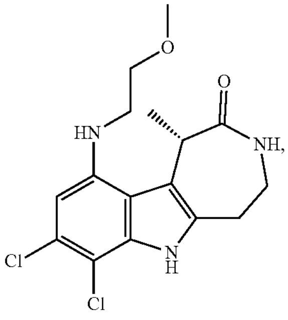

,

-continued

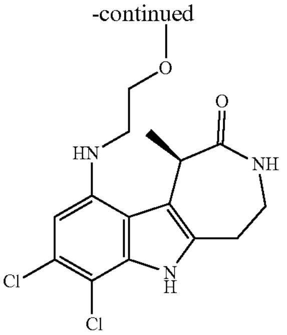

Purified racemic 7,8-dichloro-10-((2-methoxyethyl)amino)-1-methyl-3,4,5,6-tetrahydroazepino[4,5-b]indol-2(1H)-one (32.9 mg, 0.092 mmol) by SFC to give the titled compounds (Isomer 1—Rt=0.95 min (100% ee), 14.8 mg, 45%; Isomer 2—Rt=2.18 min (100% ee), 16.2 mg, 49%). Column: Chiralpak AS-H, 21×150 mm; Mobile Phase: 30° 4 MeOH with 0.5% DMEA: 70% $CO_2$; Flow Rate: 80 mL/min; Column temperature: 40° C.; Detection: 225 nM. ES/MS (m/z): ($^{35}Cl/^{37}Cl$) 355.8/357.8 (M+H).

Intermediate 48

10-((2-((tert-Butyldimethylsilyl)oxy)ethyl)amino)-7,8-dichloro-1-methyl-3,4,5,6-tetrahydroazepino[4,5-b]indol-2(1H)-one

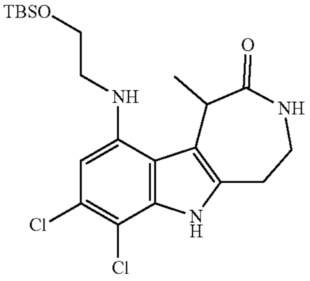 [SMILES: CC1C(=O)NCCc2[nH]c3c(Cl)c(Cl)cc(NCCO[Si](C)(C)C(C)(C)C)c3c21]

Combined 10-bromo-7,8-dichloro-1-methyl-3,4,5,6-tetrahydroazepino[4,5-b]indol-2(1H)-one (100 mg, 0.1851 mmol, 67 mass %), 2-(tert-butyldimethylsiloxy)ethanamine (80 mg, 0.407 mmol), $Pd_2(dba)_3$ (20 mg, 0.0185 mmol), 4,5-bis(diphenylphosphino)-9,9-dimethylxanthene (25 mg, 0.0370 mmol) and cesium carbonate (210 mg, 0.644 mmol) in 1,4-dioxane (20 mL) and THF (1 mL). Purged with $N_2$ and heated to 110° C. overnight. Cooled to ambient temperature. Repeated reaction on 0.5× scale and combined the crude products. Concentrated under reduced pressure. Purified by silica gel flash chromatography eluting with EtOAc in PE to give racemic 10-((2-((tert-butyldimethylsilyl)oxy)ethyl)amino)-7,8-dichloro-1-methyl-3,4,5,6-tetrahydroazepino[4,5-b]indol-2(1H)-one (150 mg, 71 mass %, 83%) as a yellow solid. ES/MS (m/z): ($^{35}Cl/^{37}Cl$) 455.9/457.9 (M+H).

Intermediate 49

(R)-10-((2-((tert-Butyldimethylsilyl)oxy)ethyl)amino)-7,8-dichloro-1-methyl-3,4,5,6-tetrahydroazepino[4,5-b]indol-2(1H)-one Or (S)-10-((2-((tert-Butyldimethylsilyl)oxy)ethyl)amino)-7,8-dichloro-1-methyl-3,4,5,6-tetrahydroazepino[4,5-b]indol-2(1H)-one (isomer 1) and Intermediate 50

(R)-10-((2-((tert-Butyldimethylsilyl)oxy)ethyl)amino)-7,8-dichloro-1-methyl-3,4,5,6-tetrahydroazepino[4,5-b]indol-2(1H)-one Or (S)-10-((2-((tert-Butyldimethylsilyl)oxy)ethyl)amino)-7,8-dichloro-1-methyl-3,4,5,6-tetrahydroazepino[4,5-b]indol-2(1H)-one (isomer 2)

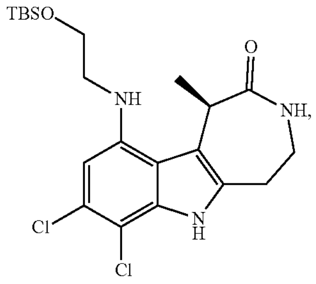

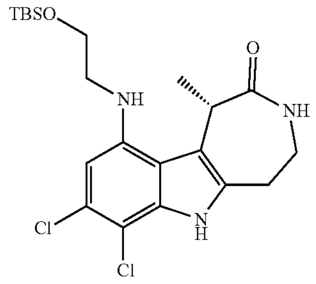

Purified racemic 10-((2-((tert-butyldimethylsilyl)oxy)ethyl)amino)-7,8-dichloro-1-methyl-3,4,5,6-tetrahydroazepino[4,5-b]indol-2(1H)-one (1.40 g, 87 mass %, 2.67 mmol) by SFC to give the title compounds (Isomer 1—Rt=2.3 min (98% ee), 546 mg, 44%; Isomer 2—Rt=2.6 min (>98% ee), 564 mg, 60% mass, 44%). Column: Chiralpak IG, 20×250 mm, 5 μm; Mobile Phase: 30% MeOH (0.5% DMEA): 70% $CO_2$; Flowrate: 80 mL/min; Column temperature: 40° C.; Outlet pressure: 100 bar; Detection: 220 nm. ES/MS (m/z): ($^{35}Cl/^{37}Cl$) 456.2/458.2 (M+H).

Example 49

7,8-Dichloro-10-((2-hydroxyethyl)amino)-1-methyl-3,4,5,6-tetrahydroazepino[4,5-b]indol-2(1H)-one

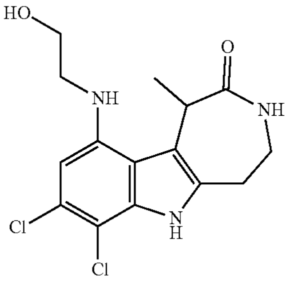 [SMILES: CC1C(=O)NCCc2[nH]c3c(Cl)c(Cl)cc(NCCO)c3c21]

Dissolved 10-((2-((tert-butyldimethylsilyl)oxy)ethyl)amino)-7,8-dichloro-1-methyl-3,4,5,6-tetrahydroazepino[4,5-b]indol-2(1H)-one (90 mg, 0.140 mmol, 71 mass %) in THF (2 mL). Added TBAF (1.0M in THF) (0.6 mL) and stirred for 2 hrs. Diluted reaction with EtOAc (50 mL) and washed with saturated aqueous ammonium chloride solution (30 mL×3). Dried organic layer with anhydrous $Na_2SO_4$, filtered, and concentrated under reduced pressure. Purified by prep-HPLC to give racemic 7,8-dichloro-10-((2-hydroxyethyl)amino)-1-methyl-3,4,5,6-tetrahydroazepino[4,5-b]indol-2(1H)-one (22.82 mg, 46%) as a gray solid. ES/MS (m/z): ($^{35}Cl/^{37}Cl$) 342.1/344.0 (M+H).

Example 50

7,8-Dichloro-10-((2-hydroxyethyl)amino)-1-methyl-3,4,5,6-tetrahydroazepino[4,5-b]indol-2(1H)-one (isomer 1)

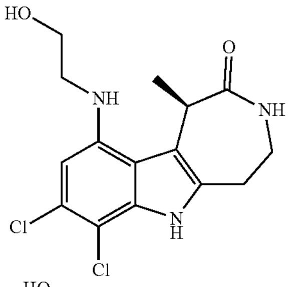

or

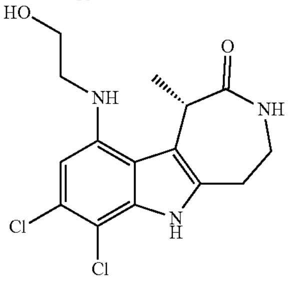

Combined single isomer of 10-((2-((tert-butyldimethylsilyl)oxy)ethyl)amino)-7,8-dichloro-1-methyl-3,4,5,6-tetrahydroazepino[4,5-b]indol-2(1H)-one (Isomer 1, 400 mg, 876 μmol) and THF (9 mL) with stirring. Sparged with nitrogen for 5 min and then added TBAF (1M in THF) (3.50 mL, 3.50 mmol). Stirred under a nitrogen atmosphere for 2 hrs, at ambient temperature. Collected the solid by filtration and washed with THF (1 mL×2). Partitioned the solid between water (10 mL) and EtOAc (15 mL), separated the phases, and extracted the aqueous with EtOAc (5 mL). Combined the organic phases, washed with saturated aqueous NaCl, dried over magnesium sulfate, filtered, and concentrated under reduced pressure at 50° C. to give a white solid. Dried the solid at 10 mbar, 40° C. for 16 hrs. R$^{e}$-slurried the solid in water (25 mL), then filtered and washed with water (2×5 mL). Dried the solid at 10 mbar, 40° C. for 16 hrs, to give 7,8-dichloro-10-((2-hydroxyethyl)amino)-1-methyl-3,4,5,6-tetrahydroazepino[4,5-b]indol-2(1H)-one (isomer 1) (199 mg (>98% ee as isomer 1), 97 mass %, 64%) as a white solid. ES/MS (m/z): ($^{35}Cl/^{37}Cl$) 456.2/458.2 (M+H).

Example 51

7,8-Dichloro-10-((2-hydroxyethyl)amino)-1,6-dimethyl-3,4,5,6-tetrahydroazepino[4,5-b]indol-2(1H)-one (isomer 1)

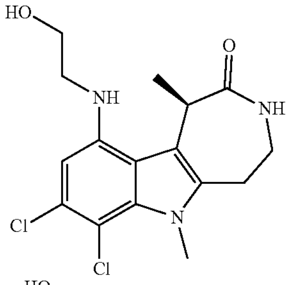

or

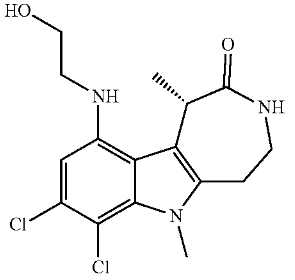

Combined single isomer 10-((2-((tert-butyldimethylsilyl)oxy)ethyl)amino)-7,8-dichloro-1-methyl-3,4,5,6-tetrahydroazepino[4,5-b]indol-2(1H)-one (Isomer 1, 50 mg, 0.11 mmol), cesium carbonate (61 mg, 0.19 mmol) and DMF (1 mL) with stirring. Added methyl iodide (7.5 μL, 0.12 mmol), capped and stirred at ambient temperature for 66 hrs. Added further methyl iodide (1.0 μL, 16 μmol) and stirred for 2 hrs, at ambient temperature. Added tetra-n-butylammonium fluoride (1M in THF, 0.55 mL, 0.55 mmol) and stirred for 1 hr, at ambient temperature. Diluted with water (6 mL) and extracted with EtOAc (4×3 mL). Combined the organic phases and concentrated under a stream of nitrogen at 40° C. Dissolved the residue in 1:1 DCM:EtOAc along with further material from a test reaction (44 μmol scale) and purified by flash chromatography on silica using EtOH in EtOAc. Concentrated fractions containing the title compound under reduced pressure and dried the residue at 10 mbar, 50° C. for 20 hrs, to give 7,8-dichloro-10-((2-hydroxyethyl)amino)-1,6-dimethyl-3,4,5,6-tetrahydroazepino[4,5-b]indol-2(1H)-one (isomer 1) (38 mg, 99+%). ES/MS (m/z): ($^{35}Cl/^{37}Cl$) 356.0/358.0 (M+H).

Example 52

7,8-Dichloro-9-fluoro-10-((2-hydroxyethyl)amino)-1-methyl-3,4,5,6-tetrahydroazepino[4,5-b]indol-2(1H)-one

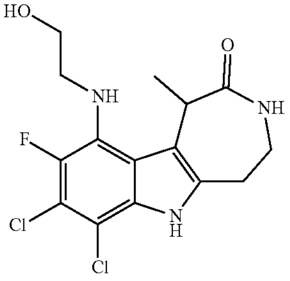 [SMILES: CC1C(=O)NCCc2[nH]c3c(Cl)c(Cl)c(F)c(NCCO)c3c21]

Added 1-fluoro-2,4,6-trimethylpyridinium tetrafluoroborate (156 mg, 687 μmol) to a suspension of racemic 10-((2-((tert-butyldimethylsilyl)oxy)ethyl)amino)-7,8-dichloro-1-methyl-3,4,5,6-tetrahydroazepino[4,5-b]indol-2(1H)-one (300 mg, 624 μmol) in ACN (12.5 mL) under nitrogen atmosphere. Stirred at ambient temperature overnight. Added 1-fluoro-2,4,6-trimethylpyridinium tetrafluoroborate (156 mg, 687 μmol) and stirred overnight. Removed volatiles, added HCl (1M), filtered the solid and washed with water. Passed through SCX cartridge eluted with MeOH and then 2M MeOH/$NH_3$. Concentrated basic fraction under reduced pressure to dryness. Purified by silica gel flash chromatography eluting with MeOH in DCM and dried under reduced pressure to obtain impure compound. Purified by SFC (Column: Luna Hilic, 5 μm 30×150 mm: Mobile phase: 20-40% $CO_2$/MeOH (10 mM $NH_4HCO_3$ pH8); Flow rate: 100 mL/min) to give racemic 7,8-dichloro-9-fluoro-10-((2-hydroxyethyl)amino)-1-methyl-3,4,5,6-tetrahydroazepino[4,5-b]indol-2(1H)-one (11 mg, 5%). ES/MS (m/z): ($^{35}Cl/^{37}Cl$) 360.0/362.0 (M+H).

Intermediate 51

10-((3-((tert-Butyldimethylsilyl)oxy)propyl)amino)-7,8-dichloro-1-methyl-3,4,5,6-tetrahydroazepino[4,5-b]indol-2(1H)-one

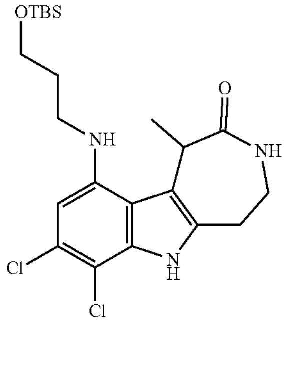 [SMILES: CC1C(=O)NCCc2[nH]c3c(Cl)c(Cl)cc(NCCCO[Si](C)(C)C(C)(C)C)c3c21]

Combined 10-bromo-7,8-dichloro-1-methyl-3,4,5,6-tetrahydroazepino[4,5-b]indol-2(1H)-one (220 mg, 0.492 mmol, 81 mass %), 3-(tert-butyldimethylsilyloxypropan-1-amine (210 mg, 1.087 mmol), $Pd_2(dba)_3$ (50 mg, 0.053 mmol), Xantphos (60 mg, 0.104 mmol) and cesium carbonate (560 mg, 1.72 mmol) in 1,4-dioxane (40 mL) and THF (2 mL). Degassed and purged with $N_2$ (×3) and stirred at 110° C. for 14-18 hrs. Repeated reaction on 0.136 times scale and combined the crude products. Concentrated under reduced pressure. Purified by silica gel flash chromatography eluting with EtOAc in PE to give racemic 10-((3-((tert-butyldimethylsilyl)oxy)propyl)amino)-7,8-dichloro-1-methyl-3,4,5,6-tetrahydroazepino[4,5-b]indol-2(1H)-one (200 mg, 62%) as a yellow solid. ES/MS (m/z): ($^{35}Cl/^{37}Cl$) 470.0/471.9 (M+H).

Example 53

(R)-7,8-Dichloro-10-((3-hydroxypropyl)amino)-1-methyl-3,4,5,6-tetrahydroazepino[4,5-b]indol-2(1H)-one Or (S)-7,8-Dichloro-10-((3-hydroxypropyl)amino)-1-methyl-3,4,5,6-tetrahydroazepino[4,5-b]indol-2(1H)-one (isomer 1) and Example 54

(R)-7,8-Dichloro-10-((3-hydroxypropyl)amino)-1-methyl-3,4,5,6-tetrahydroazepino[4,5-b]indol-2(1H)-one Or (S)-7,8-Dichloro-10-((3-hydroxypropyl)amino)-1-methyl-3,4,5,6-tetrahydroazepino[4,5-b]indol-2(1H)-one (isomer 2)

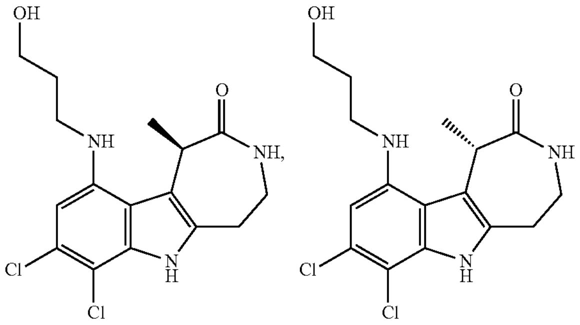 [SMILES: C[C@H]1C(=O)NCCc2[nH]c3c(Cl)c(Cl)cc(NCCCO)c3c21 ; C[C@@H]1C(=O)NCCc2[nH]c3c(Cl)c(Cl)cc(NCCCO)c3c21]

Dissolved racemic 10-((3-((tert-butyldimethylsilyl)oxy)propyl)amino)-7,8-dichloro-1-methyl-3,4,5,6-tetrahydroazepino[4,5-b]indol-2(1H)-one (200 mg, 0.344 mmol) in THF (4 mL). Added TBAF (1M in THF) (1.4 mL, 1.4 mmol) at ambient temperature. Stirred for 2 hrs. Diluted with EtOAc and washed with saturated aqueous ammonium chloride solution (×2) and saturated aqueous NaCl. Dried the organic layer over anhydrous $Na_2SO_4$, filtered, and concentrated under reduced pressure. Triturated with ACN and purified by SFC to give the titled compounds (Isomer 1—Rt=1.55 min (99% ee), 21 mg, 16%, Isomer 2—Rt=1.95 min (>99% ee), 48 mg, 37%. Column: DAICEL CHIRALCEL OD (250×30 mm, 10 μm); Mobile Phase: 40% EtOH (0.1% $NH_3H_2O$); 60% $CO_2$; Flow Rate: 80 mL/min. ES/MS (m/z): ($^{35}Cl/^{37}Cl$) 356.0/357.9 (M+H).

Intermediate 52

7,8-Dichloro-10-(((R)-2-hydroxypropyl)amino)-1-methyl-3,4,5,6-tetrahydroazepino[4,5-b]indol-2(1H)-one

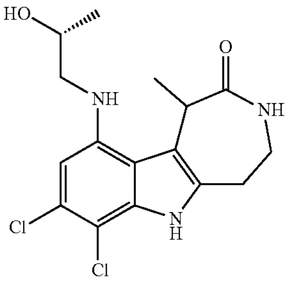 [SMILES: CC1C(=O)NCCc2[nH]c3c(Cl)c(Cl)cc(NC[C@@H](C)O)c3c21]

Combined racemic 10-bromo-7,8-dichloro-1-methyl-3,4,5,6-tetrahydroazepino[4,5-b]indol-2(1H)-one (100 mg, 71 mass %, 196 μmol), (2R)-(−)-1-aminopropan-2-ol (29 mg, 0.39 mmol), XantPhos-Pd-G2 (26 mg, 27 μmol), tripotassium phosphate (162 mg, 763 μmol) and 1,4-dioxane (4.0 mL) were combined in a glass tube with stirring. Sparged with nitrogen for 5 min, then started heating with setpoint 100° C. (block). Removed sparge needle after 5 min. Continued heating for approximately 17 hrs. Removed from heat, diluted with water (15 mL) and adjusted to pH 1 using 10% aqueous hydrochloric acid. Loaded onto a SCX-2 cartridge and eluted successively with water, MeOH and 2 N ammonia in MeOH (each 3× bed volume). Concentrated basic fractions under reduced pressure at 50° C. and combined the residue with material from two similar reactions. Purified by reverse phase column chromatography to give 7,8-dichloro-10-(((R)-2-hydroxypropyl)amino)-1-methyl-3,4,5,6-tetrahydroazepino[4,5-b]indol-2(1H)-one (86 mg, 37%) as a beige solid. ES/MS (m/z): ($^{35}Cl/^{37}Cl$) 356.0/358.0 (M+H).

Example 55

7,8-Dichloro-10-(((R)-2-hydroxypropyl)amino)-1-(R)-methyl-3,4,5,6-tetrahydroazepino[4,5-b]indol-2(1H)-one Or 7,8-Dichloro-10-(((R)-2-hydroxypropyl)amino)-1-(S)-methyl-3,4,5,6-tetrahydroazepino[4,5-b]indol-2(1H)-one (isomer 1) and Example 56

7,8-Dichloro-10-(((R)-2-hydroxypropyl)amino)-1-(R)-methyl-3,4,5,6-tetrahydroazepino[4,5-b]indol-2(1H)-one Or 7,8-Dichloro-10-(((R)-2-hydroxypropyl)amino)-1-(S)-methyl-3,4,5,6-tetrahydroazepino[4,5-b]indol-2(1H)-one (isomer 2)

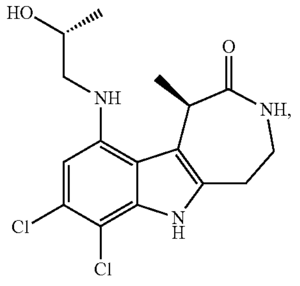

-continued

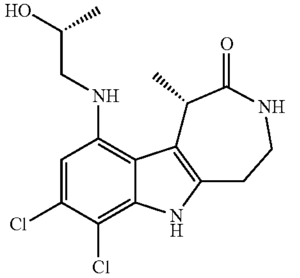

Purified 7,8-dichloro-10-(((R)-2-hydroxypropyl)amino)-1-methyl-3,4,5,6 tetrahydroazepino[4,5-b]indol-2(1H)-one (86 mg, 0.22 mmol) as a mixture of diastereomers by SFC to give the title compounds (Isomer 1—Rt=2.19 min (>98% de), 31.8 mg, 41%; Isomer 2-Rt=4.03 min (>98% de), 35.4 mg, 45%) as pale brown solids. Column: Chiralpak AD, 20×250 mm, 5 μm; Mobile Phase: 35% MeOH (0.5% DMEA): 65% $CO_2$; Flowrate: 80 mL/min; Column temperature: 40° C.; Detection: 220 nm. ES/MS (m/z): ($^{35}Cl/^{37}Cl$) 356.0/358.0 (M+H).

Example 57

7,8-Dichloro-1-methyl-10-((oxazol-4-ylmethyl) amino)-3,4,5,6-tetrahydroazepino[4,5-b]indol-2(1H)-one

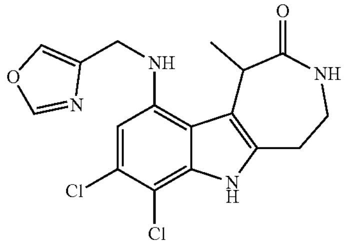 [SMILES: CC1C(=O)NCCc2[nH]c3c(Cl)c(Cl)cc(NCc4cocn4)c3c21]

Combined 10-bromo-7,8-dichloro-1-methyl-3,4,5,6-tetrahydroazepino[4,5-b]indol-2(1H)-one (150 mg, 0.414 mmol), oxazol-4-ylmethanamine hydrochloride (176 mg, 1.24 mmol), $Pd_2(dba)_3$ (38 mg, 0.041 mmol), Xantphos (49 mg, 0.083 mmol) and cesium carbonate (473 mg, 1.45 mmol) in 1,4-dioxane (15 mL) and THF (1.5 mL). Degassed and purged with $N_2$ (×3). Stirred at 110° C. for 16 hrs, under $N_2$ atmosphere. Concentrated under reduced pressure and purified by flash silica gel chromatography eluting with MeOH in DCM, and further purified by prep-HPLC. Concentrated under reduced pressure and lyophilized to give 7,8-dichloro-1-methyl-10-((oxazol-4-ylmethyl)amino)-3,4,5,6-tetrahydroazepino[4,5-b]indol-2(1H)-one (74 mg, 47%) as a white solid. ES/MS (m/z): ($^{35}Cl/^{37}Cl$) 379.1/381.1 (M+H).

Example 58

(S)-7,8-Dichloro-1-methyl-10-((oxazol-4-ylmethyl) amino)-3,4,5,6-tetrahydroazepino[4,5-b]indol-2(1H)-one Or (R)-7,8-Dichloro-1-methyl-10-((oxazol-4-ylmethyl)amino)-3,4,5,6-tetrahydroazepino[4,5-b] indol-2(1H)-one (isomer 1) and

Example 59

(S)-7,8-Dichloro-1-methyl-10-((oxazol-4-ylmethyl) amino)-3,4,5,6-tetrahydroazepino[4,5-b]indol-2(1H)-one Or (R)-7,8-Dichloro-1-methyl-10-((oxazol-4-ylmethyl)amino)-3,4,5,6-tetrahydroazepino[4,5-b] indol-2(1H)-one (isomer 2)

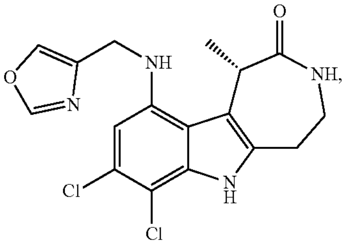

,

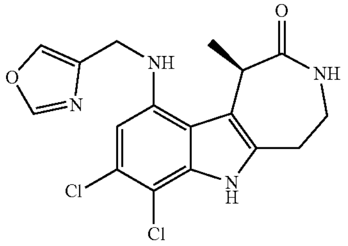

Purified racemic 7,8-dichloro-1-methyl-10-((oxazol-4-ylmethyl)amino)-3,4,5,6-tetrahydroazepino[4,5-b]indol-2(1H)-one (60 mg, 0.16 mmol) by SFC to give the titled compounds (Isomer 1—Rt=0.735 min (100% ee), 27 mg, 45%; Isomer 2—Rt=1.739 min (100% ee), 27 mg, 45%). Column: Chiralpak AS-H, 21×150 mm, 5 μm; Mobile Phase: 40% MeOH: 60% $CO_2$; Flow Rate: 80 mL/min. ES/MS (m/z): ($^{35}Cl/^{37}Cl$) 379.0/381.0 (M+H).

Example 60

7,8-Dichloro-1-methyl-10-(oxetan-3-ylamino)-3,4,5,6-tetrahydroazepino[4,5-b]indol-2(1H)-one

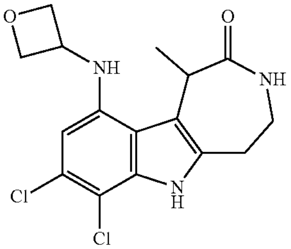 [SMILES: CC1C(=O)NCCc2[nH]c3c(Cl)c(Cl)cc(NC4COC4)c3c21]

Combined 10-bromo-7,8-dichloro-1-methyl-3,4,5,6-tetrahydroazepino[4,5-b]indol-2(1H)-one (100 mg, 0.185 mmol, 67 mass %), 3-oxetanamine (30 mg, 0.407 mmol), $Pd_2(dba)_3$ (20 mg, 0.0185 mmol), Xantphos (22 mg, 0.0370 mmol) and cesium carbonate (215 mg, 0.660 mmol) in 1,4-dioxane (20 mL) and THF (1 mL). Purged with $N_2$ and stirred at 110° C. overnight. Repeated reaction on 0.3× scale and combined the crude products. Concentrated under reduced pressure. Purified the residue by flash silica gel column chromatography eluting with MeOH in DCM to give racemic 7,8-dichloro-1-methyl-10-(oxetan-3-ylamino)-3,4,5,6-tetrahydroazepino[4,5-b]indol-2(1H)-one (23 mg, 25%) as a yellow solid. ES/MS (m/z): ($^{35}Cl/^{37}Cl$) 354.0/355.8 (M+H).

Example 61

7,8-Dichloro-1-methyl-10-(((S)-tetrahydrofuran-3-yl)amino)-3,4,5,6-tetrahydroazepino[4,5-b]indol-2(1H)-one

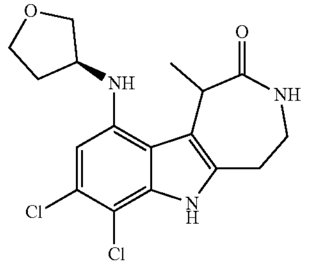 [SMILES: CC1C(=O)NCCc2[nH]c3c(Cl)c(Cl)cc(N[C@H]4CCOC4)c3c21]

Combined 10-bromo-7,8-dichloro-1-methyl-3,4,5,6-tetrahydroazepino[4,5-b]indol-2(1H)-one (200 mg, 0.403 mmol, 73 mass %), (S)-tetrahydrofuran-3-amine (77 mg, 0.887 mmol), $Pd_2(dba)_3$ (37 mg, 0.040 mmol), Xantphos (47 mg, 0.081 mmol), and cesium carbonate (460 mg, 1.41 mmol) in 1,4-dioxane (10 mL) and THF (1 mL). Degassed and purged with $N_2$ (×3). Stirred at 110° C. for 16 hrs, under $N_2$ atmosphere. Cooled to ambient temperature, filtered, added water to the filtrate, extracted with EtOAc. Combined the organic layer, washed with saturated aqueous NaCl, dried over anhydrous $Na_2SO_4$, filtered, and concentrated under reduced pressure. Purified by flash silica gel chromatography eluting with MeOH in DCM and concentrated under reduced pressure. Further purified by prep-HPLC to give a mixture of diastereomers 7,8-dichloro-1-methyl-10-(((S)-tetrahydrofuran-3-yl)amino)-3,4,5,6-tetrahydroazepino[4,5-b]indol-2(1H)-one (58 mg, 39%) as a brown solid. ES/MS (m/z): ($^{35}Cl/^{37}Cl$) 368.1/370.0 (M+H).

Example 62

(S)-7,8-Dichloro-1-methyl-10-(((S)-tetrahydrofuran-3-yl)amino)-3,4,5,6-tetrahydroazepino[4,5-b]indol-2(1H)-one Or (R)-7,8-Dichloro-1-methyl-10-(((S)-tetrahydrofuran-3-yl)amino)-3,4,5,6-tetrahydroazepino[4,5-b]indol-2(1H)-one (isomer 1) and Example 63

(S)-7,8-Dichloro-1-methyl-10-(((S)-tetrahydrofuran-3-yl)amino)-3,4,5,6-tetrahydroazepino[4,5-b]indol-2(1H)-one Or (R)-7,8-Dichloro-1-methyl-10-(((S)-tetrahydrofuran-3-yl)amino)-3,4,5,6-tetrahydroazepino[4,5-b]indol-2(1H)-one (isomer 2)

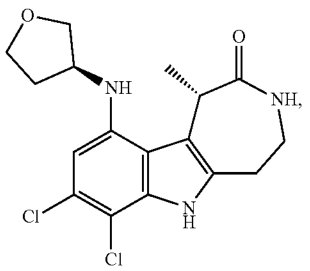

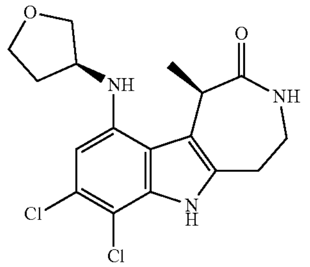

Purified mixture of (S)-7,8-dichloro-1-methyl-10-(((S)-tetrahydrofuran-3-yl)amino)-3,4,5,6-tetrahydroazepino[4,5-b]indol-2(1H)-one and (R)-7,8-dichloro-1-methyl-10-(((S)-tetrahydrofuran-3-yl)amino)-3,4,5,6-tetrahydroazepino[4,5-b]indol-2(1H)-one (55 mg, 0.15 mmol) by SFC to give the titled compounds (Isomer 1—RT=0.88 min (100% de), 26 mg, 47%; Isomer 2—RT=2.97 min (100% de), 17 mg, 31%). Column: Chiralpak AS-H, 21×150 mm; Mobile Phase: 35% MeOH (0.5% DMEA): 65% $CO_2$; Flow Rate: 80 mL/min; Column temperature: 40° C.; Detection: 225 nM. ES/MS (m/z): ($^{35}Cl/^{37}Cl$) 368.0/370.0 (M+H).

Intermediate 53

7,8-Dichloro-1-methyl-10-(((R)-tetrahydrofuran-3-yl)amino)-3,4,5,6-tetrahydroazepino[4,5-b]indol-2(1H)-one

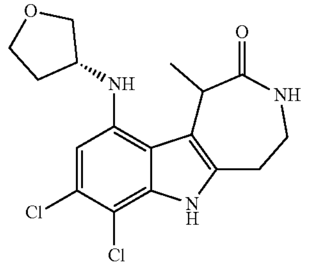 [SMILES: CC1C(=O)NCCc2[nH]c3c(Cl)c(Cl)cc(N[C@@H]4CCOC4)c3c21]

Combined 10-bromo-7,8-dichloro-1-methyl-3,4,5,6-tetrahydroazepino[4,5-b]indol-2(1H)-one (500 mg, 1.38 mmol), (3R)-oxolan-3-amine (241 mg, 2.76 mmol), XantPhos-Pd-G2 (123 mg, 138 μmol), Xantphos (79.9 mg, 138 μmol), tripotassium phosphate monohydrate (1.27 g, 5.52 mmol), and 1,4-dioxane (10 mL). Sealed and heated to 100° C. for 18 hrs. Added (3R)-oxolan-3-amine (241 mg, 2.76 mmol), XantPhos-Pd-G2 (123 mg, 138 μmol), and Xantphos (79.9 mg, 138 μmol). Sealed and heated to 100° C. overnight. Cooled the reaction to ambient temperature. Diluted the reaction mixture with EtOAc and washed with saturated ammonium chloride solution. Dried the organic layer over anhydrous magnesium sulfate, filtered and evaporated under reduced pressure. Purified the residue by silica gel flash chromatography eluting with MeOH in DCM to give 7,8-dichloro-1-methyl-10-(((R)-tetrahydrofuran-3-yl)amino)-3,4,5,6-tetrahydroazepino[4,5-b]indol-2(1H)-one as a brown solid (229.7 mg, 45%). ES/MS (m/z): ($^{35}$Cl/$^{37}$Cl) 368.0/370.0 (M+H).

Example 64

(R)-7,8-Dichloro-1-methyl-10-(((R)-tetrahydrofuran-3-yl)amino)-3,4,5,6-tetrahydroazepino[4,5-b]indol-2(1H)-one Or (S)-7,8-Dichloro-1-methyl-10-(((R)-tetrahydrofuran-3-yl)amino)-3,4,5,6-tetrahydroazepino[4,5-b]indol-2(1H)-one and Example 65

(R)-7,8-Dichloro-1-methyl-10-(((R)-tetrahydrofuran-3-yl)amino)-3,4,5,6-tetrahydroazepino[4,5-b]indol-2(1H)-one Or (S)-7,8-Dichloro-1-methyl-10-(((R)-tetrahydrofuran-3-yl)amino)-3,4,5,6-tetrahydroazepino[4,5-b]indol-2(1H)-one

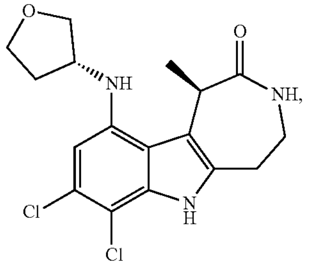

-continued

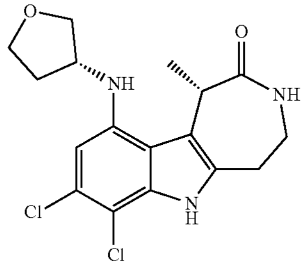

Purified the mixture of diastereomers 7,8-dichloro-1-methyl-10-(((R)-tetrahydrofuran-3-yl)amino)-3,4,5,6-tetrahydroazepino[4,5-b]indol-2(1H)-one (229.7 mg, 0.624 mmol) by SFC to give the titled compounds (Isomer 1—Rt=1.16 min (100% de), 42.9 mg, 19%; Isomer 2—Rt=2.34 min (100% de), 47.4 mg, 21%). Column: Chiralpak AS-H, 21×150 mm; Mobile Phase: 30% MeOH with 0.5% DMEA: 70% $CO_2$; Flow Rate: 80 mL/min; Column temperature: 40° C.; Detection: 225 nM. ES/MS (m/z): ($^{35}$Cl/$^{37}$Cl) 368.2/370.2 (M+H).

Example 66

7,8-Dichloro-1-methyl-10-(((R)-tetrahydrofuran-3-yl)amino)-3,4,5,6-tetrahydroazepino[4,5-b]indol-2(1H)-one

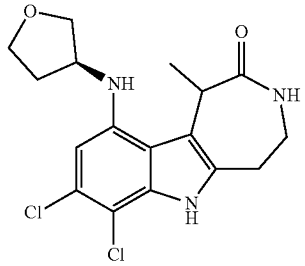 [SMILES: CC1C(=O)NCCc2[nH]c3c(Cl)c(Cl)cc(N[C@H]4CCOC4)c3c21]

Added 10-bromo-7,8-dichloro-1-methyl-3,4,5,6-tetrahydroazepino[4,5-b]indol-2(1H)-one (80 mg, 0.22 mmol), (R)-tetrahydrofuran-3-amine (0.44 mmol), XantPhos-Pd-G2 (39 mg, 0.044 mmol), potassium phosphate tribasic monohydrate (0.20 g, 0.88 mmol) in 1,4-dioxane (2 mL) to a screw cap vial under $N_2$. Sealed and heated at 100° C. overnight. Added 0.5 mL saturated NaCl solution. Extracted with 1 mL EtOAc. Separated organic layer and dried over diatomaceous earth cartridge and washed with additional EtOAc. Organic layer concentrated under a $N_2$ stream to give 7,8-dichloro-1-methyl-10-(((R)-tetrahydrofuran-3-yl)amino)-3,4,5,6-tetrahydroazepino[4,5-b]indol-2(1H)-one (1.7 mg, 2%). ES/MS (m/z): ($^{35}$Cl/$^{37}$Cl) 368.2/370.0 (M+H).

Intermediate 54

4-Methylisoxazol-3-amine

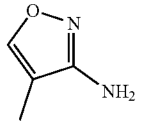

Added bromine (14.3 g, 4.61 mL, 89.4 mmol) to a solution of methacrylonitrile (5.00 g, 74.5 mmol) in MeOH (70 mL) at 0° C. Stirred at 35° C. for 2 hrs. Then added a solution of NaOH (8.94 g, 224 mmol) and hydroxyurea (7.37 g, 96.9 mmol) in $H_2O$ (12 mL) to above reaction mixture at 0° C. Stirred at 90° C. for 4 hrs. Concentrated under reduced pressure to remove MeOH and diluted with water and extracted with DCM. Combined the organic layer, washed with water, saturated aqueous NaCl, dried over anhydrous $Na_2SO_4$, filtered, and concentrated under reduced pressure. Purified by flash silica gel chromatography eluting with EtOAc in PE and concentrated under reduced pressure to give 4-methylisoxazol-3-amine (1.40 g, 17%) as a yellow solid. $^1H$ NMR (DMSO-d6): 8.08 (s, 1H), 5.42 (br s, 2H), 1.81 (s, 3H).

Example 67

7,8-Dichloro-1-methyl-10-((4-methylisoxazol-3-yl)amino)-3,4,5,6-tetrahydroazepino[4,5-b]indol-2(1H)-one

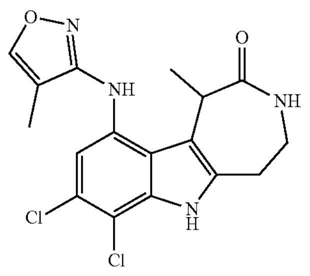 [SMILES: Cc1conc1Nc1cc(Cl)c(Cl)c2[nH]c3c(c12)C(C)C(=O)NCC3]

Combined 10-bromo-7,8-dichloro-1-methyl-3,4,5,6-tetrahydroazepino[4,5-b]indol-2(1H)-one (300 mg, 0.704 mmol, 85 mass %), 4-methylisoxazol-3-amine (230 mg, 2.11 mmol, 90 mass %), $(t\text{-}Bu_3P)_2Pd$ (72 mg, 0.14 mmol), and cesium carbonate (803 mg, 2.47 mmol) in 1,4-dioxane (10 mL) and THF (1 mL). Degassed and purged with $N_2$ (×3). Stirred at 110° C. for 16 hrs, under $N_2$ atmosphere. Concentrated under reduced pressure and purified by flash silica gel chromatography eluting with MeOH in DCM, and further purified by prep-HPLC and SFC separation. Column: DAICEL CHIRALPAK IC, 30×250 mm, 10 μm; Mobile Phase: 30% EtOH (0.1% $NH_3 \cdot H_2O$); 70% $CO_2$; Flow Rate: 80 mL/min. Concentrated under reduced pressure and lyophilized to give 7,8-dichloro-1-methyl-10-((4-methylisoxazol-3-yl)amino)-3,4,5,6-tetrahydroazepino[4,5-b]indol-2(1H)-one (14 mg, 5%) as a yellow solid. ES/MS (m/z): ($^{35}Cl/^{37}Cl$) 379.1/381.0 (M+H).

Intermediate 55

7,8-Dichloro-10-((2,2-difluoro-3-hydroxypropyl)amino)-1-methyl-3,4,5,6-tetrahydroazepino[4,5-b]indol-2(1H)-one

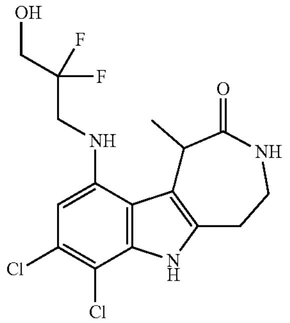

Combined 10-bromo-7,8-dichloro-1-methyl-3,4,5,6-tetrahydroazepino[4,5-b]indol-2(1H)-one (150 mg, 0.365 mmol, 88 mass %), 3-amino-2,2-difluoropropan-1-ol (128 mg, 1.09 mmol), $Pd_2(dba)_3$ (34 mg, 0.037 mmol), Xantphos (43 mg, 0.073 mmol), and cesium carbonate (420 mg, 1.28 mmol) in 1,4-dioxane (5 mL) and DMF (0.25 mL). Degassed and purged with $N_2$ (×3). Stirred at 110° C. for 16 hrs. Concentrated under reduced pressure and purified by silica gel flash chromatography eluting with MeOH in DCM, then further purified by prep-HPLC. Concentrated under reduced pressure and lyophilized to give racemic 7,8-dichloro-10-((2,2-difluoro-3-hydroxypropyl)amino)-1-methyl-3,4,5,6-tetrahydroazepino[4,5-b]indol-2(1H)-one (54 mg, 34%). ES/MS (m/z): ($^{35}Cl/^{37}Cl$) 392.0/393.9 (M+H).

Example 68

(R)-7,8-Dichloro-10-((2,2-difluoro-3-hydroxypropyl)amino)-1-methyl-3,4,5,6-tetrahydroazepino[4,5-b]indol-2(1H)-one or (S)-7,8-Dichloro-10-((2,2-difluoro-3-hydroxypropyl)amino)-1-methyl-3,4,5,6-tetrahydroazepino[4,5-b]indol-2(1H)-one (isomer 1)

and

Example 69

(R)-7,8-Dichloro-10-((2,2-difluoro-3-hydroxypropyl)amino)-1-methyl-3,4,5,6-tetrahydroazepino[4,5-b]indol-2(1H)-one or (S)-7,8-Dichloro-10-((2,2-difluoro-3-hydroxypropyl)amino)-1-methyl-3,4,5,6-tetrahydroazepino[4,5-b]indol-2(1H)-one (isomer 2)

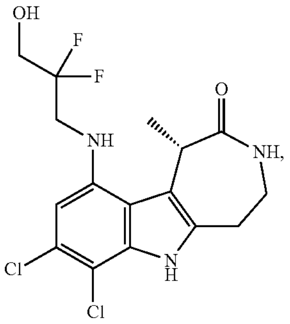

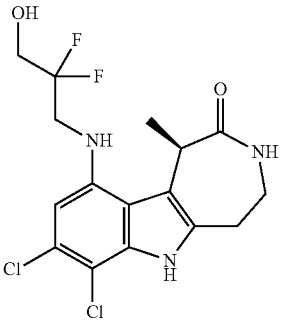 [SMILES: CC1C(=O)NCCc2[nH]c3c(Cl)c(Cl)cc(NCC(F)(F)CO)c3c21]

Purified racemic 7,8-dichloro-10-((2,2-difluoro-3-hydroxypropyl)amino)-1-methyl-3,4,5,6-tetrahydroazepino[4,5-b]indol-2(1H)-one (54 mg, 0.12 mmol) by SFC to give isomer 1—Rt=1.94 min (97.4% ee), 20.10 mg, 40% as an off-white solid). Purified second peak by trituration with ACN to give Isomer 2—Rt=2.28 min (95.9% ee), 16.12 mg, 32% as a white solid). Column: DAICEL CHIRALPAK AD, 30×250 mm 10 μm; Mobile Phase: 40'%/G MeOH: 60% $CO_2$; Flow Rate: 80 mL/min; Column temperature: 40° C. ES/MS (m/z): ($^{35}Cl/^{37}Cl$) 392.0/394.0 (M+H).

Example 70

7,8-Dichloro-10-((2,2-difluoroethyl)amino)-1-methyl-3,4,5,6-tetrahydroazepino[4,5-b]indol-2(1H)-one

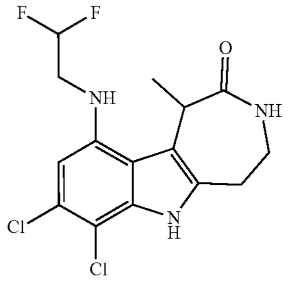 [SMILES: CC1C(=O)NCCc2[nH]c3c(Cl)c(Cl)cc(NCC(F)F)c3c21]

Combined (10-bromo-7,8-dichloro-1-methyl-3,4,5,6-tetrahydroazepino[4,5-b]indol-2(1H)-one (150 mg, 0.367 mmol, 89 mass %), 2,2-difluoroethane-1-amine (94 mg, 1.1 mmol), $Pd_2(dba)_3$ (34 mg, 0.037 mmol), Xantphos (43 mg, 0.074 mmol), and cesium carbonate (299 mg, 0.919 mmol) in 1,4-dioxane (2 mL) and THF (0.17 mL). Stirred at 100° C. for 12 hrs, under $N_2$ atmosphere. Concentrated under reduced pressure and purified by silica gel flash chromatography eluting with EtOAc in PE, and further purified by prep-HPLC. Concentrated under reduced pressure, and lyophilized to give 7,8-dichloro-10-((2,2-difluoroethyl)amino)-1-methyl-3,4,5,6-tetrahydroazepino[4,5-b]indol-2(1H)-one (44.08 mg, 33%) as a brown solid. ES/MS (m/z): ($^{35}Cl/^{37}Cl$) 362.1/364.1 (M+H).

Example 71

7,8-Dichloro-10-((3,3-difluoropropyl)amino)-1-methyl-3,4,5,6-tetrahydroazepino[4,5-b]indol-2(1H)-one

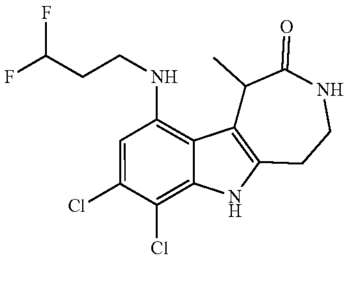 [SMILES: CC1C(=O)NCCc2[nH]c3c(Cl)c(Cl)cc(NCCC(F)F)c3c21]

Combined 10-bromo-7,8-dichloro-1-methyl-3,4,5,6-tetrahydroazepino[4,5-b]indol-2(1H)-one (100 mg, 0.243 mmol, 88 mass %), 3,3-difluoropropan-1-amine hydrochloride (96 mg, 0.73 mmol), $Pd_2(dba)_3$ (23 mg, 0.024 mmol), Xantphos (28 mg, 0.049 mmol), and cesium carbonate (400 mg, 1.22 mmol) in 1,4-dioxane (5 mL) and THF (0.25 mL). Degassed and purged with $N_2$ (3×). Stirred at 120° C. for 2 hrs. Concentrated under reduced pressure and purified by silica gel flash chromatography eluting with MeOH in DCM, and further purified by prep-HPLC. Concentrated under reduced pressure and lyophilized to give 7,8-dichloro-10-((3,3-difluoropropyl)amino)-1-methyl-3,4,5,6-tetrahydroazepino[4,5-b]indol-2(1H)-one (40.64 mg, 44%) as a yellow solid. ES/MS (m/z): ($^{35}Cl/^{37}Cl$) 375.9/378.0 (M+H).

Intermediate 56

3-((tert-Butyldimethylsilyl)oxy)-2,2-difluoropropan-1-ol

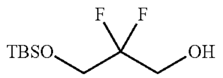

Combined 2,2-difluoropropane-1,3-diol (1.00 g, 8.92 mmol) and imidazole (911 mg, 13.4 mmol) in DCM (15 mL) at 0° C. Stirred at 0° C. for 0.5 hr. Added tert-butyldimethylsilyl chloride (1.34 g, 8.92 mmol) at 0° C. Stirred at ambient temperature for 2 hrs. Diluted with water and extracted with EtOAc. Washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give 3-((tert-butyldimethylsilyl)oxy)-2,2-difluoropropan-1-ol (550 mg, 22%). $^1H$ NMR (DMSO-d6): 5.44 (t, J=6.0 Hz, 1H), 3.81 (t, J=13.2 Hz, 2H), 3.61 (td, J=13.6, 6.0 Hz, 2H), 0.87 (s, 9H), 0.07 (s, 6H).

Intermediate 57

3-((tert-Butyldimethylsilyl)oxy)-2,2-difluoropropyl trifluoromethanesulfonate

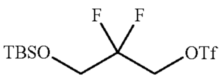 [SMILES: CC(C)(C)[Si](C)(C)OCC(F)(F)COS(=O)(=O)C(F)(F)F]

Combined 3-((tert-butyldimethylsilyl)oxy)-2,2-difluoropropan-1-ol (500 mg, 1.77 mmol, 80 mass %), pyridine (280 mg, 3.53 mmol) in DCM (10 mL). Added trifluoromethanesulfonic anhydride (748 mg, 2.65 mmol) at 0° C. Stirred at ambient temperature for 2 hrs. Diluted with water and extracted with DCM. Washed with saturated aqueous NaCl, dried over $Na_2SO_4$, filtered, and concentrated under reduced pressure. Purified by silica gel flash chromatography eluting with EtOAc in PE and concentrated under reduced pressure to give 3-((tert-butyldimethylsilyl)oxy)-2,2-difluoropropyl trifluoromethanesulfonate (450 mg, 64%). $^1H$ NMR (DMSO-d6): 5.08 (t, J=13.6 Hz, 2H), 3.97 (t, J=13.0 Hz, 2H), 0.87 (s, 9H), 0.09 (s, 6H).

Intermediate 58

10-(3-((tert-Butyldimethyl silyl)oxy)-2,2-difluoropropoxy)-7,8-dichloro-1-methyl-3,4,5,6-tetrahydroazepino[4,5-b]indol-2(1H)-one

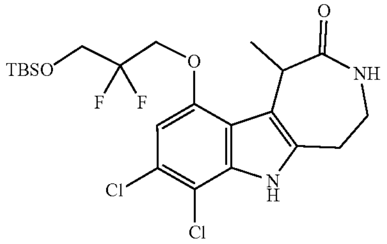 [SMILES: CC1C(=O)NCCc2[nH]c3c(Cl)c(Cl)cc(OCC(F)(F)CO[Si](C)(C)C(C)(C)C)c3c21]

Combined 7,8-dichloro-10-hydroxy-1-methyl-3,4,5,6-tetrahydroazepino[4,5-b]indol-2(1H)-one (140 mg, 0.328 mmol, 70 mass %) and $K_2CO_3$ (136 mg, 0.983 mmol) in DMF (3 mL). Added 3-((tert-butyldimethyl silyl)oxy)-2,2-difluoropropyl trifluoromethanesulfonate (391 mg, 0.983 mmol, 90 mass %). Stirred at 50° C. for 16 hrs. Diluted with water and extracted with EtOAc. Washed with saturated aqueous NaCl, dried over $Na_2SO_4$, filtered, and concentrated under reduced pressure to give 10-(3-((tert-butyldimethylsilyl)oxy)-2,2-difluoropropoxy)-7,8-dichloro-1-methyl-3,4,5,6-tetrahydroazepino[4,5-b]indol-2(1H)-one (180 mg, 65%). ES/MS (m/z): ($^{35}Cl/^{37}Cl$) 507.0/509.0 (M+H).

Example 72

7,8-Dichloro-10-(2,2-difluoro-3-hydroxypropoxy)-1-methyl-3,4,5,6-tetrahydroazepino[4,5-b]indol-2(1H)-one

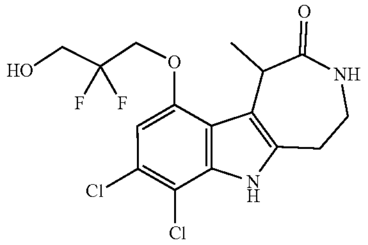 [SMILES: CC1C(=O)NCCc2[nH]c3c(Cl)c(Cl)cc(OCC(F)(F)CO)c3c21]

Added 2M aqueous HCl (1 mL) to 10-(3-((tert-butyldimethylsilyl)oxy)-2,2-difluoropropoxy)-7,8-dichloro-1-methyl-3,4,5,6-tetrahydroazepino[4,5-b]indol-2(1H)-one (180 mg, 0.213 mmol, 60 mass %) in THF (4 mL). Stirred at ambient temperature for 2 hrs. Diluted with water and extracted with EtOAc. Washed with saturated aqueous NaCl, dried over $Na_2SO_4$, filtered, and concentrated under reduced pressure. Purified by prep-HPLC to give 7,8-dichloro-10-(2,2-difluoro-3-hydroxypropoxy)-1-methyl-3,4,5,6-tetrahydroazepino[4,5-b]indol-2(1H)-one (51.76 mg, 61%) as a pink solid. ES/MS (m/z): ($^{35}Cl/^{37}Cl$) 393.0/395.0 (M+H).

Example 73

(S)-7,8-Dichloro-10-(2,2-difluoro-3-hydroxypropoxy)-1-methyl-3,4,5,6-tetrahydroazepino[4,5-b]indol-2(1H)-one Or (R)-7,8-Dichloro-10-(2,2-difluoro-3-hydroxypropoxy)-1-methyl-3,4,5,6-tetrahydroazepino[4,5-b]indol-2(1H)-one (isomer 1) and Example 74

(S)-7,8-Dichloro-10-(2,2-difluoro-3-hydroxypropoxy)-1-methyl-3,4,5,6-tetrahydroazepino[4,5-b]indol-2(1H)-one Or (R)-7,8-Dichloro-10-(2,2-difluoro-3-hydroxypropoxy)-1-methyl-3,4,5,6-tetrahydroazepino[4,5-b]indol-2(1H)-one (isomer 2)

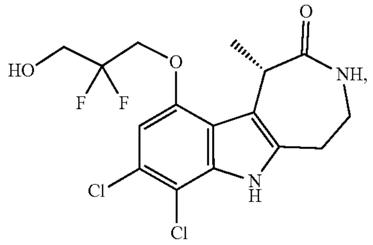

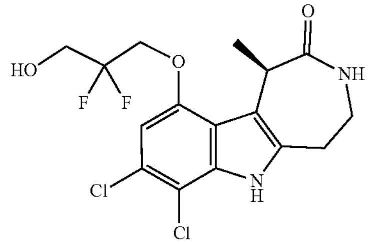

Purified racemic 7,8-dichloro-10-(2,2-difluoro-3-hydroxypropoxy)-1-methyl-3,4,5,6-tetrahydroazepino[4,5-b]indol-2(1H)-one (49 mg, 0.12 mmol) by SFC to give the titled compounds (Isomer 1—RT=0.74 min (100% ee), 17 mg, 35%; Isomer 2—RT=3.35 min (100% ee), 18 mg, 36%). Column: Chiralpak AS-H, 21×150 mm; Mobile Phase: 30% MeOH: 70% $CO_2$, Flow Rate: 80 mL/min; Column temperature: 40° C.; Detection: 225 nM. ES/MS (m/z): ($^{35}Cl/^{37}Cl$) 393.0/395.0 (M+H).

Example 75

7,8-Dichloro-10-(2-fluoroethoxy)-1-methyl-3,4,5,6-tetrahydroazepino[4,5-b]indol-2(1H)-one

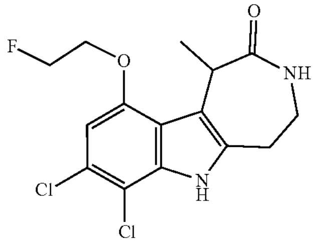 [SMILES: CC1C(=O)NCCc2[nH]c3c(Cl)c(Cl)cc(OCCF)c3c21]

Combined 7,8-dichloro-10-hydroxy-1-methyl-3,4,5,6-tetrahydroazepino[4,5-b]indol-2(1H)-one (200 mg, 0.468 mmol, 70 mass %), 1-bromo-2-fluoro-ethane (1.78 g, 14.0 mmol) and $K_2CO_3$ (194 mg, 1.40 mmol) in ACN (4 mL). Degassed and purged with $N_2$ (×3). Stirred at ambient temperature for 64 hrs, under $N_2$ atmosphere. Diluted with water and extracted with EtOAc, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure, and further purified by prep-HPLC to give 7,8-dichloro-10-(2-fluoroethoxy)-1-methyl-3,4,5,6-tetrahydroazepino[4,5-b]indol-2(1H)-one (55.31 mg, 34%) as a white solid. ES/MS (m/z): ($^{35}Cl/^{37}Cl$) 345.0/346.9 (M+H).

Example 76

7,8-Dichloro-10-(2,2-difluoroethoxy)-1-methyl-3,4,5,6-tetrahydroazepino[4,5-b]indol-2(1H)-one

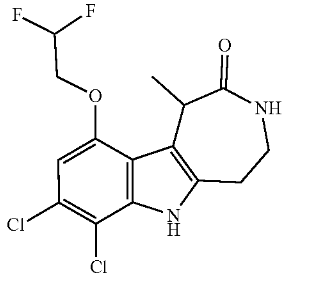 [SMILES: CC1C(=O)NCCc2[nH]c3c(Cl)c(Cl)cc(OCC(F)F)c3c21]

Combined anhydrous DMF (0.67 mL), racemic 7,8-dichloro-10-hydroxy-1-methyl-3,4,5,6-tetrahydroazepino[4,5-b]indol-2(1H)-one (50 mg, 0.17 mmol) and cesium carbonate (55 mg, 0.17 mmol) under $N_2$. Stirred at ambient temperature for 20 min. Added 2-bromo-1,1-difluoroethane (15 μL, 0.18 mmol) and stirred overnight. Added water, filtered the solid and dried under vacuum. Purified by silica gel flash chromatography eluting with MeOH in DCM and dried under reduced pressure to give racemic 7,8-dichloro-10-(2,2-difluoroethoxy)-1-methyl-3,4,5,6-tetrahydroazepino[4,5-b]indol-2(1H)-one (14 mg, 22%) as a white solid. ES/MS (m/z): ($^{35}Cl/^{37}Cl$) 363.0/365.0 (M+H).

Intermediate 59

10-(3-((tert-Butyldimethylsilyl)oxy)propoxy)-7,8-dichloro-1-methyl-3,4,5,6-tetrahydroazepino[4,5-b]indol-2(1H)-one

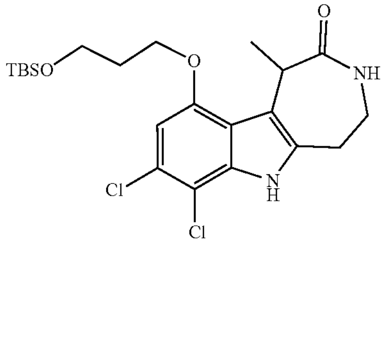 [SMILES: CC1C(=O)NCCc2[nH]c3c(Cl)c(Cl)cc(OCCCO[Si](C)(C)C(C)(C)C)c3c21]

Combined 7,8-dichloro-10-hydroxy-1-methyl-3,4,5,6-tetrahydroazepino[4,5-b]indol-2(1H)-one (100 mg, 0.207 mmol, 62 mass %), (3-iodopropoxy)(tert-butyl)dimethylsilane (124 mg, 0.415 mmol) and $K_2CO_3$ (86 mg, 0.622 mmol) in DMF (2 mL). Stirred at 25° C. for 16 hrs. Diluted with $H_2O$ and extracted with EtOAc. Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated to give 10-(3-((tert-butyldimethylsilyl)oxy)propoxy)-7,8-dichloro-1-methyl-3,4,5,6-tetrahydroazepino[4,5-b]indol-2(1H)-one (80 mg, 61%). ES/MS (m/z): 471.0/473.0 (M+H).

Intermediate 60

10-(3-((tert-Butyldimethylsilyl)oxy)propoxy)-7,8-dichloro-1,6-dimethyl-3,4,5,6-tetrahydroazepino[4,5-b]indol-2(1H)-one

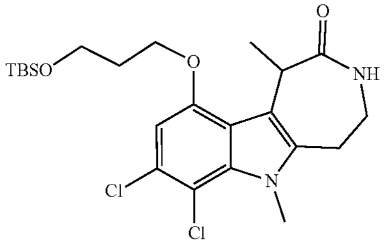 [SMILES: CC1C(=O)NCCc2c1c1c(OCCCO[Si](C)(C)C(C)(C)C)cc(Cl)c(Cl)c1n2C]

To a stirring solution of 10-(3-((tert-butyldimethylsilyl)oxy)propoxy)-7,8-dichloro-1-methyl-3,4,5,6-tetrahydroazepino[4,5-b]indol-2(1H)-one (80 mg, 0.13 mmol, 75 mass %) in DMF (2 mL), added cesium carbonate (0.15 g, 0.45 mmol) and iodomethane (22 mg, 0.15 mmol). Stirred at 25° C. for 2 hrs. Diluted with $H_2O$ and extracted with EtOAc. Combined organic layers, washed with saturated aqueous NaCl, dried over anhydrous $Na_2SO_4$, filtered, and concentrated under reduced pressure to give 10-(3-((tert-butyldimethylsilyl)oxy)propoxy)-7,8-dichloro-1,6-dimethyl-3,4,5,6-tetrahydroazepino[4,5-b]indol-2(1H)-one (70 mg, 93%). ES/MS (m/z): ($^{35}Cl/^{37}Cl$) 485.0/487.0 (M+H).

Example 77

7,8-Dichloro-10-(3-hydroxypropoxy)-1,6-dimethyl-3,4,5,6-tetrahydroazepino[4,5-b]indol-2(1H)-one

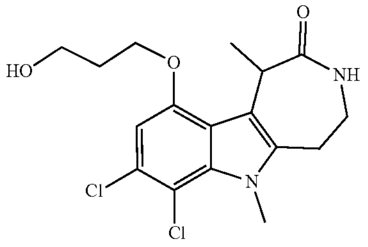 [SMILES: CC1C(=O)NCCc2c1c1c(OCCCO)cc(Cl)c(Cl)c1n2C]

To a solution of 10-(3-((tert-butyldimethylsilyl)oxy)propoxy)-7,8-dichloro-1,6-dimethyl-3,4,5,6-tetrahydroazepino[4,5-b]indol-2(1H)-one (70 mg, 0.12 mmol, 82 mass %) in THF (2 mL), added TBAF (0.47 mL, 0.47 mmol, 1M in THF). Stirred at 25° C. for 2 hrs. Diluted with EtOAc and washed with saturated aqueous $NH_4Cl$, saturated aqueous NaCl, dried over anhydrous $Na_2SO_4$, filtered, and concentrated under reduced pressure. Repeated reaction on 0.47× scale and combined the crude products. Purified by reverse phase prep-HPLC to give 7,8-dichloro-10-(3-hydroxy-propoxy)-1,6-dimethyl-3,4,5,6-tetrahydroazepino[4,5-b]indol-2(1H)-one (28 mg, 42%) as a white solid. ES/MS (m/z): ($^{35}Cl/^{37}Cl$) 371.0/373.0 (M+H).

Intermediate 61

2-((7,8-Dichloro-1-methyl-2-oxo-1,2,3,4,5,6-hexahydroazepino[4,5-b]indol-10-yl)oxy)acetonitrile

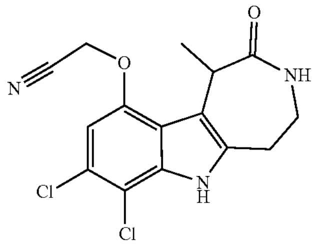 [SMILES: CC1C(=O)NCCc2[nH]c3c(Cl)c(Cl)cc(OCC#N)c3c21]

To a solution of 7,8-dichloro-10-hydroxy-1-methyl-3,4,5,6-tetrahydro-1H-azepino[4,5-b]indol-2-one (80 mg, 0.15 mmol, 56 mass %) in DMF (2 mL), added bromoacetonitrile (40 mg, 0.33 mmol) and $K_2CO_3$ (30 mg, 0.22 mmol) at ambient temperature. Stirred at ambient temperature for 2 hrs. Diluted with water and extracted with EtOAc (3×). Combined organic layers, washed with saturated aqueous NaCl, dried over anhydrous $Na_2SO_4$, filtered, and concentrated under reduced pressure. Purified by flash silica gel chromatography eluting with MeOH in DCM and concentrated to give 2-((7,8-dichloro-1-methyl-2-oxo-1,2,3,4,5,6-hexahydroazepino[4,5-b]indol-10-yl)oxy)acetonitrile (60 mg, 100%) as a yellow gum. ES/MS (m/z): ($^{35}Cl/^{37}Cl$) 337.9/339.9 (M+H).

Example 78

2-((7,8-Dichloro-1,6-dimethyl-2-oxo-1,2,3,4,5,6-hexahydroazepino[4,5-b]indol-10-yl)oxy)acetonitrile

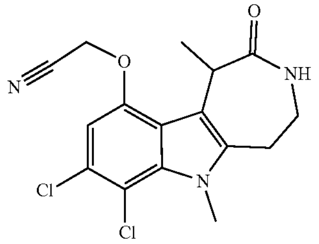 [SMILES: CC1C(=O)NCCc2c1c1c(OCC#N)cc(Cl)c(Cl)c1n2C]

Combined 2-((7,8-dichloro-1-methyl-2-oxo-1,2,3,4,5,6-hexahydroazepino[4,5-b]indol-10-yl)oxy)acetonitrile (60 mg, 0.15 mmol, 84 mass %) and cesium carbonate (170 mg, 0.522 mmol) in DMF (2 mL), added MeI (30 mg, 0.21 mmol) at 0° C. Stirred at ambient temperature for 2 hrs. Quenched with water and extracted with EtOAc (3×). Combined organic layers and washed with saturated aqueous NaCl, dried over anhydrous $Na_2SO_4$, and concentrated under reduced pressure. Purified by prep-HPLC. Concentrated under reduced pressure and lyophilized to give 2-((7,8-dichloro-1,6-dimethyl-2-oxo-1,2,3,4,5,6-hexahydroazepino[4,5-b]indol-10-yl)oxy)acetonitrile (27.15 mg, 50%) as a white solid. ES/MS (m/z): ($^{35}Cl/^{37}Cl$) 352.0/353.9 (M+H).

Example 79

7,8-Dichloro-10-(2-methoxyethoxy)-1-methyl-3,4,5,6-tetrahydroazepino[4,5-b]indol-2(1H)-one

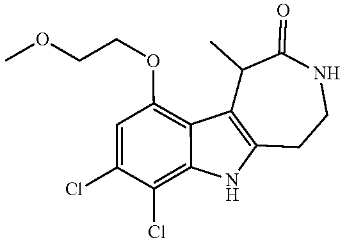 [SMILES: COCCOc1cc(Cl)c(Cl)c2[nH]c3c(c12)C(C)C(=O)NCC3]

Combined 7,8-dichloro-10-hydroxy-1-methyl-3,4,5,6-tetrahydroazepino[4,5-b]indol-2(1H)-one (70.0 mg, 0.183 mmol, 78 mass %), 1-iodo-2-methoxyethane (102 mg, 0.548 mmol) and $K_2CO_3$ (75.7 mg, 0.548 mmol) in DMF (2 mL). Stirred at 60° C. for 3 hrs. Repeated reaction on 0.71× scale and combined both crude lots. Diluted with water and extracted with EtOAc (3×). Combined the organic layers, washed with saturated aqueous NaCl (3×), dried over anhydrous $Na_2SO_4$, filtered and concentrated. Purified by prep-HPLC to give impure product as a yellow solid. Repeated reaction and purification on 1.20× scale while increasing the reaction time to 16 hrs. and combined both impure product lots. Further purified by prep-TLC eluting with MeOH in DCM (1/10, V/V), concentrated under reduced pressure, added water, and lyophilized to give 7,8-dichloro-10-(2-methoxyethoxy)-1-methyl-3,4,5,6-tetrahydroazepino[4,5-b]indol-2(1H)-one (49.6 mg, 21%) as a white solid. ES/MS (m/z): ($^{35}Cl/^{37}Cl$) 357.0/359.0 (M+H).

Example 80

(S)-7,8-Dichloro-10-(2-methoxyethoxy)-1-methyl-3,4,5,6-tetrahydroazepino[4,5-b]indol-2(1H)-one Or (R)-7,8-Dichloro-10-(2-methoxyethoxy)-1-methyl-3,4,5,6-tetrahydroazepino[4,5-b]indol-2(1H)-one (isomer 1) and Example 81

(S)-7,8-Dichloro-10-(2-methoxyethoxy)-1-methyl-3,4,5,6-tetrahydroazepino[4,5-b]indol-2(1H)-one Or (R)-7,8-Dichloro-10-(2-methoxyethoxy)-1-methyl-3,4,5,6-tetrahydroazepino[4,5-b]indol-2(1H)-one (isomer 2)

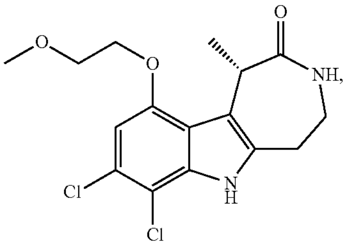

-continued

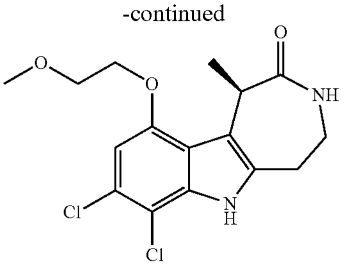

Purified racemic 7,8-dichloro-10-(2-methoxyethoxy)-1-methyl-3,4,5,6-tetrahydroazepino[4,5-b]indol-2(1H)-one (150 mg, 85.5% mass, 0.359 mmol) by SFC to give the titled compounds (Isomer 1—Rt=1.407 min (100% ee), 52.8 mg, 40%; Isomer 2—Rt=1.626 min (99.7% ee), 51.85 mg, 39%). Column: DAICEL CHIRALPAK AD, 250×30 mm, 10 μm; Mobile Phase: 40% EtOH (0.1% $NH_3H_2O$); 60% $CO_2$; Flow Rate: 80 mL/min. ES/MS (m/z): ($^{35}Cl/^{37}Cl$) 357.1/359.1 (M+H).

Intermediate 62

7,8-Dichloro-10-((R)-2-hydroxypropoxy)-1-methyl-3,4,5,6-tetrahydroazepino[4,5-b]indol-2(1H)-one

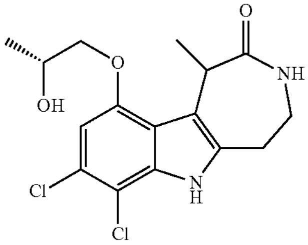 [SMILES: CC1C(=O)NCCc2[nH]c3c(Cl)c(Cl)cc(OC[C@@H](C)O)c3c21]

Combined 10-bromo-7,8-dichloro-1-methyl-3,4,5,6-tetrahydroazepino[4,5-b]indol-2(1H)-one (260 mg, 0.589 mmol, 82 mass %), (R)-propane-1,2-diol (10 mL, 140 mmol), tert-BuBrettPhos-Pd-$G_3$ (79 mg, 0.088 mmol) and t-BuONa (179 mg, 1.77 mmol) in 1,4-dioxane (10 mL). Degassed and purged with $N_2$ (×3). Stirred at 65° C. for 80 min under $N_2$ atmosphere. Cooled to ambient temperature. Repeated the reaction on 0.06× scale and combined the reaction mixtures. Diluted with water, extracted with EtOAc (×2). Combined organic layers, washed with saturated aqueous NaCl (×2), dried over anhydrous $Na_2SO_4$, filtered, and concentrated under reduced pressure. Purified by silica gel flash chromatography eluting with MeOH in DCM and concentrated under reduced pressure, and further purified by prep-HPLC to give 7,8-dichloro-10-((R)-2-hydroxypropoxy)-1-methyl-3,4,5,6-tetrahydroazepino[4,5-b]indol-2(1H)-one (90 mg, 42%) as a mixture of diastereomers. ES/MS (m/z): ($^{35}Cl/^{37}Cl$) 356.9/358.9 (M+H).

Example 82

(S)-7,8-Dichloro-10-((R)-2-hydroxypropoxy)-1-methyl-3,4,5,6-tetrahydroazepino[4,5-b]indol-2(1H)-one Or (R)-7,8-Dichloro-10-((R)-2-hydroxypropoxy)-1-methyl-3,4,5,6-tetrahydroazepino[4,5-b]indol-2(1H)-one (isomer 1) and Example 83

(S)-7,8-Dichloro-10-((R)-2-hydroxypropoxy)-1-methyl-3,4,5,6-tetrahydroazepino[4,5-b]indol-2(1H)-one Or (R)-7,8-Dichloro-10-((R)-2-hydroxypropoxy)-1-methyl-3,4,5,6-tetrahydroazepino[4,5-b]indol-2(1H)-one (isomer 2)

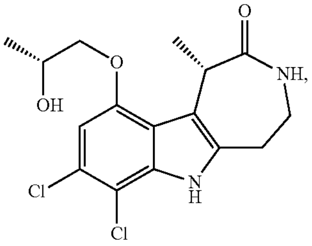

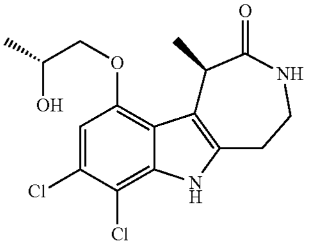

Purified diastereomeric mixture 7,8-dichloro-10-((R)-2-hydroxypropoxy)-1-methyl-3,4,5,6-tetrahydroazepino[4,5-b]indol-2(1H)-one (90 mg, 0.25 mmol, 97 mass %) by SFC to give the titled compounds (Isomer 1—Rt=1.570 min (99.1% de), 37.02 mg, 42% as a white solid; Isomer 2—Rt=2.211 min (99.6% de), 33.08 mg, 38% as a white solid). Column: DAICEL CHIRALPAK AD, 30×250 mm, 10 μm; Mobile Phase: 40% MeOH (0.1% $NH_3H_2O$): 60% $CO_2$; Flow Rate: 80 mL/min. ES/MS (m/z): ($^{35}Cl/^{37}Cl$) 357.1/359.0 (M+H).

Intermediate 63

7,8-Dichloro-10-((S)-2-hydroxypropoxy)-1-methyl-3,4,5,6-tetrahydroazepino[4,5-b]indol-2(1H)-one

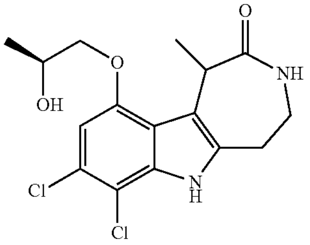 [SMILES: CC1C(=O)NCCc2[nH]c3c(Cl)c(Cl)cc(OC[C@H](C)O)c3c21]

Combined 10-bromo-7,8-dichloro-1-methyl-3,4,5,6-tetrahydroazepino[4,5-b]indol-2(1H)-one (180 mg, 0.423 mmol, 85 mass %), (S)-propane-1,2-diol (12 mL, 160 mmol), tert-BuBrettPhos-Pd-$G_3$ (57 mg, 0.063 mmol) and t-BuONa (128 mg, 1.27 mmol) in 1,4-dioxane (12 mL). Degassed and purged with $N_2$ (×3). Stirred at 65° C. for 80 min under $N_2$ atmosphere. Cooled to ambient temperature. Repeated the reaction on 0.11× scale and combined the reaction mixtures. Diluted with water, extracted with EtOAc (×2). Combined the organic layers, washed with saturated aqueous NaCl (×2), dried over anhydrous $Na_2SO_4$, filtered, and concentrated under reduced pressure. Purified by silica gel flash chromatography eluting with MeOH in DCM and concentrated under reduced pressure, and further purified by prep-HPLC to give 7,8-dichloro-10-((S)-2-hydroxypropoxy)-1-methyl-3,4,5,6-tetrahydroazepino[4,5-b]indol-2 (1H)-one (80 mg, 52%) as a mixture of diastereomers. ES/MS (m/z): ($^{35}Cl/^{37}Cl$) 356.9/358.9 (M+H).

Example 84

(S)-7,8-Dichloro-10-((S)-2-hydroxypropoxy)-1-methyl-3,4,5,6-tetrahydroazepino[4,5-b]indol-2(1H)-one Or (R)-7,8-Dichloro-10-((S)-2-hydroxypropoxy)-1-methyl-3,4,5,6-tetrahydroazepino[4,5-b]indol-2(1H)-one (isomer 1) and Example 85

(S)-7,8-Dichloro-10-((S)-2-hydroxypropoxy)-1-methyl-3,4,5,6-tetrahydroazepino[4,5-b]indol-2(1H)-one Or (R)-7,8-Dichloro-10-((S)-2-hydroxypropoxy)-1-methyl-3,4,5,6-tetrahydroazepino[4,5-b]indol-2(1H)-one (isomer 2)

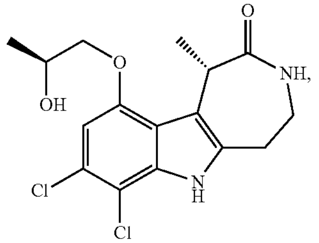

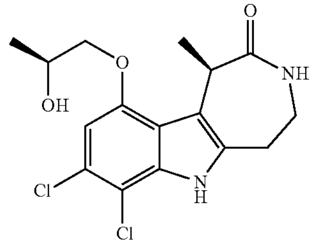

Purified diastereomeric mixture 7,8-dichloro-10-((S)-2-hydroxypropoxy)-1-methyl-3,4,5,6-tetrahydroazepino[4,5-b]indol-2(1H)-one (80 mg, 0.22 mmol) by SFC to give the titled compounds (Isomer 1—Rt=1.710 min (99.6% de), 28.62 mg, 36% as a white solid; Isomer 2—Rt=2.085 min (97.4% de), 32.40 mg, 40% as a white solid). Column: DAICEL CHIRALPAK AD, 30×250 mm, 10 μm; Mobile Phase: 35% MeOH (0.1% $NH_3H_2O$): 65% $CO_2$; Flow Rate: 80 mL/min. ES/MS (m/z): ($^{35}Cl/^{37}Cl$) 357.0/359.0 (M+H).

Example 86

7,8-Dichloro-1-methyl-10-((tetrahydrofuran-3-yl)oxy)-3,4,5,6-tetrahydroazepino[4,5-b]indol-2(1H)-one

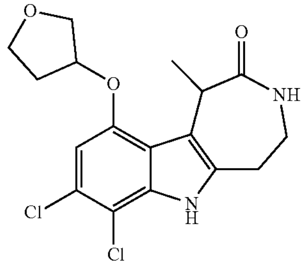 [SMILES: CC1C(=O)NCCc2[nH]c3c(Cl)c(Cl)cc(OC4CCOC4)c3c21]

Combined 7,8-dichloro-10-hydroxy-1-methyl-3,4,5,6-tetrahydroazepino[4,5-b]indol-2(1H)-one (320 mg, 0.749 mmol, 70 mass %), 3-iodotetrahydrofuran (445 mg, 2.25 mmol) and $K_2CO_3$ (517 mg, 3.74 mmol) in DMF (8 mL). Degassed and purged with $N_2$ 3 times. Stirred at 60° C. for 3 hrs, under $N_2$ atmosphere. Cooled to ambient temperature, diluted with water, and extracted with EtOAc. Washed with saturated aqueous NaCl, dried over anhydrous $Na_2SO_4$, filtered, and concentrated under reduced pressure. Purified by silica gel flash chromatography eluting with MeOH in DCM and concentrated under reduced pressure. Purified by prep-HPLC to give 7,8-dichloro-1-methyl-10-((tetrahydrofuran-3-yl)oxy)-3,4,5,6-tetrahydroazepino[4,5-b]indol-2 (1H)-one (52 mg, 19%) as a white solid mixture of diastereomers. ES/MS (m/z): ($^{35}Cl/^{37}Cl$) 369.0/371.0 (M+H).

Intermediate 64

7,8-Dichloro-10-(2-oxopropoxy)-3,4,5,6-tetrahydroazepino[4,5-b]indol-2(1H)-one

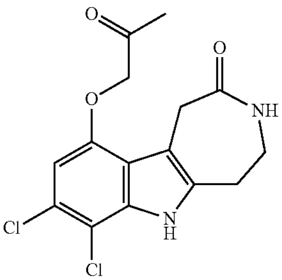 [SMILES: CC(=O)COc1cc(Cl)c(Cl)c2[nH]c3c(c12)CC(=O)NCC3]

Dissolved 7,8-dichloro-10-hydroxy-1-methyl-3,4,5,6-tetrahydroazepino[4,5-b]indol-2(1H)-one (200 mg, 0.449 mmol, 64 mass %), potassium iodide (85 mg, 0.512 mmol) and potassium carbonate (220 mg, 1.59 mmol) in acetone (5 mL). Added chloroacetone (170 mg, 1.84 mmol). Stirred at 65° C. for 3 hrs. Quenched with saturated aqueous sodium bicarbonate solution (1 mL) and concentrated under reduced pressure. Purified the residue by silica gel flash chromatography eluting with MeOH in DCM to give 7,8-dichloro-10-(2-oxopropoxy)-3,4,5,6-tetrahydroazepino[4,5-b]indol-2 (1H)-one (75 mg, 44%) as a brown solid. ES/MS (m/z): ($^{35}Cl/^{37}Cl$) 340.9/342.9 (M+H).

Example 87

7,8-Dichloro-10-(2-hydroxypropoxy)-3,4,5,6-tetrahydroazepino[4,5-b]indol-2(1H)-one

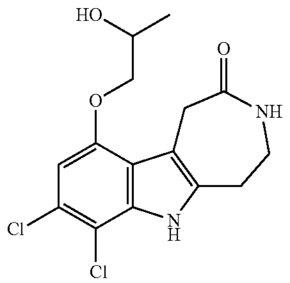 [SMILES: CC(O)COc1cc(Cl)c(Cl)c2[nH]c3c(c12)CC(=O)NCC3]

Dissolved 7,8-dichloro-10-(2-oxopropoxy)-3,4,5,6-tetrahydroazepino[4,5-b]indol-2(1H)-one (75 mg, 0.198 mmol) in MeOH (6 mL). Added sodium borohydride (60 mg, 1.59 mmol) at 0° C. Stirred at 0° C. for 0.5 hr. The reaction is quenched with aqueous 1M HCl (2 mL) at 0° C. and diluted with water (10 mL). The mixture is extracted with EtOAc (10 mL×2). Dried the combined organic layers over anhydrous $Na_2SO_4$, filtered, and concentrated under reduced pressure. Purified by prep-HPLC to give 7,8-dichloro-10-(2-hydroxypropoxy)-3,4,5,6-tetrahydroazepino[4,5-b]indol-2(1H)-one (29.54 mg, 43%) as a white solid. ES/MS (m/z): ($^{35}Cl/^{37}Cl$) 343.0/344.9 (M+H).

Intermediate 65

10-(3-((tert-Butyldimethylsilyl)oxy)prop-1-yn-1-yl)-7,8-dichloro-1-methyl-3,4,5,6-tetrahydroazepino[4,5-b]indol-2(1H)-one

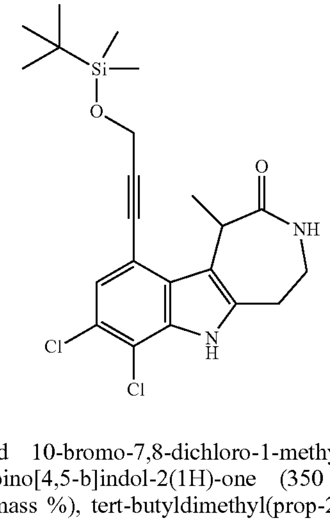

Combined 10-bromo-7,8-dichloro-1-methyl-3,4,5,6-tetrahydroazepino[4,5-b]indol-2(1H)-one (350 mg, 0.822 mmol, 85 mass %), tert-butyldimethyl(prop-2-yn-1-yloxy) silane (420 mg, 2.47 mmol), $Pd(dppf)Cl_2$ (61 mg, 0.082 mmol), copper(I) iodide (32 mg, 0.16 mmol) and $Et_3N$ (840 mg, 8.22 mmol) in DMF (8 mL). Degassed and purged with $N_2$ (×3). Stirred at 80° C. for 16 hrs. Diluted with water at 0° C. and extracted with EtOAc (3×). Combined organic layers, washed with saturated aqueous NaCl (×2), dried over anhydrous $Na_2SO_4$, filtered, and concentrated under reduced pressure. Purified by silica gel flash chromatography eluting with EtOAc in PE and concentrated under reduced pressure to give 10-(3-((tert-butyldimethylsilyl)oxy)prop-1-yn-1-yl)-7,8-dichloro-1-methyl-3,4,5,6-tetrahydroazepino[4,5-b]indol-2(1H)-one (75 mg, 19%). $^1H$ NMR ($CD_3OD$): 7.17 (s, 1H), 4.76 (q, J=7.4 Hz, 1H), 3.94-3.85 (m, 1H), 3.45 (dt, J=14.9, 3.5 Hz, 1H), 3.10-2.99 (m, 2H), 1.69 (d, J=7.4 Hz, 3H), 0.96 (s, 9H), 0.19 (s, 6H).

Example 88

7,8-Dichloro-10-(3-hydroxypropyl)-1-methyl-3,4,5,6-tetrahydroazepino[4,5-b]indol-2(1H)-one

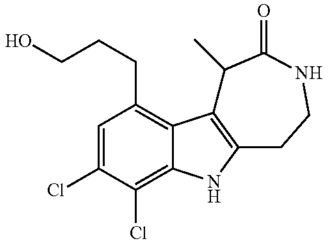 [SMILES: CC1C(=O)NCCc2[nH]c3c(Cl)c(Cl)cc(CCCO)c3c21]

Combined 10-(3-((tert-butyldimethylsilyl)oxy)prop-1-yn-1-yl)-7,8-dichloro-1-methyl-3,4,5,6-tetrahydroazepino[4,5-b]indol-2(1H)-one (75 mg, 0.16 mmol, 95 mass %) and wet $Pd(OH)_2$ on carbon (25 mg, 20 mass %) in THF (2.5 mL) and MeOH (2.5 mL). Stirred under $H_2$ (30 psi) at 20° C. for 24 hrs. Filtered and concentrated the filtrate. Purified by prep-HPLC. Concentrated under reduced pressure and lyophilized to give 7,8-dichloro-10-(3-hydroxypropyl)-1-methyl-3,4,5,6-tetrahydroazepino[4,5-b]indol-2(1H)-one (12 mg, 22%) as a white solid. ES/MS (m/z): ($^{35}Cl/^{37}Cl$) 341.1/343.1 (M+H).

Example 89

(R)-2-(7,8-Dichloro-1-methyl-2-oxo-1,2,3,4,5,6-hexahydroazepino[4,5-b]indol-10-yl)acetonitrile Or (S)-2-(7,8-Dichloro-1-methyl-2-oxo-1,2,3,4,5,6-hexahydroazepino[4,5-b]indol-10-yl)acetonitrile (isomer 1) and Example 90

(R)-2-(7,8-Dichloro-1-methyl-2-oxo-1,2,3,4,5,6-hexahydroazepino[4,5-b]indol-10-yl)acetonitrile Or (S)-2-(7,8-Dichloro-1-methyl-2-oxo-1,2,3,4,5,6-hexahydroazepino[4,5-b]indol-10-yl)acetonitrile (isomer 2)

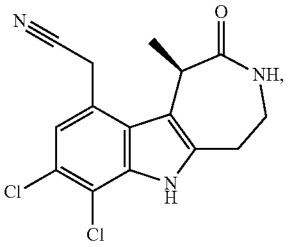

-continued

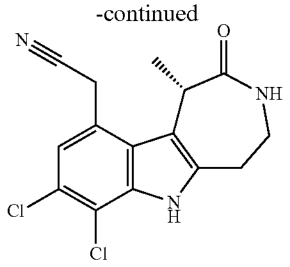

Purified racemic 2-(7,8-dichloro-1-methyl-2-oxo-1,2,3,4,5,6-hexahydroazepino[4,5-b]indol-10-yl)acetonitrile (20.82 mg, 0.0646 mmol) by SFC to give the titled compounds (Isomer 1—Rt=2.244 min (95.2% ee), 8.81 mg, 42%; Isomer 2—Rt=2.918 min (90.6% ee) 8.67 mg, 42%). Column: Chiralpak AD-H, 20×150 mm; Mobile Phase: 25% MeOH: 75% CO; Flow Rate: 80 mL/min; Column Temperature: 40° C.; Detection: 225 nM. ES/MS (m/z): ($^{35}Cl/^{37}Cl$) 322.0/324.0 (M+H)$^1$H NMR (DMSO-d6): 11.59 (s, 1H), 7.80 (t, J=5.9 Hz, 1H), 7.22 (s, 1H), 4.35-4.24 (m, 2H), 4.11-4.06 (m, 1H), 4.04-4.01 (m, 1H), 3.75-3.67 (m, 1H), 3.18 (d, J=4.7 Hz, 2H), 1.59 (d, J=7.4 Hz, 3H).

Intermediate 66

10-Bromo-7,8-dichloro-1,6-dimethyl-3,4,5,6-tetrahydroazepino[4,5-b]indol-2(1H)-one

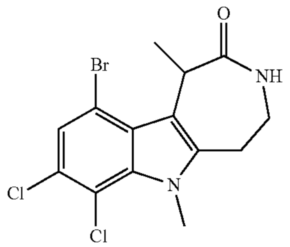 [SMILES: CC1C(=O)NCCc2c1c1c(Br)cc(Cl)c(Cl)c1n2C]

Combined 10-bromo-7,8-dichloro-1-methyl-3,4,5,6-tetrahydroazepino[4,5-b]indol-2(1H)-one (300 mg, 0.746 mmol, 90 mass %) and cesium carbonate (868 mg, 2.61 mmol) in DMF (10 mL). Added iodomethane (130 mg, 0.895 mmol) at 0° C. Stirred at ambient temperature for 2 hrs. Diluted with water, extracted with EtOAc (2×). Combined organic layers, washed with saturated aqueous NaCl (×2), dried over anhydrous $Na_2SO_4$, filtered, and concentrated under reduced pressure. Purified by silica gel flash chromatography eluting with MeOH in DCM and concentrated under reduced pressure to give 10-bromo-7,8-dichloro-1,6-dimethyl-3,4,5,6-tetrahydroazepino[4,5-b]indol-2(1H)-one (300 mg, 94%) as a light-yellow oil. ES/MS (m/z): 374.7/376.8/378.7 (M+H).

Intermediate 67

1-((2-(Trimethyl silyl)ethoxy)methyl)-1H-imidazole-4-carbonitrile

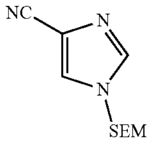 [SMILES: C[Si](C)(C)CCOCn1cnc(C#N)c1]

To a stirred solution of 1H-imidazole-5-carbonitrile (2.00 g, 21.1 mmol) in ACN (40 mL) added $K_2CO_3$ (5.82 g, 42.1 mmol) at 0° C., followed by addition of SEM-Cl (4.30 g, 25.3 mmol) dropwise. Stirred at 90° C. for 6 hrs. Filtered and washed the cake with EtOAc. Concentrated the filtrate under reduced pressure, then diluted with water, extracted with EtOAc (3×). Combined organic layers and dried over anhydrous $Na_2SO_4$, filtered and concentrated under reduced pressure. Purified by silica gel flash chromatography eluting with MeOH in DCM to give 1-((2-(trimethylsilyl)ethoxy)methyl)-1H-imidazole-4-carbonitrile (3.30 g, 67%) as a light yellow oil. ES/MS (m/z): 224.2 (M+H). $^1$H NMR (DMSO-d6): 8.29 (d, J=0.8 Hz, 1H), 8.06 (d, J=0.8 Hz, 1H), 5.40 (s, 2H), 3.49 (dd, J=8.4, 7.7 Hz, 2H), 0.84 (dd, J=8.4, 7.7 Hz, 2H), −0.04 (s, 9H).

Intermediate 68

(1-((2-(Trimethyl silyl)ethoxy)methyl)-1H-imidazol-4-yl)methanamine

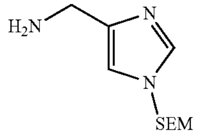 [SMILES: C[Si](C)(C)CCOCn1cnc(CN)c1]

To a solution of 1-((2-(trimethyl silyl)ethoxy)methyl)-1H-imidazole-4-carbonitrile (2.00 g, 8.51 mmol, 95 mass %) in THF (20 mL), added $LiAlH_4$ (646 mg, 17.0 mmol) portionwise at 0° C. Stirred at 0° C. for 2 hrs, under $N_2$ atmosphere. Quenched by addition of water (0.6 mL) at 0° C., followed by addition of 15% aqueous NaOH (0.6 mL) and water (1.8 mL). Diluted with THF (15 mL) and dried over anhydrous $Na_2SO_4$. Stirred at ambient temperature for 30 min., filtered, and concentrated under reduced pressure. Purified by silica gel flash chromatography eluting with MeOH in DCM to give (1-((2-(trimethyl silyl)ethoxy)methyl)-1H-imidazol-4-yl)methanamine (970 mg, 46%) as a yellow oil. ES/MS (m/z): 228.1 (M+H).

Intermediate 69

7,8-Dichloro-1,6-dimethyl-10-(((1-((2-(trimethylsilyl)ethoxy)methyl)-1H-imidazol-4-yl)methyl)amino)-3,4,5,6-tetrahydroazepino[4,5-b]indol-2(1H)-one

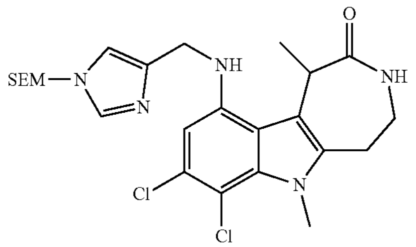 [SMILES: CC1C(=O)NCCc2c1c1c(NCc3cn(COCC[Si](C)(C)C)cn3)cc(Cl)c(Cl)c1n2C]

Combined 10-bromo-7,8-dichloro-1,6-dimethyl-3,4,5,6-tetrahydroazepino[4,5-b]indol-2(1H)-one (200 mg, 0.500 mmol, 94 mass %), (1-((2-(trimethylsilyl)ethoxy)methyl)-1H-imidazol-4-yl)methanamine (250 mg, 1.00 mmol, 91 mass %), $Pd_2(dba)_3$ (56 mg, 0.060 mmol), Xantphos (70 mg, 0.12 mmol) and cesium carbonate (489 mg, 1.50 mmol) in 1,4-dioxane (10 mL) and THF (1 mL). Degassed and purged with $N_2$ (×3). Stirred 100° C. for 16 hrs. Concentrated under reduced pressure and purified by silica gel flash chromatography eluting with MeOH in DCM to give 7,8-dichloro-1,6-dimethyl-10-(((1-((2-(trimethylsilyl)ethoxy)methyl)-1H-imidazol-4-yl)methyl)amino)-3,4,5,6-tetrahydroazepino[4,5-b]indol-2(1H)-one (220 mg, 67%) as a yellow oil. ES/MS (m/z): ($^{35}Cl/^{37}Cl$) 522.0/524.0 (M+H).

Example 91

10-(((1H-Imidazol-5-yl)methyl)amino)-7,8-dichloro-1,6-dimethyl-3,4,5,6-tetrahydroazepino[4,5-b]indol-2(1H)-one

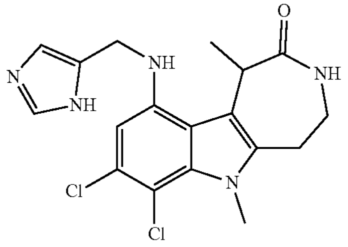 [SMILES: CC1C(=O)NCCc2c1c1c(NCc3cnc[nH]3)cc(Cl)c(Cl)c1n2C]

To a solution of 7,8 dichloro-1,6-dimethyl-10-(((1-((2-(trimethylsilyl)ethoxy)methyl)-1H-imidazol-4-yl)methyl)amino)-3,4,5,6-tetrahydroazepizio[4,5-b]indol-2(1H)-one (190 mg, 0.2.87 mmol, 79 mass %) in THF (4 mL), was added 1,2-diaminoethane (352 mg, 5.74 mmol) and TBAF (5.7 mL, 5.7 mmol, 1M in THF) dropwise. Stirred at 60° C. for 16 hrs, under $N_2$ atmosphere. Repeated reaction on a 0.05× scale and combined the reaction mixtures. Diluted with EtOAc, washed with saturation aqueous $NH_4Cl$ (10×), dried over anhydrous $Na_2SO_4$, filtered, and concentrated under reduced pressure. Purified by prep-HPLC twice. Further purified by SFC (Column: DAICEL CHIRALPAK AD (250×30 mm, 10 μm); Mobile Phase: 55% EtOH (0.1% $NH_3H_2O$); 45% $CO_2$; Flow Rate: 80 mL/min to give 10-(((1H-imidazol-5-yl)methyl)amino)-7,8-dichloro-1,6-dimethyl-3,4,5,6-tetrahydroazepino[4,5-b]indol-2(1H)-one (12.88 mg, 11%) as a yellow solid. ES/MS (m/z): ($^{35}Cl/^{37}Cl$) 392.1/394.1 (M+H).

Example 92

(S)—N-(7,8-Dichloro-1,6-dimethyl-2-oxo-1,2,3,4,5,6-hexahydroazepino[4,5-b]indol-10-yl)-2-hydroxyacetamide Or (R)—N-(7,8-Dichloro-1,6-dimethyl-2-oxo-1,2,3,4,5,6-hexahydroazepino[4,5-b]indol-10-yl)-2-hydroxyacetamide (isomer 1) and Example 93

(S)—N-(7,8-Dichloro-1,6-dimethyl-2-oxo-1,2,3,4,5,6-hexahydroazepino[4,5-b]indol-10-yl)-2-hydroxyacetamide Or (R)—N-(7,8-Dichloro-1,6-dimethyl-2-oxo-1,2,3,4,5,6-hexahydroazepino[4,5-b]indol-10-yl)-2-hydroxyacetamide (isomer 2)

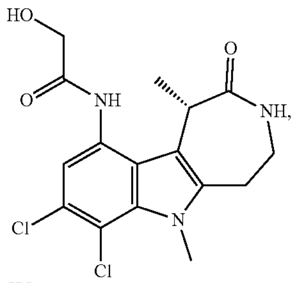

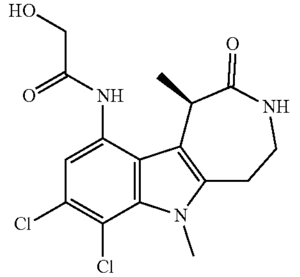

Combined 10-bromo-7,8-dichloro-1,6-dimethyl-1,3,4,5-tetrahydroazepino[4,5-b]indol-2-one (270 mg, 0.517 mmol, 72 mass %), 2-hydroxyacetamide (90 mg, 1.175 mmol), $Pd_2(dba)_3$ (50 mg, 0.0530 mmol), Xantphos (60 mg, 0.104 mmol) and cesium carbonate (600 mg, 1.84 mmol) in 1,4-dioxane (60 mL) and THF (3 mL). Degassed and purged with $N_2$ (×3) and stirred at 110° C. for 14-18 hrs. Concentrated reaction under reduced pressure and purified by silica flash column chromatography eluting with MeOH in DCM. Triturated the resulting residue with 5 mL of MeOH in DCM (1/5) and further purified by SFC to give the titled compounds (Isomer 1—Rt=2.297 min (100% ee), 47.64 mg, 24% as a white solid; Isomer 2—Rt=2.804 min (100% ee), 51.07 mg, 26% as a white solid). Purification Conditions: Column: DAICEL CHIRALPAK AD (30×250 mm, 10 μm); Mobile phase: 50% EtOH (0.1% $NH_3H_2O$): 50% $CO_2$; FlowRate: 80 mL/min. ES/MS (m/z): ($^{35}Cl/^{37}Cl$) 392.0/393.9 (M+Na). (Chiral analysis used—Column: Chiralpak IC-3, 50×4.6 mm, 3 μm; Mobile Phase: 20-40% EtOH (0.05% DEA): 80-60% $CO_2$; Flow Rate: 4 mL/min).

Intermediate 70

(2S)—N-(7,8-Dichloro-1,6-dimethyl-2-oxo-1,2,3,4,5,6-hexahydroazepino[4,5-b]indol-10-yl)-2-hydroxypropanamide

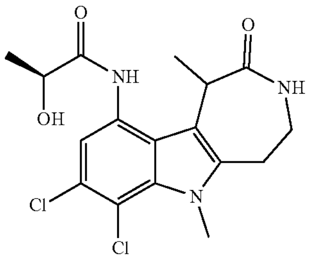 [SMILES: CC1C(=O)NCCc2c1c1c(NC(=O)[C@H](C)O)cc(Cl)c(Cl)c1n2C]

Combined racemic 10-bromo-7,8-dichloro-1,6-dimethyl-3,4,5,6-tetrahydroazepino[4,5-b]indol-2(1H)-one (300 mg, 0.702 mmol, 88 mass %), (S)-2-hydroxypropanamide (197 mg, 2.11 mmol), $Pd_2(dba)_3$ (66 mg, 0.070 mmol), Xantphos (83 mg, 0.14 mmol) and cesium carbonate (817 mg, 2.46 mmol) in 1,4-dioxane (10 mL) and THF (1 mL). Degassed and purged with $N_2$ (×3). Stirred at 110° C. for 16 hrs, under $N_2$ atmosphere. Cooled to ambient temperature. Concentrated under reduced pressure. Purified by silica gel flash chromatography eluting with MeOH in DCM and concentrated under reduced pressure to give (2S)—N-(7,8-dichloro-1,6-dimethyl-2-oxo-1,2,3,4,5,6-hexahydroazepino[4,5-b]indol-10-yl)-2-hydroxypropanamide as a mixture of diastereomers (170 mg, 60%) as an off-white solid. ES/MS (m/z): ($^{35}Cl/^{37}Cl$) 384.0/385.7 (M+H); 383.8/385.7 (M+H).

Example 94

(2S)—N—((S)-7,8-Dichloro-1,6-dimethyl-2-oxo-1,2,3,4,5,6-hexahydroazepino[4,5-b]indol-10-yl)-2-hydroxypropanamide Or (2S)—N—((R)-7,8-Dichloro-1,6-dimethyl-2-oxo-1,2,3,4,5,6-hexahydroazepino[4,5-b]indol-10-yl)-2-hydroxypropanamide (isomer 1) and Example 95

(2S)—N—((S)-7,8-Dichloro-1,6-dimethyl-2-oxo-1,2,3,4,5,6-hexahydroazepino[4,5-b]indol-10-yl)-2-hydroxypropanamide Or (2S)—N—((R)-7,8-Dichloro-1,6-dimethyl-2-oxo-1,2,3,4,5,6-hexahydroazepino[4,5-b]indol-10-yl)-2-hydroxypropanamide (isomer 2)

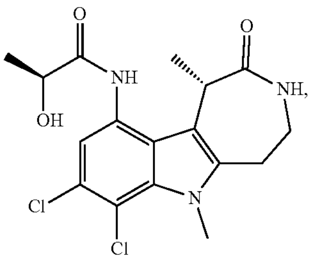

-continued

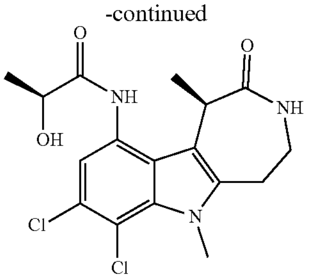

Purified diastereomeric mixture (2S)—N-(7,8-dichloro-1,6-dimethyl-2-oxo-1,2,3,4,5,6-hexahydroazepino[4,5-b]indol-10-yl)-2-hydroxypropanamide (170 mg, 0.420 mmol, 95 mass %) by SFC to give the titled compounds (Isomer 1—Rt=1.342 min (100% de), 71.17 mg, 43% as a white solid; Isomer 2—Rt=2.589 min (100% de), 61.85 mg, 38% as a white solid). Column: DAICEL CHIRALPAK IG (30×250 mm, 10 μm); Mobile Phase: 60% EtOH (w/0.1% $NH_3H_2O$): 40% $CO_2$; FlowRate: 80 mL/min. ES/MS (m/z): ($^{35}Cl/^{37}Cl$) 384.1/386.1 (M+H).

Example 96

7,8-Dichloro-10-((2-methoxyethyl)amino)-1,6-dimethyl-3,4,5,6-tetrahydroazepino[4,5-b]indol-2(1H)-one

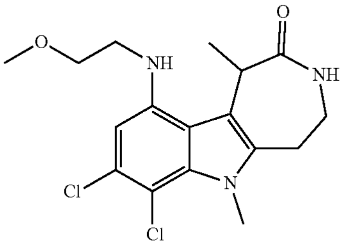 [SMILES: COCCNc1cc(Cl)c(Cl)c2c1c1c(n2C)CCNC(=O)C1C]

Combined 10-bromo-7,8-dichloro-1,6-dimethyl-3,4,5,6-tetrahydroazepino[4,5-b]indol-2(1H)-one (150 mg, 0.383 mmol, 96 mass %), 2-methoxyethan-1-amine (74 mg, 0.96 mmol), $Pd_2(dba)_3$ (36 mg, 0.038 mmol), Xantphos (45 mg, 0.077 mmol) and cesium carbonate (378 mg, 1.15 mmol) in 1,4-dioxane (8 mL) and THF (0.8 mL). Degassed and purged with $N_2$ (×3). Stirred at 100° C. for 16 hrs. Concentrated under reduced pressure and purified by silica gel flash chromatography eluting with MeOH in DCM, and further purified by prep-HPLC. Concentrated under reduced pressure and lyophilized to give 7,8-dichloro-10-((2-methoxyethyl)amino)-1,6-dimethyl-3,4,5,6-tetrahydroazepino[4,5-b]indol-2(1H)-one (50.74 mg, 35%) as a white solid. ES/MS (m/z): ($^{35}Cl/^{37}Cl$) 370.2/372.1 (M+H).

Example 97

7,8-Dichloro-10-(2-methoxyethoxy)-1,6-dimethyl-3,4,5,6-tetrahydroazepino[4,5-b]indol-2(1H)-one

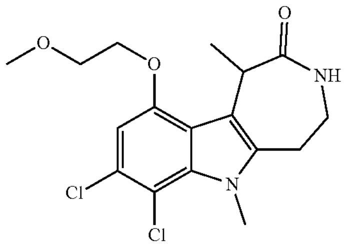 [SMILES: COCCOc1cc(Cl)c(Cl)c2c1c1c(n2C)CCNC(=O)C1C]

Combined 10-bromo-7,8-dichloro-1,6-dimethyl-3,4,5,6-tetrahydroazepino[4,5-b]indol-2(1H)-one (200 mg, 0.441 mmol, 83 mass %), sodium tert-butoxide (134 mg, 1.32 mmol), 2-methoxyethan-1-ol (1.93 g, 24.1 mmol) and t-Bu-BrettPhos-Pd-$G_3$ (40 mg, 0.044 mmol) in 1,4-dioxane (2 mL). Degassed and purged with $N_2$ (x3). Stirred at 65° C. for 1 hr, under $N_2$ atmosphere. Diluted with water and extracted with EtOAc, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure, and further purified by reverse phase prep-HPLC. Concentrated under reduced pressure and lyophilized to give 7,8-dichloro-10-(2-methoxyethoxy)-1,6-dimethyl-3,4,5,6-tetrahydroazepino[4,5-b]indol-2(1H)-one (45.35 mg, 27%) as a yellow solid. ES/MS (m/z): ($^{35}Cl/^{37}Cl$) 370.9/372.9 (M+H).

Intermediate 71

7,8-Dichloro-10-(((R)-2-hydroxypropyl)amino)-1,6-dimethyl-3,4,5,6-tetrahydroazepino[4,5-b]indol-2(1H)-one

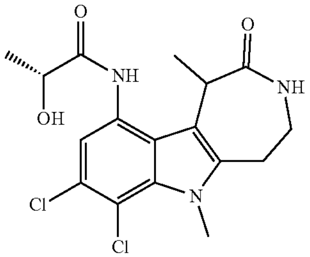 [SMILES: CC1C(=O)NCCc2c1c1c(NC(=O)[C@@H](C)O)cc(Cl)c(Cl)c1n2C]

Combined 10-bromo-7,8-dichloro-1,6-dimethyl-3,4,5,6-tetrahydroazepino[4,5-b]indol-2(1H)-one (300 mg, 0.750 mmol, 94 mass %), (R)-1-aminopropan-2-ol (178 mg, 2.25 mmol), $Pd_2(dba)_3$ (69 mg, 0.075 mmol), Xantphos (90 mg, 0.15 mmol) and cesium carbonate (611 mg, 1.87 mmol) in 1,4-dioxane (10 mL) and THF (0.8 mL). Stirred at 110° C. under $N_2$ atmosphere for 16 hrs. Concentrated under reduced pressure and purified by silica gel flash chromatography eluting with MeOH in DCM and concentrated under reduced pressure to give 7,8-dichloro-10-(((R)-2-hydroxypropyl)amino)-1,6-dimethyl-3,4,5,6-tetrahydroazepino[4,5-b]indol-2(1H)-one (165 mg, 52%) as a mixture of diastereomers. ES/MS (m/z): ($^{35}Cl/^{37}Cl$) 370.1/372.0 (M+H).

Example 98

(R)-7,8-Dichloro-10-(((R)-2-hydroxypropyl)amino)-1,6-dimethyl-3,4,5,6-tetrahydroazepino[4,5-b]indol-2(1H)-one Or (S)-7,8-Dichloro-10-(((R)-2-hydroxypropyl)amino)-1,6-dimethyl-3,4,5,6-tetrahydroazepino[4,5-b]indol-2(1H)-one (Isomer 1) and Example 99

(R)-7,8-Dichloro-10-(((R)-2-hydroxypropyl)amino)-1,6-dimethyl-3,4,5,6-tetrahydroazepino[4,5-b]indol-2(1H)-one Or (S)-7,8-Dichloro-10-(((R)-2-hydroxypropyl)amino)-1,6-dimethyl-3,4,5,6-tetrahydroazepino[4,5-b]indol-2(1H)-one (Isomer 2)

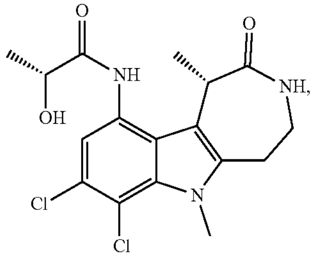

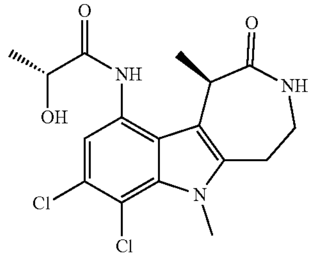

Purified diastereomeric mixture 7,8-dichloro-10-(((R)-2-hydroxypropyl)amino)-1,6-dimethyl-3,4,5,6-tetrahydroazepino[4,5-b]indol-2(1H)-one (165 mg, 0.392 mmol, 88 mass %) by SFC to give the titled compounds (Isomer 1-Rt=1.661 min (100% de), 51.39 mg, 35% as an off-white solid; Isomer 2-Rt=2.139 min (100% de), 50.23 mg, 34% as an off-white solid). Purification Conditions—Column: DAICEL CHIRALPAK AD (30x250 mm, 10 µm); Mobile Phase: 55% iPrOH (w/0.1% $NH_3H_2O$): 45% $CO_2$; FlowRate: 80 mL/min. (chiral analysis used-Column: ChiralPak IG, 50x4.6 mm, 3 µm; Mobile Phase: 40% EtOH (0.05% DEA): 60% $CO_2$; Flow Rate: 4 mL/min; Column Temperature: 35° C.). ES/MS (m/z): ($^{35}Cl/^{37}Cl$) 370.1/372.1 (M+H).

Intermediate 72

7,8-Dichloro-10-(((R)-2-hydroxypropyl)amino)-1,6-dimethyl-3,4,5,6-tetrahydroazepino[4,5-b]indol-2 (1H)-one

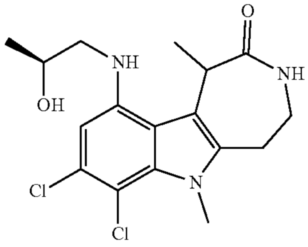 [SMILES: CC1C(=O)NCCc2c1c1c(NC[C@H](C)O)cc(Cl)c(Cl)c1n2C]

Combined 10-bromo-7,8-dichloro-1,6-dimethyl-3,4,5,6-tetrahydroazepino[4,5-b]indol-2(1H)-one (200 mg, 0.511 mmol, 96 mass %), (S)-1-aminopropan-2-ol (98 mg, 1.3 mmol), $Pd_2(dba)_3$ (48 mg, 0.051 mmol), Xantphos (60 mg, 0.10 mmol) and cesium carbonate (504 mg, 1.53 mmol) in 1,4-dioxane (10 mL) and THF (1 mL). Degassed and purged with $N_2$ (x3). Stirred at 100° C. for 16 hrs. Concentrated under reduced pressure and purified by silica gel flash chromatography eluting with MeOH in DCM. Concentrated under reduced pressure and further purified by prep-HPLC. Concentrated under reduced pressure and lyophilized to give diastereomeric mixture 7,8-dichloro-10-(((R)-2-hydroxypropyl)amino)-1,6-dimethyl-3,4,5,6-tetrahydroazepino[4,5-b]indol-2(1H)-one (100 mg, 49%) as a yellow solid. ES/MS (m/z): ($^{35}Cl/^{37}Cl$) 369.9/371.9 (M+H).

Example 100

(R)-7,8-Dichloro-10-(((R)-2-hydroxypropyl)amino)-1,6-dimethyl-3,4,5,6-tetrahydroazepino[4,5-b]indol-2(1H)-one Or (S)-7,8-Dichloro-10-(((R)-2-hydroxypropyl)amino)-1,6-dimethyl-3,4,5,6-tetrahydroazepino[4,5-b]indol-2(1H)-one (isomer 1) and Example 101

(R)-7,8-Dichloro-10-(((R)-2-hydroxypropyl)amino)-1,6-dimethyl-3,4,5,6-tetrahydroazepino[4,5-b]indol-2(1H)-one Or (S)-7,8-Dichloro-10-(((R)-2-hydroxypropyl)amino)-1,6-dimethyl-3,4,5,6-tetrahydroazepino[4,5-b]indol-2(1H)-one (isomer 2)

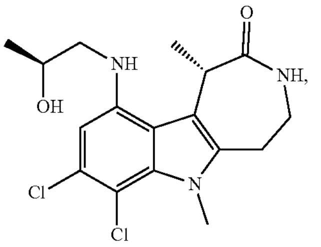

-continued

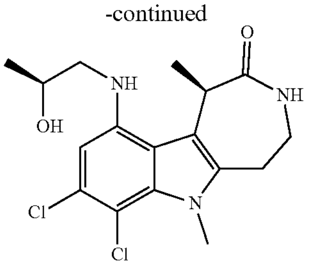

Purified diastereomeric mixture 7,8-dichloro-10-(((R)-2-hydroxypropyl)amino)-1,6-dimethyl-3,4,5,6-tetrahydroazepino[4,5-b]indol-2(1H)-one (100 mg, 0.251 mmol, 93 mass %) by SFC. Column: DAICEL CHIRALPAK AD (250×30 mm, 10 μm); Mobile Phase: 60% EtOH (w/0.1% $NH_3H_2O$): 40% $CO_2$; Flow Rate: 80 mL/min). Purified another batch of 7,8-dichloro-10-(((R)-2-hydroxypropyl)amino)-1,6-dimethyl-3,4,5,6-tetrahydroazepino[4,5-b]indol-2(1H)-one (190 mg, 0.458 mmol, 89 mass %) by SFC. Column: DAICEL CHIRALPAK IC (30×250 mm, 10 μm); Mobile Phase: 50% EtOH (w/0.1% $NH_3H_2O$): 50% $CO_2$; FlowRate: 80 mL/min). Combined the first eluting product fractions from both SFC purifications and lyophilized to give Isomer 1—Rt=1.752 min (100% de), 61.67 mg, 23% as a yellow solid. Combined the second eluting product fractions from both SFC purifications and lyophilized to give Isomer 2—Rt=2.378 min (98.9% de), 63.06 mg, 23% as a yellow solid. (Chiral analysis used—Column: Chiralpak AD-3, 50×4.6 mm, 3 μm; Mobile Phase: 5-40% EtOH (0.05% DEA)/$CO_2$; Flow Rate: 4 mL/min). ES/MS m/z: ($^{35}Cl/^{37}Cl$) 370.1/372.1 (M+H).

Intermediate 73

10-Bromo-7,8-dichloro-5-(2-hydroxy-2-methylpropyl)-3,4,5,6-tetrahydroazepino[4,5-b]indol-2(1H)-one

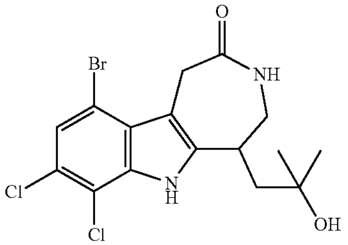 [SMILES: CC(C)(O)CC1CNC(=O)Cc2c1[nH]c1c(Cl)c(Cl)cc(Br)c21]

To a solution of ethyl 2-(10-bromo-7,8-dichloro-2-oxo-1,2,3,4,5,6-hexahydroazepino[4,5-b]indol-5-yl)acetate (200 mg, 0.392 mmol, 85 mass %) in THF (6 mL), added MeMgBr (0.65 mL, 1.96 mmol, 3M in $Et_2O$) at 0° C. Stirred at 0° C. for 2 hrs. Repeated the reaction on 0.25× scale and combined the reaction mixtures. Quenched with saturated aqueous $NH_4Cl$ and diluted with $H_2O$, extracted with EtOAc. Combined organic layers, washed with saturated aqueous $NH_4Cl$, saturated aqueous NaCl, dried over anhydrous $Na_2SO_4$, filtered, and concentrated under reduced pressure. Purified by silica gel flash chromatography eluting with MeOH in DCM and concentrated under reduced pressure to give 10-bromo-7,8-dichloro-5-(2-hydroxy-2-methylpropyl)-3,4,5,6-tetrahydroazepino[4,5-b]indol-2(1H)-one (200 mg, 57%). ES/MS (m/z): 418.8/420.8/422.8 (M+H).

Example 102

7,8-Dichloro-5-(2-hydroxy-2-methylpropyl)-10-(2-methyl-2H-1,2,3-triazol-4-yl)-3,4,5,6-tetrahydroazepino[4,5-b]indol-2(1H)-one

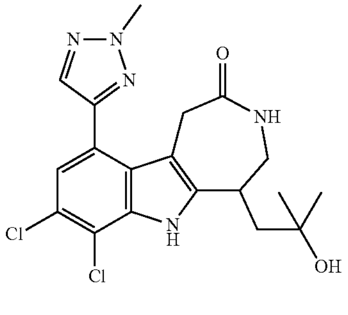 [SMILES: Cn1ncc(-c2cc(Cl)c(Cl)c3[nH]c4c(c23)CC(=O)NCC4CC(C)(C)O)n1]

Combined 10-bromo-7,8-dichloro-5-(2-hydroxy-2-methylpropyl)-3,4,5,6-tetrahydroazepino[4,5-b]indol-2(1H)-one (150 mg, 0.207 mmol, 58 mass %), 2-methyl-4-(4,4,5,5-tetramethyl-1,3,2-dioxaborolan-2-yl)-2H-1,2,3-triazole (173 mg, 0.414 mmol), Pd(dppf)$Cl_2$ (15 mg, 0.021 mmol), $Na_2CO_3$ (66 mg, 0.62 mmol) in 1,4-dioxane (12 mL) and $H_2O$ (3 mL). Degassed and purged with $N_2$ (x3). Stirred at 90° C. for 2 hrs. Repeated the reaction on 0.33× scale and combined the reaction mixtures and concentrated under reduced pressure. Purified by silica gel flash chromatography eluting with MeOH in DCM and concentrated under reduced pressure, and further purified by reverse phase prep-HPLC to give 7,8-dichloro-5-(2-hydroxy-2-methylpropyl)-10-(2-methyl-2H-1,2,3-triazol-4-yl)-3,4,5,6-tetrahydroazepino[4,5-b]indol-2(1H)-one (76.42 mg, 65%) as a white solid. ES/MS (m/z): ($^{35}Cl/^{37}Cl$) 422.0/423.8 (M+H).

Example 103

(R)-7,8-Dichloro-5-(2-hydroxy-2-methylpropyl)-10-(2-methyl-2H-1,2,3-triazol-4-yl)-3,4,5,6-tetrahydroazepino[4,5-b]indol-2(1H)-one Or (S)-7,8-Dichloro-5-(2-hydroxy-2-methylpropyl)-10-(2-methyl-2H-1,2,3-triazol-4-yl)-3,4,5,6-tetrahydroazepino[4,5-b]indol-2(1H)-one (isomer 1) and Example 104

(R)-7,8-Dichloro-5-(2-hydroxy-2-methylpropyl)-10-(2-methyl-2H-1,2,3-triazol-4-yl)-3,4,5,6-tetrahydroazepino[4,5-b]indol-2(1H)-one Or (S)-7,8-Dichloro-5-(2-hydroxy-2-methylpropyl)-10-(2-methyl-2H-1,2,3-triazol-4-yl)-3,4,5,6-tetrahydroazepino[4,5-b]indol-2(1H)-one (isomer 2)

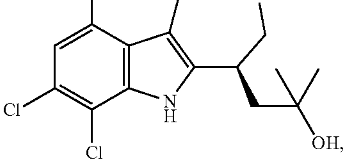

-continued

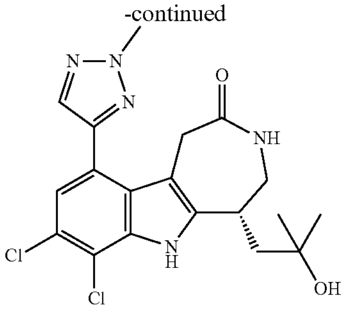

Purified racemic 7,8-dichloro-5-(2-hydroxy-2-methylpropyl)-10-(2-methyl-2H-1,2,3-triazol-4-yl)-3,4,5,6-tetrahydroazepino[4,5-b]indol-2(1H)-one (21 mg, 0.050 mmol) by SFC to give the titled compounds (Isomer 1—RT=1.79 min (100% ee), 8 mg, 40%; Isomer 2—RT=3.06 min (100% ee), 7 mg, 30%). Column: Chiralpak AD-H, 21×150 mm; Mobile Phase: 20% MeOH: 80% $CO_2$; Flow Rate: 80 mL/min; Column temperature: 40° C.; Detection: 225 nM. ES/MS (m/z): ($^{35}Cl/^{37}Cl$) 422.2/424.2 (M+H).

Example 105

7,8-Dichloro-5-(2-hydroxy-2-methylpropyl)-6-methyl-10-(2-methyl-2H-1,2,3-triazol-4-yl)-3,4,5,6-tetrahydroazepino[4,5-b]indol-2(1H)-one

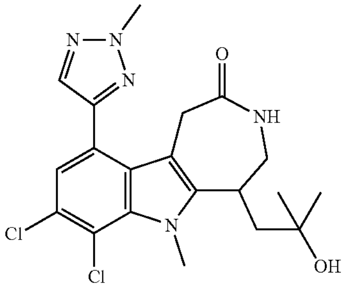 [SMILES: Cn1ncc(-c2cc(Cl)c(Cl)c3c2c2c(n3C)C(CC(C)(C)O)CNC(=O)C2)n1]

To a stirring solution of 7,8-dichloro-5-(2-hydroxy-2-methylpropyl)-6-methyl-10-(2-methyl-2H-1,2,3-triazol-4-yl)-3,4,5,6-tetrahydroazepino[4,5-b]indol-2(1H)-one (40 mg, 0.093 mmol, 98 mass %) in DMF (2 mL), added cesium carbonate (106 mg, 0.326 mmol) and iodomethane (13 mg, 0.093 mmol). Stirred at 25° C. for 2 hrs. Repeated the reaction on 0.25× scale and combined the reaction mixtures. Diluted with $H_2O$ and extracted with EtOAc. Combined organic layers, washed with saturated aqueous NaCl, dried over anhydrous $Na_2SO_4$, filtered, and concentrated under reduced pressure. Purified by reverse phase prep-HPLC to give 7,8-dichloro-5-(2-hydroxy-2-methylpropyl)-6-methyl-10-(2-methyl-2H-1,2,3-triazol-4-yl)-3,4,5,6-tetrahydroazepino[4,5-b]indol-2(1H)-one (26 mg, 49%) as a white solid. ES/MS (m/z): ($^{35}Cl/^{37}Cl$) 436.1/438.0 (M+H).

Example 106

(R)-2-(7,8-Dichloro-5-(2-hydroxy-2-methylpropyl)-2-oxo-1,2,3,4,5,6-hexahydroazepino[4,5-b]indol-10-yl)acetonitrile Or (S)-2-(7,8-dichloro-5-(2-hydroxy-2-methylpropyl)-2-oxo-1,2,3,4,5,6-hexahydroazepino[4,5-b]indol-10-yl)acetonitrile (isomer 1) and Example 107

(R)-2-(7,8-dichloro-5-(2-hydroxy-2-methylpropyl)-2-oxo-1,2,3,4,5,6-hexahydroazepino[4,5-b]indol-10-yl)acetonitrile Or (S)-2-(7,8-Dichloro-5-(2-hydroxy-2-methylpropyl)-2-oxo-1,2,3,4,5,6-hexahydroazepino[4,5-b]indol-10-yl)acetonitrile (isomer 2)

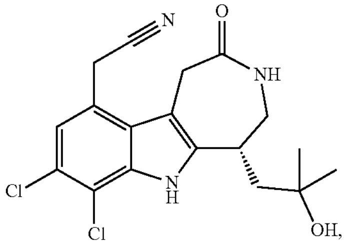
,
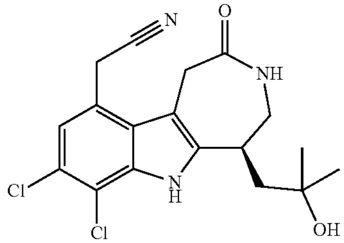

Combined 10-bromo-7,8-dichloro-5-(2-hydroxy-2-methylpropyl)-3,4,5,6-tetrahydroazepino[4,5-b]indol-2(1H)-one (310 mg, 0.568 mmol, 77 mass %), 4-(4,4,5,5-tetramethyl-[1,3,2]dioxaborolan-2-yl)-isoxazole (133 mg, 0.682 mmol), Pd(dppf)$Cl_2$ (42 mg, 0.057 mmol) and KF (99 mg, 1.7 mmol) in DMSO (12 mL) and $H_2O$ (3 mL). Degassed and purged with $N_2$ (x3). Stirred at 100° C. for 1 hr, under $N_2$ atmosphere. Diluted with $H_2O$ and extracted with EtOAc (x3). Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure. Combined the residue and KF (205 mg, 3.53 mmol) in DMF (3 mL) and $H_2O$ (3 mL). Stirred at 100° C. for 16 hrs. Diluted with $H_2O$ and extracted with EtOAc (x3). Combined the organic layers, washed with saturated aqueous NaCl, dried over anhydrous $Na_2SO_4$, filtered, and concentrated under reduced pressure. Purified by reverse phase prep-HPLC, and further purified by SFC to give the titled compounds (Isomer 1-Rt=1.308 min (99.6% ee), 29.26 mg, 17% as a white solid; Isomer 2—Rt=1.386 min (99.2% ee), 29.42 mg, 18% as a white solid). Column: DAICEL CHIRALPAK AD (30×2 50 mm, 10 μm); Method: 45% EtOH (0.1% $NH_3H_2O$): 55% $CO_2$; FlowRate: 80 mL/min. (chiral analysis used—Column: Chiralpak AD, 50×4.6 mm, 3 μm; Mobile Phase: 5-40% EtOH (0.05% DEA)/$CO_2$; Flow Rate: 4 mL/min). ES/MS (m/z): ($^{35}Cl/^{37}Cl$) 380.0/382.0 (M+H).

Intermediate 74

7,8-Dichloro-10-hydroxy-5-(2-hydroxy-2-methylpropyl)-3,4,5,6-tetrahydroazepino[4,5-b]indol-2(1H)-one

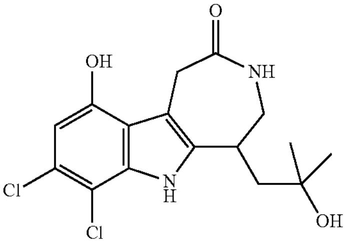 [SMILES: CC(C)(O)CC1CNC(=O)Cc2c1[nH]c1c(Cl)c(Cl)cc(O)c21]

Combined 10-bromo-7,8-dichloro-5-(2-hydroxy-2-methylpropyl)-3,4,5,6-tetrahydroazepino[4,5-b]indol-2(1H)-one (470 mg, 0.839 mmol, 75 mass %), t-BuBrettPhos-Pd-$G_3$ (72 mg, 0.084 mmol) and t-BuONa (202 mg, 2.10 mmol) in 1,4-dioxane (15 mL) and $H_2O$ (3 mL). Degassed and purged with $N_2$ (x3). Stirred at 65° C. for 2 hrs, under $N_2$ atmosphere. Added 1N aqueous HCl to adjust pH=5 and extracted with EtOAc (x3). Combined organic layers, washed with saturated aqueous NaCl, dried over anhydrous $Na_2SO_4$, filtered, and concentrated under reduced pressure. Purified by trituration with EtOAc to give 7,8-dichloro-10-hydroxy-5-(2-hydroxy-2-methylpropyl)-3,4,5,6-tetrahydroazepino[4,5-b]indol-2(1H)-one (300 mg, 76%) as a brown solid. ES/MS (m/z): ($^{35}Cl/^{37}Cl$) 356.9/358.8 (M+H).

Intermediate 75

2-((7,8-Dichloro-5-(2-hydroxy-2-methylpropyl)-2-oxo-1,2,3,4,5,6-hexahydroazepino[4,5-b]indol-10-yl)oxy)acetonitrile

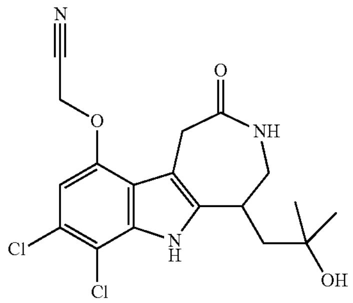 [SMILES: CC(C)(O)CC1CNC(=O)Cc2c1[nH]c1c(Cl)c(Cl)cc(OCC#N)c21]

Combined 7,8-dichloro-10-hydroxy-5-(2-hydroxy-2-methylpropyl)-3,4,5,6-tetrahydroazepino[4,5-b]indol-2(1H)-one (270 mg, 0.574 mmol, 76 mass %), $K_2CO_3$ (238 mg, 1.72 mmol) and KI (95 mg, 0.57 mmol) in DMF (8 mL), added 2-chloroacetonitrile (87 mg, 1.2 mmol) at 0° C. Stirred at 25° C. for 6 hrs. Diluted with $H_2O$ and extracted with EtOAc (3×). Combined organic layers, washed with saturated aqueous NaCl, dried over anhydrous $Na_2SO_4$, filtered, and concentrated under reduced pressure. Purified by reverse phase prep-HPLC to give 2-((7,8-dichloro-5-(2-hydroxy-2-methylpropyl)-2-oxo-1,2,3,4,5,6-hexahydroazepino[4,5-b]indol-10-yl)oxy)acetonitrile (150 mg, 63%) as a yellow solid. ES/MS (m/z): ($^{35}Cl/^{37}Cl$) 396.0/398.0 (M+H).

Example 108

(R)-2-((7,8-Dichloro-5-(2-hydroxy-2-methylpropyl)-2-oxo-1,2,3,4,5,6-hexahydroazepino[4,5-b]indol-10-yl)oxy)acetonitrile Or (S)-2-((7,8-Dichloro-5-(2-hydroxy-2-methylpropyl)-2-oxo-1,2,3,4,5,6-hexahydroazepino[4,5-b]indol-10-yl)oxy)acetonitrile (isomer 1) and Example 109

(R)-2-((7,8-Dichloro-5-(2-hydroxy-2-methylpropyl)-2-oxo-1,2,3,4,5,6-hexahydroazepino[4,5-b]indol-10-yl)oxy)acetonitrile Or (S)-2-((7,8-Dichloro-5-(2-hydroxy-2-methylpropyl)-2-oxo-1,2,3,4,5,6-hexahydroazepino[4,5-b]indol-10-yl)oxy)acetonitrile (isomer 2)

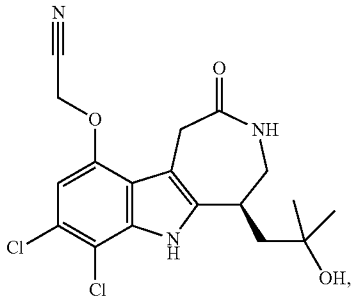

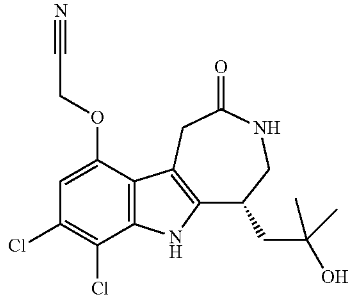

Purified racemic 2-((7,8-dichloro-5-(2-hydroxy-2-methylpropyl)-2-oxo-1,2,3,4,5,6-hexahydroazepino[4,5-b]indol-10-yl)oxy)acetonitrile (150 mg, 0.363 mmol, 96 mass %) by SFC to give the titled compounds (Isomer 1—Rt=1.505 min (99.4% ee), 63.48 mg, 43% as an off-white solid; Isomer 2—Rt=1.711 min (99.1% ee), 68.42 mg, 47% as an off-white solid). Column: REGIS (S, S) WHELK-O1 (30×250 mm, 5 μm); Mobile Phase: 45% iPrOH (0.1% $NH_3H_2O$): 55% $CO_2$. ES/MS (m/z): ($^{35}Cl/^{37}Cl$) 396.0/398.0 (M+H).

Intermediate 77

7,8-Dichloro-10-hydroxy-5-(2-hydroxy-2-methylpropyl)-6-methyl-3,4,5,6-tetrahydroazepino[4,5-b]indol-2(1H)-one

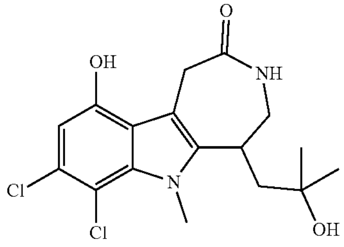 [SMILES: Cn1c2c(c3c(O)cc(Cl)c(Cl)c31)CC(=O)NCC2CC(C)(C)O]

Combined 10-bromo-7,8-dichloro-5-(2-hydroxy-2-methylpropyl)-6-methyl-3,4,5,6-tetrahydroazepino[4,5-b]indol-2(1H)-one (500 mg, 1.09 mmol, 95 mass %), t-BuONa (263 mg, 2.74 mmol), t-BuBrettphos-Pd-$G_3$ (94 mg, 0.11 mmol) in 1,4-dioxane (6 mL) and $H_2O$ (2 mL). Degassed and purged with $N_2$ (×3) times and stirred at 65° C. for 3 hrs, under $N_2$ atmosphere. Diluted with water and acidified with 2N aqueous HCl until pH=5, then extracted with EtOAc. Combined organic layers, washed with saturated aqueous NaCl, dried over anhydrous $Na_2SO_4$, filtered, and concentrated under reduced pressure. Triturated with EtOAc to give 7,8-dichloro-10-hydroxy-5-(2-hydroxy-2-methylpropyl)-6-methyl-3,4,5,6-tetrahydroazepino[4,5-b]indol-2(1H)-one (200 mg, 35%) as a brown solid. ES/MS (m/z): ($^{35}Cl/^{37}Cl$) 371.0/373.0 (M+H).

Intermediate 78

2-((7,8-Dichloro-5-(2-hydroxy-2-methylpropyl)-6-methyl-2-oxo-1,2,3,4,5,6-hexahydroazepino[4,5-b]indol-10-yl)oxy)acetonitrile

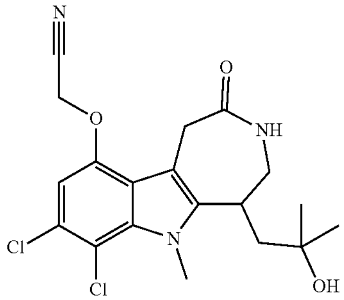 [SMILES: Cn1c2c(c3c(OCC#N)cc(Cl)c(Cl)c31)CC(=O)NCC2CC(C)(C)O]

Combined 7,8-dichloro-10-hydroxy-5-(2-hydroxy-2-methylpropyl)-6-methyl-3,4,5,6-tetrahydroazepino[4,5-b]indol-2(1H)-one (180 mg, 0.349 mmol, 72 mass %), $K_2CO_3$ (145 mg, 1.05 mmol) and KI (58 mg, 0.35 mmol) in DMF (3 mL), added 2-chloroacetonitrile (53 mg, 0.70 mmol) at 0° C. Stirred at 25° C. for 3 hrs. Diluted with water and extracted with EtOAc. Combined organic layers, washed with saturated aqueous NaCl, dried over anhydrous $Na_2SO_4$, filtered, and concentrated under reduced pressure. Purified by prep-HPLC to give racemic 2-((7,8-dichloro-5-(2-hydroxy-2-methylpropyl)-6-methyl-2-oxo-1,2,3,4,5,6-hexahydroazepino[4,5-b]indol-10-yl)oxy)acetonitrile (77 mg, 49%) as a white solid. ES/MS (m/z): ($^{35}Cl/^{37}Cl$) 410.0/412.0 (M+H).

Example 110

(R)-2-((7,8-Dichloro-5-(2-hydroxy-2-methylpropyl)-6-methyl-2-oxo-1,2,3,4,5,6-hexahydroazepino[4,5-b]indol-10-yl)oxy)acetonitrile or (S)-2-((7,8-Dichloro-5-(2-hydroxy-2-methylpropyl)-6-methyl-2-oxo-1,2,3,4,5,6-hexahydroazepino[4,5-b]indol-10-yl)oxy)acetonitrile (isomer 1) and Example 111

(R)-2-((7,8-Dichloro-5-(2-hydroxy-2-methylpropyl)-6-methyl-2-oxo-1,2,3,4,5,6-hexahydroazepino[4,5-b]indol-10-yl)oxy)acetonitrile or (S)-2-((7,8-Dichloro-5-(2-hydroxy-2-methylpropyl)-6-methyl-2-oxo-1,2,3,4,5,6-hexahydroazepino[4,5-b]indol-10-yl)oxy)acetonitrile (isomer 2)

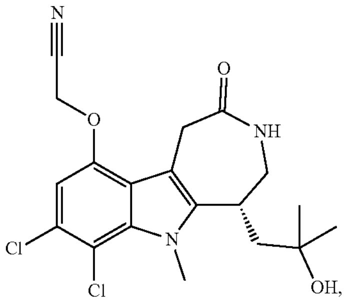

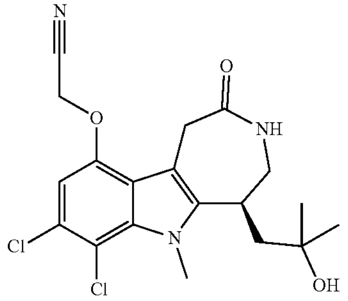

Purified racemic 2-((7,8-dichloro-5-(2-hydroxy-2-methylpropyl)-6-methyl-2-oxo-1,2,3,4,5,6-hexahydroazepino[4,5-b]indol-10-yl)oxy)acetonitrile (77 mg, 0.17 mmol) by SFC to give the title compounds (Isomer 1—Rt=1.617 min (100% ee), 26 mg, 36% as an off-white solid; Isomer 2—Rt=1.991 min (99.7% ee), 22 mg, 32% as an off-white solid). Column: DAICEL CHIRALPAK IC-3, 30×250 mm, 10 μm; Mobile Phase: 60% EtOH (0.1% $NH_3H_2O$); 40% $CO_2$; FlowRate: 80 mL/min. ES/MS (m/z): ($^{35}Cl/^{37}Cl$) 410.0/411.8 (M+H).

Intermediate 78

10-Bromo-7,8-dichloro-5-(2-((2,2,2-trifluoroethyl)amino)ethyl)-3,4,5,6-tetrahydroazepino[4,5-b]indol-2(1H)-one

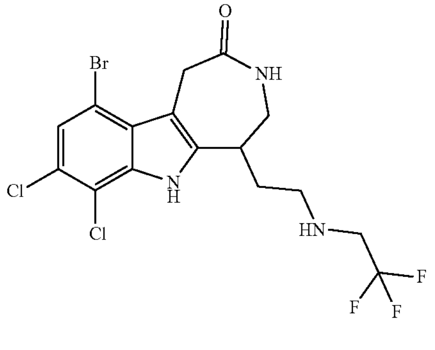 [SMILES: O=C1Cc2c([nH]c3c(Cl)c(Cl)cc(Br)c23)C(CCNCC(F)(F)F)CN1]

To a solution of 10-bromo-7,8-dichloro-5-(2-hydroxyethyl)-3,4,5,6-tetrahydroazepino[4,5-b]indol-2(1H)-one (500 mg, 0.778 mmol, 61 mass %), $Et_3N$ (249 mg, 2.33 mmol) and DMAP (10 mg, 0.078 mmol) in DMF (10 mL), was added methanesulfonic anhydride (419 mg, 2.33 mmol) at 0° C. under $N_2$ atmosphere. Stirred at 25° C. for 2 hrs, under $N_2$ atmosphere. Then added 2,2,2-trifluoroethan-1-amine (10 mL, 120 mmol) to above mixture at 25° C. Stirred at 60° C. for 16 hrs. Diluted with $H_2O$ and extracted with EtOAc (2×). Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure to give 10-bromo-7,8-dichloro-5-(2-((2,2,2-trifluoroethyl)amino)ethyl)-3,4,5,6-tetrahydroazepino[4,5-b]indol-2(1H)-one (330 mg, 82%) as a white solid. ES/MS (m/z): 471.8/473.7/475.6 (M+H).

Example 112

7,8-Dichloro-10-(2-methyl-2H-1,2,3-triazol-4-yl)-5-(2-((2,2,2-trifluoroethyl)amino)ethyl)-3,4,5,6-tetrahydroazepino[4,5-b]indol-2(1H)-one

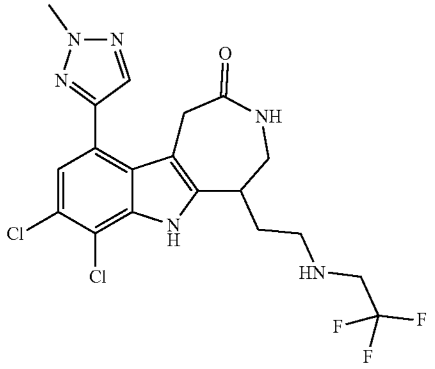 [SMILES: Cn1ncc(-c2cc(Cl)c(Cl)c3[nH]c4c(c23)CC(=O)NCC4CCNCC(F)(F)F)n1]

Combined 10-bromo-7,8-dichloro-5-(2-((2,2,2-trifluoroethyl)amino)ethyl)-3,4,5,6-tetrahydroazepino[4,5-b]indol-2(1H)-one (330 mg, 0.635 mmol, 91 mass %), 2-methyl-4-(4,4,5,5-tetramethyl-1,3,2-dioxaborolan-2-yl)-2H-1,2,3- triazole (199 mg, 0.952 mmol), Pd(dppf)$Cl_2$ (49 mg, 0.064 mmol) and $Na_2CO_3$ (212 mg, 1.90 mmol) in 1,4-dioxane (12 mL) and $H_2O$ (3 mL). Degassed and purged with $N_2$ (×3). Stirred at 90° C. for 2 hrs. Concentrated under reduced pressure. Purified by silica gel flash chromatography eluting with MeOH in DCM and concentrated under reduced pressure, then purified by reverse phase prep-HPLC and further purified by SFC. Column: achiral; Mobile Phase: 30% EtOH (0.1% $NH_3H_2O$); 70% $CO_2$; Flow Rate: 80 mL/min; to give 7,8-dichloro-10-(2-methyl-2H-1,2,3-triazol-4-yl)-5-(2-((2,2,2-trifluoroethyl)amino)ethyl)-3,4,5,6-tetrahydroazepino[4,5-b]indol-2(1H)-one (151.53 mg, 49%) as a white solid. ES/MS (m/z): ($^{35}Cl/^{37}Cl$) 475.1/477.1 (M+H).

Intermediate 79

2-(10-Bromo-7,8-dichloro-2-oxo-1,2,3,4,5,6-hexahydroazepino[4,5-b]indol-5-yl)acetic acid

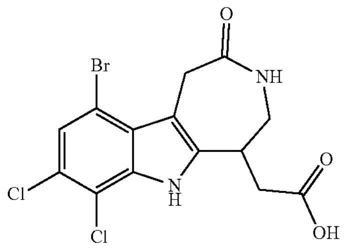 [SMILES: O=C(O)CC1CNC(=O)Cc2c1[nH]c1c(Cl)c(Cl)cc(Br)c21]

To a solution of ethyl 2-(10-bromo-7,8-dichloro-2-oxo-1,2,3,4,5,6-hexahydroazepino[4,5-b]indol-5-yl)acetate (1.00 g, 1.96 mmol, 85 mass %) in THF (8 mL), MeOH (8 mL), and $H_2O$ (4 mL), added NaOH (392 mg, 9.79 mmol). Stirred at 20° C. for 16 hrs. Quenched with 1N aqueous HCl to pH=4. Collected the solids by vacuum filtration and dried to give 2-(10-bromo-7,8-dichloro-2-oxo-1,2,3,4,5,6-hexahydroazepino[4,5-b]indol-5-yl)acetic acid (937 mg, 90%) as a yellow solid. ES/MS (m/z): 404.8/406.8/408.8 (M+H).

Intermediate 80

10-Bromo-7,8-dichloro-5-(2-hydroxyethyl)-3,4,5,6-tetrahydroazepino[4,5-b]indol-2(1H)-one

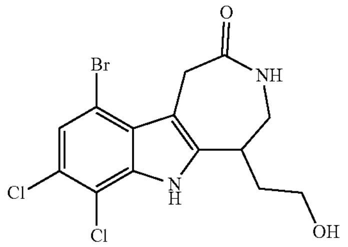 [SMILES: O=C1Cc2c([nH]c3c(Cl)c(Cl)cc(Br)c23)C(CCO)CN1]

To a solution of ethyl 2-(10-bromo-7,8-dichloro-2-oxo-1,2,3,4,5,6-hexahydroazepino[4,5-b]indol-5-yl)acetate (950 mg, 1.75 mmol, 80 mass %) in THF (20 mL), added lithium borohydride (140 mg, 6.43 mmol) at 0° C. under $N_2$ atmosphere. Stirred at 25° C. for 2 hrs. Quenched with saturated aqueous $NH_4Cl$ and extracted with EtOAc. Combined organic layers, washed with saturated aqueous $NH_4Cl$, saturated aqueous NaCl, dried over anhydrous $Na_2SO_4$, filtered, and concentrated under reduced pressure. Purified by trituration with EtOAc in PE to give 10-bromo-7,8-dichloro-5-(2-hydroxyethyl)-3,4,5,6-tetrahydroazepino[4,5-b]indol-2(1H)-one (550 mg, 60%). ES/MS (m/z): 390.8/392.8/394.7 (M+H).

Example 113

2-(7,8-Dichloro-5-(2-hydroxyethyl)-2-oxo-1,2,3,4,5,6-hexahydroazepino[4,5-b]indol-10-yl)acetonitrile

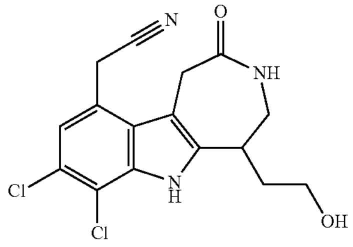 [SMILES: N#CCc1cc(Cl)c(Cl)c2[nH]c3c(c12)CC(=O)NCC3CCO]

Combined 10-bromo-7,8-dichloro-5-(2-hydroxyethyl)-3,4,5,6-tetrahydroazepino[4,5-b]indol-2(1H)-one (150 mg, 0.287 mmol, 75 mass %), 4-(4,4,5,5-tetramethyl-[1,3,2]dioxaborolan-2-yl)-isoxazole (67 mg, 0.34 mmol), Pd(dppf)$Cl_2$ (21 mg, 0.029 mmol) and KF (50 mg, 0.86 mmol) in DMSO (12 mL) and $H_2O$ (3 mL). Degassed and purged with $N_2$ (×3). Stirred at 100° C. for 1 hr. Repeated the reaction on 0.33× scale and combined the reaction mixtures. Diluted with $H_2O$ and extracted with EtOAc. Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure. Combined the residue and KF (124 mg, 2.13 mmol) in DMF (3 mL) and $H_2O$ (3 mL). Stirred at 100° C. for 16 hrs. Diluted with $H_2O$ and extracted with EtOAc. Combined organic layers, washed with saturated aqueous NaCl, dried over anhydrous $Na_2SO_4$, filtered, and concentrated under reduced pressure. Purified by reverse phase prep-HPLC, and further purified by SFC to give 2-(7,8-dichloro-5-(2-hydroxyethyl)-2-oxo-1,2,3,4,5,6-hexahydroazepino[4,5-b]indol-10-yl)acetonitrile (38.93 mg, 41%) as a white solid. ES/MS (m/z): ($^{35}Cl/^{37}Cl$) 352.0/353.9 (M+H).

Example 114

2-(8,9-Dichloro-2-oxo-2,3,4,4a, 5,6-hexahydro-1H-azepino[3,4,5-gh]benzo[b]pyrrolizin-11-yl)acetonitrile

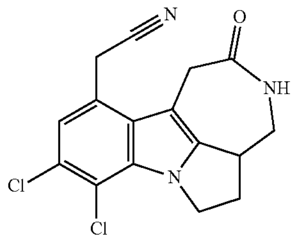 [SMILES: N#CCc1cc(Cl)c(Cl)c2c1c1c3n2CCC3CNC(=O)C1]

Combined racemic 2-(7,8-dichloro-5-(2-hydroxyethyl)-2-oxo-1,2,3,4,5,6-hexahydroazepino[4,5-b]indol-10-yl)acetonitrile (30 mg, 0.085 mmol) and THF (2 mL) at ambient temperature under $N_2$ and cooled to 0° C. Added triphenylphosphine (34 mg, 0.13 mmol) and diisopropyl azodicarboxylate (26 mg, 0.13 mmol) then allowed to slowly warm to ambient temperature overnight. Concentrated the reaction under reduced pressure and purified the material via reverse phase chromatography to give 2-(8,9-dichloro-2-oxo-2,3,4,4a,5,6-hexahydro-1H-azepino[3,4,5-gh]benzo[b]pyrrolizin-11-yl)acetonitrile (9 mg, 30%). ES/MS (m/z): ($^{35}Cl/^{37}Cl$) 334.0/336.0 (M+H).

Intermediate 81

7,8-Dichloro-10-hydroxy-5-(2-hydroxyethyl)-3,4,5,6-tetrahydroazepino[4,5-b]indol-2(1H)-one

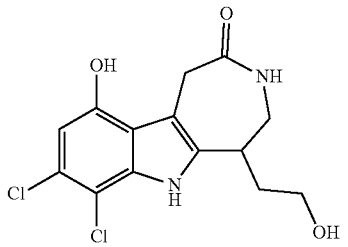 [SMILES: O=C1Cc2c([nH]c3c(Cl)c(Cl)cc(O)c23)C(CCO)CN1]

Combined 10-bromo-7,8-dichloro-5-(2-hydroxyethyl)-3,4,5,6-tetrahydroazepino[4,5-b]indol-2(1H)-one (300 mg, 0.574 mmol, 75 mass %), t-BuBrettphos-Pd-$G_3$ (49 mg, 0.057 mmol), and t-BuONa (138 mg, 1.43 mmol) in 1,4-dioxane (15 mL) and $H_2O$ (3 mL). Degassed and purged with $N_2$ (x3). Stirred at 65° C. for 2 hrs. Diluted with 1N aqueous HCl and extracted with EtOAc. Combined organic layers, washed with saturated aqueous NaCl, dried over anhydrous $Na_2SO_4$, filtered, and concentrated under reduced pressure to give 7,8-dichloro-10-hydroxy-5-(2-hydroxyethyl)-3,4,5,6-tetrahydroazepino[4,5-b]indol-2(1H)-one (300 mg, crude). ES/MS (m/z): ($^{35}Cl/^{37}Cl$) 328.9/330.8 (M+H).

Intermediate 82

2-((7,8-Dichloro-5-(2-hydroxyethyl)-2-oxo-1,2,3,4,5,6-hexahydroazepino[4,5-b]indol-10-yl)oxy)acetonitrile

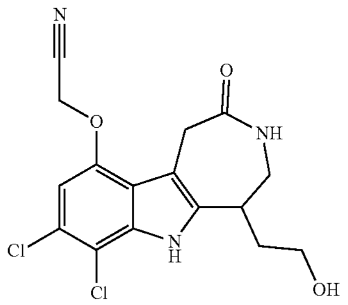 [SMILES: N#CCOc1cc(Cl)c(Cl)c2[nH]c3c(c12)CC(=O)NCC3CCO]

Combined 7,8-dichloro-10-hydroxy-5-(2-hydroxyethyl)-3,4,5,6-tetrahydroazepino[4,5-b]indol-2(1H)-one (300 mg, 0.638 mmol, 70 mass %), $K_2CO_3$ (264 mg, 1.91 mmol), potassium iodide (106 mg, 0.638 mmol) in DMF (6 mL), then added 2-chloroacetonitrile (96 mg, 1.28 mmol). Stirred at 25° C. for 16 hrs. Diluted with $H_2O$ and extracted with EtOAc. Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure to give 2-((7,8-dichloro-5-(2-hydroxyethyl)-2-oxo-1,2,3,4,5,6-hexahydroazepino[4,5-b]indol-10-yl)oxy)acetonitrile (130 mg, 43%). ES/MS (m/z): ($^{35}Cl/^{37}Cl$) 367.9/369.9 (M+H).

Example 115

2-((8,9-Dichloro-2-oxo-2,3,4,4a, 5,6-hexahydro-1H-azepino[3,4,5-gh]benzo[b]pyrrolizin-11-yl)oxy)acetonitrile

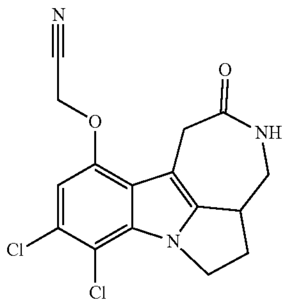 [SMILES: N#CCOc1cc(Cl)c(Cl)c2c1c1c3n2CCC3CNC(=O)C1]

Combined 2-((7,8-dichloro-5-(2-hydroxyethyl)-2-oxo-1,2,3,4,5,6-hexahydroazepino[4,5-b]indol-10-yl)oxy)acetonitrile (100 mg, 0.212 mmol, 78 mass %), triphenylphosphine (111 mg, 0.424 mmol) in THF (2 mL), added diisopropyl azodicarboxylate (86 mg, 0.424 mmol). Stirred at 25° C. for 16 hrs. Repeated the reaction on 0.30× scale and combined the reaction mixtures. Diluted with $H_2O$ and extracted with EtOAc. Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure and further purified by reverse phase prep-HPLC to give 2-((8,9-dichloro-2-oxo-2,3,4,4a, 5,6-hexahydro-1H-azepino[3,4,5-gh]benzo[b]pyrrolizin-11-yl)oxy)acetonitrile (26 mg, 26%) as a white solid. ES/MS (m/z): ($^{35}Cl/^{37}Cl$) 349.9/351.9 (M+H).

Intermediate 83

11-Bromo-8,9-dichloro-1,3,4,4a, 5,6-hexahydro-2H-azepino[3,4,5-gh]benzo[b]pyrrolizin-2-one

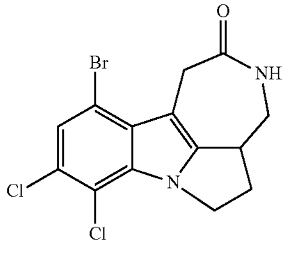 [SMILES: O=C1Cc2c3n(c4c(Cl)c(Cl)cc(Br)c24)CCC3CN1]

Combined 10-bromo-7,8-dichloro-5-(2-hydroxyethyl)-3,4,5,6-tetrahydroazepino[4,5-b]indol-2(1H)-one (170 mg, 0.347 mmol, 80 mass %), triphenylphosphine (182 mg, 0.694 mmol) in THF (4 mL) added diisopropyl azodicarboxylate (140 mg, 0.694 mmol). Stirred at 25° C. for 16 hrs. Diluted with $H_2O$ and extracted with EtOAc. Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure to give 11-bromo-8,9-dichloro-1,3,4,4a,5,6-hexahydro-2H-azepino[3,4,5-gh]benzo[b]pyrrolizin-2-one (220 mg, 61%). ES/MS (m/z): 372.9/374.9/377.0 (M+H).

Example 116

8,9-Dichloro-11-(2-methyl-2H-1,2,3-triazol-4-yl)-1,3,4,4a, 5,6-hexahydro-2H-azepino[3,4,5-gh]benzo[b]pyrrolizin-2-one

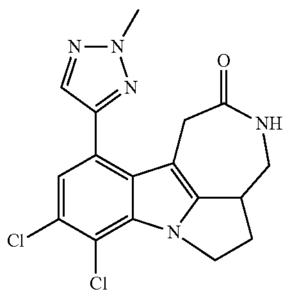 [SMILES: Cn1ncc(-c2cc(Cl)c(Cl)c3c2c2c4n3CCC4CNC(=O)C2)n1]

Combined 11-bromo-8,9-dichloro-1,3,4,4a,5,6-hexahydro-2H-azepino[3,4,5-gh]benzo[b]pyrrolizin-2-one (170 mg, 0.164 mmol, 36 mass %), 2-methyl-4-(4,4,5,5-tetramethyl-1,3,2-dioxaborolan-2-yl)-2H-1,2,3-triazole (137 mg, 0.327 mmol), Pd(dppf)$Cl_2$ (12 mg, 0.0164 mmol) and $Na_2CO_3$ (52 mg, 0.491 mmol) in 1,4-dioxane (12 mL) and $H_2O$ (3 mL). Degassed and purged with $N_2$ (x3). Stirred at 90° C. for 2 hrs. Repeated the reaction on 0.29× scale and combined the reaction mixtures. Concentrated under reduced pressure. Purified by silica gel flash chromatography eluting with MeOH in DCM and concentrated under reduced pressure, and further purified by reverse phase prep-HPLC to give 8,9-dichloro-11-(2-methyl-2H-1,2,3-triazol-4-yl)-1,3,4,4a,5,6-hexahydro-2H-azepino[3,4,5-gh]benzo[b]pyrrolizin-2-one (22 mg, 27%) as a white solid. ES/MS (m/z): ($^{35}Cl/^{37}Cl$) 376.0/378.0 (M+H).

Intermediate 84

2-(10-Bromo-7,8-dichloro-2-oxo-1,2,3,4,5,6-hexahydroazepino[4,5-b]indol-5-yl)-N,N-dimethylacetamide

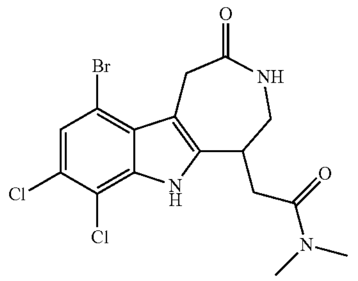 [SMILES: CN(C)C(=O)CC1CNC(=O)Cc2c1[nH]c1c(Cl)c(Cl)cc(Br)c21]

Combined 2-(10-bromo-7,8-dichloro-2-oxo-1,2,3,4,5,6-hexahydroazepino[4,5-b]indol-5-yl)acetic acid (837 mg, 1.57 mmol, 76 mass %), dimethylamine hydrochloride (153 mg, 1.88 mmol), DIPEA (607 mg, 4.70 mmol) and HATU (715 mg, 1.88 mmol) in DMF (25 mL). Stirred at 25° C. for 2 hrs. Diluted with water and extracted the aqueous layer with EtOAc. Washed with saturated aqueous NaCl, dried over anhydrous $Na_2SO_4$, filtered, and concentrated under reduced pressure. Purified by silica gel flash chromatography eluting with MeOH in DCM and concentrated under reduced pressure to give 2-(10-bromo-7,8-dichloro-2-oxo-1,2,3,4,5,6-hexahydroazepino[4,5-b]indol-5-yl)-N,N-dimethylacetamide (740 mg, 55%) as a yellow oil. ES/MS (m/z): 431.8/433.8/435.7 (M+H).

Example 117

2-(7,8-Dichloro-10-(cyanomethyl)-2-oxo-1,2,3,4,5,6-hexahydroazepino[4,5-b]indol-5-yl)-N,N-dimethylacetamide

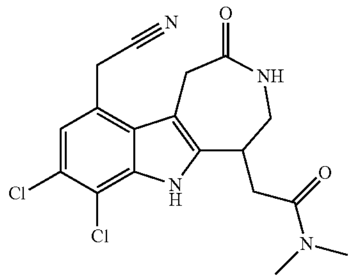 [SMILES: CN(C)C(=O)CC1CNC(=O)Cc2c1[nH]c1c(Cl)c(Cl)cc(CC#N)c21]

Combined 2-(10-bromo-7,8-dichloro-2-oxo-1,2,3,4,5,6-hexahydroazepino[4,5-b]indol-5-yl)-N,N-dimethylacetamide (740 mg, 0.854 mmol, 50 mass %), 4-(4,4,5,5-tetramethyl-[1,3,2]dioxaborolan-2-yl)-isoxazole (200 mg, 1.03 mmol), Pd(dppf)$Cl_2$ (63 mg, 0.85 mmol) and potassium fluoride (149 mg, 2.56 mmol) in DMSO (32 mL) and water (8 mL). Degassed and purged with $N_2$. Stirred at 100° C. for 1 hr. Diluted with water and extracted with EtOAc. Washed with saturated aqueous NaCl, dried over anhydrous $Na_2SO_4$, filtered, and concentrated under reduced pressure. Purified by silica gel flash chromatography eluting with MeOH in DCM and concentrated under reduced pressure. Combined the residue and KF (348 mg, 6.00 mmol) in DMF (22 mL) and $H_2O$ (22 mL). Degassed and purged with $N_2$, then stirred at 100° C. for 16 hrs. Repeated the reaction on 0.12× scale and combined the reaction mixtures. Diluted with water and extracted with EtOAc. Washed with saturated aqueous NaCl, dried over anhydrous $Na_2SO_4$, filtered, and concentrated under reduced pressure. Purified by prep-HPLC. Then further purified by SFC Column: DAICEL CHIRALPAK IC (30×250 mm, 10 μm); Mobile Phase: 50% EtOH (0.1% $NH_3H_2O$); 50% $CO_2$; Flow Rate: 80 mL/min. Concentrated under reduced pressure and lyophilized to give 2-(7,8-dichloro-10-(cyanomethyl)-2-oxo-1,2,3,4,5,6-hexahydroazepino[4,5-b]indol-5-yl)-N,N-dimethylacetamide (88.43 mg, 26%) as a white solid. ES/MS (m/z): ($^{35}Cl/^{37}Cl$) 393.1/395.1 (M+H).

Intermediate 85

2-(10-Bromo-7,8-dichloro-2-oxo-1,2,3,4,5,6-hexahydroazepino[4,5-b]indol-5-yl)ethyl methanesulfonate

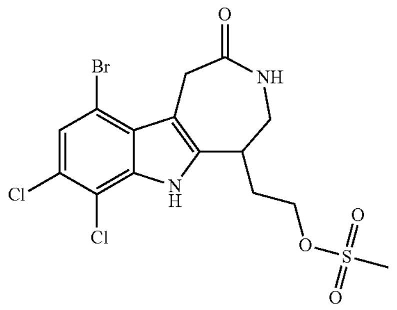 [SMILES: CS(=O)(=O)OCCC1CNC(=O)Cc2c1[nH]c1c(Cl)c(Cl)cc(Br)c21]

To a solution of 10-bromo-7,8-dichloro-5-(2-hydroxyethyl)-3,4,5,6-tetrahydroazepino[4,5-b]indol-2(1H)-one (350 mg, 0.670 mmol, 75 mass %), $Et_3N$ (203 mg, 2.01 mmol) and DMAP (8 mg, 0.07 mmol) in DCM (10 mL), added methanesulfonyl chloride (470 mg, 4.10 mmol) at 0° C. under $N_2$ atmosphere. Stirred at 25° C. for 16 hrs. Then added additional methanesulfonyl chloride (230 mg, 2.01 mmol) and stirred at 25° C. for another 3 hrs. Quenched with saturated aqueous $NaHCO_3$ and extracted with DCM. Combined organic layers, washed with saturated aqueous NaCl, dried over anhydrous $Na_2SO_4$, filtered and concentrated under reduced pressure to give 2-(10-bromo-7,8-dichloro-2-oxo-1,2,3,4,5,6-hexahydroazepino[4,5-b]indol-5-yl)ethyl methanesulfonate (300 mg, 29%). ES/MS (m/z): 468.8/470.8/472.8 (M+H).

Intermediate 86

10-Bromo-7,8-dichloro-5-(2-(dimethylamino)ethyl)-3,4,5,6-tetrahydroazepino[4,5-b]indol-2(1H)-one

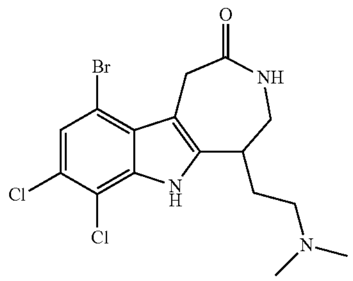 [SMILES: CN(C)CCC1CNC(=O)Cc2c1[nH]c1c(Cl)c(Cl)cc(Br)c21]

To a solution of 2-(10-bromo-7,8-dichloro-2-oxo-1,2,3,4,5,6-hexahydroazepino[4,5-b]indol-5-yl)ethyl methanesulfonate (300 mg, 0.191 mmol, 30 mass %) and DIPEA (74 mg, 0.57 mmol) in DCM (10 mL), added dimethylamine hydrochloride (31 mg, 0.38 mmol). Stirred at 25° C. for 16 hrs. Concentrated under reduced pressure and purified by silica gel flash chromatography eluting with MeOH in DCM and concentrated under reduced pressure to give 10-bromo-7,8-dichloro-5-(2-(dimethylamino)ethyl)-3,4,5,6-tetrahydroazepino[4,5-b]indol-2(1H)-one (100 mg, 83%). ES/MS (m/z): 417.8/419.8/421.8 (M+H).

Example 118

7,8-Dichloro-5-(2-(dimethylamino)ethyl)-10-(2-methyl-2H-1,2,3-triazol-4-yl)-3,4,5,6-tetrahydroazepino[4,5-b]indol-2(1H)-one

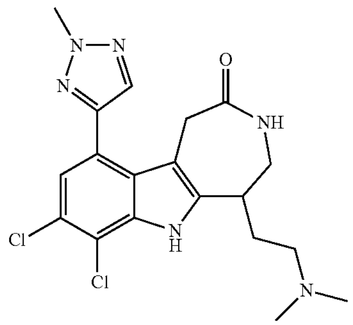 [SMILES: CN(C)CCC1CNC(=O)Cc2c1[nH]c1c(Cl)c(Cl)cc(-c3cnn(C)n3)c21]

Combined 10-bromo-7,8-dichloro-5-(2-(dimethylamino)ethyl)-3,4,5,6-tetrahydroazepino[4,5-b]indol-2(1H)-one (70 mg, 0.16 mmol, 95 mass %), 2-methyl-4-(4,4,5,5-tetramethyl-1,3,2-dioxaborolan-2-yl)-2H-1,2,3-triazole (133 mg, 0.317 mmol), Pd(dppf)$Cl_2$ (12 mg, 0.016 mmol) and $Na_2CO_3$ (50 mg, 0.48 mmol) in 1,4-dioxane (4 mL) and $H_2O$ (1 mL). Degassed and purged with $N_2$ (×3). Stirred at 90° C. for 2 hrs. Concentrated under reduced pressure, and purified by silica gel flash chromatography eluting with MeOH in DCM and concentrated under reduced pressure, and further purified by reverse phase prep-HPLC to give 7,8-dichloro-5-(2-(dimethylamino)ethyl)-10-(2-methyl-2H-1,2,3-triazol-4-yl)-3,4,5,6-tetrahydroazepino[4,5-b]indol-2(1H)-one (20.32 mg, 27%, formic acid salt) as a white solid. ES/MS (m/z): ($^{35}Cl/^{37}Cl$) 421.0/423.0 (M+H).

Intermediate 87

2-(10-Bromo-7,8-dichloro-2-oxo-1,2,3,4,5,6-hexahydroazepino[4,5-b]indol-5-yl)-N-methoxy-N-methylacetamide

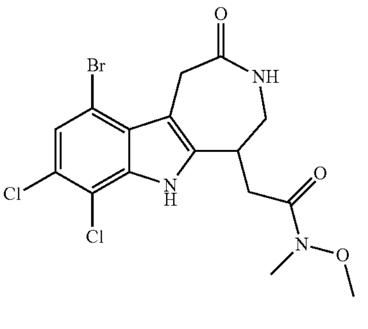 [SMILES: CON(C)C(=O)CC1CNC(=O)Cc2c1[nH]c1c(Cl)c(Cl)cc(Br)c21]

To a solution of 2-(10-bromo-7,8-dichloro-2-oxo-1,2,3,4,5,6-hexahydroazepino[4,5-b]indol-5-yl)acetic acid (750 mg, 1.31 mmol, 71 mass %) and DIPEA (508 mg, 3.93 mmol) in DMF (10 mL), added N,O-dimethylhydroxylamine hydrochloride (153 mg, 1.57 mmol) and HATU (598 mg, 1.57 mmol). Stirred at 25° C. for 2 hrs. Diluted with $H_2O$ and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with MeOH in DCM and dried under reduced pressure to give 2-(10-bromo-7,8-dichloro-2-oxo-1,2,3,4,5,6-hexahydroazepino[4,5-b]indol-5-yl)-N-methoxy-N-methylacetamide (700 mg, 99+%) as a brown solid. ES/MS (m/z): 447.8/449.8/451.8 (M+H).

Intermediate 88

10-Bromo-7,8-dichloro-5-(2-oxopropyl)-3,4,5,6-tetrahydroazepino[4,5-b]indol-2(1H)-one

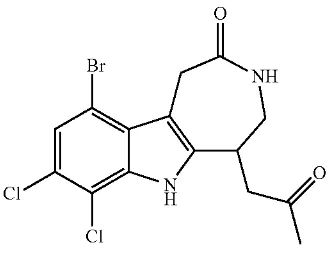 [SMILES: CC(=O)CC1CNC(=O)Cc2c1[nH]c1c(Cl)c(Cl)cc(Br)c21]

To a solution of 2-(10-bromo-7,8-dichloro-2-oxo-1,2,3,4,5,6-hexahydroazepino[4,5-b]indol-5-yl)-N-methoxy-N-methylacetamide (500 mg, 1.02 mmol, 92 mass %) in THF (15 mL), added MeMgBr (1.71 mL, 5.12 mmol, 3M in $Et_2O$) dropwise at −65° C. under $N_2$ atmosphere. Stirred at 20° C. for 5 hrs, under $N_2$ atmosphere. Quenched with saturated aqueous $NH_4Cl$ and extracted with EtOAc (2×). Combined organic layers, washed with saturated aqueous $NH_4Cl$, saturated aqueous NaCl, dried over anhydrous $Na_2SO_4$, filtered, and concentrated under reduced pressure. Purified by silica gel flash chromatography eluting with MeOH in DCM and concentrated under reduced pressure to give 10-bromo-7,8-dichloro-5-(2-oxopropyl)-3,4,5,6-tetrahydroazepino[4,5-b]indol-2(1H)-one (335 mg, 80% mass, 54%) as a yellow solid. ES/MS (m/z): 402.8/404.7/406.9 (M+H).

Intermediate 89

7,8-Dichloro-10-(2-methyl-2H-1,2,3-triazol-4-yl)-5-(2-oxopropyl)-3,4,5,6-tetrahydroazepino[4,5-b]indol-2(1H)-one

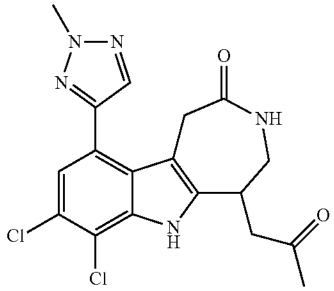 [SMILES: CC(=O)CC1CNC(=O)Cc2c1[nH]c1c(Cl)c(Cl)cc(-c3cnn(C)n3)c21]

Combined 10-bromo-7,8-dichloro-5-(2-oxopropyl)-3,4,5,6-tetrahydroazepino[4,5-b]indol-2(1H)-one (285 mg, 0.564 mmol, 80 mass %), 2-methyl-4-(4,4,5,5-tetramethyl-1,3,2-dioxaborolan-2-yl)-2H-1,2,3-triazole (472 mg, 1.13 mmol), Pd(dppf)$Cl_2$ (41 mg, 0.056 mmol) and $Na_2CO_3$ (179 mg, 1.69 mmol) in 1,4-dioxane (12 mL) and $H_2O$ (3 mL). Degassed and purged with $N_2$ (×3). Stirred at 90° C. for 2 hrs. Concentrated under reduced pressure. Purified by silica gel flash chromatography eluting with MeOH in DCM and concentrated under reduced pressure to give 7,8-dichloro-10-(2-methyl-2H-1,2,3-triazol-4-yl)-5-(2-oxopropyl)-3,4,5,6-tetrahydroazepino[4,5-b]indol-2(1H)-one (300 mg, 60% mass, 79%) as a brown solid. ES/MS (m/z): ($^{35}Cl/^{37}Cl$) 405.9/407.7 (M+H).

Example 119

7,8-Dichloro-5-(2-hydroxypropyl)-10-(2-methyl-2H-1,2,3-triazol-4-yl)-3,4,5,6-tetrahydroazepino[4,5-b]indol-2(1H)-one

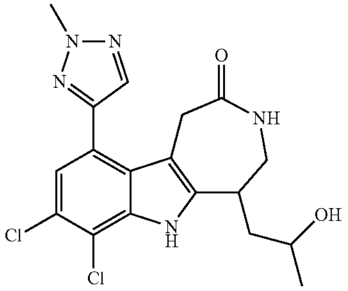 [SMILES: CC(O)CC1CNC(=O)Cc2c1[nH]c1c(Cl)c(Cl)cc(-c3cnn(C)n3)c21]

To a solution of 7,8-dichloro-10-(2-methyl-2H-1,2,3-triazol-4-yl)-5-(2-oxopropyl)-3,4,5,6-tetrahydroazepino[4,5-b]indol-2(1H)-one (100 mg, 0.148 mmol, 60 mass %) in MeOH (4 mL), added $NaBH_4$ (17 mg, 0.44 mmol) portionwise at 0° C. Stirred at 20° C. for 2 hrs, under $N_2$ atmosphere. Quenched with saturated aqueous $NH_4Cl$ and extracted with EtOAc (2×). Combined organic layers, washed with saturated aqueous NaCl, dried over anhydrous $Na_2SO_4$, filtered, and concentrated under reduced pressure. Purified by reverse phase prep-HPLC to give 7,8-dichloro-5-(2-hydroxypropyl)-10-(2-methyl-2H-1,2,3-triazol-4-yl)-3,4,5,6-tetrahydroazepino[4,5-b]indol-2(1H)-one (29.58 mg, 48%) as a white solid. ES/MS (m/z): ($^{35}Cl/^{37}Cl$) 408.0/410.0 (M+H).

Intermediate 90

10-Bromo-7,8-dichloro-5-(2-hydroxypropyl)-3,4,5,6-tetrahydroazepino[4,5-b]indol-2(1H)-one

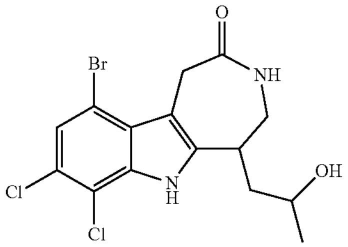 [SMILES: CC(O)CC1CNC(=O)Cc2c1[nH]c1c(Cl)c(Cl)cc(Br)c21]

To a solution of 10-bromo-7,8-dichloro-5-(2-oxopropyl)-3,4,5,6-tetrahydroazepino[4,5-b]indol-2(1H)-one (250 mg, 0.600 mmol, 97 mass %) in MeOH (8 mL), added $NaBH_4$ (68 mg, 1.8 mmol) portion-wise at 0° C. Stirred at 20° C. for 2 hrs, under $N_2$ atmosphere. Quenched with saturated aqueous $NH_4Cl$, filtered to collect the filter cake, washed with $H_2O$ (2×) and dried under reduced pressure to give 10-bromo-7,8-dichloro-5-(2-hydroxypropyl)-3,4,5,6-tetrahydroazepino[4,5-b]indol-2(1H)-one (220 mg, 85%) as a yellow solid. ES/MS (m/z): 405.0/406.9/408.9 (M+H).

Example 120

2-(7,8-Dichloro-5-(2-hydroxypropyl)-2-oxo-1,2,3,4,5,6-hexahydroazepino[4,5-b]indol-10-yl)acetonitrile

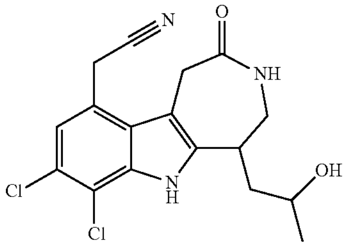 [SMILES: CC(O)CC1CNC(=O)Cc2c1[nH]c1c(Cl)c(Cl)cc(CC#N)c21]

Combined 10-bromo-7,8-dichloro-5-(2-hydroxypropyl)-3,4,5,6-tetrahydroazepino[4,5-b]indol-2(1H)-one (220 mg, 0.509 mmol, 94 mass %), 4-(4,4,5,5-tetramethyl-[1,3,2]dioxaborolan-2-yl)-isoxazole (119 mg, 0.611 mmol), $Pd(dppf)Cl_2$ (37 mg, 0.051 mmol), KF (89 mg, 1.5 mmol) in DMSO (12 mL) and $H_2O$ (3 mL). Degassed and purged with $N_2$ (×3). Stirred at 100° C. for 1 hr, under $N_2$ atmosphere. Diluted with $H_2O$ and extracted with EtOAc (×3). Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated. Combined the residue and KF (133 mg, 2.29 mmol) in DMF (2 mL) and $H_2O$ (2 mL). Degassed and purged with $N_2$ (×3). Stirred at 100° C. for 16 hrs, under $N_2$ atmosphere. Diluted with $H_2O$ and extracted with EtOAc (3×). Combined organic layers, washed with saturated aqueous NaCl, dried over anhydrous $Na_2SO_4$, filtered, and concentrated under reduced pressure. Purified by reverse phase prep-HPLC to give 2-(7,8-dichloro-5-(2-hydroxypropyl)-2-oxo-1,2,3,4,5,6-hexahydroazepino[4,5-b]indol-10-yl)acetonitrile (69 mg, 65%) as a white solid. ES/MS (m/z): ($^{35}Cl/^{37}Cl$) 366.0/367.9 (M+H).

Intermediate 91

Ethyl 2-(5-bromo-7,8-dichloro-9-methyl-1,2,4,9-tetrahydrospiro[carb azole-3,2'-[1,3]dioxolan]-1-yl) acetate

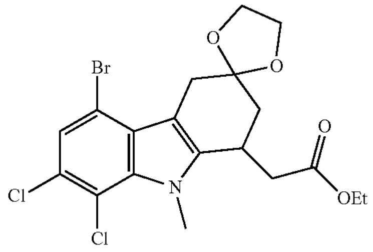 [SMILES: CCOC(=O)CC1CC2(Cc3c1n(C)c1c(Cl)c(Cl)cc(Br)c31)OCCO2]

To a stirring solution of ethyl 2-(5-bromo-7,8-dichloro-1,2,4,9-tetrahydrospiro[carbazole-3,2'-[1,3]dioxolan]-1-yl)acetate (650 mg, 1.33 mmol, 95 mass %) in DMF (10 mL), added cesium carbonate (1.52 g, 4.67 mmol) and iodomethane (568 mg, 4.00 mmol). Stirred at 25° C. for 8 hrs. Then added additional iodomethane (378 mg, 2.67 mmol) and stirred at 50° C. for 2 hrs. Repeated the reaction on 0.23× scale and combined the reaction mixtures. Diluted with $H_2O$ and extracted with EtOAc. Combined organic layers, washed with saturated aqueous NaCl, dried over anhydrous $Na_2SO_4$, filtered, and concentrated under reduced pressure to give ethyl 2-(5-bromo-7,8-dichloro-9-methyl-1,2,4,9-tetrahydrospiro[carbazole-3,2'-[1,3]dioxolan]-1-yl)acetate (650 mg, 80%). ES/MS (m/z): 475.8/477.8/479.8 (M+H).

Intermediate 92

Ethyl 2-(5-bromo-7,8-dichloro-9-methyl-3-oxo-2,3,4,9-tetrahydro-1H-carbazol-1-yl)acetate

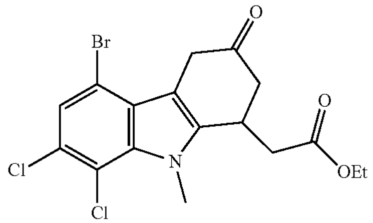 [SMILES: CCOC(=O)CC1CC(=O)Cc2c1n(C)c1c(Cl)c(Cl)cc(Br)c21]

Dissolved ethyl 2-(5-bromo-7,8-dichloro-9-methyl-1,2,4,9-tetrahydrospiro[carbazole-3,2'-[1,3]dioxolan]-1-yl)acetate (650 mg, 1.25 mmol, 92 mass %) in acetone (15 mL), added TFA (714 mg, 6.27 mmol) by syringe under $N_2$ atmosphere. Stirred at 80° C. for 3 days. Concentrated under reduced pressure. Purified by silica gel flash chromatography eluting with EtOAc in PE and concentrated under reduced pressure to give ethyl 2-(5-bromo-7,8-dichloro-9-methyl-3-oxo-2,3,4,9-tetrahydro-1H-carbazol-1-yl)acetate (230 mg, 36%). ES/MS (m/z): 431.8/433.8/435.7 (M+H).

Intermediate 93

Ethyl 2-(10-bromo-7,8-dichloro-6-methyl-2-oxo-1,2,3,4,5,6-hexahydroazepino[4,5-b]indol-5-yl)acetate

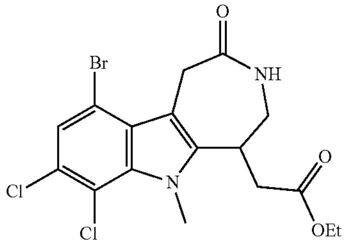 [SMILES: CCOC(=O)CC1CNC(=O)Cc2c1n(C)c1c(Cl)c(Cl)cc(Br)c21]

Dissolved ethyl 2-(5-bromo-7,8-dichloro-9-methyl-3-oxo-2,3,4,9-tetrahydro-1H-carbazol-1-yl)acetate (230 mg, 0.451 mmol, 85 mass %) in methanesulfonic acid (5 mL), added $NaN_3$ (70 mg, 1.10 mmol) slowly at 0° C. Stirred at 0° C. for 30 min and 25° C. for 16 hrs. Poured into ice-water and extracted with EtOAc. Combined organic layers, washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give ethyl 2-(10-bromo-7,8-dichloro-6-methyl-2-oxo-1,2,3,4,5,6-hexahydroazepino[4,5-b]indol-5-yl)acetate (130 mg, 58%). ES/MS (m/z): 446.9/448.8/450.8 (M+H).

Intermediate 94

10-Bromo-7,8-dichloro-5-(2-hydroxyethyl)-6-methyl-3,4,5,6-tetrahydroazepino[4,5-b]indol-2(1H)-one

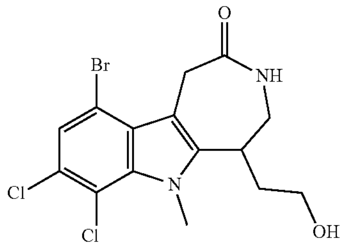 [SMILES: Cn1c2c(c3c(Br)cc(Cl)c(Cl)c31)CC(=O)NCC2CCO]

To a solution of ethyl 2-(10-bromo-7,8-dichloro-6-methyl-2-oxo-1,2,3,4,5,6-hexahydroazepino[4,5-b]indol-5-yl)acetate (130 mg, 0.261 mmol, 90 mass %) in THF (3 mL), added $LiBH_4$ (10 mg, 0.46 mmol) at 0° C. under $N_2$ atmosphere. Stirred at 25° C. for 16 hrs. Quenched with saturated aqueous $NH_4Cl$ and extracted with EtOAc. Combined organic layers, washed with saturated aqueous $NH_4Cl$, saturated aqueous NaCl, dried over anhydrous $Na_2SO_4$, filtered, and concentrated under reduced pressure. Purified by trituration with PE/EtOAc (1/1, V/V) to give 10-bromo-7,8-dichloro-5-(2-hydroxyethyl)-6-methyl-3,4,5,6-tetrahydroazepino[4,5-b]indol-2(1H)-one (100 mg, 85%). ES/MS (m/z): 404.8/406.8/408.8 (M+H).

Example 121

2-(7,8-Dichloro-5-(2-hydroxyethyl)-6-methyl-2-oxo-1,2,3,4,5,6-hexahydroazepino[4,5-b]indol-10-yl)acetonitrile

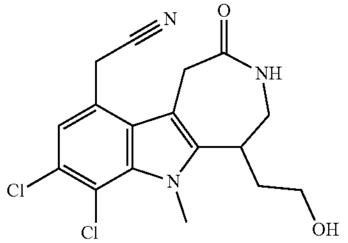 [SMILES: Cn1c2c(c3c(CC#N)cc(Cl)c(Cl)c31)CC(=O)NCC2CCO]

Combined 10-bromo-7,8-dichloro-5-(2-hydroxyethyl)-6-methyl-3,4,5,6-tetrahydroazepino[4,5-b]indol-2(1H)-one (150 mg, 0.332 mmol, 90 mass %), 4-(4,4,5,5-tetramethyl-[1,3,2]dioxaborolan-2-yl)-isoxazole (78 mg, 0.40 mmol), $Pd(dppf)Cl_2$ (24 mg, 0.033 mmol) and KF (58 mg, 0.99 mmol), in DMSO (12 mL) and $H_2O$ (3 mL). Degassed and purged with $N_2$ (3×). Stirred at 100° C. for 1 hr. Repeated the reaction on 0.33× scale and combined the reaction mixtures. Diluted with $H_2O$ and extracted with EtOAc. Combined organic layers, washed with saturated aqueous NaCl, dried over anhydrous $Na_2SO_4$, filtered, and concentrated under reduced pressure. The aqueous layer was concentrated under reduced pressure. Combined the residue and KF (200 mg, 3.45 mmol) in DMSO (10 mL) and $H_2O$ (10 mL). Stirred at 100° C. for 16 hrs. Diluted with $H_2O$ and extracted with EtOAc. Combined organic layers, washed with saturated aqueous NaCl, dried over anhydrous $Na_2SO_4$, filtered, and concentrated under reduced pressure. Purified by reverse phase prep-HPLC. Then further purified by SFC to give 2-(7,8-dichloro-5-(2-hydroxyethyl)-6-methyl-2-oxo-1,2,3,4,5,6-hexahydroazepino[4,5-b]indol-10-yl)acetonitrile (66.18 mg, 42%) as a white solid. ES/MS (m/z): ($^{35}Cl/^{37}Cl$) 366.0/367.8 (M+H).

Example 122

(R)-2-(7,8-Dichloro-5-(2-hydroxyethyl)-6-methyl-2-oxo-1,2,3,4,5,6-hexahydroazepino[4,5-b]indol-10-yl)acetonitrile Or (S)-2-(7,8-Dichloro-5-(2-hydroxyethyl)-6-methyl-2-oxo-1,2,3,4,5,6-hexahydroazepino[4,5-b]indol-10-yl)acetonitrile (isomer 1) and Example 123

(R)-2-(7,8-Dichloro-5-(2-hydroxyethyl)-6-methyl-2-oxo-1,2,3,4,5,6-hexahydroazepino[4,5-b]indol-10-yl)acetonitrile Or (S)-2-(7,8-Dichloro-5-(2-hydroxyethyl)-6-methyl-2-oxo-1,2,3,4,5,6-hexahydroazepino[4,5-b]indol-10-yl)acetonitrile (isomer 2)

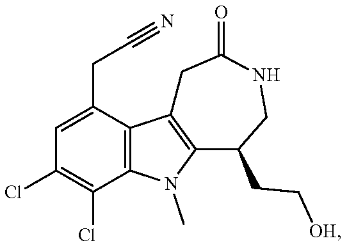
,

-continued

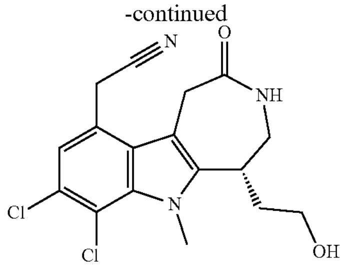

Purified racemic 2-(7,8-dichloro-5-(2-hydroxyethyl)-6-methyl-2-oxo-1,2,3,4,5,6-hexahydroazepino[4,5-b]indol-10-yl)acetonitrile (58.1 mg, 0.159 mmol) by SFC to give the titled compounds (Isomer 1—Rt=0.84 min (100% ee), 26.3 mg, 45%; Isomer 2—Rt=1.40 min (100% ee), 27.8 mg, 48%). Column: Chiralpak AD-H, 21×150 mm; Mobile Phase: 25% iPrOH: 75% $CO_2$; Flow Rate: 80 mL/min; Column temperature: 40° C.; Detection: 225 nM. ES/MS (m/z): ($^{35}Cl/^{37}Cl$) 366.2/368.2 (M+H).

Intermediate 95

7,8-Dichloro-10-hydroxy-5-(2-hydroxyethyl)-6-methyl-3,4,5,6-tetrahydroazepino[4,5-b]indol-2(1H)-one

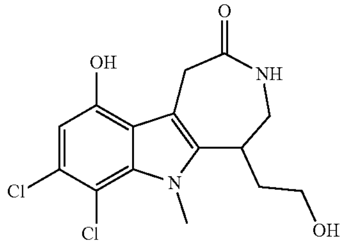 [SMILES: Cn1c2c(c3c(O)cc(Cl)c(Cl)c31)CC(=O)NCC2CCO]

Combined 10-bromo-7,8-dichloro-5-(2-hydroxyethyl)-6-methyl-3,4,5,6-tetrahydroazepino[4,5-b]indol-2(1H)-one (150 mg, 0.332 mmol, 90 mass %), t-BuBrettphos-Pd-$G_3$ (28 mg, 0.033 mmol), t-BuONa (80 mg, 0.83 mmol) in 1,4-dioxane (10 mL) and $H_2O$ (2 mL). Degassed and purged with $N_2$ (×3). Stirred at 65° C. for 2 hrs. Repeated the reaction on 0.33× scale and combined the reaction mixtures. Diluted with 1N aqueous HCl and extracted with EtOAc. Combined organic layers, washed with saturated aqueous NaCl, dried over anhydrous $Na_2SO_4$, filtered, and concentrated under reduced pressure to give 7,8-dichloro-10-hydroxy-5-(2-hydroxyethyl)-6-methyl-3,4,5,6-tetrahydroazepino[4,5-b]indol-2(1H)-one (250 mg, 63%). ES/MS (m/z): ($^{35}Cl/^{37}Cl$) 342.9/344.8 (M+H).

Example 124

2-((7,8-Dichloro-5-(2-hydroxyethyl)-6-methyl-2-oxo-1,2,3,4,5,6-hexahydroazepino[4,5-b]indol-10-yl)oxy)acetonitrile

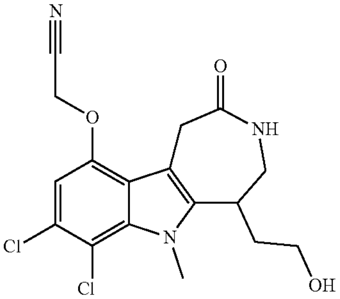 [SMILES: Cn1c2c(c3c(OCC#N)cc(Cl)c(Cl)c31)CC(=O)NCC2CCO]

Combined 7,8-dichloro-10-hydroxy-5-(2-hydroxyethyl)-6-methyl-3,4,5,6-tetrahydroazepino[4,5-b]indol-2(1H)-one (200 mg, 0.227 mmol, 39 mass %), $K_2CO_3$ (94 mg, 0.68 mmol), KI (38 mg, 0.23 mmol) in DMF (5 mL), then added 2-chloroacetonitrile (34 mg, 0.46 mmol). Stirred at 25° C. for 16 hrs. Repeated the reaction on 0.25× scale and combined the reaction mixtures. Diluted with $H_2O$ and extracted with EtOAc. Combined organic layers, washed with saturated aqueous NaCl, dried over anhydrous $Na_2SO_4$, filtered, and concentrated under reduced pressure. Purified by reverse phase prep-HPLC to give 2-((7,8-dichloro-5-(2-hydroxyethyl)-6-methyl-2-oxo-1,2,3,4,5,6-hexahydroazepino[4,5-b]indol-10-yl)oxy)acetonitrile (31 mg, 28%) as a yellow solid. ES/MS (m/z): ($^{35}Cl/^{37}Cl$) 382.0/383.8 (M+H).

Example 125

(R)-2-((7,8-Dichloro-5-(2-hydroxyethyl)-6-methyl-2-oxo-1,2,3,4,5,6-hexahydroazepino[4,5-b]indol-10-yl)oxy)acetonitrile Or (S)-2-((7,8-Dichloro-5-(2-hydroxyethyl)-6-methyl-2-oxo-1,2,3,4,5,6-hexahydroazepino[4,5-b]indol-10-yl)oxy)acetonitrile (isomer 1) and Example 126

(R)-2-((7,8-Dichloro-5-(2-hydroxyethyl)-6-methyl-2-oxo-1,2,3,4,5,6-hexahydroazepino[4,5-b]indol-10-yl)oxy)acetonitrile Or (S)-2-((7,8-Dichloro-5-(2-hydroxyethyl)-6-methyl-2-oxo-1,2,3,4,5,6-hexahydroazepino[4,5-b]indol-10-yl)oxy)acetonitrile (isomer 2)

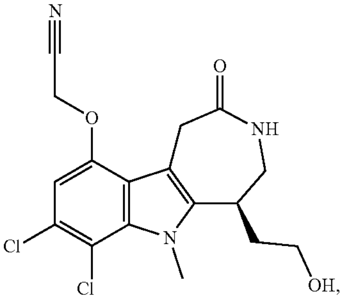
,

-continued

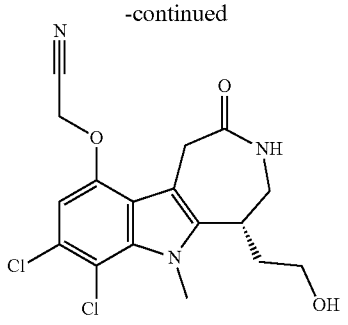

Purified racemic 2-((7,8-dichloro-5-(2-hydroxyethyl)-6-methyl-2-oxo-1,2,3,4,5,6-hexahydroazepino[4,5-b]indol-10-yl)oxy)acetonitrile (26 mg, 0.068 mmol) by SFC to give the titled compounds (Isomer 1—RT=1.83 min (100% ee), 8 mg, 30%; Isomer 2—RT=3.73 min (100% ee), 8 mg, 30%; chiral analysis used 25% MeOH: 75% $CO_2$). Column: Chiralpak AD-H, 21×150 mm; Mobile Phase: 40% MeOH: 601' $CO_2$, Flow Rate: 80 nL/min; Column temperature: 40° C.; Detection: 225 nM, ES/MS (m/z): ($^{35}Cl/^{37}Cl$) 382.0/384.0 (M+H).

Example 127

7,8-Dichloro-5-(2-hydroxyethyl)-6-methyl-10-(2-methyl-2H-1,2,3-triazol-4-yl)-3,4,5,6-tetrahydroazepino[4,5-b]indol-2(1H)-one

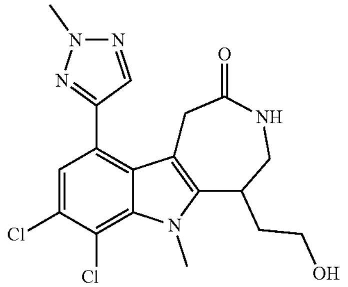 [SMILES: Cn1ncc(-c2cc(Cl)c(Cl)c3c2c2c(n3C)C(CCO)CNC(=O)C2)n1]

Combined 10-bromo-7,8-dichloro-5-(2-hydroxyethyl)-6-methyl-3,4,5,6-tetrahydroazepino[4,5-b]indol-2(1H)-one (70 mg, 0.16 mmol, 90 mass %), 2-methyl-4-(4,4,5,5-tetramethyl-1,3,2-dioxaborolan-2-yl)-2H-1,2,3-triazole (130 mg, 0.310 mmol), Pd(dppf)$Cl_2$ (11 mg, 0.016 mmol) and $Na_2CO_3$ (49 mg, 0.47 mmol) in 1,4-dioxane (8 mL) and $H_2O$ (2 mL). Degassed and purged with $N_2$ (×3). Stirred at 90° C. for 2 hrs. Repeated the reaction on 0.43× scale and combined the reaction mixtures. Concentrated under reduced pressure. Purified by silica gel flash chromatography eluting with MeOH in DCM and concentrated under reduced pressure and further purified by reverse phase prep-HPLC to give 7,8-dichloro-5-(2-hydroxyethyl)-6-methyl-10-(2-methyl-2H-1,2,3-triazol-4-yl)-3,4,5,6-tetrahydroazepino[4,5-b]indol-2(1H)-one (28 mg, 31%) as a white solid. ES/MS (m/z): ($^{35}Cl/^{37}Cl$) 408.1/410.0 (M+H).

Intermediate 96

2-(10-Bromo-7,8-dichloro-6-methyl-2-oxo-1,2,3,4,5,6-hexahydroazepino[4,5-b]indol-5-yl)acetic acid

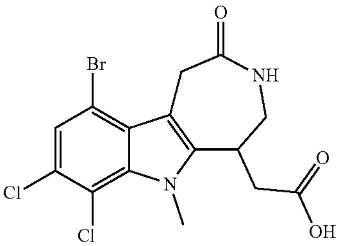 [SMILES: Cn1c2c(c3c(Br)cc(Cl)c(Cl)c31)CC(=O)NCC2CC(=O)O]

To a solution of ethyl 2-(10-bromo-7,8-dichloro-6-methyl-2-oxo-1,2,3,4,5,6-hexahydroazepino[4,5-b]indol-5-yl)acetate (500 mg, 1.00 mmol, 90 mass %) in THF (4 mL)/MeOH (4 mL) was added a solution of NaOH (201 mg, 5.02 mmol) in $H_2O$ (2 mL). Stirred at 20° C. for 16 hrs. Adjusted the pH to 5 with 1N aqueous HCl and filtered, then dried to give 2-(10-bromo-7,8-dichloro-6-methyl-2-oxo-1,2,3,4,5,6-hexahydroazepino[4,5-b]indol-5-yl)acetic acid (450 mg, 82% mass, 87%) as a yellow solid. ES/MS (m/z): 419.0/420.9/422.8 (M+H).

Intermediate 97

2-(10-Bromo-7,8-dichloro-6-methyl-2-oxo-1,2,3,4,5,6-hexahydroazepino[4,5-b]indol-5-yl)-N-methoxy-N-methylacetamide

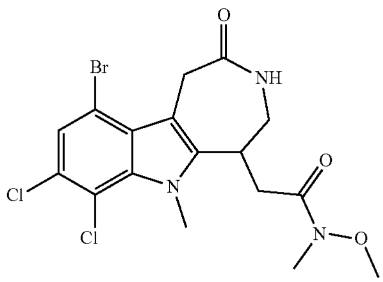 [SMILES: CON(C)C(=O)CC1CNC(=O)Cc2c1n(C)c1c(Cl)c(Cl)cc(Br)c21]

Combined 2-(10-bromo-7,8-dichloro-6-methyl-2-oxo-1,2,3,4,5,6-hexahydroazepino[4,5-b]indol-5-yl)acetic acid (450 mg, 0.878 mmol, 82 mass %), N,O-dimethylhydroxylamine hydrochloride (103 mg, 1.05 mmol), HATU (401 mg, 1.05 mmol) and DIPEA (341 mg, 2.64 mmol) in DMF (10 mL). Stirred at 25° C. for 2 hrs. Diluted with water and extracted with EtOAc, washed with saturated aqueous NaCl, dried over anhydrous $Na_2SO_4$, filtered, and concentrated under reduced pressure. Purified by flash column chromatography eluting with MeOH in DCM and concentrated under reduced pressure to give 2-(10-bromo-7,8-dichloro-6-methyl-2-oxo-1,2,3,4,5,6-hexahydroazepino[4,5-b]indol-5-yl)-N-methoxy-N-methylacetamide (380 mg, 88% mass, 82%) as a brown solid. ES/MS (m/z): 462.0/464.0/466.0 (M+H).

Intermediate 98

10-Bromo-7,8-dichloro-6-methyl-5-(2-oxopropyl)-3,4,5,6-tetrahydroazepino[4,5-b]indol-2(1H)-one

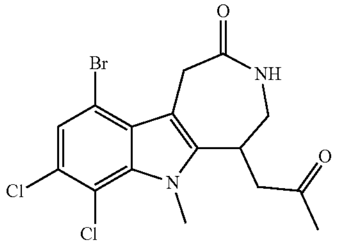 [SMILES: CC(=O)CC1CNC(=O)Cc2c1n(C)c1c(Cl)c(Cl)cc(Br)c21]

Added MeMgBr (1.20 mL, 3.61 mmol, 3M in diethyl ether) dropwise at −65° C. and under $N_2$ atmosphere to a solution of 2-(10-bromo-7,8-dichloro-6-methyl-2-oxo-1,2,3,4,5,6-hexahydroazepino[4,5-b]indol-5-yl)-N-methoxy-N-methylacetamide (380 mg, 0.722 mmol, 88 mass %) in THF (10 mL). Stirred the mixture at 25° C. for 2 hrs. Quenched with saturated aqueous $NH_4Cl$ and extracted with EtOAc, washed with saturated aqueous NaCl, dried over anhydrous $Na_2SO_4$, filtered, and concentrated under reduced pressure. Purified by flash column chromatography eluting with MeOH in DCM and concentrated under reduced pressure to give 10-bromo-7,8-dichloro-6-methyl-5-(2-oxopropyl)-3,4,5,6-tetrahydroazepino[4,5-b]indol-2(1H)-one (250 mg, 83% mass, 69%) as a white solid. ES/MS (m/z): 416.8/418.8/420.8 (M+H).

Intermediate 99

10-Bromo-7,8-dichloro-5-(2-hydroxypropyl)-6-methyl-3,4,5,6-tetrahydroazepino[4,5-b]indol-2(1H)-one

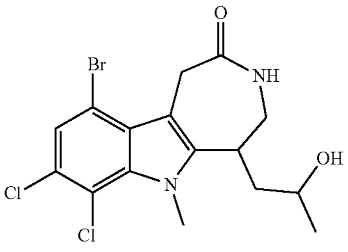 [SMILES: CC(O)CC1CNC(=O)Cc2c1n(C)c1c(Cl)c(Cl)cc(Br)c21]

Combined 10-bromo-7,8-dichloro-6-methyl-5-(2-oxopropyl)-3,4,5,6-tetrahydroazepino[4,5-b]indol-2(1H)-one (250 mg, 0.496 mmol, 83 mass %) in MeOH (3 mL), added $NaBH_4$ (60 mg, 1.6 mmol) portion-wise at 0° C. Stirred at 25° C. for 3 hrs, under $N_2$. Quenched with saturated aqueous $NH_4Cl$ and removed MeOH under reduced pressure. Diluted with water and filtered, then washed the precipitate with water and dried to give 10-bromo-7,8-dichloro-5-(2-hydroxypropyl)-6-methyl-3,4,5,6-tetrahydroazepino[4,5-b]indol-2(1H)-one (170 mg, 75%) as a white solid. ES/MS (m/z): 418.8/420.8/422.7 (M+H).

Example 128

2-(7,8-Dichloro-5-(2-hydroxypropyl)-6-methyl-2-oxo-1,2,3,4,5,6-hexahydroazepino[4,5-b]indol-10-yl)acetonitrile

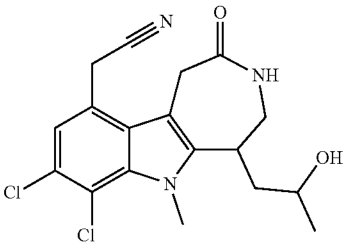 [SMILES: CC(O)CC1CNC(=O)Cc2c1n(C)c1c(Cl)c(Cl)cc(CC#N)c21]

Combined 10-bromo-7,8-dichloro-5-(2-hydroxypropyl)-6-methyl-3,4,5,6-tetrahydroazepino[4,5-b]indol-2(1H)-one (170 mg, 0.372 mmol, 92 mass %), 4-(4,4,5,5-tetramethyl-[1,3,2]dioxaborolan-2-yl)-isoxazole (87 mg, 0.45 mmol) and KF (65 mg, 1.1 mmol), $Pd(dppf)Cl_2$ (27 mg, 0.037 mmol) in DMSO (4 mL) and $H_2O$ (1 mL). Degassed and purged with $N_2$ (x3). Stirred at 100° C. for 1 hr, under $N_2$ atmosphere. Diluted with water, extracted with EtOAc, washed with saturated aqueous NaCl and dried over anhydrous $Na_2SO_4$, filtered, and concentrated under reduced pressure. Purified by flash column chromatography eluting with MeOH in DCM and concentrated under reduced pressure. Diluted residue in DMF (2 mL) and $H_2O$ (2 mL). Added KF (99 mg, 1.7 mmol) and stirred at 100° C. for 16 hrs. Diluted with $H_2O$ and extracted with EtOAc. Washed with saturated aqueous NaCl, dried over anhydrous $Na_2SO_4$, filtered, and concentrated under reduced pressure. Purified by flash column chromatography eluting with MeOH in DCM, concentrated under reduced pressure, and further purified by prep-HPLC to give a mixture of diastereomers of 2-(7,8-dichloro-5-(2-hydroxypropyl)-6-methyl-2-oxo-1,2,3,4,5,6-hexahydroazepino[4,5-b]indol-10-yl)acetonitrile (25.26 mg, 30%) as a white solid. ES/MS (m/z): ES/MS m/z: ($^{35}Cl/^{37}Cl$) 380.0/382.0 (M+H); 380.1/382.0 (M+H).

Intermediate 100

10-Bromo-7,8-dichloro-5-(2-hydroxy-2-methylpropyl)-6-methyl-3,4,5,6-tetrahydroazepino[4,5-b]indol-2(1H)-one

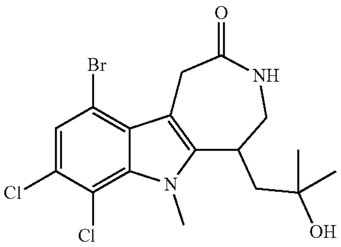 [SMILES: Cn1c2c(c3c(Br)cc(Cl)c(Cl)c31)CC(=O)NCC2CC(C)(C)O]

To a solution of ethyl 2-(10-bromo-7,8-dichloro-6-methyl-2-oxo-1,2,3,4,5,6-hexahydroazepino[4,5-b]indol-5-yl)acetate (2.28 g, 4.78 mmol, 94 mass %) in THF (10 mL), added MeMgBr (7.97 mL, 23.9 mmol, 3 M in diethyl ether) at −65° C. Stirred at 25° C. for 2 hrs. Quenched with saturated aqueous $NH_4Cl$ and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with MeOH in DCM and dried under reduced pressure to give 10-bromo-7,8-dichloro-5-(2-hydroxy-2-methylpropyl)-6-methyl-3,4,5,6-tetrahydroazepino[4,5-b]indol-2(1H)-one (1.50 g, 69%). ES/MS (m/z): 432.8/434.8/436.8 (M+H).

Intermediate 101

2-(7,8-Dichloro-5-(2-hydroxy-2-methylpropyl)-6-methyl-2-oxo-1,2,3,4,5,6-hexahydroazepino[4,5-b]indol-10-yl)acetonitrile

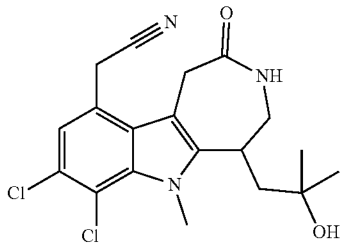 [SMILES: Cn1c2c(c3c(CC#N)cc(Cl)c(Cl)c31)CC(=O)NCC2CC(C)(C)O]

Combined 10-bromo-7,8-dichloro-5-(2-hydroxy-2-methylpropyl)-6-methyl-3,4,5,6-tetrahydroazepino[4,5-b]indol-2(1H)-one (300 mg, 0.656 mmol, 95 mass %), 4-(4,4,5,5-tetramethyl-[1,3,2]dioxaborolan-2-yl)-isoxazole (154 mg, 0.788 mmol), $Pd(dppf)Cl_2$ (48 mg, 0.066 mmol) and KF (114 mg, 1.97 mmol) in DMSO (8 mL) and $H_2O$ (2 mL). Degassed and purged with $N_2$ (×3). Stirred at 100° C. for 1 hr, under $N_2$ atmosphere. Diluted with $H_2O$ and extracted with EtOAc (×3). Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure. Combined residue and KF (134 mg, 2.30 mmol) in DMF (3 mL) and $H_2O$ (3 mL). Degassed and purged with $N_2$ (×3). Stirred at 100° C. for 16 hrs, under $N_2$ atmosphere. Diluted with $H_2O$ and extracted with EtOAc (×3). Combined the organic layers, washed with saturated aqueous NaCl, dried over anhydrous $Na_2SO_4$, filtered, and concentrated under reduced pressure. Purified by reverse phase prep-HPLC to give 2-(7,8-dichloro-5-(2-hydroxy-2-methylpropyl)-6-methyl-2-oxo-1,2,3,4,5,6-hexahydroazepino[4,5-b]indol-10-yl)acetonitrile (70 mg, 59%) as a white solid. ES/MS (m/z): ($^{35}Cl/^{37}Cl$) 393.9/395.9 (M+H).

Example 129

(R)-2-(7,8-Dichloro-5-(2-hydroxy-2-methylpropyl)-6-methyl-2-oxo-1,2,3,4,5,6-hexahydroazepino[4,5-b]indol-10-yl)acetonitrile Or (S)-2-(7,8-Dichloro-5-(2-hydroxy-2-methylpropyl)-6-methyl-2-oxo-1,2,3,4,5,6-hexahydroazepino[4,5-b]indol-10-yl)acetonitrile (isomer 1) and Example 130

(R)-2-(7,8-Dichloro-5-(2-hydroxy-2-methylpropyl)-6-methyl-2-oxo-1,2,3,4,5,6-hexahydroazepino[4,5-b]indol-10-yl)acetonitrile Or (S)-2-(7,8-Dichloro-5-(2-hydroxy-2-methylpropyl)-6-methyl-2-oxo-1,2,3,4,5,6-hexahydroazepino[4,5-b]indol-10-yl)acetonitrile (isomer 2)

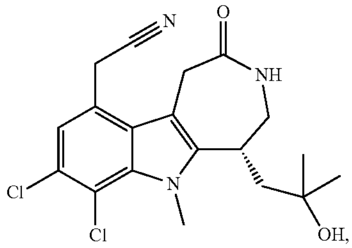

,

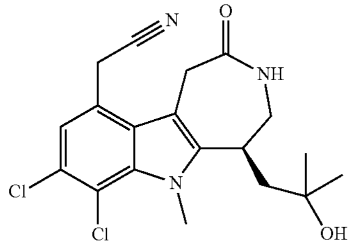

Purified racemic 2-(7,8-dichloro-5-(2-hydroxy-2-methylpropyl)-6-methyl-2-oxo-1,2,3,4,5,6-hexahydroazepino[4,5-b]indol-10-yl)acetonitrile (70 mg, 0.17 mmol, 96 mass %) by SFC to give the titled compounds (Isomer 1—Rt=1.604 min (100% ee), 33 mg, 48% as a white solid; Isomer 2—Rt=2.247 min (99.8% ee), 29 mg, 42% as a white solid). Column: DAICEL CHIRALPAK IC (250×30 mm, 10 μm); Mobile Phase: 60% EtOH (0.1% $NH_3H_2O$), 400, $CO_2$; Flow Rate: 80 mL/min, ES/MS (m/z): ($^{35}Cl/^{37}Cl$) 394.1/396.0 (M+H).

Intermediate 102

7,7-Dimethyl-1,4-dioxaspiro[4.5]decan-8-one

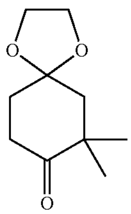

To a solution of 1,4-dioxaspiro[4.5]decan-8-one (20.0 g, 128 mmol) in t-BuOH (450 mL), added t-BuOK (35.9 g, 320 mmol) slowly at ambient temperature under $N_2$ atmosphere and stirred for 1 hr. Added iodomethane (39.1 g, 275 mmol) dropwise over 1 hr. Stirred at ambient temperature for 16 hrs, under $N_2$ atmosphere. Quenched with water and extracted with EtOAc (3×). Combined the organic layers, washed with saturated aqueous NaCl (×3), dried over anhydrous $Na_2SO_4$, filtered, and concentrated under reduced pressure. Purified by silica gel flash chromatography eluting with EtOAc in PE and concentrated under reduced pressure to give 7,7-dimethyl-1,4-dioxaspiro[4.5]decan-8-one (11.8 g, 45%). $^1$H NMR (DMSO-d6): 3.92 (s, 4H), 2.44 (dd, J=7.6, 6.8 Hz, 2H), 1.93 (ddd, J=7.6, 6.8, 1.0 Hz, 2H), 1.84 (s, 2H), 1.06 (s, 6H).

Intermediate 103

(E)-1-(5-Bromo-2,3-dichlorophenyl)-2-(7,7-dimethyl-1,4-dioxaspiro[4.5]decan-8-ylidene)hydrazine

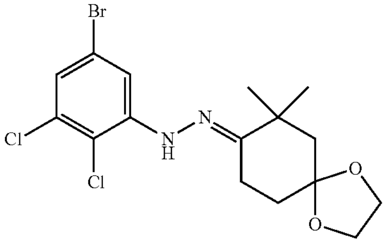 [SMILES: CC1(C)CC2(CC/C1=N\Nc1cc(Br)cc(Cl)c1Cl)OCCO2]

Combined 5-bromo-2,3-dichlorophenyl)hydrazine (21 g, 73 mmol, 90 mass %), 7,7-dimethyl-1,4-dioxaspiro[4.5]decan-8-one (15 g, 73 mmol, 90 mass %) and acetic acid (4.2 mL, 73 mmol) in MeOH (150 mL). Stirred at 75° C. for 3 hrs, under $N_2$ atmosphere. Concentrated under reduced pressure and diluted with EtOAc and water. Separated the layers and extracted the aqueous layer with EtOAc (3×). Combined organic layers, washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give (E)-1-(5-bromo-2,3-dichlorophenyl)-2-(7,7-dimethyl-1,4-dioxaspiro[4.5]decan-8-ylidene)hydrazine (14 g, 38%) as a brown oil. ES/MS (m/z): 420.8/422.8/424.8 (M+H).

Intermediate 104

5-Bromo-7,8-dichloro-1,1-dimethyl-1,2,4,9-tetrahydrospiro[carbazole-3,2'-[1,3]dioxolane]

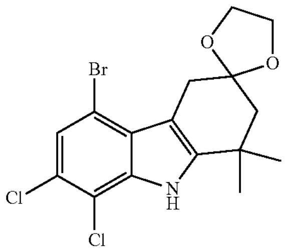 [SMILES: CC1(C)CC2(Cc3c1[nH]c1c(Cl)c(Cl)cc(Br)c31)OCCO2]

Charged a separate flask with $ZnCl_2$ (9.22 g, 67.7 mmol) and heated at 140° C. under reduced pressure until the $ZnCl_2$ became a white free-flowing solid. Cooled to ambient temperature. Dissolved (E)-1-(5-bromo-2,3-dichlorophenyl)-2-(7,7-dimethyl-1,4-dioxaspiro[4.5]decan-8-ylidene)hydrazine (14.0 g, 28.2 mmol, 85 mass %) in dry toluene (90 mL) and added to the above dried $ZnCl_2$ under $N_2$ atmosphere. Stirred at 130° C. for 2 days. Concentrated under reduced pressure and suspended in dry xylene (90 mL), added the suspension to dry $ZnCl_2$ (9.22 g, 67.7 mmol) and stirred at 140° C. for 3 days under $N_2$ atmosphere. Cooled to ambient temperature and concentrated under reduced pressure. Diluted with EtOAc and saturated aqueous sodium bicarbonate to form precipitate. Added 2N aqueous HCl to pH=7 to dissolve the solids. Separated and extracted the aqueous layer with EtOAc (2×). Combined organic layers, washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give 5-bromo-7,8-dichloro-1,1-dimethyl-1,2,4,9-tetrahydrospiro[carbazole-3,2'-[1,3]dioxolane] (3.30 g, 23%). ES/MS (m/z): 404.0/405.9/407.9 (M+H).

Intermediate 105

5-Bromo-7,8-dichloro-1,1-dimethyl-1,2,4,9-tetrahydro-3H-carbazol-3-one

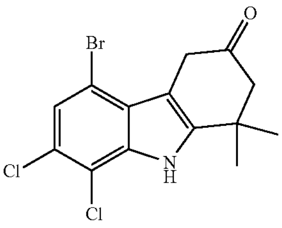 [SMILES: CC1(C)CC(=O)Cc2c1[nH]c1c(Cl)c(Cl)cc(Br)c21]

To a solution of 5-bromo-7,8-dichloro-1,1-dimethyl-1,2,4,9-tetrahydrospiro[carbazole-3,2'-[1,3]dioxolane] (1.90 g, 4.13 mmol, 88 mass %) in acetone (50 mL), added TFA (2.35 g, 20.6 mmol) under $N_2$ atmosphere. Stirred at 80° C. for 16 hrs, under $N_2$ atmosphere. Concentrated under reduced pressure, diluted with water, and extracted with EtOAc (3×). Combined the organic layers, washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give 5-bromo-7,8-dichloro-1,1-dimethyl-1,2,4,9-tetrahydro-3H-carbazol-3-one (1.10 g, 66%) as a yellow solid. ES/MS (m/z): 360.0.0/362.0/363.9 (M+H).

Intermediate 106

10-Bromo-7,8-dichloro-5,5-dimethyl-3,4,5,6-tetrahydroazepino[4,5-b]indol-2(1H)-one

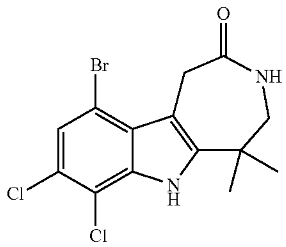 [SMILES: CC1(C)CNC(=O)Cc2c1[nH]c1c(Cl)c(Cl)cc(Br)c21]

To a solution of 5-bromo-7,8-dichloro-1,1-dimethyl-1,2,4,9-tetrahydro-3H-carbazol-3-one (1.10 g, 2.74 mmol, 90 mass %) in methanesulfonic acid (22 mL), added sodium azide (180 mg, 2.77 mmol) slowly at 0° C. Stirred at 0° C. for 30 min and then at 20° C. for 16 hrs. Poured the reaction mixture into ice-water and basified with 6N aqueous NaOH to pH=10, extracted with EtOAc (3×). Combined the organic layers, washed with saturated aqueous NaCl, dried over anhydrous $Na_2SO_4$, filtered, and concentrated under reduced pressure. Purified by silica gel flash chromatography eluting with MeOH in DCM, then suspended the product in DCM, stirred at ambient temperature for 30 min and collected the solids by vacuum filtration and dried to give 10-bromo-7,8-dichloro-5,5-dimethyl-3,4,5,6-tetrahydroazepino[4,5-b]indol-2(1H)-one (520 mg, 40%) as a white solid. ES/MS (m/z): 374.8.0/376.8/378.7 (M+H). $^1$H NMR (DMSO-d6): 11.46 (s, 1H), 7.95 (t, J=6.4 Hz, 1H), 7.42 (s, 1H), 4.15 (s, 2H), 3.30 (s, 2H), 1.34 (s, 6H).

Intermediate 107

1-(10-Bromo-7,8-dichloro-5,5-dimethyl-2-oxo-1,2,3,4,5,6-hexahydroazepino[4,5-b]indol-1-yl)pyrrolidine-2,5-dione

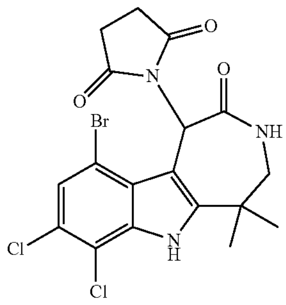 [SMILES: CC1(C)CNC(=O)C(N2C(=O)CCC2=O)c2c1[nH]c1c(Cl)c(Cl)cc(Br)c21]

Combined 10-bromo-7,8-dichloro-5,5-dimethyl-3,4,5,6-tetrahydroazepino[4,5-b]indol-2(1H)-one (600 mg, 1.47 mmol, 92 mass %), NIS (396 mg, 1.76 mmol) and cesium carbonate (574 mg, 1.76 mmol) in DMF (10 mL) at 0° C. Stirred at 25° C. for 6 hrs, and allowed to stand at 25° C. for 2.5 days. Added NIS (198 mg, 0.881 mmol), stirred at 25° C. for 16 hrs. Quenched with 10% aqueous lithium chloride dropwise at 0° C. and stirred at 0° C. for 0.5 hr. Filtered and dried the precipitate under reduced pressure to give brown solids. Extracted the filtrate with EtOAc (×2). Combined organic layers, washed with saturated aqueous NaCl, dried over anhydrous $Na_2SO_4$, filtered, and concentrated under reduced pressure to give a brown gum. Combined brown solids and gum to give 1-(10-bromo-7,8-dichloro-5,5-dimethyl-2-oxo-1,2,3,4,5,6-hexahydroazepino[4,5-b]indol-1-yl)pyrrolidine-2,5-dione (750 mg, 54%). ES/MS (m/z): 372.9/374.9/376.7 (M+H-succinimide).

Intermediate 108

10-Bromo-7,8-dichloro-1,5,5-trimethyl-3,4,5,6-tetrahydroazepino[4,5-b]indol-2(1H)-one

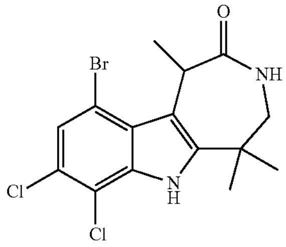 [SMILES: CC1C(=O)NCC(C)(C)c2[nH]c3c(Cl)c(Cl)cc(Br)c3c21]

To a solution of MeMgBr (1.32 mL, 3.96 mmol, 3M in diethyl ether) in THF (20 mL), added a solution of 1-(10-bromo-7,8-dichloro-5,5-dimethyl-2-oxo-1,2,3,4,5,6-hexahydroazepino[4,5-b]indol-1-yl)pyrrolidine-2,5-dione (750 mg, 0.793 mmol, 50 mass %) in THF (15 mL) dropwise at 0° C. under $N_2$ atmosphere. Stirred at 0° C. for 1 hr. Quenched with 10% aqueous citric acid, extracted with EtOAc (3×). Combined organic layers, washed with saturated aqueous NaCl, dried over anhydrous $Na_2SO_4$, filtered, concentrated under reduced pressure. Purified by silica gel flash chromatography eluting with MeOH in DCM and concentrated under reduced pressure to give 10-bromo-7,8-dichloro-1,5,5-trimethyl-3,4,5,6-tetrahydroazepino[4,5-b]indol-2(1H)-one (420 mg, 96%) as a brown gum. ES/MS (m/z): 388.9/390.9/392.8 (M+H).

Example 131

7,8-Dichloro-10-((2-hydroxyethyl)amino)-1,5,5-trimethyl-3,4,5,6-tetrahydroazepino[4,5-b]indol-2(1H)-one

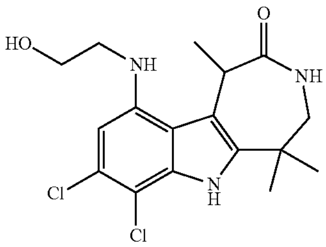 [SMILES: CC1C(=O)NCC(C)(C)c2[nH]c3c(Cl)c(Cl)cc(NCCO)c3c21]

Combined 10-bromo-7,8-dichloro-1,5,5-trimethyl-3,4,5,6-tetrahydroazepino[4,5-b]indol-2(1H)-one (250 mg, 0.429 mmol, 67 mass %), 2-aminoethan-1-ol (58 mg, 0.95 mmol), $Pd_2(dba)_3$ (40 mg, 0.043 mmol), Xantphos (51 mg, 0.086 mmol) and cesium carbonate (500 mg, 1.50 mmol) in 1,4-dioxane (20 mL) and THF (2 mL). Degassed and purged with $N_2$ (×3). Stirred at 110° C. for 16 hrs, under $N_2$ atmosphere. Concentrated under reduced pressure and purified by silica gel flash chromatography eluting with MeOH in DCM. Azeotroped with ACN (4×) and lyophilized to give 7,8-dichloro-10-((2-hydroxyethyl)amino)-1,5,5-trimethyl-3,4,5,6-tetrahydroazepino[4,5-b]indol-2(1H)-one (95.95 mg, 59%) as a yellow solid. ES/MS (m/z): ($^{35}Cl/^{37}Cl$) 370.0/371.9 (M+H).

Intermediate 109

N-(7,8-Dichloro-1,5,5-trimethyl-2-oxo-1,2,3,4,5,6-hexahydroazepino[4,5-b]indol-10-yl)-2-hydroxyacetamide

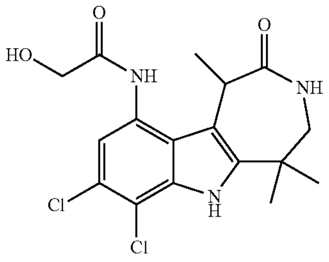 [SMILES: CC1C(=O)NCC(C)(C)c2[nH]c3c(Cl)c(Cl)cc(NC(=O)CO)c3c21]

Combined 10-bromo-7,8-dichloro-1,5,5-trimethyl-3,4,5,6-tetrahydroazepino[4,5-b]indol-2(1H)-one (450 mg, 0.773 mmol, 67 mass %), 2-hydroxyacetamide (130 mg, 1.70 mmol), $Pd_2(dba)_3$ (72 mg, 0.077 mmol), Xantphos (92 mg, 0.16 mmol) and cesium carbonate (899 mg, 2.71 mmol) in 1,4-dioxane (20 mL) and THF (2 mL). Degassed and purged with $N_2$ (×3). Stirred at 110° C. for 16 hrs, under $N_2$ atmosphere. Concentrated under reduced pressure and purified by silica gel flash chromatography eluting with MeOH in DCM. Further purified by trituration with ACN at 20° C. for 30 min to give racemic N-(7,8-dichloro-1,5,5-trimethyl-2-oxo-1,2,3,4,5,6-hexahydroazepino[4,5-b]indol-10-yl)-2-hydroxyacetamide (180 mg, 59%) as a white solid. ES/MS (m/z): ($^{35}Cl/^{37}Cl$) 384.0/386.0 (M+H).

Example 132

(R)—N-(7,8-Dichloro-1,5,5-trimethyl-2-oxo-1,2,3,4,5,6-hexahydroazepino[4,5-b]indol-10-yl)-2-hydroxyacetamide Or (S)—N-(7,8-Dichloro-1,5,5-trimethyl-2-oxo-1,2,3,4,5,6-hexahydroazepino[4,5-b]indol-10-yl)-2-hydroxyacetamide (isomer 1) and Example 133

(R)—N-(7,8-Dichloro-1,5,5-trimethyl-2-oxo-1,2,3,4,5,6-hexahydroazepino[4,5-b]indol-10-yl)-2-hydroxyacetamide Or (S)—N-(7,8-Dichloro-1,5,5-trimethyl-2-oxo-1,2,3,4,5,6-hexahydroazepino[4,5-b]indol-10-yl)-2-hydroxyacetamide (isomer 2)

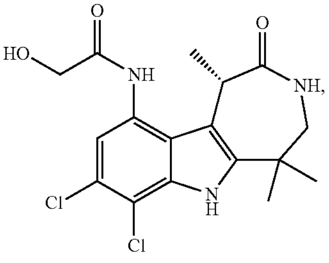

-continued

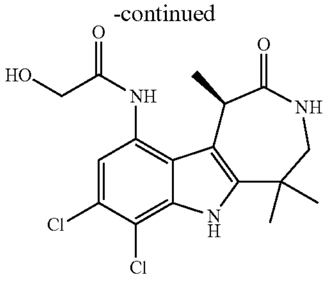

Purified racemic N-(7,8-dichloro-1,5,5-trimethyl-2-oxo-1,2,3,4,5,6-hexahydroazepino[4,5-b]indol-10-yl)-2-hydroxyacetamide (180 mg, 0.454 mmol, 97 mass %) by SFC to give the titled compounds (Isomer 1—Rt=1.135 min (100% ee), 72.58 mg, 41% as a white solid; Isomer 2—Rt=1.560 min (100% ee), 71.71 mg, 40% as a white solid). Column: DAICEL CHIRALPAK AD, 30×250 mm, 10 μm; Mobile Phase: 45% EtOH (w/0.1% $NH_3H_2O$): 55% $CO_2$; Flow Rate: 80 mL/min. ES/MS (m/z): ($^{35}Cl/^{37}Cl$) 384.1/386.1 (M+H).

Intermediate 110

10-Bromo-7,8-dichloro-1,5,5,6-tetramethyl-3,4,5,6-tetrahydroazepino[4,5-b]indol-2(1H)-one

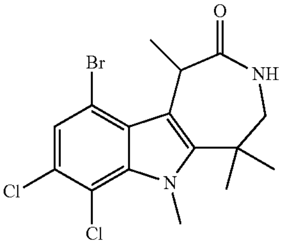 [SMILES: CC1C(=O)NCC(C)(C)c2c1c1c(Br)cc(Cl)c(Cl)c1n2C]

Combined 10-bromo-7,8-dichloro-1,5,5-trimethyl-3,4,5,6-tetrahydroazepino[4,5-b]indol-2(1H)-one (420 mg, 0.764 mmol, 71 mass %) and cesium carbonate (503 mg, 1.53 mmol) in DMF (10 mL). Stirred at 20° C. for 30 min. Added iodomethane (221 mg, 1.53 mmol) slowly at 0° C. and stirred at 20° C. for 3 hrs. Diluted with water and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with MeOH in DCM, then triturated with ACN at 25° C. for 30 min to give 10-bromo-7,8-dichloro-1,5,5,6-tetramethyl-3,4,5,6-tetrahydroazepino[4,5-b]indol-2(1H)-one (300 mg, 95%) as a white solid. ES/MS (m/z): 403.0/405.0/407.0 (M+H).

Intermediate 111

N-(7,8-Dichloro-1,5,5,6-tetramethyl-2-oxo-1,2,3,4,5,6-hexahydroazepino[4,5-b]indol-10-yl)-2-hydroxy-acetamide

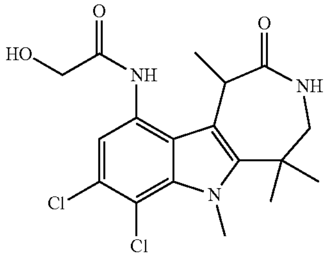 [SMILES: CC1C(=O)NCC(C)(C)c2c1c1c(NC(=O)CO)cc(Cl)c(Cl)c1n2C]

Combined 10-bromo-7,8-dichloro-1,5,5,6-tetramethyl-3,4,5,6-tetrahydroazepino[4,5-b]indol-2(1H)-one (300 mg, 0.727 mmol, 98 mass %), 2-hydroxyacetamide (123 mg, 1.60 mmol), $Pd_2(dba)_3$ (67 mg, 0.073 mmol), Xantphos (87 mg, 0.15 mmol) and cesium carbonate (847 mg, 2.55 mmol) in 1,4-dioxane (20 mL) and THF (2 mL). Degassed and purged with $N_2$ (×3) and stirred at 110° C. for 16 hrs, under $N_2$ atmosphere. Concentrated under reduced pressure and purified by silica gel flash chromatography eluting with MeOH in DCM. Then triturated with ACN at 20° C. for 30 min to give racemic N-(7,8-dichloro-1,5,5,6-tetramethyl-2-oxo-1,2,3,4,5,6-hexahydroazepino[4,5-b]indol-10-yl)-2-hydroxyacetamide (120 mg, 38%) as a white solid. ES/MS (m/z): ($^{35}Cl/^{37}Cl$) 398.1/400.0 (M+H).

Example 134

(R)—N-(7,8-Dichloro-1,5,5,6-tetramethyl-2-oxo-1,2,3,4,5,6-hexahydroazepino[4,5-b]indol-10-yl)-2-hydroxyacetamide or (S)—N-(7,8-Dichloro-1,5,5,6-tetramethyl-2-oxo-1,2,3,4,5,6-hexahydroazepino[4,5-b]indol-10-yl)-2-hydroxyacetamide (isomer 1)
and Example 135

(R)—N-(7,8-Dichloro-1,5,5,6-tetramethyl-2-oxo-1,2,3,4,5,6-hexahydroazepino[4,5-b]indol-10-yl)-2-hydroxyacetamide or (S)—N-(7,8-Dichloro-1,5,5,6-tetramethyl-2-oxo-1,2,3,4,5,6-hexahydroazepino[4,5-b]indol-10-yl)-2-hydroxyacetamide (isomer 2)

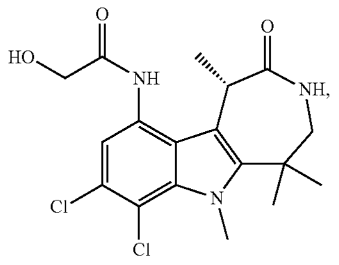

-continued

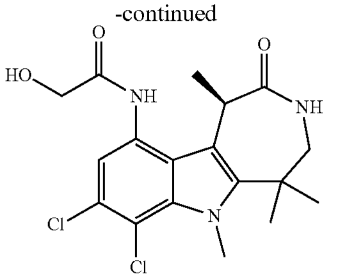

Purified racemic N-(7,8-dichloro-1,5,5,6-tetramethyl-2-oxo-1,2,3,4,5,6-hexahydroazepino[4,5-b]indol-10-yl)-2-hydroxyacetamide (120 mg, 0.274 mmol, 91 mass %) by SFC to give the titled compounds (Isomer 1—Rt=1.436 min (100% ee), 41.63 mg, 37% as a white solid; Isomer 2—Rt=2.114 min (100% ee), 42.04 mg, 38% as a white solid). Column: REGIS (S, S) WHELK-O1, 30×250 mm, 5 μm; Mobile Phase: 45% EtOH (w/0.1% $NH_3H_2O$): 55% $CO_2$, Flow Rate: 80 mL/min. ES/MS (m/z): ($^{35}Cl/^{37}Cl$) 398.1/400.1 (M+H).

Intermediate 112

2-(5-Bromo-7,8-dichloro-1,2,4,9-tetrahydrospiro[carbazole-3,2'-[1,3]dioxolan]-1-yl)acetic acid

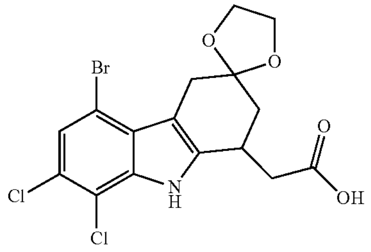 [SMILES: O=C(O)CC1CC2(Cc3c1[nH]c1c(Cl)c(Cl)cc(Br)c31)OCCO2]

To a solution of ethyl 2-(5-bromo-7,8-dichloro-1,2,4,9-tetrahydrospiro[carbazole-3,2'-[1,3]dioxolan]-1-yl)acetate (7.32 g, 14.5 mmol, 92 mass %) in THF (20 mL) and MeOH (20 mL), added a solution of sodium hydroxide (2.91 g, 72.7 mmol) in $H_2O$ (10 mL). Stirred at 20° C. for 16 hrs. Added 1N aqueous HCl to adjust pH to 5, collected the resulting solid via filtration and vacuum dried. Purified by trituration with EtOAc in PE to give 2-(5-bromo-7,8-dichloro-1,2,4,9-tetrahydrospiro[carbazole-3,2'-[1,3]dioxolan]-1-yl)acetic acid (5.30 g, 80%) as a yellow solid. ES/MS (m/z): 433.9/435.6/437.7 (M+H).

Intermediate 113

2-(5-Bromo-7,8-dichloro-1,2,4,9-tetrahydrospiro[carbazole-3,2'-[1,3]dioxolan]-1-yl)-N-methoxy-N-methylacetamide

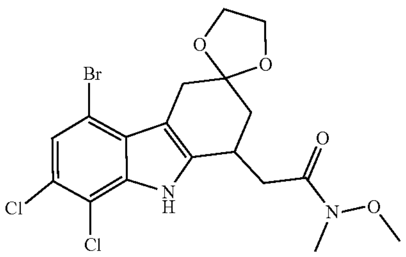 [SMILES: CON(C)C(=O)CC1CC2(Cc3c1[nH]c1c(Cl)c(Cl)cc(Br)c31)OCCO2]

To a solution of 2-(5-bromo-7,8-dichloro-1,2,4,9-tetrahydrospiro[carbazole-3,2'-[1,3]dioxolan]-1-yl)acetic acid (5.30 g, 11.7 mmol, 96 mass %) and DIPEA (4.53 g, 35.1 mmol) in DMF (50 mL), added N, O-dimethylhydroxylamine hydrochloride (1.37 g, 14.0 mmol) and HATU (5.34 g, 14.0 mmol). Stirred at 25° C. for 2 hrs. Diluted with $H_2O$ and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give 2-(5-bromo-7,8-dichloro-1,2,4,9-tetrahydrospiro[carbazole-3,2'-[1,3]dioxolan]-1-yl)-N-methoxy-N-methylacetamide (5.00 g, 87%) as a yellow oil. ES/MS (m/z): 476.8/478.7/480.7 (M+H).

Intermediate 114

1-(5-Bromo-7,8-dichloro-1,2,4,9-tetrahydrospiro[carbazole-3,2'-[1,3]dioxolan]-1-yl)propan-2-one

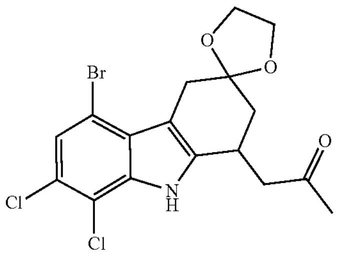 [SMILES: CC(=O)CC1CC2(Cc3c1[nH]c1c(Cl)c(Cl)cc(Br)c31)OCCO2]

To a solution of 2-(5-bromo-7,8-dichloro-1,2,4,9-tetrahydrospiro[carbazole-3,2'-[1,3]dioxolan]-1-yl)-N-methoxy-N-methylacetamide (5.00 g, 10.1 mmol, 97 mass %) in THF (50 mL), added MeMgBr (16.9 mL, 50.7 mmol, 3M in diethyl ether) dropwise at −65° C. under $N_2$ atmosphere. Stirred at 20° C. for 3 hrs, under $N_2$ atmosphere. Quenched with saturated aqueous ammonium chloride and extracted with EtOAc (3×). Combined organic layers, washed with saturated aqueous ammonium chloride, saturated aqueous NaCl, dried over anhydrous $Na_2SO_4$, filtered, and concentrated under reduced pressure. Purified by silica gel flash chromatography eluting with EtOAc in PE and concentrated under reduced pressure to give 1-(5-bromo-7,8-dichloro-1,2,4,9-tetrahydrospiro[carbazole-3,2'-[1,3]dioxolan]-1-yl)propan-2-one (2.86 g, 64%) as a yellow solid. ES/MS (m/z): 431.8/433.8/435.7 (M+H).

Intermediate 115

5-Bromo-7,8-dichloro-1-(2,2-difluoropropyl)-1,2,4,9-tetrahydrospiro[carbazole-3,2'-[1,3]dioxolane]

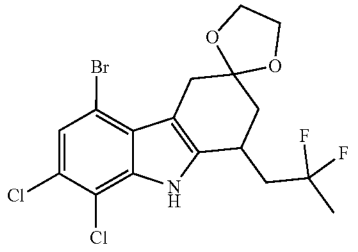 [SMILES: CC(F)(F)CC1CC2(Cc3c1[nH]c1c(Cl)c(Cl)cc(Br)c31)OCCO2]

To a solution of 1-(5-bromo-7,8-dichloro-1,2,4,9-tetrahydrospiro[carbazole-3,2'-[1,3]dioxolan]-1-yl)propan-2-one (860 mg, 1.95 mmol, 98 mass %) in DCM (15 mL), added diethylaminosulfur trifluoride (1.25 g, 7.78 mmol) at −65° C. under $N_2$ atmosphere. Stirred at 45° C. for 3 days under $N_2$ atmosphere. Quenched with saturated aqueous $NaHCO_3$ and extracted with DCM (3×). Combined organic layers, washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give 5-bromo-7,8-dichloro-1-(2,2-difluoropropyl)-1,2,4,9-tetrahydrospiro[carbazole-3,2'-[1,3]dioxolane](570 mg, 63%) as a yellow gum. ES/MS (m/z): 453.8/455.8/457.7 (M+H).

Intermediate 116

5-Bromo-7,8-dichloro-1-(2,2-difluoropropyl)-1,2,4,9-tetrahydro-3H-carbazol-3-one

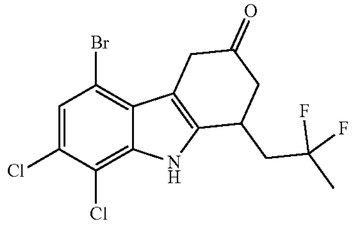 [SMILES: CC(F)(F)CC1CC(=O)Cc2c1[nH]c1c(Cl)c(Cl)cc(Br)c21]

To a solution of 5-bromo-7,8-dichloro-1-(2,2-difluoropropyl)-1,2,4,9-tetrahydrospiro[carbazole-3,2'-[1,3]dioxolane] (570 mg, 1.23 mmol, 98 mass %) in acetone (15 mL), added TFA (1.12 g, 9.82 mmol) by syringe under $N_2$ atmosphere. Stirred at 80° C. for 2 days under $N_2$ atmosphere. Concentrated under reduced pressure and triturated with EtOAc in PE to give 5-bromo-7,8-dichloro-1-(2,2-difluoropropyl)-1,2,4,9-tetrahydro-3H-carbazol-3-one (410 mg, 79%) as a white solid. ES/MS (m/z): 409.7/411.8/413.7 (M+H).

Intermediate 117

10-Bromo-7,8-dichloro-5-(2,2-difluoropropyl)-3,4,5,6-tetrahydroazepino[4,5-b]indol-2(1H)-one

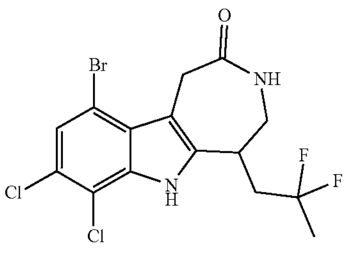 [SMILES: CC(F)(F)CC1CNC(=O)Cc2c1[nH]c1c(Cl)c(Cl)cc(Br)c21]

To a solution of 5-bromo-7,8-dichloro-1-(2,2-difluoropropyl)-1,2,4,9-tetrahydro-3H-carbazol-3-one (410 mg, 0.967 mmol, 97 mass %) in methanesulfonic acid (10 mL), added $NaN_3$ (70 mg, 1.1 mmol) slowly at 0° C. Stirred at 0° C. for 30 min, then at 25° C. for 16 hrs. Poured into ice-water and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with EtOAc in PE and concentrated under reduced pressure to give 10-bromo-7,8-dichloro-5-(2,2-difluoropropyl)-3,4,5,6-tetrahydroazepino[4,5-b]indol-2(1H)-one (160 mg, 37%) as a yellow solid. ES/MS (m/z): 424.8/426.7/428.5 (M+H).

Intermediate 118

7,8-Dichloro-5-(2,2-difluoropropyl)-10-(2-methyl-2H-1,2,3-triazol-4-yl)-3,4,5,6-tetrahydroazepino[4,5-b]indol-2(1H)-one

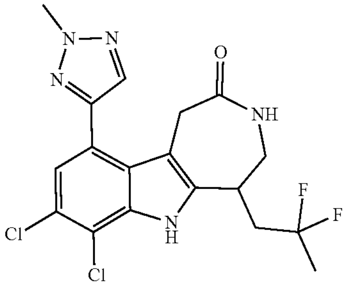 [SMILES: Cn1ncc(-c2cc(Cl)c(Cl)c3[nH]c4c(c23)CC(=O)NCC4CC(C)(F)F)n1]

Combined 10-bromo-7,8-dichloro-5-(2,2-difluoropropyl)-3,4,5,6-tetrahydroazepino[4,5-b]indol-2(1H)-one (160 mg, 0.360 mmol, 96 mass %), 2-methyl-4-(4,4,5,5-tetramethyl-1,3,2-dioxaborolan-2-yl)-2H-1,2,3-triazole (113 mg, 0.541 mmol), $Pd(dppf)Cl_2$ (26 mg, 0.036 mmol) and $Na_2CO_3$ (115 mg, 1.08 mmol) in 1,4-dioxane (8 mL) and $H_2O$ (2 mL). Degassed and purged with $N_2$ (×3). Stirred at 90° C. for 2 hrs. Concentrated under reduced pressure. Purified by silica gel flash chromatography eluting with EtOAc in PE, concentrated under reduced pressure, and further purified by reverse phase prep-HPLC to give 7,8-dichloro-5-(2,2-difluoropropyl)-10-(2-methyl-2H-1,2,3-triazol-4-yl)-3,4,5,6-tetrahydroazepino[4,5-b]indol-2(1H)-one (80 mg, 51%) as a yellow solid. ES/MS (m/z): ($^{35}Cl/^{37}Cl$) 428.1/430.1 (M+H).

Example 136

(R)-7,8-Dichloro-5-(2,2-difluoropropyl)-10-(2-methyl-2H-1,2,3-triazol-4-yl)-3,4,5,6-tetrahydroazepino[4,5-b]indol-2(1H)-one Or (S)-7,8-Dichloro-5-(2,2-difluoropropyl)-10-(2-methyl-2H-1,2,3-triazol-4-yl)-3,4,5,6-tetrahydroazepino[4,5-b]indol-2(1H)-one (isomer 1) and Example 137

(R)-7,8-Dichloro-5-(2,2-difluoropropyl)-10-(2-methyl-2H-1,2,3-triazol-4-yl)-3,4,5,6-tetrahydroazepino[4,5-b]indol-2(1H)-one Or (S)-7,8-Dichloro-5-(2,2-difluoropropyl)-10-(2-methyl-2H-1,2,3-triazol-4-yl)-3,4,5,6-tetrahydroazepino[4,5-b]indol-2(1H)-one (isomer 2)

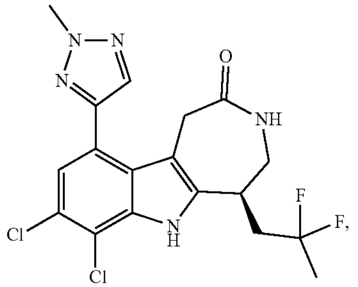

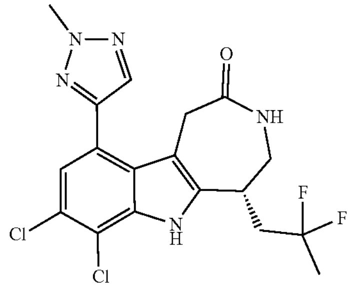

Purified 7,8-dichloro-5-(2,2-difluoropropyl)-10-(2-methyl-2H-1,2,3-triazol-4-yl)-3,4,5,6-tetrahydroazepino[4,5-b]indol-2(1H)-one (80 mg, 0.18 mmol, 98 mass %) by SFC to give the titled compounds (Isomer 1—Rt=1.996 min (100% ee), 32 mg, 40% as a white solid; Isomer 2-Rt=2.141 min (98.5% ee), 36 mg, 45% as a white solid). Column: DAICEL CHIRALCEL OX (30×250 mm, 10 μm); Mobile Phase: 30% EtOH (w/0.1% $NH_3H_2O$): 70% $CO_2$; FlowRate: 80 mL/min. ES/MS (m/z): ($^{35}Cl/^{37}Cl$) 428.1/430.0 (M+H).

Intermediate 119

2-(7,8-Dichloro-5-(2,2-difluoropropyl)-2-oxo-1,2,3,4,5,6-hexahydroazepino[4,5-b]indol-10-yl)acetonitrile

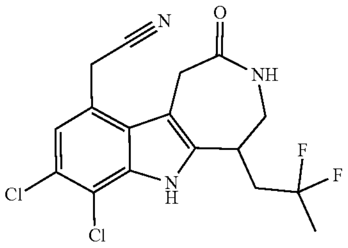 [SMILES: CC(F)(F)CC1CNC(=O)Cc2c1[nH]c1c(Cl)c(Cl)cc(CC#N)c21]

Combined 10-bromo-7,8-dichloro-5-(2,2-difluoropropyl)-3,4,5,6-tetrahydroazepino[4,5-b]indol-2(1H)-one (250 mg, 0.557 mmol, 95 mass %), 4-(4,4,5,5-tetramethyl-[1,3,2]dioxaborolan-2-yl)-isoxazole (134 mg, 0.669 mmol), $Pd(dppf)Cl_2$ (43 mg, 0.056 mmol) and KF (102 mg, 1.67 mmol) in DMSO (12 mL) and water (3 mL). Degassed and purged with $N_2$ (×3). Stirred at 100° C. for 1 hr, under $N_2$ atmosphere. Diluted with water and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with MeOH in DCM and concentrated under reduced pressure. Combined the residue and KF (186 mg, 3.04 mmol) in DMF (3 mL) and water (3 mL). Degassed and purged with $N_2$ (×3). Stirred at 100° C. for 16 hrs, under $N_2$ atmosphere. Diluted with water and extracted with EtOAc (3×). Combined organic layers, washed with saturated aqueous NaCl, dried over anhydrous $Na_2SO_4$, filtered, and concentrated under reduced pressure. Purified by reverse phase prep-HPLC to give 2-(7,8-dichloro-5-(2,2-difluoropropyl)-2-oxo-1,2,3,4,5,6-hexahydroazepino[4,5-b]indol-10-yl)acetonitrile (70 mg, 46%) as a white solid. ES/MS (m/z): ($^{35}Cl/^{37}Cl$) 386.0/388.0 (M+H).

Example 138

(R)-2-(7,8-Dichloro-5-(2,2-difluoropropyl)-2-oxo-1,2,3,4,5,6-hexahydroazepino[4,5-b]indol-10-yl)acetonitrile Or (S)-2-(7,8-Dichloro-5-(2,2-difluoropropyl)-2-oxo-1,2,3,4,5,6-hexahydroazepino[4,5-b]indol-10-yl)acetonitrile (isomer 1) and Example 139

(R)-2-(7,8-Dichloro-5-(2,2-difluoropropyl)-2-oxo-1,2,3,4,5,6-hexahydroazepino[4,5-b]indol-10-yl)acetonitrile Or (S)-2-(7,8-Dichloro-5-(2,2-difluoropropyl)-2-oxo-1,2,3,4,5,6-hexahydroazepino[4,5-b]indol-10-yl)acetonitrile (isomer 2)

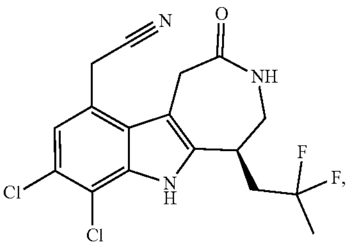

-continued

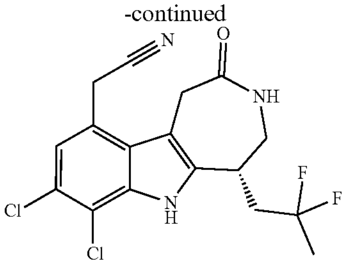

Purified racemic 2-(7,8-dichloro-5-(2,2-difluoropropyl)-2-oxo-1,2,3,4,5,6-hexahydroazepino[4,5-b]indol-10-yl)acetonitrile (70 mg, 0.18 mmol, 97 mass %) by SFC to give the titled compounds (Isomer 1—Rt=1.275 min (99.6% ee), 27.62 mg, 40% as a white solid; Isomer 2—Rt=1.466 min (98.7% ee), 25.35 mg, 37% as a white solid). Column: REGIS (S, S) WHELK-O1 (30×250 mm, 5 μm); Mobile Phase: 45% iPrOH (w/0.1% $NH_3H_2O$): 55% $CO_2$; Flow Rate: 80 mL/min. ES/MS (m/z): ($^{35}Cl/^{37}Cl$) 386.0/388.0 (M+H).

Intermediate 120

10-Bromo-7,8-dichloro-6-(difluoromethyl)-1-methyl-3,4,5,6-tetrahydroazepino[4,5-b]indol-2(1H)-one

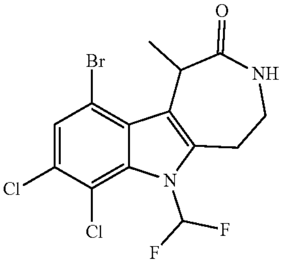 [SMILES: CC1C(=O)NCCc2c1c1c(Br)cc(Cl)c(Cl)c1n2C(F)F]

To a solution of 10-bromo-7,8-dichloro-1-methyl-3,4,5,6-tetrahydroazepino[4,5-b]indol-2(1H)-one (1.50 g, 4.14 mmol) in DMF (20 mL), added sodium hydride (331 mg, 8.29 mmol, 60 mass %) at 10° C. Stirred at 10° C. for 30 min. Added ethyl-2-bromo-2,2-difluoroacetate (1.02 g, 4.97 mmol) dropwise at 10° C. Stirred at 60° C. for 2 hrs. Quenched with saturated aqueous $NH_4Cl$ and extracted with EtOAc (3×). Combined organic layers, washed with saturated aqueous NaCl, dried over $Na_2SO_4$, filtered, and concentrated under reduced pressure. Purified by flash silica gel chromatography eluting with MeOH in DCM and concentrated under reduced pressure to give 10-bromo-7,8-dichloro-6-(difluoromethyl)-1-methyl-3,4,5,6-tetrahydroazepino[4,5-b]indol-2(1H)-one (800 mg, 38%). ES/MS (m/z): 410.8/412.8/414.7 (M+H).

Intermediate 121

10-((2-((tert-Butyldimethylsilyl)oxy)ethyl)amino)-7,8-dichloro-6-(difluoromethyl)-1-methyl-3,4,5,6-tetrahydroazepino[4,5-b]indol-2(1H)-one

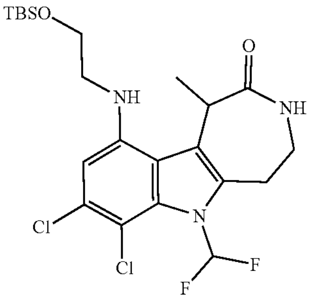 [SMILES: CC1C(=O)NCCc2c1c1c(NCCO[Si](C)(C)C(C)(C)C)cc(Cl)c(Cl)c1n2C(F)F]

Suspended 10-bromo-7,8-dichloro-6-(difluoromethyl)-1-methyl-3,4,5,6-tetrahydroazepino[4,5-b]indol-2(1H)-one (130 mg, 0.315 mmol) in 1,4-dioxane (5 mL) in a vial and purged with $N_2$ for 5 min. Added tris(dibezylideneacetone) dipalladium (29 mg, 0.031 mmol) and 4,5-bis(diphenylphosphino)-9,9-dimethyl xanthene (44 mg, 0.076 mmol) followed by 2-((tert-butyldimethylsilyl)oxy)ethan-1-amine (111 mg, 0.631 mmol) and potassium phosphate, tribasic (201 mg, 0.946 mmol). Sealed vial and heated to 100° C. for 18 hrs. Cooled to ambient temperature and poured into 1:1 water and saturated aqueous sodium bicarbonate. Extracted aqueous layer with EtOAc (×2). Combined the organics and washed with saturated sodium bicarbonate (2×) and saturated aqueous NaCl. Dried the organics over $Na_2SO_4$, filtered and concentrated under reduced pressure. Purified via flash chromatography eluting with hexanes/acetone to give 10-((2-((tert-butyldimethylsilyl)oxy)ethyl)amino)-7,8-dichloro-6-(difluoromethyl)-1-methyl-3,4,5,6-tetrahydroazepino[4,5-b]indol-2(1H)-one (75 mg, 47%). ES/MS (m/z): ($^{35}Cl/^{37}Cl$) 506.2/508.2 (M+H).

Example 140

7,8-Dichloro-6-(difluoromethyl)-10-((2-hydroxyethyl)amino)-1-methyl-3,4,5,6-tetrahydroazepino[4,5-b]indol-2(1H)-one

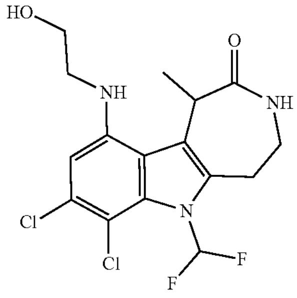 [SMILES: CC1C(=O)NCCc2c1c1c(NCCO)cc(Cl)c(Cl)c1n2C(F)F]

Dissolved 10-((2-((tert-butyldimethylsilyl)oxy)ethyl)amino)-7,8-dichloro-6-(difluoromethyl)-1-methyl-3,4,5,6-tetrahydroazepino[4,5-b]indol-2(1H)-one (75 mg, 0.15 mmol) in THF (2 mL), added TBAF (1.0M in THF) (0.44 mL, 0.44 mmol) and stirred at ambient temperature for 30 mins. Poured into water and extracted with EtOAc. Washed with 1:1 water and saturated aqueous sodium bicarbonate and saturated aqueous NaCl. Dried the organics over $Na_2SO_4$, filtered, and concentrated under reduced pressure. Purified via flash chromatography eluting with MeOH in DCM to give racemic 7,8-dichloro-6-(difluoromethyl)-10-((2-hydroxyethyl)amino)-1-methyl-3,4,5,6-tetrahydroazepino[4,5-b]indol-2(1H)-one (41 mg, 71%). ES/MS (m/z): ($^{35}Cl/^{37}Cl$) 392.0/394.0 (M+H).

Example 141

7,8-Dichloro-6-(difluoromethyl)-10-((2-methoxyethyl)amino)-1-methyl-3,4,5,6-tetrahydroazepino[4,5-b]indol-2(1H)-one

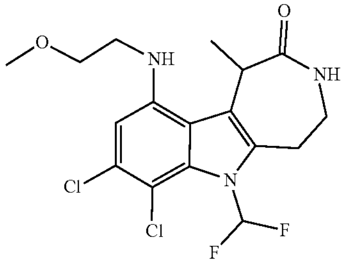 [SMILES: COCCNc1cc(Cl)c(Cl)c2c1c1c(n2C(F)F)CCNC(=O)C1C]

Combined 10-bromo-7,8-dichloro-6-(difluoromethyl)-1-methyl-3,4,5,6-tetrahydroazepino[4,5-b]indol-2(1H)-one (200 mg, 0.393 mmol, 81 mass %), 2-methoxyethan-1-amine (93 mg, 1.2 mmol), $Pd_2(dba)_3$ (38 mg, 0.039 mmol), Xantphos (48 mg, 0.079 mmol) and cesium carbonate (405 mg, 1.18 mmol) in 1,4-dioxane (8 mL) and THF (0.8 mL). Degassed and purged with $N_2$ (×3). Stirred at 110° C. for 16 hrs, under $N_2$ atmosphere. Cooled to ambient temperature. Concentrated under reduced pressure. Purified by silica gel flash chromatography eluting with MeOH in DCM and concentrated under reduced pressure. Purified further by prep-HPLC to give 7,8-dichloro-6-(difluoromethyl)-10-((2-methoxyethyl)amino)-1-methyl-3,4,5,6-tetrahydroazepino[4,5-b]indol-2(1H)-one (68.59 mg, 42%) as a white solid. ES/MS (m/z): ($^{35}Cl/^{37}Cl$) 406.1/408.1 (M+H).

Intermediate 122

(2S)—N-(7,8-Dichloro-6-(difluoromethyl)-1-methyl-2-oxo-1,2,3,4,5,6-hexahydroazepino[4,5-b]indol-10-yl)-2-hydroxypropanamide

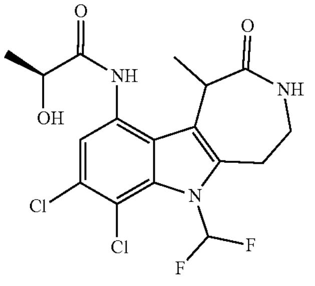 [SMILES: CC1C(=O)NCCc2c1c1c(NC(=O)[C@H](C)O)cc(Cl)c(Cl)c1n2C(F)F]

Combined 10-bromo-7,8-dichloro-6-(difluoromethyl)-1-methyl-3,4,5,6-tetrahydroazepino[4,5-b]indol-2(1H)-one (200 mg, 0.393 mmol, 81 mass %), (S)-2-hydroxypropanamide (81 mg, 0.87 mmol), $Pd_2(dba)_3$ (36 mg, 0.039 mmol), Xantphos (47 mg, 0.079 mmol) and cesium carbonate (453 mg, 1.38 mmol) in 1,4-dioxane (20 mL) and THF (1 mL). Degassed and purged with $N_2$ (×3). Stirred at 110° C. for 16 hrs. Concentrated under reduced pressure. Purified by silica gel flash chromatography eluting with MeOH in DCM and concentrated under reduced pressure. Purified further by SFC (Column: DAICEL CHIRALPAK IG (30×250 mm, 10 μm); Mobile Phase: 30% iPrOH (w/0.1% $NH_3H_2O$): 70% $CO_2$; FlowRate: 80 mL/min) to give diastereomeric mixture (2S)—N-(7,8-dichloro-6-(difluoromethyl)-1-methyl-2-oxo-1,2,3,4,5,6-hexahydroazepino[4,5-b]indol-10-yl)-2-hydroxypropanamide (50 mg, 30%) as a yellow solid. ES/MS (m/z): ($^{35}Cl/^{37}Cl$) 419.9/421.8 (M+H).

Example 142

(2S)—N—((S)-7,8-Dichloro-6-(difluoromethyl)-1-methyl-2-oxo-1,2,3,4,5,6-hexahydroazepino[4,5-b]indol-10-yl)-2-hydroxypropanamide Or (2S)—N—((R)-7,8-Dichloro-6-(difluoromethyl)-1-methyl-2-oxo-1,2,3,4,5,6-hexahydroazepino[4,5-b]indol-10-yl)-2-hydroxypropanamide (isomer 1) and Example 143

(2S)—N—((S)-7,8-Dichloro-6-(difluoromethyl)-1-methyl-2-oxo-1,2,3,4,5,6-hexahydroazepino[4,5-b]indol-10-yl)-2-hydroxypropanamide Or (2S)—N—((R)-7,8-Dichloro-6-(difluoromethyl)-1-methyl-2-oxo-1,2,3,4,5,6-hexahydroazepino[4,5-b]indol-10-yl)-2-hydroxypropanamide (isomer 2)

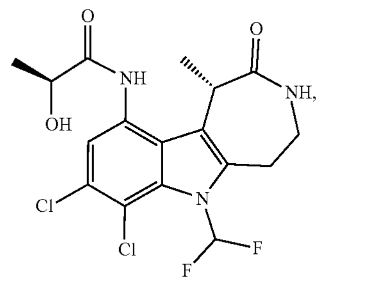

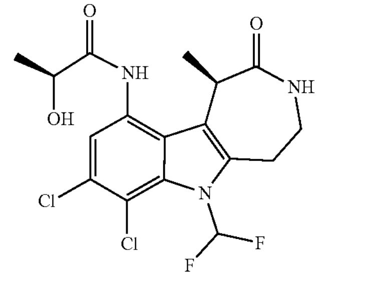

Purified diastereomeric mixture (2S)—N-(7,8-dichloro-6-(difluoromethyl)-1-methyl-2-oxo-1,2,3,4,5,6-hexahydroazepino[4,5-b]indol-10-yl)-2-hydroxypropanamide (206 mg, 0.483 mmol) by SFC to give the titled compounds (Isomer 1-Rt=1.212 min (99.1% de), 97.70 mg, 46% as an off-white solid; Isomer 2—Rt=1.603 min (98.4% de), 75.01 mg, 36% as an off-white solid). Column: ChiralPak IH, 30×250 mm, 10 μm); Mobile Please: 40% EtOH (w/ 0.1% $NH_3H_2O$): 60% $CO_2$; FlowRate: 80 mL/min. ES/MS m/z: ($^{35}Cl/^{37}Cl$) 420.1/422.1 (M+H).

Example 144

N-(7,8-Dichloro-6-(difluoromethyl)-1-methyl-2-oxo-1,2,3,4,5,6-hexahydroazepino[4,5-b]indol-10-yl)-2-hydroxyacetamide

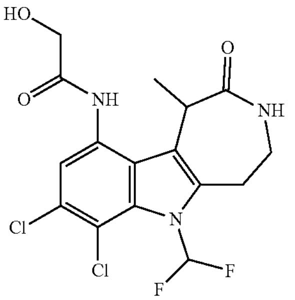 [SMILES: CC1C(=O)NCCc2c1c1c(NC(=O)CO)cc(Cl)c(Cl)c1n2C(F)F]

Suspended racemic 10-bromo-7,8-dichloro-6-(difluoromethyl)-1-methyl-3,4,5,6-tetrahydroazepino[4,5-b]indol-2(1H)-one (130 mg, 0.315 mmol) in 1,4-dioxane (5 mL) in a vial and purged with $N_2$ for 5 min. Added tris(dibenzylideneacetone)dipalladium (29 mg, 0.031 mmol) and 4,5-bis(diphenylphosphino)-9,9-dimethyl xanthene (44 mg, 0.075 mmol) followed by 2-hydroxyacetamide (47 mg, 0.63 mmol) and tripotassium phosphate (201 mg, 0.946 mmol). Sealed vial and heated to 100° C. for 18 hrs. Cooled to ambient temperature and poured into 1:1 water and saturated aqueous sodium bicarbonate. Extracted aqueous layer with EtOAc (2×). Combined the organics and washed with saturated sodium bicarbonate (2×) and saturated aqueous NaCl. Dried the organics over $Na_2SO_4$, filtered, and concentrated under reduced pressure. Purified via flash chromatography eluting with hexanes/acetone to give N-(7,8-dichloro-6-(difluoromethyl)-1-methyl-2-oxo-1,2,3,4,5,6-hexahydroazepino[4,5-b]indol-10-yl)-2-hydroxyacetamide (16 mg, 12%). ES/MS (m/z): ($^{35}Cl/^{37}Cl$) 406.0/408.0 (M+H).

Intermediate 123

2-((tert-Butyldimethylsilyl)oxy)-N-(7,8-dichloro-6-(difluoromethyl)-1-methyl-2-oxo-1,2,3,4,5,6-hexahydroazepino[4,5-b]indol-10-yl)acetamide

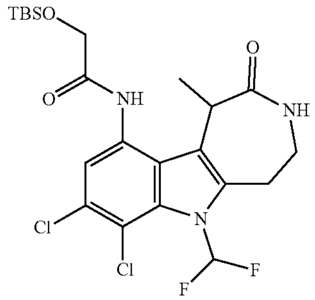 [SMILES: CC1C(=O)NCCc2c1c1c(NC(=O)CO[Si](C)(C)C(C)(C)C)cc(Cl)c(Cl)c1n2C(F)F]

Suspended 10-bromo-7,8-dichloro-6-(difluoromethyl)-1-methyl-3,4,5,6-tetrahydroazepino[4,5-b]indol-2(1H)-one (0.70 g, 1.7 mmol) in 1,4-dioxane (13 mL) and purged with $N_2$ for 5 mins. Added 2-((tert-butyldimethylsilyl)oxy)acetamide (0.80 mg, 4.2 mmol), potassium phosphate, tribasic (1.3 g, 5.9 mmol), tris(dibenzylideneacetone)dipalladium(0) (39 mg, 0.042 mmol) 4,5-bis(diphenylphosphino)9,9-dimethyl xanthene (59 mg, 0.10 mmol) then heated to reflux for 4 hrs. Cooled reaction to −70° C., then added 100 mL EtOAc and water. Separated the layers and extracted with EtOAc. Washed the combined organics with 1:1 saturated aqueous sodium bicarbonate/water and saturated aqueous NaCl. Dried over $Na_2SO_4$, filtered, and concentrated under reduced pressure. Purified the material by flash chromatography eluting with hexanes/acetone to give 2-((tert-butyldimethylsilyl)oxy)-N-(7,8-dichloro-6-(difluoromethyl)-1-methyl-2-oxo-1,2,3,4,5,6-hexahydroazepino[4,5-b]indol-10-yl)acetamide (0.43 g, 49%). ES/MS (m/z): ($^{35}Cl/^{37}Cl$) 520.2/522.2 (M+H).

Intermediates 124

(R)-2-((tert-Butyl dimethyl silyl)oxy)-N-(7,8-dichloro-6-(difluoromethyl)-1-methyl-2-oxo-1,2,3,4,5,6-hexahydroazepino[4,5-b]indol-10-yl)acetamide Or (S)-2-((tert-Butyldimethylsilyl)oxy)-N-(7,8-dichloro-6-(difluoromethyl)-1-methyl-2-oxo-1,2,3,4,5,6-hexahydroazepino[4,5-b]indol-10-yl)acetamide (isomer 1) and Intermediates 125

(R)-2-((tert-Butyl dimethyl silyl)oxy)-N-(7,8-dichloro-6-(difluoromethyl)-1-methyl-2-oxo-1,2,3,4,5,6-hexahydroazepino[4,5-b]indol-10-yl)acetamide Or (S)-2-((tert-Butyldimethylsilyl)oxy)-N-(7,8-dichloro-6-(difluoromethyl)-1-methyl-2-oxo-1,2,3,4,5,6-hexahydroazepino[4,5-b]indol-10-yl)acetamide (isomer 2)

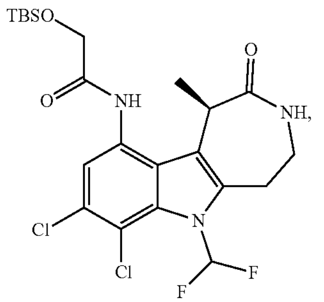

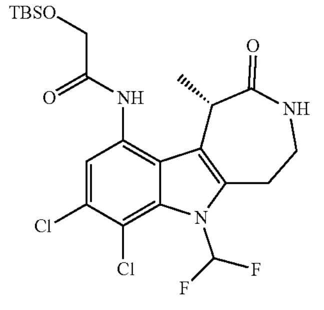

Purified racemic 2-((tert-butyldimethylsilyl)oxy)-N-(7,8-dichloro-6-(difluoromethyl)-1-methyl-2-oxo-1,2,3,4,5,6-hexahydroazepino[4,5-b]indol-10-yl)acetamide (0.42 g, 0.81 mmol) by SFC to give the titled compounds (Isomer 1—RT=1.267 min (99% ee), 191 mg, 45%; Isomer-2—RT=2.353 min (99% ee), 201 mg, 48%). Column: Chiralpak IC, 21×150 mm; Mobile Phase: 25% MeOH (0.5% DMEA): 75% $CO_2$; Flow Rate: 80 mL/min; Column temperature: 40° C.; Detection: 225 nM, ES/MS (m/z): ($^{35}Cl/^{37}Cl$) 520.0.0/522.0 (M+H).

Example 145

(R)—N-(7,8-Dichloro-6-(difluoromethyl)-1-methyl-2-oxo-1,2,3,4,5,6-hexahydroazepino[4,5-b]indol-10-yl)-2-hydroxyacetamide or (S)—N-(7,8-Dichloro-6-(difluoromethyl)-1-methyl-2-oxo-1,2,3,4,5,6-hexahydroazepino[4,5-b]indol-10-yl)-2-hydroxyacetamide

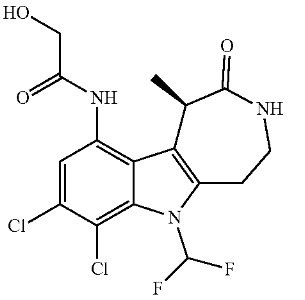

or

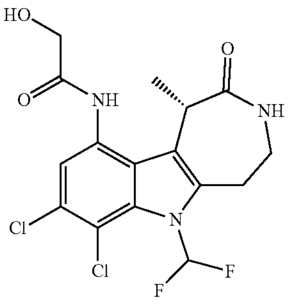

Dissolved single isomer 2-((tert-butyldimethylsilyl)oxy)-N-(7,8-dichloro-6-(difluoromethyl)-1-methyl-2-oxo-1,2,3,4,5,6-hexahydroazepino[4,5-b]indol-10-yl)acetamide (Isomer 1, 0.191 g, 0.367 mmol) in THF (4 mL) and added TBAF (1.0M in THF) (1.4 mL, 1.47 mmol). Stirred at ambient temperature for 1 hr. Added ethyl acetate and washed with water (2×) and saturated aqueous NaCl (2×). Dried organics over $Na_2SO_4$, filtered, and concentrated under reduced pressure. Purified via flash chromatography eluting with MeOH in DCM to give (R)—N (7,8-dichloro-6-(difluoromethyl)-1-methyl-2-oxo-1,2,3,4,5,6-hexahydroazepino[4,5-b]indol-10-yl)-2-hydroxyacetamide or (S)—N-(7,8-dichloro-6-(difluoromethyl)-1-methyl-2-oxo-1,2,3,4,5,6-hexahydroazepino[4,5-b]indol-10-yl)-2-hydroxyacetamide (119 mg, 97%). ES/MS (m/z): ($^{35}Cl/^{37}Cl$) 406.0/408.0 (M+H).

Intermediate 126

Methyl 8-oxo-1,4-dioxaspiro[4.5]decane-7-carboxylate

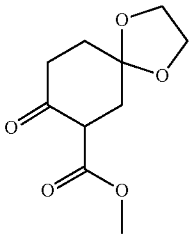

Rinsed sodium hydride (20.5 g, 512 mmol, 60% in mineral oil) with hexanes three times in a 2 L flask and purged the flask with $N_2$. Added a solution of 1,4-dioxaspiro[4.5]decan-8-one (40.0 g, 256 mmol) in THF (1.0 L) over 15 minutes at ambient temperature. Stirred at ambient temperature for 30 min and added dimethyl carbonate (46.1 g, 512 mmol). Stirred the resulting suspension for 3 days and then filtered allowing the filtrate to flow into a stirring mixture of water and EtOAc. Brought the aqueous layer to pH 7 by the slow addition of 5M HCl and separated the layers. Washed the organic layer with water and saturated aqueous sodium chloride, filtered, and dried over anhydrous $Na_2SO_4$. Repeated the reaction on an identical scale and combined the crude product solutions. Concentrated under reduced pressure to give an amber oil. Dissolved the oil in toluene, concentrated under reduced pressure, and further dried under reduced pressure to give methyl 8-oxo-1,4-dioxaspiro[4.5]decane-7-carboxylate (96.78 g, 80%, 90% purity) as an amber oil that crystallized to a light amber solid upon standing. ES/MS (m/z): 215.0 (M+H).

Intermediate 127

Methyl 7-methyl-8-oxo-1,4-dioxaspiro[4.5]decane-7-carboxylate

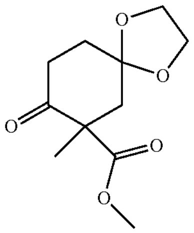 [SMILES: COC(=O)C1(C)CC2(CCC1=O)OCCO2]

Combined methyl 8-oxo-1,4-dioxaspiro[4.5]decane-7-carboxylate (8.40 g, 32.9 mmol, 84% purity), potassium carbonate (6.57 g, 47.1 mmol), and DMF (105 mL). Purged with $N_2$, stirred at ambient temperature for 15 min, and added iodomethane (2.93 mL, 47.0 mmol) dropwise. Stirred at ambient temperature for 22 hours, added 50 mL of water, and added 5M HCl slowly until pH 7. Concentrated under reduced pressure, partitioned the residue between EtOAc and water, and separated the layers. Washed the organic layer with water and saturated aqueous NaCl, filtered, dried over anhydrous $Na_2SO_4$, and concentrated under reduced pressure. Purified by silica gel flash chromatography eluting with EtOAc in hexanes and dried under reduced pressure to give methyl 7-methyl-8-oxo-1,4-dioxaspiro[4.5]decane-7-carboxylate (7.66 g, 100%) as a colorless oil. GCMS (m/z): 228.1. $^1$H NMR ($CDCl_3$): 4.08-3.93 (m, 4H), 3.72 (s, 3H), 3.07-2.97 (m, 1H), 2.68 (ddd, J=14.0, 2.4, 1.4 Hz, 1H), 2.54-2.48 (ddd, J=14.8, 4.5, 4.0 Hz, 1H), 2.05-1.98 (m, 2H), 1.72 (d, J=14.0 Hz, 1H), 1.29 (s, 3H).

Intermediate 128

Methyl (E)-8-(2-(5-bromo-2,3-dichlorophenyl)hydrazineylidene)-7-methyl-1,4-dioxaspiro[4.5]decane-7-carboxylate

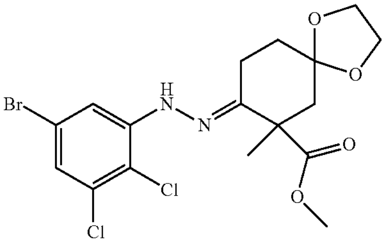 [SMILES: COC(=O)C1(C)CC2(CC/C1=N\Nc1cc(Br)cc(Cl)c1Cl)OCCO2]

Combined methyl 7-methyl-8-oxo-1,4-dioxaspiro[4.5]decane-7-carboxylate (7.13 g, 30.6 mmol), (5-bromo-2,3-dichlorophenyl)hydrazine (8.00 g, 30.6 mmol), MeOH (61 mL), and acetic acid (1.8 mL, 31 mmol) under $N_2$. Refluxed for 3 hrs, cooled to ambient temperature, and placed into an ice water bath for 1 hr. Collected the solids by vacuum filtration, washed with MeOH (3×), and dried to give methyl (E)-8-(2-(5-bromo-2,3-dichlorophenyl)hydrazineylidene)-7-methyl-1,4-dioxaspiro[4.5]decane-7-carboxylate (13.43 g, 94%) as a white solid. ES/MS (m/z): 464.8/466.8/468.8 (M+H).

Intermediate 129

Methyl 5-bromo-7,8-dichloro-1-methyl-1,2,4,9-tetrahydrospiro[carb azole-3,2'-[1,3]dioxolane]-1-carboxylate

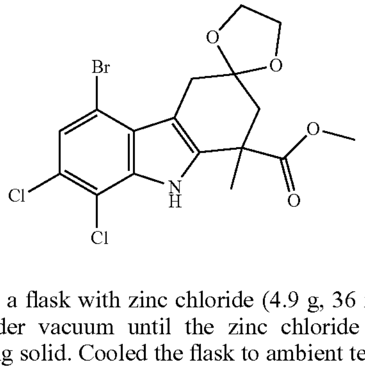

Charged a flask with zinc chloride (4.9 g, 36 mmol) and heated under vacuum until the zinc chloride became a free-flowing solid. Cooled the flask to ambient temperature, and added methyl (E)-8-(2-(5-bromo-2,3-dichlorophenyl)hydrazineylidene)-7-methyl-1,4-dioxaspiro[4.5]decane-7-carboxylate (14.0 g, 30.0 mmol, azeotroped with 50 mL of toluene immediately before use) and toluene (200 mL) under $N_2$. Purged with $N_2$ and refluxed for 2 days. Concentrated under reduced pressure, added zinc chloride (4.9 g, 36 mmol, dried as above) and xylenes (100 mL). Purged with $N_2$ and refluxed for 4 days. Cooled to ambient temperature, added EtOAc and saturated aqueous sodium bicarbonate, and then added 5M HCl slowly until pH 7. Separated the layers and extracted the aqueous layer with EtOAc (2×). Washed the combined organic layers with saturated aqueous sodium chloride, filtered, dried over anhydrous $Na_2SO_4$, and concentrated under reduced pressure. Purified by silica gel flash chromatography eluting with DCM. Concentrated the mixed fractions under reduced pressure and recrystallized the residue from DCM. Combined the crystals with the pure chromatography fractions, concentrated under reduced pressure, and further dried under reduced pressure at 80° C. to give methyl 5-bromo-7,8-dichloro-1-methyl-1,2,4,9-tetrahydrospiro[carbazole-3,2'-[1,3]dioxolane]-1-carboxylate (6.96 g, 50%) as a tan solid. ES/MS (m/z): 447.8/449.8/451.8 (M+H).

Intermediate 130

5-Bromo-7,8-dichloro-1-methyl-1,2,4,9-tetrahydrospiro[carbazole-3,2'-[1,3]dioxolane]-1-carboxylic acid

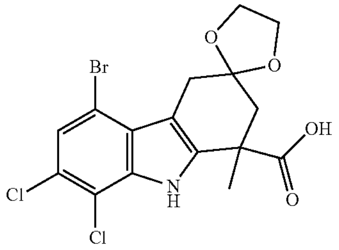 [SMILES: CC1(C(=O)O)CC2(Cc3c1[nH]c1c(Cl)c(Cl)cc(Br)c31)OCCO2]

Combined methyl 5-bromo-7,8-dichloro-1-methyl-1,2,4,9-tetrahydrospiro[carbazole-3,2'-[1,3]dioxolane]-1-carboxylate (5.69 g, 12.2 mmol), THF (61 mL), and MeOH (61 mL). Added 5M aqueous sodium hydroxide (4.87 mL, 24.4 mmol) and stirred at ambient temperature for 28 hrs. Added 5M aqueous HCl (4.87 mL, 24.4 mmol) dropwise and concentrated under reduced pressure. Suspended the residue in DCM, filtered, and rinsed the solids with DCM. Dried the filtrate over anhydrous $Na_2SO_4$, concentrated under reduced pressure, and further dried under reduced pressure to give 5-bromo-7,8-dichloro-1-methyl-1,2,4,9-tetrahydrospiro[carbazole-3,2'-[1,3]dioxolane]-1-carboxylic acid (5.40 g, 90%, 88% purity) as a brown solid. ES/MS (m/z): 433.8/435.8/437.8 (M+H).

Intermediate 131

5-Bromo-7,8-dichloro-1-methyl-1,2,4,9-tetrahydro-3H-carbazol-3-one

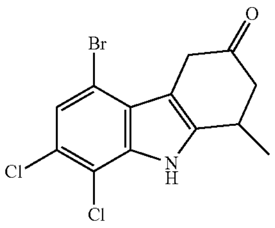 [SMILES: CC1CC(=O)Cc2c1[nH]c1c(Cl)c(Cl)cc(Br)c21]

Combined 5-bromo-7,8-dichloro-1-methyl-1,2,4,9-tetrahydrospiro[carbazole-3,2'-[1,3]dioxolane]-1-carboxylic acid (5.40 g, 10.9 mmol, 88% purity, azeotroped with toluene immediately before use) and acetic acid (44 mL) under $N_2$. Purged with nitrogen and stirred at 120° C. for 4 days. Cooled to ambient temperature, concentrated under reduced pressure, and azeotroped twice with toluene to give 5-bromo-7,8-dichloro-1-methyl-1,2,4,9-tetrahydro-3H-carbazol-3-one (5.37 g, >99%, 72% purity) as an orangish-brown solid. ES/MS (m/z): 343.8/345.8/347.8 (M−H).

Intermediate 132

10-Bromo-7,8-dichloro-5-methyl-3,4,5,6-tetrahydroazepino[4,5-b]indol-2(1H)-one

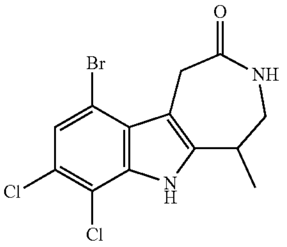 [SMILES: CC1CNC(=O)Cc2c1[nH]c1c(Cl)c(Cl)cc(Br)c21]

Cooled a suspension of 5-bromo-7,8-dichloro-1-methyl-1,2,4,9-tetrahydro-3H-carbazol-3-one (5.37 g, 11.1 mmol, 72% purity) in methanesulfonic acid (74 mL) in an ice water bath until the solvent was almost frozen. Added sodium azide (732 mg, 11.1 mmol) slowly and stirred the mixture at ambient temperature for 1 hr. Added more sodium azide (241 mg, 3.67 mmol) slowly and stirred the mixture at ambient temperature for 30 min. Added the reaction mixture dropwise to a mixture of ice and 2M aqueous potassium carbonate with stirring. Diluted the resulting suspension with EtOAc and separated the layers. Washed the organic layer with saturated aqueous NaCl, filtered, dried over anhydrous $Na_2SO_4$, and concentrated under reduced pressure. Suspended the residue in 9:1 DCM/MeOH, collected the solids by vacuum filtration, washed with DCM (2×), and dried to give 10-bromo-7,8-dichloro-5-methyl-3,4,5,6-tetrahydroazepino[4,5-b]indol-2(1H)-one (2.095 g, 45%, 86% purity) as a yellow solid. ES/MS (m/z): 358.8/360.8/362.8 (M−H).

Intermediate 133

7,8-Dichloro-5-methyl-10-(2-methyl-2H-1,2,3-triazol-4-yl)-3,4,5,6-tetrahydroazepino[4,5-b]indol-2(1H)-one

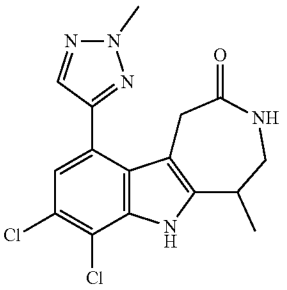 [SMILES: CC1CNC(=O)Cc2c1[nH]c1c(Cl)c(Cl)cc(-c3cnn(C)n3)c21]

Combined 10-bromo-7,8-dichloro-5-methyl-3,4,5,6-tetrahydroazepino[4,5-b]indol-2(1H)-one (1.00 g, 2.26 mmol, 82% purity), 2-methyl-4-(4,4,5,5-tetramethyl-1,3,2-dioxaborolan-2-yl)-2H-1,2,3-triazole (710 mg, 3.40 mmol), potassium carbonate (939 mg, 6.79 mmol), Pd(dppf)$Cl_2$ (222 mg, 0.272 mmol), 1,4-dioxane (15 mL), and water (3 mL). Purged with $N_2$ and heated to 100° C. for 2 hrs. Cooled to ambient temperature, diluted with EtOAc, filtered through a plug of silica gel, rinsed thoroughly through the silica with 90% EtOAc/10% MeOH, and concentrated the filtrate under reduced pressure to give a residue. Suspended the residue in DCM/MeOH (9:1), sonicated, collected the solids by vacuum filtration, and washed with DCM/MeOH (9:1) and then with DCM. Purified the filtrate by flash column chromatography eluting with MeOH in EtOAc and combined the product-containing fractions with the solids from the filtration. Purified further by reverse phase chromatography to give racemic 7,8-dichloro-5-methyl-10-(2-methyl-2H-1,2,3-triazol-4-yl)-3,4,5,6-tetrahydroazepino[4,5-b]indol-2(1H)-one (513 mg, 62%) as an off-white solid. ES-MS (m/z): ($^{35}Cl/^{37}Cl$) 364.0/366.0 (M+H).

Example 146

(R)-7,8-Dichloro-5-methyl-10-(2-methyl-2H-1,2,3-triazol-4-yl)-3,4,5,6-tetrahydroazepino[4,5-b]indol-2(1H)-one Or (S)-7,8-Dichloro-5-methyl-10-(2-methyl-2H-1,2,3-triazol-4-yl)-3,4,5,6-tetrahydroazepino[4,5-b]indol-2(1H)-one (isomer 1) and Example 147

(R)-7,8-Dichloro-5-methyl-10-(2-methyl-2H-1,2,3-triazol-4-yl)-3,4,5,6-tetrahydroazepino[4,5-b]indol-2(1H)-one Or (S)-7,8-Dichloro-5-methyl-10-(2-methyl-2H-1,2,3-triazol-4-yl)-3,4,5,6-tetrahydroazepino[4,5-b]indol-2(1H)-one (isomer 2)

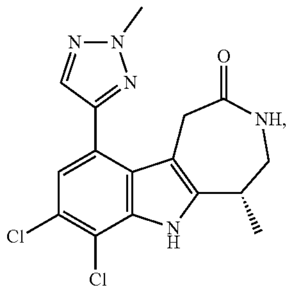

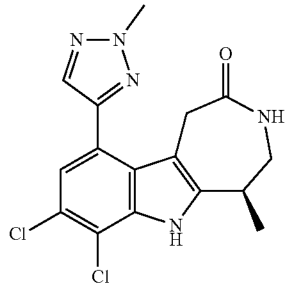

Purified racemic 7,8-dichloro-5-methyl-10-(2-methyl-2H-1,2,3-triazol-4-yl)-3,4,5,6-tetrahydroazepino[4,5-b]indol-2(1H)-one (513 mg, 1.41 mmol) by SFC to give the titled compounds (Isomer 1—RT=0.90 min (100% ee), 201 mg, 39%; Isomer 2—RT=1.38 min (100% ee), 229 mg, 45%; chiral analysis used 30% MeOH (0.5% DMEA): 70% $CO_2$). Column: Chiralpak AD-H, 30×250 mm; Mobile Phase: 40% MeOH (0.5% DMEA): 60% $CO_2$; Flow Rate: 100 mL/min; Column temperature: 40° C.; (Detection: 235 nM, ES/MS (m/z): ($^{35}Cl/^{37}Cl$) 364.0/366.0 (M+H). $^1H$ NMR (DMSO-d6): 11.54 (s, 1H), 7.96 (s, 1H), 7.73 (t, J=6.4 Hz, 1H), 7.15 (s, 1H), 4.24 (s, 3H), 3.55 (ddd, J=14.6, 6.5, 3.3 Hz, 1H), 3.35-3.28 (m, 2H), 3.27 (dd, J=14.6, 6.5 Hz, 1H), 3.16-3.06 (m, 1H), 1.30 (d, J=7.0 Hz, 3H).

Intermediate 134

7,8-Dichloro-10-hydroxy-5-methyl-3,4,5,6-tetrahydroazepino[4,5-b]indol-2(1H)-one

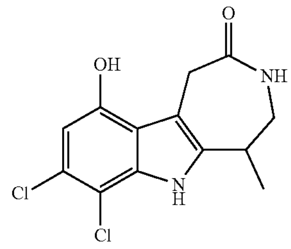 [SMILES: CC1CNC(=O)Cc2c1[nH]c1c(Cl)c(Cl)cc(O)c21]

Dissolved 10-bromo-7,8-dichloro-5-methyl-3,4,5,6-tetrahydroazepino[4,5-b]indol-2(1H)-one (430 mg, 0.950 mmol, 80 mass %) in 1,4-dioxane (9 mL) and water (3 mL). Added sodium tert-butoxide (280 mg, 2.83 mmol) and tert-BuBrettPhos-Pd-G3 (100 mg, 0.115 mmol). Degassed and purged with $N_2$ (×3) and stirred at 65° C. for 3 hrs. Diluted with water (100 mL) and extracted with 100 mL of EtOAc (3×). Washed the organic layer with saturated aqueous NaCl and dried over anhydrous $Na_2SO_4$. Filtered and concentrated under reduced pressure. Purified the residue by silica gel flash column chromatography eluting with MeOH in DCM to give racemic 7,8-dichloro-10-hydroxy-5-methyl-3,4,5,6-tetrahydroazepino[4,5-b]indol-2(1H)-one (70 mg, 90 mass %, 22%) as a yellow oil. ES/MS (m/z): ($^{35}Cl/^{37}Cl$) 299.1/300.9 (M+H).

Intermediate 135

2-((7,8-Dichloro-5-methyl-2-oxo-1,2,3,4,5,6-hexahydroazepino[4,5-b]indol-10-yl)oxy)acetonitrile

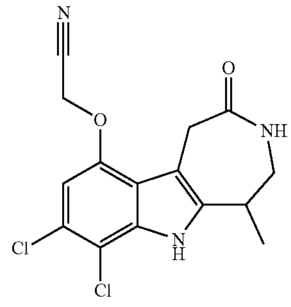 [SMILES: CC1CNC(=O)Cc2c1[nH]c1c(Cl)c(Cl)cc(OCC#N)c21]

Dissolved 7,8-dichloro-10-hydroxy-5-methyl-3,4,5,6-tetrahydroazepino[4,5-b]indol-2(1H)-one (70 mg, 0.187 mmol, 80 mass %) in DMF (4 mL). Added potassium carbonate (80 mg, 0.579 mmol) and bromoacetonitrile (30 μL, 0.430 mmol). Stirred at ambient temperature for 3 hrs. The reaction was diluted with water (100 mL), extracted with EtOAc (100 mL×3), dried over anhydrous $Na_2SO_4$, filtered, and concentrated under reduced pressure. Purified by silica gel flash column chromatography eluting with MeOH in DCM to give racemic 2-((7,8-dichloro-5-methyl-2-oxo-1,2,3,4,5,6-hexahydroazepino[4,5-b]indol-10-yl)oxy) acetonitrile (60 mg, 83 mass %, 79%) as a yellow oil. ES/MS (m/z): ($^{35}Cl/^{37}Cl$) 338.1/340.0 (M+H).

Example 148

(R)-2-((7,8-Dichloro-5-methyl-2-oxo-1,2,3,4,5,6-hexahydroazepino[4,5-b]indol-10-yl)oxy)acetonitrile Or (S)-2-((7,8-Dichloro-5-methyl-2-oxo-1,2,3,4,5,6-hexahydroazepino[4,5-b]indol-10-yl)oxy)acetonitrile (isomer 1) and Example 149

(R)-2-((7,8-Dichloro-5-methyl-2-oxo-1,2,3,4,5,6-hexahydroazepino[4,5-b]indol-10-yl)oxy)acetonitrile Or (S)-2-((7,8-Dichloro-5-methyl-2-oxo-1,2,3,4,5,6-hexahydroazepino[4,5-b]indol-10-yl)oxy)acetonitrile (isomer 2)

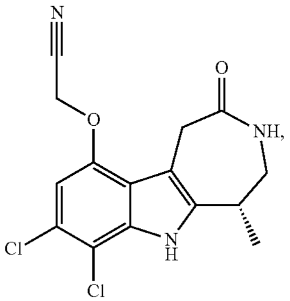

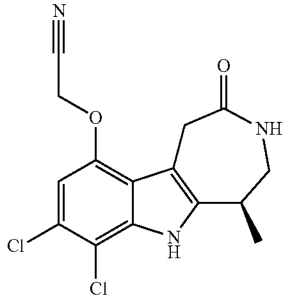

2-((7,8-Dichloro-5-methyl-2-oxo-1,2,3,4,5,6-hexahydroazepino[4,5-b]indol-10-yl)oxy)acetonitrile (60 mg, 83 mass % 0.147 mmol) was purified by SFC to give 2-((7,8-dichloro-5-methyl-2-oxo-1,2,3,4,5,6-hexahydroazepino[4,5-b]indol-10-yl)oxy)acetonitrile as separated enantiomers (Isomer 1—Rt=1.95 min (100% ee), 8.53 mg, 17%; Isomer 2—Rt=2.42 min (>99% ee), 13.05 mg, 25%). Column: DAICEL CHIRALPAK AD (250 mm×30 mm, 10 μm); Mobile Phase: 50% $CO_2$: 50% EtOH (0.1% $NH_3H_2O$); Flow Rate: 80 mL/min). (Chiral analysis used—Column: Chiralpak AD, 50×4.6 mm, 3 μm; Mobile Phase: 5-40% EtOH (0.1% $NH_3H_2O$) and $CO_2$; Flow Rate: 4 mL/min). ES/MS (m/z): ($^{35}Cl/^{37}Cl$) 338.0/339.9 (M+H).

Intermediate 136

10-Bromo-7,8-dichloro-1,5-dimethyl-3,4,5,6-tetrahydroazepino[4,5-b]indol-2(1H)-one

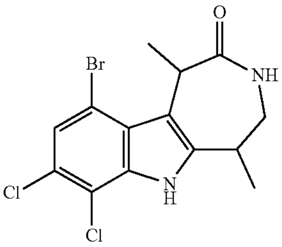

Combined 10-bromo-7,8-dichloro-5-methyl-3,4,5,6-tetrahydroazepino[4,5-b]indol-2(1H)-one (1.39 g, 3.84 mmol) and EtOAc (38.4 mL). Stirred for 5 min at ambient temperature to produce a beige slurry. Added pyridinium tribromide (1.96 g, 6.14 mmol) and stirred overnight. Cooled in an ice bath, added sodium ethoxide (11.5 mL, 30.7 mmol, 21 wt % in ethanol) dropwise, and stirred overnight. Quenched with ice/water and extracted with EtOAc (×5). Washed the combined organic layers with saturated aqueous NaCl, dried over $Na_2SO_4$, and concentrated under reduced pressure. Dissolved the residue in THF (17.1 mL) and added dropwise to a mixture of MeMgBr (7.30 mL, 21.9 mmol, 3M in diethyl ether) and THF (8.55 mL) precooled in an ice bath. Stirred at 0° C. for 30 min. Quenched with aqueous ammonium chloride and extracted with EtOAc (×5). Combined organic layers, washed with saturated aqueous NaCl, and dried over anhydrous $Na_2SO_4$. Evaporated under $N_2$ stream to give crude 10-bromo-7,8-dichloro-1,5-dimethyl-3,4,5,6-tetrahydroazepino[4,5-b]indol-2(1H)-one (1.585 g, 2.1 mmol, 77%, 50% purity) as a brown solid. ES/MS (m/z): 374.8/376.8/378.8 (M+H).

Intermediate 137

2-(7,8-Dichloro-1,5-dimethyl-2-oxo-1,2,3,4,5,6-hexahydroazepino[4,5-b]indol-10-yl)acetonitrile

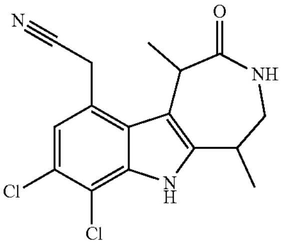 [SMILES: CC1CNC(=O)C(C)c2c1[nH]c1c(Cl)c(Cl)cc(CC#N)c21]

Combined 10-bromo-7,8-dichloro-1,5-dimethyl-3,4,5,6-tetrahydroazepino[4,5-b]indol-2(1H)-one (0.5 g, 0.7 mmol, 50% purity), 4-(4,4,5,5-tetramethyl-[1,3,2]dioxaborolan-2-yl)-isoxazole (0.4 g, 2 mmol), potassium fluoride (0.2 g, 4 mmol), Pd(dppf)$Cl_2$ (0.1 g, 0.2 mmol), DMSO (0.01 L), and water (3 mL). Purged with nitrogen, placed into a heating block set at 100° C., and stirred for 1 hr 50 min at 100° C. Cooled to ambient temperature, diluted with EtOAc, and filtered. Washed the filtrate with water, dried over $Na_2SO_4$, filtered, and concentrated under reduced pressure. Purified the crude product by silica gel flash column chromatography eluting with MeOH in EtOAc to give 2-(7,8-dichloro-1,5-dimethyl-2-oxo-1,2,3,4,5,6-hexahydroazepino[4,5-b]indol-10-yl)acetonitrile (194 mg, 82%) as a brown solid and a mixture of isomers. ES/MS (m/z): ($^{35}Cl/^{37}Cl$) 336.0/338.0 (M+H).

Examples 150

2-((1S,5R)-7,8-Dichloro-1,5-dimethyl-2-oxo-1,2,3,4,5,6-hexahydroazepino[4,5-b]indol-10-yl)acetonitrile Or 2-((1R,5S)-7,8-Dichloro-1,5-dimethyl-2-oxo-1,2,3,4,5,6-hexahydroazepino[4,5-b]indol-10-yl)acetonitrile (isomer 1) and Example 151

2-((1S,5S)-7,8-Dichloro-1,5-dimethyl-2-oxo-1,2,3,4,5,6-hexahydroazepino[4,5-b]indol-10-yl)acetonitrile Or 2-((1R,5R)-7,8-Dichloro-1,5-dimethyl-2-oxo-1,2,3,4,5,6-hexahydroazepino[4,5-b]indol-10-yl)acetonitrile (isomer 2) and Example 152

2-((1S,5S)-7,8-Dichloro-1,5-dimethyl-2-oxo-1,2,3,4,5,6-hexahydroazepino[4,5-b]indol-10-yl)acetonitrile Or 2-((1R,5R)-7,8-Dichloro-1,5-dimethyl-2-oxo-1,2,3,4,5,6-hexahydroazepino[4,5-b]indol-10-yl)acetonitrile (isomer 3) and Example 153

2-((1S,5R)-7,8-Dichloro-1,5-dimethyl-2-oxo-1,2,3,4,5,6-hexahydroazepino[4,5-b]indol-10-yl)acetonitrile Or 2-((1R,5S)-7,8-Dichloro-1,5-dimethyl-2-oxo-1,2,3,4,5,6-hexahydroazepino[4,5-b]indol-10-yl)acetonitrile (isomer 4)

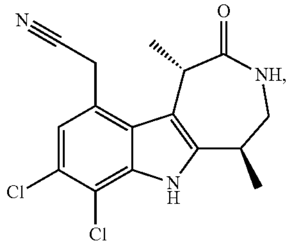

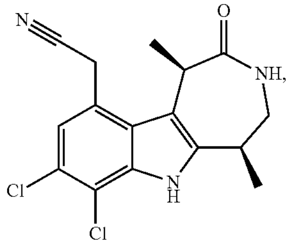

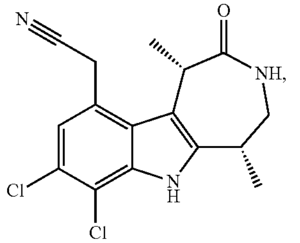

-continued

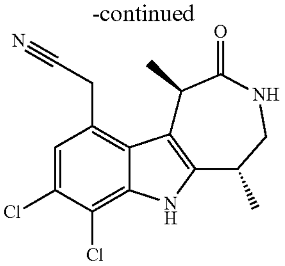

Purified 2-(7,8-dichloro-1,5-dimethyl-2-oxo-1,2,3,4,5,6-hexahydroazepino[4,5-b]indol-10-yl)acetonitrile (185 mg, 0.550 mmol) by SFC to give the titled compounds (Isomer 1—Rt=1.90 min (100% de), 27 mg, 14%; Isomer 2—Rt=2.30 min (94.4% ee), 20 mg, 10%); (Isomer 3-Rt=3.29 min (100% ee), 23 mg, 12%; Isomer 4—Rt=5.23 min (100% ee), 38 mg, 20%). Column: Chiralpak AS-H, 4.6×150 mm; Mobile Phase: 20% EtOH (0.5% DMEA):80% $CO_2$; Flow Rate: 80 mL/min; Detection: 230 nM; Column temperature: 40° C. ES/MS m/z: ($^{35}Cl/^{37}Cl$) 336.0/338.0 (M+H). Isomers 1 and 4: $^{1}H$ NMR (DMSO-d6): 11.56 (s, 1H), 7.80 (t, J=6.1 Hz, 1H), 7.21 (s, 1H), 4.31 (d, J=18.4 Hz, 1H), 4.26 (d, J=18.4 Hz, 1H), 4.01 (qd, J=7.5, 1.3 Hz, 1H), 3.86 (ddd, J=14.8, 5.6, 1.5 Hz, 1H), 3.22-3.14 (m, 1H), 3.07 (ddd, J=14.8, 7.4, 3.3 Hz, 1H), 1.54 (d, J=7.5 Hz, 3H), 1.27 (d, J=7.0 Hz, 3H). Isomers 2 and 3: $^{1}H$ NMR (DMSO-d6): 11.35 (s, 1H), 7.83-7.76 (m, 1H), 7.23 (s, 1H), 4.32 (d, J=18.4 Hz, 1H), 4.27 (d, J=18.4 Hz, 1H), 4.00 (qd, J=7.6, 1.4 Hz, 1H), 3.55 (ddd, J=14.5, 11.5, 5.0 Hz, 1H), 3.20-3.04 (m, 3H), 1.63 (d, J=7.6 Hz, 3H), 1.34 (d, J=6.6 Hz, 3H).

Intermediate 138

10-((2-((tert-Butyldimethylsilyl)oxy)ethyl)amino)-7,8-dichloro-1,5-dimethyl-3,4,5,6-tetrahydroazepino[4,5-b]indol-2(1H)-one

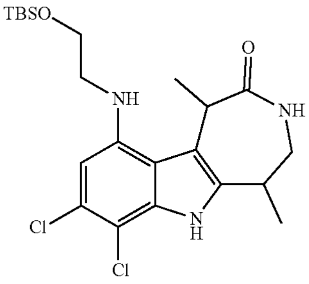 [SMILES: CC1CNC(=O)C(C)c2c1[nH]c1c(Cl)c(Cl)cc(NCCO[Si](C)(C)C(C)(C)C)c21]

Combined 10-bromo-7,8-dichloro-1,5-dimethyl-3,4,5,6-tetrahydroazepino[4,5-b]indol-2(1H)-one (0.1 g, 60% purity, 0.2 mmol), XantPhos-Pd-G2 (0.01 g, 0.02 mmol) and tripotassium phosphate (0.1 g, 0.6 mmol). Added 1,4-dioxane (2 mL) and 2-[tert-butyl(dimethyl)silyl]oxy-ethanamine (0.06 g, 0.3 mmol). The reaction is sparged with $N_2$ and stirred at 102° C. for 15 hrs. Cooled to ambient temperature, concentrated under reduced pressure, and purified by silica gel column chromatography eluting with EtOAc in hexanes. Combined fractions, concentrated under reduced pressure, and dried in vacuum oven to give the orange oil product 10-((2-((tert-butyldimethylsilyl)oxy)ethyl)amino)-7,8-dichloro-1,5-dimethyl-3,4,5,6-tetrahydroazepino[4,5-b]indol-2(1H)-one (58 mg, 80%) as a mixture of isomers. ES/MS (m/z): ($^{35}Cl/^{37}Cl$) 470.0/472.0 (M+H).

Example 154

(1S,5R)-7,8-Dichloro-10-((2-hydroxyethyl)amino)-1,5-dimethyl-3,4,5,6-tetrahydroazepino[4,5-b]indol-2(1H)-one Or (1R,5S)-7,8-Dichloro-10-((2-hydroxyethyl)amino)-1,5-dimethyl-3,4,5,6-tetrahydroazepino[4,5-b]indol-2(1H)-one (isomer 1) and Example 155

(1R,5R)-7,8-Dichloro-10-((2-hydroxyethyl)amino)-1,5-dimethyl-3,4,5,6-tetrahydroazepino[4,5-b]indol-2(1H)-one Or (1S,5S)-7,8-Dichloro-10-((2-hydroxyethyl)amino)-1,5-dimethyl-3,4,5,6-tetrahydroazepino[4,5-b]indol-2(1H)-one (isomer 2) and Example 156

(1R,5R)-7,8-Dichloro-10-((2-hydroxyethyl)amino)-1,5-dimethyl-3,4,5,6-tetrahydroazepino[4,5-b]indol-2(1H)-one Or (1S,5S)-7,8-Dichloro-10-((2-hydroxyethyl)amino)-1,5-dimethyl-3,4,5,6-tetrahydroazepino[4,5-b]indol-2(1H)-one (isomer 3) and Example 157

(1S,5R)-7,8-Dichloro-10-((2-hydroxyethyl)amino)-1,5-dimethyl-3,4,5,6-tetrahydroazepino[4,5-b]indol-2(1H)-one Or (1R,5S)-7,8-Dichloro-10-((2-hydroxyethyl)amino)-1,5-dimethyl-3,4,5,6-tetrahydroazepino[4,5-b]indol-2(1H)-one (isomer 4)

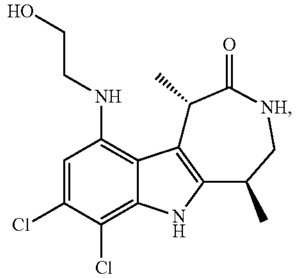

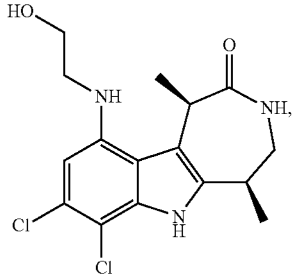

-continued

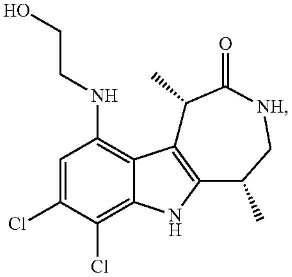

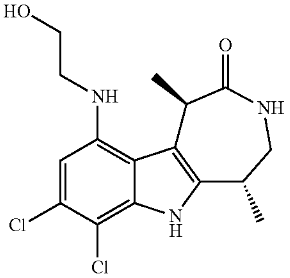

Dissolved 10-((2-((tert-butyldimethylsilyl)oxy)ethyl)amino)-7,8-dichloro-1,5-dimethyl-3,4,5,6-tetrahydroazepino[4,5-b]indol-2(1H)-one (286 mg, 0.608 mmol) in THF (6.1 mL) and purged with $N_2$. Added TBAF (2.43 mL, 2.43 mmol, 1.0M in THF), stirred for 30 min, and concentrated under a stream of $N_2$. Repeated reaction on 0.20× scale and combined the crude products. Filtered the crude product through a plug of silica gel, rinsed thoroughly through the silica with EtOAc, and concentrated the filtrate under reduced pressure to give a residue. Purified by reverse phase chromatography to give 7,8-dichloro-10-((2-hydroxyethyl)amino)-1,5-dimethyl-3,4,5,6-tetrahydroazepino[4,5-b]indol-2(1H)-one as a mixture of four diastereomers. Separated the diastereomers by SFC to give the titled compounds as white solids (Isomer 1—RT=0.77 min (98.6% de), 40.5 mg, 16%; Isomer 2—RT=1.18 min (95.8% de), 19.8 mg, 8%; Isomer 3—RT=1.90 min (100% de), 20.4 mg, 8%; Isomer 4—RT=3.06 min (98.8% de), 41.9 mg, 16%). Column: Chiralpak AS-H, 21×150 mm; Mobile Phase: 35% EtOH: 65% $CO_2$; Flow Rate: 80 mL/min; Column temperature: 40° C.; Detection: 245 nM.

Isomer 1: ES/MS m/z: 355.8/357.8 (M+H); Isomer 2-ES/MS (m/z): 356.2/358.2 (M+H); Isomer 3-ES/MS m/z: 356.2/358.2 (M+H); Isomer 4-ES/MS m/z: 356.2/358.2 (M+H). Isomers 1 and 4: $^1H$ NMR (DMSO-d6): 11.03 (s, 1H), 7.76 (t, J=6.2 Hz, 1H), 6.23 (s, 1H), 4.97 (t, J=5.3 Hz, 1H), 4.93 (s, 1H), 4.10 (q, J=7.5 Hz, 1H), 3.80 (dd, J=14.3, 6.2 Hz, 1H), 3.71-3.60 (m, 2H), 3.23-2.98 (m, 4H), 1.54 (d, J=7.5 Hz, 3H), 1.24 (d, J=6.8 Hz, 3H). Isomers 2 and 3: $^1H$ NMR (DMSO-d6): 10.82 (s, 1H), 7.78 (t, J=6.2 Hz, 1H), 6.26 (s, 1H), 4.95 (t, J=5.0 Hz, 1H), 4.88 (dd, J=4.5, 5.9 Hz, 1H), 4.13 (q, J=7.6 Hz, 1H), 3.73-3.61 (m, 2H), 3.49 (ddd, J=14.6, 11.8, 5.6 Hz, 1H), 3.23-2.97 (m, 4H), 1.62 (d, J=7.6 Hz, 3H), 1.29 (d, J=6.7 Hz, 3H).

Intermediate 139

2-((tert-Butyldimethylsilyl)oxy)-N-(7,8-dichloro-1,5-dimethyl-2-oxo-1,2,3,4,5,6-hexahydroazepino[4,5-b]indol-10-yl)acetamide

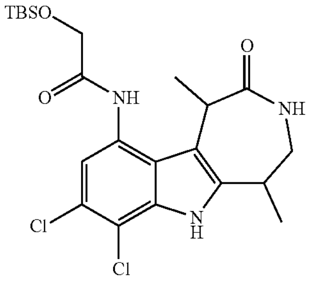 [SMILES: CC1CNC(=O)C(C)c2c1[nH]c1c(Cl)c(Cl)cc(NC(=O)CO[Si](C)(C)C(C)(C)C)c21]

Combined 10-bromo-7,8-dichloro-1,5-dimethyl-3,4,5,6-tetrahydroazepino[4,5-b]indol-2(1H)-one (558 mg, 0.890 mmol, 60% purity), tert-BuBrettPhos-Pd-G3 (79.1 mg, 89.0 μmol) and potassium phosphate, tribasic (756 mg, 3.56 mmol). Added 1,4-dioxane (12.5 mL) and 2-((tert-butyldimethylsilyl)oxy)acetamide (337 mg, 1.78 mmol). Stirred and sparged with $N_2$ using a sub surface needle for 5 min. Heated to 102° C. and stirred overnight. Cooled to ambient temperature, filtered through diatomaceous earth, and concentrated under reduced pressure. Purified by silica gel flash column chromatography eluting with EtOAc in hexanes to give 2-((tert-butyldimethylsilyl)oxy)-N-(7,8-dichloro-1,5-dimethyl-2-oxo-1,2,3,4,5,6-hexahydroazepino[4,5-b]indol-10-yl)acetamide (0.68 g, 95%, 60% purity) as a mixture of isomers. ES/MS (m/z): ($^{35}Cl/^{37}Cl$) 484.2/486.2 (M+H).

Example 158 trans-N-(7,8-dichloro-1,5-dimethyl-2-oxo-1,2,3,4,5,6-hexahydroazepino[4,5-b]indol-10-yl)-2-hydroxyacetamide

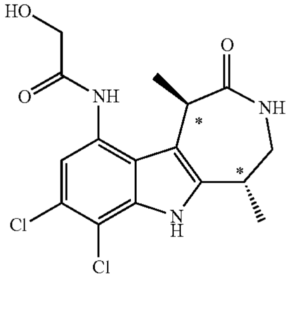 [SMILES: C[C@H]1CNC(=O)[C@H](C)c2c1[nH]c1c(Cl)c(Cl)cc(NC(=O)CO)c21]

and

Example 159 cis-N-(7,8-dichloro-1,5-dimethyl-2-oxo-1,2,3,4,5,6-hexahydroazepino[4,5-b]indol-10-yl)-2-hydroxyacetamide

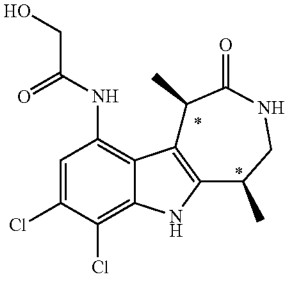 [SMILES: C[C@@H]1CNC(=O)[C@H](C)c2c1[nH]c1c(Cl)c(Cl)cc(NC(=O)CO)c21]

Dissolved 2-((tert-butyldimethylsilyl)oxy)-N-(7,8-dichloro-1,5-dimethyl-2-oxo-1,2,3,4,5,6-hexahydroazepino[4,5-b]indol-10-yl)acetamide (0.680 g, 60% purity, 842 μmol) in THF (8.42 mL). Purged with $N_2$ and added TBAF (3.37 mL, 3.37 mmol, 1.0M in THF). Purged again with $N_2$ and stirred for 30 min. Concentrated under a stream of $N_2$, purified by reverse phase column chromatography, triturated with MeOH, and dried to give the titled compounds as white solids. ES/MS (m/z): ($^{35}Cl/^{37}Cl$) 369.8/371.8 (M+H).

trans- (73.8 mg, 24%)—$^1$H NMR (DMSO-d6): 11.42 (br s, 1H), 9.54 (br s, 1H), 7.76 (t, J=6.2 Hz, 1H), 7.39 (s, 1H), 6.04 (br s, 1H), 4.11 (q, J=7.5 Hz, 1H), 4.04 (s, 2H), 3.81 (dd, J=14.0, 4.9 Hz, 1H), 3.20-3.10 (m, 1H), 3.10-3.01 (m, 1H), 1.48 (d, J=7.5 Hz, 3H), 1.26 (d, J=6.9 Hz, 3H).

cis- (28 mg, 9%)—$^1$H NMR (DMSO-d6): 11.21 (s, 1H), 9.51 (s, 1H), 7.81-7.74 (m, 1H), 7.38 (s, 1H), 6.50 (s, 1H), 4.13 (q, J=7.6 Hz, 1H), 4.04 (s, 2H), 3.56-3.44 (m, 1H), 3.18-3.02 (m, 2H), 1.56 (d, J=7.6 Hz, 3H), 1.33 (d, J=6.6 Hz, 3H).

Example 160

N-((1S,5R)-7,8-Dichloro-1,5-dimethyl-2-oxo-1,2,3,4,5,6-hexahydroazepino[4,5-b]indol-10-yl)-2-hydroxyacetamide or N-((1R,5S)-7,8-Dichloro-1,5-dimethyl-2-oxo-1,2,3,4,5,6-hexahydroazepino[4,5-b]indol-10-yl)-2-hydroxyacetamide (isomer 1) and Example 161

N-((1S,5R)-7,8-Dichloro-1,5-dimethyl-2-oxo-1,2,3,4,5,6-hexahydroazepino[4,5-b]indol-10-yl)-2-hydroxyacetamide or N-((1R,5S)-7,8-Dichloro-1,5-dimethyl-2-oxo-1,2,3,4,5,6-hexahydroazepino[4,5-b]indol-10-yl)-2-hydroxyacetamide (isomer 2)

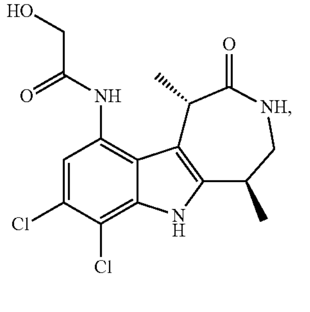

-continued

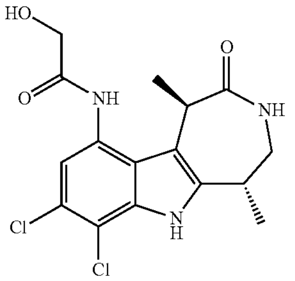

Purified racemic trans-N-(7,8-dichloro-1,5-dimethyl-2-oxo-1,2,3,4,5,6-hexahydroazepino[4,5-b]indol-10-yl)-2-hydroxyacetamide (65 mg, 0.18 mmol) by SFC to give the titled compounds (Isomer 1—RT=1.24 min (100% ee), 33.51 mg, 52%; Isomer 2—RT=1.74 min (100% ee), 27.51 mg, 42%). Column: (S, S) Whelk-01, 21.2×250 mm; Mobile Phase: 40% EtOH: 60° 4 $CO_2$; Flow Rate: 80 mL/min; Column temperature: 40° C.; Detection: 225 nM, ES/MS (m/z): ($^{35}Cl/^{37}Cl$) 369.8/371.8 (M+H).

Intermediate 140

Methyl 7-ethyl-8-oxo-1,4-dioxaspiro[4.5]decane-7-carboxylate

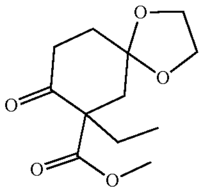 [SMILES: CCC1(C(=O)OC)CC2(CCC1=O)OCCO2]

To NaH (300 mg, 10.0 mmol, 60 mass %) in toluene (50 mL) and DMF (50 mL), added a solution of methyl 8-oxo-1,4-dioxaspiro[4.5]decane-7-carboxylate (3.00 g, 10.0 mmol, 85 mass %) in toluene (10 mL) and DMF (10 mL) dropwise at 0° C. Stirred at ambient temperature for 1 hr. Added iodoethane (6.00 g, 40.0 mmol) to above reaction mixture, stirred at 25° C. for 16 hrs. Quenched with $H_2O$, extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with EtOAc in PE to give methyl 7-ethyl-8-oxo-1,4-dioxaspiro[4.5]decane-7-carboxylate (2 g, 85% mass, 60%). $^1H$ NMR (DMSO-d6): 4.00-3.80 (m, 4H), 3.65 (s, 3H), 2.82 (td, J=14.0, 6.5 Hz, 1H), 2.43 (dd, J=13.8, 3.4 Hz, 1H), 2.36-2.26 (m, 1H), 1.99 (td, J=13.3, 5.1 Hz, 1H), 1.90-1.84 (m, 1H), 1.81 (d, J=14.0 Hz, 1H), 1.70 (dq, J=13.7, 7.4 Hz, 1H), 1.49 (dq, J=13.7, 7.4 Hz, 1H), 0.78 (t, J=7.4 Hz, 3H).

Intermediate 141

Methyl 5-bromo-7,8-dichloro-1-ethyl-1,2,4,9-tetrahydrospiro[carbazole-3,2'-[1,3]dioxolane]-1-carboxylate

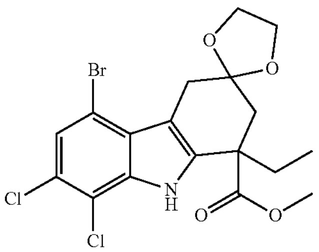 [SMILES: CCC1(C(=O)OC)CC2(Cc3c1[nH]c1c(Cl)c(Cl)cc(Br)c31)OCCO2]

Combined (5-bromo-2,3-dichlorophenyl)hydrazine (1.06 g, 3.72 mmol, 90 mass %), methyl 7-ethyl-8-oxo-1,4-dioxaspiro[4.5]decane-7-carboxylate (1.00 g, 3.72 mmol, 90 mass %) and acetic acid (223 mg, 3.72 mmol) in EtOH (15 mL). Stirred at 75° C. for 2 hrs, under $N_2$ atmosphere. Cooled to ambient temperature, filtered, and dried the filter cake under reduced pressure to give a yellow solid. Dissolved the solid in toluene (120 mL), added dry $ZnCl_2$ (2.70 g, 20.0 mmol). Stirred at 145° C. for 2 days under $N_2$ atmosphere. Concentrated under reduced pressure and dissolved the residue in xylene (56 mL). Added dry $ZnCl_2$ (2.70 g, 20.0 mmol) and stirred at 145° C. for 4 days under $N_2$ atmosphere. Cooled to ambient temperature, diluted with EtOAc, and $H_2O$ and added 2N aqueous NaOH to the above mixture and separated. Neutralized the cloudy aqueous layer with 6N aqueous HCl to pH=7, extracted with EtOAc. Combined the organic layers, washed with saturated aqueous NaCl, dried over anhydrous $Na_2SO_4$, filtered, and concentrated under reduced pressure. Purified by silica gel flash chromatography eluting with EtOAc in PE to give methyl 5-bromo-7,8-dichloro-1-ethyl-1,2,4,9-tetrahydrospiro[carbazole-3,2'-[1,3]dioxolane]-1-carboxylate (6 g, 70% mass, 50%). ES/MS (m/z): 462.0/463.9/465.9 (M+H).

Intermediate 142

5-Bromo-7,8-dichloro-1-ethyl-1,2,4,9-tetrahydrospiro[carbazole-3,2'-[1,3]dioxolane]-1-carboxylic acid

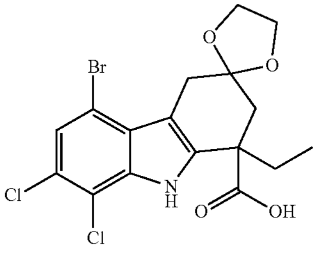 [SMILES: CCC1(C(=O)O)CC2(Cc3c1[nH]c1c(Cl)c(Cl)cc(Br)c31)OCCO2]

To a solution of methyl 5-bromo-7,8-dichloro-1-ethyl-1,2,4,9-tetrahydrospiro[carbazole-3,2'-[1,3]dioxolane]-1-carboxylate (6.00 g, 9.07 mmol, 70 mass %) in MeOH (45 mL) and THF (45 mL), added 5N aqueous NaOH (3.6 mL, 18.1 mmol). Stirred at 50° C. for 16 hrs. Diluted with water and acidified by addition of 6N aqueous HCl to pH=3 and concentrated to remove most of solvent under reduced pressure. Extracted with DCM (3×) and dried over anhydrous $Na_2SO_4$, filtered, and concentrated under reduced pressure. Solidified in a mixture of EtOAc and PE, filtered and dried. Triturated the crude product with DCM in EtOAc/PE to give 5-bromo-7,8-dichloro-1-ethyl-1,2,4,9-tetrahydrospiro[carbazole-3,2'-[1,3]dioxolane]-1-carboxylic acid (4.36 g, 95% mass, 99+%). ES/MS (m/z): 447.9/449.9/451.8 (M+H).

Intermediate 143

5-Bromo-7,8-dichloro-1-ethyl-1,2,4,9-tetrahydro-3H-carbazol-3-one

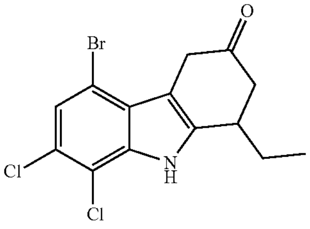 [SMILES: CCC1CC(=O)Cc2c1[nH]c1c(Cl)c(Cl)cc(Br)c21]

Stirred a solution of 5-bromo-7,8-dichloro-1-ethyl-1,2,4,9-tetrahydrospiro[carbazole-3,2'-[1,3]dioxolane]-1-carboxylic acid (3.30 g, 7.00 mmol, 95 mass %) in acetic acid (29 mL) at 120° C. for 16 hrs, under $N_2$ atmosphere. Concentrated under reduced pressure and purified the crude product by trituration with EtOAc in PE to give 5-bromo-7,8-dichloro-1-ethyl-1,2,4,9-tetrahydro-3H-carbazol-3-one (750 mg, 80% mass, 23%). ES/MS (m/z): 359.8/361.7/363.9 (M+H).

Intermediate 144

10-Bromo-7,8-dichloro-5-ethyl-3,4,5,6-tetrahydroazepino[4,5-b]indol-2(1H)-one

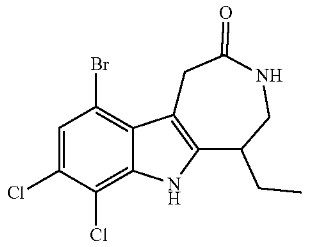 [SMILES: CCC1CNC(=O)Cc2c1[nH]c1c(Cl)c(Cl)cc(Br)c21]

To a mixture of 5-bromo-7,8-dichloro-1-ethyl-1,2,4,9-tetrahydro-3H-carbazol-3-one (250 mg, 0.554 mmol, 80 mass %) in methanesulfonic acid (9.00 g, 93.7 mmol) at 0° C., added $NaN_3$ (70 mg, 1.1 mmol) slowly. Stirred at 0° C. for 30 mm, then at 20° C. for 16 hrs, Poured the reaction mixture into ice water and basified with 6N aqueous NaOH to pH=10, extracted with EtOAc (3×). Combined organic layers, washed with saturated aqueous NaCl and dried over anhydrous $Na_2SO_4$, filtered and concentrated under reduced pressure. Purified by silica gel flash chromatography eluting with MeOH in DCM to give 10-bromo-7,8-dichloro-5-ethyl-3,4,5,6-tetrahydroazepino[4,5-b]indol-2(1H)-one (110 mg, 84% purity, 44%). ES/MS (m/z): 374.9/376.8/378.7 (M+H).

Example 162

7,8-Dichloro-5-ethyl-10-(2-methyl-2H-1,2,3-triazol-4-yl)-3,4,5,6-tetrahydroazepino[4,5-b]indol-2(1H)-one

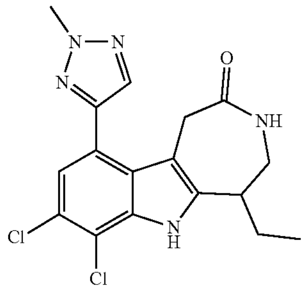 [SMILES: CCC1CNC(=O)Cc2c1[nH]c1c(Cl)c(Cl)cc(-c3cnn(C)n3)c21]

Combined 10-bromo-7,8-dichloro-5-ethyl-3,4,5,6-tetrahydroazepino[4,5-b]indol-2(1H)-one (110 mg, 0.246 mmol, 84 mass %), 2-methyl-4-(4,4,5,5-tetramethyl-1,3,2-dioxaborolan-2-yl)-2H-1,2,3-triazole (144 mg, 0.344 mmol, 50 mass %), Pd(dppf)$Cl_2$ (18 mg, 0.025 mmol) and $Na_2CO_3$ (78 mg, 0.74 mmol) in 1,4-dioxane (4 mL) and $H_2O$ (1 mL). Degassed and purged with $N_2$ (3×). Stirred at 90° C. for 2 hrs under $N_2$ atmosphere. Concentrated under reduced pressure and diluted with water, extracted with EtOAc (3×) and dried over anhydrous $Na_2SO_4$, filtered, and concentrated under reduced pressure. Purified by prep-HPLC, and further purified by SFC (Column: DAICEL CHIRALPAK AD (250×30 mm, 10 μm); Mobile Phase: 45% EtOH (0.1% $NH_3H_2O$); 55% $CO_2$; FlowRate: 80 mL/min). Concentrated under reduced pressure, and lyophilized, then triturated with ACN to give 7,8-dichloro-5-ethyl-10-(2-methyl-2H-1,2,3-triazol-4-yl)-3,4,5,6-tetrahydroazepino[4,5-b]indol-2(1H)-one (23.05 mg, 26%) as a white solid. ES/MS (m/z): ($^{35}Cl/^{37}Cl$) 378.0/379.8 (M+H).

Example 163

7,8-Dichloro-5-ethyl-10-((2-hydroxyethyl)amino)-3,4,5,6-tetrahydroazepino[4,5-b]indol-2(1H)-one

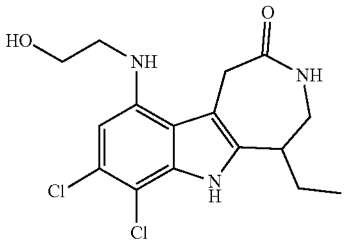 [SMILES: CCC1CNC(=O)Cc2c1[nH]c1c(Cl)c(Cl)cc(NCCO)c21]

Combined 10-bromo-7,8-dichloro-5-ethyl-3,4,5,6-tetrahydroazepino[4,5-b]indol-2(1H)-one (120 mg, 0.287 mmol, 90 mass %), 2-aminoethan-1-ol (35 mg, 0.57 mmol), $Pd_2(dba)_3$ (26 mg, 0.029 mmol), Xantphos (33 mg, 0.057 mmol) and cesium carbonate (327 mg, 1.01 mmol) in 1,4-dioxane (20 mL) and THF (1 mL). Degassed and purged with $N_2$ (x3). Stirred at 110° C. for 16 hrs. Concentrated under reduced pressure. Purified by silica gel flash chromatography eluting with MeOH in DCM and concentrated under reduced pressure. Then purified by reverse phase prep-HPLC to give 7,8-dichloro-5-ethyl-10-((2-hydroxyethyl)amino)-3,4,5,6-tetrahydroazepino[4,5-b]indol-2(1H)-one (27.91 mg, 27%) as a yellow solid. ES/MS (m/z): ($^{35}Cl/^{37}Cl$) 355.8/357.9 (M+H).

Intermediate 145

Methyl 8-oxo-7-propyl-1,4-dioxaspiro[4.5]decane-7-carboxylate

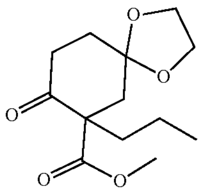 [SMILES: CCCC1(C(=O)OC)CC2(CCC1=O)OCCO2]

To sodium hydride (1.1 g, 48.0 mmol, 60 mass %) in toluene (50 mL) and DMF (50 mL), added a solution of methyl 8-oxo-1,4-dioxaspiro[4.5]decane-7-carboxylate (10 g, 40.0 mmol, 85 mass %) in toluene (10 mL) and DMF (10 mL) dropwise at 0° C. Stirred at 25° C. for 1 hr. Added propyl iodide (20.0 g, 120 mmol) to above reaction mixture and stirred at 25° C. for 16 hrs. Quenched with water and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with EtOAc in PE to give methyl 8-oxo-7-propyl-1,4-dioxaspiro[4.5]decane-7-carboxylate (7 g, 60%). $^1$H NMR (DMSO-d6): 4.00-3.80 (m, 4H), 3.64 (s, 3H), 2.82 (td, J=14.0, 6.5 Hz, 1H), 2.44 (dd, J=13.8, 3.5 Hz, 1H), 2.31 (ddd, J=14.4, 4.9, 3.4 Hz, 1H), 1.98 (td, J=13.3, 5.1 Hz, 1H), 1.90-1.84 (m, 1H), 1.81 (d, J=14.0 Hz, 1H), 1.66-1.55 (m, 1H), 1.44-1.28 (m, 2H), 1.06-0.90 (m, 1H), 0.82 (t, J=7.0 Hz, 3H).

Intermediate 146

Methyl 8-(2-(5-bromo-2,3-dichlorophenyl)hydrazinylidene)-7-propyl-1,4-dioxaspiro[4.5]decane-7-carboxylate

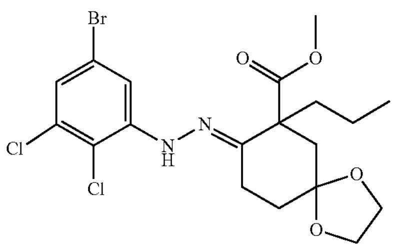 [SMILES: CCCC1(C(=O)OC)CC2(CC/C1=N\Nc1cc(Br)cc(Cl)c1Cl)OCCO2]

To a solution of (5-bromo-2,3-dichlorophenyl)hydrazine (6.99 g, 24.6 mmol, 90 mass %) and methyl 8-oxo-7-propyl-1,4-dioxaspiro[4.5]decane-7-carboxylate (7.00 g, 24.6 mmol, 90 mass %) in EtOH (100 mL), added acetic acid (1.48 g, 24.6 mmol). Stirred at 75° C. for 2 hrs, under $N_2$ atmosphere. Cooled to ambient temperature, filtered, and dried the filter cake under reduced pressure to give methyl 8-(2-(5-bromo-2,3-dichlorophenyl)hydrazinylidene)-7-propyl-1,4-dioxaspiro[4.5]decane-7-carboxylate (10 g, 70%). $^1$H NMR (DMSO-d6): 8.83 (s, 1H), 7.47 (d, J=2.3 Hz, 1H), 7.28 (d, J=2.3 Hz, 1H), 3.98-3.89 (m, 2H), 3.88-3.77 (m, 2H), 3.63 (s, 3H), 2.92 (dt, J=15.0, 4.4 Hz, 1H), 2.41-2.31 (m, 1H), 2.40 (d, J=13.8 Hz, 1H), 1.88 (td, J=12.4, 3.0 Hz, 1H), 1.79-1.68 (m, 2H), 1.68-1.48 (m, 2H), 1.66 (d, J=13.8 Hz, 1H), 1.21-1.08 (m, 1H), 0.93 (t, J=7.1 Hz, 3H).

Intermediate 147

Methyl 5-bromo-7,8-dichloro-1-propyl-1,2,4,9-tetrahydrospiro[carbazole-3,2'-[1,3]dioxolane]-1-carboxylate

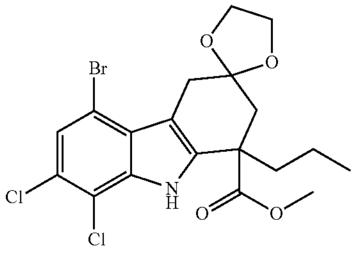 [SMILES: CCCC1(C(=O)OC)CC2(Cc3c1[nH]c1c(Cl)c(Cl)cc(Br)c31)OCCO2]

To a solution of methyl 8-(2-(5-bromo-2,3-dichlorophenyl)hydrazinylidene)-7-propyl-1,4-dioxaspiro[4.5]decane-7-carboxylate (10.0 g, 17.0 mmol, 85 mass %) in toluene (120 mL), added dry $ZnCl_2$ (2.80 g, 21.0 mmol). Stirred at 145° C. for 2 days under $N_2$ atmosphere. Concentrated under reduced pressure and dissolved the residue in xylene (57 mL). Added dry $ZnCl_2$ (2.80 g, 21.0 mmol) and stirred at 145° C. for 4 days under $N_2$ atmosphere. Cooled to ambient temperature and diluted with EtOAc and $H_2O$. Added 2N aqueous NaOH to the above mixture and separated. Neutralized the cloudy aqueous layer with 6N aqueous HCl to pH=7 and extracted with EtOAc. Combined the organic layers, washed with saturated aqueous NaCl, dried over anhydrous $Na_2SO_4$, filtered, and concentrated under reduced pressure. Purified by silica gel flash chromatography eluting with EtOAc in PE to give methyl 5-bromo-7,8-dichloro-1-propyl-1,2,4,9-tetrahydrospiro[carbazole-3,2'-[1,3]dioxolane]-1-carboxylate (2.50 g, 27%). ES/MS (m/z): 475.9/477.9/479.8 (M+H).

Intermediate 148

5-Bromo-7,8-dichloro-1-propyl-1,2,4,9-tetrahydrospiro[carbazole-3,2'-[1,3]dioxolane]-1-carboxylic acid

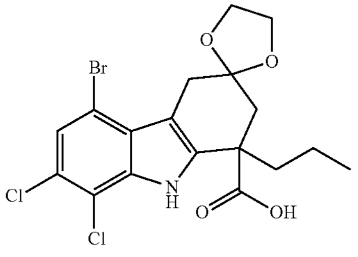 [SMILES: CCCC1(C(=O)O)CC2(Cc3c1[nH]c1c(Cl)c(Cl)cc(Br)c31)OCCO2]

To a solution of methyl 5-bromo-7,8-dichloro-1-propyl-1,2,4,9-tetrahydrospiro[carbazole-3,2'-[1,3]dioxolane]-1-carboxylate (2.50 g, 4.98 mmol, 90 mass %) in MeOH (24 mL) and THF (24 mL), added 5N aqueous NaOH (1.9 mL). Stirred at 50° C. for 16 hrs. Diluted with water, acidified with 5N aqueous HCl to pH=3, then extracted with DCM (2×). Combined organic layers, dried over anhydrous $Na_2SO_4$, filtered, and concentrated under reduced pressure. Purified by trituration with DCM in EtOAc/PE to give 5-bromo-7,8-dichloro-1-propyl-1,2,4,9-tetrahydrospiro[carbazole-3,2'-[1,3]dioxolane]-1-carboxylic acid (1.85 g, 80%). ES/MS (m/z): 461.8/463.8/465.8 (M+H).

Intermediate 149

5-Bromo-7,8-dichloro-1-propyl-1,2,4,9-tetrahydro-3H-carbazol-3-one

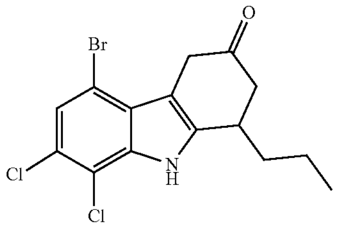 [SMILES: CCCC1CC(=O)Cc2c1[nH]c1c(Cl)c(Cl)cc(Br)c21]

Degassed and purged a solution of 5-bromo-7,8-dichloro-1-propyl-1,2,4,9-tetrahydrospiro[carbazole-3,2'-[1,3]dioxolane]-1-carboxylic acid (930 mg, 1.91 mmol, 95 mass %) in acetic acid (7 mL) with $N_2$ (×10). Stirred at 125° C. for 40 hrs. Concentrated under reduced pressure and purified by trituration with PE/DCM to give 5-bromo-7,8-dichloro-1-propyl-1,2,4,9-tetrahydro-3H-carbazol-3-one (280 mg, 37%). $^1H$ NMR (DMSO-d6): 11.81 (s, 1H), 7.41 (s, 1H), 3.90 (d, J=20.4 Hz, 1H), 3.68 (d, J=20.4 Hz, 1H), 3.40-3.28 (m, 1H), 2.93 (dd, J=14.2, 6.7 Hz, 1H), 1.73-1.62 (m, 1H), 1.54-1.42 (m, 1H), 1.41-1.16 (m, 2H), 0.86 (t, J=7.3 Hz, 3H).

Intermediate 150

10-Bromo-7,8-dichloro-5-propyl-3,4,5,6-tetrahydroazepino[4,5-b]indol-2(1H)-one

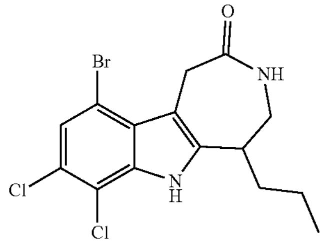 [SMILES: CCCC1CNC(=O)Cc2c1[nH]c1c(Cl)c(Cl)cc(Br)c21]

To a solution of 5-bromo-7,8-dichloro-1-propyl-1,2,4,9-tetrahydro-3H-carbazol-3-one (280 mg, 0.709 mmol, 95 mass %) in methanesulfonic acid (6 mL), added $NaN_3$ (20 mg, 0.31 mmol) slowly at 0° C. Stirred at 0° C. for 30 min, then at 20° C. for 16 hrs. Poured into ice water and basified with 6N aqueous NaOH to pH=10 and extracted with EtOAc (3×). Combined organic layers, washed with saturated aqueous NaCl, dried over anhydrous $Na_2SO_4$, filtered, and concentrated under reduced pressure. Purified by silica gel flash chromatography eluting with MeOH in DCM to give 10-bromo-7,8-dichloro-5-propyl-3,4,5,6-tetrahydroazepino[4,5-b]indol-2(1H)-one (145 mg, 47%). ES/MS (m/z): 388.8/390.8/392.8 (M+H).

Example 164

7,8-Dichloro-10-(2-methyl-2H-1,2,3-triazol-4-yl)-5-propyl-3,4,5,6-tetrahydroazepino[4,5-b]indol-2(1H)-one

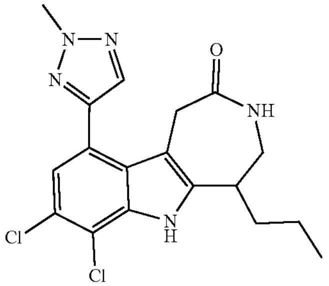 [SMILES: CCCC1CNC(=O)Cc2c1[nH]c1c(Cl)c(Cl)cc(-c3cnn(C)n3)c21]

Combined 10-bromo-7,8-dichloro-5-propyl-3,4,5,6-tetrahydroazepino[4,5-b]indol-2(1H)-one (145 mg, 0.335 mmol, 90 mass %), 2-methyl-4-(4,4,5,5-tetramethyl-1,3,2-dioxaborolan-2-yl)-2H-1,2,3-triazole (196 mg, 0.468 mmol, 50 mass %), $Pd(dppf)Cl_2$ (25 mg, 0.034 mmol) and $Na_2CO_3$ (106 mg, 1.00 mmol) in 1,4-dioxane (5 mL) and $H_2O$ (1.25 mL). Stirred at 90° C. for 6 hrs, under $N_2$ atmosphere. Concentrated under reduced pressure, and diluted with water, extracted with EtOAc (3×). Combined organic layers and dried over anhydrous $Na_2SO_4$, filtered, and concentrated under reduced pressure. Purified by silica gel flash chromatography eluting with MeOH in DCM and concentrated under reduced pressure. Then triturated with DCM, further purified by SFC (Column: DAICEL CHIRALPAK AD (250×30 mm, 10 μm). Mobile Phase: 35% EtOH (0.1% $NH_3H_2O$); 65% $CO_2$; FlowRate (ml/min): 80). Concentrated under reduced pressure, and lyophilized to give 7,8-dichloro-10-(2-methyl-2H-1,2,3-triazol-4-yl)-5-propyl-3,4,5,6-tetrahydroazepino[4,5-b]indol-2(1H)-one (31.60 mg, 23%) as a white solid. ES/MS (m/z): ($^{35}Cl/^{37}Cl$) 392.1/394.0 (M+H).

Intermediate 151

7-Methyl-1,4-dioxaspiro[4.5]decan-8-one

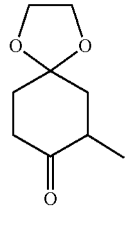

To a solution of lithium bis(trimethylsilyl)amide (170 mL, 170 mmol, 1M in THF) in THF (100 mL), added a solution of 1,4-dioxaspiro[4.5]decan-8-one (20.0 g, 0.13 mol) in THF (200 mL) dropwise over 15 min at −78° C. under $N_2$. Stirred at −78° C. for 30 min. Added iodomethane (22.0 g, 150 mmol) to above reaction and stirred at −78° C. for 20 min, warmed to ambient temperature and stirred at ambient temperature for 2 hrs, under $N_2$ atmosphere. Quenched with saturated aqueous $NH_4Cl$ and extracted with EtOAc. Combined organic layers, washed with saturated aqueous NaCl, dried over $Na_2SO_4$, filtered, and concentrated under reduced pressure. Purified by flash silica gel chromatography eluting with EtOAc in PE and concentrated under reduced pressure to give 7-methyl-1,4-dioxaspiro[4.5]decan-8-one (11.5 g, 90% mass, 47%). $^1$H NMR (DMSO-d6): 4.02-3.87 (m, 4H), 2.70-2.48 (m, 2H), 2.22-2.14 (m, 1H), 2.05-1.82 (m, 3H), 1.65 (t, J=13.1 Hz, 1H), 0.89 (d, J=6.6 Hz, 3H).

Intermediate 152

2-Methylcyclohexane-1,4-dione

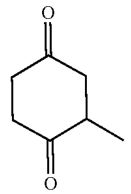

To a solution of 7-methyl-1,4-dioxaspiro[4.5]decan-8-one (11.5 g, 60.8 mmol, 90 mass %) in DCM (150 mL), added TFA (92.6 mL, 1.22 mol). Stirred at 25° C. for 16 hrs. Quenched with $NaHCO_3$ and extracted with EtOAc. Combined organic layers, washed with saturated aqueous NaCl, dried over $Na_2SO_4$, filtered, and concentrated under reduced pressure. Purified by flash silica gel chromatography eluting with EtOAc in PE and concentrated under reduced pressure to give 2-methylcyclohexane-1,4-dione (5.40 g, 90% mass, 63%). $^1$H NMR (DMSO-d6): 2.93-2.75 (m, 2H), 2.68-2.43 (m, 5H), 0.98 (d, J=6.8 Hz, 3H).

Intermediate 153

5-Bromo-7,8-dichloro-2-methyl-1,2,4,9-tetrahydro-3H-carbazol-3-one

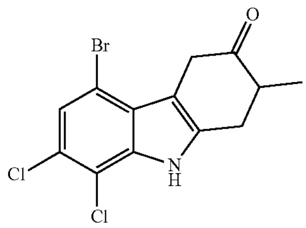 [SMILES: CC1Cc2[nH]c3c(Cl)c(Cl)cc(Br)c3c2CC1=O]

Combined 2-methylcyclohexane-1,4-dione (5.4 g, 39 mmol, 90 mass %) and (5-bromo-2,3-dichlorophenyl)hydrazine (8.8 g, 31 mmol, 90 mass %) in toluene (300 mL) and stirred at 130° C. for 3 hrs with a Dean-Stark trap under $N_2$ atmosphere. Concentrated under reduced pressure to give the crude hydrazone as a yellow solid (14 g). Combined the crude hydrazone with dry $ZnCl_2$ (6.30 g, 46.0 mmol) in toluene and refluxed at 130° C. for 3 days with a Dean-Stark trap under $N_2$ atmosphere. Added another batch of dry $ZnCl_2$ (6.30 g, 46.0 mmol) and stirred at 130° C. for another 2 days. Cooled to ambient temperature and concentrated under reduced pressure. Diluted with EtOAc and saturated aqueous $NaHCO_3$ to produce lots of solids. Adjusted the pH of the mixture to 7 by addition of 2 M aqueous HCl slowly to dissolve the solids. Separated and extracted the aqueous layer with EtOAc. Combined the organic layers, washed with saturated aqueous NaCl, dried over anhydrous $Na_2SO_4$, filtered, and concentrated under reduced pressure. Purified by flash silica gel chromatography eluting with EtOAc in PE to give 5-bromo-7,8-dichloro-2-methyl-1,2,4,9-tetrahydro-3H-carbazol-3-one (1.50 g, 9%). $^1$H NMR (DMSO-d6): 11.82 (s, 1H), 7.38 (s, 1H), 3.92 (d, J=19.8 Hz, 1H), 3.67 (d, J=19.8 Hz, 1H), 3.24 (dd, J=16.2, 6.9 Hz, 1H), 3.01-2.89 (m, 1H), 2.75 (dd, J=16.2, 11.0 Hz, 1H), 1.12 (d, J=6.5 Hz, 3H).

Intermediate 154

10-Bromo-7,8-dichloro-4-methyl-3,4,5,6-tetrahydroazepino[4,5-b]indol-2(1H)-one

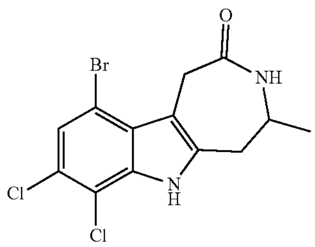 [SMILES: CC1Cc2[nH]c3c(Cl)c(Cl)cc(Br)c3c2CC(=O)N1]

To a mixture of 5-bromo-7,8-dichloro-2-methyl-1,2,4,9-tetrahydro-3H-carbazol-3-one (500 mg, 11.15 mmol, 80 mass %) in methanesulfonic acid (10 mL) added $NaN_3$ (230 mg, 3.54 mmol) portion-wise at 0° C. Stirred at 25° C. for 16 hrs. Poured into ice-water and extracted with EtOAc. Filtered to collect the solids and extracted the filtrate with EtOAc. Combined organic layers, washed with saturated aqueous NaCl (100 mL), dried over anhydrous $Na_2SO_4$, filtered, and concentrated under reduced pressure. Purified the solids and extracts by flash silica gel chromatography eluting with MeOH in DCM, then concentrated under reduced pressure to give 10-bromo-7,8-dichloro-4-methyl-3,4,5,6-tetrahydroazepino[4,5-b]indol-2(1H)-one (400 mg, 89% mass, 85%). ES/MS (m/z): 361.0/363.0/364.9 (M+H).

Example 165

7,8-Dichloro-10-((2-hydroxyethyl)amino)-4-methyl-3,4,5,6-tetrahydroazepino[4,5-b]indol-2(1H)-one

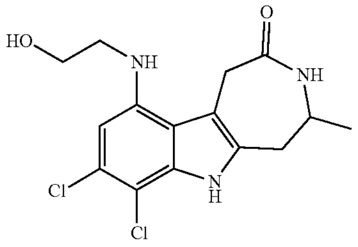 [SMILES: CC1Cc2[nH]c3c(Cl)c(Cl)cc(NCCO)c3c2CC(=O)N1]

Combined 10-bromo-7,8-dichloro-4-methyl-3,4,5,6-tetrahydroazepino[4,5-b]indol-2(1H)-one (150 mg, 0.331 mmol, 80 mass %), 2-aminoethane-1-ol (41 mg, 0.66 mmol), $Pd_2(dba)_3$ (30 mg, 0.033 mmol), Xantphos (19 mg, 0.033 mmol) and cesium carbonate (270 mg, 0.829 mmol) in 1,4-dioxane. Degassed and purged with $N_2$ (x3). Stirred at 100° C. for 16 hrs, under $N_2$ atmosphere. Filtered and diluted the filtrate with water, then extracted with EtOAc. Combined organic layers, dried over anhydrous $Na_2SO_4$, filtered, and concentrated under reduced pressure. Purified by prep-HPLC. Concentrated under reduced pressure and lyophilized to give 7,8-dichloro-10-((2-hydroxyethyl)amino)-4-methyl-3,4,5,6-tetrahydroazepino[4,5-b]indol-2(1H)-one (17.70 mg, 16%) as a yellow solid. ES/MS (m/z): ($^{35}Cl/^{37}Cl$) 342.0/344.0 (M+H).

Intermediate 155

Methyl 7-(2-methoxyethyl)-8-oxo-1,4-dioxaspiro[4.5]decane-7-carboxylate

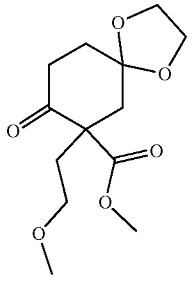 [SMILES: COCCC1(C(=O)OC)CC2(CCC1=O)OCCO2]

Combined methyl 8-oxo-1,4-dioxaspiro[4.5]decane-7-carboxylate (6.42 g, 25.2 mmol, 84% purity), potassium carbonate (5.27 g, 37.8 mmol), potassium iodide (2.11 g, 12.6 mmol), and DMF (50 mL). Purged with $N_2$ and added 1-bromo-2-methoxyethane (2.93 mL, 47.0 mmol). Stirred at 80° C. for 24 hrs, filtered, added 50 mL of water to the filtrate, and added 5M HCl slowly until pH 7. Concentrated under reduced pressure, partitioned the residue between EtOAc and water, and separated the layers. Washed the organic layer with water and saturated aqueous NaCl, filtered, dried over anhydrous $Na_2SO_4$, and concentrated under reduced pressure. Purified by silica gel flash chromatography eluting with hexanes/EtOAc and dried under reduced pressure to give methyl 7-(2-methoxyethyl)-8-oxo-1,4-dioxaspiro[4.5]decane-7-carboxylate (4.75 g, 69%) as a colorless oil that crystallized to a white solid upon standing. GCMS (m/z): 272.1. $^1H$ NMR ($CDCl_3$): 4.07-3.92 (m, 4H), 3.72 (s, 3H), 3.53-3.47 (ddd, J=9.8, 6.6, 5.8 Hz, 1H), 3.37 (dt, J=9.8, 6.8 Hz, 1H), 3.25 (s, 3H), 3.02 (ddd, J=14.5, 11.4, 8.8 Hz, 1H), 2.63 (dd, J=14.0, 2.3 Hz, 1H), 2.48 (dt, J=14.5, 4.2 Hz, 1H), 2.07-1.96 (m, 3H), 1.89 (quintet, J=6.9 Hz, 1H), 1.81 (d, J=14.0 Hz, 1H).

Intermediate 156

Methyl (E)-8-(2-(5-bromo-2,3-dichlorophenyl)hydrazineylidene)-7-(2-methoxyethyl)-1,4-dioxaspiro[4.5]decane-7-carboxylate

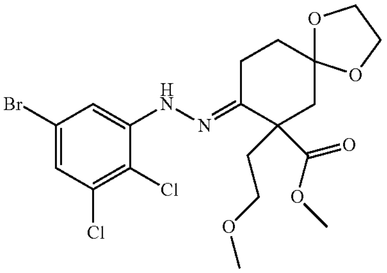 [SMILES: COCCC1(C(=O)OC)CC2(CC/C1=N\Nc1cc(Br)cc(Cl)c1Cl)OCCO2]

Combined methyl 7-(2-methoxyethyl)-8-oxo-1,4-dioxaspiro[4.5]decane-7-carboxylate (14.3 g, 52.4 mmol), MeOH (105 mL), acetic acid (3.0 mL, 52 mmol), and (5-bromo-2,3-dichlorophenyl)hydrazine (13.7 g, 52.5 mmol) under $N_2$. Refluxed for 20 hrs, cooled to ambient temperature, azeotroped with toluene (3×), and dried under reduced pressure at 70° C. to give methyl (E)-8-(2-(5-bromo-2,3-dichlorophenyl)hydrazineylidene)-7-(2-methoxyethyl)-1,4-dioxaspiro[4.5]decane-7-carboxylate (28.5 g, 99+%, 94% purity) as an orange syrup. ES/MS (m/z): 508.8/510.8/512.8 (M+H).

Intermediate 157

Methyl 5-bromo-7,8-dichloro-1-(2-methoxyethyl)-1,2,4,9-tetrahydrospiro[carbazole-3,2'-[1,3]dioxolane]-1-carboxylate

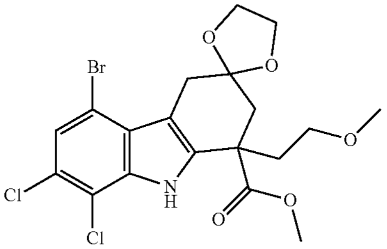 [SMILES: COCCC1(C(=O)OC)CC2(Cc3c1[nH]c1c(Cl)c(Cl)cc(Br)c31)OCCO2]

Charged a flask with zinc chloride (17.2 g, 126 mmol) and heated under vacuum until the zinc chloride became a free-flowing solid. Cooled the flask to ambient temperature and added a solution of methyl (E)-8-(2-(5-bromo-2,3-dichlorophenyl)hydrazineylidene)-7-(2-methoxyethyl)-1,4-dioxaspiro[4.5]decane-7-carboxylate (28.5 g, 52.5 mmol) in xylenes (175 mL) under $N_2$. Purged with nitrogen and refluxed for 5 days. Cooled to ambient temperature, added EtOAc and saturated aqueous sodium bicarbonate, and then added 5M HCl slowly until pH 7. Separated the layers and extracted the aqueous layer with EtOAc (4×). Washed the combined organic layers with saturated aqueous NaCl, filtered, dried over anhydrous $Na_2SO_4$, and concentrated under reduced pressure. Purified by silica gel flash chromatography eluting with EtOAc in hexanes. Further purified by silica gel flash chromatography eluting with EtOAc in DCM and dried under reduced pressure to give methyl 5-bromo-7,8-dichloro-1-(2-methoxyethyl)-1,2,4,9-tetrahydrospiro [carbazole-3,2'-[1,3]dioxolane]-1-carboxylate (11.46 g, 44%) as a yellow solid. ES/MS (m/z): 491.8/493.8/495.8 (M+H).

Intermediate 158

5-Bromo-7,8-dichloro-1-(2-methoxyethyl)-1,2,4,9-tetrahydrospiro[carbazole-3,2'-[1,3]dioxolane]-1-carboxylic acid

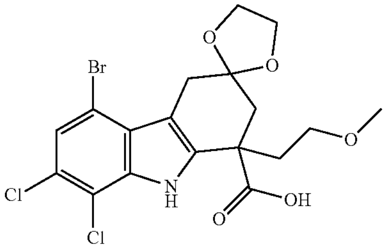 [SMILES: COCCC1(C(=O)O)CC2(Cc3c1[nH]c1c(Cl)c(Cl)cc(Br)c31)OCCO2]

Combined methyl 5-bromo-7,8-dichloro-1-(2-methoxyethyl)-1,2,4,9-tetrahydrospiro[carbazole-3,2'-[1,3]dioxolane]-1-carboxylate (11.46 g, 23.00 mmol), THF (100 mL), and MeOH (100 mL). Added 5M aqueous sodium hydroxide (9.20 mL, 46.0 mmol) and stirred at ambient temperature for 3 days. Added 5M aqueous HCl (9.20 mL, 46.0 mmol) dropwise and concentrated under reduced pressure. Suspended the residue in MeOH in DCM (1:9), sonicated, filtered, and rinsed the solids with DCM. Dried the filtrate over anhydrous $Na_2SO_4$, concentrated under reduced pressure, azeotroped with DCM, and dried under reduced pressure to give 5-bromo-7,8-dichloro-1-(2-methoxyethyl)-1,2,4,9-tetrahydrospiro[carbazole-3,2'-[1,3]dioxolane]-1-carboxylic acid (11.84 g, 95%, 88% purity) as a light orange solid. ES/MS (m/z): 477.8/479.8/481.8 (M+H).

Intermediate 159

5-Bromo-7,8-dichloro-1-(2-methoxyethyl)-1,2,4,9-tetrahydro-3H-carbazol-3-one

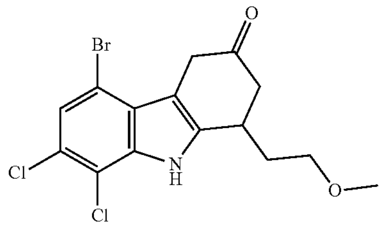 [SMILES: COCCC1CC(=O)Cc2c1[nH]c1c(Cl)c(Cl)cc(Br)c21]

Combined 5-bromo-7,8-dichloro-1-(2-methoxyethyl)-1,2,4,9-tetrahydrospiro[carbazole-3,2'-[1,3]dioxolane]-1-carboxylic acid (11.84 g, 21.75 mmol, 88% purity, azeotroped with toluene immediately before use) and acetic acid (87 mL) under $N_2$. Purged with $N_2$ and stirred at 125° C. for 3 days. Cooled to ambient temperature, concentrated under reduced pressure, and azeotroped twice with toluene. Suspended the residue in 2:1 hexanes/toluene, collected the solids by vacuum filtration, washed with hexanes (2×), and dried to give 5-bromo-7,8-dichloro-1-(2-methoxyethyl)-1,2,4,9-tetrahydro-3H-carbazol-3-one (8.09 g, 94%) as a cream-colored solid. ES/MS (m/z): 389.8/391.8/393.8 (M+H).

Intermediate 160

10-Bromo-7,8-dichloro-5-(2-methoxyethyl)-3,4,5,6-tetrahydroazepino[4,5-b]indol-2(1H)-one

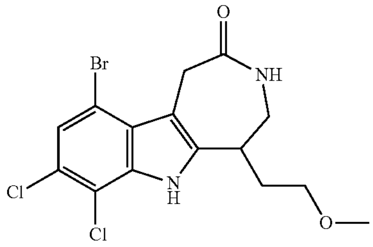 [SMILES: COCCC1CNC(=O)Cc2c1[nH]c1c(Cl)c(Cl)cc(Br)c21]

Cooled a suspension of 5-bromo-7,8-dichloro-1-(2-methoxyethyl)-1,2,4,9-tetrahydro-3H-carbazol-3-one (4.00 g, 10.2 mmol) in methanesulfonic acid (68 mL) in an ice water bath until the solvent was almost frozen. Added sodium azide (798 mg, 12.3 mmol) slowly, stirred at 0° C. for 30 min, warmed to ambient temperature, and stirred the mixture at ambient temperature for 30 min. Added the reaction mixture dropwise to a mixture of ice and 2M aqueous potassium carbonate with stirring causing a precipitate to form. Collected the solids by vacuum filtration, washed with water (3×), and dried to give a light brown solid. Suspended the solid in MeOH in DCM (1:9), sonicated, collected the solids by vacuum filtration, and washed with MeOH in DCM (1:9) and then with DCM, and dried to give 10-bromo-7,8-dichloro-5-(2-methoxyethyl)-3,4,5,6-tetrahydroazepino[4,5-b]indol-2(1H)-one (1.94 g, 44%) as a cream-colored solid. ES/MS (m/z): 404.8/406.8/408.8 (M+H).

Example 166

7,8-Dichloro-5-(2-methoxyethyl)-10-(2-methyl-2H-1,2,3-triazol-4-yl)-3,4,5,6-tetrahydroazepino[4,5-b]indol-2(1H)-one

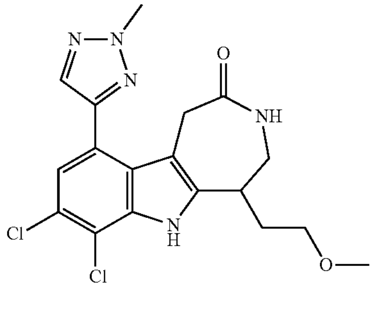 [SMILES: COCCC1CNC(=O)Cc2c1[nH]c1c(Cl)c(Cl)cc(-c3cnn(C)n3)c21]

Combined 10-bromo-7,8-dichloro-5-(2-methoxyethyl)-3,4,5,6-tetrahydroazepino[4,5-b]indol-2(1H)-one (300 mg, 0.702 mmol), 2-methyl-4-(4,4,5,5-tetramethyl-1,3,2-dioxaborolan-2-yl)-2H-1,2,3-triazole (229 mg, 1.05 mmol), potassium carbonate (291 mg, 2.11 mmol), Pd(dppf)$Cl_2$ (86 mg, 0.105 mmol), 1,4-dioxane (4.7 mL), and water (0.9 mL). Purged with $N_2$ and heated to 100° C. for 2 hrs. Cooled to ambient temperature, diluted with 90% EtOAc/10% MeOH, filtered through a plug of silica gel, rinsed thoroughly through the silica with 90% EtOAc/10% MeOH, and concentrated the filtrate under reduced pressure to give a residue. Purified the crude product by flash column chromatography eluting with MeOH in EtOAc. Purified further by reverse phase chromatography to give 7,8-dichloro-5-(2-methoxyethyl)-10-(2-methyl-2H-1,2,3-triazol-4-yl)-3,4,5,6-tetrahydroazepino[4,5-b]indol-2(1H)-one (66 mg, 23%) as a cream-colored solid. ES/MS (m/z): ($^{35}Cl/^{37}Cl$) 407.8/409.8 (M+H).

Example 167

(R)-7,8-Dichloro-5-(2-methoxyethyl)-10-(2-methyl-2H-1,2,3-triazol-4-yl)-3,4,5,6-tetrahydroazepino[4,5-b]indol-2(1H)-one (isomer 1) and Example 168

(S)-7,8-Dichloro-5-(2-methoxyethyl)-10-(2-methyl-2H-1,2,3-triazol-4-yl)-3,4,5,6-tetrahydroazepino[4,5-b]indol-2(1H)-one (isomer 2)

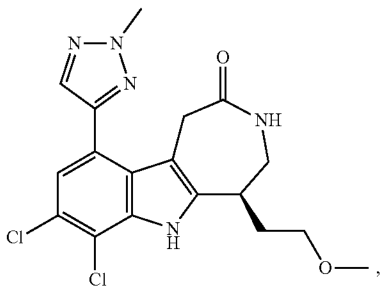
,
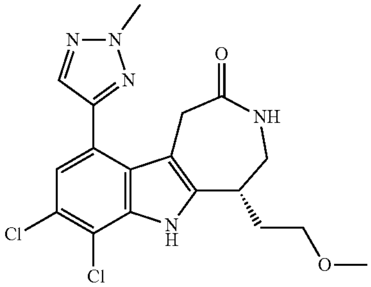

Purified racemic 7,8-dichloro-5-(2-methoxyethyl)-10-(2-methyl-2H-1,2,3-triazol-4-yl)-3,4,5,6-tetrahydroazepino[4,5-b]indol-2(1H)-one (61 mg, 0.15 mmol) by SFC to give (R)-7,8-dichloro-5-(2-methoxyethyl)-10-(2-methyl-2H-1,2,3-triazol-4-yl)-3,4,5,6-tetrahydroazepino[4,5-b]indol-2(1H)-one (Isomer 1—RT=1.42 min (100% ee), 24 mg, 39%; chiral analysis used 25% MeOH: 75% $CO_2$) and (S)-7,8-dichloro-5-(2-methoxyethyl)-10-(2-methyl-2H-1,2,3-triazol-4-yl)-3,4,5,6-tetrahydroazepino[4,5-b]indol-2(1H)-one (Isomer 2—RT=3.04 min (99% ee), 24 mg, 39%; chiral analysis used 25% MeOH: 75% $CO_2$). Column: Chiralpak AD-H, 21×150 mm; Mobile Phase: 40% MeOH: 60% $CO_2$; Flow Rate: 80 mL/min; Column temperature: 40° C.; Detection: 225 nM. ES/MS (m/z): ($^{35}Cl/^{37}Cl$) 408.0/410.0 (M+H).

Intermediate 161

10-Bromo-7,8-dichloro-1-ethoxy-5-(2-methoxyethyl)-3,4,5,6-tetrahydroazepino[4,5-b]indole-2(1H)-one

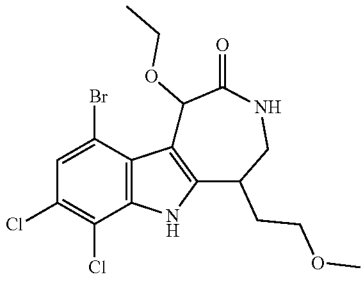 [SMILES: CCOC1C(=O)NCC(CCOC)c2[nH]c3c(Cl)c(Cl)cc(Br)c3c21]

Dissolved 10-bromo-7,8-dichloro-5-(2-methoxyethyl)-3,4,5,6-tetrahydroazepino[4,5-b]indol-2(1H)-one (622 mg, 1.53 mmol) in EtOAc (10 mL). Stirred for 5 min at ambient temperature, then added pyridinium bromide perbromide (735 mg, 2.30 mmol). After 24 hrs, cooled the reaction in an ice-water bath. After 10 min, added sodium ethoxide (1.94 g, 2.23 mL, 5.97 mmol, 21 wt % in ethanol). Stirred for 5 min in the ice-water bath, then at ambient temperature for an additional 24 hrs. Diluted the mixture with EtOAc (100 mL). Added a small amount of diatomaceous earth, filtered, rinsed with EtOAc (200 mL) and water (200 mL). Transferred filtrate to a separatory funnel. Extracted with EtOAc, washed with saturated aqueous NaCl, dried over anhydrous $Na_2SO_4$, filtered and concentrated under reduced pressure to give impure 10-bromo-7,8-dichloro-1-ethoxy-5-(2-methoxyethyl)-3,4,5,6-tetrahydroazepino[4,5-b]indole-2(1H)-one (700 mg, 99+%). ES/MS (m/z): 448.8/450.8 (M+H).

Intermediate 162

10-Bromo-7,8-dichloro-5-(2-methoxyethyl)-1-methyl-3,4,5,6-tetrahydroazepino[4,5-b]indol-2(1H)-one

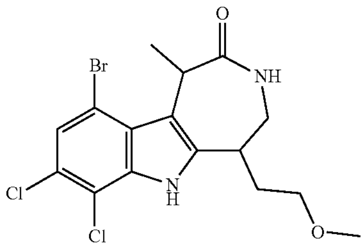 [SMILES: COCCC1CNC(=O)C(C)c2c1[nH]c1c(Cl)c(Cl)cc(Br)c21]

Diluted MeMgBr (3.11 mL, 9.33 mmol, 3M in diethyl ether) in THF (6 mL) and cooled to 0° C. Added slowly dropwise a solution of 10-bromo-7,8-dichloro-1-ethoxy-5-(2-methoxyethyl)-3,4,5,6-tetrahydroazepino[4,5-b]indole-2(1H)-one (700 mg, 1.56 mmol) in THF (6 mL). Stirred at 0°

C. for 8 hrs. Quenched slowly with 10% aqueous citric acid (50 mL) and transferred to a separatory funnel. Extracted with EtOAc, washed with saturated aqueous NaCl, dried over anhydrous $Na_2SO_4$, filtered, and concentrated under reduced pressure. Purified by silica gel flash chromatography eluting with DCM/EtOAc/MeOH to give 10-bromo-7,8-dichloro-5-(2-methoxyethyl)-1-methyl-3,4,5,6-tetrahydroazepino[4,5-b]indol-2(1H)-one (300 mg, 46%) as a yellow solid mixture of diastereomers. ES/MS (m/z): 418.8/420.8/422.8 (M+H).

Intermediate 163 trans-10-((2-((tert-Butyldimethylsilyl)oxy)ethyl)amino)-7,8-dichloro-5-(2-methoxyethyl)-1-methyl-3,4,5,6-tetrahydroazepino[4,5-b]indol-2(1H)-one

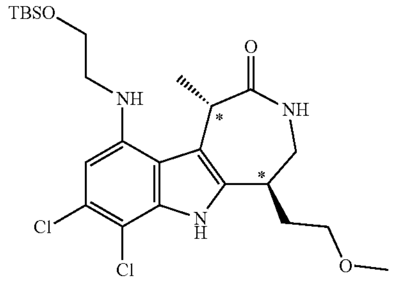 [SMILES: COCC[C@@H]1CNC(=O)[C@@H](C)c2c1[nH]c1c(Cl)c(Cl)cc(NCCO[Si](C)(C)C(C)(C)C)c21]

and

Intermediate 164 cis-10-((2-((tert-Butyldimethylsilyl)oxy)ethyl)amino)-7,8-dichloro-5-(2-methoxyethyl)-1-methyl-3,4,5,6-tetrahydroazepino[4,5-b]indol-2(1H)-one

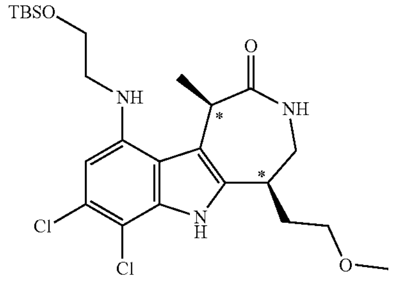 [SMILES: COCC[C@@H]1CNC(=O)[C@H](C)c2c1[nH]c1c(Cl)c(Cl)cc(NCCO[Si](C)(C)C(C)(C)C)c21]

Combined 10-bromo-7,8-dichloro-5-(2-methoxyethyl)-1-methyl-3,4,5,6-tetrahydroazepino[4,5-b]indol-2(1H)-one (450 mg, 1.07 mmol), 2-((tert-butyldimethylsilyl)oxy)ethan-1-amine (188 mg, 1.07 mmol), tripotassium phosphate (909 mg, 4.28 mmol) and XantPhos-Pd-G2 (190 mg, 0.214 mmol) in 1,4-dioxane (5 mL). Purged with $N_2$ and heated to 100° C. Stirred overnight. Cooled to ambient temperature and diluted with EtOAc. Washed with saturated sodium bicarbonate solution and saturated aqueous NaCl. Dried organic layer over anhydrous $Na_2SO_4$, filtered and concentrated under reduced pressure. Purified by silica gel flash chromatography eluting with DCM in EtOAc and MeOH. Concentrated mixture of diastereomers and purified by reverse phase chromatography to give separated cis and trans isomers. ES/MS (m/z): 514.4/516.4 (M+H).

trans- (237 mg, 43%)—$^1$H NMR (DMSO-d6): 11.04 (s, 1H), 7.73 (t, J=6.3 Hz, 1H), 6.27 (s, 1H), 4.94 (t, J=5.4 Hz, 1H), 4.10 (q, J=7.5 Hz, 1H), 3.87-3.81 (m, 3H), 3.72 (dd, J=5.5, 14.5 Hz, 1H), 3.52-3.46 (m, 3H), 3.30-3.30 (m, 5H), 3.25-3.16 (m, 4H), 2.03-1.95 (m, 1H), 1.77-1.70 (m, 1H), 1.55 (d, J=7.5 Hz, 4H), 0.89 (s, 9H), 0.08 (s, 6H)

cis- (212 mg, 39%)—$^1$H NMR (DMSO-d6): 10.92 (s, 1H), 7.72 (t, J=6.2 Hz, 1H), 6.29 (s, 1H), 4.80 (t, J=5.3 Hz, 1H), 4.13 (q, J=7.6 Hz, 1H), 3.89-3.83 (m, 2H), 3.67-3.59 (m, 1H), 3.38 (t, J=6.4 Hz, 2H), 3.32 (s, 2H), 3.25 (s, 7H), 3.12-3.05 (m, 1H), 2.45-2.33 (m, 1H), 2.22-2.14 (m, 1H), 1.92-1.82 (m, 1H), 1.62 (d, J=7.7 Hz, 4H), 0.88 (s, 9H), 0.08 (s, 6H).

Example 169 trans-7,8-Dichloro-10-((2-hydroxyethyl)amino)-5-(2-methoxyethyl)-1-methyl-3,4,5,6-tetrahydroazepino[4,5-b]indol-2(1H)-one

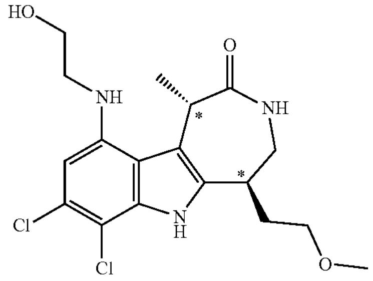 [SMILES: COCC[C@@H]1CNC(=O)[C@@H](C)c2c1[nH]c1c(Cl)c(Cl)cc(NCCO)c21]

Combined racemic trans-10-((2-((tert-butyldimethylsilyl)oxy)ethyl)amino)-7,8-dichloro-5-(2-methoxyethyl)-1-methyl-3,4,5,6-tetrahydroazepino[4,5-b]indol-2(1H)-one (95 mg, 0.18 mmol) and THF (2 mL). Added TBAF (0.74 mL, 0.74 mmol, 1.0M in THF) and stirred at ambient temperature for 1 hr. Concentrated the reaction under reduced pressure, diluted with EtOAc (50 mL) and washed with saturated ammonium chloride solution and saturated aqueous NaCl. Dried the organic layer over anhydrous $Na_2SO_4$, filtered and concentrated under reduced pressure to give racemic trans-7,8-dichloro-10-((2-hydroxyethyl)amino)-5-(2-methoxyethyl)-1-methyl-3,4,5,6-tetrahydroazepino[4,5-b]indol-2(1H)-one (75 mg, 100%). ES/MS (m/z): ($^{35}$Cl/$^{37}$Cl) 400.2/402.2 (M+H).

Example 170 cis 7,8-Dichloro-10-((2-hydroxyethyl)amino)-5-(2-methoxyethyl)-1-methyl-3,4,5,6-tetrahydroazepino [4,5-b]indol-2(1H)-one

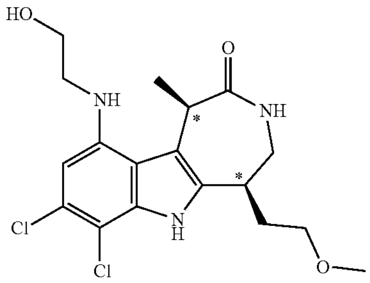 [SMILES: COCC[C@@H]1CNC(=O)[C@H](C)c2c1[nH]c1c(Cl)c(Cl)cc(NCCO)c21]

Combined racemic cis-10-((2-((tert-butyldimethylsilyl) oxy)ethyl)amino)-7,8-dichloro-5-(2-methoxyethyl)-1-methyl-3,4,5,6-tetrahydroazepino[4,5-b]indol-2(1H)-one (95 mg, 0.18 mmol) and THF (2 mL). Added TBAF (0.74 mL, 0.74 mmol, 1.0M in THF) and stirred at ambient temperature for 1 hr. Concentrated the reaction, diluted with EtOAc (50 mL) and washed with saturated ammonium chloride solution and saturated aqueous NaCl. Dried the organic layer over anhydrous $Na_2SO_4$, filtered and concentrated to give racemic cis 7,8-dichloro-10-((2-hydroxyethyl) amino)-5-(2-methoxyethyl)-1-methyl-3,4,5,6-tetrahydroazepino[4,5-b]indol-2(1H)-one (70 mg, 95%). ES/MS (m/z): ($^{35}Cl/^{37}Cl$) 400.2/402.2 (M+H).

Example 171

(1R,5S)-7,8-Dichloro-10-((2-hydroxyethyl)amino)-5-(2-methoxyethyl)-1-methyl-3,4,5,6-tetrahydroazepino[4,5-b]indol-2(1H)-one Or (1S,5R)-7,8-Dichloro-10-((2-hydroxyethyl)amino)-5-(2-methoxyethyl)-1-methyl-3,4,5,6-tetrahydroazepino [4,5-b]indol-2(1H)-one (isomer 1) and Example 172

(1R,5S)-7,8-Dichloro-10-((2-hydroxyethyl)amino)-5-(2-methoxyethyl)-1-methyl-3,4,5,6-tetrahydroazepino[4,5-b]indol-2(1H)-one Or (1S,5R)-7,8-Dichloro-10-((2-hydroxyethyl)amino)-5-(2-methoxyethyl)-1-methyl-3,4,5,6-tetrahydroazepino [4,5-b]indol-2(1H)-one (isomer 2)

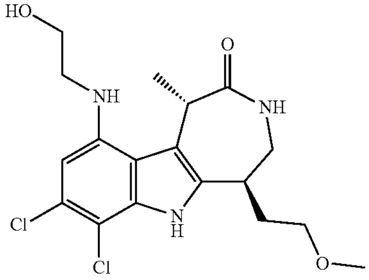

,

-continued

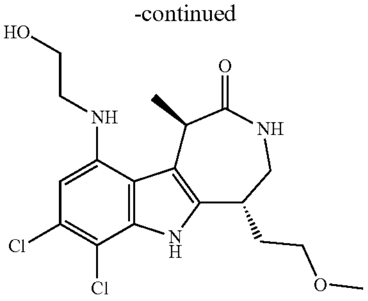

Purified racemic trans-7,8-dichloro-10-((2-hydroxyethyl) amino)-5-(2-methoxyethyl)-1-methyl-3,4,5,6-tetrahydroazepino[4,5-b]indol-2(1H)-one (70 mg, 0.17 mmol) by SFC to give the titled compounds (Isomer 1—Rt=0.98 min (97% ee) 22 mg, 32%; Isomer 2—Rt=1.71 min (99% ee) 21 mg, 31%). Column: Chiralpak AD-H, 21×150 mm; Mobile Phase: 25% MeOH: 75% $CO_2$; Flow Rate: 80 mL/min; Detection: 225 nM. ES/MS (m/z): ($^{35}Cl/^{37}Cl$) 400.2/402.2 (M+H).

Example 173

(1S,5S)-7,8-Dichloro-10-((2-hydroxyethyl)amino)-5-(2-methoxyethyl)-1-methyl-3,4,5,6-tetrahydroazepino[4,5-b]indol-2(1H)-one Or (1R,5R)-7,8-Dichloro-10-((2-hydroxyethyl)amino)-5-(2-methoxyethyl)-1-methyl-3,4,5,6-tetrahydroazepino [4,5-b]indol-2(1H)-one (isomer 1) and Example 174

(1S,5S)-7,8-Dichloro-10-((2-hydroxyethyl)amino)-5-(2-methoxyethyl)-1-methyl-3,4,5,6-tetrahydroazepino[4,5-b]indol-2(1H)-one Or (1R,5R)-7,8-Dichloro-10-((2-hydroxyethyl)amino)-5-(2-methoxyethyl)-1-methyl-3,4,5,6-tetrahydroazepino [4,5-b]indol-2(1H)-one (isomer 2)

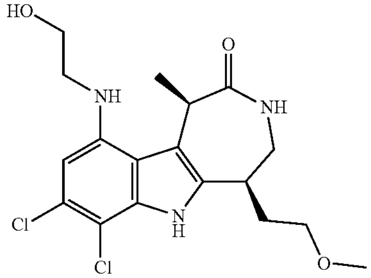

,

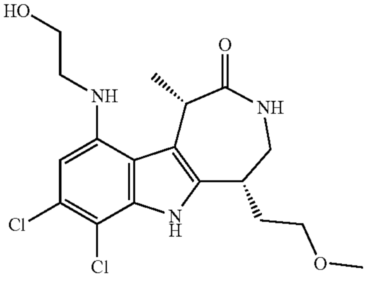

Purified racemic cis-7,8-dichloro-10-((2-hydroxyethyl) amino)-5-(2-methoxyethyl)-1-methyl-3,4,5,6-tetrahydroazepino[4,5-b]indol-2(1H)-one (70 mg, 0.17 mmol) by SFC to give the titled compounds (Isomer 1—Rt=1.98 min (96% ee) 18 mg, 26%; Isomer 2—Rt=2.80 min (93% ee) 19 mg, 27%). Column: Chiralpak AD-H, 21×150 mm; Mobile Phase: 25% MeOH: 75% $CO_2$; Flow Rate: 80 mL/min; Detection: 225 nM. ES/MS (m/z): ($^{35}Cl/^{37}Cl$) 400.2/402.2 (M+H).

Example 175

(R)-7,8-Dichloro-10-(2-methyl-2H-1,2,3-triazol-4-yl)-5-(2-morpholinoethyl)-3,4,5,6-tetrahydroazepino [4,5-b]indol-2(1H)-one Or (S)-7,8-Dichloro-10-(2-methyl-2H-1,2,3-triazol-4-yl)-5-(2-morpholinoethyl)-3,4,5,6-tetrahydroazepino[4,5-b] indol-2(1H)-one

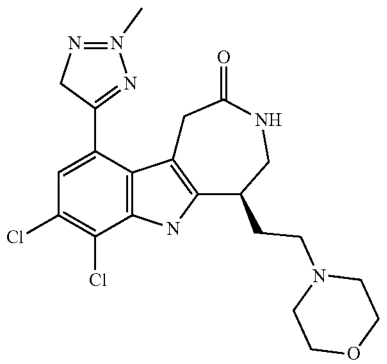

or

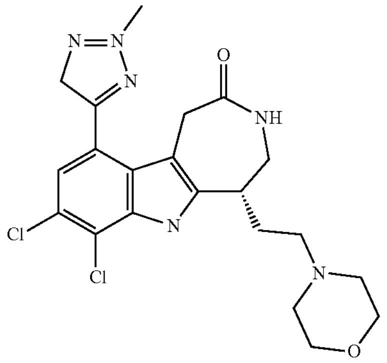

Dissolved single enantiomer 7,8-dichloro-5-(2-hydroxyethyl)-10-(2-methyl-2H-1,2,3-triazol-4-yl)-3,4,5,6-tetrahydroazepino[4,5-b]indol-2(1H)-one (Isomer 1, 0.29 g, 0.74 mmol) in DCM (3 mL). Added TEA (74 mg, 0.74 mmol) followed by methanesulfonyl chloride (84 mg, 0.74 mmol) under $N_2$ at ambient temperature. Stirred for 8 hrs. Added morpholine (63 μL, 0.74 mmol) and heated to 50° C. Stirred at 50° C. overnight. Cooled to ambient temperature and loaded directly onto a silica precolumn. Purified by silica gel column chromatography eluting with DCM and 7N ammonia in MeOH and further purified by reverse phase chromatography to give (R)-7,8-dichloro-10-(2-methyl-2H-1,2,3-triazol-4-yl)-5-(2-morpholinoethyl)-3,4,5,6-tetrahydroazepino[4,5-b]indol-2(1H)-one or (S)-7,8-dichloro-10-(2-methyl-2H-1,2,3-triazol-4-yl)-5-(2-morpholinoethyl)-3,4,5,6-tetrahydroazepino[4,5-b]indol-2 (1H)-one (61 mg, 18%) as an off-white solid. ES/MS (m/z): ($^{35}Cl/^{37}Cl$) 463.2/465.2 (M+H).

Intermediate 165

2-(7,8-Dichloro-10-(cyanomethyl)-2-oxo-1,2,3,4,5,6-hexahydroazepino[4,5-b]indol-5-yl)acetic acid

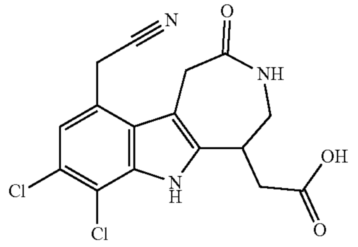 [SMILES: N#CCc1cc(Cl)c(Cl)c2[nH]c3c(c12)CC(=O)NCC3CC(=O)O]

Combined ethyl 2-(10-bromo-7,8-dichloro-2-oxo-1,2,3,4,5,6-hexahydroazepino[4,5-b]indol-5-yl)acetate (0.16 g, 0.368 mmol), DMSO (5 mL), water (1.25 mL), 4-isoxazoleboronic acid pinacol ester (0.16 mg, 0.804 mmol), Pd(dppf)$Cl_2$ (0.05 g, 0.068 mmol), and KF (0.150 g, 2.58 mmol). Stirred at 100° C. for 1 hr, via microwave. Quenched with water and extracted with EtOAc. Dried the organic layer over magnesium sulfate, filtered, and concentrated mixture to dryness under reduced pressure. Purified the residue via silica gel chromatography eluting with MeOH in DCM. Combined the purified material, DMF (3 mL), water (3 mL), and KF (0.09 g, 1.5 mmol). Stirred at 100° C. for 18 hrs. Concentrated mixture to dryness under reduced pressure. Purified the residue via reverse phase column chromatography to give 2-(7,8-dichloro-10-(cyanomethyl)-2-oxo-1,2,3,4,5,6-hexahydroazepino[4,5-b]indol-5-yl)acetic acid as a brown solid (20 mg, 28.2%). ES/MS (m/z): ($^{35}Cl/^{37}Cl$) 366.0/368.0 (M+H).

Example 176

Methyl 2-(7,8-dichloro-10-(cyanomethyl)-2-oxo-1,2,3,4,5,6-hexahydroazepino[4,5-b]indol-5-yl)acetate

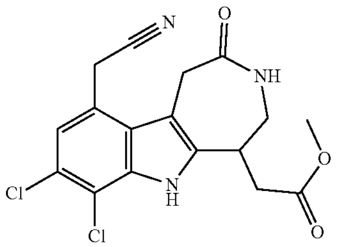 [SMILES: COC(=O)CC1CNC(=O)Cc2c1[nH]c1c(Cl)c(Cl)cc(CC#N)c21]

Combined 2-(7,8-dichloro-10-(cyanomethyl)-2-oxo-3,4,5,6-tetrahydro-1H-azepino[4,5-b]indol-5-yl)acetic acid (20 mg, 0.055 mmol), methanol (1 mL), and sulfuric acid (0.01 mL, 0.2 mmol). Stirred at ambient temperature for 18 hrs. Evaporated mixture to dryness under reduced pressure. Purified the residue via reverse phase chromatography to give methyl 2-(7,8-dichloro-10-(cyanomethyl)-2-oxo-1,2,3,4,5,6-hexahydroazepino[4,5-b]indol-5-yl)acetate as a white solid (14.9 mg, 72%). ES/MS (m/z): ($^{35}Cl/^{37}Cl$) 380.0/382.0 (M+H).

Intermediate 166

7,8-Dichloro-5-(2-iodoethyl)-10-(2-methyl-2H-1,2,3-triazol-4-yl)-3,4,5,6-tetrahydroazepino[4,5-b]indol-2(1H)-one

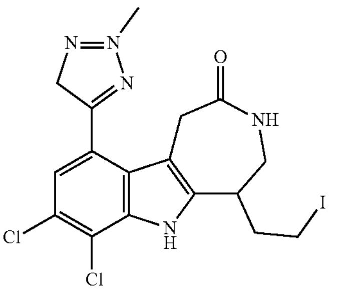

Combined triphenylphosphine (0.32 g, 1.2 mmol), imidazole (82 mg, 1.2 mmol), and iodine (0.31 g, 1.2 mmol) in anhydrous DCM (4.0 mL). Added racemic 7,8-dichloro-5-(2-hydroxyethyl)-10-(2-methyl-2H-1,2,3-triazol-4-yl)-3,4,5,6-tetrahydroazepino[4,5-b]indol-2(1H)-one (0.49 g, 65% purity, 0.81 mmol) portion-wise at 0° C. Warmed to ambient temperature and stirred overnight. Washed with an aqueous 20% (w/v) solution of $Na_2S_2O_3$, water, and saturated aqueous NaCl. Dried organic layer over $Na_2SO_4$, filtered, and concentrated under reduced pressure. Purified by flash chromatography eluting with MeOH in EtOAc to give 7,8-dichloro-5-(2-iodoethyl)-10-(2-methyl-2H-1,2,3-triazol-4-yl)-3,4,5,6-tetrahydroazepino[4,5-b]indol-2(1H)-one (270 mg, 63%) as a brown solid. ES/MS (m/z): ($^{35}Cl/^{37}Cl$) 503.8/505.8 (M+H).

Example 177

7,8-Dichloro-5-(3,3-difluoropropyl)-10-(2-methyl-2H-1,2,3-triazol-4-yl)-3,4,5,6-tetrahydroazepino[4,5-b]indol-2(1H)-one

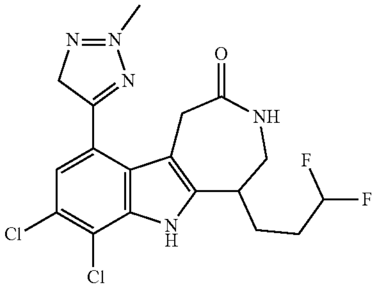

Combined racemic 7,8-dichloro-5-(2-iodoethyl)-10-(2-methyl-2H-1,2,3-triazol-4-yl)-3,4,5,6-tetrahydroazepino[4,5-b]indol-2(1H)-one (133 mg, 0.251 mmol), copper(II) trifluoromethanesulfonate (12.4 mg, 34.3 μmol), and 2,2';6',2"-terpyridine (8.00 mg, 34.3 μmol). Purged with nitrogen, added DMSO (343 μL), and stirred for 1 min. Added a solution of $(DMPU)_2Zn(CF_2H)_2$ (109 mg, 257 μmol) in DMSO (343 μL) while simultaneously adding a solution of 2,4,6-trimethylbenzenediazonium tetrafluoroborate (100 mg, 0.429 mmol) in DMSO (343 μL) dropwise. Stirred for 2 hrs, added $(DMPU)_2Zn(CF_2H)_2$ (109 mg, 257 μmol) in DMSO (343 μL), and stirred for an additional hour. Added 2,4,6-trimethylbenzenediazonium tetrafluoroborate (40 mg, 0.172 mmol) in 0.2 mL DMSO, and stirred for 3 hrs. Diluted with water (3 mL) and extracted with EtOAc (10 mL×3). Combined the organic layers, washed with saturated aqueous NaCl, and concentrated under reduced pressure. Purified the crude product by reverse phase chromatography and further purified by silica gel chromatography, eluting with EtOAc in hexanes followed by MeOH in EtOAc. Purified again by reverse phase chromatography and dried in a vacuum oven to give racemic 7,8-dichloro-5-(3,3-difluoropropyl)-10-(2-methyl-2H-1,2,3-triazol-4-yl)-3,4,5,6-tetrahydroazepino[4,5-b]indol-2(1H)-one (19 mg, 23%, 90% purity) as a white solid. ES/MS (m/z): ($^{35}Cl/^{37}Cl$) 428.0/430.0 (M+H).

Intermediate 167

7,8-Dichloro-1-methyl-10-(oxazol-4-ylmethoxy)-3,4,5,6-tetrahydroazepino[4,5-b]indol-2(1H)-one

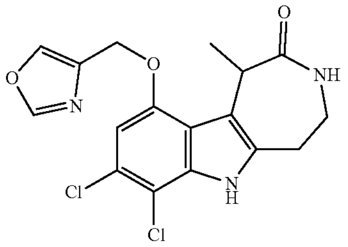 [SMILES: CC1C(=O)NCCc2[nH]c3c(Cl)c(Cl)cc(OCc4cocn4)c3c21]

To a mixture of 7,8-dichloro-10-hydroxy-1-methyl-3,4,5,6-tetrahydroazepino[4,5-b]indol-2(1H)-one (215 mg, 0.696 mmol) and potassium carbonate (389 mg, 2.78 mmol) in DMF (5 mL) was added 4-(bromomethyl)oxazole (343 mg, 2.09 mmol). The mixture was stirred at 20° C. for 16 hrs. The mixture was diluted with water and extracted with EtOAc (3×). The combined organic layers were washed with saturated aqueous NaCl, dried over anhydrous $Na_2SO_4$, filtered, and concentrated under reduced pressure. Purification was performed by prep-HPLC to give 7,8-dichloro-1-methyl-10-(oxazol-4-ylmethoxy)-3,4,5,6-tetrahydroazepino[4,5-b]indol-2(1H)-one (85 mg, 32%) as a yellow solid. ES/MS (m/z): ($^{35}Cl/^{37}Cl$) 380.0/382.1 (M+H).

Example 178

(S)-7,8-Dichloro-1-methyl-10-(oxazol-4-ylmethoxy)-3,4,5,6-tetrahydroazepino[4,5-b]indol-2(1H)-one or (R)-7,8-dichloro-1-methyl-10-(oxazol-4-ylmethoxy)-3,4,5,6-tetrahydroazepino[4,5-b]indol-2(1H)-one (isomer 1) and Example 179

(S)-7,8-Dichloro-1-methyl-10-(oxazol-4-ylmethoxy)-3,4,5,6-tetrahydroazepino[4,5-b]indol-2(1H)-one or (R)-7,8-dichloro-1-methyl-10-(oxazol-4-ylmethoxy)-3,4,5,6-tetrahydroazepino[4,5-b]indol-2(1H)-one (isomer 2)

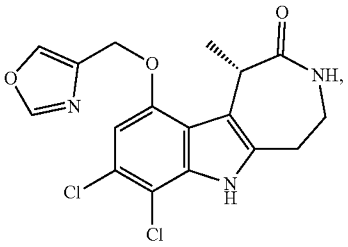

,

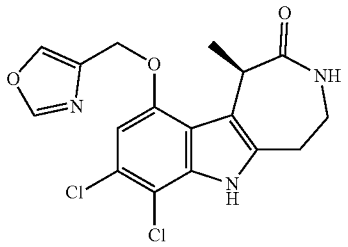

Purified racemic 7,8-dichloro-1-methyl-10-(oxazol-4-ylmethoxy)-3,4,5,6-tetrahydroazepino[4,5-b]indol-2(1H)-one (85 mg, 0.22 mmol) by SFC to give the titled compounds (Isomer 1—Rt=1.57 min (99% ee) 23 mg, 27%; Isomer 2—Rt=2.06 min (99% ee) 21 mg, 25%). Column: Chiralpak AD, 250×30 mm; Mobile Phase: 40% iPrOH: 60% $CO_2$; Flow Rate: 80 mL/min; Detection: 225 nM. ES/MS (m/z): ($^{35}Cl/^{37}Cl$) 380.1/382.0 (M+H). (Chiral analysis used—Column: Chiralpak AD-3, 50×4.6 mm, 3 μm; Mobile phase: A: $CO_2$ B: IPA (0.05% DEA). Gradient: from 5% to 40% of B in 1.5 min and hold 40% of 1 min, then 5% of B for 0.5 min. Flow Rate: 4 mL/min).

Intermediate 168

7,8-Dichloro-1-methyl-10-(((R)-oxetan-2-yl)methoxy)-6-((2-(trimethylsilyl)ethoxy)methyl)-3,4,5,6-tetrahydroazepino[4,5-b]indol-2(1H)-one

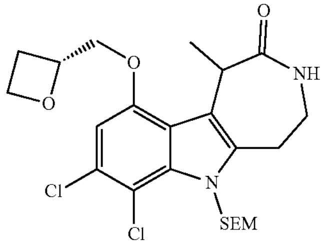 [SMILES: CC1C(=O)NCCc2c1c1c(OC[C@H]3CCO3)cc(Cl)c(Cl)c1n2COCC[Si](C)(C)C]

To a mixture of 7,8-dichloro-10-hydroxy-1-methyl-6-((2-(trimethylsilyl)ethoxy)methyl)-3,4,5,6-tetrahydroazepino[4,5-b]indol-2(1H)-one (300 mg, 46 weight %, 0.321 mmol) and $Cs_2CO_3$ (276 mg, 0.803 mmol) in DMF (8 mL) was added (R)-oxetan-2-ylmethyl 4-methylbenzenesulfonate (105 mg, 0.418 mmol). The mixture was stirred at 80° C. for 2 hrs. The reaction mixture was diluted with water and extracted with EtOAc (3×). The combined organic phase was washed with saturated aqueous NaCl, dried over anhydrous $Na_2SO_4$, filtered, and concentrated under reduced pressure to give a residue that was purified by column chromatography (MeOH/DCM). 7,8-dichloro-1-methyl-10-(((R)-oxetan-2-yl)methoxy)-6-((2-(trimethylsilyl)ethoxy)methyl)-3,4,5,6-tetrahydroazepino[4,5-b]indol-2(1H)-one (200 mg, 93%) was obtained as brown gum. ES/MS (m/z): ($^{35}Cl/^{37}Cl$) 499.2/501.1 (M+H).

Example 180

7,8-Dichloro-1-methyl-10-(((R)-oxetan-2-yl)methoxy)-3,4,5,6-tetrahydroazepino[4,5-b]indol-2(1H)-one

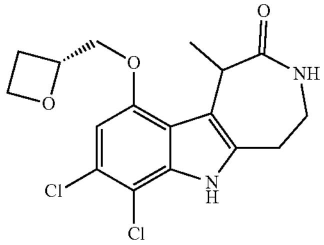 [SMILES: CC1C(=O)NCCc2[nH]c3c(Cl)c(Cl)cc(OC[C@H]4CCO4)c3c21]

To a solution of 7,8-dichloro-1-methyl-10-(((R)-oxetan-2-yl)methoxy)-6-((2-(trimethylsilyl)ethoxy)methyl)-3,4,5,6-tetrahydroazepino[4,5-b]indol-2(1H)-one (200 mg, 75% purity, 0.300 mmol) in THF (3 mL) was added TBAF (1M in THF, 6.01 mL, 6.01 mmol) and 1,2-diaminoethane (0.502 mL, 7.11 mmol). The resulting mixture was stirred at 60° C. for 16 hrs. The heat was increased to 80° C. for 2 hrs. The reaction mixture was cooled, diluted with EtOAc, washed sequentially with saturated aqueous $NH_4Cl$ (6×) and saturated aqueous NaCl, dried over $Na_2SO_4$, filtered, and concentrated under reduced pressure to give a residue that was purified by prep-HPLC to give 7,8-dichloro-1-methyl-10-(((R)-oxetan-2-yl)methoxy)-3,4,5,6-tetrahydroazepino[4,5- b]indol-2(1H)-one (29 mg, 26%) as a white solid. ES/MS (m/z): ($^{35}Cl/^{37}Cl$) 369.1/371.1 (M+H).

Intermediate 169

(2S)—N-(7,8-Dichloro-1,5,5-trimethyl-2-oxo-1,2,3,4,5,6-hexahydroazepino[4,5-b]indol-10-yl)-2-hydroxypropanamide

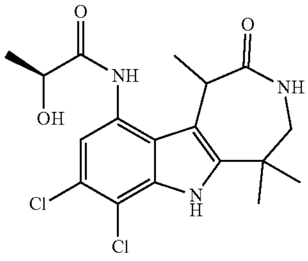 [SMILES: CC1C(=O)NCC(C)(C)c2[nH]c3c(Cl)c(Cl)cc(NC(=O)[C@H](C)O)c3c21]

A mixture of 10-bromo-7,8-dichloro-1,5,5-trimethyl-3,4,5,6-tetrahydroazepino[4,5-b]indol-2(1H)-one (250 mg, 67 weight %, 0.429 mmol), tris(dibezylideneacetone)dipalladium (39.7 mg, 0.0429 mmol), 4,5-bis(diphenylphosphino)-9,9-dimethyl xanthene (51.2 mg, 0.0859 µmol), cesium carbonate (495 mg, 1.50 mmol) and (S)-2-hydroxypropanamide (88.6 mg, 0.945 mmol) in 1,4-dioxane (20 mL) and THF (1.0 mL) was degassed and purged with $N_2$ (x3). The mixture was stirred at 110° C. for 16 hrs., under $N_2$. The mixture was concentrated and purified by column chromatography eluting with MeOH in DCM to give (2S)—N-(7,8-dichloro-1,5,5-trimethyl-2-oxo-1,2,3,4,5,6-hexahydroazepino[4,5-b]indol-10-yl)-2-hydroxypropanamide (160 mg, 88%) as a yellow solid. ES/MS (m/z): ($^{35}Cl/^{37}Cl$) 398.0/400.0 (M+H).

Example 181

(S)—N—((R)-7,8-Dichloro-1,5,5-trimethyl-2-oxo-1,2,3,4,5,6-hexahydroazepino[4,5-b]indol-10-yl)-2-hydroxypropanamide or (S)—N—((S)-7,8-dichloro-1,5,5-trimethyl-2-oxo-1,2,3,4,5,6-hexahydroazepino[4,5-b]indol-10-yl)-2-hydroxypropanamide (isomer 1) and Example 182

(S)—N—((R)-7,8-Dichloro-1,5,5-trimethyl-2-oxo-1,2,3,4,5,6-hexahydroazepino[4,5-b]indol-10-yl)-2-hydroxypropanamide or (S)—N—((S)-7,8-dichloro-1,5,5-trimethyl-2-oxo-1,2,3,4,5,6-hexahydroazepino[4,5-b]indol-10-yl)-2-hydroxypropanamide (isomer 2)

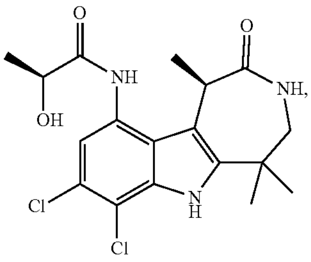

-continued

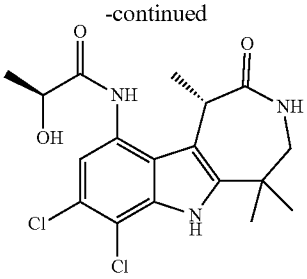

Purified diastereomeric (2S)—N-(7,8-dichloro-1,5,5-trimethyl-2-oxo-1,2,3,4,5,6-hexahydroazepino[4,5-b]indol-10-yl)-2-hydroxypropanamide (160 mg, 0.38 mmol) by SFC to give the titled compounds (Isomer 1—Rt=1.08 min (>99% ee) 60 mg, 39%; Isomer 2—Rt=1.76 min (>99% ee) 69 mg, 46%). Column: Chiralpak AD, 250x30 mm; Mobile Phase: 50% EtOH (0.1% $NH_4OH$): 50% $CO_2$; Flow Rate: 80 mL/min; Detection: 225 nM. ES/MS (m/z): ($^{35}Cl/^{37}Cl$) 398.5/400.2 (M+H). (Chiral analysis used—Column: Chiralpak AD-3, 50x4.6 mm, 3 µm; Mobile phase: A: $CO_2$ B: IPA (0.05% DEA). Gradient: from 5% to 40% of B in 1.5 min and hold 40% of 1 min, then 5% of B for 0.5 min. Flow rate: 4 mL/min).

Example 183

7,8-Dichloro-1-methyl-10-(oxetan-3-yloxy)-3,4,5,6-tetrahydroazepino[4,5-b]indol-2(1H)-one

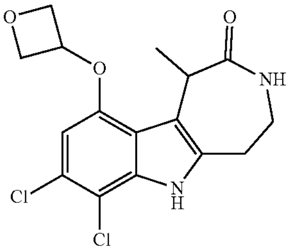 [SMILES: CC1C(=O)NCCc2[nH]c3c(Cl)c(Cl)cc(OC4COC4)c3c21]

To a mixture of 7,8-dichloro-10-hydroxy-1-methyl-3,4,5,6-tetrahydroazepino[4,5-b]indol-2(1H)-one (100 mg, 0.234 mmol, 70% by weight) and $Cs_2CO_3$ (233 mg, 0.702 mmol) in DMF (2 mL) was added 3-iodooxetane (52.7 mg, 0.281 mmol) at 25° C. The reaction mixture was stirred for 16 hrs. The mixture was diluted with water and extracted with EtOAc (3x). The combined organic layers were washed with saturated aqueous NaCl, dried over anhydrous $Na_2SO_4$, filtered, and concentrated under reduced pressure to give a residue that was purified by prep. HPLC to give 7,8-dichloro-1-methyl-10-(oxetan-3-yloxy)-3,4,5,6-tetrahydroazepino[4,5-b]indol-2(1H)-one (9.10 mg, 11%) as a white solid. ES/MS (m/z): ($^{35}Cl/^{37}Cl$) 355.1/357.0 (M+H).

Intermediate 170

7,8-Dichloro-10-(2-methoxyethoxy)-1,5,5-trimethyl-3,4,5,6-tetrahydroazepino[4,5-b]indol-2(1H)-one

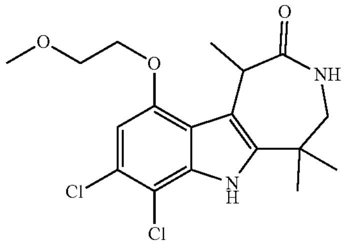

To a mixture of 7,8-dichloro-10-hydroxy-1,5,5-trimethyl-3,4,5,6-tetrahydroazepino[4,5-b]indol-2(1H)-one (150 mg, 0.344 mmol, 75% by weight) and potassium carbonate (150 mg, 1.03 mmol) in DMF (10 mL) was added 1-iodo-2-methoxyethane (202 mg, 1.03 mmol). The mixture was stirred at 25° C. for 16 hrs. The reaction mixture was diluted with water and extracted with EtOAc (3×). The combined organics were washed with saturated aqueous NaCl (2×), dried over anhydrous $Na_2SO_4$, filtered, and concentrated under reduced pressure. The residue was purified by prep-HPLC to give 7,8-dichloro-10-(2-methoxyethoxy)-1,5,5-trimethyl-3,4,5,6-tetrahydroazepino[4,5-b]indol-2(1H)-one (100 mg, 74%) as a white solid.

solid. ES/MS (m/z): ($^{35}Cl/^{37}Cl$) 385.1/387.1 (M+H).

Example 184

(S)-7,8-Dichloro-10-(2-methoxyethoxy)-1,5,5-trimethyl-3,4,5,6-tetrahydroazepino[4,5-b]indol-2(1H)-one or (R)-7,8-dichloro-10-(2-methoxyethoxy)-1,5,5-trimethyl-3,4,5,6-tetrahydroazepino[4,5-b]indol-2(1H)-one (isomer 1) and Example 185

(S)-7,8-Dichloro-10-(2-methoxyethoxy)-1,5,5-trimethyl-3,4,5,6-tetrahydroazepino[4,5-b]indol-2(1H)-one or (R)-7,8-Dichloro-10-(2-methoxyethoxy)-1,5,5-trimethyl-3,4,5,6-tetrahydroazepino[4,5-b]indol-2(1H)-one (isomer 2)

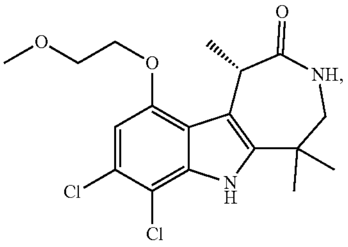

-continued

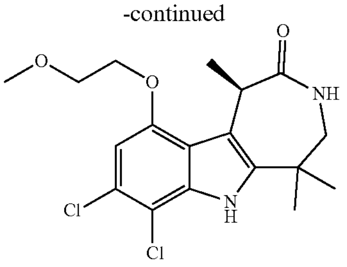

Purified enantiomeric 7,8-dichloro-10-(2-methoxyethoxy)-1,5,5-trimethyl-3,4,5,6-tetrahydroazepino[4,5-b]indol-2(1H)-one (100 mg, 0.253 mmol) by SFC to give the titled compounds (Isomer 1—Rt=1.18 min (>99% ee) 36 mg, 37%; Isomer 2—Rt=1.41 min (97% ee) 32 mg, 33%). Column: Chiralpak AD, 250×30 mm; Mobile Phase: 35% EtOH (0.1% $NH_4OH$): 65% $CO_2$; Flow Rate: 80 mL/min; Detection: 225 nM. ES/MS (m/z): ($^{35}Cl/^{37}Cl$) 385.2/387.1 (M+H). (Chiral analysis used—Column: Chiralpak AD-3, 50×4.6 mm, 3 μm; Mobile phase: A: $CO_2$ B: IPA (0.05% DEA). Gradient: from 5% to 40% of B in 1.5 min and hold 40% of 1 min, then 5% of B for 0.5 min. Flow rate: 4 mL/min).

Intermediate 171

10-Bromo-7,8-dichloro-1-methyl-6-(2,2,2-trifluoroethyl)-3,4,5,6-tetrahydroazepino[4,5-b]indol-2(1H)-one

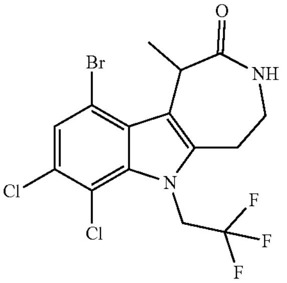 [SMILES: CC1C(=O)NCCc2c1c1c(Br)cc(Cl)c(Cl)c1n2CC(F)(F)F]

To a solution of 10-bromo-7,8-dichloro-1-methyl-3,4,5,6-tetrahydroazepino[4,5-b]indol-2(1H)-one (500 mg, 1.22 mmol, 88% by weight) and $Cs_2CO_3$ (1.19 g, 3.65 mmol) in DMF (5 mL) was added 2,2,2-trifluoroethyl trifluoromethylsulfonate (863 mg, 3.65 mmol) at 0° C. The reaction was allowed to warm to ambient temperature and stirred for 2 hrs., under $N_2$. The mixture was concentrated, suspended in water, and extracted with EtOAc (×3). The combined organic layers were washed with saturated aqueous NaCl (×3), dried over anhydrous $Na_2SO_4$, filtered, and concentrated under reduced pressure. The residue was purified by silica gel column chromatography eluting with MeOH in DCM to give 10-bromo-7,8-dichloro-1-methyl-6-(2,2,2-trifluoroethyl)-3,4,5,6-tetrahydroazepino[4,5-b]indol-2(1H)-one (500 mg, 79%) as a green oil. ES/MS (m/z): 443.0/445.0/446.9 (M+H).

Intermediate 172

N-(7,8-Dichloro-1-methyl-2-oxo-6-(2,2,2-trifluoroethyl)-1,2,3,4,5,6-hexahydroazepino[4,5-b]indol-10-yl)-2-hydroxyacetamide

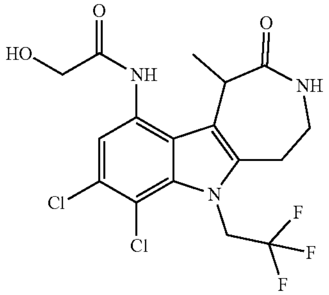 [SMILES: CC1C(=O)NCCc2c1c1c(NC(=O)CO)cc(Cl)c(Cl)c1n2CC(F)(F)F]

A mixture of 10-bromo-7,8-dichloro-1-methyl-6-(2,2,2-trifluoroethyl)-3,4,5,6-tetrahydroazepino[4,5-b]indol-2(1H)-one (300 mg, 0.574 mmol, 85% by weight), 2-hydroxyacetamide (136 mg, 1.72 mmol), tris(dibezylideneacetone)dipalladium (53.1 mg, 0.0574 mmol), 4,5-bis(diphenylphosphino)-9,9-dimethyl xanthene (67.8 mg, 0.115 mmol), $Cs_2CO_3$(562 mg, 1.72 mmol) in 1,4-dioxane (20 mL) and THF (2.0 mL) was stirred at 100° C. for 16 hrs., under $N_2$. ES/MS (m/z): ($^{35}Cl/^{37}Cl$) 385.1/387.1 (M+H). The mixture was concentrated and purified sequentially by silica gel column chromatography eluting with MeOH in DCM and prep-HPLC to give N-(7,8-dichloro-1-methyl-2-oxo-6-(2,2,2-trifluoroethyl)-1,2,3,4,5,6-hexahydroazepino[4,5-b]indol-10-yl)-2-hydroxyacetamide (140 mg, 53%) as a white solid. ES/MS (m/z): ($^{35}Cl/^{37}Cl$) 437.7/439.8 (M+H).

Example 186

(S)—N-(7,8-Dichloro-1-methyl-2-oxo-6-(2,2,2-trifluoroethyl)-1,2,3,4,5,6-hexahydroazepino[4,5-b]indol-10-yl)-2-hydroxyacetamide or (R)—N-(7,8-Dichloro-1-methyl-2-oxo-6-(2,2,2-trifluoroethyl)-1,2,3,4,5,6-hexahydroazepino[4,5-b]indol-10-yl)-2-hydroxyacetamide (isomer 1) and Example 187

(S)—N-(7,8-Dichloro-1-methyl-2-oxo-6-(2,2,2-trifluoroethyl)-1,2,3,4,5,6-hexahydroazepino[4,5-b]indol-10-yl)-2-hydroxyacetamide or (R)—N-(7,8-Dichloro-1-methyl-2-oxo-6-(2,2,2-trifluoroethyl)-1,2,3,4,5,6-hexahydroazepino[4,5-b]indol-10-yl)-2-hydroxyacetamide (isomer 2)

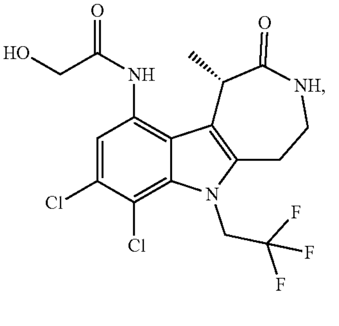

-continued

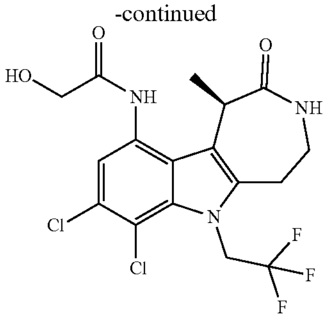

Purified enantiomeric N-(7,8-dichloro-1-methyl-2-oxo-6-(2,2,2-trifluoroethyl)-1,2,3,4,5,6-hexahydroazepino[4,5-b]indol-10-yl)-2-hydroxyacetamide (140 mg, 0.303 mmol) by SFC to give the titled compounds (Isomer 1—Rt=1.01 min (>99% ee) 54 mg, 41%; Isomer 2—Rt=1.25 min (>99% ee) 61 mg, 46%). Column: (S,S)-Whelk-O 1, 250×30 mm; Mobile Phase: 35% EtOH (0.1% $NH_4OH$): 65% $CO_2$; Flow Rate: 80 mL/min; Detection: 225 nM. ES/MS (m/z): ($^{35}Cl/^{37}Cl$) 438.1/440.0 (M+H). (Chiral analysis used—Column: (S,S)-Whelk-0-1.8, 50×4.6 mm, 3 μm; Mobile phase: A: $CO_2$ B: 35% of ethanol (0.05% DEA); flow rate: 2.8 mL/min).

Assay

Expression and Purification of Recombinant cGAS Protein: Insert cDNA encoding full-length of human cGAS into a modified bacterial expression vector containing an in-frame His6-tag. Induce the *E. coli* strain BL21(DE3) harboring the plasmid with 1 mM IPTG (Isopropyl β-D-1-thiogalactopyranoside) at 18° C. overnight. Purify the His6-tagged cGAS protein over HISpur Ni-NTA resin in the presence of benzonase and RNase followed by Superdex 200 size exclusion chromatography with storage buffer (50 mM Tris-HCl pH 7.5, 300 mM NaCl, 1 mM DTT, 10% glycerol).

In vitro inhibition assay of cGAS activity: Add a 5 μL mixture containing 10 mM Tris-Cl pH 7.5, 50 mM NaCl, 5 mM $MgCl_2$, 1 mM DTT, 0.01% Triton X-100, 60 nM 75-bp dsDNA, 50 μM ATP, 50 μM GTP, 10 nM of recombinant human cGAS, and serial dilutions of a test compound in DMSO to a 384-well plate and incubate at ambient temperature for 3 hrs. Quench the reaction by the addition of 100 μL of stop solution containing 0.1% formic acid and 0.1 μM internal standard (3'3'-difluoro cGAMP). Measure the amount of cGAMP produced by RapidFire 365 mass spectrometry and evaluate inhibitory effect of a compound by plotting percent specific inhibition of cGAMP production against log concentration of the test compound. Calculate $IC_{50}$ values using a 4-parameter non-linear logistic equation (y=(S0+((Sinf−S0)/(1+((qAC50/x)^nHill))))).

Cellular assay to measure cGAS activity: Use THP1 cell line from ATCC to determine inhibition of cGAS activity by test compounds in human cells. Plate cells on 96-well plates at $0.2\times10^6$/well and differentiate with phorbol myristate acetate (PMA) at 37° C./5% $CO_2$. After 24 hours, replace PMA containing media with media lacking PMA and further incubate overnight. Stimulate cells were then by RDG-Adenovirus-GFP (Vector Biolabs #1768) at 1000 MOI for 4 hours prior to the addition of test compounds. After overnight incubation, transfer 10 μL of the media from each well to a new plate for IFNb analysis as a marker for cGAS activity. Measure quantification of IFNb with an IFNb AlphaLISA Detection kit (Perkin Elmer AL3133F) by mixing the acceptor beads with the cell supernatant followed by the addition of the biotinylated antibody and donor beads. Measure the relative fluorescence signal produced from the interaction of the donor and acceptor beads by a PHERAStar AlphaLISA protocol and evaluate the inhibitory effect of a compound by plotting specific inhibition of IFNb production against log concentration of the test compound. Calculate $IC_{50}$ values using a 4-parameter non-linear logistic equation (y=(S0+((SInf−S0)/(1+((qAC50/x)^nHill))))).

cGAS inhibitory activity data for the Examples is summarized in Table 2 below.

TABLE 2 cGAS activity as measured by different assays (Examples 1-31)

| Example No. | In vitro inhibition assay $IC_{50}$ (μM) | Cellular Assay $IC_{50}$ (μM) |
|---|---|---|
| 1 | 0.0334 | 2.64 |
| 2 | 0.0205 | 0.819 |
| 3 | 0.111 | — |
| 4 | 0.0262 | 3.57 |
| 5 | 0.00512 | >10.0 |
| 6 | 0.0156 | >10.0 |
| 7 | 0.0281 | 0.661 |
| 8 | 0.019 | 0.42 |
| 8A | 0.0156 | 0.168 |
| 8B | 0.214 | 3.14 |
| 9 | 0.087 | 2.16 |
| 10 | 0.124 | 2.73 |
| 11 | 0.0454 | 1.76 |
| 12A | 0.0163 | 0.356 |
| 12B | 0.748 | 1.7 |
| 13 | 9.05 | 0.582 |
| 14A | 0.0073 | 0.344 |
| 14B | 0.302 | 4.45 |
| 15A | 0.0224 | 0.793 |
| 15B | 1.09 | 8.14 |
| 16A | 0.00218 | 0.871 |
| 16B | 0.998 | 1.01 |
| 17A | 0.0224 | 0.856 |
| 17B | 1.54 | 4.08 |
| 18 | 0.0709 | 2.07 |
| 19 | 0.0936 | >10.0 |
| 20 | 0.132 | >10.0 |
| 21 | 0.141 | — |
| 22 | 0.0459 | 4.58 |
| 23 | 0.118 | 7.79 |
| 24 | 0.0884 | 6.91 |
| 25 | 0.0271 | >10.0 |
| 26 | 0.133 | >10.0 |
| 27 | 0.11 | >10.0 |
| 28 | 0.0581 | 0.914 |
| 29 | 0.122 | >10.0 |
| 30 | 0.119 | 3.73 |
| 31 | 0.0395 | 1.12 |

The symbol "—" denotes data not collected.

TABLE 2A cGAS activity as measured by different assays (Examples 32-177)

| Example No. | In vitro inhibition assay $IC_{50}$ (μM) | Cellular Assay $IC_{50}$ (μM) |
|---|---|---|
| 32 | 0.0333 | 1.4 |
| 33 | 0.0204 | 1.2 |
| 34 | 0.0395 | 1.73 |
| 35 | 0.0438 | 3.69 |
| 36 | 3.95 | 1.2 |
| 37 | 0.0304 | 0.802 |
| 38 | 1.65 | 9.8 |
| 39 | 0.0544 | 0.892 |
| 40 | 0.0273 | 0.787 |
| 41 | 7.17 | >10 |
| 42 | 6.44 | >10 |
| 43 | 0.0149 | 0.498 |

TABLE 2A-continued cGAS activity as measured by different assays (Examples 32-177)

| Example No. | In vitro inhibition assay $IC_{50}$ (μM) | Cellular Assay $IC_{50}$ (μM) |
|---|---|---|
| 44 | 0.0389 | 2.79 |
| 45 | 0.0466 | 2.23 |
| 46 | 0.0226 | 0.885 |
| 47 | 0.0201 | 0.596 |
| 48 | 6.49 | >10 |
| 49 | 0.015 | 0.39 |
| 50 | 0.00962 | 0.286 |
| 51 | 0.00834 | 1.34 |
| 52 | 0.0291 | 2.22 |
| 53 | 0.0173 | 0.471 |
| 54 | 4.25 | 5.66 |
| 55 | 0.0465 | 1.92 |
| 56 | 3.56 | 6.23 |
| 57 | 0.0421 | 0.558 |
| 58 | 0.0165 | 0.577 |
| 59 | 2.00 | >10 |
| 60 | 0.0533 | 0.974 |
| 61 | 0.0345 | 1.91 |
| 62 | 0.0445 | 1.9 |
| 63 | 1.67 | >10 |
| 64 | 0.0379 | 2.42 |
| 65 | 0.89 | 10 |
| 66 | 0.0375 | 4.15 |
| 67 | 0.0306 | 1.03 |
| 68 | 0.00844 | 0.49 |
| 69 | 0.63 | >10 |
| 70 | 0.0305 | 1.29 |
| 71 | 0.043 | 2.32 |
| 72 | 0.0233 | 0.662 |
| 73 | 0.0112 | 0.755 |
| 74 | 3.44 | >10 |
| 75 | 0.019 | 1.15 |
| 76 | 0.0386 | 1.47 |
| 77 | 0.0141 | 0.843 |
| 78 | 0.0465 | 0.81 |
| 79 | 0.0142 | 0.591 |
| 80 | 0.00812 | 0.28 |
| 81 | 1.20 | 7.06 |
| 82 | 0.0325 | 0.91 |
| 83 | 4.74 | >10 |
| 84 | 0.0442 | 1.43 |
| 85 | 2.77 | 7.26 |
| 86 | 0.0519 | 3.47 |
| 87 | 0.036 | 5.97 |
| 88 | 0.0361 | 3.23 |
| 89 | 0.02 | 1.13 |
| 90 | 0.552 | 0.993 |
| 91 | 0.0207 | 1.19 |
| 92 | 0.0173 | 0.259 |
| 93 | 2.76 | >10 |
| 94 | 0.0247 | 0.663 |
| 95 | 7.58 | 10 |
| 96 | 0.0186 | >10 |
| 97 | 0.018 | 1.15 |
| 98 | 0.0424 | 2.18 |
| 99 | 1.64 | >10 |
| 100 | 0.0304 | 1.13 |
| 101 | 1.26 | >10 |
| 102 | 0.0232 | 0.727 |
| 103 | 0.0176 | 0.398 |
| 104 | 0.0422 | 1.57 |
| 105 | 0.0388 | 3.25 |
| 106 | 0.188 | 0.861 |
| 107 | 0.0125 | 0.649 |
| 108 | 0.0257 | 0.676 |
| 109 | 0.159 | 1.86 |
| 110 | 2.61 | 3.12 |
| 111 | 0.0131 | 0.231 |
| 112 | 0.0515 | 2.6 |
| 113 | 0.0373 | 1.74 |
| 114 | 0.0384 | 1.27 |
| 115 | 0.0224 | 1.95 |
| 116 | 0.0148 | 0.64 |
| 117 | 0.0186 | 1.32 |
| 118 | 0.0424 | 0.577 |

TABLE 2A-continued

| cGAS activity as measured by different assays (Examples 32-177) | | |
|---|---|---|
| Example No. | In vitro inhibition assay $IC_{50}$ (μM) | Cellular Assay $IC_{50}$ (μM) |
| 119 | 0.0232 | 0.487 |
| 120 | 0.0119 | 0.716 |
| 121 | 0.0172 | 0.18 |
| 122 | 0.934 | 2.94 |
| 123 | 0.0141 | 0.181 |
| 124 | 0.0323 | 0.468 |
| 125 | 0.018 | 0.272 |
| 126 | 0.997 | 0.501 |
| 127 | 0.0344 | 1.21 |
| 128 | 0.0136 | 0.217 |
| 129 | 1.55 | 1.32 |
| 130 | 0.0123 | 0.205 |
| 131 | 0.0533 | 2.72 |
| 132 | 39.8 | >10 |
| 133 | 0.02 | 0.82 |
| 134 | 0.0175 | 0.787 |
| 135 | 20.2 | 10 |
| 136 | 0.016 | 1.57 |
| 137 | 0.683 | >10 |
| 138 | 0.008 | 0.431 |
| 139 | 0.824 | 4.61 |
| 140 | 0.0164 | 1.28 |
| 141 | 0.0354 | 2.44 |
| 142 | 0.0296 | 0.293 |
| 143 | 1.51 | >10 |
| 144 | 0.0225 | 0.649 |
| 145 | 0.0123 | 0.287 |
| 146 | 0.0272 | 0.3 |
| 147 | 0.237 | 5.17 |
| 148 | 0.0414 | 1.39 |
| 149 | 1.56 | 3.08 |
| 150 | 0.0259 | 2.12 |
| 151 | 0.0197 | 1.77 |
| 152 | 0.948 | 5.31 |
| 153 | 2.42 | >10 |
| 154 | 0.0124 | 0.394 |
| 155 | 0.0177 | 0.655 |
| 156 | 1.81 | >10 |
| 157 | 6.68 | >10 |
| 158 | 0.0197 | 0.341 |
| 159 | 0.0606 | 1.39 |
| 160 | 0.013 | 0.256 |
| 161 | 3.73 | >10 |
| 162 | 0.0487 | 1.28 |
| 163 | 0.0231 | 1.62 |
| 164 | 0.0189 | 1.38 |
| 165 | 0.0442 | 1.73 |
| 166 | 0.0207 | 1.02 |
| 167 | 0.0128 | 0.624 |
| 168 | 0.109 | 4.6 |
| 169 | 0.0262 | 1.13 |
| 170 | 0.0277 | 0.473 |
| 171 | 0.00784 | 0.483 |
| 172 | 1.81 | >10 |
| 173 | 0.0147 | 1.61 |
| 174 | 0.361 | >10 |
| 175 | 0.0546 | 1.44 |
| 176 | 0.0389 | 7.11 |
| 177 | 0.0231 | 0.841 |

TABLE 2B

| cGAS activity as measured by different assays (Examples 178-187) | | |
|---|---|---|
| Example No. | In vitro inhibition assay $IC_{50}$ (μM) | Cellular Assay $IC_{50}$ (μM) |
| 178 | 0.0108 | 0.311 |
| 179 | 2.12 | >10 |
| 180 | 0.0237 | 0.793 |
| 181 | >39.8 | >10 |
| 182 | 0.0456 | 1.18 |
| 183 | 0.0409 | 1.85 |
| 184 | 0.0174 | 1.37 |
| 185 | 1.89 | >10 |
| 186 | 0.0489 | 4.34 |
| 187 | >39.8 | >10 |

The data in Tables 2 and 2A-2B shows that the compounds of the invention are effective cGAS inhibitors. Other compounds of the disclosure not specifically exemplified can also be similarly tested and verified to be effective cGAS inhibitors.

We claim:

1. A compound of formula:

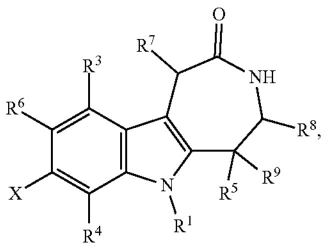

wherein:

X and $R^4$ are independently halo;

$R^1$, $R^7$, $R^8$, and $R^9$ are independently $R^b$;

$R^6$ is H or F;

$R^3$ is —NH—$R^{bb}$—$OR^b$, —NHC(O)—$R^{bb}$—$OR^b$, —NHC(O)—C(O)—$NH_2$, —NH—$R^c$, —NH—C(O)—$R^c$, —O—$R^c$, —O—$CH_2$—$R^c$, —O—$R^{bb}$—C(O)$NH_2$, —O—$R^{bb}$—$OR^b$, —O—$R^{bb}$—O—C(O)—$R^b$, —O—$R^{bb}$—H, —O—$R^{bb}$—CN, —NH—$R^{bb}$—H, —$R^{bb}$—OH, —$R^{bb}$—CN, —NH—$R^e$, —O—$CH_2$—$R^e$, —NH—$CH_2$—$R^e$, or a five-membered or six-membered heteroaryl each with 2 or 3 heteroatoms, wherein the heteroaryl is optionally substituted with —$NH_2$, —$R^{bb}$—H, or —$R^{bb}$—OH;

$R^5$ is H, —$R^{bb}$H, —$R^{bb}$C(O)$OR^b$, —$R^{bb}$C(O)N$(R^b)_2$, —$R^{bb}$N$(R^b)_2$, —$R^{bb}$N$(R^b)$($R^{bb}$$CF_3$), —$R^{bb}$$OR^b$, or

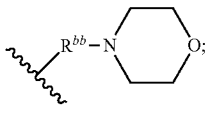

or $R^1$ and $R^5$ with atoms attached therewith collectively form a 5-member heterocycle;

each occurrence of $R^b$ is independently H or —$R^{bb}$H;

each occurrence of $R^{bb}$ is independently $C_{1-3}$ alkylene optionally substituted with fluoro or methyl;

each occurrence of $R^c$ is a $C_{4-6}$ carbocycle substituted with hydroxy or a 4- to 6-membered heterocycle of oxygen; and each occurrence of $R^e$ is 5-membered heteroaryl including N, or a pharmaceutically acceptable salt thereof.

2. The compound of claim 1, having the formula:

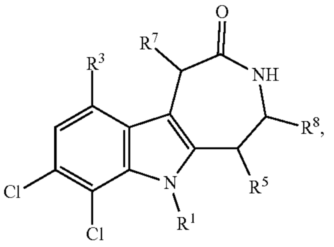

or a pharmaceutically acceptable salt thereof.

3. The compound of claim 1, wherein $R^5$ is H, —$R^{bb}$H, —$R^{bb}$C(O)O$R^b$, —$R^{bb}$C(O)N($R^b$)$_2$, —$R^{bb}$N($R^b$)$_2$, —$R^{bb}$N ($R^b$)($R^{bb}$C$F_3$), —$R^{bb}$—O$R^b$, or

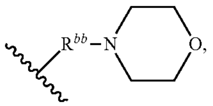

or a pharmaceutically acceptable salt thereof.

4. The compound of claim 1, wherein $R^5$ is H, —$CH_3$, —$CH_2CH_3$, —$CH_2CH_2CH_3$,

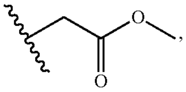 , 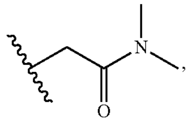 , 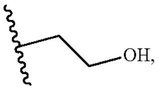

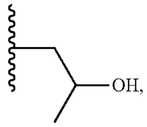 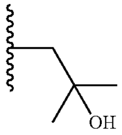 , 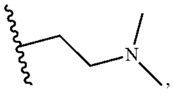

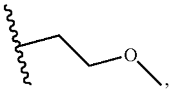 , 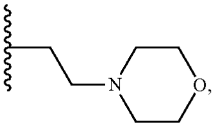 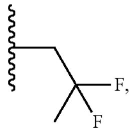

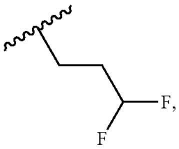 or 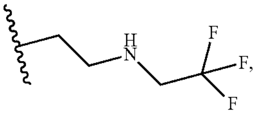

or a pharmaceutically acceptable salt thereof.

5. The compound of claim 1, wherein $R^5$ is —$R^{bb}$H, —$R^{bb}$C(O)O$R^b$, —$R^{bb}$C(O)N($R^b$)$_2$, —$R^{bb}$N($R^b$)$_2$, —$R^{bb}$N ($R^b$)($R^{bb}$C$F_3$), —$R^{bb}$—O$R^b$,

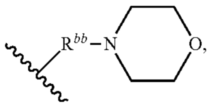

and the

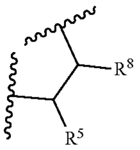

is

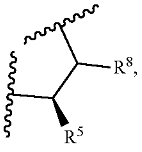

or a pharmaceutically acceptable salt thereof.

6. The compound of claim 1, wherein $R^5$ is H, or a pharmaceutically acceptable salt thereof.

7. The compound of claim 1, wherein $R^7$ is H, or a pharmaceutically acceptable salt thereof.

8. The compound of claim 1, wherein $R^7$ is —$R^{bb}$H, and the

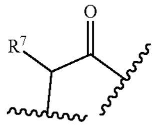

is

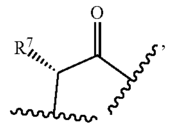

or a pharmaceutically acceptable salt thereof.

9. The compound of claim 1, wherein $R^7$ is methyl, or a pharmaceutically acceptable salt thereof.

10. The compound of claim 1, wherein $R^3$ is —NH—$R^{bb}$—O$R^b$, —NHC(O)—$R^{bb}$—O$R^b$, —NHC(O)—C(O)—$NH_2$, —O—$R^{bb}$—C(O)$NH_2$, —O—$R^{bb}$—O$R^b$, —O—$R^{bb}$—O—C(O)—$R^b$, —O—$R^{bb}$—H, —O—$R^{bb}$—CN, —NH—$R^{bb}$—H, —$R^{bb}$—OH, or —$R^{bb}$—CN, or a pharmaceutically acceptable salt thereof.

11. The compound of claim 1, wherein $R^3$ is —NH—$R^c$, —NH—C(O)—$R^c$, or —O—$R^c$, or a pharmaceutically acceptable salt thereof.

12. The compound of claim 1, wherein $R^3$ is selected from

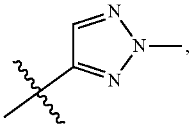 , 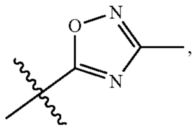 , 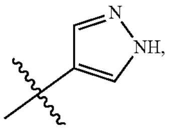

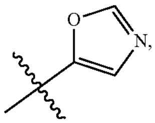 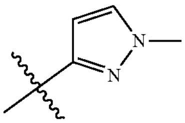 , 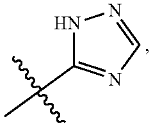 ,

-continued

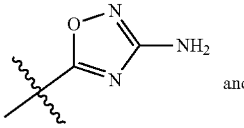 and 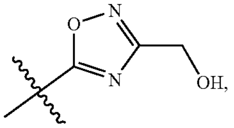

or a pharmaceutically acceptable salt thereof.

13. The compound of claim 1, wherein $R^3$ is selected from —NH—$(CH_2)_2$—OH, —NH—$(CH_2)_2$—O$(CH_3)$, —NH—$(CH_2)((CH)(CH_3))$—OH, —NHC(O)—$CH_2$—OH, —NHC(O)—$CH_2$—O$(CH_3)$, —NHC(O)—CH$(CH_3)$—OH, —NH—$(CH_2)(CF_2)(CH_2)$—OH, —NH—$(CH_2)$—$CHF_2$, —NH—$(CH_2)_2$—$CHF_2$, —O—$CH_2$—C(O)$NH_2$, —O—$(CH_2)(CH(CH_3))$—OH, —O$(CH_2)_3$—OH, —O$(CH_2)_2$—O$(CH_3)$, —O—$(CH_2)(CF_2)(CH_2)$—OH, —NH—$(CH_2)(CF_2)(CH_2)$—OH, —O$(CH_2)CH_2F$, —O$(CH_2)_2CH_2F$, —O—$CH_2$—CN, —NH$(CH_2)_3$, —$(CH_2)_3$OH, and —$CH_2$—CN, or a pharmaceutically acceptable salt thereof.

14. The compound of claim 1, wherein $R^8$ is H, or a pharmaceutically acceptable salt thereof.

15. The compound of claim 1, wherein $R^8$ is methyl, or a pharmaceutically acceptable salt thereof.

16. The compound of claim 1, wherein $R^1$ is H, or a pharmaceutically acceptable salt thereof.

17. The compound of claim 1, wherein $R^1$ is methyl, or a pharmaceutically acceptable salt thereof.

18. The compound of claim 1, having a formula:

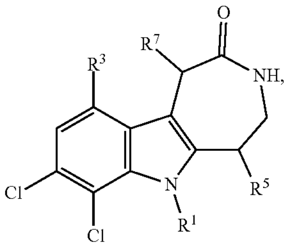

wherein:

$R^1$ is H, —$CH_3$, or —$CHF_2$;

$R^5$ is H, —$CH_3$, $CH_2CH_3$, or —$CH_2CH_2CH_3$;

$R^7$ is H, —$CH_3$, $CH_2CH_3$, or —$CH_2CH_2CH_3$;

$R^3$ is —NH—$(CH_2)_2$—OH, —NH—$(CH_2)_2$—O$(CH_3)$, —NH—$(CH_2)((CH)(CH_3))$—OH, NHC(O)—$CH_2$—OH, —NHC(O)—$CH_2$—O$(CH_3)$, —NHC(O)—CH$(CH_3)$—OH, NH—$(CH_2)(CF_2)(CH_2)$—OH, —NH—$(CH_2)$—$CHF_2$, —NH—$(CH_2)_2$—$CHF_2$, —O—$CH_2$—C(O)$NH_2$, O—$(CH_2)(CH(CH_3))$—OH, —O$(CH_2)_3$—OH, —O$(CH_2)_2$—O$(CH_3)$, —O—$(CH_2)(CF_2)(CH_2)$—OH, NH—$(CH_2)(CF_2)(CH_2)$—OH, —O$(CH_2)CH_2F$, —O$(CH_2)_2CH_2F$, —O—$CH_2$—CN, —NH$(CH_2)_3$, —$(CH_2)_3$OH, —$CH_2$—CN,

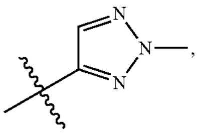 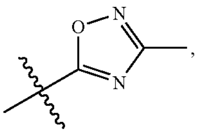 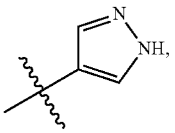

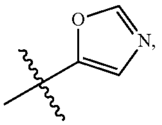 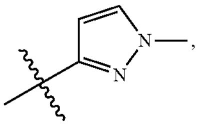 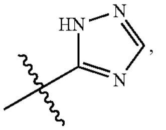

-continued

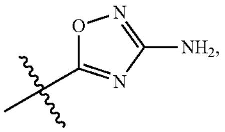 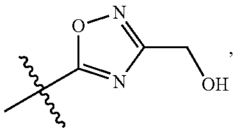

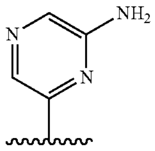 , 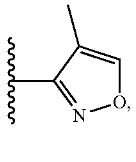 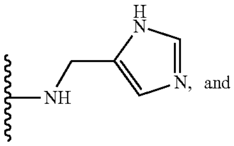 and

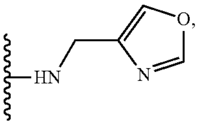

or a pharmaceutically acceptable salt thereof.

19. The compound of claim 1, having a formula:

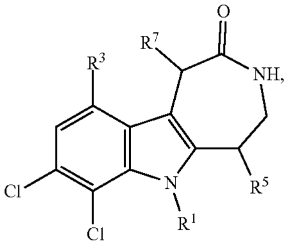

wherein $R^1$, $R^5$, and $R^7$ is each independently H or —$CHF_2$, and $R^3$ is —NHC(O)—$CH_2$—OH, —O—$(CH_2)_2$—O—$(CH_3)$, —NH—C(O)—CH$(CH_3)$—OH, or

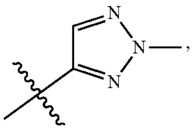 [SMILES: *c1cnn(C)n1]

or a pharmaceutically acceptable salt thereof.

20. The compound of claim 1, wherein the compound is selected from:

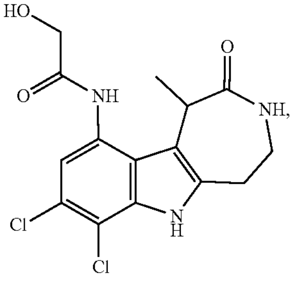

-continued
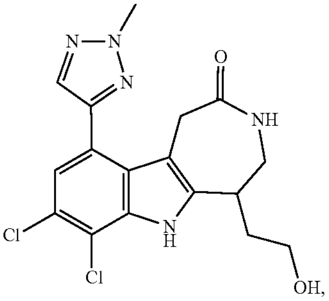
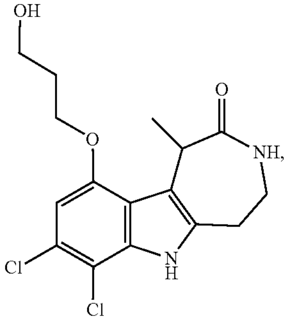
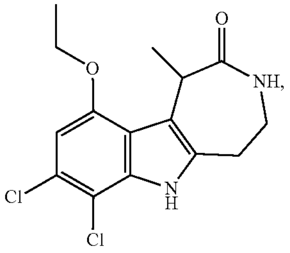
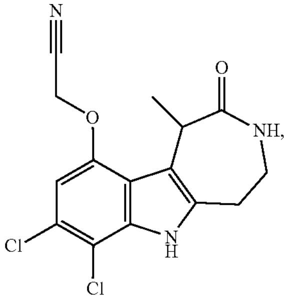
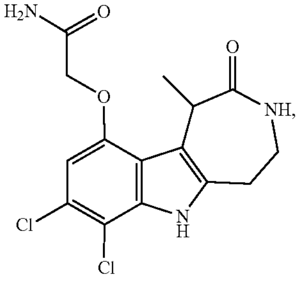
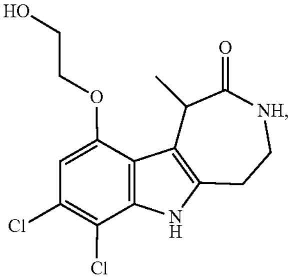
-continued
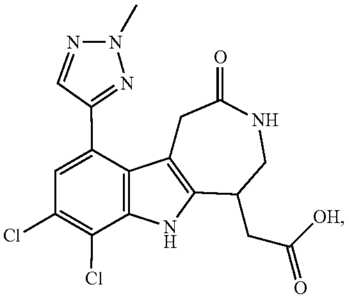
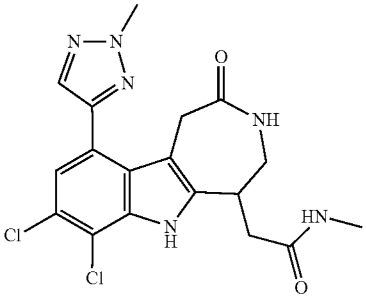
,
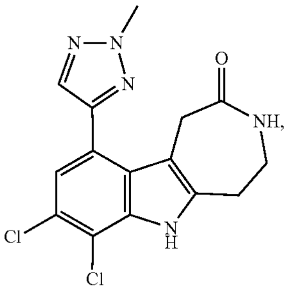
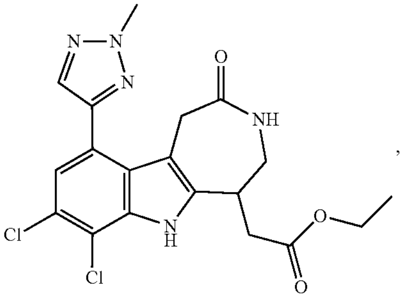
,
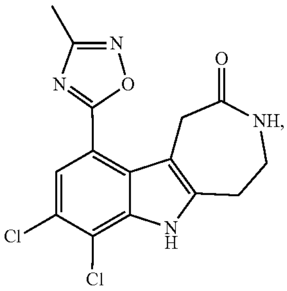

-continued
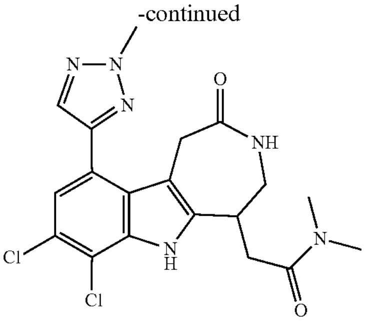
,
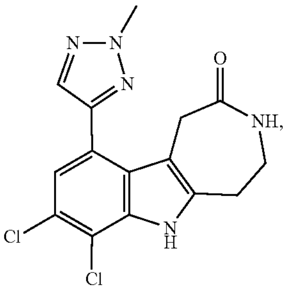
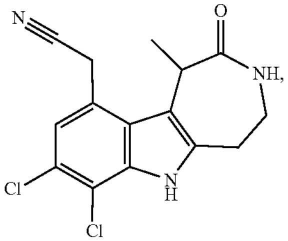
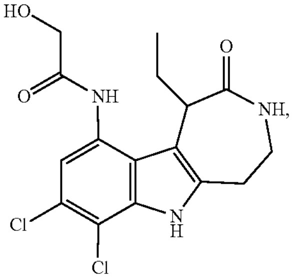
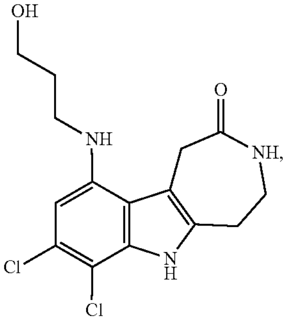
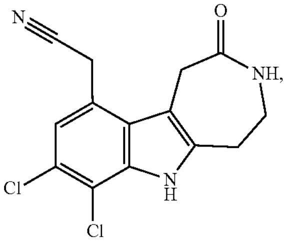
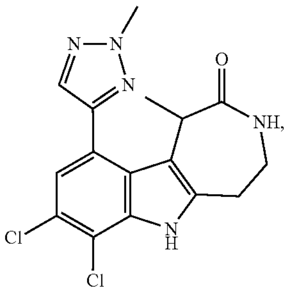
-continued
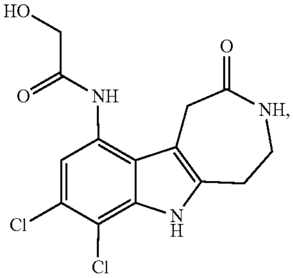
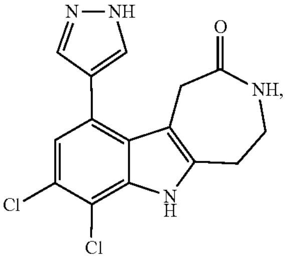
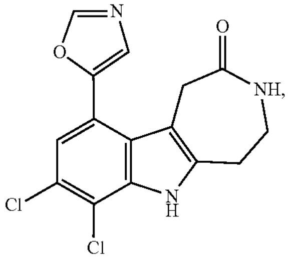
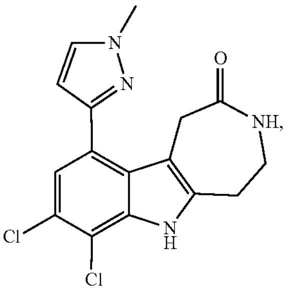
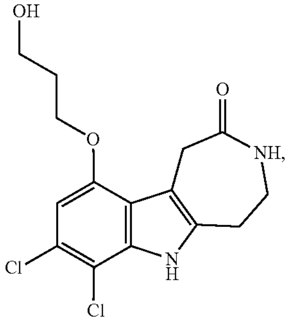
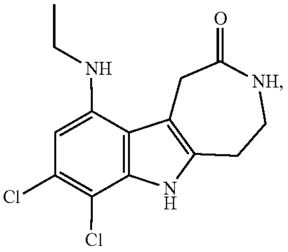
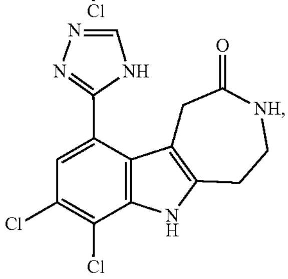
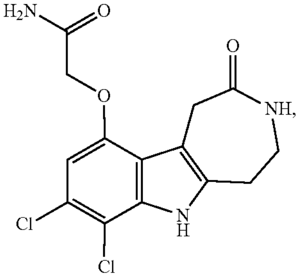
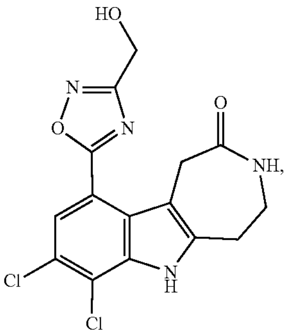
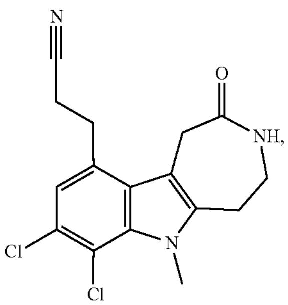

-continued
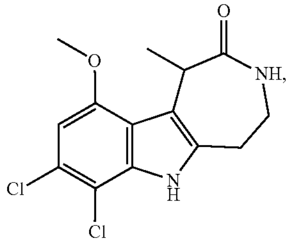
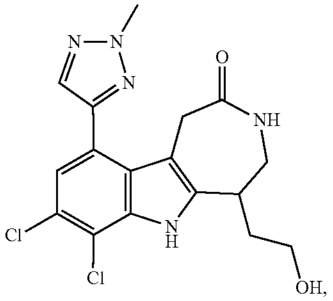
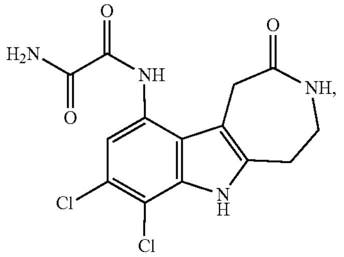
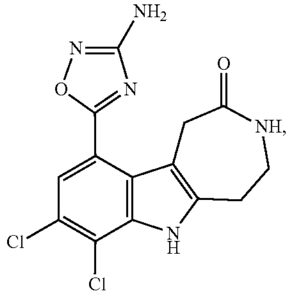
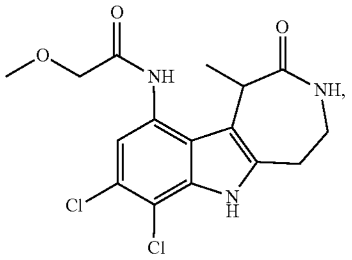
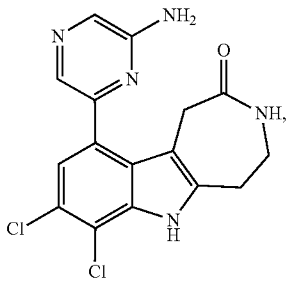
-continued
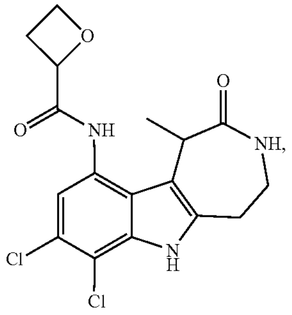
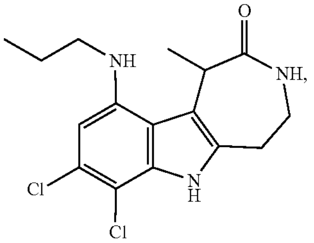
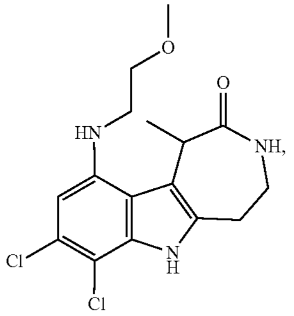
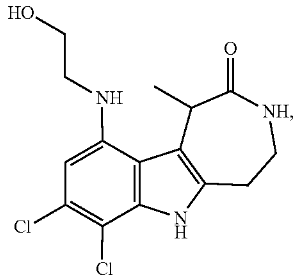
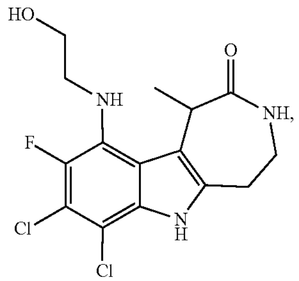 [SMILES: CC1C(=O)NCCc2[nH]c3c(Cl)c(Cl)c(F)c(NCCO)c3c21]
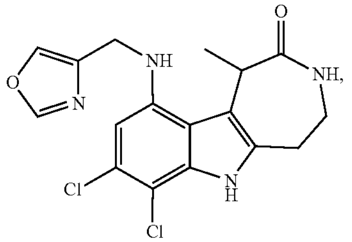

-continued
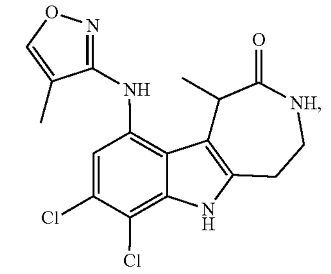
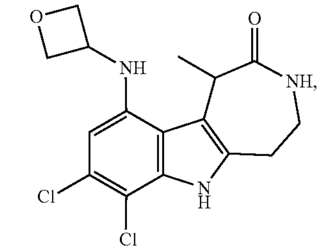
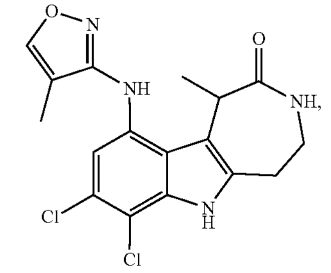
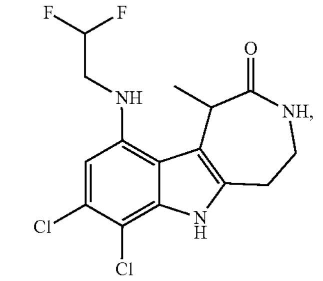
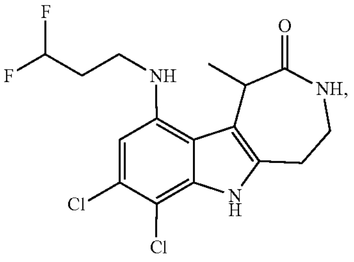
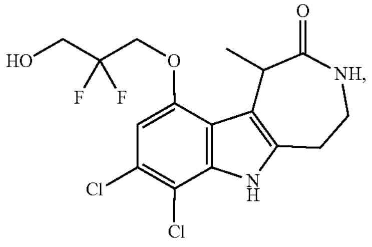
-continued
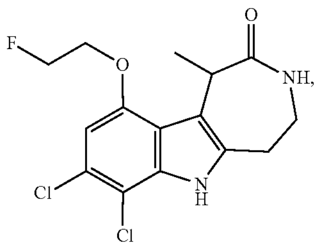
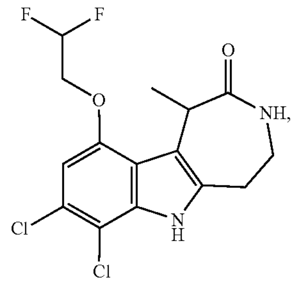
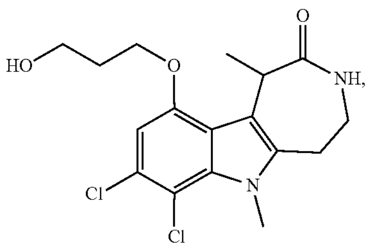
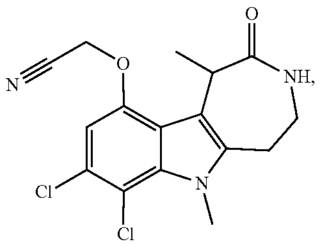
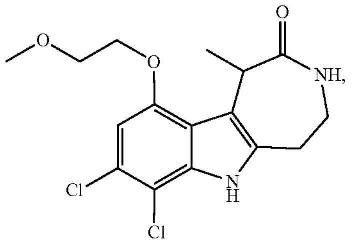
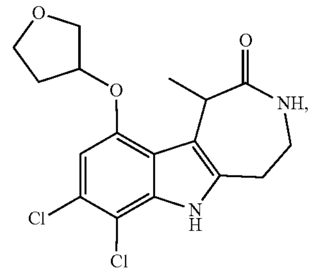

-continued
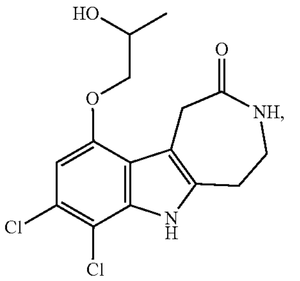
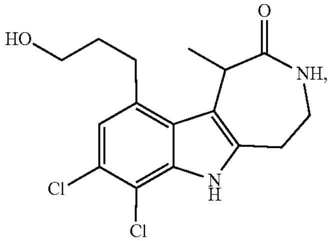
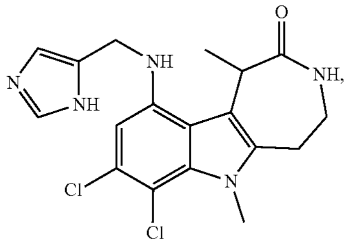
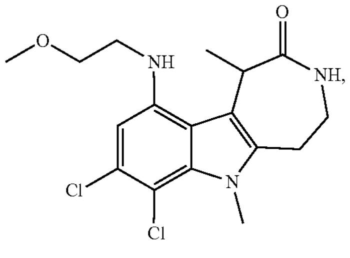
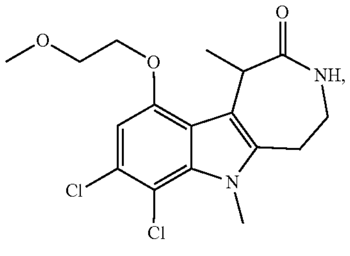
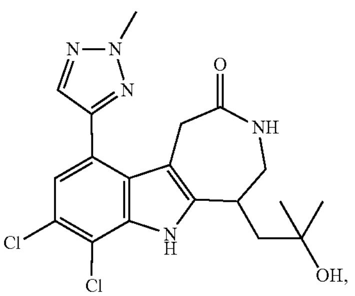
-continued
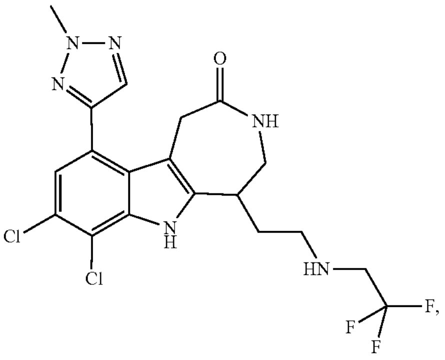
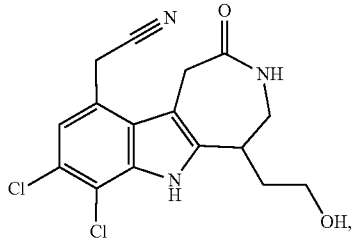
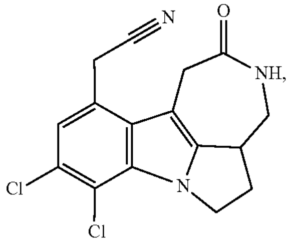
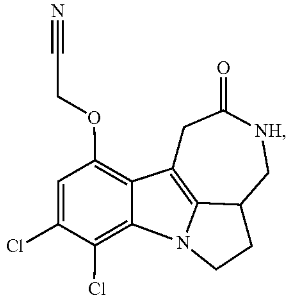
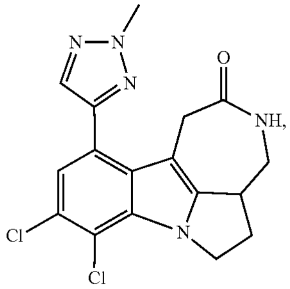
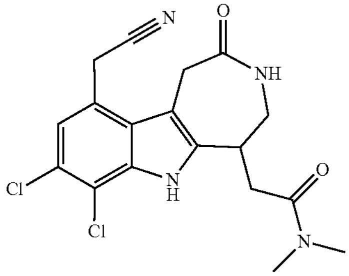
, -continued
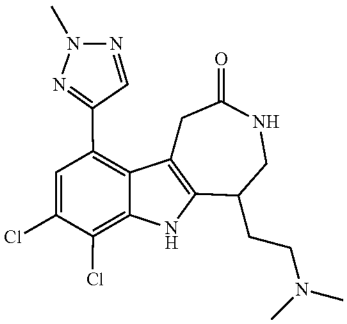
,
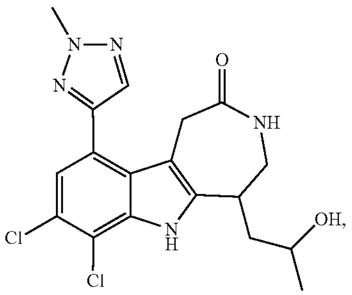
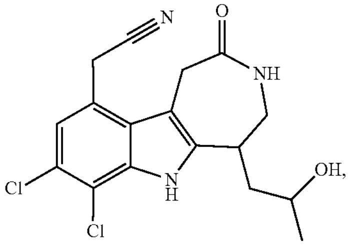
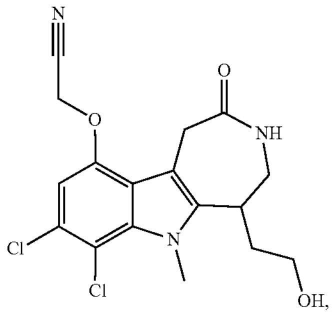
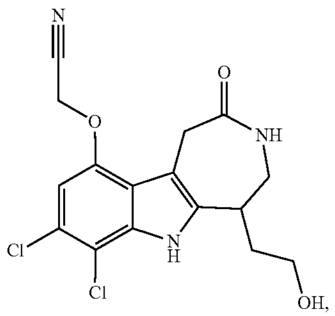
-continued
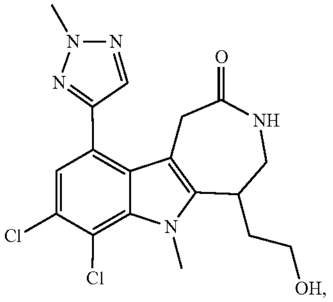
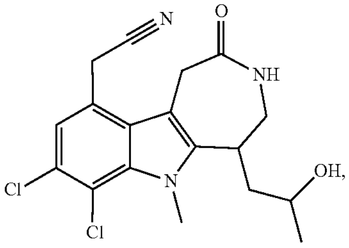
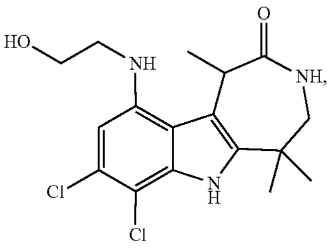
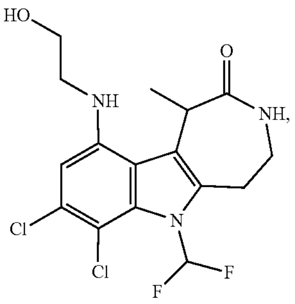
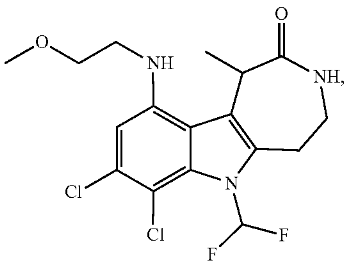
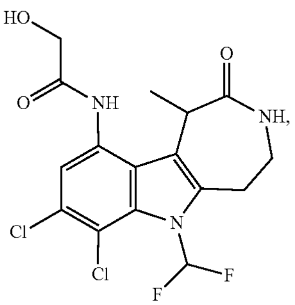

-continued
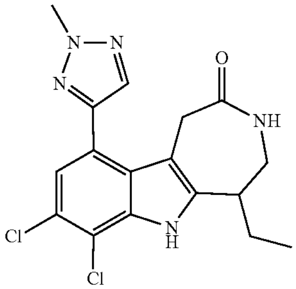
,
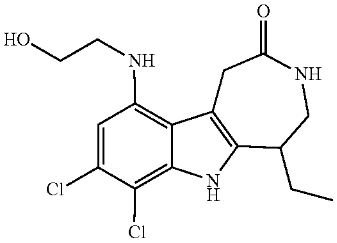
,
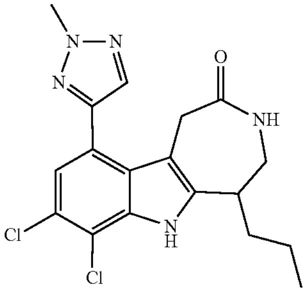
,
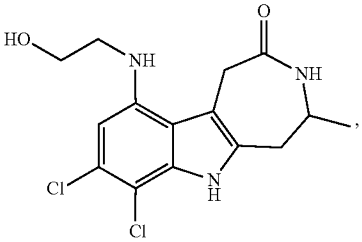
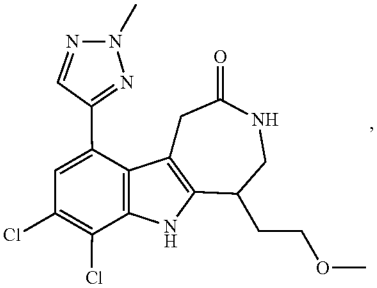
,
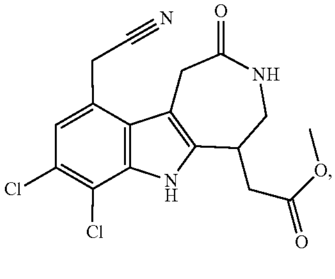
-continued
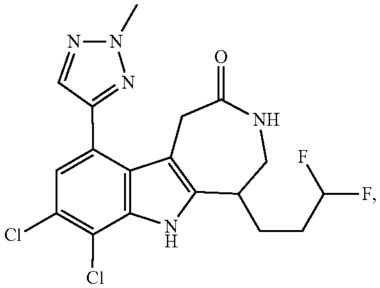
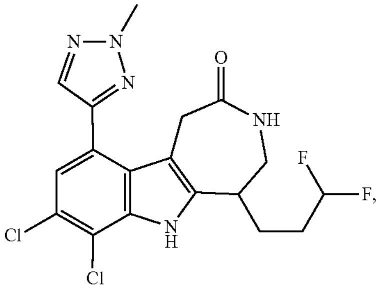
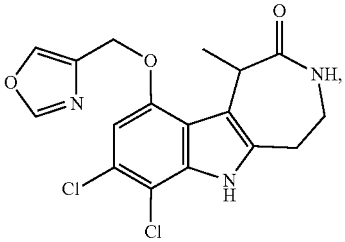
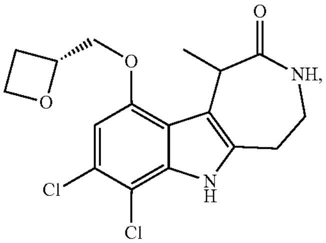
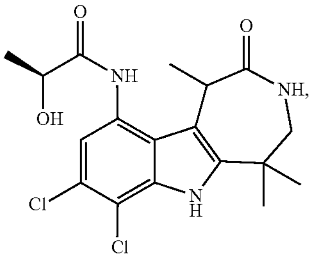
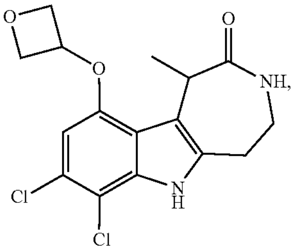

-continued
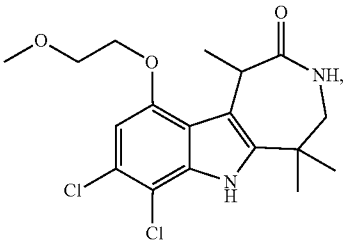
and
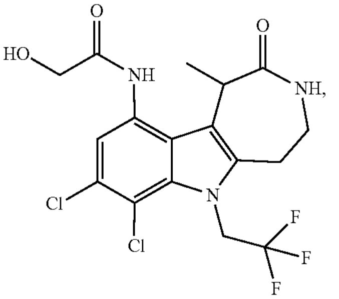
or a pharmaceutically acceptable salt thereof.
21. The compound of claim 1, wherein the compound is selected from:
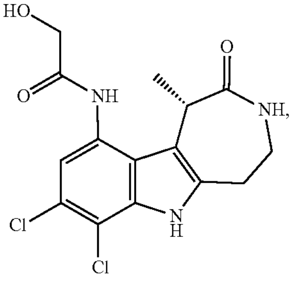
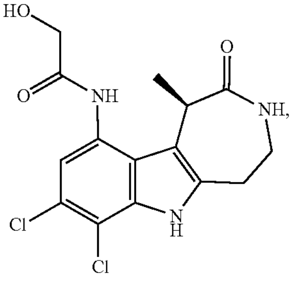
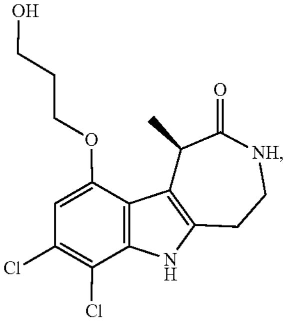
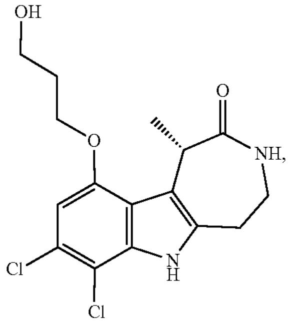
-continued
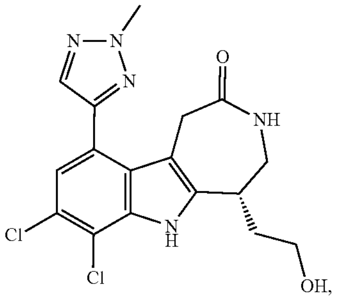
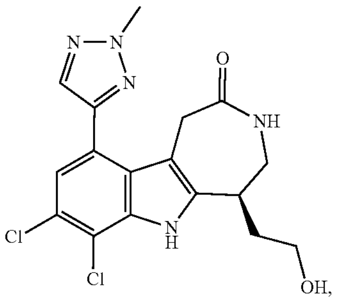
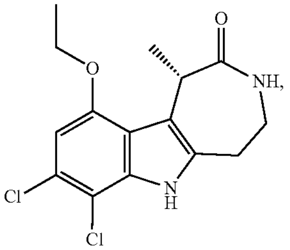
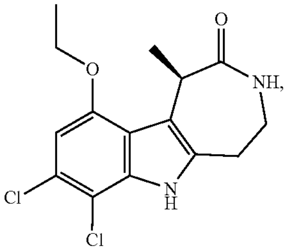
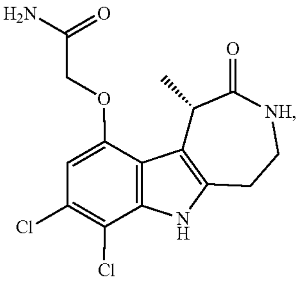
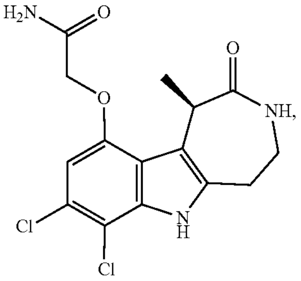

-continued
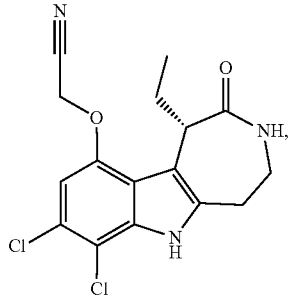,
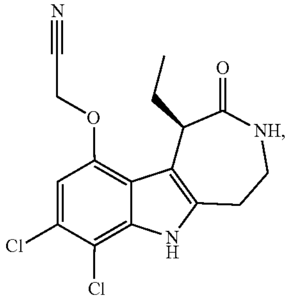,
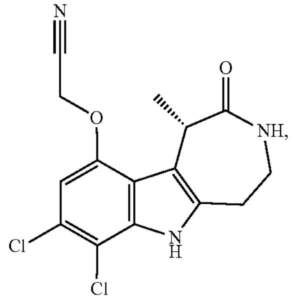,
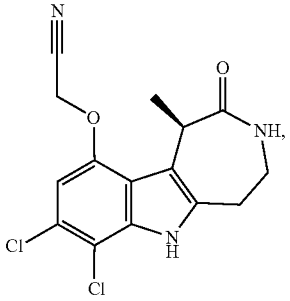,
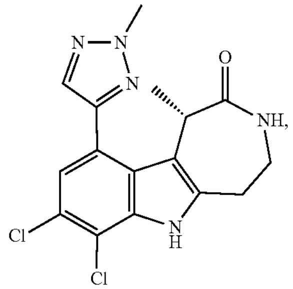,
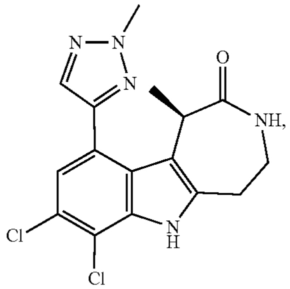,
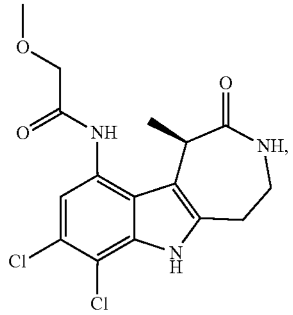,
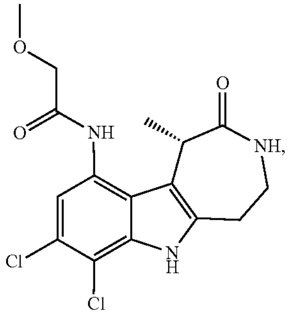,
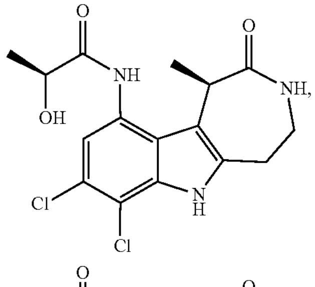,
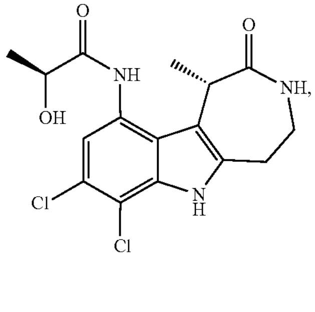,
-continued
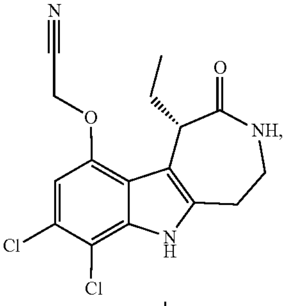,
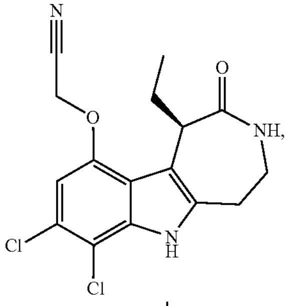,
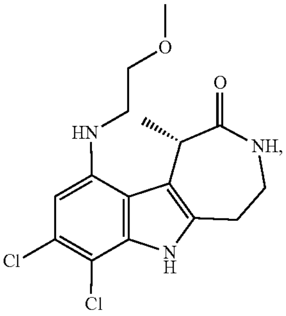,
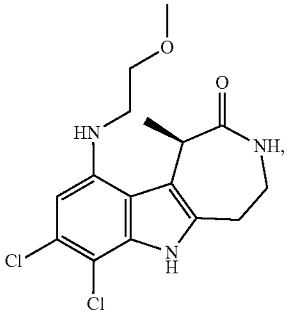,
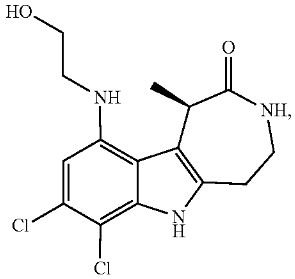,
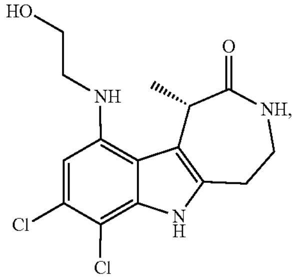,
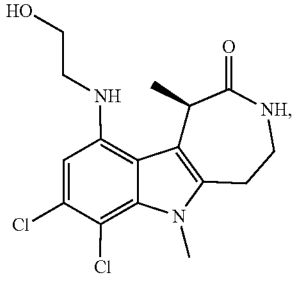,
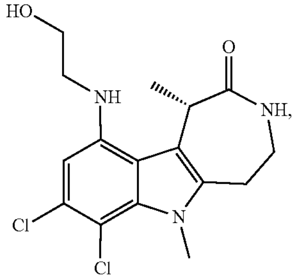, -continued
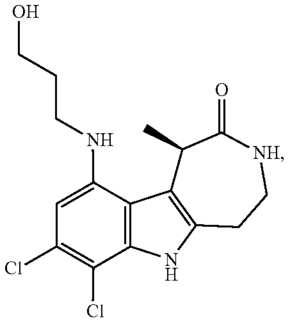
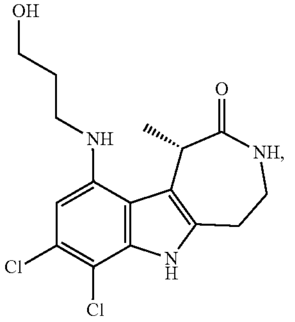 [SMILES: C[C@@H]1C(=O)NCCc2[nH]c3c(Cl)c(Cl)cc(NCCCO)c3c21]
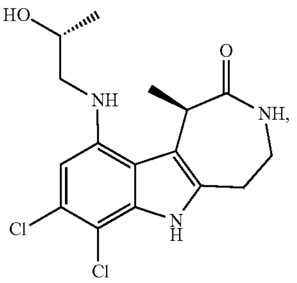
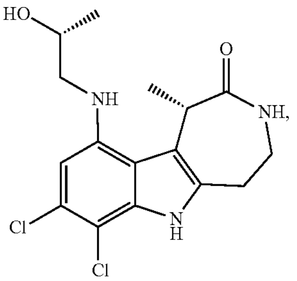
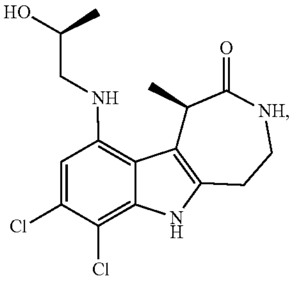
-continued
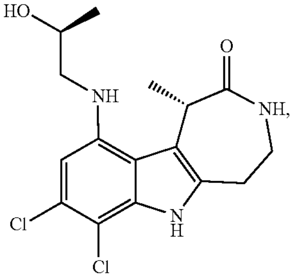
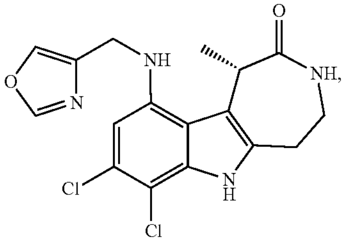
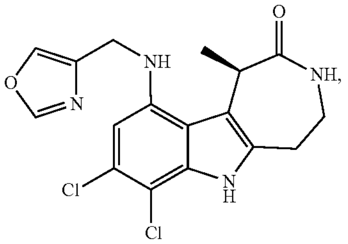
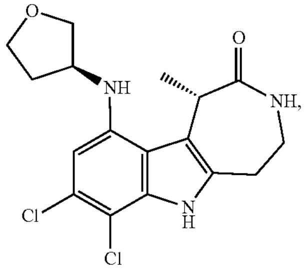
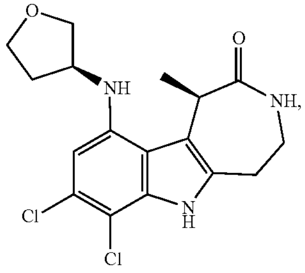
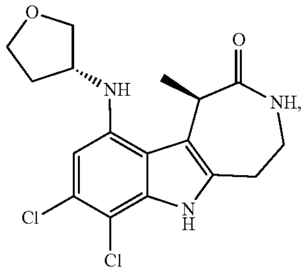

-continued
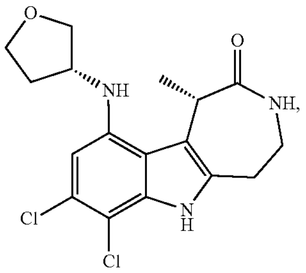
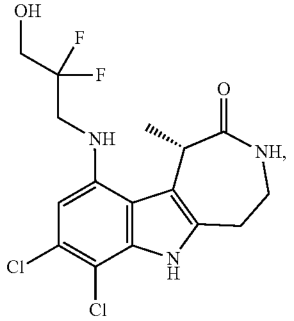
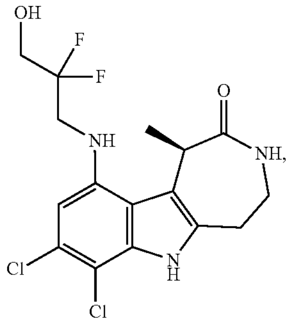
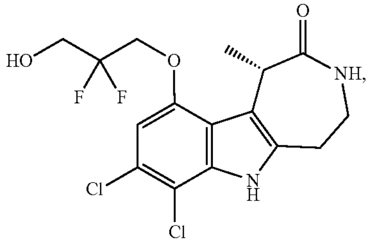
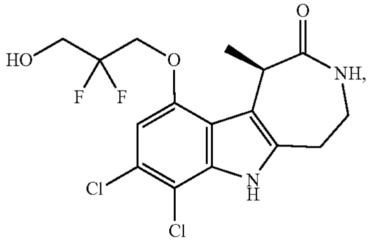
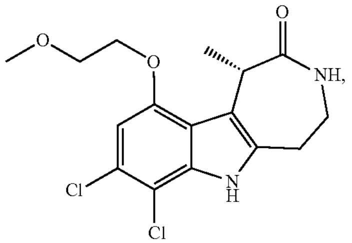
-continued
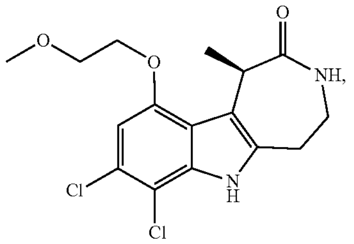
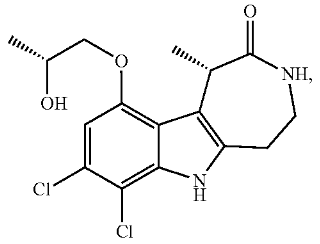
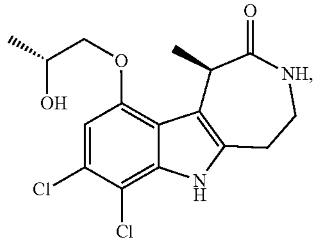
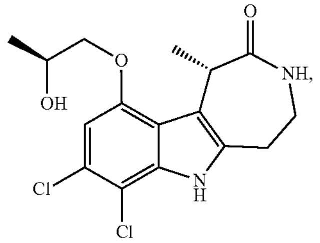
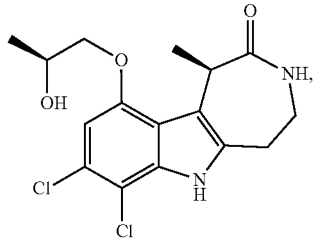
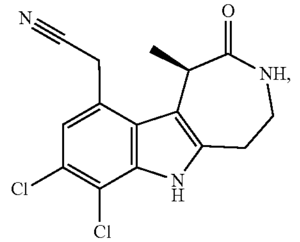
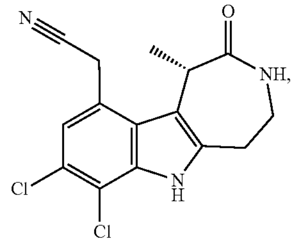

-continued
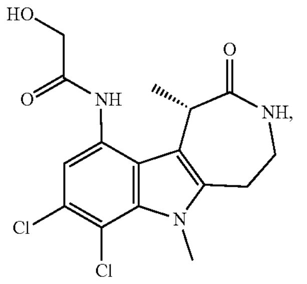
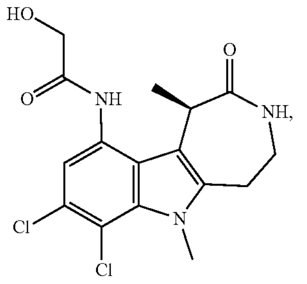
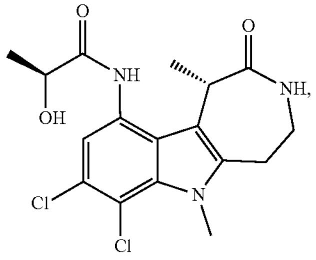
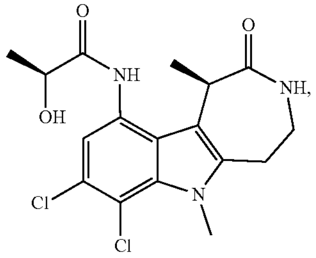
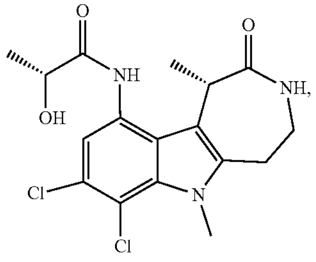
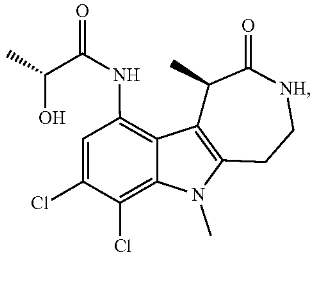
-continued
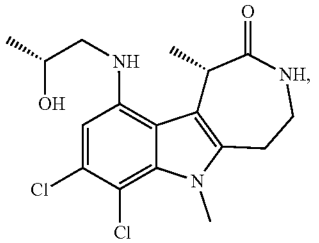
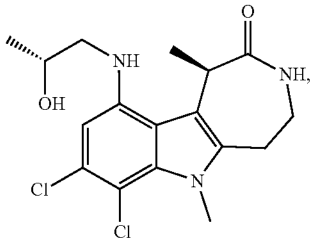
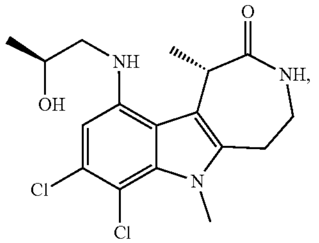
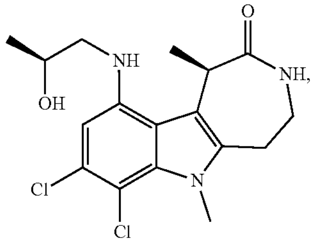
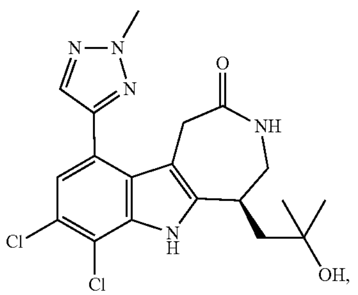
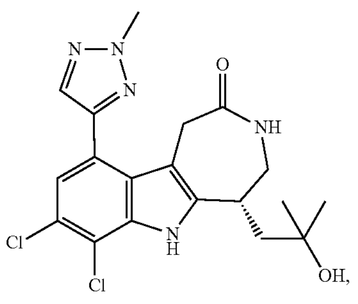

-continued
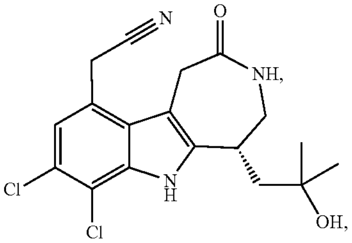
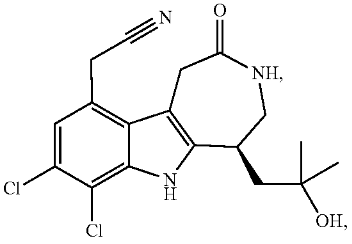
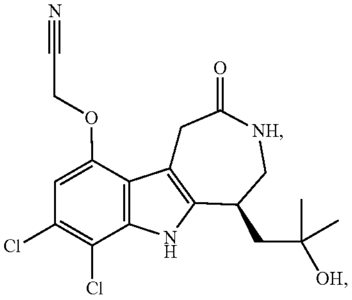
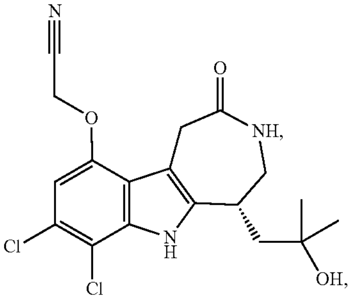
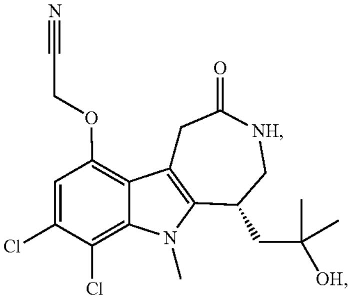
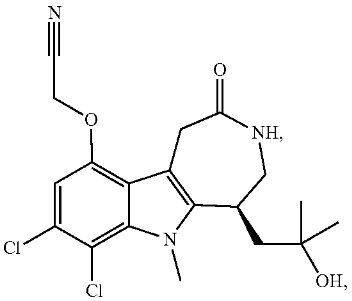
-continued
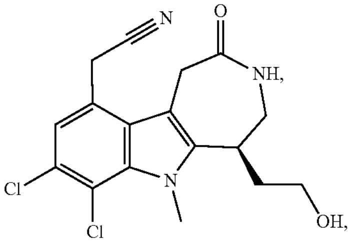
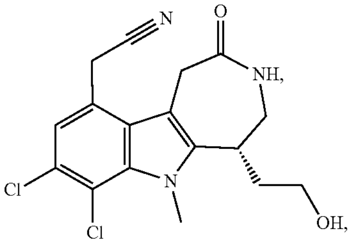
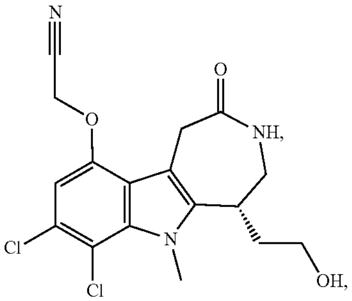
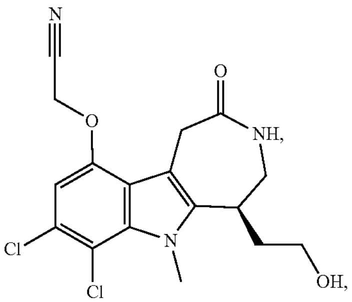
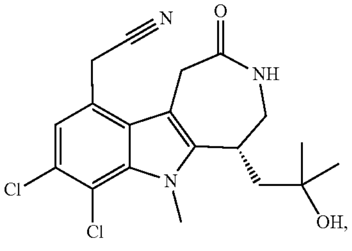
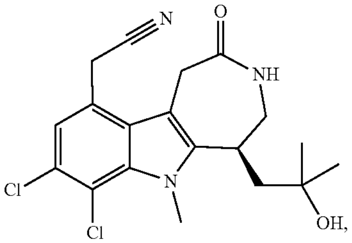

-continued
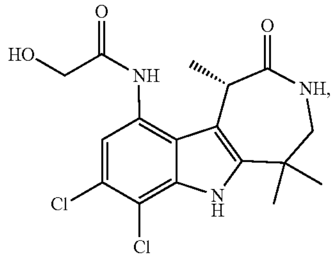
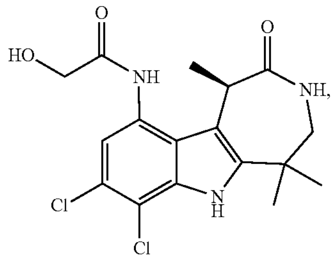
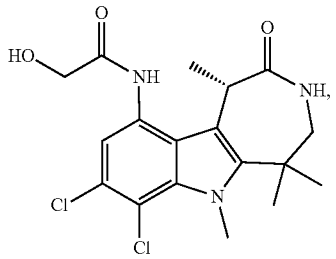
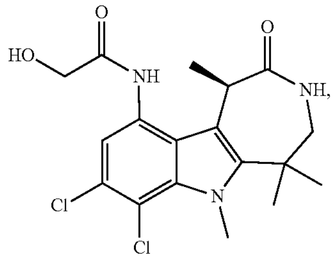
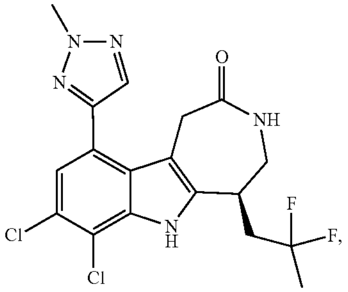
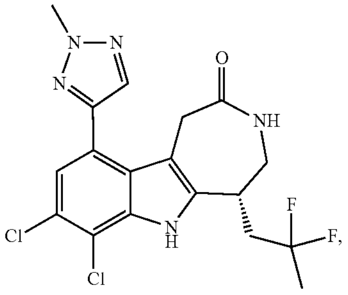
-continued
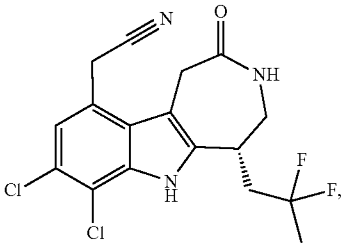
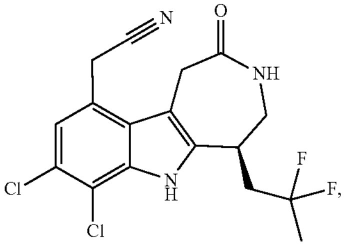
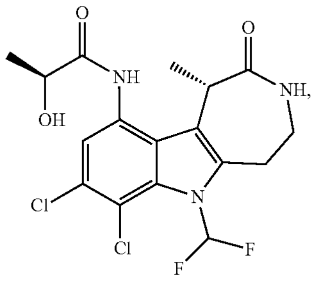
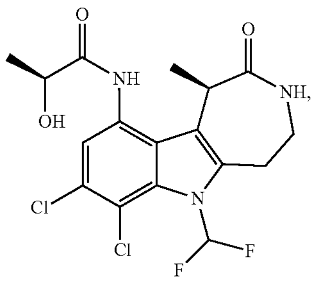
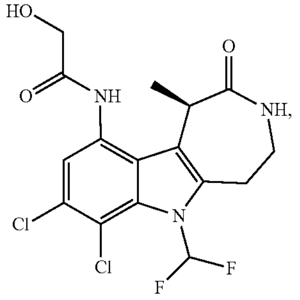
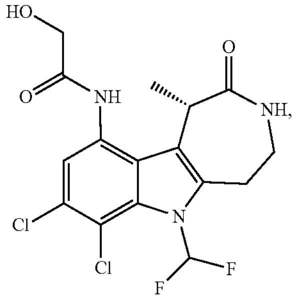

-continued
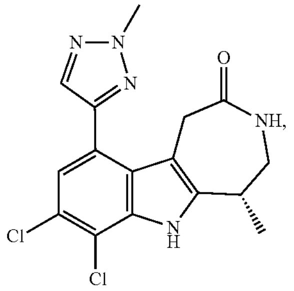
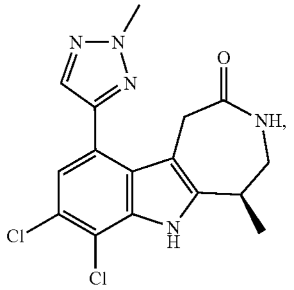
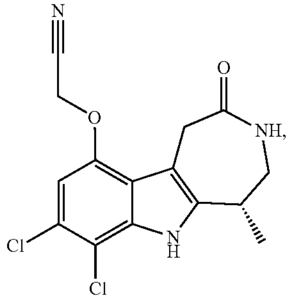
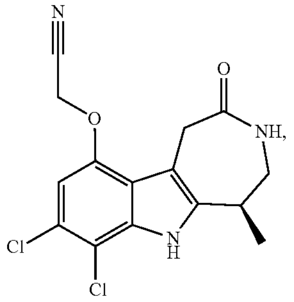
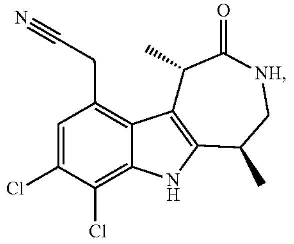
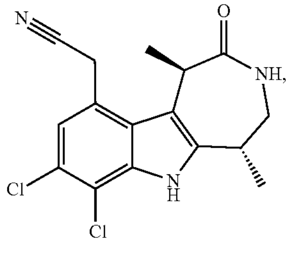
-continued
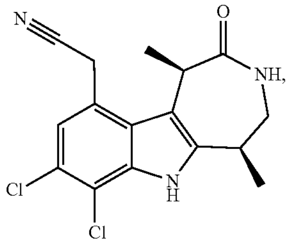
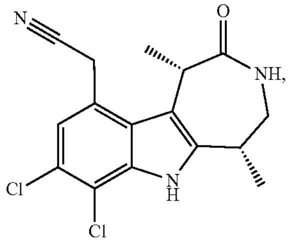
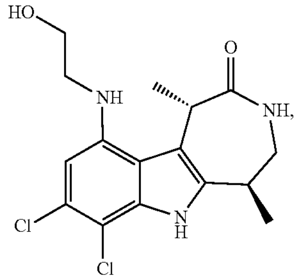
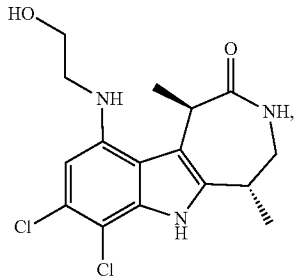
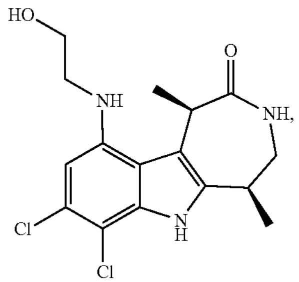
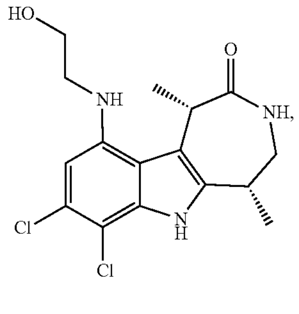

-continued
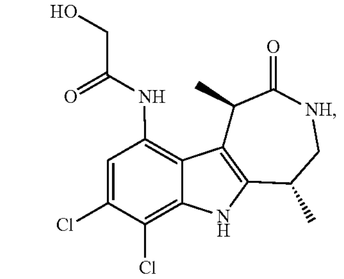
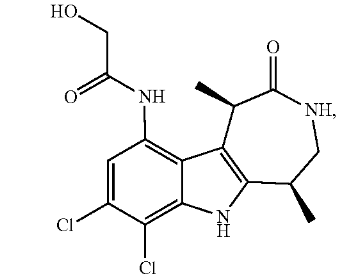
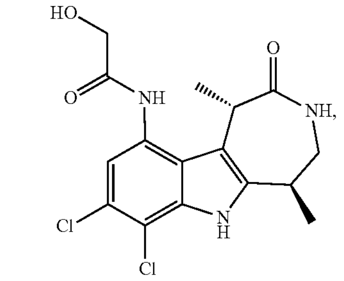
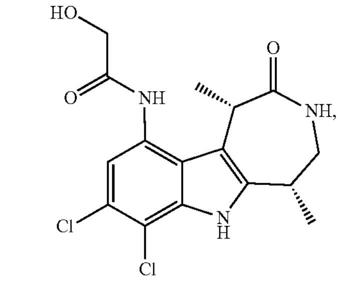
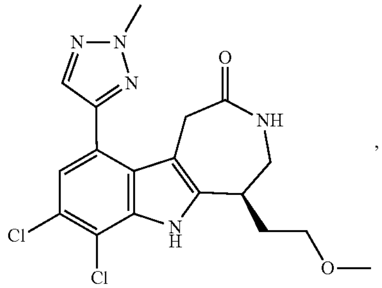
,
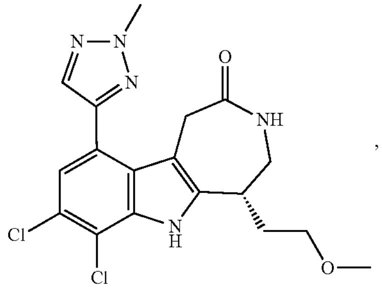
,
-continued
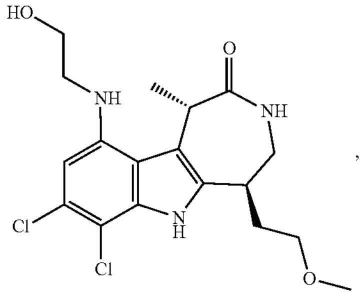
,
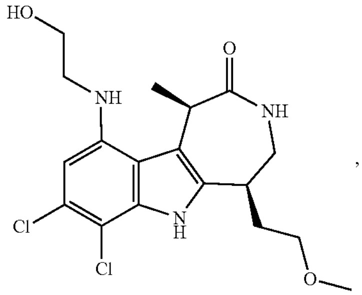
,
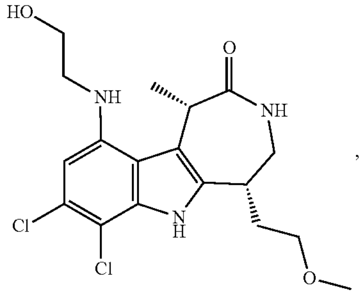
,
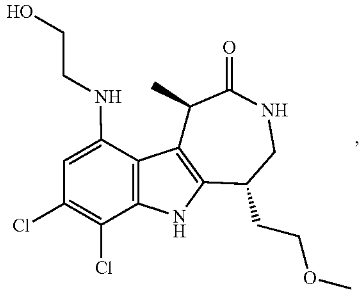
,
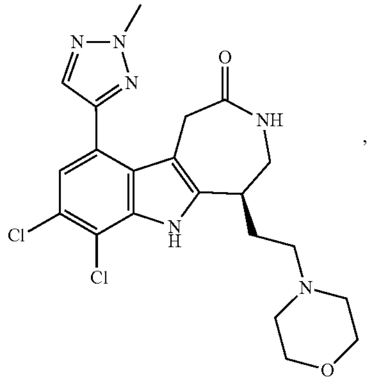
, -continued
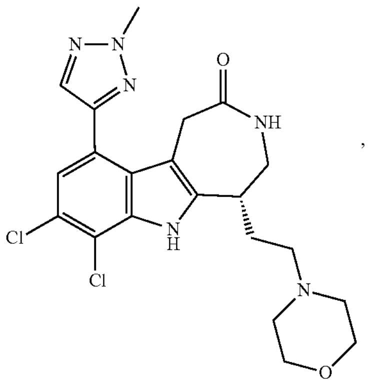
,
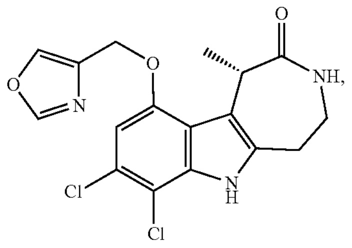
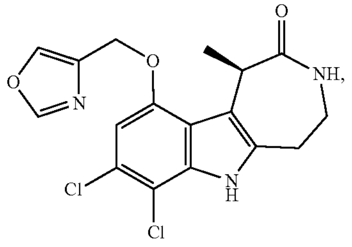
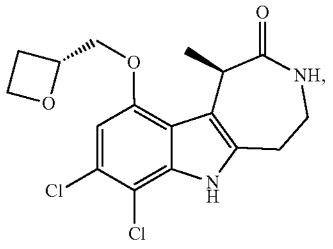
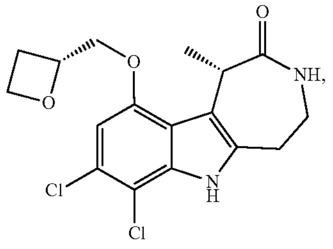
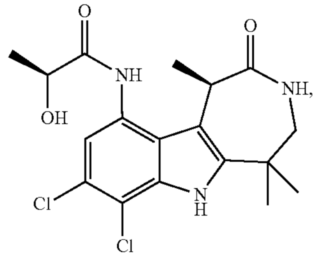
-continued
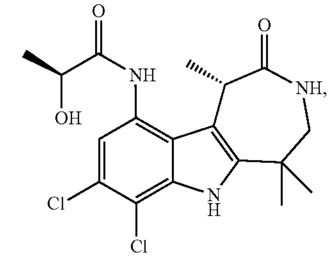
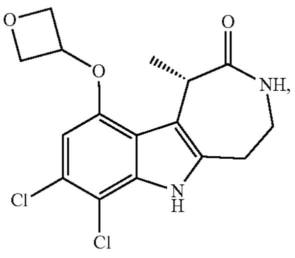
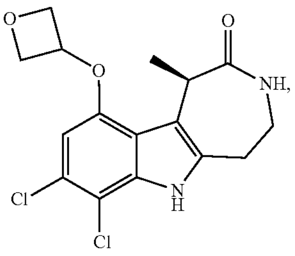
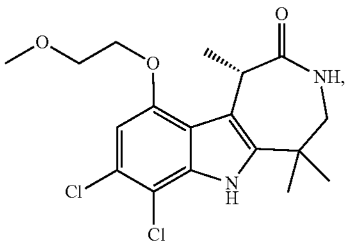
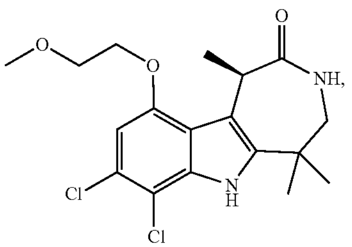
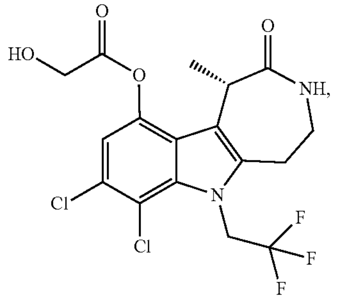
and -continued
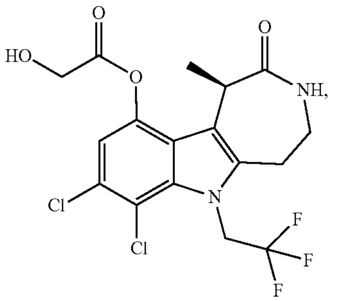
or a pharmaceutically acceptable salt thereof.
22. A compound selected from:
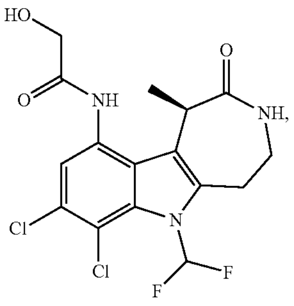
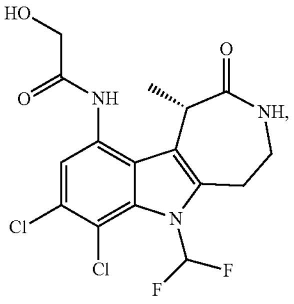
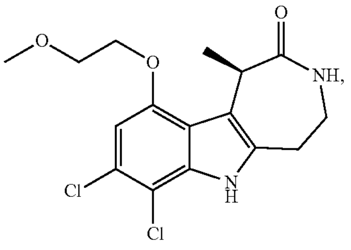
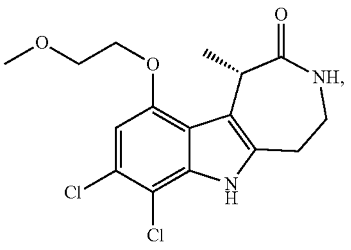
-continued
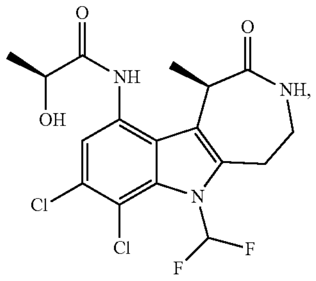
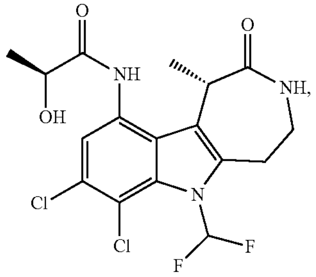
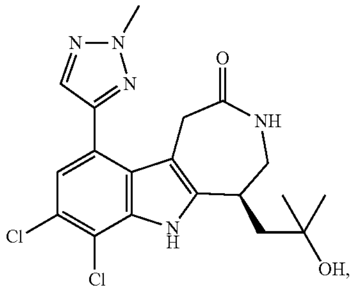
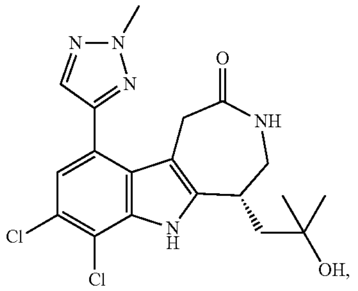
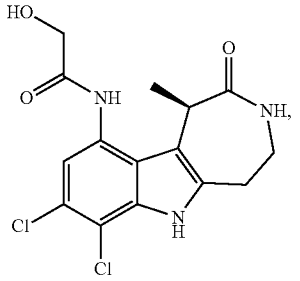
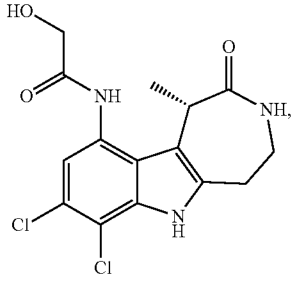

-continued

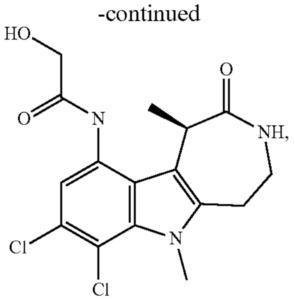

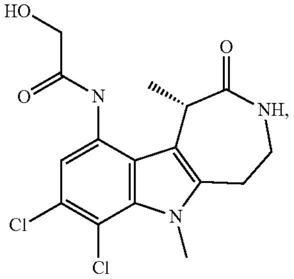

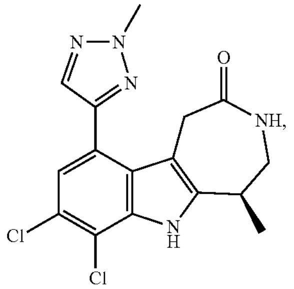

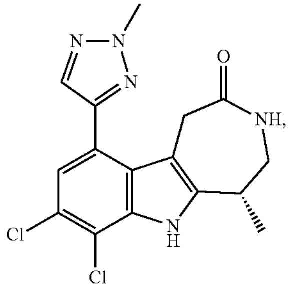

-continued

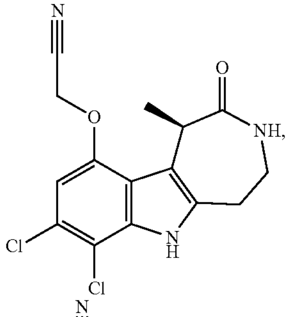

and

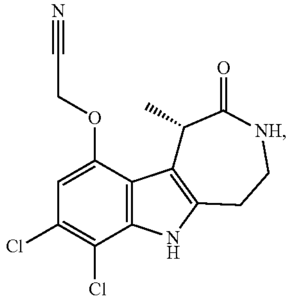

or a pharmaceutically acceptable salt thereof.

23. A pharmaceutical composition, comprising a compound according to claim 1, or a pharmaceutically acceptable salt thereof, with one or more pharmaceutically acceptable carriers, diluents, or excipients.

24. A method of treating an immune-mediated disease in a patient, comprising administering to a patient in need of such treatment an effective amount of a compound according to claim 1, or a pharmaceutically acceptable salt thereof, or a pharmaceutically composition thereof.

25. The method of claim 24, wherein the immune-mediated disease is selected from systemic lupus erythematosus, lupus nephritis, dermatomyositis, and Aicardi-Goutières syndrome.

26. A method of treating a disease associated with cGAS activation in a patient, comprising administering to a patient in need of such treatment an effective amount of a compound according to claim 1, or a pharmaceutically acceptable salt thereof, or a pharmaceutically composition thereof.

* * * * *